US012509459B2

(12) United States Patent
Hartman et al.

(10) Patent No.: US 12,509,459 B2
(45) Date of Patent: Dec. 30, 2025

(54) INHIBITORS OF NLRP3 INFLAMMASOME

(71) Applicant: BioAge Labs, Inc., Richmond, CA (US)

(72) Inventors: George Hartman, Lansdale, PA (US); Yan Wang, Richmond, CA (US); Paul Humphries, Richmond, CA (US); Rusty Montgomery, Richmond, CA (US); Matthias Geyer, Bonn (DE); Kevin Wilhelmsen, Richmond, CA (US); Shijun Yan, Richmond, CA (US)

( * ) Notice: Subject to any disclaimer, the term of this patent is extended or adjusted under 35 U.S.C. 154(b) by 0 days.

(21) Appl. No.: 19/089,839

(22) Filed: Mar. 25, 2025

(65) Prior Publication Data

US 2025/0304581 A1 Oct. 2, 2025

Related U.S. Application Data

(60) Provisional application No. 63/708,034, filed on Oct. 16, 2024, provisional application No. 63/669,006, filed on Jul. 9, 2024, provisional application No. 63/656,967, filed on Jun. 6, 2024, provisional application No. 63/570,087, filed on Mar. 26, 2024.

(51) Int. Cl.

| | |
|---|---|
| ***C07D 471/04*** | (2006.01) |
| ***A61K 31/416*** | (2006.01) |
| ***A61K 31/437*** | (2006.01) |
| ***A61K 31/4545*** | (2006.01) |
| ***A61K 31/5377*** | (2006.01) |
| ***A61P 3/04*** | (2006.01) |
| ***A61P 19/06*** | (2006.01) |
| ***C07D 231/56*** | (2006.01) |
| ***C07D 403/06*** | (2006.01) |

(52) U.S. Cl.

CPC .......... *C07D 471/04* (2013.01); *A61K 31/416* (2013.01); *A61K 31/437* (2013.01); *A61K 31/4545* (2013.01); *A61K 31/5377* (2013.01); *A61P 3/04* (2018.01); *A61P 19/06* (2018.01); *C07D 231/56* (2013.01); *C07D 403/06* (2013.01)

(58) Field of Classification Search

CPC .................................................... C07D 471/04
USPC .................................................... 514/210.21
See application file for complete search history.

(56) References Cited

U.S. PATENT DOCUMENTS

| | | | |
|---|---|---|---|
| 7,511,062 | B2 | 3/2009 | Kuang et al. |
| 11,702,391 | B2 | 7/2023 | Hartman et al. |
| 11,708,334 | B2 | 7/2023 | Hartman et al. |
| 11,787,805 | B2 | 10/2023 | Hartman |
| 12,129,251 | B2 | 10/2024 | Hartman |
| 12,215,087 | B2 | 2/2025 | Hartman et al. |
| 2023/0365507 | A1 | 11/2023 | Hartman et al. |
| 2024/0116933 | A1 | 4/2024 | Hartman |
| 2025/0084080 | A1 | 3/2025 | Kothari |

FOREIGN PATENT DOCUMENTS

| | | | | | |
|---|---|---|---|---|---|
| CN | 111 329 993 | A | | 6/2020 | |
| EP | 2 269 990 | A1 | | 1/2011 | |
| EP | 3 660 003 | A1 | | 6/2020 | |
| WO | WO 2004/099143 | A1 | | 11/2004 | |
| WO | WO 2008/006561 | A1 | | 1/2008 | |
| WO | WO 2012/101453 | A1 | | 8/2012 | |
| WO | WO 2013/126856 | A1 | | 8/2013 | |
| WO | WO 2016/081290 | A1 | | 5/2016 | |
| WO | WO 2019/001416 | A1 | | 1/2019 | |
| WO | WO 2019/193342 | A1 | | 10/2019 | |
| WO | WO 2020/097389 | A1 | | 5/2020 | |
| WO | WO 2021/209539 | A1 | | 10/2021 | |
| WO | WO 2022/006433 | A1 | | 1/2022 | |
| WO | 2022204227 | | * | 9/2022 | |
| WO | WO-2022204227 | A1 | * | 9/2022 | ........... C07D 471/04 |
| WO | 2023147468 | | * | 8/2023 | |
| WO | WO-2023147468 | A1 | * | 8/2023 | ........... C07D 487/04 |
| WO | 2024064655 | | * | 3/2024 | |
| WO | WO-2024064655 | A1 | * | 3/2024 | .............. A61P 43/00 |

OTHER PUBLICATIONS

Caira, "Crystalline Polymorphism of Organic Compounds", *Topics in Current Chemistry* 198:163-208 (1998).
Fischer et al., "Age-Dependent Changes in the Cochlea", *Gerontology* 1-7 (2019).
Franceshi et al., "Inflamm-aging: An Evolutionary Perspective on Immunosenescence", *Annals of the New York Academy of Sciences* 908(1):244-254 (2000).
Hubbard et al., "Frailty, inflammation and the elderly" *Biogerontology* 11(5):635-641 (2010).
Kang et al., "Synthesis and structure-activity relationships of novel fused ring analogues of Q203 as antitubercular agents", *European Journal of Medicinal Chemistry* 136(1):420-427 (2017), doi:10.1016/j.ejmech.2017.05.021.
Le Prell et al., "Noise-induced hearing loss and its prevention: current issues in mammalian hearing" *Current Opinion in Physiology* 18:32-36 (2020).
Montalvao et al., "Synthesis and Biological Evaluation of 2-Aminobenzothiazole and Benzimidazole Analogs Based on the Clathrodin Structure", *Archiv der Pharmazie—Chemistry in Life Sciences* 349(2):137-149 (2016); doi:10.1002/ardp.201500365.
Nakanishi et al., "NLRP3 mutation and cochlear autoinflammation cause syndromic and nonsyndromic hearing loss DFNA34 responsive to anakinra therapy", *PNAS* 114(37):E7766-E7775 (2017).
Nakanishi et al., "Genetic Hearing Loss Associated With Autoinflammation", *Frontiers in Neurology* 11(Art. 141):1-7 (2020).
Schwaid et al., "Strategies for Targeting the NLRP3 Inflammasome in the Clinical and Preclinical Space", *Journal of Medicinal Chemistry* 64(1):101-122 (2021).

(Continued)

*Primary Examiner* — Niloofar Rahmani
(74) *Attorney, Agent, or Firm* — Lathrop GPM LLP; Brian C. Trinque; Nicole Sassu

(57) ABSTRACT

The present disclosure relates to compounds that act as inhibitors of NLRP3 inflammasomes; pharmaceutical compositions comprising the compounds; and methods of treating cancer and disorders associated with inflammation and inflammaging.

29 Claims, 21 Drawing Sheets

Specification includes a Sequence Listing.

(56) References Cited

OTHER PUBLICATIONS

Yao et al., "Inflammation and Immune Systems Alterations in Frailty", *Clinics in Geriatric Medicine* 27(1):79-87 (2011).
Yee et al., "Zika virus infection causes widespread damage to the inner ear", *Hearing Research* 395:1-15 (2020).
Zahid et al., "Pharmacological Inhibitors of the MLRP3 Inflammasome", *Frontiers in Immunology* vol. 10, Article 2538 (2019); doi:10.3389/fimmu.2019.02538.
U.S. Appl. No. 17/701,856 / 2022-0324812 A1 / U.S. Pat. No. 11,702,391, filed Mar. 23, 2022 / Oct. 13, 2022 / Jul. 18, 2023, George Hartman.
U.S. Appl. No. 17/930,895 / 2023-0051130 A1 / U.S. Pat. No. 11,708,334, filed Sep. 9, 2022 / Feb. 16, 2023 / Jul. 25, 2023, George Hartman.
U.S. Appl. No. 18/323,939 / 2023-0365507 A1, filed May 25, 2023 / Nov. 16, 2023, George Hartman.
U.S. Appl. No. 18/353,410 / 2024-0059659 A1, filed Jul. 17, 2023 / Feb. 22, 2024, George Hartman.
U.S. Appl. No. 18/353,422 / 2024-0067610 A1 / U.S. Pat. No. 12,215,087, filed Jul. 17, 2023 / Feb. 29, 2024 / Feb. 4, 2025, George Hartman.
U.S. Appl. No. 18/353,370 / 2024-0051923 A1, filed Jul. 17, 2023 / Feb. 15, 2024, George Hartman.
U.S. Appl. No. 18/160,594 / 2023-0242528 A1 / U.S. Pat. No. 11,787,805, filed Jan. 27, 2023 / Aug. 3, 2023 / Oct. 17, 2023, George Hartman.
U.S. Appl. No. 18/462,015 / 2024-0067648 A1 / U.S. Pat. No. 12,129,251, filed Sep. 6, 2023 / Feb. 29, 2024 / Oct. 29, 2024, George Hartman.
U.S. Appl. No. 18/896,259 / 2025-0092037 A1, filed Sep. 25, 2024 / Mar. 20, 2025, George Hartman.
U.S. Appl. No. 18/470,105 / 2024-0116933 A1, filed Sep. 19, 2023 / Apr. 11, 2024, George Hartman.
U.S. Appl. No. 18/882,356 / 2025-0084080 A1, filed Sep. 11, 2024 / Mar. 13, 2025, Sanjeev Hukmichand Kothari.
International Search Report and Written Opinion for International Application No. PCT/US2025/021357 mailed Aug. 7, 2025, 16 pages.

* cited by examiner

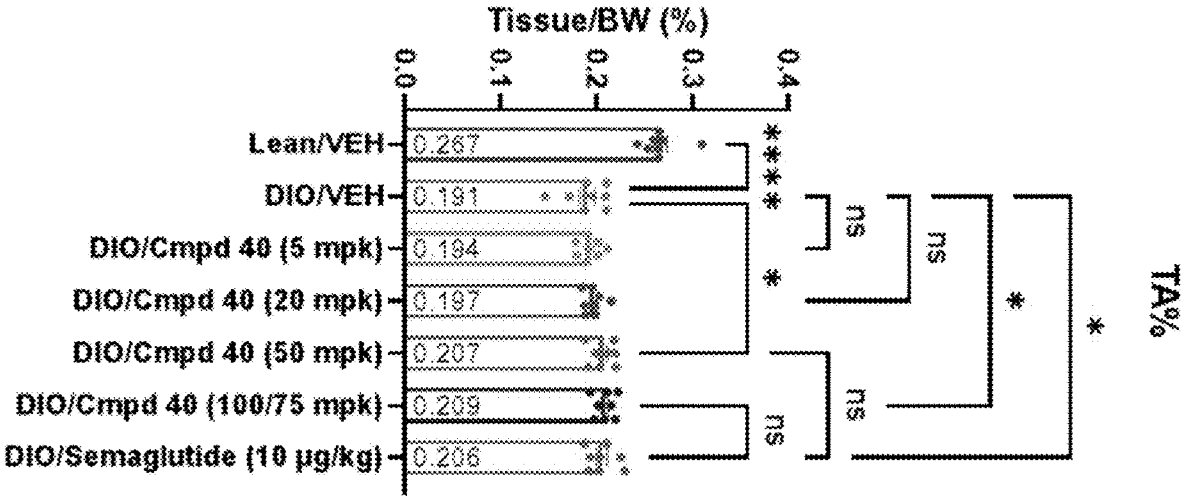
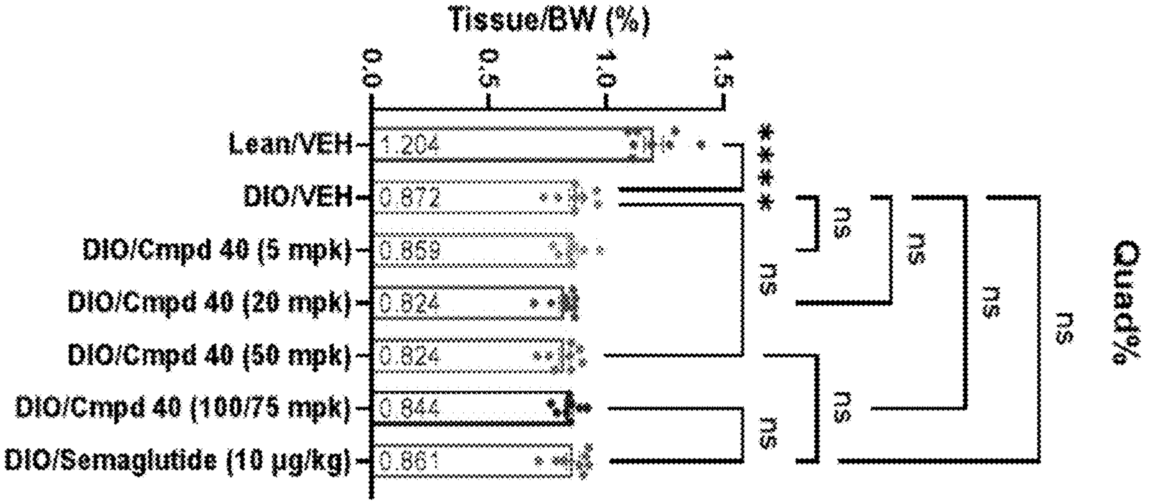
Fig. 13, cont'd

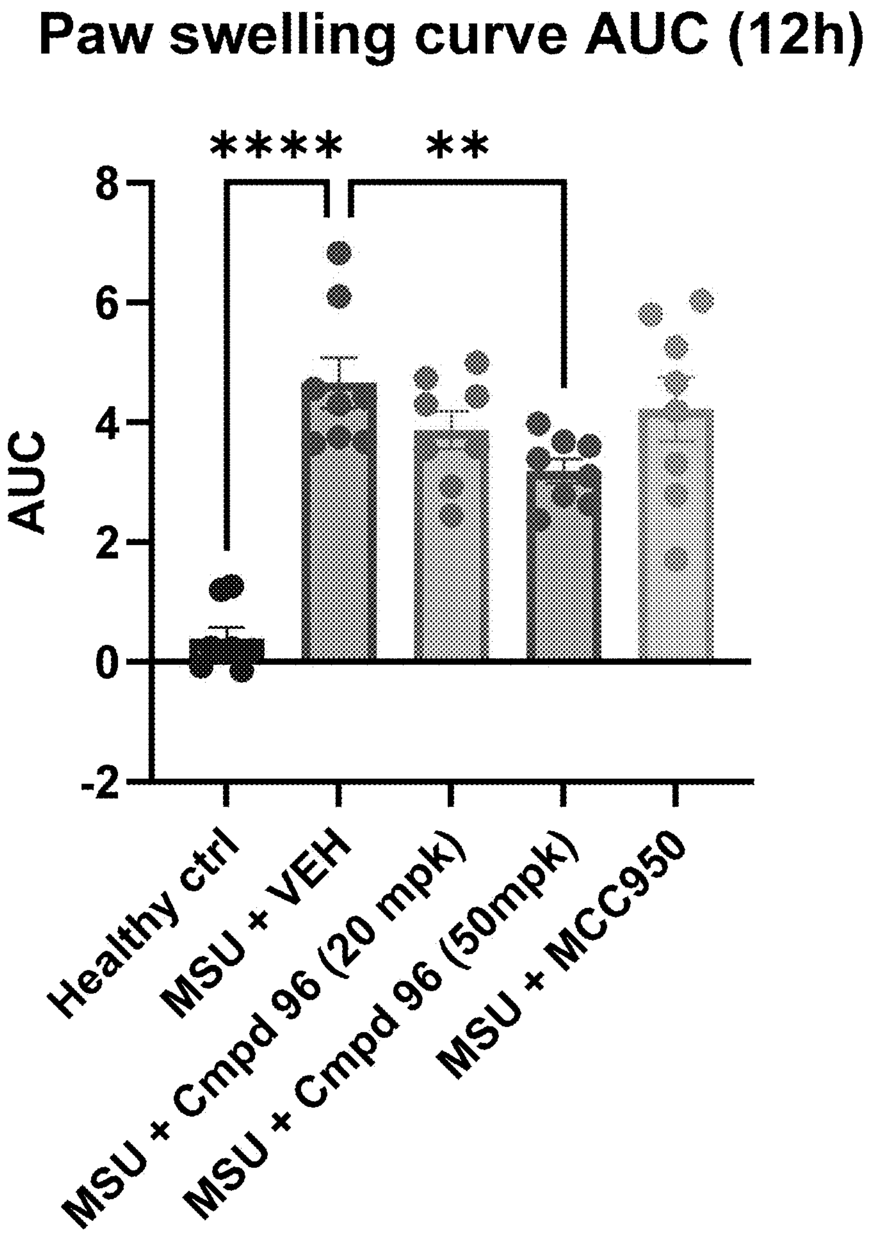
Fig. 16, cont'd

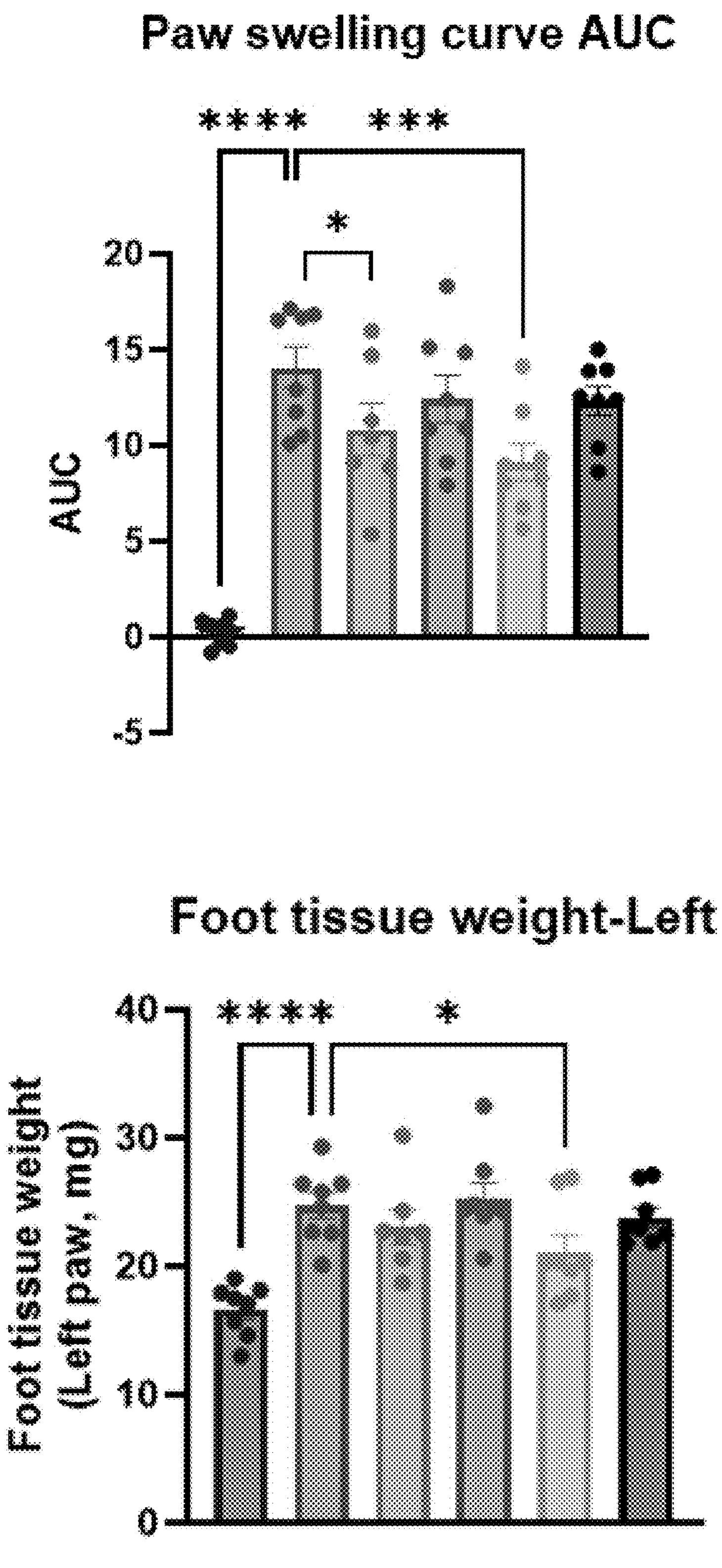
Fig. 17, cont'd

SEQUENCE LISTING

```
Sequence total quantity: 1
SEQ ID NO: 1            moltype = AA  length = 1036
FEATURE                 Location/Qualifiers
source                  1..1036
                        mol_type = protein
                        organism = Homo sapiens
SEQUENCE: 1
MKMASTRCKL ARYLEDLEDV DLKKFKMHLE DYPPQKGCIP LPRGQTEKAD HVDLATLMID  60
FNGEEKAWAM AVWIFAAINR RDLYEKAKRD EPKWGSDNAR VSNPTVICQE DSIEEEWMGL  120
LEYLSRISIC KMKKDYRKKY RKYVRSRFQC IEDRNARLGE SVSLNKRYTR LRLIKEHRSQ  180
QEREQELLAI GKTKTCESPV SPIKMELLFD PDDEHSEPVH TVVFQGAAGI GKTILARKMM  240
LDWASGTLYQ DRFDYLFYIH CREVSLVTQR SLGDLIMSCC PDPNPPIHKI VRKPSRILFL  300
MDGFDELQGA FDEHIGPLCT DWQKAERGDI LLSSLIRKKL LPEASLLITT RPVALEKLQH  360
LLDHPRHVEI LGFSEAKRKE YFFKYFSDEA QARAAFSLIQ ENEVLFTMCF IPLVCWIVCT  420
GLKQQMESGK SLAQTSKTTT AVYVFFLSSL LQPRGGSQEH GLCAHLWGLC SLAADGIWNQ  480
KILFEESDLR NHGLQKADVS AFLRMNLFQK EVDCEKFYSF IHMTFQEFFA AMYYLLEEEK  540
EGRTNVPGSR LKLPSRDVTV LLENYGKFEK GYLIFVVRFL FGLVNQERTS YLEKKLSCKI  600
SQQIRLELLK WIEVKAKAKK LQIQPSQLEL FYCLYEMQEE DFVQRAMDYF PKIEINLSTR  660
MDHMVSSFCI ENCHRVESLS LGFLHNMPKE EEEEEKEGRH LDMVQCVLPS SSHAACSHGL  720
VNSHLTSSFC RGLFSVLSTS QSLTELDLSD NSLGDPGMRV LCETLQHPGC NIRRLWLGRC  780
GLSHECCFDI SLVLSSNQKL VELDLSDNAL GDFGIRLLCV GLKHLLCNLK KLWLVSCCLT  840
SACCQDLASV LSTSHSLTRL YVGENALGDS GVAILCEKAK NPQCNLQKLG LVNSGLTSVC  900
CSALSSVLST NQNLTHLYLR GNTLGDKGIK LLCEGLLHPD CKLQVLELDN CNLTSHCCWD  960
LSTLLTSSQS LRKLSLGNND LGDLGVMMFC EVLKQQSCLL QNLGLSEMYF NYETKSALET  1020
LQEEKPELTV VFEPSW                                                 1036
```

INHIBITORS OF NLRP3 INFLAMMASOME

REFERENCE TO SEQUENCE LISTING SUBMITTED ELECTRONICALLY

The content of the electronically submitted sequence listing in XML file (Name: 762525_BIOT-007PC_ST26.xml; Size: 2,722 bytes; Date of Creation: Mar. 24, 2025) is incorporated herein by reference in its entirety.

RELATED APPLICATIONS

This application is related to U.S. Provisional Application No. 63/570,087 filed Mar. 26, 2024, U.S. Provisional Application No. 63/656,967, filed Jun. 6, 2024, U.S. Provisional Application No. 63/669,006, filed Jul. 9, 2024, and U.S. Provisional Application No. 63/708,034, filed Oct. 16, 2024, the entire contents of each are incorporated herein.

BACKGROUND

Aging frailty poses a very concerning problem for the overall health and well-being of individuals and is characterized as a syndrome of multisystem physiological dysregulation. Aging frailty is a geriatric syndrome characterized by weakness, low physical activity, slowed motor performance, exhaustion, and unintentional weight loss (Yao, X. et al., Clinics in Geriatric Medicine 27(1): 79-87 (2011)). Furthermore, there are many studies showing a direct correlation between aging frailty and inflammation (Hubbard, R. E., et al., Biogerontology 11(5):635-641 (2010)). Immunosenescence is characterized by a low grade, chronic systemic inflammatory state known as inflammaging (Franceshi, C. et al., Annals of the New York Academy of Sciences 908:244-254 (2000)). This heightened inflammatory state or chronic inflammation found in aging and aging frailty leads to immune dysregulation and a complex remodeling of both innate and adaptive immunity.

Inhibiting the NLRP3 inflammasome, an oligomeric protein complex that includes ASC and caspase-1, mediates inflammation in an extensive number of preclinical models (Schwaid, A. G., *J. Med. Chem.* 2021, 64(1), 101-122). At the same time, the NLRP3 inflammasome is part of a larger pro-inflammatory pathway, whose modulation is also being explored. NLRP3 is an inflammasome sensor protein that has been well studied in a number of disease contexts. Many different indications are associated with the NLRP3 inflammasome including diseases related to aging, cryopyrin-associated periodic syndrome (CAPS), nonalcoholic steatohepatitis (NASH), gout, coronary artery disease, Crohn's disease, osteoarthritis, rheumatoid arthritis, Alzheimer's disease, Parkinson's disease, intestinal disorders, acute respiratory distress syndrome (ARDS), amyotrophic lateral sclerosis (ALS), cancer, and dermatological diseases.

Inflammation, as well as activation of the NLRP3 inflammasome, have also been shown to result in hearing loss (Nakanishi, H., et al., *Frontiers in Neurology,* 2020, 11, 1-7; Nakanishi, H., et al., *PNAS,* 2017, E7766-E7775). The inflammation-related hearing loss can be age-dependent (Fischer, N., et al., *Gerontology,* 2019, 1-7), noise-induced (Le Prell, C. G., et al. *Current Opinion in Physiology,* 2020, 18, 32-36), and the result of a viral infection such as Zika virus and coronavirus (Yee, K. T., et al., *Hearing Research,* 2020, 395, 1-15).

Inactivation of NLRP3 inflammasome significantly alleviates obesity-mediated metabolic disorders, such as non-alcoholic fatty liver disease (NAFLD) (Wani, K., et. al., Int. J. Environ. Res. Public Health, 2021, 18, 511) and has been shown to reverse obesity in the diet-induced obesity mice model (Thornton, P., *J. Pharmacol. Exp. Ther.,* 2024, 388, 813-826). Other metabolic disorders linked to NLRP3 include insulin resistance (Vandanmagsar, B., et. al., *Nature Medicine,* 2011 17, 179-188), obesity-induced inflammation (Sokolova, M., *Scientific Reports,* 2020, 10, 21006), diabetes-associated atherosclerosis (Sharma, A., et al., *Diabetes* 2021; 70(3):772-787), and ischemic stroke concomitant with diabetes (Hong, P., et al., *J. Neuroinflammation,* 2019; 16:121). Inhibiting the NLRP3 inflammasome has also been shown to ameliorate kidney injury in diabetic nephropathy (Yang, M., et al., *Curr. Med. Chem.,* 2022, 30, 3261-3270) and play a role in obesity-related low-grade inflammation and insulin resistance in skeletal muscle (Jorquera, G., et al., *Int. J. Mol. Sci.,* 2021, 21, 3254).

NLRPs, including NLRP3, have been implicated in various eye diseases with not all being related to aging (Niu, L., et al., PLoS ONE 10(5): e0126277; and Mugisho, O., et al., Experimental Eye Research 215 (2022) 108911). For example, the NLRP3 inflammasome has been shown to play a role in both glaucoma, an ocular disease most commonly occurring in older adults, and dry eye, which can occur in people of any age.

The NLRP3 inflammasome is therefore a promising drug target. The breadth of the indications it is implicated in speak to the need for therapeutics that target the NLRP3 inflammasome.

SUMMARY

Provided here are compounds that inhibit the NLRP3 inflammasome. As such, these compounds are useful in the treatment of a variety of indications, including inflammaging and inflammation.

In particular, provided herein is a compound that binds to amino acids of Y143, R147, F257, Y258, H260, E263, V264, L272, L275, I276, C279, F299, G328, L331, L332, L335, and C514 of a NLRP3 amino acid sequence of SEQ ID NO: 1. Such a compound is useful for the treatment of a variety of conditions in a subject, such as cancer, inflammaging, inflammation, and age-related diseases.

In an aspect, provided herein is a compound of Formula I:

(I)

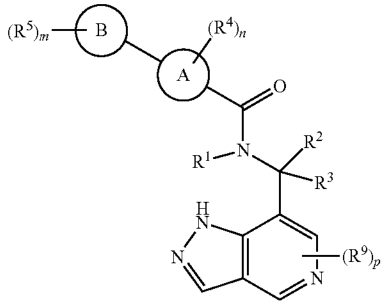

or a pharmaceutically acceptable salt thereof.

In another aspect, provided herein is a compound of Formula II:

(II)

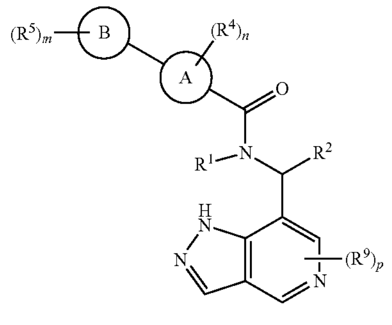

or a pharmaceutically acceptable salt thereof.

In another aspect, provided herein is a compound of Formula III:

(III)

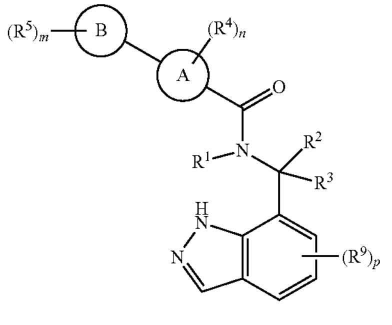

or a pharmaceutically acceptable salt thereof.

In yet another aspect, provided herein is a pharmaceutical composition comprising a compound described herein, or a pharmaceutically acceptable salt thereof, and a pharmaceutically acceptable carrier.

In yet another aspect, provided herein is a method of inhibiting NLRP3 inflammasome in a subject in need thereof comprising administering to the subject a therapeutically effective amount of a compound described herein.

DETAILED DESCRIPTION

Figure 1:
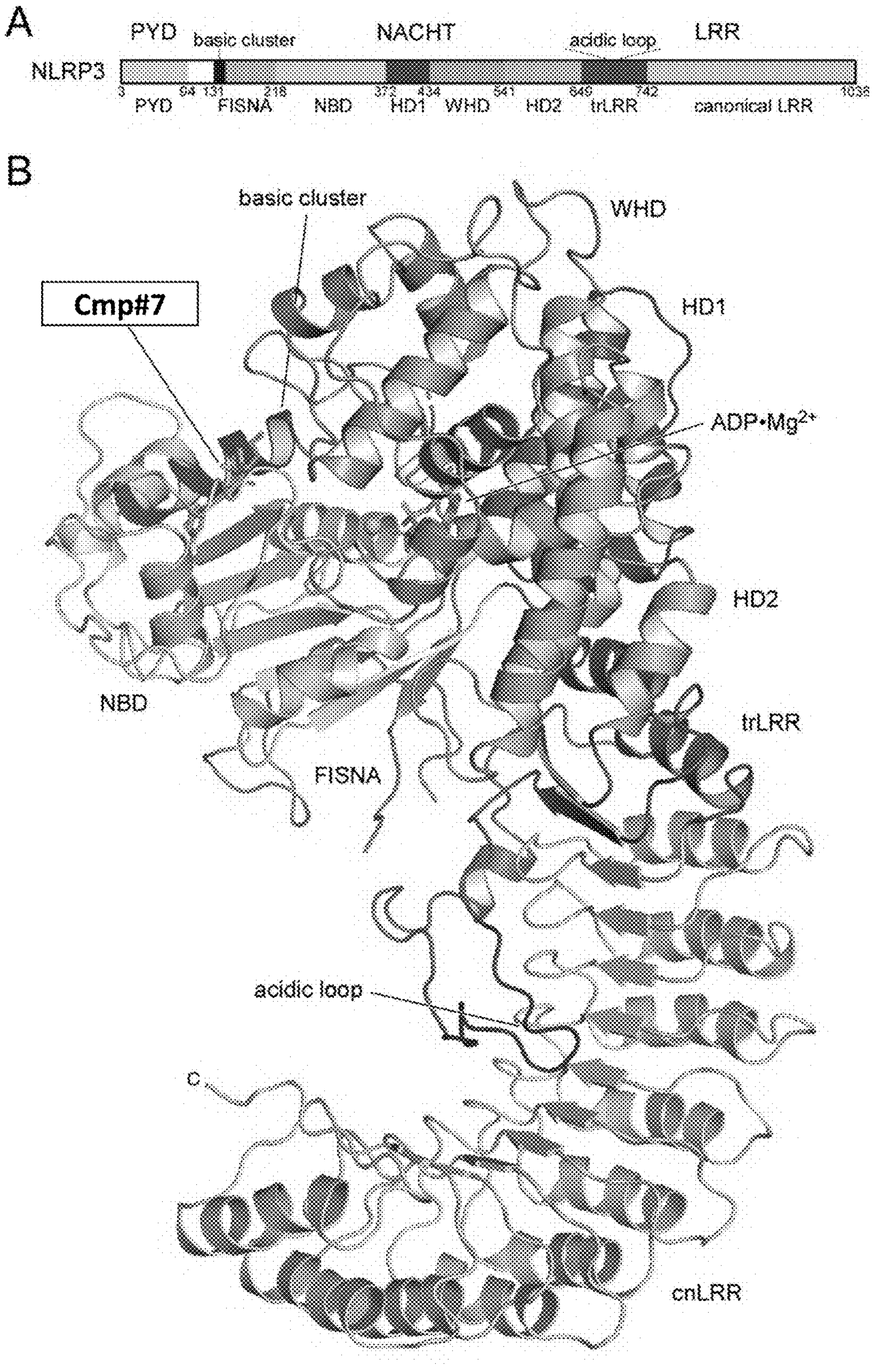
FIG. 1 depicts a cryo-EM image of Compound 007 binding into a characteristic pocket on the NACHT domain of NLRP3.
Figure 1:
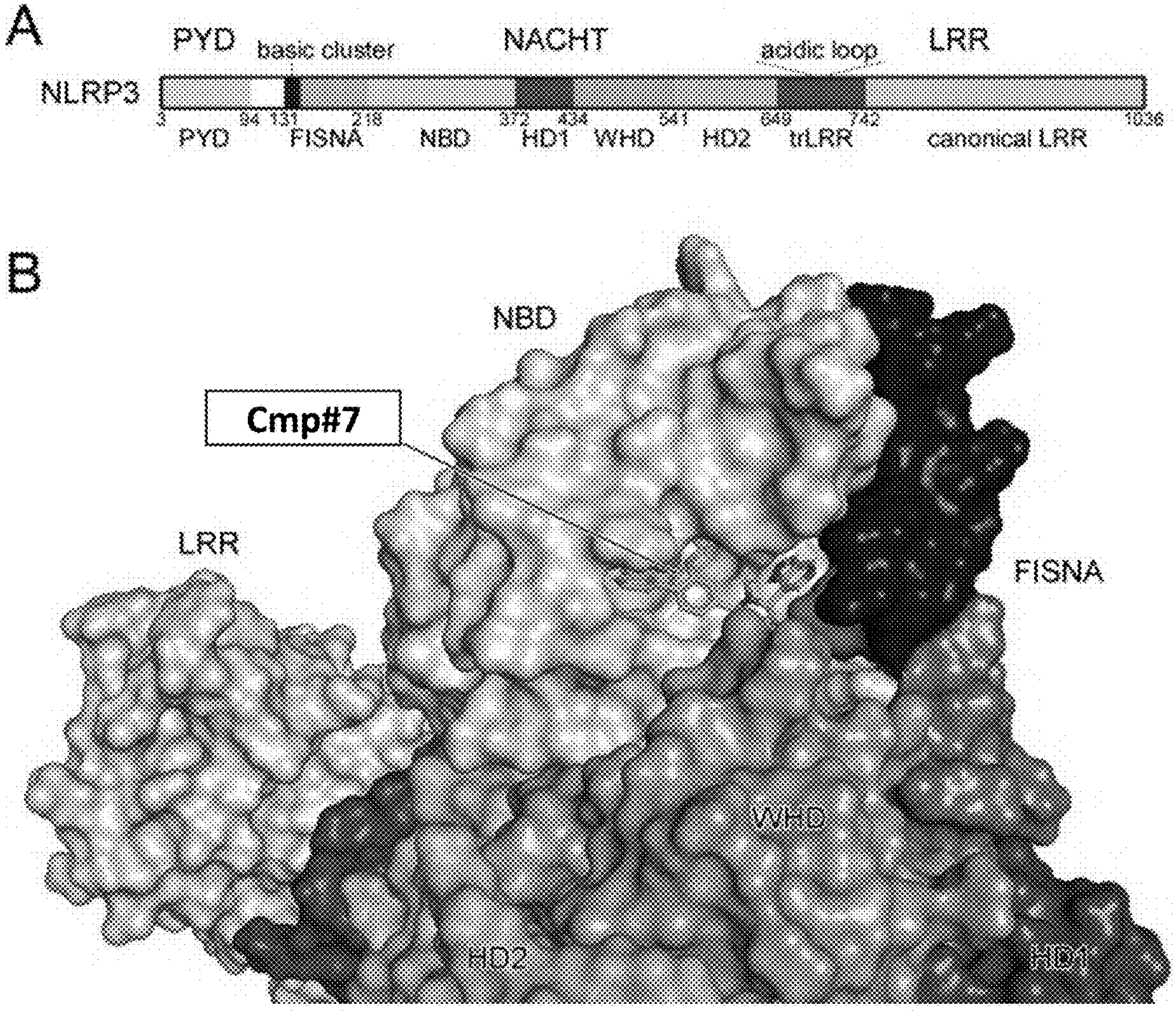

Provided here are compounds that inhibit the NLRP3 inflammasome. In a non-limiting embodiment, the compounds bind to amino acids of Y143, R147, F257, Y258, H260, E263, V264, L272, L275, I276, C279, F299, G328, L331, L332, L335, and C514 of a NLRP3 amino acid sequence of SEQ ID NO: 1. Such compounds are useful for the treatment of a variety of conditions in a subject, such as cancer, inflammaging, inflammation, and age-related diseases. As such, these compounds, as well as pharmaceutical compositions that comprise these compounds, are useful in the treatment of a variety of indications, including cancer, inflammaging, inflammation, and age-related diseases. These compounds are also useful for treating obesity and obesity-related disorders.

DEFINITIONS

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

As used herein, the term "contacting" refers to the bringing together of indicated moieties in an in vitro system or an in vivo system. For example, "contacting" a cell with a compound includes the administration of a compound of the present invention to an individual, subject, or patient, such as a human, as well as, for example, introducing a compound into a sample containing a purified preparation containing the cell.

The term "treat," "treated," "treating," or "treatment" includes the diminishment or alleviation of at least one symptom associated or caused by the state, disorder or disease being treated. In certain embodiments, the treatment comprises alleviating the symptoms of inflammaging and age-related disorders.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, an "epitope" refers to a surface or region on one or more entities (e.g., an NLRP3 polypeptide) that is capable of interacting with a binding molecule (e.g., the compounds of the disclosure). For example, a protein epitope may contain one or more amino acids and/or post-translational modifications (e.g., phosphorylated residues) which interact with the binding molecule. In some embodiments, an epitope may be a "conformational epitope," which refers to an epitope involving a specific three-dimensional arrangement of the entity(ies) having or forming the epitope. For example, conformational epitopes of proteins may include combinations of amino acids and/or post-translational modifications from folded, non-linear stretches of amino acid chains.

As used herein, "inflammaging" is defined as chronic sterile inflammation that is associated with numerous age-related diseases.

As used herein, "age-related disorder" refers to disorders that are associated with the aging process Stated alternatively, age-related disorders are diseases associated with the elderly. Non-limiting examples of age-related diseases include atherosclerosis and cardiovascular disease, cancer, arthritis, cataracts, osteoporosis, type 2 diabetes, hypertension, and Alzheimer's disease. The incidence of all of these diseases increases exponentially with age.

As used herein, "GLP-1" refers to glucagon-like peptide-1, which is a 30- or 31-amino-acid-long peptide hormone deriving from the tissue-specific posttranslational processing of the proglucagon peptide. It is produced and secreted by intestinal enteroendocrine L-cells and certain neurons within the nucleus of the solitary tract in the brainstem upon food consumption. Beside the insulinotropic effects, GLP-1 has been associated with numerous regulatory and protective effects. Glucagon-like peptide-1 receptor agonists have gained approval as drugs to treat diabetes and obesity.

As used herein, "comorbidity" refers to a disease or medical condition that is simultaneously present with another disease or medical condition in a patient.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

In some embodiments, the compounds herein are substantially isolated. As used herein, "substantially isolated" means that the compound is at least partially or substantially separated from the environment in which it was formed or detected. Partial separation can include, for example, a composition enriched in a compound of the present disclosure. Substantial separation can include compositions containing at least about 50%, at least about 60%, at least about 70%, at least about 80%, at least about 90%, at least about 95%, at least about 97%, or at least about 99% by weight of the compound.

The term "$C_{n-m}$" indicates a range which includes the endpoints, wherein n and m are integers and indicate the number of carbons. Examples include $C_{1-4}$, $C_{1-6}$ and the like.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

As used herein, the term "haloalkyl" refers to an alkyl group, as defined above, substituted with one or more halo substituents, wherein alkyl and halo are as defined herein.

Haloalkyl includes, by way of example, chloromethyl, trifluoromethyl, bromoethyl, chlorofluoroethyl, and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, "cycloalkyl" is $C_{3-10}$ cycloalkyl. In another embodiment, "cycloalkyl" is $C_{3-6}$ cycloalkyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, "heterocycloalkyl" refers to 3-10 membered heterocycloalkyl. In another embodiment, "heterocycloalkyl" refers to 4-10 membered heterocycloalkyl. In yet another embodiment, "heterocycloalkyl" refers to 3-, 4-, 5-, or 6-membered heterocycloalkyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In an embodiment, "heteroaryl" refers to 5-10 membered heteroaryl. In another embodiment, "heteroaryl" refers to 5-6 membered heterocycloalkyl. In yet another embodiment, "heteroaryl" refers to 5-, 6-, 7-, 8-, 9-, or 10-membered heteroaryl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

NLRP3

As used herein, the term "Nucleotide-binding oligomerization domain, Leucine rich Repeat and Pyrin domain containing 3" or "NOD-, LRR-, and pyrin domain-containing protein 3" or "NLRP3" refers to UNIPROT reference number Q96P20 and the amino acid sequence of SEQ ID NO: 1, shown below.

```
                                       (SEQ ID NO: 1)
MKMASTRCKLARYLEDLEDVDLKKFKMHLEDYPPQKGCIPLPRGQTEKA

DHVDLATLMIDFNGEEKAWAMAVWIFAAINRRDLYEKAKRDEPKWGSDN

ARVSNPTVICQEDSIEEEWMGLLEYLSRISICKMKKDYRKKYRKYVRSR

FQCIEDRNARLGESVSLNKRYTRLRLIKEHRSQQEREQELLAIGKTKTC

ESPVSPIKMELLFDPDDEHSEPVHTVVFQGAAGIGKTILARKMMLDWAS

GTLYQDRFDYLFYIHCREVSLVTQRSLGDLIMSCCPDPNPPIHKIVRKP

SRILFLMDGFDELQGAFDEHIGPLCTDWQKAERGDILLSSLIRKKLLPE

ASLLITTRPVALEKLQHLLDHPRHVEILGFSEAKRKEYFFKYFSDEAQA

RAAFSLIQENEVLFTMCFIPLVCWIVCTGLKQQMESGKSLAQTSKTTTA

VYVFFLSSLLQPRGGSQEHGLCAHLWGLCSLAADGIWNQKILFEESDLR

NHGLQKADVSAFLRMNLFQKEVDCEKFYSFIHMTFQEFFAAMYYLLEEE

KEGRTNVPGSRLKLPSRDVTVLLENYGKFEKGYLIFVVRFLFGLVNQER
```

-continued

TSYLEKKLSCKISQQIRLELLKWIEVKAKAKKLQIQPSQLELFYCLYEM

QEEDFVQRAMDYFPKIEINLSTRMDHMVSSFCIENCHRVESLSLGFLHN

MPKEEEEEEKEGRHLDMVQCVLPSSSHAACSHGLVNSHLTSSFCRGLFS

VLSTSQSLTELDLSDNSLGDPGMRVLCETLQHPGCNIRRLWLGRCGLSH

ECCFDISLVLSSNQKLVELDLSDNALGDFGIRLLCVGLKHLLCNLKKLW

LVSCCLTSACCQDLASVLSTSHSLTRLYVGENALGDSGVAILCEKAKNP

QCNLQKLGLVNSGLTSVCCSALSSVLSTNQNLTHLYLRGNTLGDKGIKL

LCEGLLHPDCKLQVLELDNCNLTSHCCWDLSTLLTSSQSLRKLSLGNND

LGDLGVMMFCEVLKQQSCLLQNLGLSEMYFNYETKSALETLQEEKPELT

VVFEPSW

NLRP3 is a member of the Nod-like receptor (NLR) family of proteins. NLRP3 is an intracellular sensor that detects a broad range of danger signals and environmental insults resulting in a protective pro-inflammatory response designed to impair pathogens and repair tissue damage via the formation and activation of the NLRP3 inflammasome (Coll, R. C., et al., *Trends Pharmacol. Sci.,* 2022, 43(8), 653-668). NLRP3 is highly expressed in subsets of peripheral leukocytes and microglia of the central nervous system.

NLRP3 displays a tripartite structure consisting of a Pyrin Domain (PYD), a central nucleotide binding and oligomerization domain of the NACHT subfamily of NTPases, and a Leucine Rich Repeat domain (LRR). The NACHT domain has ATPase activity that is required to induce an inactive ADP-bound decameric assembly in cells (Hochheiser, I., et al., *Nature,* 2022, 604, 184-189), (Brinkschulte, R., et al., *Commun. Biol.,* 2022, 5, 1176).

Assembly of the NLRP3 inflammasome leads to caspase 1-dependent secretory release of the pro-inflammatory cytokines IL-1p and IL-18 as well as to gasdermin D-mediated pyroptotic cell death.

In an aspect, provided herein is a compound that binds to one or more amino acids of Y143, R147, F257, Y258, H260, E263, V264, L272, L275, I276, C279, F299, G328, L331, L332, L335, and C514 of a NLRP3 amino acid sequence of SEQ ID NO: 1.

In an embodiment, the compound binds to at least amino acids of L275 and C279 of a NLRP3 amino acid sequence of SEQ ID NO: 1. In another embodiment, the compound binds to amino acids of Y143, R147, F257, Y258, H260, E263, V264, L272, L275, I276, C279, F299, G328, L331, L332, L335, and C514 of a NLRP3 amino acid sequence of SEQ ID NO: 1.

Compounds

Provided herein are compounds that are inhibitors of the NLRP3 inflammasome and are thus useful in the treatment of inflammatory disorders, including cancer and other proliferation diseases.

In an aspect, provided herein is a compound of Formula I:

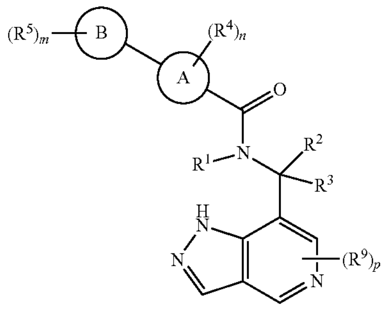

(I)

or a pharmaceutically acceptable salt thereof;

wherein

- Ring A is selected from the group consisting of $C_{6-10}$ aryl, 5-10 membered heteroaryl, $C_{3-10}$ cycloalkyl, and 4-10 membered heterocycloalkyl;
- Ring B is selected from the group consisting of $C_{6-10}$ aryl, 5-6 membered heteroaryl, $C_{3-6}$ cycloalkyl, and 3-6 membered heterocycloalkyl;
- alternatively, Ring B and $R^5$ are absent;
- $R^1$ is selected from the group consisting of H, $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo;
- each $R^a$ is independently H, $C_{1-6}$ alkyl, $C_{3-6}$ cycloalkyl, and $C(O)C_{1-6}$ alkyl;
- $R^2$ is H or $C_{1-6}$ alkyl;
- $R^3$ is selected from the group consisting of $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; the nitrogen atom of $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized; and one or more carbon atoms of the alkyl groups on the nitrogen atom are optionally substituted with 1-6 deuterium atoms or $C_{1-6}$ alkoxy;
- alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;
- each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;
- alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In an embodiment, $R^3$ is selected from the group consisting of $C_{1-6}$ alkyl, $C_{3-6}$ cycloalkyl, and 3-6 membered heterocycloalkyl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo, or $C_{0-3}$ alkylene-5-10 membered heteroaryl, wherein 3-6 membered heterocycloalkyl is optionally substituted by $C_{1-6}$ alkyl; and the nitrogen atom of $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized.

In another embodiment, $R^3$ is selected from the group consisting of $C_{1-6}$ alkyl, $C_{3-6}$ cycloalkyl, and 3-6 membered heterocycloalkyl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^1$, 3-6 membered heterocycloalkyl optionally substituted with one or two halo or OH, or $C_{0-3}$ alkylene-5-10 membered heteroaryl, wherein 3-6 membered heterocycloalkyl is optionally substituted by $C_{1-6}$ alkyl; and the nitrogen atom of $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized. In another embodiment, $R^3$ is $C_{1-6}$ alkyl substituted by OH, $NH(C_{1-6}$ alkyl), $N(C_{1-6}$ alkyl$)_2$, or $C_{1-3}$ alkoxy. In another embodiment, $R^3$ is $C_{1-6}$ alkyl substituted by $NH(C_{1-6}$ alkyl), $N(C_{1-6}$ alkyl$)_2$, or $C_{1-3}$ alkoxy. In yet another embodiment, $R^3$ is $C_{1-6}$ alkyl substituted by $NH(C_{1-6}$ alkyl) or $N(C_{1-6}$ alkyl$)_2$.

In yet another embodiment, $R^3$ is selected from the group consisting of $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; and the nitrogen atom of $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized and the carbon atom of the alkyl groups on the nitrogen atom are optionally substituted with 1-6 deuterium atoms or $C_{1-6}$ alkoxy.

In an embodiment, $R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo; and $R^3$ is selected from the group consisting of $C_{1-6}$ alkyl, $C_{3-6}$ cycloalkyl, and 3-6 membered heterocycloalkyl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo, or $C_{0-3}$ alkylene-5-10 membered heteroaryl, and wherein 3-6 membered heterocycloalkyl is optionally substituted by $C_{1-6}$ alkyl.

In an embodiment,

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

$R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{0-3}$ alkylene-5-10 membered heteroaryl;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In another embodiment,

Ring A is C6-10 aryl;

Ring B is $C_{6-10}$ aryl;

$R^1$ is $C_{1-6}$ alkyl;

$R^2$ is H;

$R^3$ is selected from the group consisting of $C_{1-6}$ alkyl, $C_{3-6}$ cycloalkyl, and 3-6 membered heterocycloalkyl, all of which are substituted by OH or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which is substituted by OH;

each $R^4$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $NHC(O)C_{1-6}$ alkyl, CN, and $C_{1-6}$ haloalkyl;

each $R^5$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $CONH_2$, $CONH(C_{1-6}$ alkyl), CN, and $C_{1-6}$ haloalkyl;

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

In yet another embodiment,

Ring A is $C_{6-10}$ aryl;

Ring B is $C_{6-10}$ aryl;

$R^1$ is $C_{1-6}$ alkyl;

$R^2$ is H;

$R^3$ is selected from the group consisting of $C_{1-6}$ alkyl, $C_{3-6}$ cycloalkyl, and 3-6 membered heterocycloalkyl, all of which are substituted by OH, $NH(C_{1-6}$ alkyl), $N(C_{1-6}$ alkyl$)_2$, or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which is substituted by OH;

each $R^4$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $NHC(O)C_{1-6}$ alkyl, CN, and $C_{1-6}$ haloalkyl;

each $R^5$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $CONH_2$, $CONH(C_{1-6}$ alkyl), CN, and $C_{1-6}$ haloalkyl;

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

In another embodiment,

Ring A is phenyl;

Ring B is phenyl;

$R^1$ is $C_{1-6}$ alkyl;

$R^2$ is H;

$R^3$ is $C_{1-6}$ alkyl substituted by $N(R^a)_2$;

each $R^a$ is independently H or $C_{1-6}$ alkyl;

$R^4$ is $C_{1-6}$ alkoxy;

$R^5$ is selected from the group consisting of $C_{1-6}$ alkyl, halo, OH, $C_{1-6}$ alkoxy, CN, and $C_{1-6}$ haloalkyl;

m is 1;

n is 1; and p is 0.

In yet another embodiment, the compound of Formula I is a compound of Formula Ia:

(Ia)

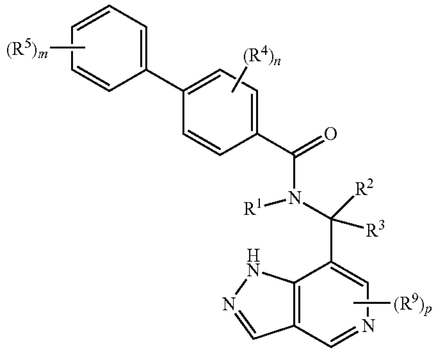

or a pharmaceutically acceptable salt thereof.

In still another embodiment, Ring A is phenyl.

In an embodiment, Ring B is selected from the group consisting of $C_{6-10}$ aryl, 5-6 membered heteroaryl, $C_{3-6}$ cycloalkyl, and 3-6 membered heterocycloalkyl. In another embodiment, Ring B is phenyl. In yet another embodiment, Ring B and $R^5$ are absent.

In still another embodiment, $R^1$ is $C_{1-6}$ alkyl. In an embodiment, $R^1$ is methyl. In another embodiment, $R^1$ is ethyl. In an embodiment, $R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl. In yet another embodiment, $R^1$ is $C_{1-6}$ alkyl or $C_{3-6}$ cycloalkyl, wherein alkyl and cycloalkyl are optionally substituted with OH, $OC(O)C_{1-6}$ alkyl, $C(O)C_{1-6}$ alkyl, $N(R^a)_2$, and halo. In still another embodiment, $R^1$ is $C_{1-6}$ alkyl or $C_{3-6}$ cycloalkyl, wherein alkyl and cycloalkyl are optionally substituted with OH, $OC(O)C_{1-3}$ alkyl, $C(O)C_{1-3}$ alkyl, $NH_2$, $NHC_{1-3}$ alkyl, $N(C_{1-3}$ alkyl$)_2$, and halo.

In another embodiment, $R^2$ is H.

In an embodiment, $R^3$ is $C_{1-6}$ alkyl substituted by OH or $C_{1-3}$ alkoxy. In still another embodiment, $R^3$ is $C_{1-6}$ alkyl substituted by OH. In an embodiment, $R^3$ is $C_{1-6}$ alkyl substituted by $C_{1-3}$ alkoxy. In an embodiment, $R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{0-3}$ alkylene-5-10 membered heteroaryl. In another embodiment, $R^3$ is $C_{1-6}$ alkyl substituted by 3-6 membered heterocycloalkyl optionally substituted with one or two halo or OH. In yet another embodiment, $R^3$ is 3-6 membered heterocycloalkyl is optionally substituted by $C_{1-6}$ alkyl. In an embodiment, $R^3$ is $C_{1-6}$ alkyl substituted by $N(R^a)_2$. In another embodiment, each $R^a$ is independently H or $C_{1-6}$ alkyl.

In yet another embodiment, $R^3$ is $C_{1-6}$ alkyl substituted by OH or $C_{1-3}$ alkoxy. In still another embodiment, $R^3$ is $C_{1-6}$ alkyl substituted by OH. In an embodiment, $R^3$ is $C_{1-6}$ alkyl substituted by $C_{1-3}$ alkoxy. In an embodiment, $R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{0-3}$ alkylene-5-10 membered heteroaryl. In another embodiment, $R^3$ is $C_{1-6}$ alkyl substituted by 3-6 membered heterocycloalkyl optionally substituted with one or two halo. In yet another embodiment, $R^3$ is 3-6 membered heterocycloalkyl is optionally substituted by $C_{1-6}$ alkyl. In an embodiment, $R^3$ is $C_{1-6}$ alkyl substituted by $N(R^a)_2$. In another embodiment, each $R^a$ is independently H or $C_{1-6}$ alkyl.

In an embodiment, $R^3$ is $C_{1-6}$ alkyl substituted by OH, $NH(C_{1-6}$ alkyl), $N(C_{1-6}$ alkyl$)_2$, or $C_{1-3}$ alkoxy. In another embodiment, $R^3$ is $C_{1-6}$ alkyl substituted by $NH(C_{1-6}$ alkyl), $N(C_{1-6}$ alkyl$)_2$, or $C_{1-3}$ alkoxy. In yet another embodiment, $R^3$ is $C_{1-6}$ alkyl substituted by $NH(C_{1-6}$ alkyl) or $N(C_{1-6}$ alkyl$)_2$.

In another embodiment, $R^2$ and $R^3$, together with the atom to which they are attached, form a ring selected from the group consisting of $C_{3-6}$ cycloalkyl and 3-6 membered heterocycloalkyl, both of which is substituted by OH. In yet another embodiment, $R^2$ and $R^3$, together with the atom to which they are attached, form $C_{3-6}$ cycloalkyl substituted by OH. In still another embodiment, $R^2$ and $R^3$, together with the atom to which they are attached, form 3-6 membered heterocycloalkyl substituted by OH.

In an embodiment, each $R^4$ is independently selected from the group consisting of halo, $C_{1-6}$ alkoxy, $OC_{3-6}$ cycloalkyl, and $C_{1-6}$ haloalkyl. In another embodiment, each $R^4$ is independently selected from the group consisting of halo, $C_{1-3}$ alkoxy, O-cyclopropyl, and $C_{1-3}$ haloalkyl. In an embodiment, $R^4$ is $C_{1-6}$ alkoxy.

In yet another embodiment, each $R^5$ is independently selected from the group consisting of $C_{1-6}$ alkyl, halo, CN, and $C(O)NH(C_{1-6}$ alkyl). In still another embodiment, each $R^5$ is independently selected from the group consisting of $C_{1-3}$ alkyl, halo, CN, and $C(O)NH(C_{1-3}$ alkyl). In another embodiment, $R^5$ is selected from the group consisting of $C_{1-6}$ alkyl, halo, OH, $C_{1-6}$ alkoxy, CN, and $C_{1-6}$ haloalkyl.

In an embodiment, each $R^9$ is independently selected from the group consisting of $C_{1-3}$ alkyl, $C_{1-6}$ alkoxy, $C_{1-3}$ alkyl-OH, and halo.

In another embodiment, m is 0, 1, or 2. In yet another embodiment, m is 0. In still another embodiment, m is 1. In an embodiment, m is 2.

In another embodiment, n is 1. In yet another embodiment, n is 0. In still another embodiment, n is 2.

In another embodiment, p is 0, 1, or 2. In yet another embodiment, p is 0. In still another embodiment, p is 1. In an embodiment, p is 2.

In another embodiment, the compound of Formula I is selected from the group consisting of a compound in Table 1.

TABLE 1

| Ex. No. | Structure |
| --- | --- |
| 001 | 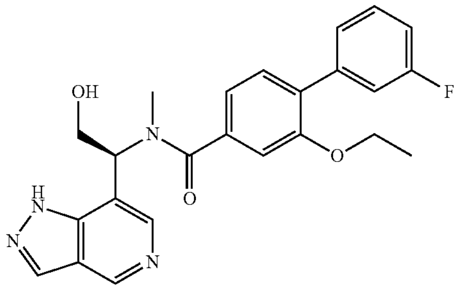 [SMILES: CCOc1cc(C(=O)N(C)[C@H](CO)c2cncc3cn[nH]c23)ccc1-c1cccc(F)c1] |
| 002 | 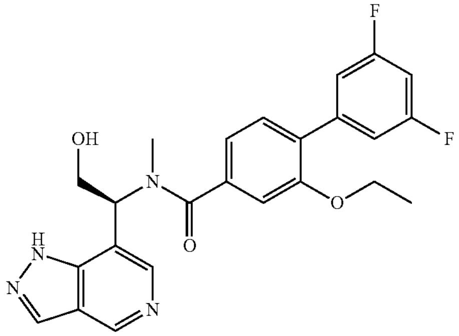 [SMILES: CCOc1cc(C(=O)N(C)[C@H](CO)c2cncc3cn[nH]c23)ccc1-c1cc(F)cc(F)c1] |
| 003 | 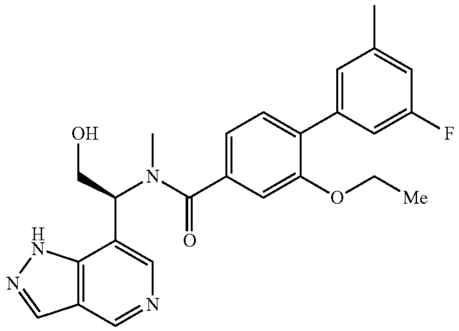 [SMILES: CCOc1cc(C(=O)N(C)[C@H](CO)c2cncc3cn[nH]c23)ccc1-c1cc(C)cc(F)c1] |
| 004 | 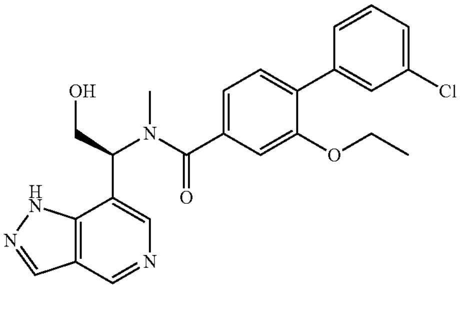 [SMILES: CCOc1cc(C(=O)N(C)[C@H](CO)c2cncc3cn[nH]c23)ccc1-c1cccc(Cl)c1] |

TABLE 1-continued
| Ex. No. | Structure |
|---|---|
| 005 | 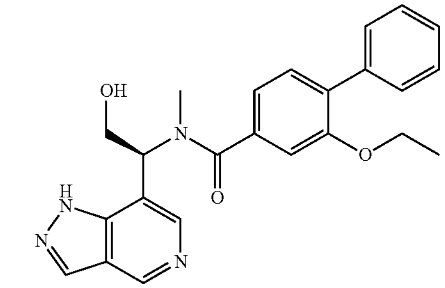 [SMILES: CCOc1cc(C(=O)N(C)[C@H](CO)c2cncc3cn[nH]c23)ccc1-c1ccccc1] |
| 006 | 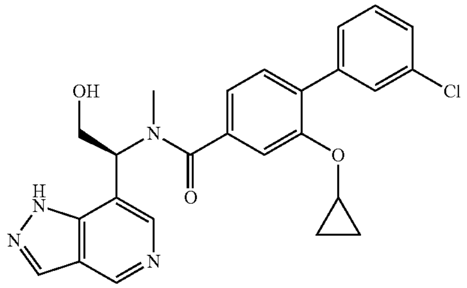 [SMILES: CN(C(=O)c1ccc(-c2cccc(Cl)c2)c(OC2CC2)c1)[C@H](CO)c1cncc2cn[nH]c12] |
| 007 | 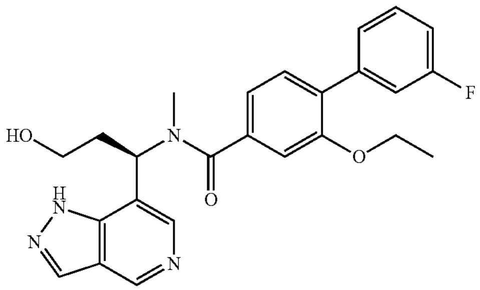 [SMILES: CCOc1cc(C(=O)N(C)[C@H](CCO)c2cncc3cn[nH]c23)ccc1-c1cccc(F)c1] |
| 008 | 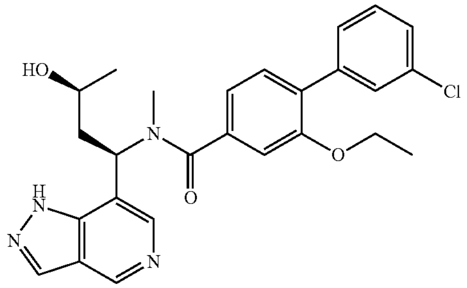 [SMILES: CCOc1cc(C(=O)N(C)[C@H](C[C@H](C)O)c2cncc3cn[nH]c23)ccc1-c1cccc(Cl)c1] |
| 009 | 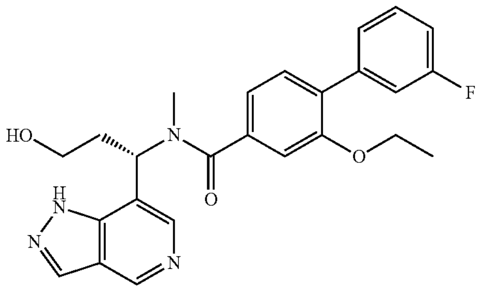 [SMILES: CCOc1cc(C(=O)N(C)[C@@H](CCO)c2cncc3cn[nH]c23)ccc1-c1cccc(F)c1] |
| 010 | 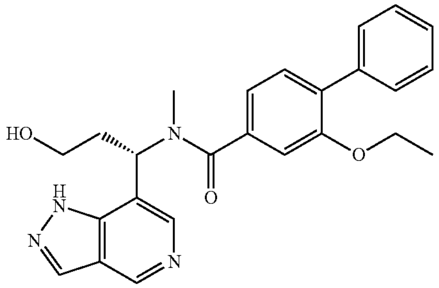 [SMILES: CCOc1cc(C(=O)N(C)[C@@H](CCO)c2cncc3cn[nH]c23)ccc1-c1ccccc1] |
| 011 | 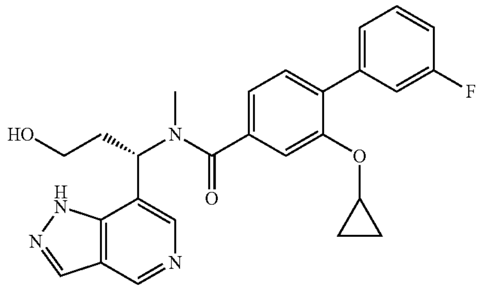 [SMILES: CN(C(=O)c1ccc(-c2cccc(F)c2)c(OC2CC2)c1)[C@@H](CCO)c1cncc2cn[nH]c12] |
| 012 | 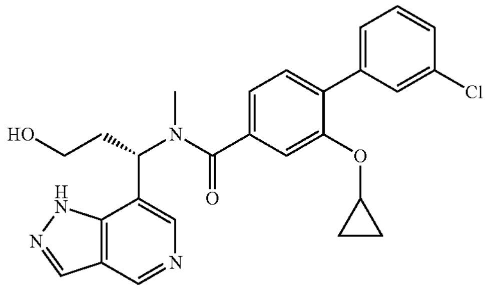 [SMILES: CN(C(=O)c1ccc(-c2cccc(Cl)c2)c(OC2CC2)c1)[C@@H](CCO)c1cncc2cn[nH]c12] |
| 013 | 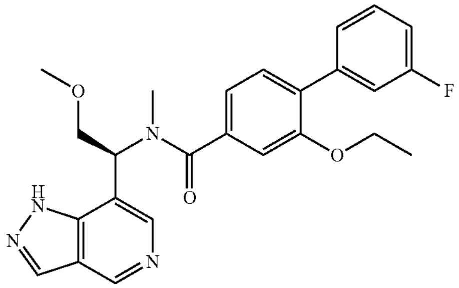 [SMILES: CCOc1cc(C(=O)N(C)[C@H](COC)c2cncc3cn[nH]c23)ccc1-c1cccc(F)c1] |
| 014 | 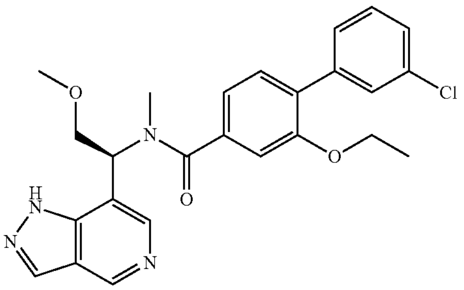 [SMILES: CCOc1cc(C(=O)N(C)[C@H](COC)c2cncc3cn[nH]c23)ccc1-c1cccc(Cl)c1] |

TABLE 1-continued
| Ex. No. | Structure |
|---|---|
| 015 | 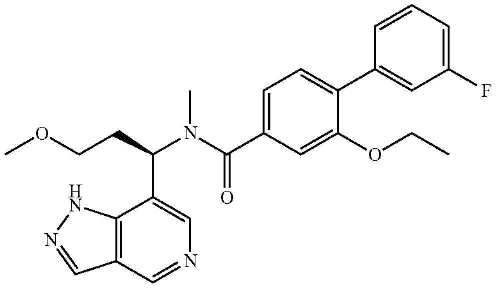 [SMILES: CCOc1cc(C(=O)N(C)[C@H](CCOC)c2cncc3cn[nH]c23)ccc1-c1cccc(F)c1] |
| 016 | 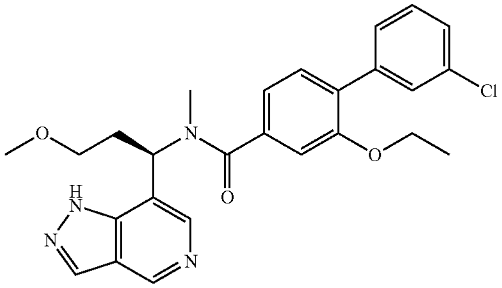 [SMILES: CCOc1cc(C(=O)N(C)[C@H](CCOC)c2cncc3cn[nH]c23)ccc1-c1cccc(Cl)c1] |
| 017 | 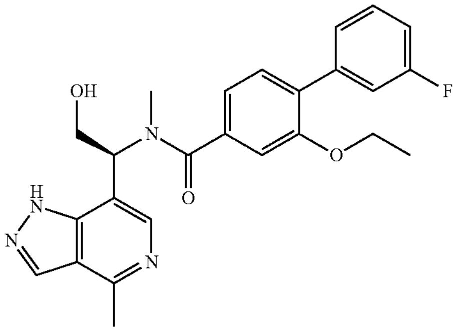 [SMILES: CCOc1cc(C(=O)N(C)[C@H](CO)c2cnc(C)c3cn[nH]c23)ccc1-c1cccc(F)c1] |
| 018 | 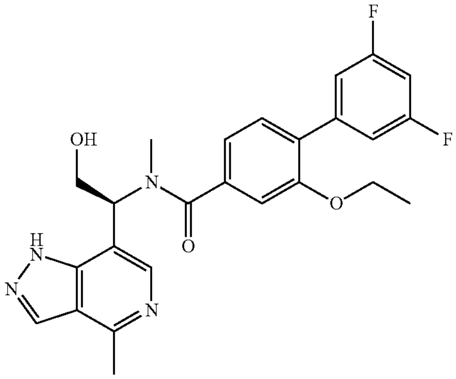 [SMILES: CCOc1cc(C(=O)N(C)[C@H](CO)c2cnc(C)c3cn[nH]c23)ccc1-c1cc(F)cc(F)c1] |
TABLE 1-continued
| Ex. No. | Structure |
|---|---|
| 019 | 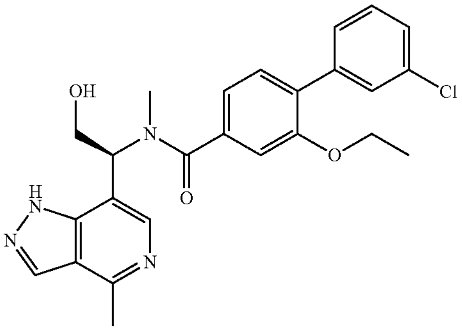 [SMILES: CCOc1cc(C(=O)N(C)[C@H](CO)c2cnc(C)c3cn[nH]c23)ccc1-c1cccc(Cl)c1] |
| 020 | 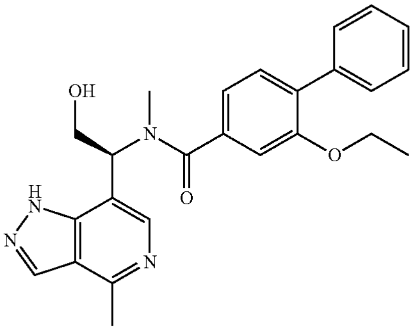 [SMILES: CCOc1cc(C(=O)N(C)[C@H](CO)c2cnc(C)c3cn[nH]c23)ccc1-c1ccccc1] |
| 021 | 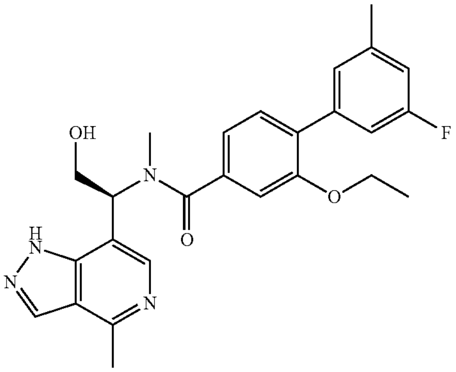 [SMILES: CCOc1cc(C(=O)N(C)[C@H](CO)c2cnc(C)c3cn[nH]c23)ccc1-c1cc(C)cc(F)c1] |
| 022 | 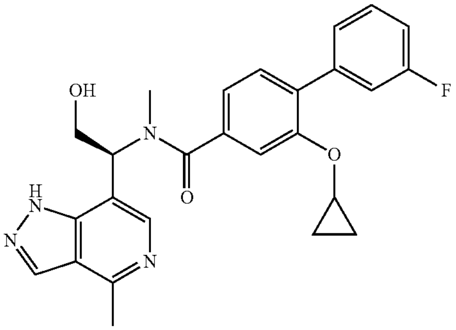 [SMILES: Cc1ncc([C@@H](CO)N(C)C(=O)c2ccc(-c3cccc(F)c3)c(OC3CC3)c2)c2[nH]ncc12] |

TABLE 1-continued
| Ex. No. | Structure |
|---|---|
| 023 | 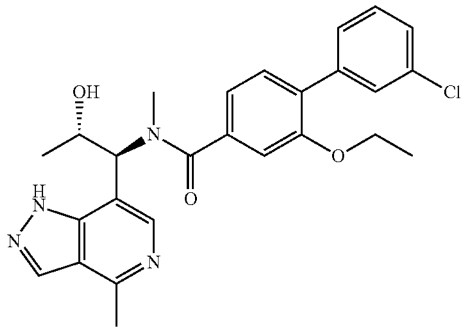 [SMILES: CCOc1cc(C(=O)N(C)[C@@H](c2cnc(C)c3cn[nH]c23)[C@H](C)O)ccc1-c1cccc(Cl)c1] |
| 024 | 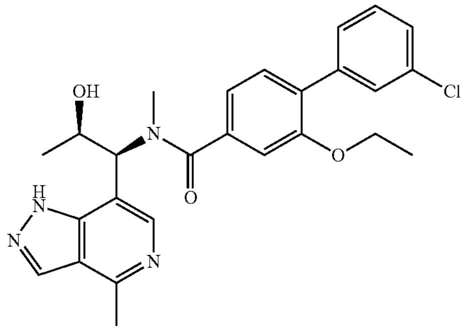 [SMILES: CCOc1cc(C(=O)N(C)[C@@H](c2cnc(C)c3cn[nH]c23)[C@@H](C)O)ccc1-c1cccc(Cl)c1] |
| 025 | 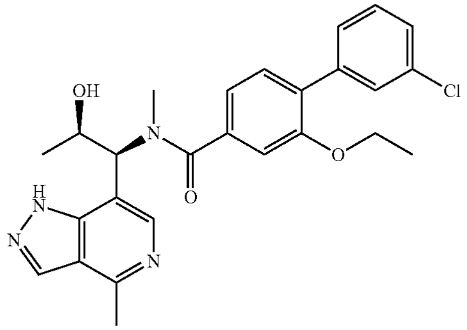 [SMILES: CCOc1cc(C(=O)N(C)[C@@H](c2cnc(C)c3cn[nH]c23)[C@@H](C)O)ccc1-c1cccc(Cl)c1] |
| 026 | 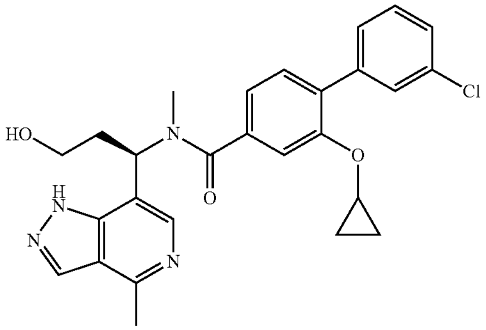 [SMILES: Cc1ncc([C@@H](CCO)N(C)C(=O)c2ccc(-c3cccc(Cl)c3)c(OC3CC3)c2)c2[nH]ncc12] |
TABLE 1-continued
| Ex. No. | Structure |
|---|---|
| 027 | 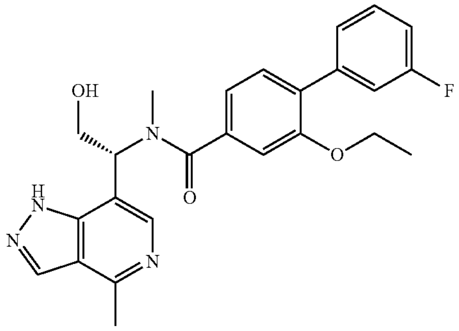 [SMILES: CCOc1cc(C(=O)N(C)[C@@H](CO)c2cnc(C)c3cn[nH]c23)ccc1-c1cccc(F)c1] |
| 028 | 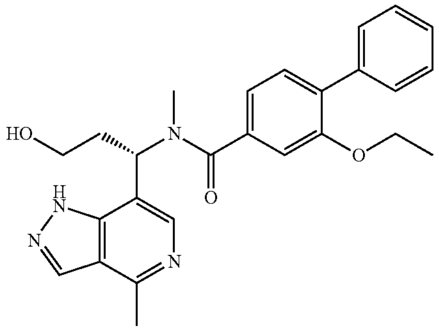 [SMILES: CCOc1cc(C(=O)N(C)[C@@H](CCO)c2cnc(C)c3cn[nH]c23)ccc1-c1ccccc1] |
| 029 | 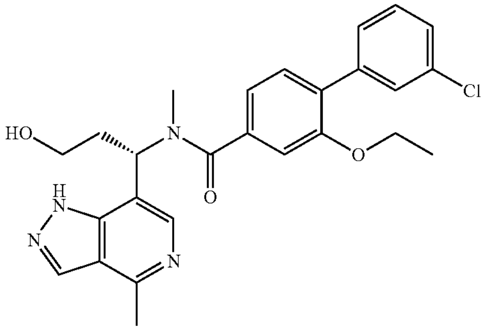 [SMILES: CCOc1cc(C(=O)N(C)[C@@H](CCO)c2cnc(C)c3cn[nH]c23)ccc1-c1cccc(Cl)c1] |
| 030 | 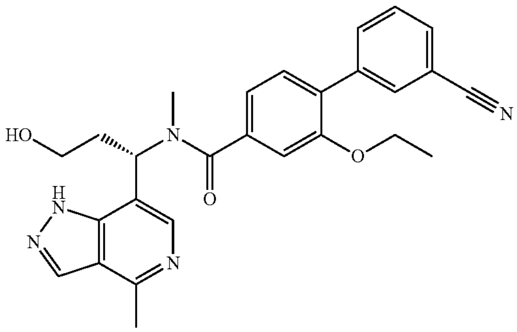 [SMILES: CCOc1cc(C(=O)N(C)[C@@H](CCO)c2cnc(C)c3cn[nH]c23)ccc1-c1cccc(C#N)c1] |

TABLE 1-continued
| Ex. No. | Structure |
|---|---|
| 031 | 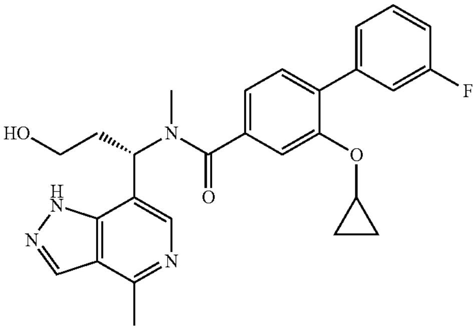 [SMILES: Cc1ncc([C@H](CCO)N(C)C(=O)c2ccc(-c3cccc(F)c3)c(OC3CC3)c2)c2[nH]ncc12] |
| 032 | 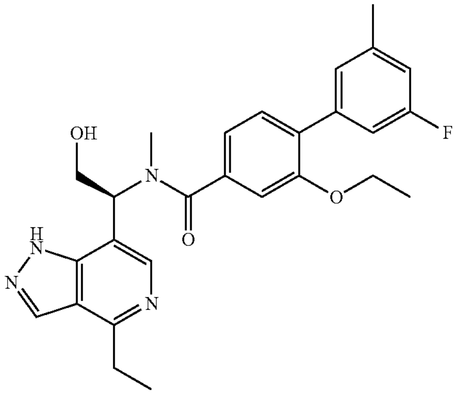 [SMILES: CCOc1cc(C(=O)N(C)[C@H](CO)c2cnc(CC)c3cn[nH]c23)ccc1-c1cc(C)cc(F)c1] |
| 033 | 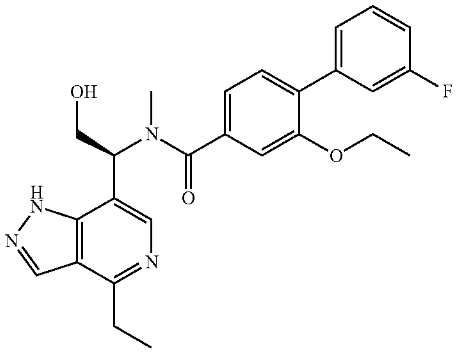 [SMILES: CCOc1cc(C(=O)N(C)[C@H](CO)c2cnc(CC)c3cn[nH]c23)ccc1-c1cccc(F)c1] |
| 034 | 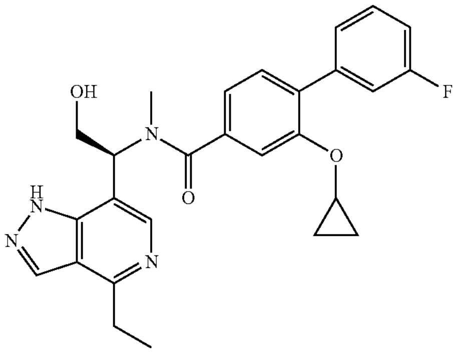 [SMILES: CCc1ncc([C@@H](CO)N(C)C(=O)c2ccc(-c3cccc(F)c3)c(OC3CC3)c2)c2[nH]ncc12] |
TABLE 1-continued
| Ex. No. | Structure |
|---|---|
| 035 | 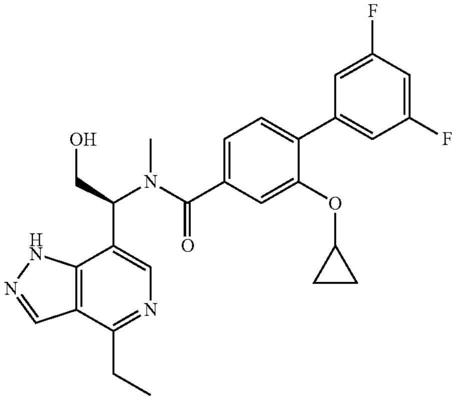 [SMILES: CCc1ncc([C@@H](CO)N(C)C(=O)c2ccc(-c3cc(F)cc(F)c3)c(OC3CC3)c2)c2[nH]ncc12] |
| 036 | 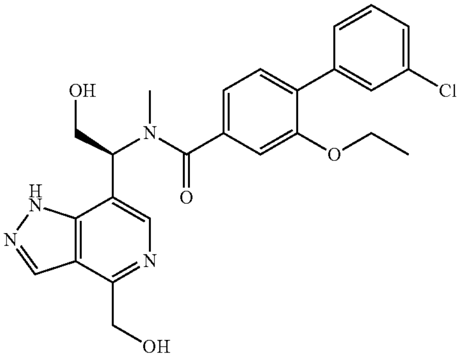 [SMILES: CCOc1cc(C(=O)N(C)[C@H](CO)c2cnc(CO)c3cn[nH]c23)ccc1-c1cccc(Cl)c1] |
| 037 | 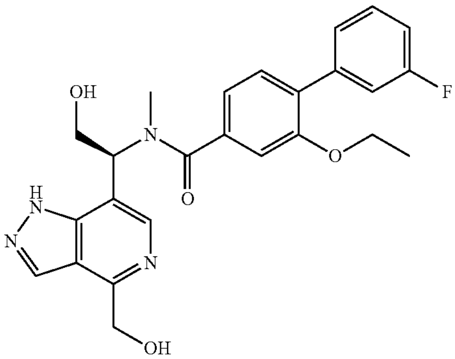 [SMILES: CCOc1cc(C(=O)N(C)[C@H](CO)c2cnc(CO)c3cn[nH]c23)ccc1-c1cccc(F)c1] |
| 038 | 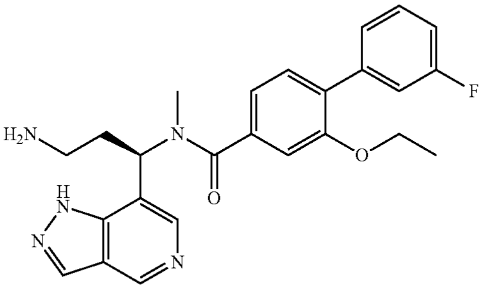 [SMILES: CCOc1cc(C(=O)N(C)[C@H](CCN)c2cncc3cn[nH]c23)ccc1-c1cccc(F)c1] |

TABLE 1-continued
| Ex. No. | Structure |
| --- | --- |
| 039 | 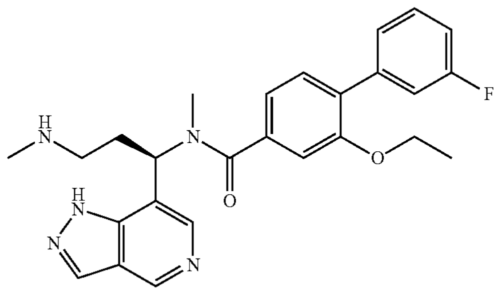 [SMILES: CCOc1cc(C(=O)N(C)[C@H](CCNC)c2cncc3cn[nH]c23)ccc1-c1cccc(F)c1] |
| 040 | 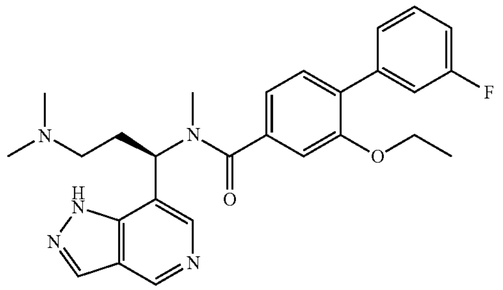 [SMILES: CCOc1cc(C(=O)N(C)[C@H](CCN(C)C)c2cncc3cn[nH]c23)ccc1-c1cccc(F)c1] |
or a pharmaceutically acceptable salt thereof.
In another embodiment, the compound of Formula I is selected from the group consisting of a compound in Table 1A.
TABLE 1A
| Ex. No. | Structure |
| --- | --- |
| 063 | 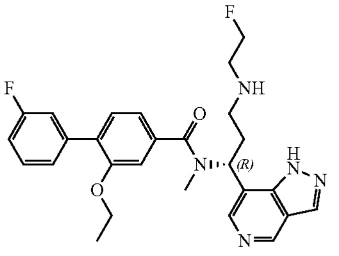 |
| 064 | 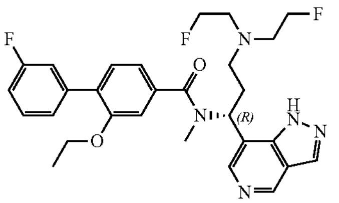 |
| 065 | 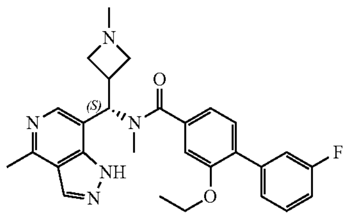 |
TABLE 1A-continued
| Ex. No. | Structure |
| --- | --- |
| 066 | 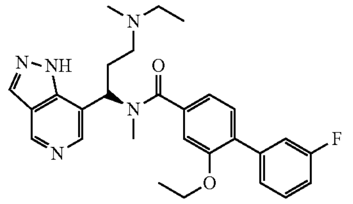 |
| 067 | 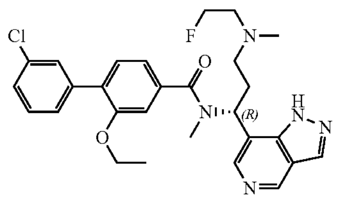 |
| 068 | 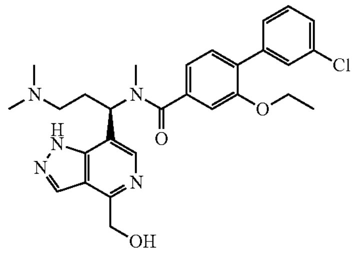 [SMILES: CCOc1cc(C(=O)N(C)[C@H](CCN(C)C)c2cnc(CO)c3cn[nH]c23)ccc1-c1cccc(Cl)c1] |
| 069 | 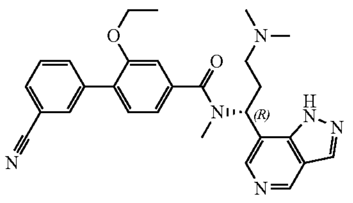 |
| 070 | 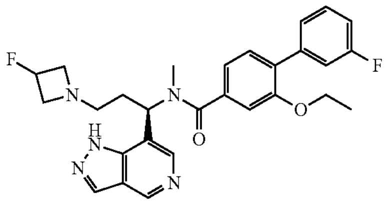 [SMILES: CCOc1cc(C(=O)N(C)[C@H](CCN2CC(F)C2)c2cncc3cn[nH]c23)ccc1-c1cccc(F)c1] |
| 071 | 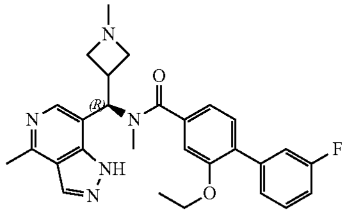 |
| 072 | 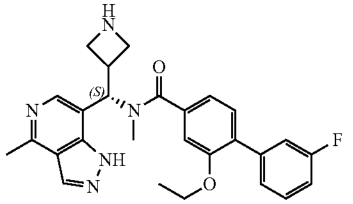 |

TABLE 1A-continued
| Ex. No. | Structure |
| --- | --- |
| 073 | 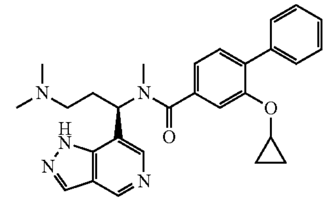 [SMILES: CN(C)CC[C@H](c1cncc2cn[nH]c12)N(C)C(=O)c1ccc(-c2ccccc2)c(OC2CC2)c1] |
| 074 | 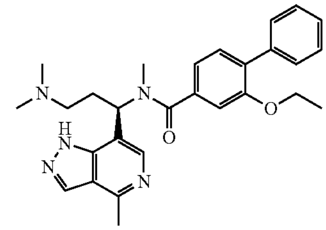 [SMILES: CCOc1cc(C(=O)N(C)[C@H](CCN(C)C)c2cnc(C)c3cn[nH]c23)ccc1-c1ccccc1] |
| 075 | 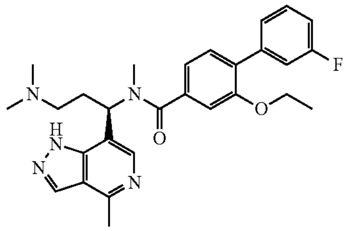 [SMILES: CCOc1cc(C(=O)N(C)[C@H](CCN(C)C)c2cnc(C)c3cn[nH]c23)ccc1-c1cccc(F)c1] |
| 076 | 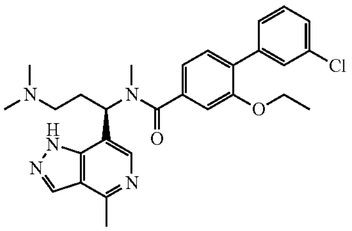 [SMILES: CCOc1cc(C(=O)N(C)[C@H](CCN(C)C)c2cnc(C)c3cn[nH]c23)ccc1-c1cccc(Cl)c1] |
| 077 | 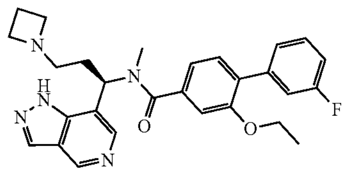 [SMILES: CCOc1cc(C(=O)N(C)[C@H](CCN2CCC2)c2cncc3cn[nH]c23)ccc1-c1cccc(F)c1] |
| 078 | 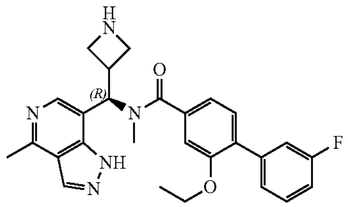 |
| 079 | 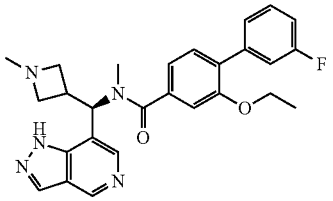 [SMILES: CCOc1cc(C(=O)N(C)[C@@H](c2cncc3cn[nH]c23)C2CN(C)C2)ccc1-c1cccc(F)c1] |
| 080 | 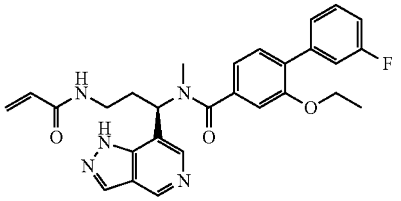 [SMILES: C=CC(=O)NCC[C@H](c1cncc2cn[nH]c12)N(C)C(=O)c1ccc(-c2cccc(F)c2)c(OCC)c1] |
| 081 | 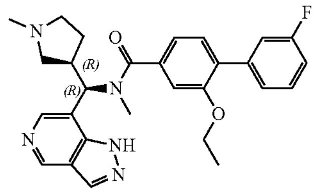 |
| 082 | 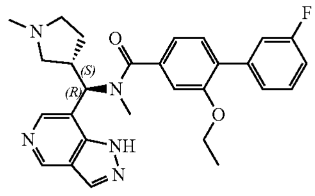 |
| 083 | 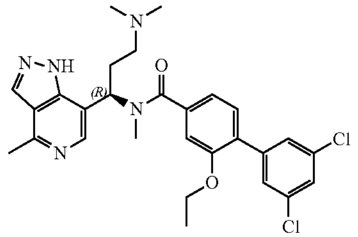 |
| 084 | 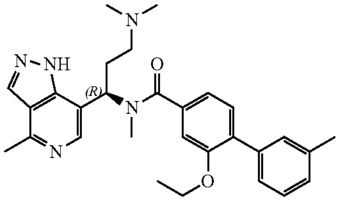 |
| 085 | 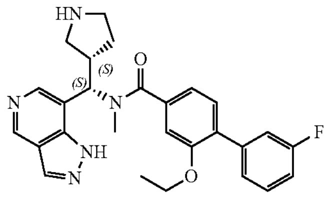 |
| 086 | 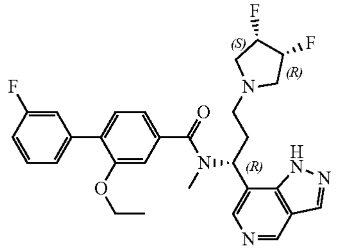 |

TABLE 1A-continued
| Ex. No. | Structure |
|---|---|
| 087 | 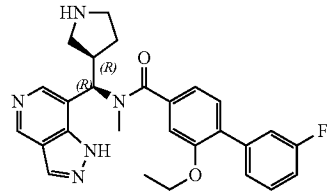 |
| 088 | 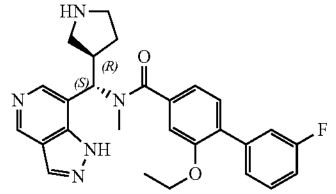 |
| 089 | 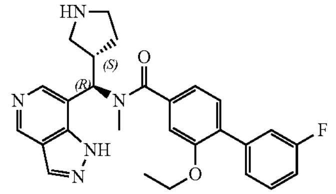 |
| 090 | 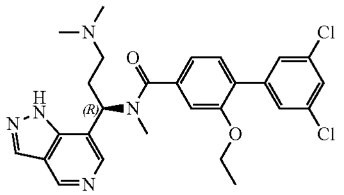 |
| 091 | 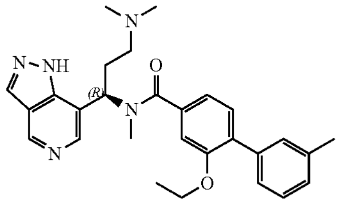 |
| 092 | 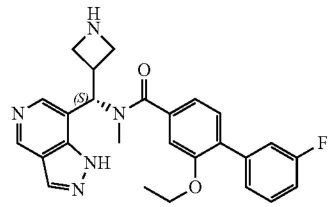 |
| 093 | 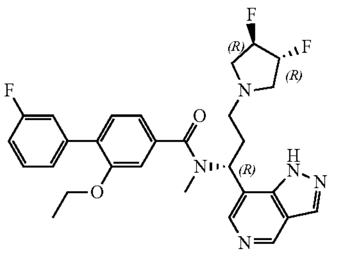 |
TABLE 1A-continued
| Ex. No. | Structure |
|---|---|
| 094 | 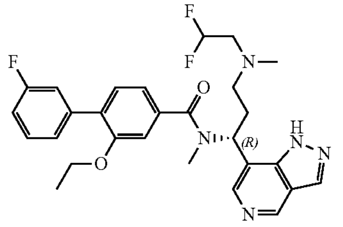 |
| 095 | 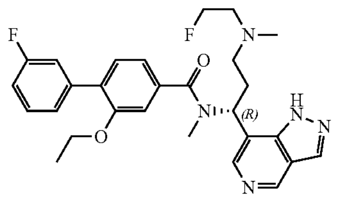 |
| 096 | 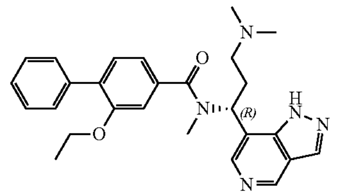 |
| 097 | 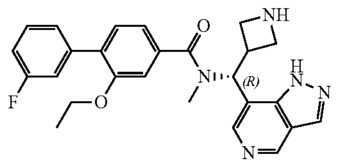 |
| 098 | 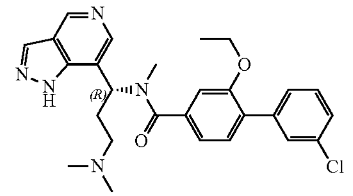 |
| 099 | 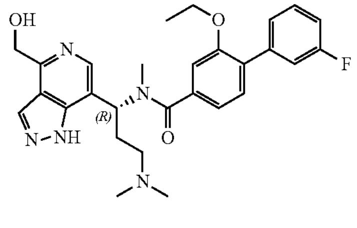 |
| 100 | 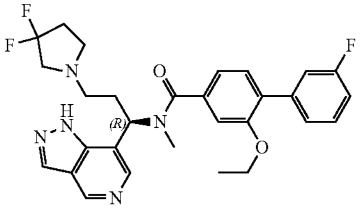 |

TABLE 1A-continued
| Ex. No. | Structure |
| --- | --- |
| 101 | 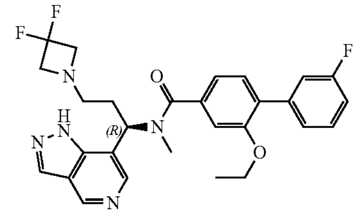 |
| 102 | 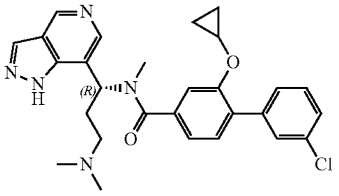 |
| 103 | 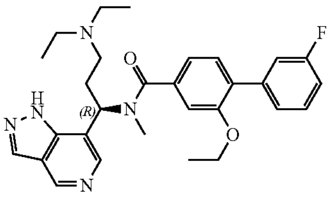 |
| 104 | 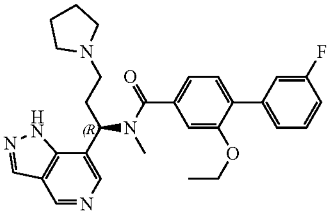 |
or a pharmaceutically acceptable salt thereof.
In another embodiment, the compound of Formula I is selected from the group consisting of a compound in Table 1B.
TABLE 1B
| Ex. No. | Structure |
| --- | --- |
| 121 | 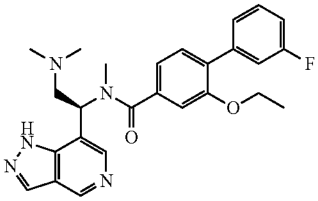 [SMILES: CCOc1cc(C(=O)N(C)[C@H](CN(C)C)c2cncc3cn[nH]c23)ccc1-c1cccc(F)c1] |
| 122 | 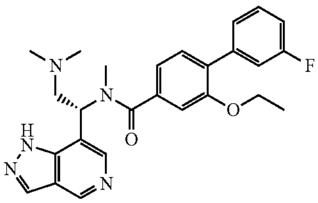 [SMILES: CCOc1cc(C(=O)N(C)[C@@H](CN(C)C)c2cncc3cn[nH]c23)ccc1-c1cccc(F)c1] |
TABLE 1B-continued
| Ex. No. | Structure |
| --- | --- |
| 123 | 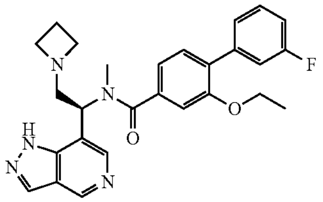 [SMILES: CCOc1cc(C(=O)N(C)[C@H](CN2CCC2)c2cncc3cn[nH]c23)ccc1-c1cccc(F)c1] |
| 124 | 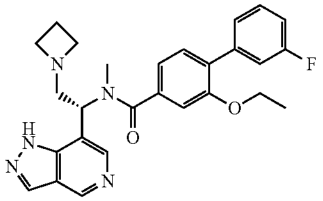 [SMILES: CCOc1cc(C(=O)N(C)[C@@H](CN2CCC2)c2cncc3cn[nH]c23)ccc1-c1cccc(F)c1] |
| 125 | 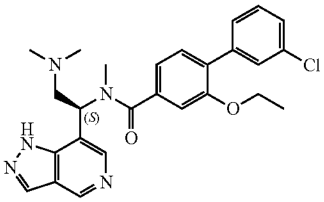 |
| 126 | 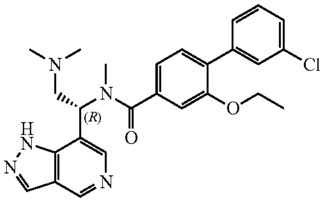 |
| 127 | 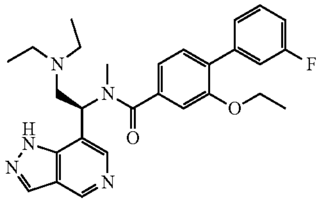 [SMILES: CCOc1cc(C(=O)N(C)[C@H](CN(CC)CC)c2cncc3cn[nH]c23)ccc1-c1cccc(F)c1] |
| 128 | 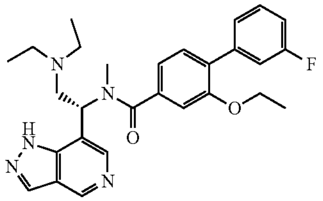 [SMILES: CCOc1cc(C(=O)N(C)[C@@H](CN(CC)CC)c2cncc3cn[nH]c23)ccc1-c1cccc(F)c1] |
| 129 | 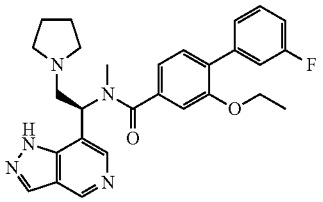 [SMILES: CCOc1cc(C(=O)N(C)[C@H](CN2CCCC2)c2cncc3cn[nH]c23)ccc1-c1cccc(F)c1] |

TABLE 1B-continued
| Ex. No. | Structure |
|---|---|
| 130 | 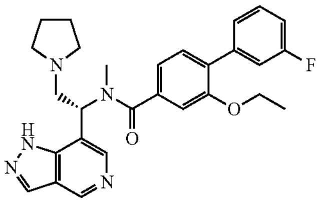 [SMILES: CCOc1cc(C(=O)N(C)[C@@H](CN2CCCC2)c2cncc3cn[nH]c23)ccc1-c1cccc(F)c1] |
| 131 | 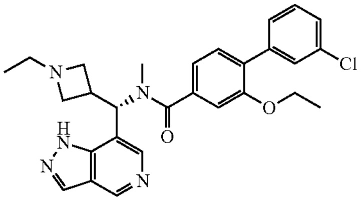 [SMILES: CCOc1cc(C(=O)N(C)[C@H](c2cncc3cn[nH]c23)C2CN(CC)C2)ccc1-c1cccc(Cl)c1] |
| 132 | 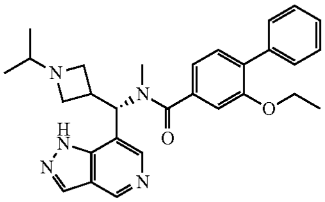 |
| 133 | 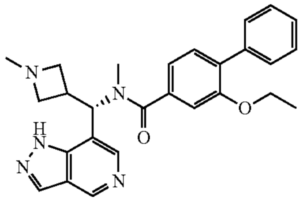 [SMILES: CCOc1cc(C(=O)N(C)[C@H](c2cncc3cn[nH]c23)C2CN(C)C2)ccc1-c1ccccc1] |
| 134 | 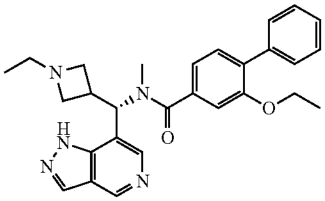 [SMILES: CCOc1cc(C(=O)N(C)[C@H](c2cncc3cn[nH]c23)C2CN(CC)C2)ccc1-c1ccccc1] |
| 136 | 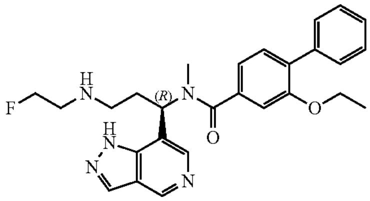 |
| 137 | 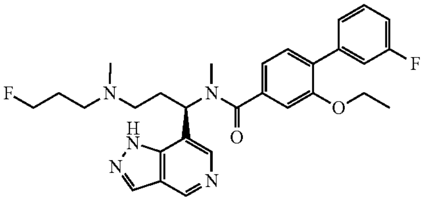 [SMILES: CCOc1cc(C(=O)N(C)[C@H](CCN(C)CCCF)c2cncc3cn[nH]c23)ccc1-c1cccc(F)c1] |
TABLE 1B-continued
| Ex. No. | Structure |
|---|---|
| 138 | 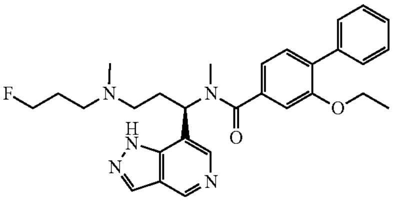 [SMILES: CCOc1cc(C(=O)N(C)[C@H](CCN(C)CCCF)c2cncc3cn[nH]c23)ccc1-c1ccccc1] |
| 139 | 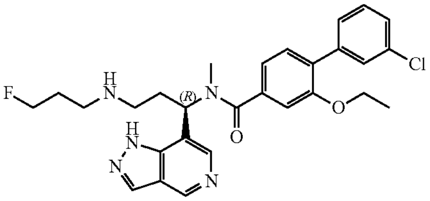 |
| 140 | 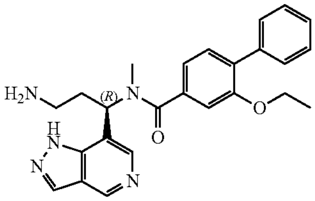 |
| 141 | 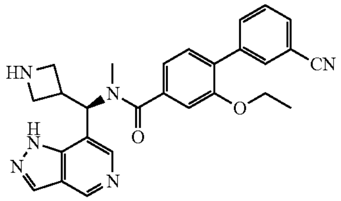 [SMILES: CCOc1cc(C(=O)N(C)[C@@H](c2cncc3cn[nH]c23)C2CNC2)ccc1-c1cccc(C#N)c1] |
| 142 | 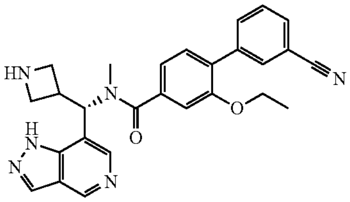 [SMILES: CCOc1cc(C(=O)N(C)[C@H](c2cncc3cn[nH]c23)C2CNC2)ccc1-c1cccc(C#N)c1] |
| 143 | 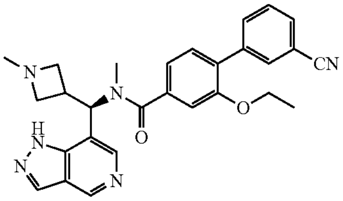 [SMILES: CCOc1cc(C(=O)N(C)[C@@H](c2cncc3cn[nH]c23)C2CN(C)C2)ccc1-c1cccc(C#N)c1] |
| 144 | 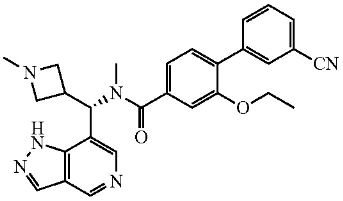 [SMILES: CCOc1cc(C(=O)N(C)[C@H](c2cncc3cn[nH]c23)C2CN(C)C2)ccc1-c1cccc(C#N)c1] |

TABLE 1B-continued
| Ex. No. | Structure |
|---|---|
| 145 | 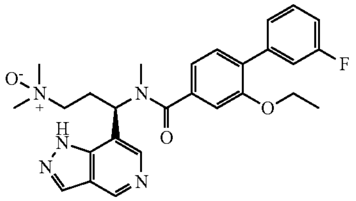 |
| 146 | 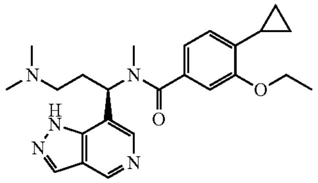 [SMILES: CCOc1cc(C(=O)N(C)[C@H](CCN(C)C)c2cncc3cn[nH]c23)ccc1C1CC1] |
| 147 | 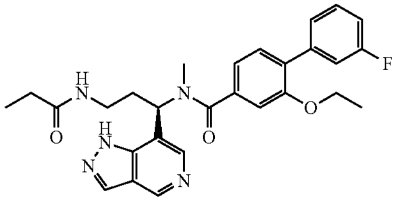 [SMILES: CCOc1cc(C(=O)N(C)[C@H](CCNC(=O)CC)c2cncc3cn[nH]c23)ccc1-c1cccc(F)c1] |
| 148 | 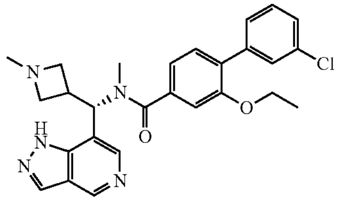 [SMILES: CCOc1cc(C(=O)N(C)[C@H](c2cncc3cn[nH]c23)C2CN(C)C2)ccc1-c1cccc(Cl)c1] |
| 149 | 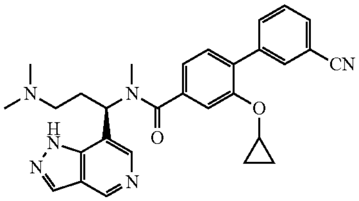 [SMILES: CN(C)CC[C@H](c1cncc2cn[nH]c12)N(C)C(=O)c1ccc(-c2cccc(C#N)c2)c(OC2CC2)c1] |
| 150 | 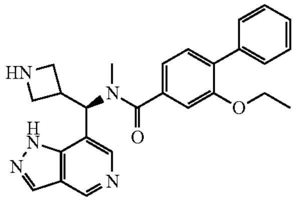 [SMILES: CCOc1cc(C(=O)N(C)[C@@H](c2cncc3cn[nH]c23)C2CNC2)ccc1-c1ccccc1] |
| 151 | 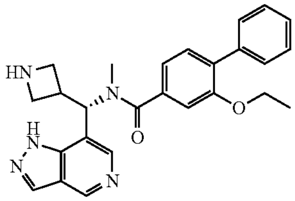 [SMILES: CCOc1cc(C(=O)N(C)[C@H](c2cncc3cn[nH]c23)C2CNC2)ccc1-c1ccccc1] |
TABLE 1B-continued
| Ex. No. | Structure |
|---|---|
| 152 | 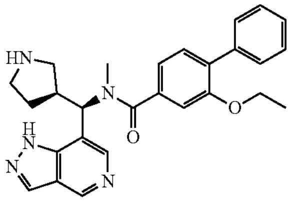 [SMILES: CCOc1cc(C(=O)N(C)[C@@H](c2cncc3cn[nH]c23)[C@H]2CCNC2)ccc1-c1ccccc1] |
| 153 | 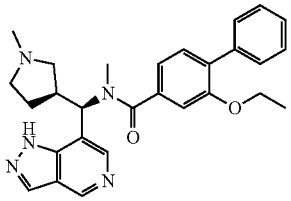 [SMILES: CCOc1cc(C(=O)N(C)[C@@H](c2cncc3cn[nH]c23)[C@H]2CCN(C)C2)ccc1-c1ccccc1] |
| 154 | 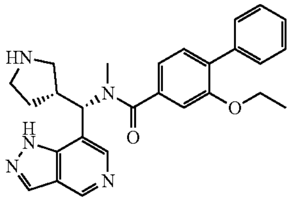 [SMILES: CCOc1cc(C(=O)N(C)[C@H](c2cncc3cn[nH]c23)[C@@H]2CCNC2)ccc1-c1ccccc1] |
| 155 | 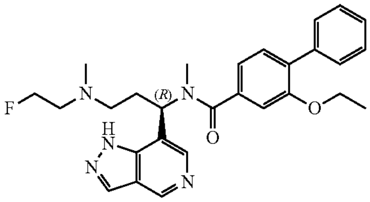 |
| 156 | 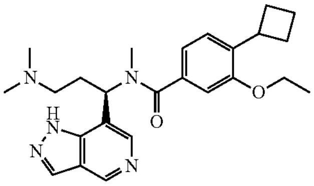 [SMILES: CCOc1cc(C(=O)N(C)[C@H](CCN(C)C)c2cncc3cn[nH]c23)ccc1C1CCC1] |
| 157 | 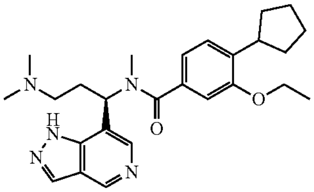 [SMILES: CCOc1cc(C(=O)N(C)[C@H](CCN(C)C)c2cncc3cn[nH]c23)ccc1C1CCCC1] |
| 158 | 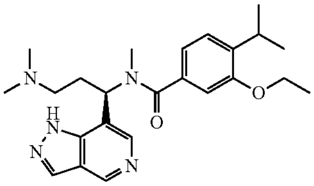 [SMILES: CCOc1cc(C(=O)N(C)[C@H](CCN(C)C)c2cncc3cn[nH]c23)ccc1C(C)C] |

TABLE 1B-continued
| Ex. No. | Structure |
|---|---|
| 159 | 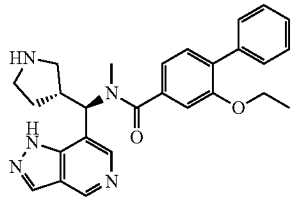 [SMILES: CCOc1cc(C(=O)N(C)[C@@H](c2cncc3cn[nH]c23)[C@@H]2CCNC2)ccc1-c1ccccc1] |
| 160 | 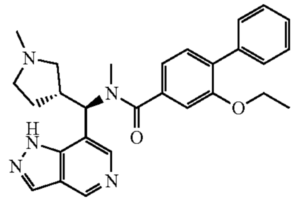 [SMILES: CCOc1cc(C(=O)N(C)[C@@H](c2cncc3cn[nH]c23)[C@@H]2CCN(C)C2)ccc1-c1ccccc1] |
| 161 | 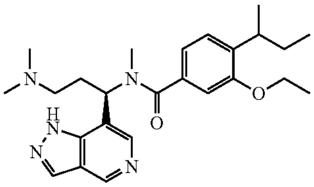 [SMILES: CCOc1cc(C(=O)N(C)[C@H](CCN(C)C)c2cncc3cn[nH]c23)ccc1C(C)CC] |
| 162 | 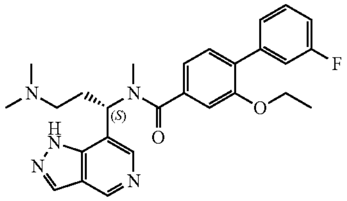 |
| 163 | 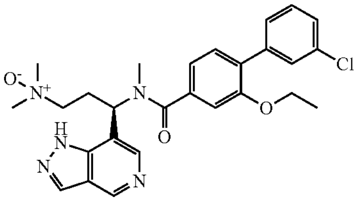 [SMILES: CCOc1cc(C(=O)N(C)[C@H](CC[N+](C)(C)[O-])c2cncc3cn[nH]c23)ccc1-c1cccc(Cl)c1] |
| 164 | 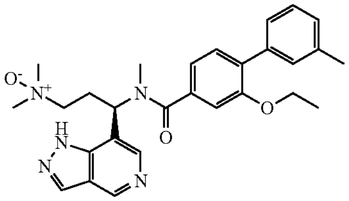 |
| 165 | 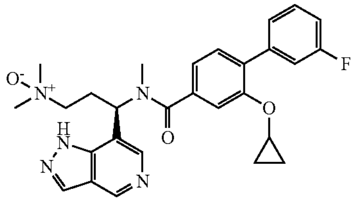 [SMILES: CN(C(=O)c1ccc(-c2cccc(F)c2)c(OC2CC2)c1)[C@H](CC[N+](C)(C)[O-])c1cncc2cn[nH]c12] |
TABLE 1B-continued
| Ex. No. | Structure |
|---|---|
| 166 | 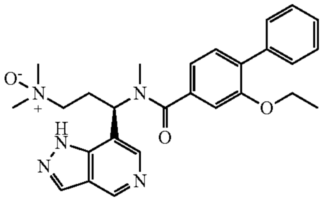 |
| 167 | 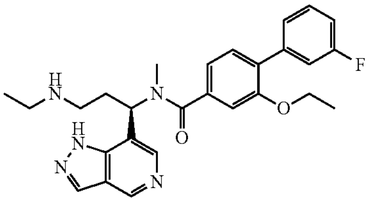 [SMILES: CCNCC[C@H](c1cncc2cn[nH]c12)N(C)C(=O)c1ccc(-c2cccc(F)c2)c(OCC)c1] |
| 168 | 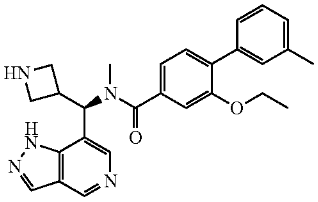 [SMILES: CCOc1cc(C(=O)N(C)[C@@H](c2cncc3cn[nH]c23)C2CNC2)ccc1-c1cccc(C)c1] |
| 169 | 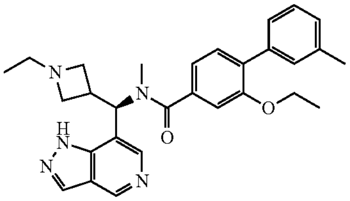 [SMILES: CCOc1cc(C(=O)N(C)[C@@H](c2cncc3cn[nH]c23)C2CN(CC)C2)ccc1-c1cccc(C)c1] |
| 170 | 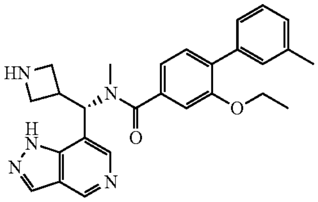 [SMILES: CCOc1cc(C(=O)N(C)[C@H](c2cncc3cn[nH]c23)C2CNC2)ccc1-c1cccc(C)c1] |
| 171 | 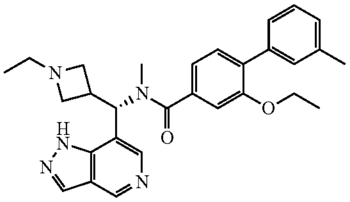 [SMILES: CCOc1cc(C(=O)N(C)[C@H](c2cncc3cn[nH]c23)C2CN(CC)C2)ccc1-c1cccc(C)c1] |
| 172 | 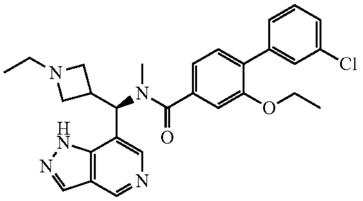 [SMILES: CCOc1cc(C(=O)N(C)[C@@H](c2cncc3cn[nH]c23)C2CN(CC)C2)ccc1-c1cccc(Cl)c1] |

TABLE 1B-continued
| Ex. No. | Structure |
|---|---|
| 173 | 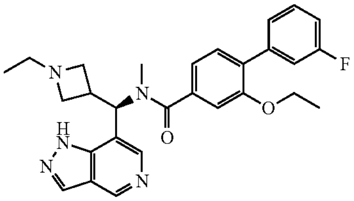 [SMILES: CCOc1cc(C(=O)N(C)[C@@H](c2cncc3cn[nH]c23)C2CN(CC)C2)ccc1-c1cccc(F)c1] |
| 174 | 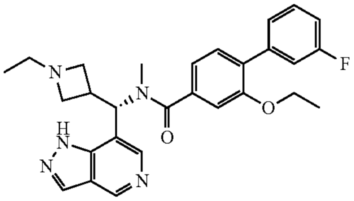 [SMILES: CCOc1cc(C(=O)N(C)[C@H](c2cncc3cn[nH]c23)C2CN(CC)C2)ccc1-c1cccc(F)c1] |
| 175 | 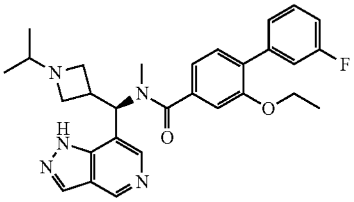 [SMILES: CCOc1cc(C(=O)N(C)[C@@H](c2cncc3cn[nH]c23)C2CN(C(C)C)C2)ccc1-c1cccc(F)c1] |
| 176 | 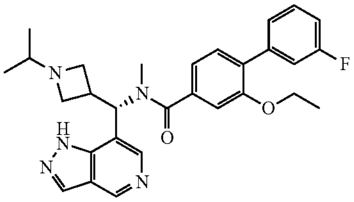 [SMILES: CCOc1cc(C(=O)N(C)[C@H](c2cncc3cn[nH]c23)C2CN(C(C)C)C2)ccc1-c1cccc(F)c1] |
| 177 | 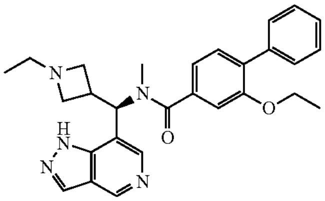 [SMILES: CCOc1cc(C(=O)N(C)[C@@H](c2cncc3cn[nH]c23)C2CN(CC)C2)ccc1-c1ccccc1] |
| 178 | 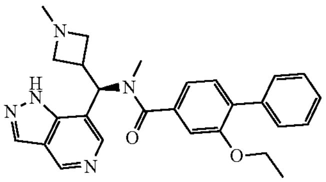 [SMILES: CCOc1cc(C(=O)N(C)[C@@H](c2cncc3cn[nH]c23)C2CN(C)C2)ccc1-c1ccccc1] |
| 179 | 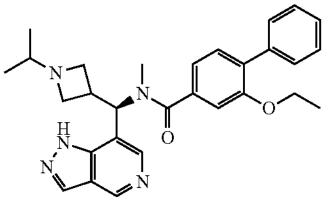 [SMILES: CCOc1cc(C(=O)N(C)[C@@H](c2cncc3cn[nH]c23)C2CN(C(C)C)C2)ccc1-c1ccccc1] |
TABLE 1B-continued
| Ex. No. | Structure |
|---|---|
| 180 | 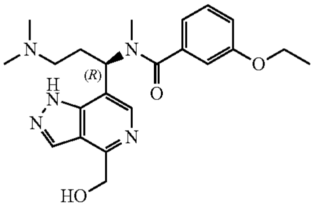 |
| 181 | 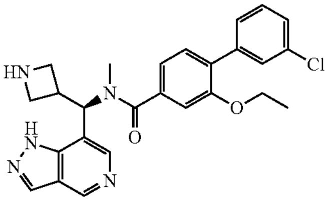 [SMILES: CCOc1cc(C(=O)N(C)[C@@H](c2cncc3cn[nH]c23)C2CNC2)ccc1-c1cccc(Cl)c1] |
| 182 | 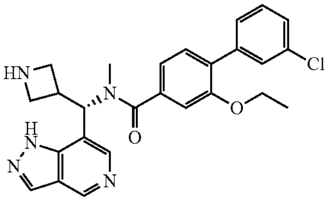 [SMILES: CCOc1cc(C(=O)N(C)[C@H](c2cncc3cn[nH]c23)C2CNC2)ccc1-c1cccc(Cl)c1] |
| 183 | 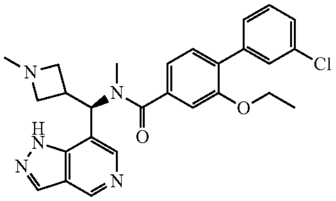 [SMILES: CCOc1cc(C(=O)N(C)[C@@H](c2cncc3cn[nH]c23)C2CN(C)C2)ccc1-c1cccc(Cl)c1] |
| 184 | 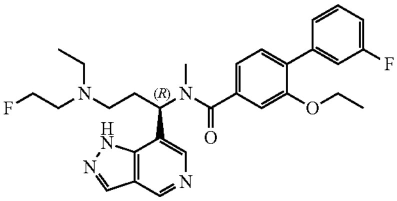 |
| 185 | 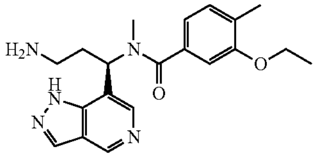 [SMILES: CCOc1cc(C(=O)N(C)[C@H](CCN)c2cncc3cn[nH]c23)ccc1C] |
In another embodiment, the compound of Formula I is selected from the group consisting of a compound in Table 1C.

TABLE 1C
| Ex. No. | Structure |
|---|---|
| 187 | 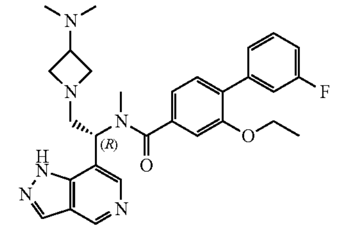 |
| 188 | 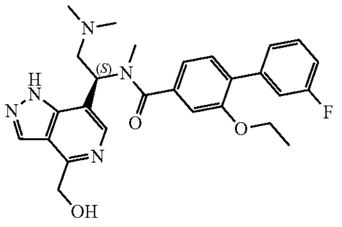 |
| 190 | 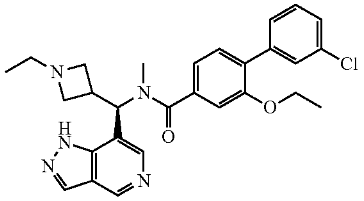 [SMILES: CCOc1cc(C(=O)N(C)[C@@H](c2cncc3cn[nH]c23)C2CN(CC)C2)ccc1-c1cccc(Cl)c1] |
| 192 | 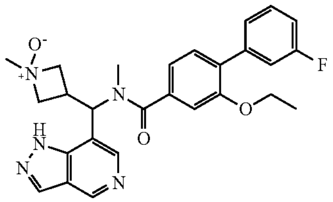 |
| 193 | 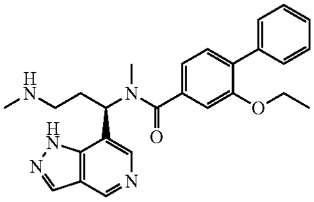 [SMILES: CCOc1cc(C(=O)N(C)[C@H](CCNC)c2cncc3cn[nH]c23)ccc1-c1ccccc1] |
| 208 | 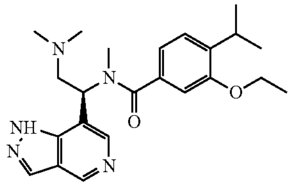 [SMILES: CCOc1cc(C(=O)N(C)[C@H](CN(C)C)c2cncc3cn[nH]c23)ccc1C(C)C] |
| 209 | 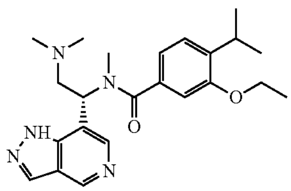 [SMILES: CCOc1cc(C(=O)N(C)[C@@H](CN(C)C)c2cncc3cn[nH]c23)ccc1C(C)C] |
TABLE 1C-continued
| Ex. No. | Structure |
|---|---|
| 210 | 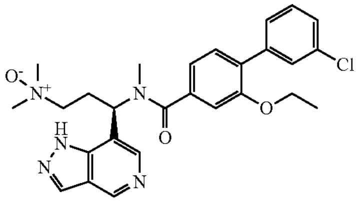 |
| 211 | 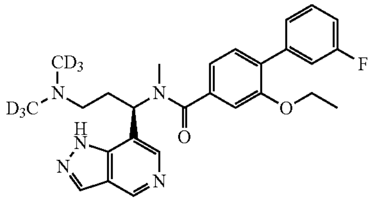 [SMILES: [2H]C([2H])([2H])N(CC[C@H](c1cncc2cn[nH]c12)N(C)C(=O)c1ccc(-c2cccc(F)c2)c(OCC)c1)C([2H])([2H])[2H]] |
| 224 | 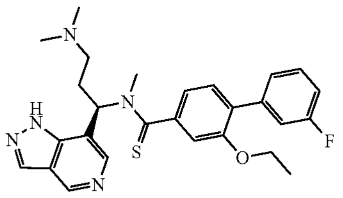 [SMILES: CCOc1cc(C(=S)N(C)[C@H](CCN(C)C)c2cncc3cn[nH]c23)ccc1-c1cccc(F)c1] |
| 225 | 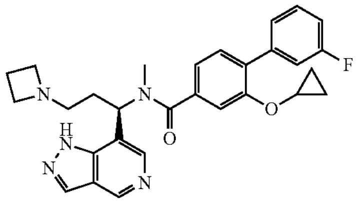 [SMILES: CN(C(=O)c1ccc(-c2cccc(F)c2)c(OC2CC2)c1)[C@H](CCN1CCC1)c1cncc2cn[nH]c12] |
| 226 | 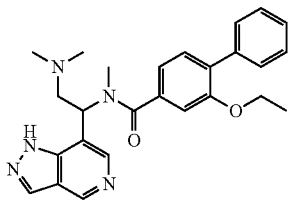 [SMILES: CCOc1cc(C(=O)N(C)C(CN(C)C)c2cncc3cn[nH]c23)ccc1-c1ccccc1] |
| 228 | 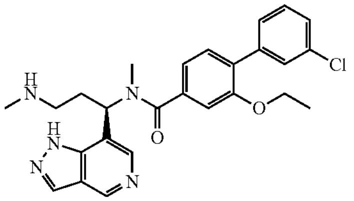 [SMILES: CCOc1cc(C(=O)N(C)[C@H](CCNC)c2cncc3cn[nH]c23)ccc1-c1cccc(Cl)c1] |
| 229 | 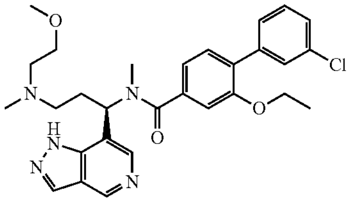 [SMILES: CCOc1cc(C(=O)N(C)[C@H](CCN(C)CCOC)c2cncc3cn[nH]c23)ccc1-c1cccc(Cl)c1] |

TABLE 1C-continued
| Ex. No. | Structure |
| --- | --- |
| 230 | 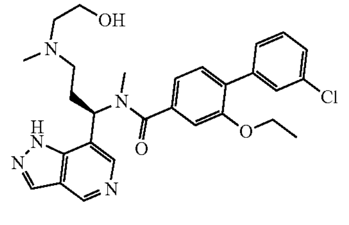 [SMILES: CCOc1cc(C(=O)N(C)[C@H](CCN(C)CCO)c2cncc3cn[nH]c23)ccc1-c1cccc(Cl)c1] |
| 231 | 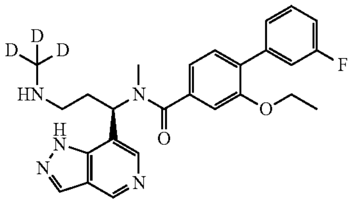 [SMILES: [2H]C([2H])([2H])NCC[C@H](c1cncc2cn[nH]c12)N(C)C(=O)c1ccc(-c2cccc(F)c2)c(OCC)c1] |
| 232 | 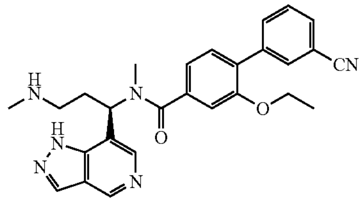 [SMILES: CCOc1cc(C(=O)N(C)[C@H](CCNC)c2cncc3cn[nH]c23)ccc1-c1cccc(C#N)c1] |
| 246 | 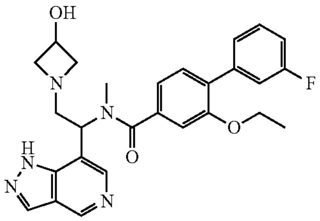 [SMILES: CCOc1cc(C(=O)N(C)C(CN2CC(O)C2)c2cncc3cn[nH]c23)ccc1-c1cccc(F)c1] |
| 247 | 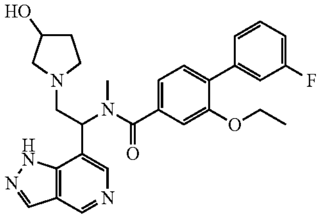 [SMILES: CCOc1cc(C(=O)N(C)C(CN2CCC(O)C2)c2cncc3cn[nH]c23)ccc1-c1cccc(F)c1] |
| 254 | 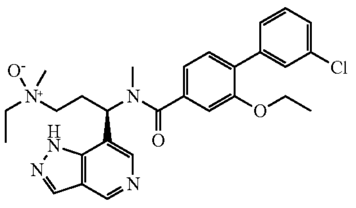 |
| 255 | 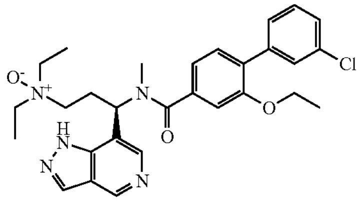 [SMILES: CCOc1cc(C(=O)N(C)[C@H](CC[N+]([O-])(CC)CC)c2cncc3cn[nH]c23)ccc1-c1cccc(Cl)c1] |
TABLE 1C-continued
| Ex. No. | Structure |
| --- | --- |
| 262 | 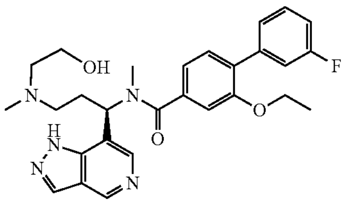 [SMILES: CCOc1cc(C(=O)N(C)[C@H](CCN(C)CCO)c2cncc3cn[nH]c23)ccc1-c1cccc(F)c1] |
| 263 | 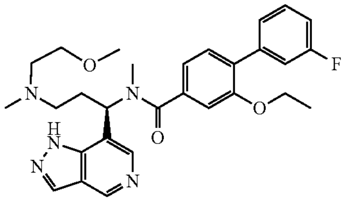 [SMILES: CCOc1cc(C(=O)N(C)[C@H](CCN(C)CCOC)c2cncc3cn[nH]c23)ccc1-c1cccc(F)c1] |
| 267 | 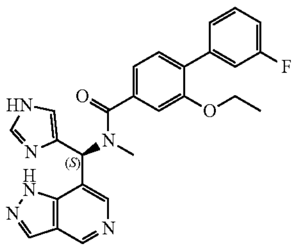 |
| 279 | 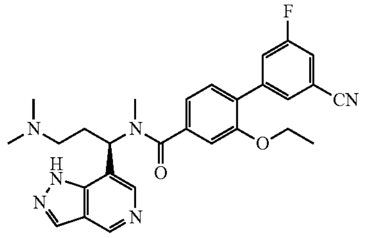 [SMILES: CCOc1cc(C(=O)N(C)[C@H](CCN(C)C)c2cncc3cn[nH]c23)ccc1-c1cc(F)cc(C#N)c1] |
| 280 | 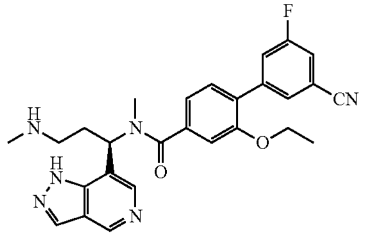 |
| 281 | 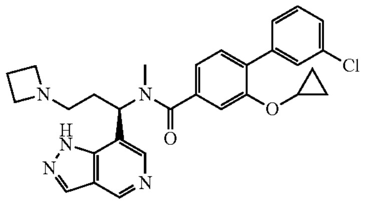 [SMILES: CN(C(=O)c1ccc(-c2cccc(Cl)c2)c(OC2CC2)c1)[C@H](CCN1CCC1)c1cncc2cn[nH]c12] |

TABLE 1C-continued

| Ex. No. | Structure |
| --- | --- |
| 299 | 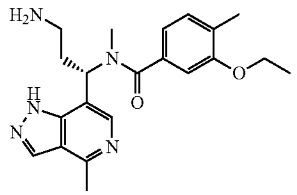 [SMILES: CCOc1cc(C(=O)N(C)[C@@H](CCN)c2cnc(C)c3cn[nH]c23)ccc1C] |

In another aspect, provided herein is a compound of Formula II:

(II)

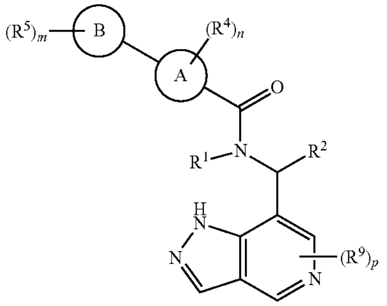

or a pharmaceutically acceptable salt thereof;

wherein

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of $C_{1-6}$ alkyl, $C_{3-6}$ cycloalkyl, $C_{0-6}$ alkylene-$C_{6-10}$ aryl, and 3-7 membered heterocycloalkyl, wherein $C_{1-6}$ alkyl, $C_{3-6}$ cycloalkyl, and $C_{0-6}$ alkylene-$C_{6-10}$ aryl are substituted with OH, halo, $SO_2R^6$, $OC(O)C_{1-6}$ alkyl, $C(O)C_{1-6}$ alkyl, 3-6 membered heterocycloalkyl, and $N(R^a)_2$, wherein 3-6 membered heterocycloalkyl is optionally substituted by one or two halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkyl-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^6$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, $C_{1-6}$ alkyl-$NH(C_{1-3}$ alkyl), halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In an embodiment,

Ring A is $C_{6-10}$ aryl;

Ring B is $C_{6-10}$ aryl;

$R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, all of which are substituted with OH, halo, $SO_2R^6$, $OC(O)C_{1-6}$ alkyl, $C(O)C_{1-6}$ alkyl, and $N(R^a)_2$;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

each $R^4$ is independently selected from the group consisting of halo, OH, $C_{1-6}$ alkoxy, $OC_{3-6}$ cycloalkyl, CN, and $C_{1-6}$ haloalkyl;

each $R^5$ is independently selected from the group consisting of $C_{1-6}$ alkyl, $C_{1-6}$ haloalkyl, halo, CN, $CONH_2$, and $CONH(C_{1-6}$ alkyl);

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In another embodiment,

Ring A is phenyl;

Ring B is phenyl;

$R^1$ is selected from the group consisting of $C_{1-6}$ alkyl and $C_{3-6}$ cycloalkyl, both of which are substituted with OH;

$R^2$ is H or $C_{1-6}$ alkyl;

each $R^4$ is independently selected from the group consisting of halo, OH, $C_{1-6}$ alkoxy, $OC_{3-6}$ cycloalkyl, and $C_{1-6}$ haloalkyl;

each $R^5$ is independently selected from the group consisting of $C_{1-6}$ alkyl, $C_{1-6}$ haloalkyl, halo, CN, $CONH_2$, and $CONH(C_{1-6}$ alkyl);

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

In yet another embodiment, the compound of Formula II is a compound of Formula IIa:

(IIa)

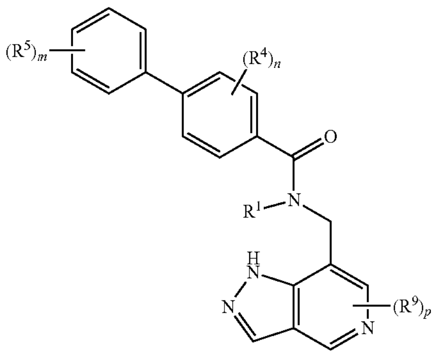

or a pharmaceutically acceptable salt thereof.

In still another embodiment, Ring A is phenyl.

In an embodiment, Ring B is selected from the group consisting of phenyl, 5-6 membered heteroaryl, $C_{3-6}$ cycloalkyl, and 3-6 membered heterocycloalkyl. In another embodiment, Ring B is phenyl. In yet another embodiment, Ring B and $R^5$ are absent.

In still another embodiment, $R^1$ is $C_{1-6}$ alkyl substituted by OH. In another embodiment $R^1$ is $C_{1-6}$ alkyl substituted by OH, halo, $SO_2R^6$, $OC(O)C_{1-3}$ alkyl, $C(O)C_{1-3}$ alkyl, $NH_2$, $NHC_{1-3}$ alkyl, or $N(C_{1-3}$ alkyl$)_2$. In an embodiment, $R^1$ is selected from the group consisting of $C_{1-6}$ alkyl, $C_{3-6}$ cycloalkyl, $C_{0-6}$ alkylene-$C_{6-10}$ aryl, and 3-7 membered heterocycloalkyl, wherein $C_{1-6}$ alkyl, $C_{3-6}$ cycloalkyl, and $C_{0-6}$ alkylene-$C_{6-10}$ aryl are substituted with OH, halo, $SO_2R^6$, $NH_2$, $NH(C_{1-6}$ alkyl), or $N(C_{1-6}$ alkyl$)_2$.

In an embodiment, $R^1$ is selected from the group consisting of $C_{1-6}$ alkyl, $C_{3-6}$ cycloalkyl, $C_{0-6}$ alkylene-$C_{6-10}$ aryl, and 3-7 membered heterocycloalkyl, wherein $C_{1-6}$ alkyl, $C_{3-6}$ cycloalkyl, and $C_{0-6}$ alkylene-$C_{6-10}$ aryl are substituted with OH, halo, $SO_2R^6$, $OC(O)C_{1-6}$ alkyl, $C(O)C_{1-6}$ alkyl, and $N(R^a)_2$.

In an embodiment, each $R^4$ is independently selected from the group consisting of $C_{1-6}$ alkoxy and $OC_{3-6}$ cycloalkyl. In another embodiment, each $R^4$ is independently selected from the group consisting of $C_{1-3}$ alkoxy and O-cyclopropyl. In yet another embodiment, $R^4$ is $C_{1-3}$ alkoxy. In still another embodiment, $R^4$ is O-cyclopropyl. In an embodiment, $R^4$ is O-cyclobutyl.

In another embodiment, each $R^5$ is independently selected from the group consisting of halo, CN, $CONH_2$, and CONH ($C_{1-6}$ alkyl). In yet another embodiment, $R^5$ is halo. In still another embodiment, $R^5$ is CN. In an embodiment, $R^5$ is $CONH_2$. In another embodiment, $CONH(C_{1-3}$ alkyl).

In yet another embodiment, each $R^9$ is independently selected from the group consisting of $C_{1-6}$ alkyl-OH, halo, OH, $NH_2$, $NH(C_{1-6}$ alkyl), and $N(C_{1-6}$ alkyl$)_2$. In still another embodiment, $R^9$ is $C_{1-6}$ alkyl-OH. In an embodiment, $R^9$ is OH. In another embodiment, $R^9$ is is halo. In yet another embodiment, $R^9$ is $NH_2$. In still another embodiment, $R^9$ is $NH(C_{1-3}$ alkyl). In an embodiment, $R^9$ is $N(C_{1-3}$ alkyl$)_2$.

In another embodiment, m is 0, 1, or 2. In yet another embodiment, m is 0. In still another embodiment, m is 1. In an embodiment, m is 2.

In another embodiment, n is 0, 1, or 2. In yet another embodiment, n is 0. In still another embodiment, n is 1. In an embodiment, n is 2.

In another embodiment, p is 0, 1, or 2. In yet another embodiment, p is 0. In still another embodiment, p is 1. In an embodiment, p is 2.

In another embodiment, the compound of Formula II is selected from the group consisting of a compound in Table 2.

TABLE 2

| Ex. No. | Structure |
|---|---|
| 041 | 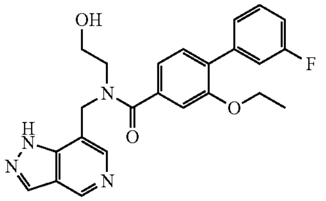 [SMILES: CCOc1cc(C(=O)N(CCO)Cc2cncc3cn[nH]c23)ccc1-c1cccc(F)c1] |
| 042 | 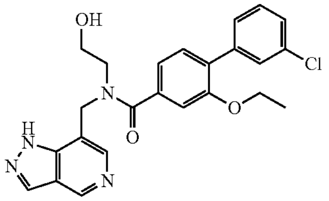 [SMILES: CCOc1cc(C(=O)N(CCO)Cc2cncc3cn[nH]c23)ccc1-c1cccc(Cl)c1] |
| 043 | 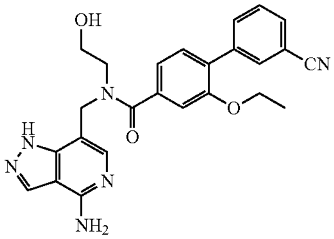 [SMILES: CCOc1cc(C(=O)N(CCO)Cc2cnc(N)c3cn[nH]c23)ccc1-c1cccc(C#N)c1] |
| 044 | 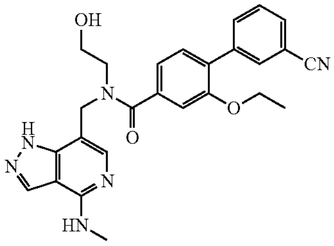 [SMILES: CCOc1cc(C(=O)N(CCO)Cc2cnc(NC)c3cn[nH]c23)ccc1-c1cccc(C#N)c1] |
| 045 | 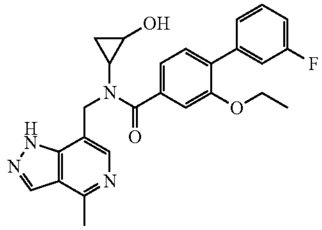 [SMILES: CCOc1cc(C(=O)N(Cc2cnc(C)c3cn[nH]c23)C2CC2O)ccc1-c1cccc(F)c1] |
| 046 | 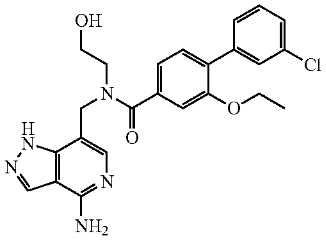 [SMILES: CCOc1cc(C(=O)N(CCO)Cc2cnc(N)c3cn[nH]c23)ccc1-c1cccc(Cl)c1] |

TABLE 2-continued
| Ex. No. | Structure |
|---|---|
| 047 | 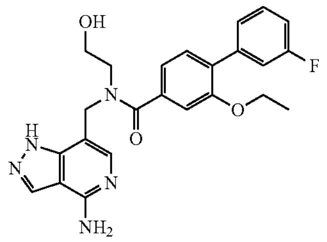 [SMILES: CCOc1cc(C(=O)N(CCO)Cc2cnc(N)c3cn[nH]c23)ccc1-c1cccc(F)c1] |
| 048 | 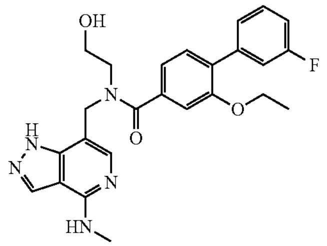 [SMILES: CCOc1cc(C(=O)N(CCO)Cc2cnc(NC)c3cn[nH]c23)ccc1-c1cccc(F)c1] |
| 049 | 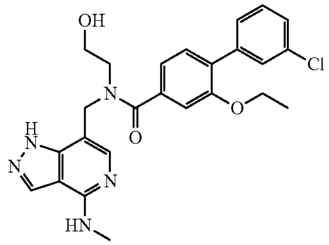 [SMILES: CCOc1cc(C(=O)N(CCO)Cc2cnc(NC)c3cn[nH]c23)ccc1-c1cccc(Cl)c1] |
| 050 | 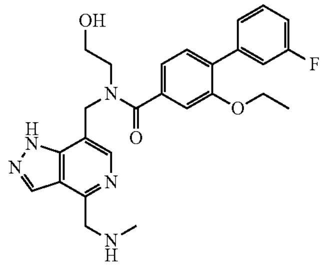 [SMILES: CCOc1cc(C(=O)N(CCO)Cc2cnc(CNC)c3cn[nH]c23)ccc1-c1cccc(F)c1] |
| 051 | 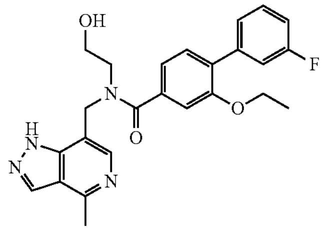 [SMILES: CCOc1cc(C(=O)N(CCO)Cc2cnc(C)c3cn[nH]c23)ccc1-c1cccc(F)c1] |
| 052 | 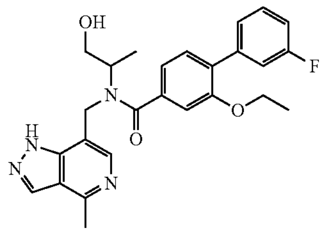 [SMILES: CCOc1cc(C(=O)N(Cc2cnc(C)c3cn[nH]c23)C(C)CO)ccc1-c1cccc(F)c1] |
TABLE 2-continued
| Ex. No. | Structure |
|---|---|
| 053 | 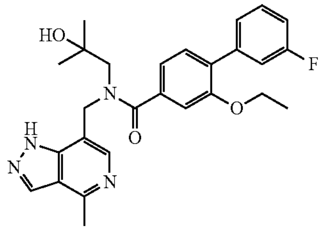 [SMILES: CCOc1cc(C(=O)N(Cc2cnc(C)c3cn[nH]c23)CC(C)(C)O)ccc1-c1cccc(F)c1] |
| 054 | 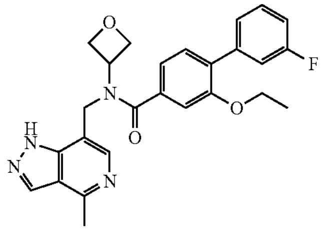 [SMILES: CCOc1cc(C(=O)N(Cc2cnc(C)c3cn[nH]c23)C2COC2)ccc1-c1cccc(F)c1] |
| 055 | 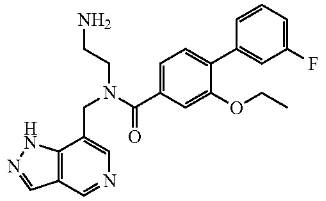 [SMILES: CCOc1cc(C(=O)N(CCN)Cc2cncc3cn[nH]c23)ccc1-c1cccc(F)c1] |
| 056 | 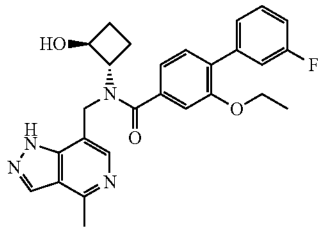 [SMILES: CCOc1cc(C(=O)N(Cc2cnc(C)c3cn[nH]c23)[C@H]2CC[C@@H]2O)ccc1-c1cccc(F)c1] |
| 057 | 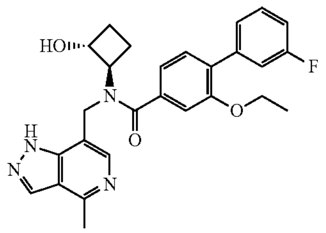 [SMILES: CCOc1cc(C(=O)N(Cc2cnc(C)c3cn[nH]c23)[C@@H]2CC[C@H]2O)ccc1-c1cccc(F)c1] |
| 058 | 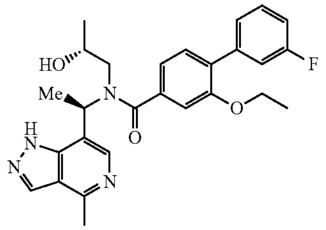 [SMILES: CCOc1cc(C(=O)N(C[C@@H](C)O)[C@H](C)c2cnc(C)c3cn[nH]c23)ccc1-c1cccc(F)c1] |

TABLE 2-continued
| Ex. No. | Structure |
|---|---|
| 059 | 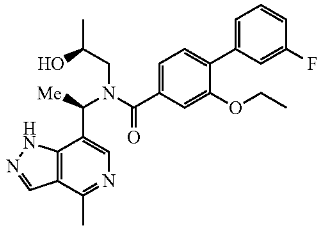 [SMILES: CCOc1cc(C(=O)N(C[C@H](C)O)[C@H](C)c2cnc(C)c3cn[nH]c23)ccc1-c1cccc(F)c1] |
| 060 | 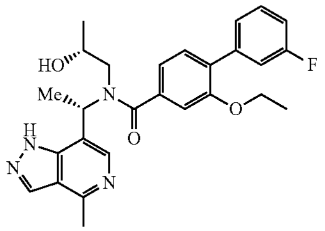 [SMILES: CCOc1cc(C(=O)N(C[C@@H](C)O)[C@@H](C)c2cnc(C)c3cn[nH]c23)ccc1-c1cccc(F)c1] |
| 061 | 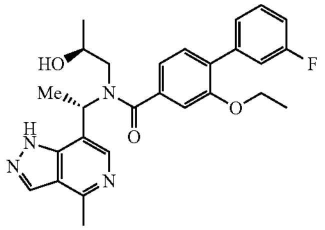 [SMILES: CCOc1cc(C(=O)N(C[C@H](C)O)[C@@H](C)c2cnc(C)c3cn[nH]c23)ccc1-c1cccc(F)c1] |
| 062 | 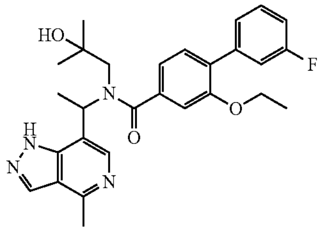 [SMILES: CCOc1cc(C(=O)N(CC(C)(C)O)C(C)c2cnc(C)c3cn[nH]c23)ccc1-c1cccc(F)c1] |
or a pharmaceutically acceptable salt thereof.
In another embodiment, the compound of Formula II is selected from the group consisting of a compound in Table 2A.
TABLE 2A
| Ex No. | Structure |
|---|---|
| 105 | 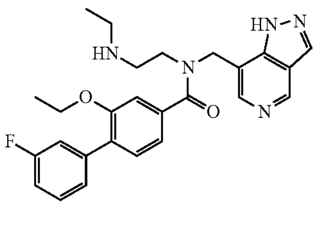 [SMILES: CCNCCN(Cc1cncc2cn[nH]c12)C(=O)c1ccc(-c2cccc(F)c2)c(OCC)c1] |
TABLE 2A-continued
| Ex No. | Structure |
|---|---|
| 106 | 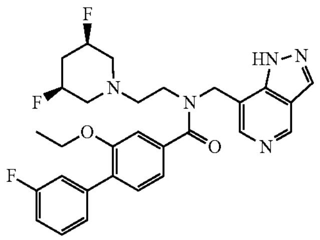 [SMILES: CCOc1cc(C(=O)N(CCN2C[C@H](F)C[C@H](F)C2)Cc2cncc3cn[nH]c23)ccc1-c1cccc(F)c1] |
| 107 | 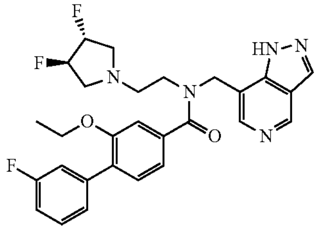 [SMILES: CCOc1cc(C(=O)N(CCN2C[C@@H](F)[C@H](F)C2)Cc2cncc3cn[nH]c23)ccc1-c1cccc(F)c1] |
| 108 | 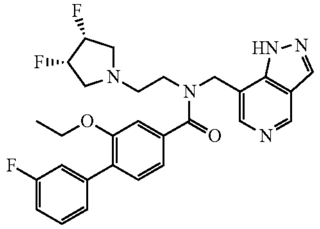 [SMILES: CCOc1cc(C(=O)N(CCN2C[C@@H](F)[C@@H](F)C2)Cc2cncc3cn[nH]c23)ccc1-c1cccc(F)c1] |
| 109 | 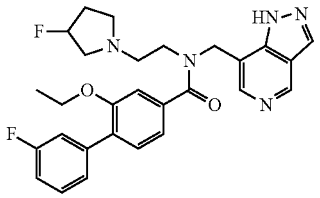 [SMILES: CCOc1cc(C(=O)N(CCN2CCC(F)C2)Cc2cncc3cn[nH]c23)ccc1-c1cccc(F)c1] |
| 110 | 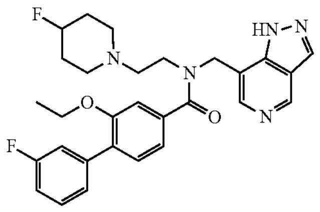 [SMILES: CCOc1cc(C(=O)N(CCN2CCC(F)CC2)Cc2cncc3cn[nH]c23)ccc1-c1cccc(F)c1] |
| 111 | 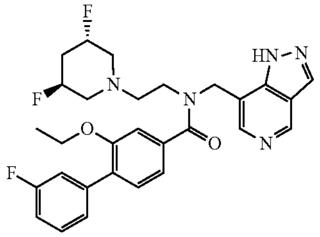 [SMILES: CCOc1cc(C(=O)N(CCN2C[C@@H](F)C[C@H](F)C2)Cc2cncc3cn[nH]c23)ccc1-c1cccc(F)c1] |
| 112 | 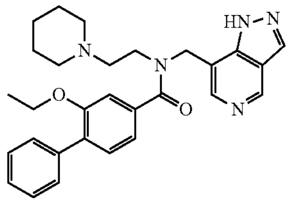 [SMILES: CCOc1cc(C(=O)N(CCN2CCCCC2)Cc2cncc3cn[nH]c23)ccc1-c1ccccc1] |

TABLE 2A-continued
| Ex No. | Structure |
|---|---|
| 113 | 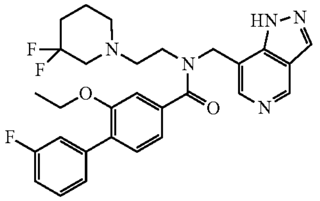 [SMILES: CCOc1cc(C(=O)N(CCN2CCCC(F)(F)C2)Cc2cncc3cn[nH]c23)ccc1-c1cccc(F)c1] |
| 114 | 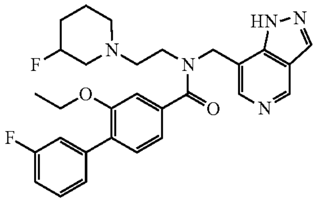 [SMILES: CCOc1cc(C(=O)N(CCN2CCCC(F)C2)Cc2cncc3cn[nH]c23)ccc1-c1cccc(F)c1] |
| 115 | 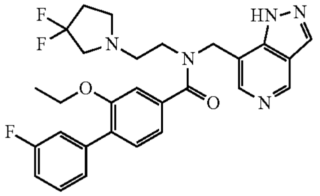 [SMILES: CCOc1cc(C(=O)N(CCN2CCC(F)(F)C2)Cc2cncc3cn[nH]c23)ccc1-c1cccc(F)c1] |
| 116 | 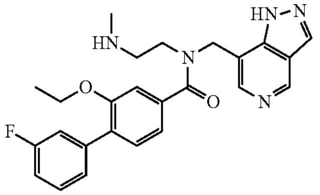 [SMILES: CCOc1cc(C(=O)N(CCNC)Cc2cncc3cn[nH]c23)ccc1-c1cccc(F)c1] |
| 117 | 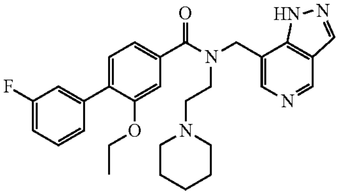 [SMILES: CCOc1cc(C(=O)N(CCN2CCCCC2)Cc2cncc3cn[nH]c23)ccc1-c1cccc(F)c1] |
| 118 | 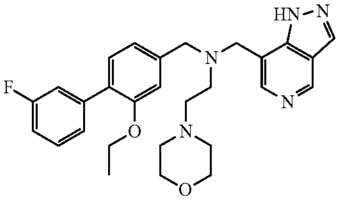 [SMILES: CCOc1cc(CN(CCN2CCOCC2)Cc2cncc3cn[nH]c23)ccc1-c1cccc(F)c1] |
| 119 | 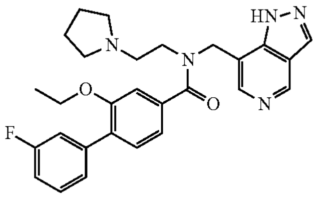 [SMILES: CCOc1cc(C(=O)N(CCN2CCCC2)Cc2cncc3cn[nH]c23)ccc1-c1cccc(F)c1] |
| 120 | 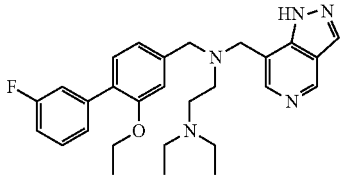 [SMILES: CCOc1cc(CN(CCN(CC)CC)Cc2cncc3cn[nH]c23)ccc1-c1cccc(F)c1] |
or a pharmaceutically acceptable salt thereof.
In another embodiment, the compound of Formula II is selected from the group consisting of a compound in Table 2B.
TABLE 2B
| Ex No. | Structure |
|---|---|
| 234 | 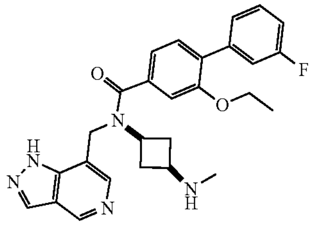 |
| 235 | 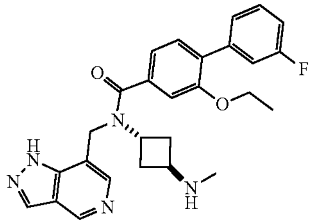 |
| 236 | 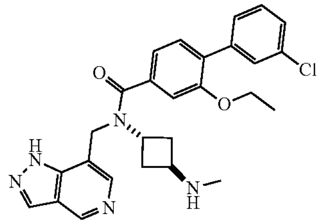 |
| 237 | 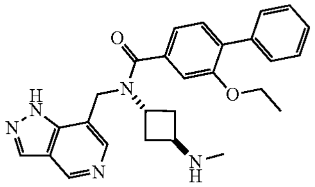 |
| 238 | 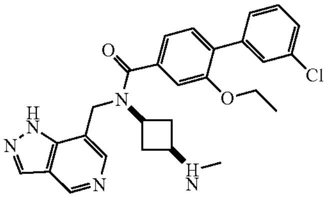 |

TABLE 2B-continued
| Ex No. | Structure |
|---|---|
| 239 | 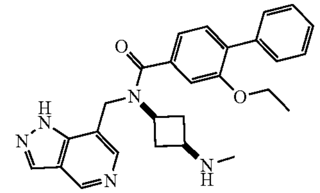 |
| 240 | 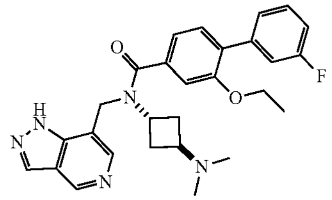 |
| 242 | 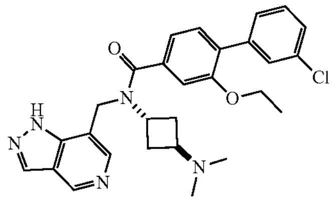 |
| 243 | 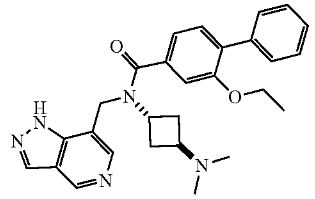 |
| 244 | 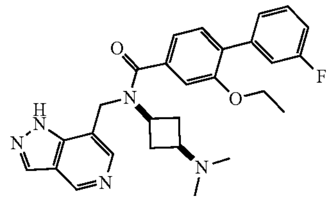 |
| 245 | 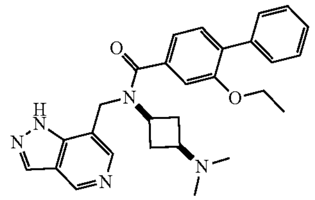 |
| 248 | 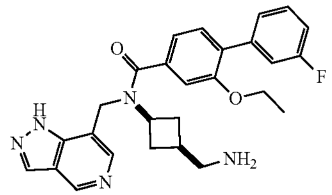 |
TABLE 2B-continued
| Ex No. | Structure |
|---|---|
| 249 | 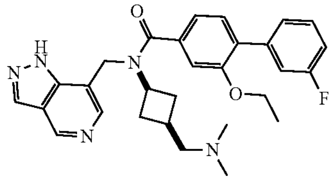 |
| 253 | 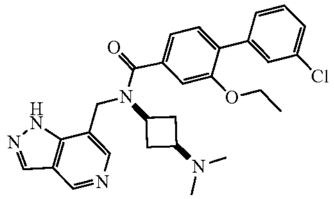 |
| 277 | 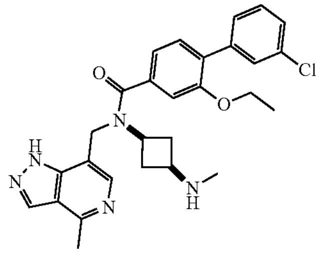 |
| 278 | 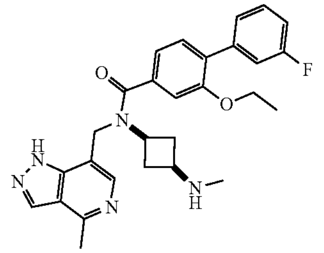 |
| 287 | 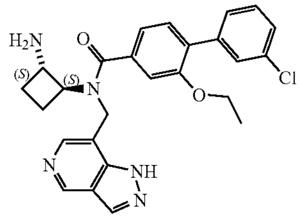 |
| 288 | 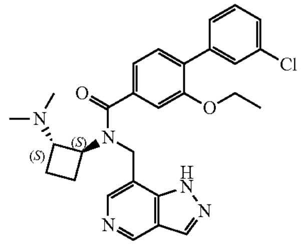 |
| 289 | 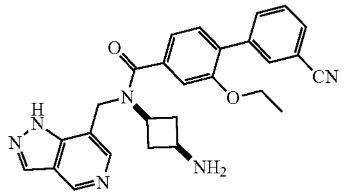 |

TABLE 2B-continued

| Ex No. | Structure |
|---|---|
| 290 | 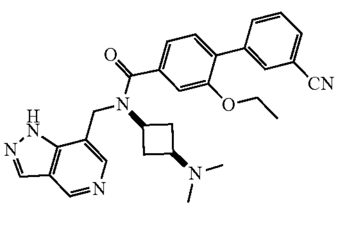 |
| 291 | 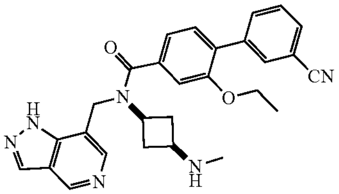 |
| 294 | 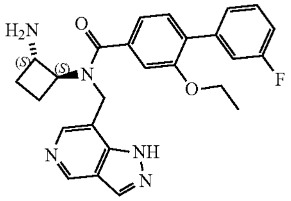 |
| 295 | 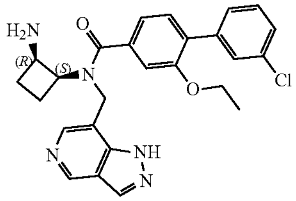 |
| 300 | 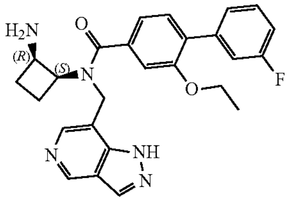 |
| 301 | 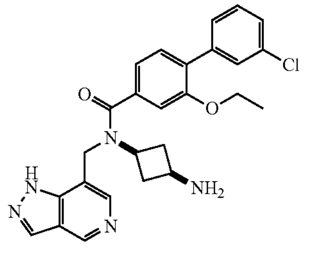 |
| 302 | 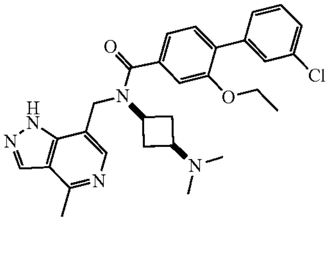 |

TABLE 2B-continued

| Ex No. | Structure |
|---|---|
| 303 | 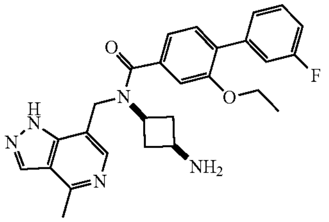 |
| 304 | 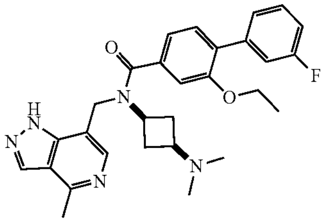 |

In an aspect, provided herein is a compound of Formula III:

(III)

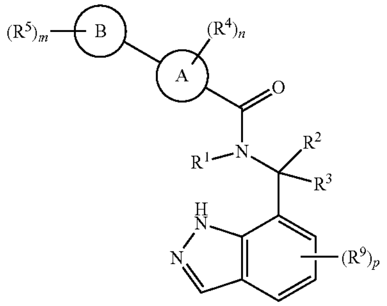

or a pharmaceutically acceptable salt thereof;

wherein

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of H, $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

$R^3$ is selected from the group consisting of H, $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; and the nitrogen atom of $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized and one or more carbon atoms of the alkyl groups on the nitrogen atom are optionally substituted with 1-6 deuterium atoms or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In an embodiment, $R^3$ is selected from the group consisting of $C_{1-6}$ alkyl, $C_{3-6}$ cycloalkyl, and 3-6 membered heterocycloalkyl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo, or $C_{0-3}$ alkylene-5-10 membered heteroaryl, wherein 3-6 membered heterocycloalkyl is optionally substituted by $C_{1-6}$ alkyl; and the nitrogen atom of $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized.

In an embodiment,

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of H, $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

$R^3$ is selected from the group consisting of $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, $N(C_{1-6}$ haloalkyl$)_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; and the nitrogen atom of $NH(C_{1-6}$ alkyl), $N(C_{1-6}$ alkyl)($C_{1-6}$ haloalkyl), $NH(C_{1-6}$ haloalkyl), $N(C_{1-6}$ alkyl$)_2$, and $N(C_{1-6}$ haloalkyl$)_2$ is optionally oxidized and the carbon atom of the alkyl groups on the nitrogen atom are optionally substituted with 1-6 deuterium atoms or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^6$, and $SO_2R8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In another embodiment,

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, $OC(O)C_{1-6}$ alkyl, $C(O)C_{1-6}$ alkyl, $N(R^a)_2$, and halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

$R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{0-3}$ alkylene-5-10 membered heteroaryl;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^6$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In another embodiment,

Ring A is $C_{6-10}$ aryl;

Ring B is $C_{6-10}$ aryl;

$R^1$ is $C_{1-6}$ alkyl;

$R^2$ is H;

$R^3$ is selected from the group consisting of $C_{1-6}$ alkyl, $C_{3-6}$ cycloalkyl, and 3-6 membered heterocycloalkyl, all of which are substituted by OH or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which is substituted by OH;

each $R^4$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $NHC(O)C_{1-6}$ alkyl, CN, and $C_{1-6}$ haloalkyl;

each $R^5$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $CONH_2$, $CONH(C_{1-6}$ alkyl), CN, and $C_{1-6}$ haloalkyl;

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

In another embodiment, the compound of Formula III is a compound of Formula IIIa:

(IIIa)

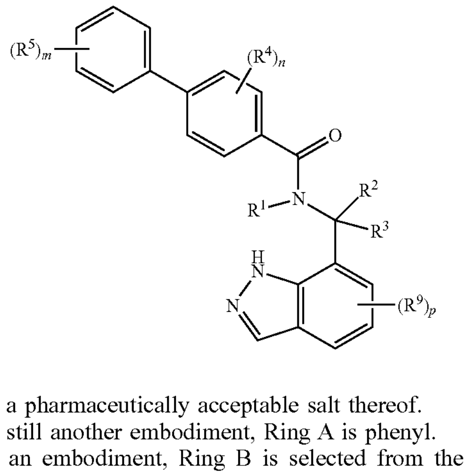

or a pharmaceutically acceptable salt thereof.

In still another embodiment, Ring A is phenyl.

In an embodiment, Ring B is selected from the group consisting of $C_{6-10}$ aryl, 5-6 membered heteroaryl, $C_{3-6}$ cycloalkyl, and 3-6 membered heterocycloalkyl. In another embodiment, Ring B is phenyl. In yet another embodiment, Ring B and $R^5$ are absent.

In still another embodiment, $R^1$ is $C_{1-6}$ alkyl. In an embodiment, $R^1$ is methyl. In another embodiment, $R^1$ is ethyl. In an embodiment, $R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl. In yet another embodiment, $R^1$ is $C_{1-6}$ alkyl or $C_{3-6}$ cycloalkyl, wherein alkyl and cycloalkyl are optionally substituted with OH, $OC(O)C_{1-6}$ alkyl, $C(O)C_{1-6}$ alkyl, $N(R^a)_2$, and halo. In still another embodiment, $R^1$ is $C_{1-6}$ alkyl or $C_{3-6}$ cycloalkyl, wherein alkyl and cycloalkyl are optionally substituted with OH, $OC(O)C_{1-3}$ alkyl, $C(O)C_{1-3}$ alkyl, $NH_2$, $NHC_{1-3}$ alkyl, $N(C_{1-3}$ alkyl$)_2$, and halo. In another embodiment, $R^1$ is $C_{3-6}$ cycloalkyl optionally substituted with $NH_2$, $NHC_{1-3}$ alkyl, or $N(C_{1-3}$ alkyl$)_2$.

In another embodiment, $R^2$ is H.

In yet another embodiment, $R^3$ is $C_{1-6}$ alkyl substituted by OH or $C_{1-3}$ alkoxy. In still another embodiment, $R^3$ is $C_{1-6}$ alkyl substituted by OH. In an embodiment, $R^3$ is $C_{1-6}$ alkyl substituted by $C_{1-3}$ alkoxy. In an embodiment, $R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{0-3}$ alkylene-5-10 membered heteroaryl. In another embodiment, $R^3$ is $C_{1-6}$ alkyl substituted by 3-6 membered heterocycloalkyl optionally substituted with one or two halo or OH. In another embodiment, $R^3$ is $C_{1-6}$ alkyl substituted by 3-6 membered heterocycloalkyl optionally substituted with one or two halo. In yet another embodiment, $R^3$ is 3-6 membered heterocycloalkyl is optionally substituted by $C_{1-6}$ alkyl. In an embodiment, $R^3$ is $C_{1-6}$ alkyl substituted by $N(R^a)_2$. In another embodiment, each $R^a$ is independently H or $C_{1-6}$ alkyl.

In another embodiment, $R^2$ and $R^3$, together with the atom to which they are attached, form a ring selected from the group consisting of $C_{3-6}$ cycloalkyl and 3-6 membered heterocycloalkyl, both of which is substituted by OH. In yet another embodiment, $R^2$ and $R^3$, together with the atom to which they are attached, form $C_{3-5}$ cycloalkyl substituted by OH. In still another embodiment, $R^2$ and $R^3$, together with the atom to which they are attached, form 3-6 membered heterocycloalkyl substituted by OH.

In an embodiment, each $R^4$ is independently selected from the group consisting of halo, $C_{1-6}$ alkoxy, $OC_{3-6}$ cycloalkyl, and $C_{1-6}$ haloalkyl. In another embodiment, each $R^4$ is independently selected from the group consisting of halo, $C_{1-3}$ alkoxy, O-cyclopropyl, and $C_{1-3}$ haloalkyl. In an embodiment, $R^4$ is $C_{1-6}$ alkoxy.

In yet another embodiment, each $R^5$ is independently selected from the group consisting of $C_{1-6}$ alkyl, halo, CN, and $C(O)NH(C_{1-6}$ alkyl). In still another embodiment, each $R^5$ is independently selected from the group consisting of $C_{1-3}$ alkyl, halo, CN, and $C(O)NH(C_{1-3}$ alkyl). In another embodiment, $R^5$ is selected from the group consisting of $C_{1-6}$ alkyl, halo, OH, $C_{1-6}$ alkoxy, CN, and $C_{1-6}$ haloalkyl.

In an embodiment, each $R^9$ is independently selected from the group consisting of $C_{1-3}$ alkyl, $C_{1-6}$ alkoxy, $C_{1-3}$ alkyl-OH, and halo.

In another embodiment, m is 0, 1, or 2. In yet another embodiment, m is 0. In still another embodiment, m is 1. In an embodiment, m is 2.

In another embodiment, n is 1. In yet another embodiment, n is 0. In still another embodiment, n is 2.

In another embodiment, p is 0, 1, or 2. In yet another embodiment, p is 0. In still another embodiment, p is 1. In an embodiment, p is 2.

In another embodiment, the compound of Formula I is selected from the group consisting of a compound in Table 3.

TABLE 3

| Ex. No. | Structure |
|---|---|
| 135 | 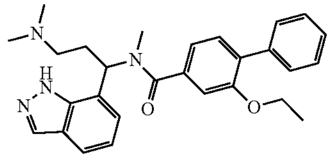 [SMILES: CCOc1cc(C(=O)N(C)C(CCN(C)C)c2cccc3cn[nH]c23)ccc1-c1ccccc1] |
| 186 | 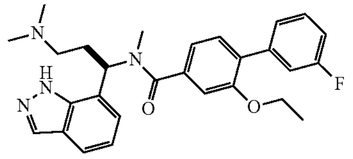 [SMILES: CCOc1cc(C(=O)N(C)[C@H](CCN(C)C)c2cccc3cn[nH]c23)ccc1-c1cccc(F)c1] |

In another embodiment, the compound of Formula I is selected from the group consisting of a compound in Table 3A.

TABLE 3A

| Ex. No. | Structure |
|---|---|
| 189 | 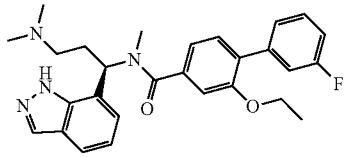 [SMILES: CCOc1cc(C(=O)N(C)[C@H](CCN(C)C)c2cccc3cn[nH]c23)ccc1-c1cccc(F)c1] |
| 194 | 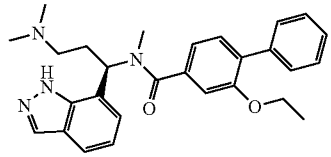 [SMILES: CCOc1cc(C(=O)N(C)[C@H](CCN(C)C)c2cccc3cn[nH]c23)ccc1-c1ccccc1] |
| 195 | 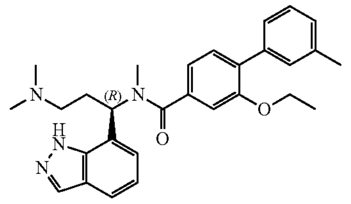 |
| 196 | 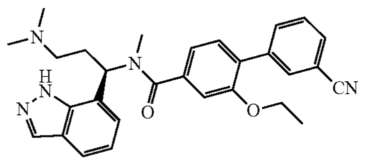 [SMILES: CCOc1cc(C(=O)N(C)[C@H](CCN(C)C)c2cccc3cn[nH]c23)ccc1-c1cccc(C#N)c1] |
| 197 | 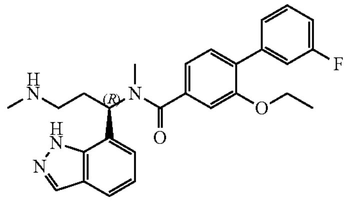 |

TABLE 3A-continued
| Ex. No. | Structure |
|---|---|
| 198 | 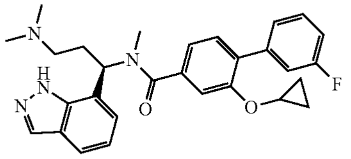 [SMILES: CN(C)CC[C@H](c1cccc2cn[nH]c12)N(C)C(=O)c1ccc(-c2cccc(F)c2)c(OC2CC2)c1] |
| 199 | 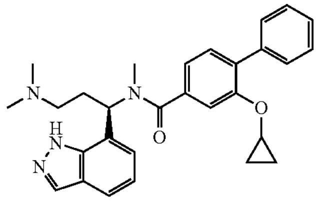 [SMILES: CN(C)CC[C@H](c1cccc2cn[nH]c12)N(C)C(=O)c1ccc(-c2ccccc2)c(OC2CC2)c1] |
| 200 | 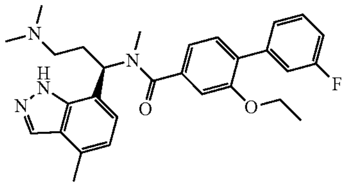 [SMILES: CCOc1cc(C(=O)N(C)[C@H](CCN(C)C)c2ccc(C)c3cn[nH]c23)ccc1-c1cccc(F)c1] |
| 201 | 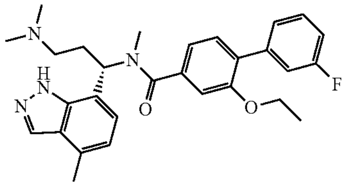 [SMILES: CCOc1cc(C(=O)N(C)[C@@H](CCN(C)C)c2ccc(C)c3cn[nH]c23)ccc1-c1cccc(F)c1] |
| 202 | 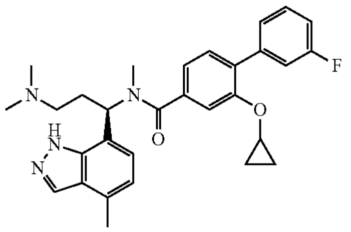 [SMILES: Cc1ccc([C@@H](CCN(C)C)N(C)C(=O)c2ccc(-c3cccc(F)c3)c(OC3CC3)c2)c2[nH]ncc12] |
| 203 | 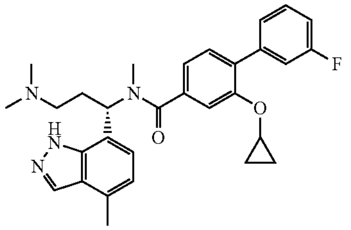 [SMILES: Cc1ccc([C@H](CCN(C)C)N(C)C(=O)c2ccc(-c3cccc(F)c3)c(OC3CC3)c2)c2[nH]ncc12] |
| 204 | 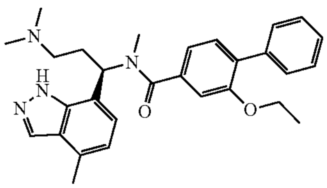 [SMILES: CCOc1cc(C(=O)N(C)[C@H](CCN(C)C)c2ccc(C)c3cn[nH]c23)ccc1-c1ccccc1] |
TABLE 3A-continued
| Ex. No. | Structure |
|---|---|
| 205 | 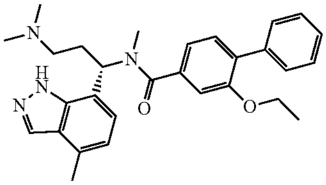 [SMILES: CCOc1cc(C(=O)N(C)[C@@H](CCN(C)C)c2ccc(C)c3cn[nH]c23)ccc1-c1ccccc1] |
| 206 | 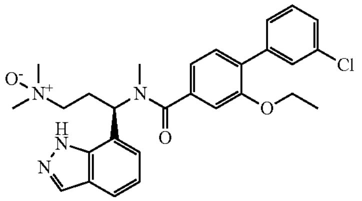 [SMILES: CCOc1cc(C(=O)N(C)[C@H](CC[N+](C)(C)[O-])c2cccc3cn[nH]c23)ccc1-c1cccc(Cl)c1] |
| 207 | 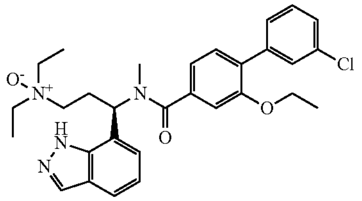 [SMILES: CCOc1cc(C(=O)N(C)[C@H](CC[N+]([O-])(CC)CC)c2cccc3cn[nH]c23)ccc1-c1cccc(Cl)c1] |
| 212 | 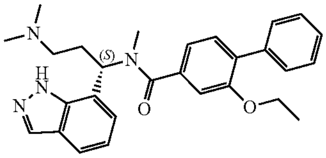 |
| 213 | 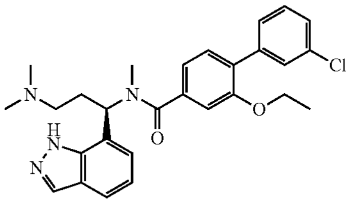 [SMILES: CCOc1cc(C(=O)N(C)[C@H](CCN(C)C)c2cccc3cn[nH]c23)ccc1-c1cccc(Cl)c1] |
| 214 | 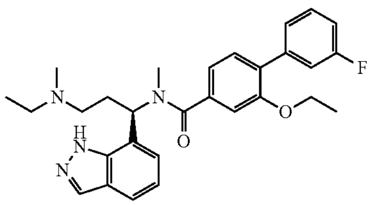 [SMILES: CCOc1cc(C(=O)N(C)[C@H](CCN(C)CC)c2cccc3cn[nH]c23)ccc1-c1cccc(F)c1] |
| 215 | 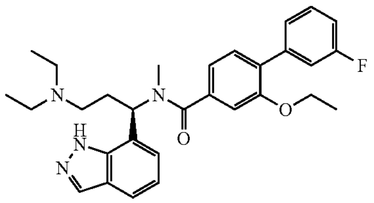 [SMILES: CCOc1cc(C(=O)N(C)[C@H](CCN(CC)CC)c2cccc3cn[nH]c23)ccc1-c1cccc(F)c1] |

TABLE 3A-continued
| Ex. No. | Structure |
|---|---|
| 216 | 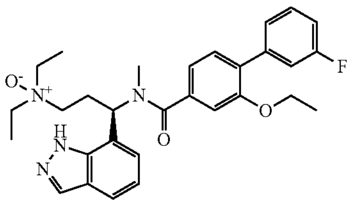 [SMILES: CCOc1cc(C(=O)N(C)[C@H](CC[N+]([O-])(CC)CC)c2cccc3cn[nH]c23)ccc1-c1cccc(F)c1] |
| 217 | 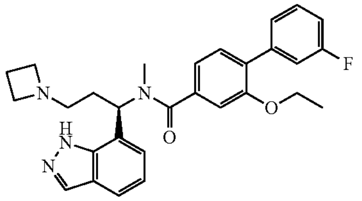 [SMILES: CCOc1cc(C(=O)N(C)[C@H](CCN2CCC2)c2cccc3cn[nH]c23)ccc1-c1cccc(F)c1] |
| 218 | 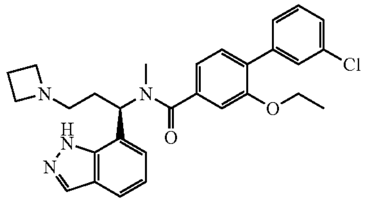 [SMILES: CCOc1cc(C(=O)N(C)[C@H](CCN2CCC2)c2cccc3cn[nH]c23)ccc1-c1cccc(Cl)c1] |
| 219 | 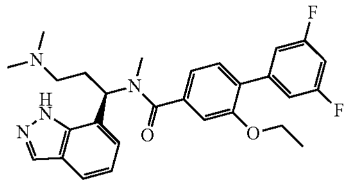 [SMILES: CCOc1cc(C(=O)N(C)[C@H](CCN(C)C)c2cccc3cn[nH]c23)ccc1-c1cc(F)cc(F)c1] |
| 220 | 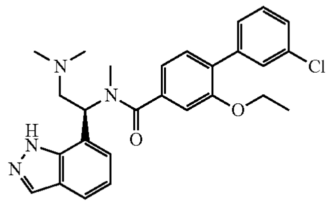 [SMILES: CCOc1cc(C(=O)N(C)[C@H](CN(C)C)c2cccc3cn[nH]c23)ccc1-c1cccc(Cl)c1] |
| 221 | 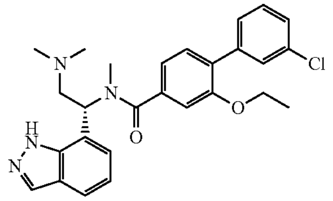 [SMILES: CCOc1cc(C(=O)N(C)[C@@H](CN(C)C)c2cccc3cn[nH]c23)ccc1-c1cccc(Cl)c1] |
| 222 | 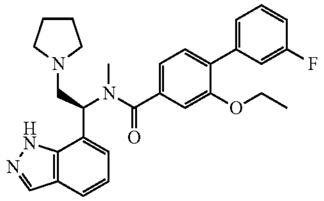 [SMILES: CCOc1cc(C(=O)N(C)[C@H](CN2CCCC2)c2cccc3cn[nH]c23)ccc1-c1cccc(F)c1] |
TABLE 3A-continued
| Ex. No. | Structure |
|---|---|
| 223 | 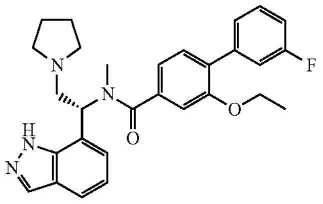 [SMILES: CCOc1cc(C(=O)N(C)[C@@H](CN2CCCC2)c2cccc3cn[nH]c23)ccc1-c1cccc(F)c1] |
| 227 | 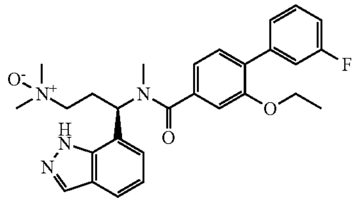 [SMILES: CCOc1cc(C(=O)N(C)[C@H](CC[N+](C)(C)[O-])c2cccc3cn[nH]c23)ccc1-c1cccc(F)c1] |
| 233 | 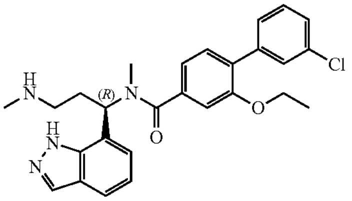 |
| 241 | 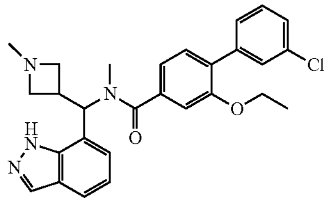 |
| 256 | 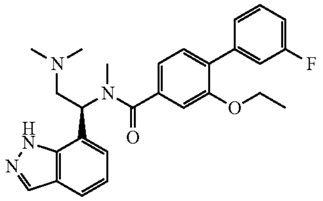 [SMILES: CCOc1cc(C(=O)N(C)[C@H](CN(C)C)c2cccc3cn[nH]c23)ccc1-c1cccc(F)c1] |
| 257 | 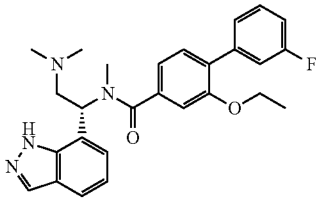 [SMILES: CCOc1cc(C(=O)N(C)[C@@H](CN(C)C)c2cccc3cn[nH]c23)ccc1-c1cccc(F)c1] |
| 258 | 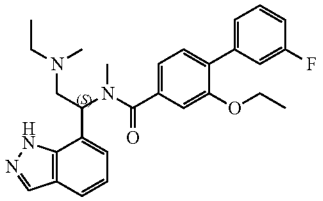 |

TABLE 3A-continued
| Ex. No. | Structure |
|---|---|
| 259 | 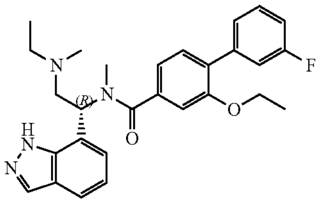 |
| 260 | 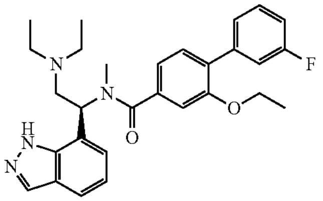 [SMILES: CCOc1cc(C(=O)N(C)[C@H](CN(CC)CC)c2cccc3cn[nH]c23)ccc1-c1cccc(F)c1] |
| 261 | 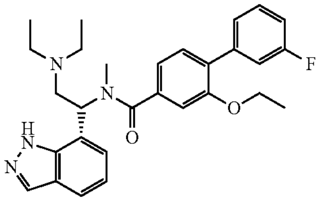 |
| 264 | 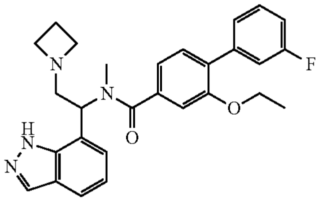 [SMILES: CCOc1cc(C(=O)N(C)C(CN2CCC2)c2cccc3cn[nH]c23)ccc1-c1cccc(F)c1] |
| 282 | 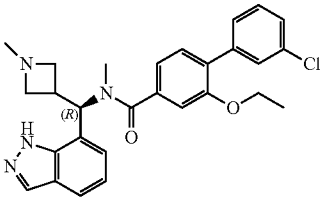 |
| 283 | 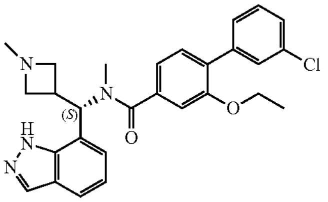 |
| 296 | 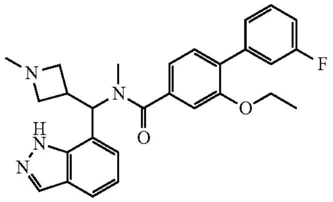 [SMILES: CCOc1cc(C(=O)N(C)C(c2cccc3cn[nH]c23)C2CN(C)C2)ccc1-c1cccc(F)c1] |
TABLE 3A-continued
| Ex. No. | Structure |
|---|---|
| 297 | 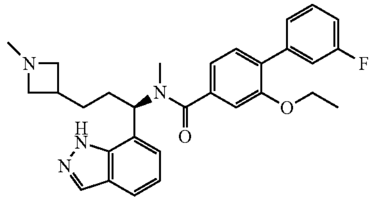 [SMILES: CCOc1cc(C(=O)N(C)[C@H](CCC2CN(C)C2)c2cccc3cn[nH]c23)ccc1-c1cccc(F)c1] |
| 298 | 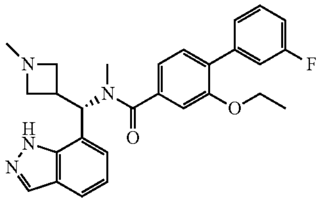 [SMILES: CCOc1cc(C(=O)N(C)[C@H](c2cccc3cn[nH]c23)C2CN(C)C2)ccc1-c1cccc(F)c1] |
| 250 | 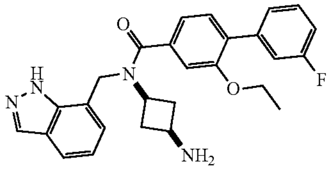 |
| 251 | 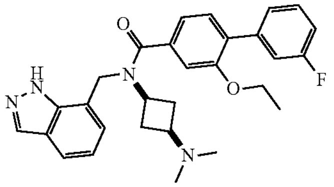 |
| 252 | 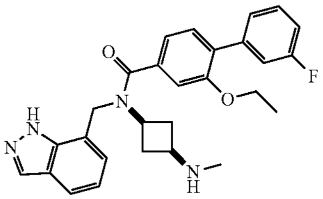 |
| 265 | 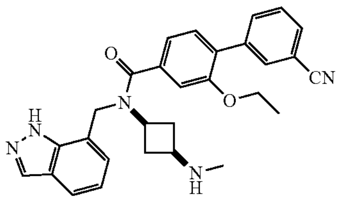 |
| 266 | 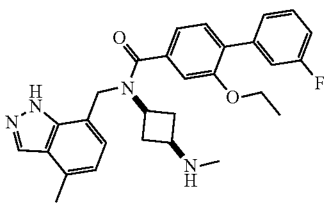 |

TABLE 3A-continued

| Ex. No. | Structure |
|---|---|
| 284 | 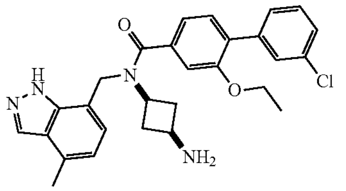 |
| 285 | 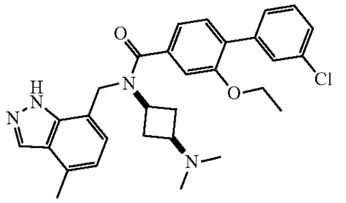 |
| 286 | 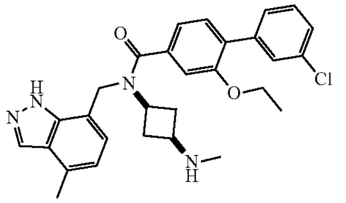 |
| 292 | 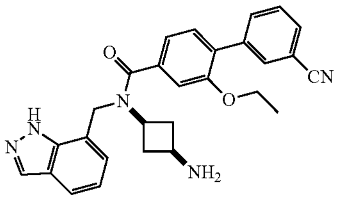 |
| 293 | 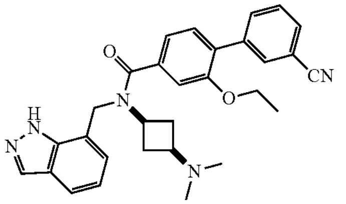 |

In another aspect, provided herein is a pharmaceutical composition comprising a compound described herein, or a pharmaceutically acceptable salt thereof, and a pharmaceutically acceptable carrier.

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound disclosed herein is a prodrug within the scope of the present disclosure.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

In embodiments, the compounds provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Methods of Treatment

In an aspect, provided herein is a method of inhibiting NLRP3 inflammasome in a subject in need thereof, comprising administering to the subject a therapeutically effective amount of a compound disclosed herein.

In another aspect, provided herein is a method of modulating GLP-1 in a subject in need thereof, comprising administering to the subject a therapeutically effective amount of a compound disclosed herein.

In another aspect, provided herein is a method of treating a disease or disorder associated with GLP-1 activity in a subject in need thereof, comprising administering to the subject a therapeutically effective amount of a compound disclosed herein.

In an embodiment, the disease or disorder associated with GLP-1 activity is obesity. In an embodiment, the obesity is dietary-induced obesity.

In another aspect, provided herein is a method of treating obesity-related comorbidity in a subject in need thereof, comprising administering to the subject a therapeutically effective amount of a compound disclosed herein.

In an embodiment, the obesity-related comorbidity is selected from the group consisting of diabetes, heart failure, metabolic dysfunction-associated steatohepatitis (MASH), and a renal disease.

In another aspect, provided herein is a method of treating obesity-related disease, disorder, or comorbidity in a subject in need thereof, comprising administering to the subject a therapeutically effective amount of a compound disclosed herein and a GLP-1 modulator.

In an embodiment, the GLP-1 modulator is selected from the group consisting of semaglutide, dulaglutide, exenatide, liraglutide, and lixisenatide.

In another aspect, provided herein is a method of treating inflammation in a subject in need thereof, comprising administering to the subject a therapeutically effective amount of a compound disclosed herein.

In another aspect, provided herein is a method of treating inflammaging in a subject in need thereof, comprising administering to the subject a therapeutically effective amount of a compound disclosed herein.

In another aspect, provided herein is a method of treating cryopyrin-associated periodic syndrome (CAPS) in a subject in need thereof, comprising administering to the subject a therapeutically effective amount of a compound disclosed herein.

In an embodiment, the CAPS is selected from the group consisting of familial cold autoinflammatory syndrome, Muckle-Wells syndrome, and neonatal-onset multisystem inflammatory disease.

In another aspect, provided herein is a method of treating a dermatologic disease in a subject in need thereof, comprising administering to the subject a therapeutically effective amount of a compound disclosed herein.

In an embodiment, the dermatologic disease is selected from the group consisting of psoriasis, urticaria, skin photoaging, and eczema.

Also provided herein is a method of using the compounds provided herein for treatment or amelioration of aging or an aging-related condition negatively impacting longevity or quality of life, wherein the aging-related condition negatively impacting longevity or quality of life is selected from the group consisting of inflammation, anemia, hyperglycemia, dyslipidemia, hyperinsulinemia, insulin resistance, immunosuppression, liver disease, iron overload, hypertriglyceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen Ill, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (1-TAC/CXCL11), interleukin (IL)-1, IL-1.alpha., IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNF.alpha.), vascular cell adhesion molecule (VCAM-1), and vascular endothelial growth factor 2 (VEGFR2), comprising: administering to a subject in need thereof a compound provided herein.

In an aspect, provided herein is a method of reversing a normal aging process in subject comprising administering to the subject a therapeutically effective amount of a compound provided herein or a pharmaceutically acceptable salt thereof.

In another aspect, provided herein is a method of reversing a normal aging process in subject comprising administering to the subject a pharmaceutical composition comprising a therapeutically effective amount of a compound provided herein or a pharmaceutically acceptable salt thereof.

In yet another aspect, provided herein is a method of extending lifespan of a subject comprising administering to the subject a therapeutically effective amount of a compound provided herein or a pharmaceutically acceptable salt thereof.

In still another aspect, provided herein is a method of extending lifespan of a subject comprising administering to the subject a pharmaceutical composition comprising a therapeutically effective amount of a compound provided herein or a pharmaceutically acceptable salt thereof.

In another aspect, provided herein is a method to slow down and mitigate the aging process in a subject comprising administering to the subject a therapeutically effective amount of a compound provided herein or a pharmaceutically acceptable salt thereof.

In another aspect, provided herein is a method of inhibiting or modulating the pro-inflammatory pathway in a cell comprising contacting the cell with a compound provided herein, or a pharmaceutically acceptable salt thereof. In yet another aspect, provided herein is a method of inhibiting or modulating NLRP3 in a cell comprising contacting the cell with a compound provided herein, or a pharmaceutically acceptable salt thereof.

Treatment of a cell (in vitro or in vivo) that expresses a NLRP3 inflammasome with a compound provided herein can result in inhibiting the pro-inflammatory pathway and inhibiting downstream events related to the signaling pathway such as inflammation or inflammaging.

In another aspect, provided herein is a method of treating a neurosensory disease in a subject in need thereof, comprising administering to the subject a therapeutically effective amount of a compound disclosed herein.

In an embodiment, the neurosensory disease is selected from the group consisting of hearing loss, hearing injury, and ocular disease.

In another aspect, provided herein is a method of treating an ocular disease in a subject in need thereof, comprising administering to the subject a therapeutically effective amount of a compound disclosed herein.

In an embodiment, the ocular disease is an age-related eye disease (ARED). In an embodiment, the ocular disease is retinal and optic nerve injury. In another embodiment, the ocular disease is age-related macular degeneration (AMD). In an embodiment, the age-related macular degeneration is non-neovascular geographic atrophic ("dry") AMD. In an embodiment, the age-related macular degeneration is neovascular exudative ("wet") AMD.

In another embodiment, the ocular disease is diabetic retinopathy. In another embodiment, the ocular disease is diabetic macular edema (DME). In another embodiment, the ocular disease is geographic atrophy. In another embodiment, the geographic atrophy is in the back of the eye. In an embodiment, the ocular disease is retinal disease.

In an embodiment, the ocular disease is dry eye. In an embodiment, the ocular disease is severe dry eye. In an embodiment, the ocular disease is Sjogren's syndrome dry eye (SSDE). In an embodiment, the ocular disease is non-Sjogren's syndrome dry eye (NSSDE).

In an embodiment, the ocular disease is glaucoma. In an embodiment, the ocular disease is cataracts.

In an embodiment, the ocular disease is not an age-related eye disease. In an embodiment, the ocular disease is selected from a corneal ulcer, a non-healing ocular burn, uveitis, a persistent corneal defect, inflammatory keratitis, retinitis pigmentosa, and retinopathy of prematurity.

In yet another aspect, provided herein is a method of treating an inflammatory disorder in a subject in need thereof, comprising administering to the subject a therapeutically effective amount of a compound disclosed herein.

In an embodiment, the inflammatory disorder is selected from the group consisting of allergy, asthma, atopic dermatitis, atherosclerosis, autoimmune diseases, coeliac disease, chronic inflammation, glomerulonephritis, hepatitis, inflammatory bowel disease, preperfusion injury, SARS-CoV-2 infection, transplant rejection, heart disease, diabetes, arthritis, Crohn's disease, ulcerative colitis, non-alcoholic steatohepatitis (NASH), gout, coronary artery disease, rheumatoid arthritis, intestinal disorders, and acute respiratory distress syndrome (ARDS). In an embodiment, the inflammatory disorder is diabetes-associated atherosclerosis. In another embodiment, the inflammatory disorder is kidney injury in diabetic nephropathy. In an embodiment, the inflammatory disorder is low-grade inflammation. In an embodiment, the inflammatory disorder is graft versus host disease (GvHD).

In another embodiment, the inflammatory disorder is a neuroinflammatory disease. In yet another embodiment, the inflammatory disorder is inner ear inflammation. In another embodiment, the inflammatory disorder is an ocular disease.

In an embodiment, a chronic inflammation comprises a tissue inflammation. Tissue inflammation is a chronic inflammation that is confined to a particular tissue or organ. In an embodiment, a tissue inflammation comprises, e.g., a skin inflammation, ocular inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the term bacteremia being applied specifically for bacterial sepsis and viremia specifically to viral sepsis. Vasodilation and organ dysfunction are serious problems associated with widespread infection that may lead to septic shock and death.

In yet another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In still another aspect, provided herein is a method of treating an age-related disorder in a subject in need thereof, comprising administering to the subject a therapeutically effective amount of a compound disclosed herein.

In an embodiment, the age-related disorder is selected from the group consisting of neurodegeneration, cardiovascular disease, insulin resistance, diabetes, osteoporosis, osteoarthritis, cognitive decline, dementia, frailty, cataracts, arthritis, obesity, hypertension, angina, congestive heart failure, dyslipidemia, myocardial infarction, vascular disease, respiratory disease, kidney disease, cerebrovascular disease, peripheral vascular disease, Alzheimer's disease, cardiac diastolic dysfunction, benign prostatic hypertrophy, aortic aneurysm, and emphysema. In an embodiment, the age-related disorder is an ischemic stroke concomitant with diabetes.

In another aspect, provided herein is a method of treating obesity-related comorbidity in a subject in need thereof, comprising administering to the subject a therapeutically effective amount of a compound disclosed herein.

In an embodiment, the obesity-related comorbidity is selected from the group consisting of diabetes, heart failure, metabolic dysfunction-associated steatohepatitis (MASH), and a renal disease.

In another aspect, provided herein is a method of treating a metabolic condition in a subject in need thereof, comprising administering to the subject a therapeutically effective amount of a compound disclosed herein.

In an embodiment, the metabolic condition is selected from the group consisting of diabetes, obesity, cystic fibrosis, and hyperthyroidism. In an embodiment, the metabolic condition is insulin resistance. In an embodiment, the metabolic condition is an ischemic stroke concomitant with diabetes.

In yet another aspect, provided herein is a method of treating a neurodegenerative disease in a subject in need thereof, comprising administering to the subject a therapeutically effective amount of a compound disclosed herein.

In an embodiment, the neurodegenerative disease is selected from the group consisting of Alzheimer's disease, Parkinson's disease, Huntington's disease, multiple sclerosis (MS), amyotrophic lateral sclerosis (ALS), and Batten disease.

In an aspect, provided herein is a method of treating a disease or disorder of the inner ear in a subject in need thereof, comprising administering to the subject a therapeutically effective amount of a compound disclosed herein.

In an embodiment, the disease or disorder of the inner ear is selected from the group consisting of hearing loss, hearing impairment, vertigo, Meniere's disease, and tinnitus. In another embodiment, the disease of the inner ear is hearing loss. In yet another embodiment, the disease of the inner ear is hearing impairment.

In another embodiment, the hearing loss is age-related, noise-induced, or the result of a viral infection. In yet another embodiment, the viral infection is Zika virus or coronavirus.

In another aspect, provided herein is a method of treating a neurosensory disease in a subject in need thereof comprising administering to the subject a therapeutically effective amount of a compound of the present disclosure.

In an embodiment, the neurosensory disease is selected from the group consisting of amyotrophic lateral sclerosis (ALS), traumatic brain injury, Parkinson's disease, and Alzheimer's disease. In another embodiment, the neurosensory disease is ALS. In yet another embodiment, the neurosensory disease is traumatic brain injury. In still another embodiment, the neurosensory disease is Parkinson's disease. In an embodiment, the neurosensory disease is Alzheimer's disease.

In yet another aspect, provided herein is a method of treating, preventing, or mitigating an adverse effect related to the administration of a T cell engaging agent in a subject in need thereof comprising administering to the subject a therapeutically effective amount of a compound disclosed herein.

In an embodiment, the adverse effect is cytokine release syndrome (CRS). In another embodiment, the adverse effect is fever, hypotension and/or hypoxia.

In yet another embodiment, the adverse effect is an elevated serum level of one of more cytokine(s), particularly one or more cytokine(s) selected from the group consisting of IL-1b, IL-6 and IL-8. In another embodiment, the adverse effect is an elevated serum level of one of more cytokine(s), particularly one or more cytokine(s) selected from the group consisting of IL-1b, IL-6, IL-18, and TNF-α. In another embodiment, the adverse effect is an elevated serum level of one of more cytokine(s), particularly one or more cytokine(s) selected from the group consisting of IL-1b, IL-6, and IL-18.

In an embodiment of the methods, the subject is a human.

In another aspect, the disclosure provides a compound disclosed herein, or a pharmaceutically acceptable salt thereof, for use in the manufacture of a medicament for treating or preventing a disease in which NLRP3 inflammasome plays a role.

In an aspect, provided herein is a method of treating a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer.

Therefore, in an aspect, provided herein is a method of treating cancer in a subject in need thereof comprising administering to the subject a therapeutically effective amount of a compound disclosed herein, or a pharmaceutically acceptable salt thereof.

In an embodiment, the cancer is a CD20-expressing cancer. In another embodiment, the cancer is a B-cell cancer.

In yet another embodiment, the cancer is selected from the group consisting of Non-Hodgkin lymphoma (NHL), acute lymphocytic leukemia (ALL), chronic lymphocytic leukemia (CLL), diffuse large B-cell lymphoma (DLBCL), high grade B cell lymphoma (HGBCL), primary mediastinal large B-cell lymphoma (PMBCL), follicular lymphoma (FL), mantle-cell lymphoma (MCL) and marginal zone lymphoma (MZL).

In an embodiment, the cancer is selected from the group consisting of breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia.

In another embodiment, the cancer is selected from the group consisting of myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

In an embodiment, the cancer is selected from the group consisting of prostate cancer, colon cancer, lung cancer, squamous cell cancer of the head and neck, esophageal cancer, hepatocellular carcinoma, melanoma, sarcoma, gastric cancer, pancreatic cancer, ovarian cancer, breast cancer.

In an embodiment, the cancer is selected from the group consisting of tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in treating are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In another aspect, provided herein is the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

In another aspect, provided herein is a method of treating obesity in a subject in need thereof, comprising administering to the subject a therapeutically effective amount of a compound disclosed herein.

In an embodiment, the obesity is dietary-induced obesity.

In another aspect, provided herein is a method of treating obesity-mediated metabolic disorders in a subject in need thereof, comprising administering to the subject a therapeutically effective amount of a compound disclosed herein.

In an embodiment, the obesity-mediated metabolic disorder is non-alcoholic fatty liver disease (NAFLD). In another embodiment, the obesity-mediated metabolic disorder is insulin resistance. In yet another embodiment, the obesity-mediated metabolic disorder is obesity-induced inflammation.

In yet another aspect, provided herein is a method of improving lipid metabolism in a subject in need thereof, comprising administering to the subject a therapeutically effective amount of a compound disclosed herein.

In still another aspect, provided herein is a method of reducing hypothalamic gliosis in a subject in need thereof, comprising administering to the subject a therapeutically effective amount of a compound disclosed herein.

In another aspect, provided herein is a method of reducing leptin levels in a subject in need thereof, comprising administering to the subject a therapeutically effective amount of a compound disclosed herein.

In another aspect, provided herein is a method of reducing low-density lipoprotein (LDL) cholesterol in a subject in need thereof, comprising administering to the subject a therapeutically effective amount of a compound disclosed herein.

In an embodiment of the methods, the method treats obesity in the subject, e.g., reduces obesity in the subject.

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In an embodiment, a compound of the present disclosure, or a pharmaceutically acceptable salt thereof, is administered orally.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present disclosure can be administered intratympanically, wherein a long, narrow, bore needle is passed through the ear canal and through the eardrum to administer medications into the middle ear space where they are absorbed by the inner ear.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting NLRP3 inflammasome activity selected from one or more compounds of disclosed herein, or pharmaceutically acceptable salts thereof, and instructions for use in treating a disorder associated with NLRP3 inflammasomes.

In another aspect, the disclosure provides a kit comprising a compound capable of inhibiting NLRP3 inflammasome activity selected from a compound disclosed herein, or a pharmaceutically acceptable salt thereof.

In yet another aspect, provided herein is a kit comprising a compound disclosed herein, or a pharmaceutically acceptable salt thereof for the treatment of any of the indications disclosed herein.

Those skilled in the art will recognize or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

ACN acetonitrile
AcOH acetic acid
DCM dichloromethane
DIPEA N,N-Diisopropylethylamine
DMAP 4-dimethylaminopyridine
DMF dimethylformamide
DMSO dimethylsulfoxide
dppf 1,1'-bis(diphenylphosphino)ferrocene
EA ethyl acetate
EDCI 1-ethyl-3-(3-dimethylaminopropyl)carbodiimide
EtOAc ethyl acetate
EtOH ethanol
FA Formic acid
HPLC high-performance liquid chromatography
LAH lithium aluminum hydride
LCMS liquid chromatography-mass spectrometry
m-CPBA meta-chloroperoxybenzoic acid
MeOH methanol
NMR nuclear magnetic resonance
PE petroleum ether
SEM-Cl 2-(trimethylsilyl)ethoxymethyl chloride
SFC Supercritical fluid chromatography
TEA triethylamine
TFA trifluoroacetic acid
THE tetrahydrofuran
TLC thin layer chromatography
TsOH para-Toluenesulfonic acid

Example 1: Synthetic Procedures

Synthesis of Common Intermediates

Scheme 1: Synthesis of intermediate 3

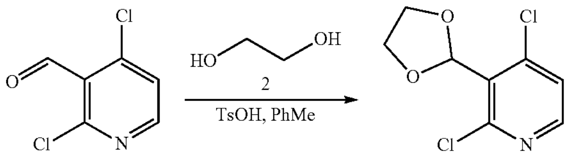

1 2 3

To a solution of starting material 1 (11 g, 62.50 mmol, 1 eq) and TsOH (1.08 g, 6.25 mmol, 0.1 eq) in toluene (150 mL) was added ethylene glycol (intermediate 2; 5.82 g, 93.75 mmol, 5.23 mL, 1.5 eq). The reaction mixture was stirred at 125° C. for 12 h under $N_2$. TLC showed desired product was formed. TLC (PE:EA=10:1) was not prove that the starting material was reaction complete. The reaction mixture was poured into $H_2O$ (300 mL) and extracted with EA (3×150 mL). The combined organic phase was dried with $Na_2SO_4$ and concentrated to give the crude product. The crude product was purified by column silica (PE:EA=1:0-10:1) and concentrated under reduced pressure to give the product ($R_f$=0.6; PE:EA=10:1). Intermediate 3 (12.3 g, 50.31 mmol, 80.49% yield, 90% purity) was obtained as light-yellow oil. NMR: $^1$H NMR (400 MHz, Chloroform-d) δ ppm 4.05-4.13 (m, 2H) 4.29-4.37 (m, 2H) 6.43 (s, 1H) 7.31 (d, J=5.26 Hz, 1H) 8.27 (d, J=5.26 Hz, 1H).

Scheme 2: Synthesis of intermediate (S)-N-tert-butanesulfinyl imines

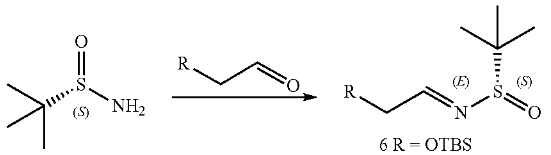

4

6 R = OTBS
7 R = $CH_2OTBS$

To a solution of starting material 4 (9 g, 74.26 mmol, 1 eq) in DCM (800 mL) was added $MgSO_4$ (178.77 g, 1.49 mol, 20 eq) and the corresponding aldehyde (25.89 g, 148.51 mmol, 28.29 mL, 2 eq), then the mixture was stirred at 25° C. for 12 h. LCMS showed the starting material was consumed completely and desired mass was detected. The crude mixture was filtered, and the filtrate was concentrated under reduced pressure.

Scheme 3: Synthesis of intermediate (R)-N-tert-butanesulfinyl imines

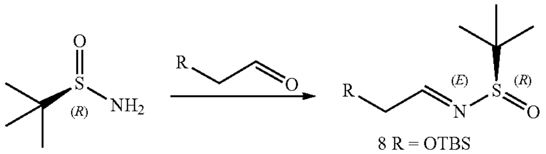

5

8 R = OTBS
9 R = $CH_2OTBS$

To a solution of starting material 5 (9 g, 74.26 mmol, 1 eq) in DCM (800 mL) was added $MgSO_4$ (178.77 g, 1.49 mol, 20 eq) and the corresponding aldehyde (25.89 g, 148.51 mmol, 28.29 mL, 2 eq), then the mixture was stirred at 25° C. for 12 h. LCMS showed the starting material was consumed completely and desired mass was detected. The crude mixture was filtered, and the filtrate was concentrated under reduced pressure.

Scheme 4: Synthesis of intermediate 4-chloro-1-((2-(trimethylsilyl)ethoxy)methyl)-1H-pyrazolo[4,3-c]pyridine-7-carbaldehyde (27)

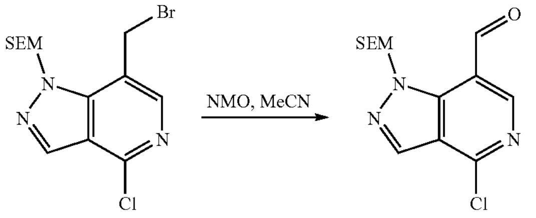

int-26 int-27

To a solution of intermediate 26 (7-(bromomethyl)-4-chloro-1-((2-(trimethylsilyl)ethoxy)methyl)-1H-pyrazolo[4,3-c]pyridine, 10 g, 26.54 mmol, 1 eq) in MeCN (100 mL) was added NMO (9.33 g, 79.63 mmol, 8.40 mL, 3 eq) at 0° C., the mixture was stirred at 0° C. for 2 h. TLC (PE:EtOAc=10:1; UV) showed starting material was consumed up and new spots were formed. The reaction mixture was concentrated to give a crude product. The crude product was purified by silica gel chromatography (8% EtOAc in PE, $R_f$=0.30) to give a product. Intermediate 27 (5.3 g, 15.30 mmol, 57.63% yield, 90% purity) was obtained as yellow oil. NMR: $^1H$ NMR (400 MHz, CHLOROFORM-d) δ=10.25 (s, 1H), 8.70 (s, 1H), 8.31 (s, 1H), 6.20 (s, 2H), 4.12 (q, J=7.2 Hz, 1H), 3.57-3.50 (m, 2H), 2.05 (s, 1H), 1.26 (t, J=7.2 Hz, 1H), 0.91-0.80 (m, 2H), −0.01--0.16 (m, 9H).

General Procedure 1 (GP1): Michael Addition to Imine

To a solution of starting material 1 (1 g, 4.54 mmol, 1 eq) in THE (20 mL) was added LDA (2 M, 1.5 eq) at −70° C. under $N_2$, then stirred at −70° C. for 0.5 h. Then the corresponding sulfinamide (1.5 eq) in THE (10 mL) was added dropwise and the reaction was stirred for 1 h under $N_2$. The reaction progress was monitored by LCMS. Upon completion, the reaction mixture was poured into a sat. aq. $NH_4Cl$ solution (150 mL), the mixture was extracted with EtOAc (3×100 mL), the combined organic phases were washed with brine (100 mL), dried over anhydrous $Na_2SO_4$, and concentrated to give a crude product. The crude material was purified by flash silica gel chromatography.

General Procedure 2 (GP2): Sulfinamide N-Methylation

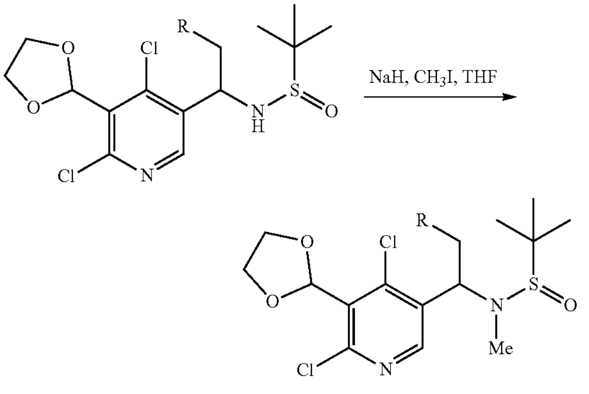

To a solution of compound 5 (730 mg, 1.47 mmol, 1 eq) in THE (10 mL) was added NaH (88.02 mg, 2.20 mmol, 60% purity, 1.5 eq) in ten batches at 0° C. under $N_2$, and stirred for 30 min at 0° C. Then the reaction was added $CH_3I$ (416.50 mg, 2.93 mmol, 182.68 μL, 2 eq) at 0° C. and stirred for 1 h at 25° C. under $N_2$. LCMS showed starting material was remained and desire product was detected. The mixture was poured into sat. aq. $NH_4Cl$ solution (50 mL) at 0° C. and the mixture was extracted with EtOAc (3×50 mL), then washed with brine (2×50 mL). The combined organic layers were dried over $Na_2SO_4$ and concentrated under reduced pressure to afford a residue. The residue was purified by column chromatography on silica and concentrated under reduced pressure.

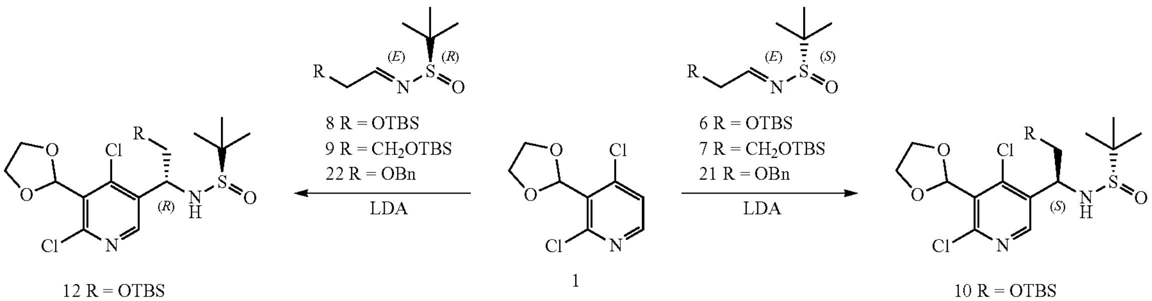

8 R = OTBS
9 R = $CH_2OTBS$
22 R = OBn

6 R = OTBS
7 R = $CH_2OTBS$
21 R = OBn

1

12 R = OTBS
13 R = $CH_2OTBS$
24 R = OBn

10 R = OTBS
11 R = $CH_2OTBS$
23 R = OBn

General Procedure 3 (GP3): Cleavage of Ellman Auxiliary

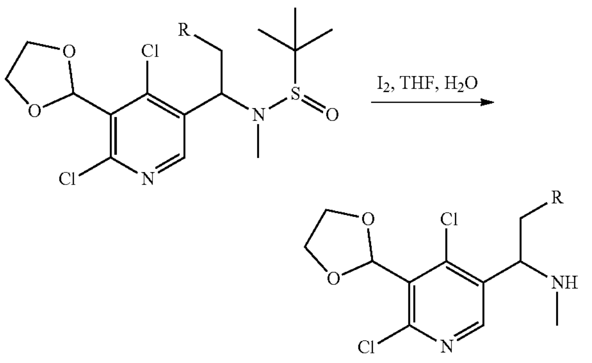

To a solution of the corresponding sulfinamide (6.1 g, 11.92 mmol, 1 eq) in THF (0.2 M) and $H_2O$ (0.2 M) was added $I_2$ (0.2 eq). The reaction mixture was stirred at 50° C. for 12 h. LCMS showed the starting material was consumed completely. The mixture was poured in sat. aq. $Na_2SO_3$ and extracted with EtOAc (3×100 mL). The combined organic layers were dried over $Na_2SO_4$ and concentrated under reduced pressure to give a residue. The residue was purified by silica column chromatography.

General Procedure 4 (GP4): Silyl Protection of Hydroxyl Group

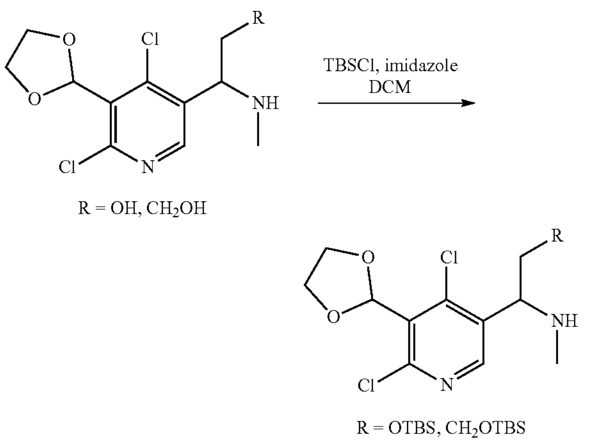

To a solution of the starting alcohol (1 eq) in DCM (0.1 M) was added imidazole (3 eq) and tert-Butyldimethylsilyl chloride (2 eq), the mixture was stirred at 20° C. for 12 h. The reaction was monitored by LCMS. Upon completion, the mixture was filtered, and the filtrate was concentrated to give a crude product. The crude product was purified by silica gel chromatography to give desire product.

General Procedure 5 (GP5): Secondary Amine Coupling

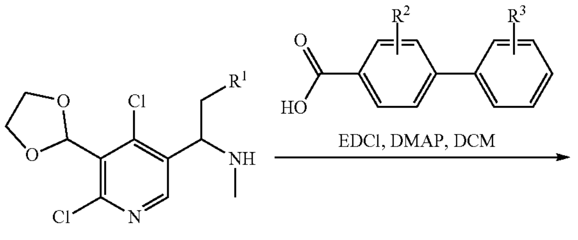

-continued

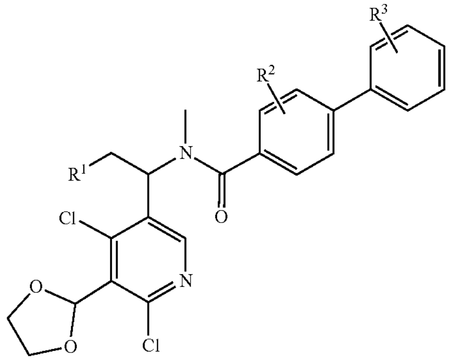

To a solution of the secondary amine (1 eq), carboxylic acid (1.1 eq), and EDCI (1.5 eq) in DCM (0.1 M) was added DMAP (0.1 eq), then stirred at 20° C. for 2 h. The reaction was monitored by LCMS. After completion, the reaction was concentrated under reduced to give a crude product. The crude product was purified by preparative-TLC.

Optionally, the following procedure can be utilized:

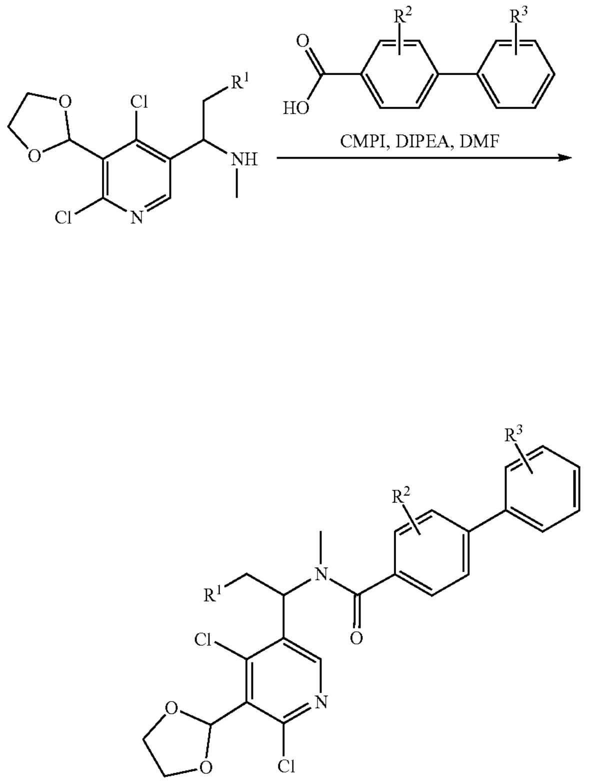

To a solution of the secondary amine (1.0 eq) and the carboxylic acid (1.0 eq) in DMF (0.25 M) was added CMPI (1.5 eq) (or other coupling agent such as HCTU, HATU or the like) and DIPEA (3 eq). The mixture was stirred at 50° C. for 12 h. After desired completion as tracked by LCMS. The mixture was poured into $H_2O$ and extracted with EtOAc. The combined organic layers were washed by brine, dried over $Na_2SO_4$, and concentrated under reduced pressure to give a crude residue.

General Procedure 6 (GP6): Global Deprotection 1

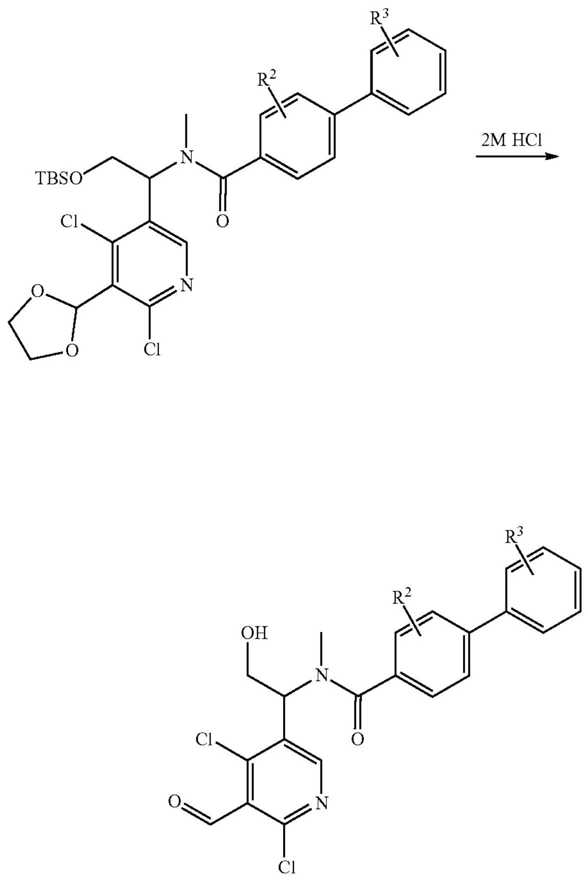

To a solution of silyl protected alcohol (100 mg, 153.93 μmol, 1 eq) in THF (0.03 M; or other applicable solvent) was added HCl (1-150 eq). Additionally, other acids can be used in conjunction with HCl, on their own. Examples of other acids include, but are not limited to, TsOH, MsOH, $H_2SO_4$, $HNO_3$, or similar (0.01-20 eq). The reaction mixture was stirred in the range of 0-90° C. for 1-24 h. The reaction mixture was adjusted to pH=7 with sat. aq. $Na_2CO_3$ and extracted with EtOAc (3×50 mL). The combined organic layers were dried over $Na_2SO_4$, then concentrated under reduced pressure to give a crude residue.

General Procedure 7 (GP7): Annulation Reaction (Pyrazole Synthesis)

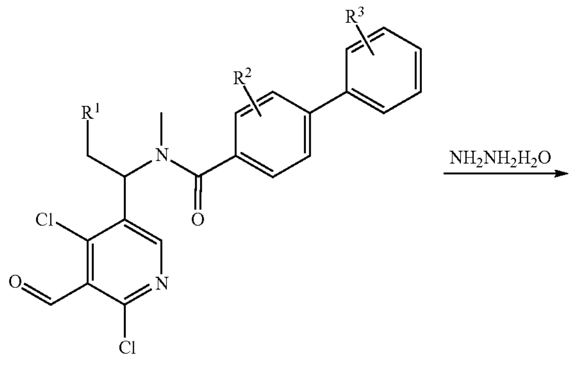

-continued

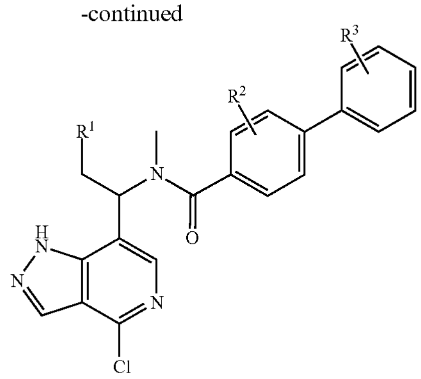

To a solution of the corresponding aldehyde (1 eq) in dioxane (0.03 M) was added hydrazine hydrate (98% purity, 2 eq), the mixture was stirred at 20° C. for 0.5 h, then stirred at 70° C. for 2 h. The reaction mixture was added into water (10 mL) at 20° C. and extracted with EtOAc (3×10 mL). The combined organic phases were dried over $Na_2SO_4$ and concentrated under reduce pressure to afford a residue. The crude product was purified by prep-TLC.

General Procedure 8 (GP8): Hydrodechlorination (HDC)

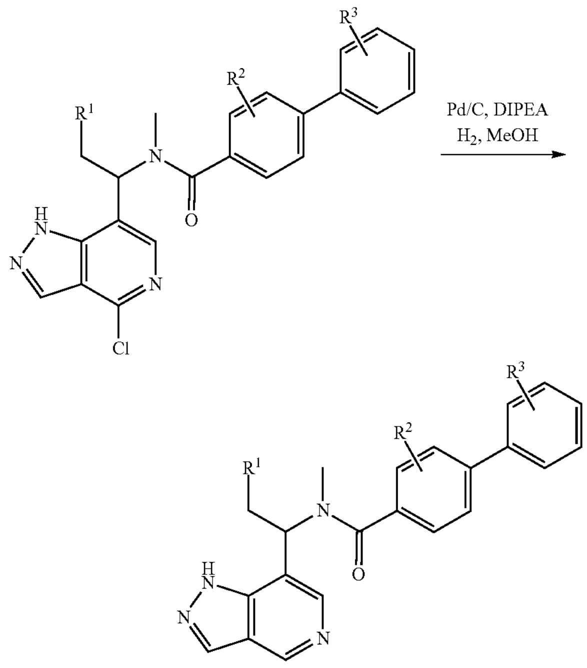

To a solution of the corresponding 4-chloro-pyrazolopyridine (1 eq), DIPEA (1 eq) in MeOH (0.06 M) was added Pd/C (10% purity, 0.0441 eq). The reaction mixture was stirred at 30° C. for 1 h under $H_2$ (15 psi). The reaction mixture was filtered with diatomite and the filtrate was concentrated to afford the crude residue.

Optional GP8 when Starting Materials Contain Other Aryl Chloride Moieties:

To a solution of the corresponding 4-chloro-pyrazolopyridine (1 eq) in THF (0.25 M) was added $Pd(dppf)Cl_2$ (0.1 eq), TMEDA (1.7 eq), and $NaBH_4$ (1.7 eq) under $N_2$ atmosphere. The mixture was stirred at 20° C. for 2 h. After completion, as judged by LCMS, the mixture was poured into $NH_4Cl$, the aqueous layer was extracted with EtOAc (×3). The combined organic layers were washed with brine (×5) dried over $Na_2SO_4$ (or similar drying agent). The solvent was removed in vacuo to afford the crude residue.

General Procedure 9 (GP9): Silyl Deprotection

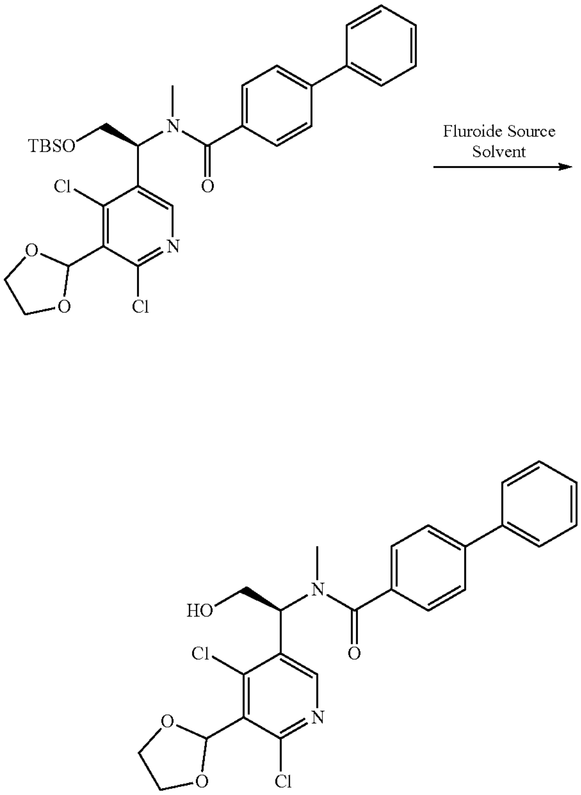

To a solution of the silyl protected compound (1 eq) in a solvent (solvent options: MeCN, $Et_2O$, dioxane, MeOH, EtOH, i-PrOH, THF, DCM, DMF, or similar) at a concentration of 0.01-0.5 M, was added a fluoride ion source (1-20 eq, examples: TBAF, $NH_4F$, HF, pyridine-HF, CsF, $LiBF_4$, or similar). The reaction was stirred at 20-80° C., for 1-20 h, until starting material was consumed. A standard aqueous work-up was performed. The solvent was removed in vacuo to afford the crude product. The crude product was purified by column chromatography on silica gel eluted with petroleum ether/ethyl acetate to give the desired product.

General Procedure 10 (GP10): Ether Synthesis

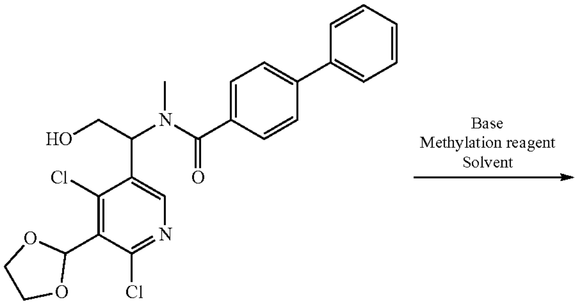

-continued

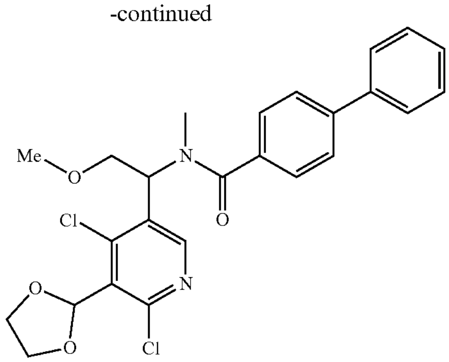

To a solution of the hydroxy containing compound (1 eq) in a solvent (solvent options: MeCN, $Et_2O$, dioxane, MeOH, EtOH, i-PrOH, THF, DCM, DMF, or similar) was added a base (1-5 eq, base options: MeLi, t-BuLi, PhLi, NaOMe, LiOMe, NaOEt, NaOt-Bu, LiOt-Bu, NaH, or similar) at −78-25° C. The reaction was stirred until consumption of starting material, and then quenched by pouring into ice sat. aq. $NH_4Cl$. The mixture was extracted with organic solvent (×3) and the combined organic phases were washed with brine. The organic phase was dried over sodium sulfate (or similar drying agent) and concentrated under reduced pressure to remove solvent. The resulting crude compound was purified by silica gel column chromatography (PE:EA, or similar applicable solvent system).

General Procedure 11 (GP11): Heteroaryl N-Protection

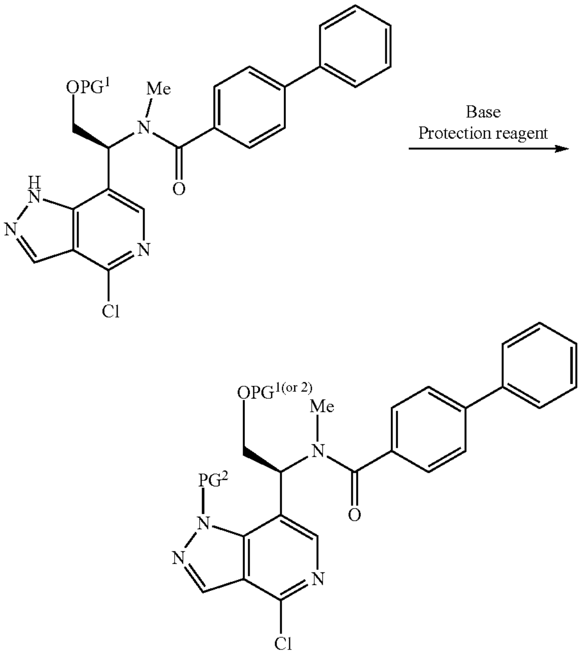

To a solution of the starting material (1 eq) in DMF (or other applicable solvent) was added a base (1.5 eq; base options: t-BuOLi, MeLi, t-BuLi, PhLi, NaOMe, LiOMe, NaOEt, NaOt-Bu, NaH, or similar) at 0° C. under $N_2$ atmosphere. The reaction was stirred at 0° C. for 0.5-2 h. Then SEM-Cl (or other protection reagent such as: MEM chloride, MOM chloride, BOM chloride, or similar) was added to the reaction and the resulting mixture was stirred at 20-30° C. for 1-6 h. The reaction mixture was quenched with $NH_4Cl$ under N2 and mixture was extracted with ethyl acetate (×3), the organic phases were combined and washed with brine (×3), then dried with anhydrous $Na_2SO_4$, filtered, and concentrated under reduced pressure to afford a crude product. The crude product was purified by flash silica gel chromatography.

General Procedure 12 (GP12): Suzuki-Miyaura Alkylation

Methylation:

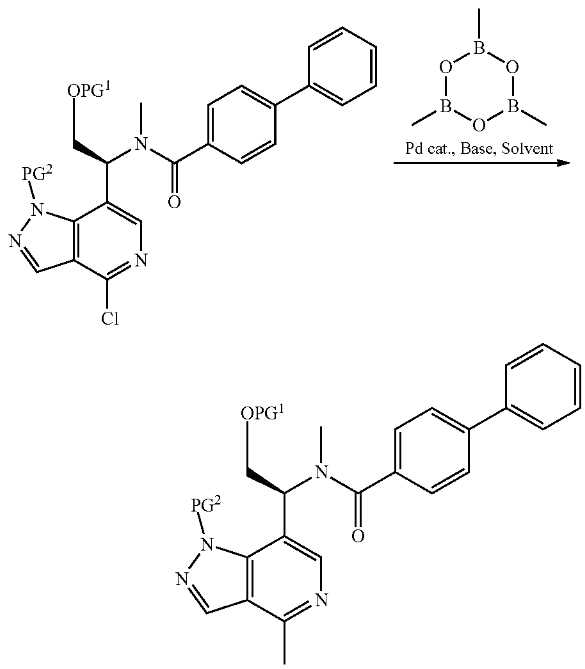

To a solution of the starting material (1 eq) and trimethylboroxine (5 eq) in 1,4-dioxane (~0.1 M; or other applicable solvent) was added $Pd(dppf)Cl_2$ (0.1 eq) (or other palladium catalyst such as: $Pd(dppf)Cl_2 \cdot CH_2Cl_2$, RuPhos Pd G3, Pd/C, or similar) and $K_2CO_3$ (3 eq), the mixture was stirred at 40-120° C. for 1-24 h. The reaction is monitored by LCMS, tracking consumption of starting material. After the reaction mixture was cooled to room temperature, the mixture was filtered through Celite®, and the filtrate was concentrated to give a crude product. The crude product was purified by flash silica gel chromatography.

Ethylation:

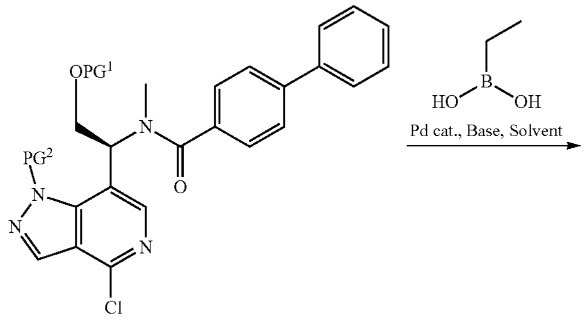

-continued

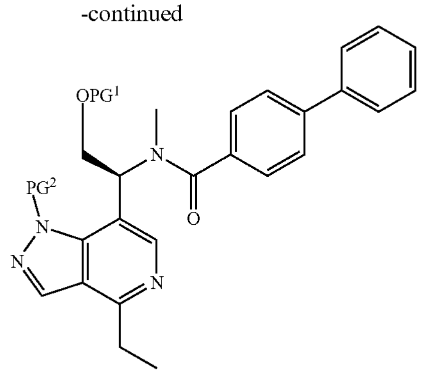

To a solution of the starting material (1 eq) and ethylboronic acid (3 eq) in 1,4-dioxane (~0.1 M; or other applicable solvent) was added $Pd(dppf)Cl_2$ (0.1 eq) (or other palladium catalyst such as: $Pd(dppf)Cl_2 \cdot CH_2Cl_2$, RuPhos Pd G3, Pd/C, or similar) and $K_2CO_3$ (3 eq), the mixture was stirred at 40-120° C. for 1-24 h. The reaction is monitored by LCMS, tracking consumption of starting material. After the reaction mixture was cooled to room temperature, the mixture was filtered through Celite®, and the filtrate was concentrated to give a crude product. The crude product was purified by flash silica gel chromatography.

General Procedure 13 (GP13): Global Deprotection 2

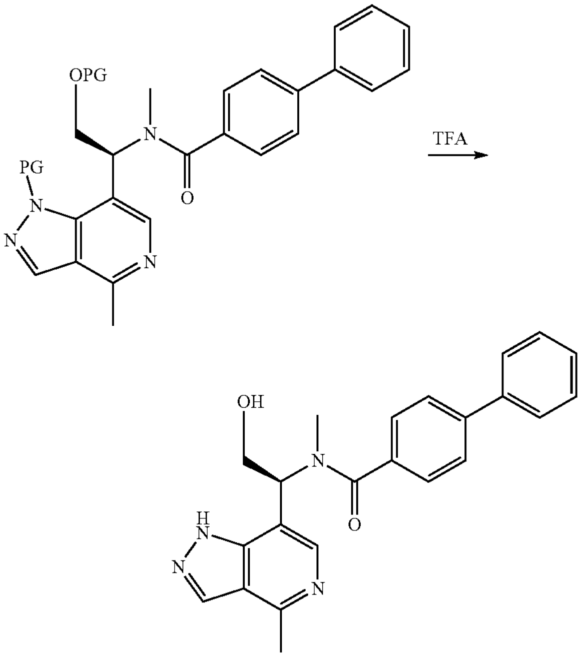

To a solution of the starting compound (1 eq) in DCM (or other applicable solvent) was added TFA (50-150 eq). The reaction mixture was stirred at 20-100° C. for 2-24 h. The reaction mixture was concentrated to give a crude residue. The residue was dissolved in a protic solvent and treated with $Et_3N$ ($NH_3 \cdot H_2O$, or similar base) to adjust to pH=8. The resulting mixture was quenched by pouring into $H_2O$. The mixture was extracted with EtOAc (×3), the combined organic phases were washed with brine and dried over anhydrous sodium sulfate (or another drying agent). The solution was concentrated under reduced pressure to remove the solvent. The crude material can be purified by prep-TLC, column chromatography, or prep-HPLC before an optional following step.

General Procedure 14 (GP14): Global Deprotection 3

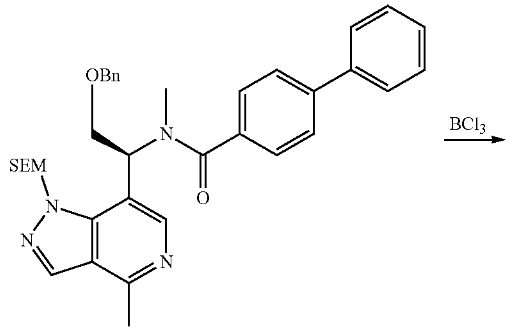

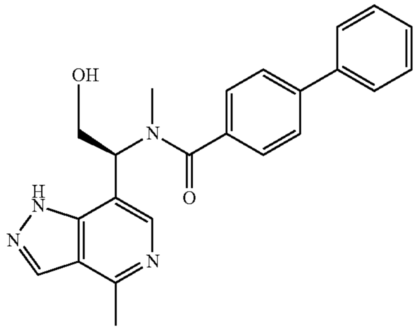

To a solution of the starting compound (1 eq) in DCM (or other applicable solvent) was added $BCl_3$ (3 eq) at 0° C. The reaction mixture was stirred at 0-20° C. for 2-24 h under $N_2$ atmosphere. The reaction was quenched with sat. aq. $NaHCO_3$, the resulting mixture was extracted with DCM (×2) and the organic phases were washed with brine, then dried over anhydrous $Na_2SO_4$, filtered, and concentrated to give a residue. The crude material can be purified by prep-TLC, column chromatography, or prep-HPLC before an optional following step.

General Procedure 15 (GP15): Reduction

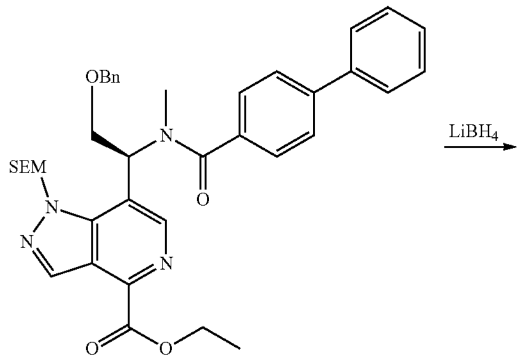

-continued

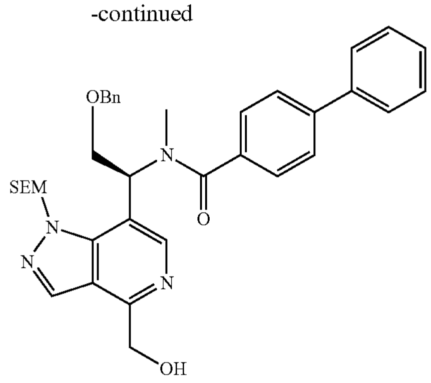

To a solution of the starting compound (1 eq) in EtOH (0.1 M) was added $LiBH_4$ (or $NaBH_4$) in THF (2 M, 5 eq) at 0° C. The reaction mixture was stirred at 20-30° C. for 1-6 hr under $N_2$ atmosphere. Upon desired completion the reaction mixture was poured into water and extracted with EA (×3). The combined organic phases were dried with $Na_2SO_4$ and concentrated to give the crude product.

General Procedure 16 (GP16): Amination

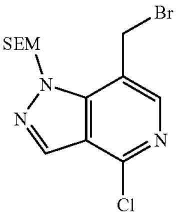

int-26

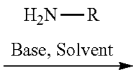

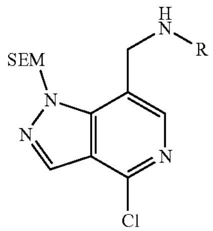

To a solution of int-26 (1 eq) and the corresponding amine (1.5 eq) in DMF or other applicable solvent (0.2 M) was added $K_2CO_3$ or another similar base (2 eq). The mixture was stirred at 20-50° C. for 2-20 h. The reaction was tracked by LCMS. After the reaction was completed, the reaction mixture was poured into $H_2O$ solution at 0° C., and extracted with EtOAc (×2), the combined organic phase was washed with brine (×3), dried over anhydrous $Na_2SO_4$, and concentrated to give a crude product. The residue was purified by silica gel chromatography and concentrated.

General Procedure 17 (GP17): Reductive Amination

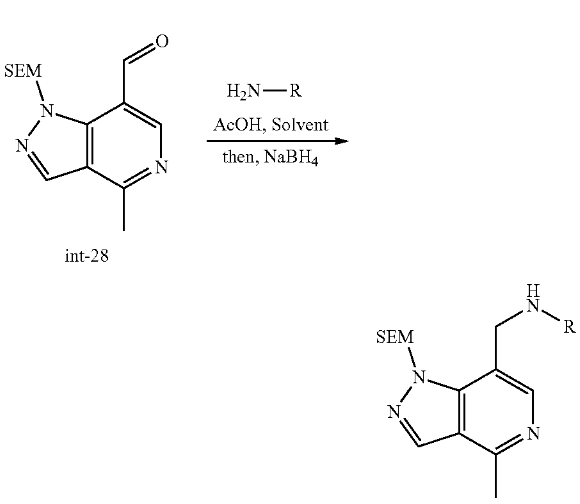

int-28

To a solution of int-28 (1 eq) in MeOH (0.2 M) was added the corresponding amine (2 eq) and AcOH (0.1 eq). The reaction was stirred at 25° C. for 1.5 h. Then $NaBH_4$ (3 eq) was added at 0° C. The reaction was stirred at 25° C. for 0.5 h under $N_2$. Upon completion the mixture was poured into sat. aq. $NH_4Cl$ at 20° C. and extracted with DCM (x3). The combined organic layers were dried over $Na_2SO_4$ and concentrated under reduced pressure to give a residue. The crude product was purified by flash silica gel chromatography.

Synthesis of Compounds 001-040 (C-Substituted):

Synthesis of Compound 001:

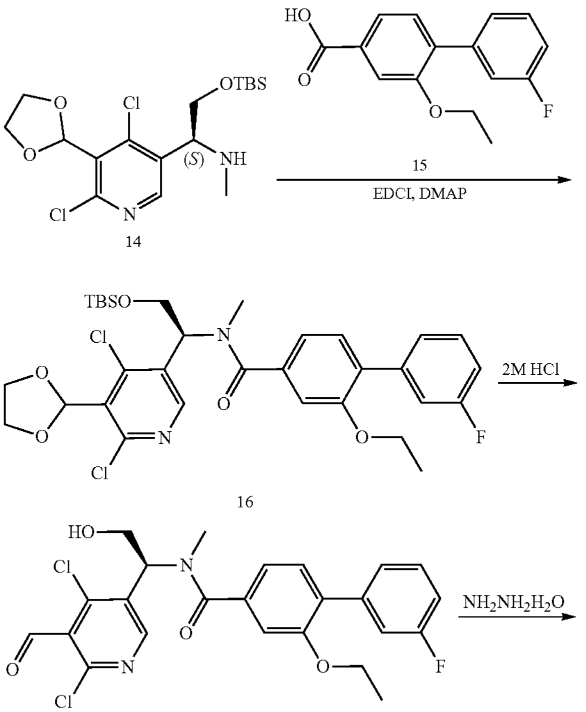

14

15

16

17

-continued

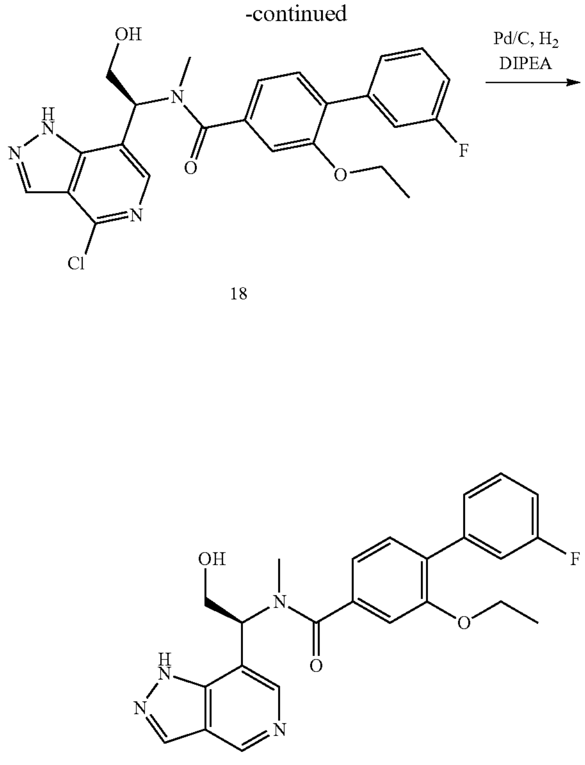

18

001

Synthesis of Intermediate 16:

Intermediate 14 was synthesized, starting from int-1, via GP1 through GP3

Intermediate 15 is commercially available.

Following GP4, the crude product was isolated and then purified by prep-TLC (Petroleum ether:Ethyl acetate=1:1). Int-16 (100 mg, 128.53 μmol, 34.91% yield, 83.5% purity) was obtained as yellow oil. LCIS: $t_R$=0.718 min, m/z=649.3 $[M+H]^+$ Synthesis of Intermediate 17:

Following GP5, int-17 (80 mg, 81.41 μmol, 52.89% yield, 50% purity) was obtained as yellow solid and used for next step without purification. LCMS: $t_R$=0.516 min, m/z=491.1 $(M+H^+)$ Synthesis of Intermediate 18:

Following GP7, the crude product was purified by prep-TLC (PE:EA=1:1). Int-18 (50 mg, 104.29 μmol, 64.05% yield, 97.8% purity) was obtained as white oil. LCMS: $t_R$=0.500 min, m/z=469.1 $[M+H]^+$ Synthesis of Compound 001:

Following GP8, the crude product was purified by prep-HPLC (column: Phenomenex luna C18, 150x25 mm, 10 um; mobile phase: A=Water+0.1% FA, B=Acetonitrile, 15%-45% B; gradient time: 1 min; flow rate: 60 mL/min). Compound 001 (2.08 mg, 4.79 μmol, 7.48% yield, 100% purity) was obtained as white solid. LCMS: $t_R$=0.433 min, m/z=435.2 $[M+H]^+$ $^1H$ NMR: (400 MHz, CHLOROFORM-d) δ=9.00 (s, 1H), 8.19 (s, 1H), 8.15 (s, 1H), 7.27-7.15 (m, 3H), 7.15 (s, 2H), 7.02 (d, J=7.8 Hz, 1H), 6.98 (s, 1H), 6.94-6.91 (m, 1H), 4.33-4.29 (m, 1H), 3.95 (dt, J=6.7, 13.4 Hz, 2H), 2.78 (s, 2H), 1.29-1.22 (m, 2H). SFC=100% ee Synthesis of Compound 002:

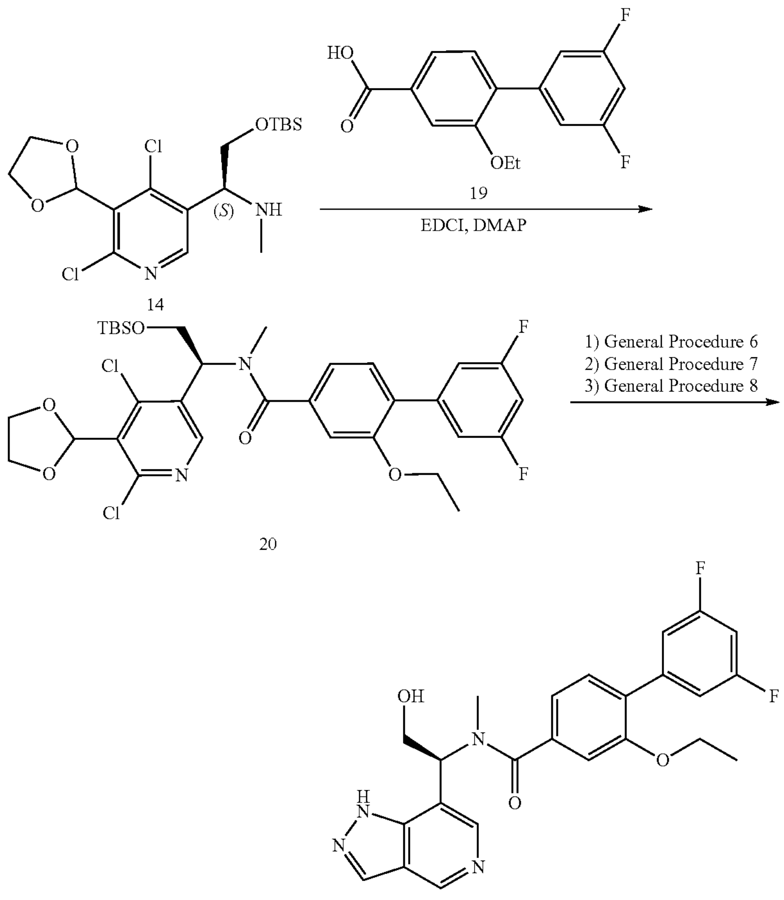

14

20

002

Synthesis of Intermediate 20:

Following a similar scheme to the synthesis of Compound 001, intermediate 20 was synthesized via GP1-GP5. The residue was purified by silica gel column chromatography (PE:EA=3:1). Compound 8 (550 mg, 617.85 μmol, 83.90% yield, 75% purity) was obtained as yellow oil. LCMS: $t_R$=0.731 min; m/z=667.2[M+H]$^+$.

Synthesis of Compound 002:

Following GP6-GP8, crude 002 was isolated and purified by prep-HPLC: (column: Phenomenex luna C18, 150×25 mm, 10 um; mobile phase: A=Water+0.1% FA, B=Acetonitrile, 19%-49% B; gradient time: 15 min; flow rate: 60 mL/min) The combined fractions were concentrated and lyophilized to afford the final product. Compound 002 (10.26 mg, 22.00 μmol, 42.84% yield, 97% purity) was obtained as pink solid. LCMS: $t_R$=0.337 min; m/z=453.1 [M+H]$^+$ $^1$H NMR (400 MHz, Chloroform-d) δ=9.58-8.91 (m, 1H), 8.57-8.13 (m, 2H), 7.26 (br d, J=7.5 Hz, 1H), 7.15-6.99 (m, 4H), 6.74 (br t, J=8.6 Hz, 1H), 6.20 (br s, 1H), 4.67-4.34 (m, 2H), 4.17-3.82 (m, 2H), 2.86 (br s, 3H), 1.33 (br t, J=6.7 Hz, 3H).

Synthesis of Compound 003:

Following a similar scheme to the synthesis of Compound 002, compound 003 was synthesized via GP5-GP8. The residue was purified by pre-HPLC (column: C18 150×30 mm; mobile phase: A=Water+0.1% FA, B=Acetonitrile; gradient: 25%-55% B over 1 min). The combined fractions were lyophilized. Compound 003 (8.32 mg, 18.37 μmol, 29.56% yield, 99% purity) was obtained as an off-white solid. LCMS: $t_R$=0.478 min; m/z=449.2 [M+H]$^+$ $^1$H NMR (400 MHz, CHLOROFORM-d) δ=9.16-9.11 (m, 1H), 8.37 (s, 1H), 8.30 (s, 1H), 7.33-7.29 (m, 1H), 7.15-7.04 (m, 4H), 6.89-6.83 (m, 1H), 6.31-6.15 (m, 1H), 4.53 (br t, J=10.3 Hz, 1H), 4.47-4.40 (m, 1H), 4.11-3.97 (m, 2H), 2.90 (s, 3H), 2.38 (s, 3H), 1.35 (br t, J=6.9 Hz, 3H). SFC: 100% ee Synthesis of Compound 004:

Following a similar procedure to the synthesis of Compound 002, starting from int-14, compound 004 was synthesized via GP5-GP8. The residue was purified by two separate methods:

Method 1: prep-HPLC (column: C18 150×30 mm; mobile phase: A=water+0.1% FA, B=Acetonitrile; gradient: 25%-55% B over 7 min).

Method 2: pre-HPLC (column: Waters Xbridge 150×25 mm, 5 um; mobile phase: A=water ($NH_4HCO_3$). B=Acetonitrile; gradient: 32%-62% B over 9 min).

The combined fractions from prep-HPLC were lyophilized. Compound 004 (2.92 mg, 6.40 μmol, 16.36% yield, 98.9% purity) was obtained as white solid. LCMS: Rt=0.485 min, m/z=451.1 [M+H]$^+$ $^1$H NMR (400 MHz, CHLOROFORM-d) δ=12.27-11.99 (m, 1H), 9.05 (s, 1H), 8.24 (s, 1H), 8.20 (s, 1H), 7.46 (s, 1H), 7.35-7.31 (m, 1H), 7.27-7.22 (m, 3H), 7.08-7.05 (m, 1H), 7.04-7.01 (m, 1H), 6.17-6.09 (m, 1H), 4.54-4.43 (m, 1H), 4.35 (dd, J=5.4, 11.4 Hz, 1H), 4.06-3.91 (m, 2H), 2.83 (s, 3H), 1.31-1.26 (m, 3H). SFC: 100% ee Synthesis of Compound 005:

Following a similar procedure to the synthesis of Compound 002, starting from int-14, compound 005 was synthesized via GP5-GP8. The crude compound 005 was purified by prep-HPLC (column: Phenomenex Luna C18 150×25 mm, 10 um; mobile phase: [water(FA)-ACN]; gradient: 15%-45% B over 9 min) and the fractions were lyophilized to give the product. Compound 005 (10.52 mg, 25.26 μmol, 17.84% yield, 100% purity) was obtained as a white solid. LCMS: $t_R$=0.435 min, m/z=417.2 $[M+H]^+$ $^1H$ NMR (400 MHz, CHLOROFORM-d) δ=12.13-11.62 (m, 1H), 8.30-8.07 (m, 2H), 7.76 (s, 1H), 7.67 (br d, J=7.9 Hz, 1H), 7.55 (br d, J=7.8 Hz, 1H), 7.48-7.39 (m, 1H), 7.22 (d, J=8.1 Hz, 1H), 7.09-6.94 (m, 2H), 6.49-6.21 (m, 1H), 4.12-3.90 (m, 2H), 3.86 (br t, J=5.6 Hz, 2H), 2.78 (s, 3H), 2.72 (s, 3H), 2.60-2.46 (m, 1H), 2.44-2.30 (m, 1H), 1.28 (t, J=6.9 Hz, 3H)

Synthesis of Compound 006:

(S)-3'-chloro-2-cyclopropoxy-N-(2-hydroxy-1-(1H-pyrazolo[4,3-c]pyridin-7-yl)ethyl)-N-methyl-[1,1'-biphenyl]-4-carboxamide Following a similar procedure to the synthesis of Compound 002, starting from int-14, compound 006 was synthesized via GP5-GP7. The final step in the synthesis of compound 006 is as follows:

To a solution of the penultimate compound (40 mg, 80.42 μmol, 1 eq) in AcOH (1 mL) was added Zn (52.59 mg, 804.23 μmol, 10 eq), the mixture was stirred at 30° C. for 2 h under $N_2$ atmosphere. The reaction mixture was filtered under $N_2$ and the filtrate was basified with 1M NaOH. The crude residue was purified by prep-HPLC (column: YMC-Actus Triart C18 150*30 mm*7 um; mobile phase: [water (FA)-ACN]; gradient: 23%-53% B over 10 min) and lyophilized to afford compound 006 (8.51 mg, 18.33 μmol, 22.79% yield, 99.7% purity) as an off-white solid. LCMS: $t_R$=0.465 min, m/z=463.2$[M+H]^+$ $^1H$ NMR (400 MHz, CHLOROFORM-d) δ=9.17 (s, 1H), 8.36 (s, 1H), 8.31 (s, 1H), 7.52 (d, J=1.1 Hz, 1H), 7.47 (d, J=1.2 Hz, 1H), 7.39-7.32 (m, 4H), 7.23-7.18 (m, 1H), 6.24 (br dd, J=5.9, 9.2 Hz, 1H), 4.65-4.56 (m, 1H), 4.47 (dd, J=5.2, 11.4 Hz, 1H), 3.85-3.75 (m, 1H), 2.96 (s, 3H), 0.88-0.73 (m, 4H).

Synthesis of Compound 007:

General procedure 1 (GP1), was used to synthesize int-11. Int-11 was subjected to GP2-GP8. The crude product was purified by reversed-phase HPLC (column: Phenomenex luna C18 150×25 mm, 10 um; mobile phase: [water (FA)-ACN]; gradient: 17%-47% B over 15 min). The product was concentrated and lyophilized to afford compound 007 (13.86 mg, 30.90 μmol, 31.09% yield, 100% purity) as an off-white solid. $^1H$ NMR (400 MHz, CHLOROFORM-d) δ ppm 1.37 (t, J=6.94 Hz, 3H) 2.44-2.67 (m, 2H) 2.81 (s, 3H) 3.86-3.98 (m, 2H) 4.00-4.13 (m, 2H) 6.48 (br dd, J=10.63, 4.75 Hz, 1H) 7.01-7.09 (m, 3H) 7.27-7.31 (m, 2H) 7.33 (d, J=8.13 Hz, 1H) 7.35-7.40 (m, 1H) 8.27 (s, 1H) 8.42 (br s, 1H) 9.12 (br s, 1H). LCMS: $t_R$=0.459 min, m/z=449.1 $[M+H]^+$ Synthesis of Compound 008:

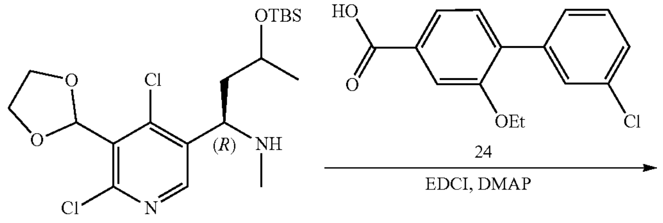

23

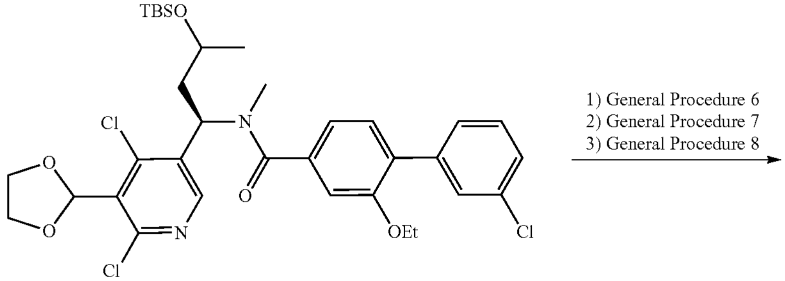

25

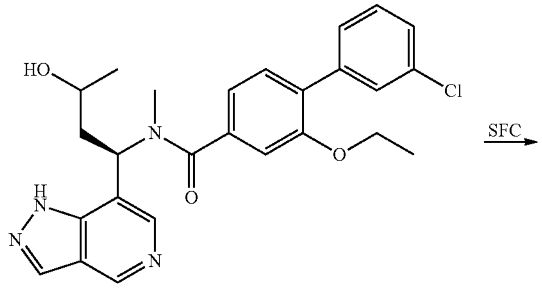

26

-continued

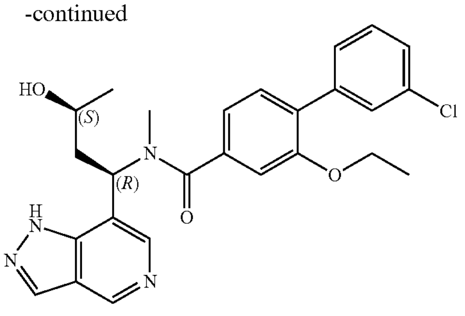

008

Intermediate 23 was synthesized, starting from int-1, via GP1 through GP3

Intermediate 24 is commercially available.

Following a similar procedure to the synthesis of Compound 002, starting from int-23, compound 008 was synthesized via GP5-GP8. In addition to the proceeding procedures, the diastereomeric mixture of compound 008 (20 mg, 41.76 μmol, 1 eq) was purified by SFC (column: DAICEL CHIRALPAK AS (250 mm×30 mm, 10 um); mobile phase: [$CO_2$:i-PrOH (0.1% $NH_3H_2O$)]; B %=30%, isocratic elution mode). After SFC, the eluent was concentrated to remove organic solvents. The residual aqueous solution was lyophilized.

Compound 008 (11.23 mg, 23.45 μmol, 56.15% yield) was obtained as white solid. LCMS: $t_R$=0.487 min, m/z=479.2 $[M+H]^+$ NMR: $^1H$ NMR (400 MHz, CHLOROFORM-d) δ=12.25-11.73 (m, 1H), 9.14 (br dd, J=2.1, 9.9 Hz, 1H), 8.59-8.31 (m, 1H), 8.29 (s, 1H), 7.52 (s, 1H), 7.39 (s, 1H), 7.36-7.29 (m, 3H), 7.09-7.02 (m, 2H), 6.57 (br d, J=11.1 Hz, 1H), 4.13-3.97 (m, 3H), 2.78 (s, 3H), 2.60 (br s, 1H), 2.20-2.12 (m, 1H), 1.44 (d, J=6.3 Hz, 3H), 1.36 (t, J=6.9 Hz, 3H)

Synthesis of Compound 009:

Following a similar procedure to the synthesis of Compound 002, starting from int-13, compound 009 was synthesized via GP2-GP8. The crude compound 009 was purified by prep-HPLC (column: C18 150×30 mm; mobile phase: [water (FA)-ACN]; gradient: 20%-50% B over 7 min), but LCMS showed the product contained impurities, Re-purified by prep-HPLC (column: C18 150×30 mm; mobile phase: [water (FA)-ACN]; gradient: 22%-52% B over 7 min). The product was concentrated and lyophilized to give the product. Compound 009 (47.64 mg, 104.10 μmol, 50.27% yield, 98% purity) was obtained as white solid. LCMS: $t_R$=0.464 min, m/z=449.2 $[M+H]^+$ NMR: $^1H$ NMR (400 MHz, CHLOROFORM-d) δ ppm 1.37 (t, J=6.94 Hz, 3H) 2.43-2.52 (m, 1H) 2.59-2.69 (m, 1H) 2.81 (s, 3H) 3.91-3.98 (m, 2H) 4.01-4.12 (m, 2H) 6.48 (br dd, J=10.51, 4.63 Hz, 1H) 7.01-7.10 (m, 3H) 7.28-7.31 (m, 2H) 7.33 (d, J=8.25 Hz, 1H) 7.35-7.41 (m, 1H) 8.27 (s, 1H) 8.42 (s, 1H) 9.13 (s, 1H). SFC=96% ee Synthesis of Compound 010:

Following a similar procedure to the synthesis of Compound 009, starting from int-13, compound 009 was synthesized via GP2-GP8. An additional silyl deprotection step GP9 was employed between GP5 and GP6, utilizing $LiBF_4$ (10 eq) in ACN:$H_2O$ (20:1; 0.8 M). The crude compound 010 product was purified by Prep-HPLC (column: Phenomenex luna C18 150×25 mm, 10 um; mobile phase: [water (FA)-ACN]; gradient: 18%-48% B over 9 min) to give compound 010 (42.85 mg, 99.54 μmol, 54.16% yield, 100% purity) as white solid. LCMS: Rt=0.431 min, m/z=431.1 $[M+H]^+$ NMR: $^1H$ NMR (400 MHz, CHLOROFORM-d) δ=9.10 (br s, 1H), 8.39 (br s, 1H), 8.25 (s, 1H), 7.50 (d, J=7.5 Hz, 2H), 7.43-7.34 (m, 2H), 7.34-7.27 (m, 2H), 7.08-7.01 (m, 2H), 6.45 (br dd, J=4.8, 10.3 Hz, 1H), 4.12-3.95 (m, 2H), 3.95-3.84 (m, 2H), 2.79 (s, 3H), 2.60 (tdd, J=4.9, 9.8, 14.5 Hz, 1H), 2.43 (dt, J=5.9, 13.1 Hz, 1H), 1.31 (t, J=6.9 Hz, 3H).

Synthesis of Compound 011:

Following a similar procedure to the synthesis of Compound 009, starting from int-13, compound 009 was synthesized via GP2-GP8. The residue was purified by prep-HPLC (column: Waters Xbridge 150×25 mm, 5 um; mobile phase: [water ($NH_4HCO_3$)-ACN]; gradient: 30%-60% B over 9 min), lyophilized. Compound 011 (19.75 mg, 44.15 μmol, 26.01% yield, 100% purity) was obtained as an off-white solid. LCMS: $t_R$=0.457 min, m/z=461.2 $[M+H]^+$ NMR: $^1H$ NMR (400 MHz, CHLOROFORM-d) δ=12.19-11.86 (m, 1H), 9.13 (s, 1H), 8.43 (s, 1H), 8.27 (s, 1H), 7.46 (s, 1H), 7.40-7.28 (m, 2H), 7.24-7.15 (m, 2H), 7.11 (br d, J=7.8 Hz, 1H), 7.03 (dt, J=1.9, 8.5 Hz, 1H), 6.53-6.45 (m, 1H), 3.96 (br t, J=5.7 Hz, 2H), 3.76 (br dd, J=3.3, 5.3 Hz, 1H), 2.83 (s, 3H), 2.73-2.58 (m, 1H), 2.55-2.41 (m, 1H), 0.89-0.65 (m, 4H). SFC: 100% ee Synthesis of Compound 012:

Following a similar procedure as compound 011, GP2-8 were utilized in the synthesis of compound 012.

The crude product was purified by prep-HPLC (column: Waters Xbridge 150×25 mm, 5 um; mobile phase: [water ($NH_4HCO_3$)-ACN]; gradient: 35%-65% B over 9 min), then lyophilized for 12 h. Compound 012 (30.65 mg, 63.94 μmol, 34.06% yield, 99.5% purity) was obtained as white solid. LCMS: $t_R$=0.477 min, m/z=477.2 $[M+H]^+$ NMR: $^1H$ NMR (400 MHz, CHLOROFORM-d) δ=12.09 (br s, 1H), 9.14 (s, 1H), 8.44 (s, 1H), 8.29 (s, 1H), 7.45 (d, J=6.4 Hz, 2H), 7.34-7.29 (m, 5H), 6.51 (br d, J=4.5 Hz, 1H), 6.48 (br d, J=4.4 Hz, 1H), 3.96 (t, J=5.9 Hz, 2H), 3.77 (br d, J=3.3 Hz, 1H), 2.84 (s, 3H), 2.70-2.61 (m, 1H), 2.53-2.45 (m, 1H), 0.86-0.71 (m, 4H). SFC: 100% ee Synthesis of Compound 013:

Following a similar procedure to compound 002, compound 013 was synthesized starting from int-10 utilizing the following steps, in order: GP2-5, GP9-10, GP6-GP8; to afford the residue of crude compound 013.

The residue was purified by prep-HPLC (column: Waters Xbridge 150×25 mm, 5 um; mobile phase: [water ($NH_4HCO_3$)-ACN]; gradient: 40%-70% B over 9 min), combined fractions were lyophilized. Compound 013 (44.69 mg, 96.62 μmol, 57.37% yield, 100% purity) was obtained as a white solid. LCMS: $t_R$=0.466 min, m/z=463.1 $[M+H]^+$ NMR: $^1H$ NMR (400 MHz, CHLOROFORM-d) δ=12.17

(br s, 1H), 9.12 (s, 1H), 8.40 (s, 1H), 8.26 (s, 1H), 7.41-7.33 (m, 2H), 7.32-7.28 (m, 2H), 7.13-7.07 (m, 2H), 7.04 (br d, J=2.0 Hz, 1H), 6.43-6.34 (m, 1H), 4.14-4.00 (m, 2H), 3.66 (br t, J=5.7 Hz, 2H), 3.42 (s, 3H), 2.82 (s, 3H), 2.72-2.61 (m, 1H), 2.54-2.43 (m, 1H), 1.37 (t, J=6.9 Hz, 3H). SFC: 100% ee

Synthesis of Compound 014:

Following a similar procedure to compound 002, compound 014 was synthesized starting from int-10 utilizing the following steps, in order: GP2-5, GP9-10, GP6-GP8; to afford the residue of crude compound 014.

The residue was purified by preparative HPLC (column: YMC-Actus Triart C18 150×30 mm×7 um; mobile phase: [water (FA)-ACN]; gradient: 28%-58% B over 10 min) and lyophilized. Compound 014 (9.04 mg, 19.19 μmol, 38.33% yield, and 98.7% purity) was obtained as yellow solid. LCMS: $t_R$=0.500 min, m/z=465.2 $[M+H]^+$. NMR: $^1H$ NMR (400 MHz, CHLOROFORM-d) δ=9.23 (br d, J=2.0 Hz, 1H), 8.46 (s, 2H), 7.54 (s, 1H), 7.41 (s, 1H), 7.33 (br d, J=4.0 Hz, 3H), 7.16-7.05 (m, 2H), 6.38 (br s, 1H), 4.35 (s, 1H), 4.11 (br d, J=4.9 Hz, 2H), 4.07-4.00 (m, 1H), 3.56 (s, 3H), 2.89 (s, 3H), 1.37 (t, J=6.9 Hz, 3H)

Synthesis of Compound 015:

Following a similar procedure to compound 002, compound 015 was synthesized starting from int-11 utilizing the following steps, in order: GP2-5, GP9-10, GP6-GP8; to afford the residue of crude compound 015. The residue was purified by prep-HPLC (column: Waters Xbridge 150×25 mm×5 um; mobile phase: [water($NH_4HCO_3$)-ACN]; gradient: 40%-70% B over 9 min), lyophilized. Compound 015 (44.69 mg, 96.62 μmol, 57.37% yield, 100% purity) was obtained as a white solid. LCMS: $t_R$=0.466 min, m/z=463.1 $[M+H]^+$. NMR: $^1H$ NMR (400 MHz, CHLOROFORM-d) δ=12.17 (br s, 1H), 9.12 (s, 1H), 8.40 (s, 1H), 8.26 (s, 1H), 7.41-7.33 (m, 2H), 7.32-7.28 (m, 2H), 7.13-7.07 (m, 2H), 7.04 (br d, J=2.0 Hz, 1H), 6.43-6.34 (m, 1H), 4.14-4.00 (m, 2H), 3.66 (br t, J=5.7 Hz, 2H), 3.42 (s, 3H), 2.82 (s, 3H), 2.72-2.61 (m, 1H), 2.54-2.43 (m, 1H), 1.37 (t, J=6.9 Hz, 3H). SFC: 100% ee Synthesis of Compound 016:

Following a similar procedure to compound 002, compound 016 was synthesized starting from int-11 utilizing the following steps, in order: GP2-5, GP9-10, GP6-GP8; to afford the residue of crude compound 015. The crude product was purified by prep-HPLC (column: Phenomenex luna C18 150×25 mm×10 um; mobile phase: [water(FA)-ACN]; gradient: 28%-58% B over 9 min) to give compound 016 (44.46 mg, 92.82 μmol, 39.00% yield, 100% purity) as white solid. LCMS: Rt=0.485 min, m/z=479.1 $[M+H]^+$ NMR: $^1H$ NMR (400 MHz, CHLOROFORM-d) δ=12.21 (br s, 1H), 9.16 (s, 1H), 8.44 (s, 1H), 8.30 (s, 1H), 7.58 (s, 1H), 7.46 (td, J=1.9, 6.6 Hz, 1H), 7.41-7.34 (m, 3H), 7.17-7.11 (m, 2H), 6.43 (br dd, J=4.8, 10.2 Hz, 1H), 4.19-4.03 (m, 2H), 3.70 (t, J=5.9 Hz, 2H), 3.46 (s, 3H), 2.86 (s, 3H), 2.77-2.66 (m, 1H), 2.59-2.48 (m, 1H), 1.41 (t, J=7.0 Hz, 3H)

Synthesis of Compound 017:

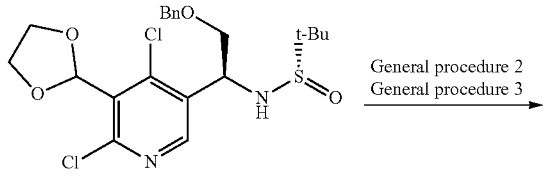

int-23

-continued

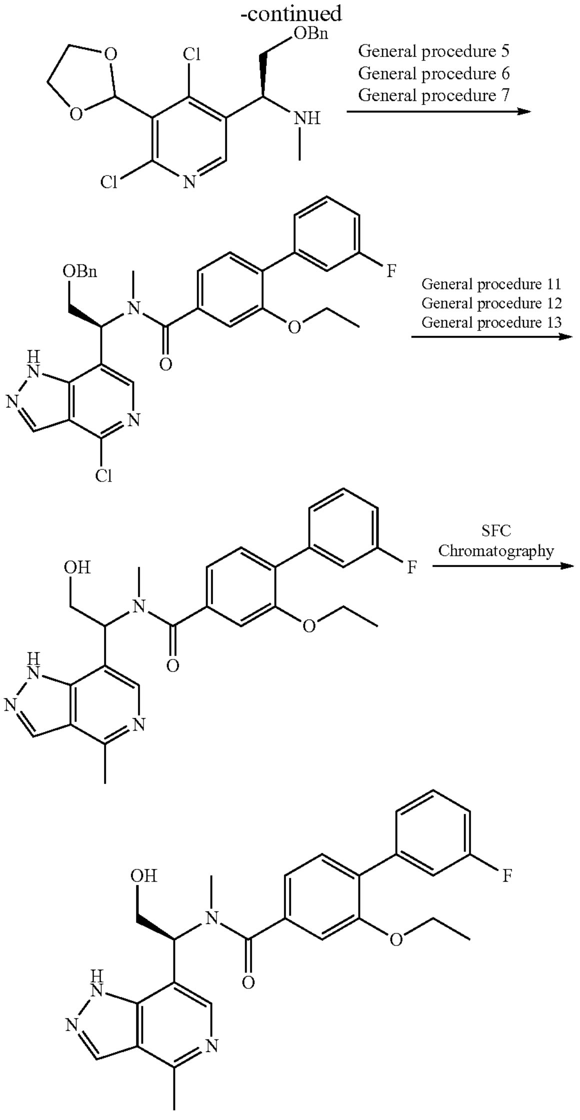

017

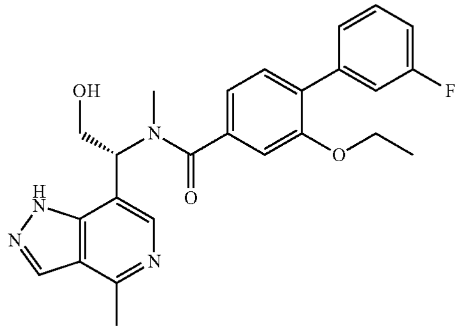

025

The synthesis of compound 017 was completed starting from int-23. The starting material was subjected GP2-3, followed by GP5-7. The resulting compound was subjected to GP11-13. Finally, the product was purified by SFC (column: DAICEL CHIRALPAK IK (250 mm×30 mm, 10 um); mobile phase: [$CO_2$:MeOH (0.1% $NH_3H_2O$)]; B %: 35%, isocratic elution mode), After SFC, the eluent was concentrated to remove organic solvents. The residual aqueous solution was lyophilized. Compound 017 (8.26 mg, 17.75 μmol, 53.08% yield, 96.4% purity) was obtained as a white solid. LCMS: $t_R$=0.417 min, 449.2 $[M+H]^+$ (ESI pos). NMR: $^1H$ NMR (400 MHz, CHLOROFORM-d) δ=8.49-8.34 (m, 1H), 8.14 (br s, 1H), 7.21 (br d, J=7.6 Hz, 1H), 7.15 (s, 1H), 7.05-6.94 (m, 1H), 6.92-6.89 (m, 1H), 6.76-6.65 (m, 1H), 4.90-4.66 (m, 1H), 4.63-4.35 (m, 3H), 3.71 (q, J=7.1 Hz, 2H), 2.73 (s, 3H), 2.34 (br s, 3H), 1.07-0.99 (m, 4H). SFC: 100% ee Synthesis of Compound 018:

Following a similar procedure to compound 017, compound 018 was synthesized starting from int-23 utilizing the following steps: GP2-3, GP5-7, then GP11-13. The crude product was purified by prep-TLC (DCM:MeOH=10:1) to give the crude product ($R_f$=0.5). Then, the still crude product was re-purified by prep-TLC (DCM:MeOH=10:1) to give the crude product ($R_f$=0.5). The product was finally purified by prep-HPLC (column: Phenomenex luna C18 150×25 mm, 10 um; mobile phase: [water (FA)-ACN]; gradient: 12%-42% B over 9 min) and lyophilized to afford the desired product. Compound 018 (8.05 mg, 17.08 μmol, 9.89% yield, 99% purity) was obtained as a white. LCMS: $t_R$=0.433 min, m/z 5=467.3 $[M+H]^+$. NMR: $^1H$ NMR (400 MHz, CHLOROFORM-d) δ=8.34-8.27 (m, 1H), 8.23 (s, 1H), 7.61 (dd, J=1.3, 7.9 Hz, 1H), 7.56 (s, 1H), 7.38 (d, J=7.9 Hz, 1H), 7.12 (br dd, J=2.0, 8.5 Hz, 2H), 6.89-6.76 (m, 1H), 4.67 (dd, J=4.3, 11.2 Hz, 1H), 4.49 (br d, J=11.1 Hz, 1H), 4.40 (dd, J=4.4, 7.5 Hz, 1H), 4.12 (d, J=7.0 Hz, 2H), 2.89 (s, 3H), 2.44 (s, 3H), 1.42 (t, J=6.9 Hz, 3H)

Synthesis of Compound 019:

Following a similar procedure to compound 017, compound 019 was synthesized starting from int-23 utilizing the following steps: GP2-3, GP5-7, then GP11-13. The final crude product was purified by SFC (column: DAICEL CHIRALPAK IC (250 mm×30 mm, 10 um); mobile phase: [$CO_2$-ACN/i-PrOH (0.1% $NH_3H_2O$)]; B %: 25%, isocratic elution mode), and concentrated under reduced pressure to give the product. Compound 019 (30.12 mg, 64.13 μmol, 74.55% yield, 99% purity) was obtained as yellow solid. LCMS: $t_R$=0.451 min, m/z=465.1 $[M+H]^+$. NMR: $^1H$ NMR (400 MHz, CHLOROFORM-d) δ ppm 1.38 (t, J=6.94 Hz, 3H) 2.50 (s, 3H) 3.02 (s, 3H) 4.08 (q, J=6.92 Hz, 2H) 4.59-4.66 (m, 2H) 4.72-4.80 (m, 1H) 7.33-7.36 (m, 3H) 7.41-7.45 (m, 1H) 7.52 (s, 1H) 7.54-7.57 (m, 2H) 8.38 (s, 1H) 8.52 (s, 1H)

Synthesis of Compound 020:

Following a similar procedure to compound 017, compound 020 was synthesized starting from int-23 utilizing the following steps: GP2-3, GP5-7, then GP11-13. The crude compound 020 (45 mg, 94.08 μmol, 1 eq) was purified by SFC (column: DAICEL CHIRALPAK AD (250 mm×30 mm, 10 um); mobile phase: [$CO_2$:i-PrOH (0.1% $NH_3H_2O$)]; B %: 45%, isocratic elution mode) to afford the desired product. Compound 020 (7.4 mg, 16.85 μmol, 17.91% yield, and 98% purity) was obtained as a white off-solid. LCMS: $t_R$=0.453 min, m/z=431.2 $[M+H]^+$. NMR: $^1H$ NMR (400 MHz, CHLOROFORM-d) δ=12.55-11.89 (m, 1H), 8.22 (s, 1H), 8.17 (s, 1H), 7.52 (d, J=7.3 Hz, 2H), 7.43-7.37 (m, 2H), 7.36-7.30 (m, 2H), 7.15-7.07 (m, 2H), 6.15 (br dd, J=5.4, 8.4 Hz, 1H), 4.57-4.45 (m, 1H), 4.45-4.36 (m, 1H), 4.08-3.96 (m, 2H), 2.89 (s, 3H), 2.83 (s, 3H), 1.33 (t, J=6.9 Hz, 3H).

Synthesis of Compound 021:

Following a similar procedure to compound 017, compound 021 was synthesized starting from int-23 utilizing the following steps: GP2-3, GP5-7, then GP11-13. The crude compound 021 (51 mg, 110.27 μmol, 1 eq) was purified by SFC (column: DAICEL CHIRALPAK AD (250 mm×50 mm, 10 um); mobile phase: [$CO_2$:i-PrOH (0.1% $NH_3H_2O$)]; B %: 30%, isocratic elution mode). The eluent was concentrated to remove organic solvents and the residual aqueous solution was lyophilized to afford the desired product. Compound 021 (18.93 mg, 40.11 μmol, 36.38% yield, 98% purity) was obtained as an off-white solid. LCMS: $t_R$=0.458 min, m/z=463.3 $[M+H]^+$. NMR: $^1H$ NMR (400 MHz, CHLOROFORM-d) δ=8.18 (s, 1H), 8.12 (s, 1H), 7.52 (dd, J=1.3, 7.9 Hz, 1H), 7.46 (s, 1H), 7.29 (d, J=7.9 Hz, 1H), 7.08-7.02 (m, 2H), 6.81 (br d, J=9.4 Hz, 1H), 4.55 (dd, J=4.3, 11.1 Hz, 1H), 4.44-4.35 (m, 1H), 4.32-4.25 (m, 1H), 4.01 (q, J=6.9 Hz, 2H), 2.77 (s, 3H), 2.33 (d, J=3.8 Hz, 6H), 1.32 (t, J=6.9 Hz, 3H).

Synthesis of Compound 022:

Following a similar procedure to compound 017, compound 022 was synthesized starting from int-23 utilizing the following steps: GP2-3, GP5-7, then GP11-13. The crude compound 022 (35 mg, 76.00 μmol, 1 eq) was purified by SFC (column: DAICEL CHIRALPAK AD (250 mm×30 mm, 10 um); mobile phase: [$CO_2$:i-PrOH (0.1% $NH_3H_2O$)]; B %: 50%, isocratic elution mode). The eluent was concentrated to remove organic solvents and the residual aqueous solution was lyophilized to afford the desired product. Compound 022 (18.93 mg, 40.11 μmol, 36.38% yield, 98% purity) was obtained as an off-white solid. LCMS: $t_R$=0.453 min, m/z=461.2 $[M+H]^+$. NMR: $^1H$ NMR (400 MHz, CHLOROFORM-d) δ=12.51-11.98 (m, 1H), 8.26 (s, 1H), 8.22 (s, 1H), 7.49 (s, 1H), 7.38-7.28 (m, 2H), 7.24-7.16 (m, 3H), 7.03 (t, J=8.2 Hz, 1H), 6.18-6.13 (m, 1H), 4.57-4.51 (m, 1H), 4.45-4.40 (m, 1H), 3.77 (br s, 1H), 2.96-2.91 (m, 3H), 2.89 (s, 3H), 0.87-0.69 (m, 5H). SFC: 100% ee.

Synthesis of Compound 023:

Compound 023 was synthesized starting from int-11 utilizing the following procedures in order: GP2-7, GP4, GP11-13. The crude product was purified by Prep-HPLC (column: Phenomenex luna C18 150×25 mm, 10 um; mobile phase: [water(FA)-ACN]; gradient: 20%-50% B over 15 min) to afford compound 023 (20.78 mg, 27.69 μmol, 19.91% yield, 100% purity) was obtained as white solid. LCMS: $t_R$=0.457 min, m/z=475.2 $[M+H]^+$. NMR: $^1H$ NMR (400 MHz, CHLOROFORM-d) δ=8.34 (s, 2H), 7.49 (d, J=1.3 Hz, 1H), 7.41-7.34 (m, 2H), 7.27-7.19 (m, 2H), 7.15 (dd, J=1.5, 7.7 Hz, 1H), 7.09-7.01 (m, 1H), 6.52-6.44 (m, 1H), 4.03-3.95 (m, 2H), 3.83-3.76 (m, 1H), 2.99 (s, 3H), 2.87 (s, 3H), 2.70-2.62 (m, 1H), 2.53-2.45 (m, 1H), 0.87-0.73 (m, 4H)

Synthesis of Compound 024:

Following a similar procedure to compound 023, compound 024 was synthesized starting from int-11 utilizing the following procedures in order: GP2-7, GP4, GP11-13. The crude product was purified by prep-HPLC (column: Phenomenex luna C18 150×25 mm, 10 um; mobile phase: [water(FA)-ACN]; gradient: 12%-42% B over 9 min) the resulting solution was concentrated and lyophilized to afford the product. Compound 024 (16.33 mg, 32.93 μmol, 14.70% yield, 99% purity) was obtained as a white solid. LCMS: $t_R$=0.484 min, m/z=491.1 $[M+H]^+$. NMR: $^1H$ NMR (400 MHz, CHLOROFORM-d) δ=12.59-11.44 (m, 1H), 8.39-8.17 (m, 2H), 7.44 (s, 2H), 7.34-7.28 (m, 4H), 7.10 (dd, J=1.3, 7.7 Hz, 1H), 6.50-6.38 (m, 1H), 3.94 (br t, J=5.2 Hz, 2H), 3.76 (br d, J=3.4 Hz, 1H), 2.87 (s, 3H), 2.82 (s, 3H), 2.68-2.55 (m, 1H), 2.52-2.41 (m, 1H), 0.87-0.68 (m, 4H).

Synthesis of Compound 025:

Following the identical procedure for the synthesis of compound 017, compound 025 was synthesized starting from int-23. The starting material was subjected GP2-3, followed by GP5-7. The resulting compound was then subjected to GP11-13 resulting in an enantiomeric mixture of compound 017 and 025. The crude enantiomers were separated by SFC (column: DAICEL CHIRALPAK IK (250 mm×50 mm, 10 um); mobile phase: [$CO_2$-EtOH (0.1% $NH_3H_2O$)]; B %: 25%, isocratic elution mode), and concentrated under reduced pressure to give the product. Compound 025 (69.20 mg, 152.75 μmol, 22.84% yield, 99% purity) was obtained as white solid. LCMS: $t_R$=0.458 min, m/z=449.1 $[M+H]^+$. NMR: $^1$H NMR (400 MHz, DMSO-d6) δ ppm 1.21-1.36 (m, 3H) 2.79 (br s, 3H) 2.91-3.09 (m, 3H) 4.09 (br s, 2H) 5.16-5.40 (m, 1H) 5.92 (br d, J=8.88 Hz, 1H) 7.04-7.11 (m, 1H) 7.13-7.20 (m, 2H) 7.32-7.40 (m, 3H) 7.42-7.47 (m, 1H) 8.15-8.30 (m, 1H) 8.54 (br s, 1H).

Synthesis of Compound 026:

Following a similar procedure to compound 023, compound 026 was synthesized starting from int-13 utilizing the following procedures in order: GP2-7, GP4, GP11-13. The crude product was purified by prep-HPLC (column: Waters Xbridge 150×25 mm, 5 um; mobile phase: [water ($NH_4OH$)-ACN]; gradient: 20%-50% B over 10 min) to afford compound 026 (15.03 mg, 33.81 μmol, 46.60% yield, 100% purity) as yellow solid. LCMS: $t_R$=0.456 min, m/z=445.2 $[M+H]^+$. NMR: $^1$H NMR (400 MHz, CHLOROFORM-d) δ=12.27-11.86 (m, 1H), 8.23-8.17 (m, 2H), 7.47-7.43 (m, 2H), 7.35-7.30 (m, 2H), 7.28-7.24 (m, 2H), 7.01-6.97 (m, 2H), 6.35 (br dd, J=4.5, 10.3 Hz, 1H), 4.02-3.91 (m, 2H), 3.89-3.82 (m, 2H), 2.84 (br s, 3H), 2.73 (s, 3H), 2.58-2.47 (m, 1H), 2.41-2.33 (m, 1H), 1.27 (t, J=6.9 Hz, 3H).

Synthesis of Compound 027:

Following a similar procedure to compound 023, compound 027 was synthesized starting from int-13 utilizing the following procedures in order: GP2-7, GP4, GP11-13. The residue was purified by prep-HPLC (column: Waters Xbridge 150×25 mm, 5 um; mobile phase: [water ($NH_4HCO_3$)-ACN]; gradient: 35%-65% B over 9 min) then concentrated and lyophilized to give the product. Compound 027 (14.37 mg, 29.40 μmol, 89.56% yield, 98% purity) was obtained as a brown solid. LCMS: $t_R$=0.460 min, m/z 479.3 $[M+H]^+$. NMR: $^1$H NMR (400 MHz, CHLOROFORM-d) δ=12.13-11.62 (m, 1H), 8.30-8.07 (m, 2H), 7.76 (s, 1H), 7.67 (br d, J=7.9 Hz, 1H), 7.55 (br d, J=7.8 Hz, 1H), 7.48-7.39 (m, 1H), 7.22 (d, J=8.1 Hz, 1H), 7.09-6.94 (m, 2H), 6.49-6.21 (m, 1H), 4.12-3.90 (m, 2H), 3.86 (br t, J=5.6 Hz, 2H), 2.78 (s, 3H), 2.72 (s, 3H), 2.60-2.46 (m, 1H), 2.44-2.30 (m, 1H), 1.28 (t, J=6.9 Hz, 3H).

Synthesis of Compound 028:

Following a similar procedure to compound 023, compound 028 was synthesized starting from int-13 utilizing the following procedures in order: GP2-7, GP4, GP11-13. The residue was purified by prep-HPLC (column: Waters Xbridge 150×25 mm, 5 um; mobile phase: [water ($NH_3H_2O$)-ACN]; gradient: 22%-52% B over 9 min) and lyophilized to give the product. Compound 028 (17 mg, 36.21 μmol, 79.93% yield, 100% purity) was obtained as a white solid. LCMS: $t_R$=0.442 min, m/z=470.2 $[M+H]^+$. NMR: $^1$H NMR (400 MHz, CHLOROFORM-d) δ=12.13-11.62 (m, 1H), 8.30-8.07 (m, 2H), 7.76 (s, 1H), 7.67 (br d, J=7.9 Hz, 1H), 7.55 (br d, J=7.8 Hz, 1H), 7.48-7.39 (m, 1H), 7.22 (d, J=8.1 Hz, 1H), 7.09-6.94 (m, 2H), 6.49-6.21 (m, 1H), 4.12-3.90 (m, 2H), 3.86 (br t, J=5.6 Hz, 2H), 2.78 (s, 3H), 2.72 (s, 3H), 2.60-2.46 (m, 1H), 2.44-2.30 (m, 1H), 1.28 (t, J=6.9 Hz, 3H)

Synthesis of Compound 029:

Following a similar procedure to compound 023, compound 029 was synthesized starting from int-13 utilizing the following procedures in order: GP2-7, GP4, GP11-13. The residue was purified by prep-HPLC (column: Waters Xbridge 150×25 mm, 5 um; mobile phase: [water ($NH_4HCO_3$)-ACN]; gradient: 32%-62% B over 9 min), lyophilized. Compound 029 (5.32 mg, 11.21 μmol, 19.37% yield, 100% purity) was obtained as an off-white solid. LCMS: $t_R$=0.465 min, m/z=475.3 $[M+H]^+$ NMR: $^1$H NMR (400 MHz, CHLOROFORM-d) δ=12.22-11.98 (m, 1H), 8.28 (br d, J=9.1 Hz, 2H), 7.46 (s, 1H), 7.39-7.29 (m, 2H), 7.25-7.16 (m, 3H), 7.11 (br d, J=7.4 Hz, 1H), 7.07-7.00 (m, 1H), 6.49-6.41 (m, 1H), 3.95 (br t, J=5.6 Hz, 2H), 3.77 (br d, J=3.0 Hz, 1H), 2.90 (s, 3H), 2.83 (s, 3H), 2.67-2.56 (m, 1H), 2.51-2.40 (m, 1H), 0.85-0.69 (m, 4H). SFC: 100% ee.

Synthesis of Compound 030:

Following a similar procedure to compound 017, compound 030 was synthesized starting from int-23. The starting material was subjected GP2-3, GP5-7, then GP11-13. The final crude product was pre-purified by prep-HPLC (column: Phenomena Luna C18 150×25 mm, 10 um; mobile phase: [water (FA)-ACN]; gradient: 15%-45% B over 9 min). Compound 030 (32 mg, 65.14 μmol, 8.90% yield, 97% purity) was obtained as a white solid. The product was then purified by SFC (column: DAICEL CHIRALPAK IK (250 mm×30 mm, 10 um); mobile phase: [$CO_2$-ACN/i-PrOH (0.1% $NH_3H_2O$)]; B %: 25%, isocratic elution mode). Compound 030 (18.15 mg, 38.09 μmol, 56.72% yield, 100% purity) was obtained as a white solid. LCMS: $t_R$=0.472 min, m/z=477.3 $[M+H]^+$. NMR: $^1$H NMR (400 MHz, CHLOROFORM-d) δ=8.28 (s, 1H), 8.18 (s, 1H), 7.51 (dd, J=1.3, 7.9 Hz, 1H), 7.45 (d. J=1.1 Hz, 1H), 7.27 (d, J=7.9 Hz, 1H), 7.06-7.00 (m, 2H), 6.80 (br d, J=9.5 Hz, 1H), 4.68-4.58 (m, 1H), 4.55-4.47 (m, 1H), 4.45-4.40 (m, 1H), 4.00 (q, J=7.0 Hz, 2H), 3.13 (q, J=7.6 Hz, 2H), 2.39 (s, 3H), 2.32 (s, 3H), 1.40 (t, J=7.6 Hz, 3H), 1.30 (t, J=6.9 Hz, 3H).

Synthesis of Compound 031:

Following a similar procedure to compound 017, compound 031 was synthesized starting from int-23. The starting material was subjected GP2-3, GP5-7, GP11-12, then GP14. The resulting crude compound was pre-purified by prep-HPLC (column: Phenomenex luna C18 150×25 mm, 10 um; mobile phase: [water(FA)-ACN]; gradient: 12%-42% B over 9 min) and lyophilized. Compound 031 (20 mg, 43.24 μmol, 29.53% yield) was obtained as white solid. The product was further purified by SFC (column: DAICEL CHIRALPAK AD (250 mm×30 mm, 10 um); mobile phase: [$CO_2$:i-PrOH (0.1% $NH_3H_2O$)]; B %: 35%, isocratic elution mode). After SFC, the eluent was concentrated to remove organic solvents and the residual aqueous solution was lyophilized. Compound 031 (30.67 mg, 66.31 μmol, 87.63% yield, and 100% purity) was obtained as white solid. LCMS: $t_R$=0.467 min, m/z=463.2 ($M+H^+$). NMR: $^1$H NMR (400 MHz, CHLOROFORM-d) δ=12.42-12.07 (m, 1H), 8.26 (d, J=18.1 Hz, 2H), 7.33 (br d, J=7.8 Hz, 2H), 7.31-7.26 (m, 2H), 7.17-7.08 (m, 2H), 7.07-6.99 (m, 1H), 6.15 (br dd, J=6.1, 8.4 Hz, 1H), 4.52 (br d, J=10.0 Hz, 1H), 4.41 (dd, J=5.6, 11.3 Hz, 1H), 4.06 (br dd, J=7.1, 13.9 Hz, 2H), 3.21 (q, J=7.6 Hz, 2H), 2.91 (s, 3H), 1.47 (t, J=7.6 Hz, 3H), 1.36 (t, J=6.9 Hz, 3H)

Synthesis of Compound 032:

Following a similar procedure to compound 017, compound 032 was synthesized starting from int-23. The starting material was subjected GP2-3, GP5-7, GP11-12, then GP14. The crude product was pre-purified by prep-HPLC (column: Phenomenex luna C18 150×40 mm, 15 um; mobile phase: [water(FA)-ACN]; gradient: 20%-50% B over 15 min) the eluent was concentrated and then lyophilized for 12 h. The isolated product was purified further by SFC (column: Phenomenex-Cellulose-2 (250 mm×30 mm, 10 um); mobile phase: [$CO_2$-EtOH (0.1% $NH_3H_2O$)]; B %: 25%, isocratic elution mode). After SFC, the eluent was concentrated to remove organic solvents and the residual aqueous solution was lyophilized. Compound 032 (38.02 mg, 77.00 μmol, 73.07% yield, 96.1% purity) was obtained as brown gum. LCMS: 0.469 min, 475.2 $[M+H]^+$ ESI pos $^1H$ NMR (400 MHz, CHLOROFORM-d) δ=12.40-12.07 (m, 1H), 8.29 (s, 1H), 8.25 (s, 1H), 7.50 (s, 1H), 7.38-7.29 (m, 2H), 7.26-7.15 (m, 4H), 7.09-6.98 (m, 1H), 6.16 (br d, J=8.9 Hz, 1H), 4.60-4.51 (m, 1H), 4.42 (dd, J=5.6, 11.3 Hz, 1H), 3.78 (br s, 1H), 3.22 (q, J=6.8 Hz, 2H), 2.94 (s, 3H), 1.49 (t, J=7.5 Hz, 4H), 0.86-0.70 (m, 4H)

Synthesis of Compound 033:

Following a similar procedure to compound 017, compound 033 was synthesized starting from int-23. The starting material was subjected GP2-3, GP5-7, GP11-12, then GP14. The crude product was pre-purified by prep-HPLC (column: Phenomenex luna C18 150×40 mm, 15 um; mobile phase: [water (FA)-ACN]; gradient: 22%-52% B over 15 min.) then lyophilized for 12 h. The resulting compound was purified by SFC (column: DAICEL CHIRALPAK AD (250 mm×30 mm, 10 um); mobile phase: [$CO_2$-EtOH (0.1% $NH_3H_2O$)]; B %: 35%, isocratic elution mode) the eluent was then concentrated and lyophilized to afford the desired product. Compound 033 (43.04 mg, 84.08 μmol, 60.36% yield, 96.3% purity) was obtained as white solid and by LCMS and $^1H$-NMR. LCMS: $t_R$=0.474 min, m/z=493.2 $[M+H]^+$. NMR: $^1H$ NMR (400 MHz, CHLOROFORM-d) δ=12.22 (br s, 1H), 8.25 (d, J=11.3 Hz, 2H), 7.49 (s, 1H), 7.17 (d, J=7.8 Hz, 1H), 7.01-6.95 (m, 2H), 6.78 (tt, J=2.3, 8.9 Hz, 1H), 6.16 (br dd, J=5.4, 9.0 Hz, 1H), 4.57-4.50 (m, 1H), 4.45-4.38 (m, 1H), 3.77 (br d, J=3.2 Hz, 1H), 3.18 (q, J=7.6 Hz, 2H), 2.92 (s, 3H), 1.46 (t, J=7.6 Hz, 3H), 0.85-0.69 (m, 4H). SFC: 100% ee.

Synthesis of Compound 034:

Following an identical procedure to compound 019, the intermediate isolated after GP11, was subject to a modified GP12, wherein the solvent is EtOH and under performed under CO atmosphere at 50 psi. The result product was subjected to GP15, then GP13 to afford the crude product. The crude material was pre-purified by prep-HPLC (column: Phenomenex luna C18 150×25 mm, 10 um; mobile phase: [water (FA)-ACN]; gradient: 15%-45% B over 9 min), and the product was concentrated and lyophilized to give the product. This material was then purified by SFC (column: DAICEL CHIRALPAK AD (250 mm×30 mm, 10 um); mobile phase: [$CO_2$-EtOH (0.1% $NH_3H_2O$)]; B %: 40%, isocratic elution mode), and concentrated under reduced pressure to give the product. Compound 034 (46.79 mg, 96.32 μmol, 66.17% yield, 99% purity) was obtained as yellow solid. LCMS: $t_R$=0.448 min, m/z=481.1 $[M+H]^+$. NMR: $^1H$ NMR (400 MHz, CHLOROFORM-d) δ ppm 1.40 (t, J=7.00 Hz, 3H) 2.44 (s, 3H) 4.10 (q, J=7.00 Hz, 2H) 4.40-4.53 (m, 2H) 4.66 (dd, J=11.07, 4.31 Hz, 1H) 5.13 (s, 2H) 7.34-7.39 (m, 3H) 7.43-7.47 (m, 1H) 7.55 (d, J=1.50 Hz, 1H) 7.57 (s, 1H) 7.61 (dd, J=7.88, 1.50 Hz, 1H) 8.23 (s, 1H) 8.33 (s, 1H).

Synthesis of Compound 035:

Following a similar procedure to compound 034, compound 035 was isolated and pre-purified before final purification by SFC (column: DAICEL CHIRALPAK IK (250 mm×30 mm, 10 um); mobile phase: [$CO_2$-EtOH (0.1% $NH_3H_2O$)]; B %: 35%, isocratic elution mode) and lyophilized to give the product. Compound 035 (41.71 mg, 88.90 μmol, 41.71% yield, 99% purity) was obtained as a white solid. LCMS: $t_R$=0.427 min, m/z=465.3 $[M+H]^+$ NMR: $^1H$ NMR (400 MHz, CHLOROFORM-d) δ=11.90-11.41 (m, 1H), 8.32 (s, 1H), 8.23 (s, 1H), 7.61 (dd, J=1.4, 7.9 Hz, 1H), 7.55 (d, J=1.1 Hz, 1H), 7.43-7.30 (m, 4H), 7.07 (br d, J=1.1 Hz, 1H), 5.12 (s, 2H), 4.64 (br d, J=4.3 Hz, 1H), 4.53-4.44 (m, 1H), 4.43-4.35 (m, 1H), 4.10 (q, J=6.9 Hz, 2H), 2.43 (s, 3H), 1.40 (t, J=6.9 Hz, 3H).

Synthesis of Compound 036:

Starting from int-11, the material was subjected to GP2-8, followed by oxidation with DMP (1.5 eq) in DCM (0.25 M) at 0° C. and stirred for 2 hr. The reaction was filtered, and the filtrate was concentrated to give the crude material which was purified by prep-TLC ($SiO_2$, DCM:MeOH=10:1, $R_f$=0.7). Int-24 (25 mg, 50.40 μmol, 64.58% yield, 90% purity) was obtained as a colorless oil. LCMS: Rt=0.457 min, m/z=447.2 $(M+H^+)$.

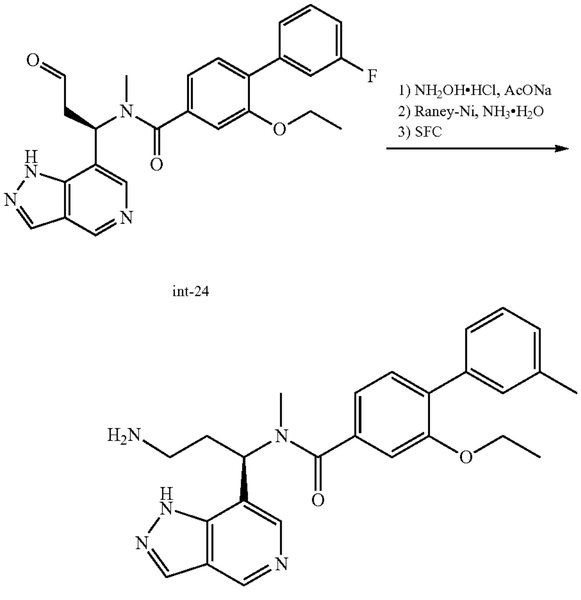

int-24

Compound 036

Int-24 (197 mg, 441.24 μmol, 1 eq) in EtOH (5 mL) was treated with $NH_2OH$·HCl (45.99 mg, 661.85 μmol, 1.5 eq) and AcONa (54.29 mg, 661.85 μmol, 1.5 eq). The reaction mixture was stirred at 40° C. for 12 h under $N_2$. Then the reaction mixture was poured into saturated ice-water (30 mL) and extracted by EA (50 mL×3). The combined organic phase was dried with $Na_2SO_4$ and concentrated to give the crude product. The crude product was used directly in the next step without further purification. To the crude material (162 mg, 351.04 μmol, 1 eq) in AcOH (2 mL) was added Zinc metal (114.77 mg, 1.76 mmol, 5 eq), the mixture was stirred at 25° C. for 12 h under $N_2$. After 12 h, zinc (229.54 mg, 3.51 mmol, 10 eq) was added again and the reaction was stirred at 25° C. for 2 h under $N_2$. The reaction mixture was filtered, and the filter liquor was basified with 1M (NaOH). The filter cake was basified with 1M (NaOH). The crude product was pre-purified by prep-HPLC (column: Phenomena Luna C18 150×25 mm, 10 um; mobile phase: [water (FA)-ACN]; gradient: 8%-38% B over 9 min), and the product was concentrated and lyophilized to give the semi-purified product. This material was purified by SFC (column: DAICEL CHIRALPAK AD (250 mm×30 mm, 10 um); mobile phase: [$CO_2$-EtOH (0.1% $NH_3$H2O)]; B %: 60%, isocratic elution mode). Compound 036 (10.85 mg, 23.28 μmol, 65.10% yield, and 96% purity) was obtained as a yellow solid. LCMS: $t_R$=0.419 min, m/z=448.3 $[M+H]^+$. NMR: $^1H$ NMR (400 MHz, CHLOROFORM-d) δ=9.03 (br s, 1H), 8.47-8.09 (m, 2H), 7.31-7.20 (m, 3H), 7.04-6.89 (m, 3H), 6.34 (br dd, J=2.0, 3.5 Hz, 1H), 4.04-3.91 (m, 2H), 3.06-2.86 (m, 2H), 2.79-2.63 (m, 3H), 2.60-2.49 (m, 1H), 2.33 (br d, J=3.5 Hz, 1H), 2.09-1.87 (m, 1H), 1.28 (br t, J=6.9 Hz, 3H), 1.19 (br d, J=5.0 Hz, 2H).

Synthesis of Compound 037:

To a solution of intermediate 24 (20 mg, 44.80 μmol, 1 eq) in MeOH (2 mL) was added $MeNH_2$ (2 M, 67.19 μL, 3.00 eq), the reaction mixture was stirred at 20° C. for 2 hr. Then $NaBH_4$ (3.39 mg, 89.59 μmol, 2 eq) was added to the solution slowly at 0° C., the reaction mixture was stirred at 20° C. for 1 hr. After the reaction was completed, the reaction mixture was poured into $NH_4Cl$ (3 mL) at 0° C., filtered, the filtrate was concentrated under reduced pressure to give a residue. Then the solution was triturated in DCM/MeOH=10:1) and collected by filtration, the filtrate was concentrated under reduced pressure to give crude product. The crude product was purified by prep-HPLC (column: Waters X bridge 150×25 mm, 5 um; mobile phase: [water ($NH_4OH$)-ACN]; gradient: 18%-48% B over 10 min). Compound 037 (4.74 mg, 10.27 μmol, 22.93% yield, and 100% purity) was obtained as a white sol d. LCMS: $t_R$=0.565 min, m/z=462.3 $[M+H]^+$. NMR: $^1H$ NMR (400 MHz, CHLOROFORM-d) δ=9.09 (br s, 1H), 8.38-8.20 (m, 2H), 7.46-7.33 (m, 4H), 7.10-7.03 (m, 3H), 4.27-3.94 (m, 4H), 3.84 (br s, 2H), 3.45-3.16 (m, 1H), 3.01 (s, 3H), 2.37-2.27 (m, 4H), 1.41-1.37 (m, 3H).

Synthesis of Compound 038:

To a solution of Intermediate 24 (60 mg, 134.39 μmol, 1 eq) in MeOH (1.5 mL) was added dimethylamine (2 M, 1.5 mL, 22.32 eq), the reaction mixture was stirred at 20° C. for 11 h. Then $NaBH_4$ (10.17 mg, 268.77 μmol, 2 eq) was added to the solution slowly at 0° C., the reaction mixture was stirred at 20° C. for 1 h. After the reaction was completed, the reaction mixture was poured into $NH_4Cl$ (10 mL) at 0° C., filtered, the filtrate was concentrated under reduced pressure to give a residue. Then the solution was triturated in DCM/MeOH=10:1) and collected by filtration, the filtrate was concentrated under reduced pressure to give crude product. The crude product was purified by prep-HPLC (column: Phenomenex luna C18 150×25 mm, 10 um; mobile phase: [water(FA)-ACN]; gradient: 5%-35% B over 9 min) and lyophilized to give the product. Compound 038 (10.74 mg, 19.97 μmol, 14.86% yield, 97% purity, FA) was obtained as a yellow solid. LCMS: $t_R$=0.417 min, m/z=476.3 $[M+H]^+$ NMR: $^1H$ NMR (400 MHz, CHLOROFORM-d) δ=9.14 (br s, 1H), 8.45 (br s, 1H), 8.34-8.18 (m, 1H), 7.45-7.29 (m, 4H), 7.20-6.97 (m, 3H), 6.31 (br s, 1H), 4.28-3.91 (m, 2H), 2.88 (br s, 3H), 2.69 (br d, J=11.3 Hz, 2H), 2.49 (br s, 6H), 1.49-1.31 (m, 3H)

Synthesis of Compound 023 & 024:

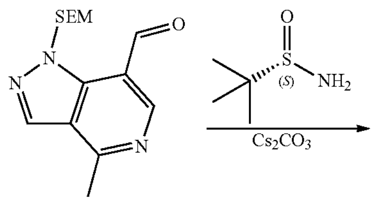

int-25

-continued

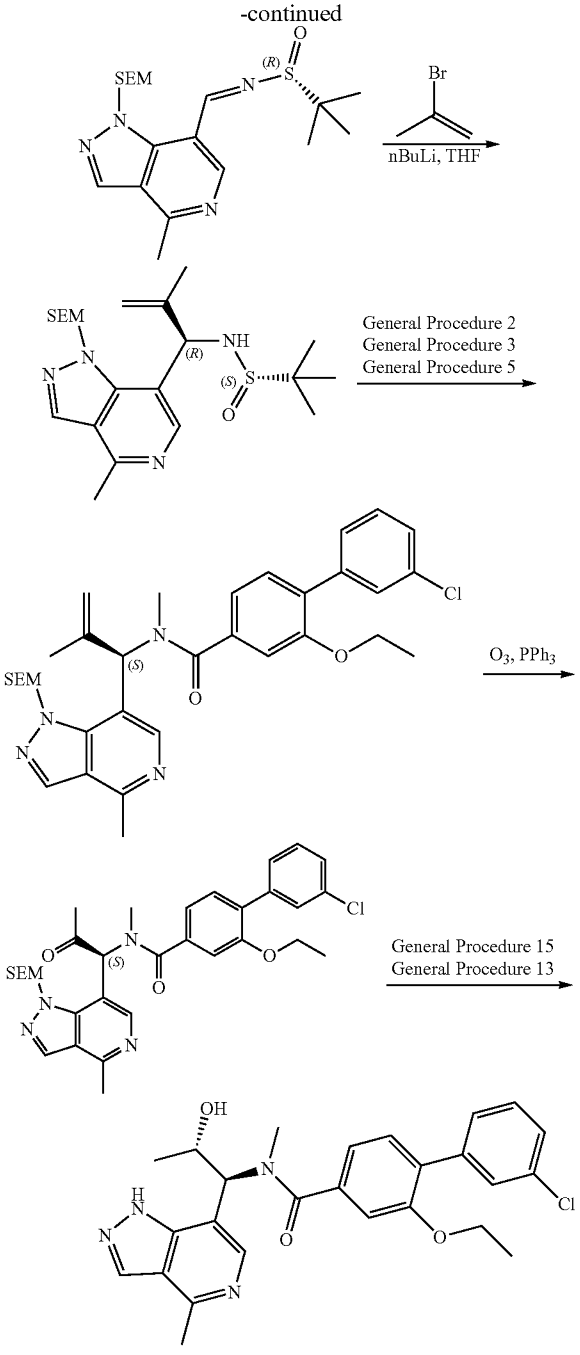

Compound 023

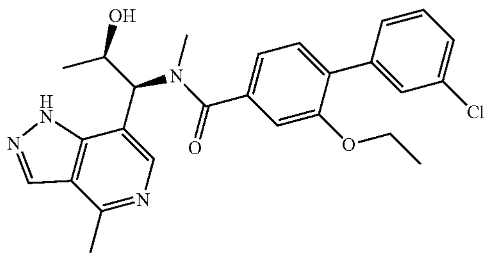

Compound 024

To a solution of int-25 (2 g, 6.86 mmol, 1 eq), int-4 (914.97 mg, 7.55 mmol, 1.1 eq) in DCM (30 mL) was added $Cs_2CO_3$ (2.68 g, 8.24 mmol, 1.2 eq), the reaction was stirred at 20° C. for 12 h. TLC (PE:EtOAc=0:1; UV&DNP) showed starting material was consumed up and new spot was formed. The reaction was filtered and concentrated to give a crude product. The crude product was purified by silica gel chromatography (50% EtOAc in PE, $R_f$=0.60).

To a solution of 2-bromoprop-1-ene (827.75 mg, 6.84 mmol, 607.74 µL, 1.2 eq) in THE (20 mL) was added n-BuLi (2.5 M, 5.47 mL, 2.4 eq) at −70° C. under $N_2$ protected, then stirred at −70° C. for 0.5 h, then a solution of the purified compound from the prior step (2.5 g, 5.70 mmol, 1 eq) in THE (5 mL) was added dropwise to this reaction, the reaction was stirred at −70° C. for 1 h. LCMS showed starting material was consumed up and desire product was detected. The solution was slowly poured into saturated aqueous $NH_4Cl$ (300 mL) at 0° C. under $N_2$. The layers were separated, the aqueous layer was extracted in EtOAc (100 mL×3), the combined organics were dried over $Na_2SO_4$ and filtered, and the solvent was evaporated in vacuo to give the crude residue. The crude product was purified by silica gel chromatography (7% EtOAc in MeOH, $R_f$=0.10) to give a product.

The product was subjected to GP2, GP3, and GP5 to give the intermediate amide product. The product (140 mg, 231.31 µmol, 1 eq) was dissolved in DCM (3 mL) and MeOH (3 mL) was treated with ozone (11.10 mg, 231.31 µmol, 1 eq) at −70° C. for 0.5 h, then the mixture was purged with nitrogen 3 times, $PPh_3$ (121.34 mg, 462.63 µmol, 2 eq) was dissolved in DCM (1 mL) was added dropwise to the mixture at −70° C. The mixture was warmed to 20° C. and stirred at 20° C. for 1 h. TLC (PE:EtOAc=0:1; UV) showed starting material was consumed up and new spots were formed. The reaction was concentrated to give a crude product. The crude product was purified by silica gel chromatography (35% EtOAc in PE, Rf=0.80) to give a product. This product was subjected to GP15 followed by GP13 and the resulting crude mixture was purified by prep-HPLC (column: Waters Xbridge 150×25 mm, 5 um; mobile phase: [water($NH_4HCO_3$)-ACN]; gradient: 32%-62% B over 15 min) and lyophilized.

Compound 023 (2.13 mg, 4.45 µmol, 10.84% yield, and 100% purity) was obtained as white solid. LCMS: $t_R$=0.493 min, m/z=479.3 $[M+H]^+$. NMR: $^1H$ NMR (400 MHz, CHLOROFORM-d) δ=12.27-11.88 (m, 1H), 8.35-8.04 (m, 2H), 7.55-7.45 (m, 1H), 7.43-7.35 (m, 1H), 7.30 (br d, J=3.8 Hz, 2H), 7.19 (br s, 1H), 7.14-6.90 (m, 2H), 5.77-5.38 (m, 1H), 4.99-4.63 (m, 1H), 4.19-3.82 (m, 2H), 2.91 (br d, J=14.9 Hz, 3H), 2.86-2.74 (m, 3H), 1.38 (br d, J=13.0 Hz, 3H), 1.35-1.23 (m, 3H)

Compound 024 (5.08 mg, 10.61 µmol, 25.85% yield, and 100% purity) was obtained as white solid. LCMS: $t_R$=0.502 min, m/z=479.3 $[M+H]^+$. NMR: $^1H$ NMR (400 MHz, CHLOROFORM-d) δ=12.16-11.85 (m, 1H), 8.39 (br s, 1H), 8.23 (s, 1H), 7.53 (s, 1H), 7.40 (s, 1H), 7.32 (br d, J=5.9 Hz, 3H), 7.06-7.00 (m, 2H), 5.94-5.69 (m, 1H), 5.07-4.75 (m, 1H), 4.05 (br dd, J=6.9, 12.9 Hz, 2H), 2.85 (s, 3H), 2.83 (s, 3H), 1.57-1.52 (m, 3H), 1.36 (t, J=6.9 Hz, 3H).

Synthesis of Compound 163

Compound 163 was prepared following the procedure for Compound 145 using Compound 098 as starting material. Compound 163 (64.95 mg, 127.85 µmol, 57.19% yield, 100% purity) was obtained as a white solid. LCMS: RT=0.527 min, m/z=508.1 [M+H]+ $^1H$ NMR (400 MHz, METHANOL-d4) δ=9.14 (s, 1H), 8.52 (br s, 1H), 8.42 (s, 1H), 8.34-8.21 (m, 1H), 7.53 (br s, 1H), 7.44-7.30 (m, 4H), 7.15 (br s, 2H), 6.35 (br s, 1H), 4.08 (br s, 2H), 3.79-3.55 (m, 2H), 3.38 (br s, 6H), 3.14-2.99 (m, 1H), 2.89 (br s, 4H), 1.32 (br s, 3H).

Synthesis of Compound 164

Compound 164 was prepared following the procedure for Compound 145 using Compound 091 as starting material. Compound 164 (33 mg, 67.68 µmol, 45.60% yield, 98.5% purity) was obtained as off-white solid. LCMS: Rt=0.459 min, m/z=488.1 (M+H+). $^1H$ NMR: (400 MHz, CHLOROFORM-d) δ=9.12 (s, 1H), 8.50 (br s, 1H), 8.26 (s, 1H), 7.33 (br s, 3H), 7.30 (br d, J=7.6 Hz, 1H), 7.18-7.09 (m, 3H), 6.30 (br s, 1H), 4.06 (br dd, J=7.2, 11.2 Hz, 2H), 3.58 (br s, 2H), 3.42-3.33 (m, 6H), 3.18 (br dd, J=2.0, 3.2 Hz, 2H), 2.91 (br s, 3H), 2.39 (s, 3H), 1.35 (br t, J=6.4 Hz, 3H).

Synthesis of Compound 165

Compound 165 was prepared following the procedure for Compound 145 using Compound 102 as starting material. Compound 165 (53.24 mg, 103.01 µmol, 50.22% yield, 97.43% purity) as a white solid. LCMS: Rt=0.471 min, m/z=504.2[M+H]+ $^1H$ NMR (400 MHz, CHLOROFORM-d) δ=9.16 (br s, 1H), 8.51 (br s, 1H), 8.34 (br s, 1H), 8.28 (s, 1H), 7.52 (s, 1H), 7.39-7.31 (m, 2H), 7.25-7.15 (m, 3H), 7.03 (dt, J=2.0, 8.4 Hz, 1H), 6.28 (br dd, J=5.2, 10.2 Hz, 1H), 3.90-3.81 (m, 2H), 3.65 (br dd, J=6.6, 11.6 Hz, 1H), 3.55 (s, 3H), 3.45 (s, 3H), 3.33 (m, 1H), 2.95 (s, 3H), 2.84-2.76 (m, 1H), 0.87-0.69 (m, 4H).

Synthesis of Compound 166

Compound 166 was prepared following the procedure for Compound 145 using Compound 096 as starting material. Compound 166 (43.06 mg, 90.56 µmol, 27.63% yield, 99.6% purity) was obtained as off-white solid. LCMS: RT=0.419 min, m/z=474.3 [M+H]+ $^1H$ NMR (400 MHz, CHLOROFORM-d) δ=9.06 (s, 1H), 8.43 (s, 1H), 8.26 (s, 1H), 8.20 (s, 1H), 7.45 (d, J=7.6 Hz, 2H), 7.34-7.29 (m, 2H), 7.28-7.24 (m, 2H), 7.10-7.05 (m, 2H), 6.20 (dd, J=4.4, 9.2 Hz, 1H), 4.08-3.89 (m, 2H), 3.85-3.76 (m, 1H), 3.62 (dd, J=7.2, 10.4 Hz, 1H), 3.48 (s, 3H), 3.39 (s, 3H), 3.19 (d, J=10.4 Hz, 1H), 2.84 (s, 3H), 2.69 (t, J=12.0 Hz, 1H), 1.26 (t, J=6.8 Hz, 3H).

Synthesis of Compounds 041-062 (N-Substituted):

Synthesis of Compound 041:

Compound 041 was synthesized starting from int-26. Intermediate 26 was subjected to GP16, GP5, GP8, and finally GP13 resulting in crude 041. The crude product was purified by prep-HPLC (column: Waters Xbridge 150×25 mm, 5 um; mobile phase: [water($NH_4HCO_3$)-ACN]; gradient: 20%-50% B over 15 min) lyophilization for 12 h. Compound 041 (31.85 mg, 72.94 µmol, 21.72% yield, 99.5% purity) was obtained as white solid. LCMS: $t_R$=0.447 min, 456.1 $[M+H]^+$. NMR: $^1H$ NMR (400 MHz, CHLOROFORM-d) δ=12.02 (br s, 1H), 12.08-11.93 (m, 1H), 9.05 (br s, 1H), 8.31 (br s, 1H), 8.20 (s, 1H), 7.32-7.21 (m, 4H), 7.03-6.99 (m, 2H), 6.98-6.94 (m, 1H), 5.08 (s, 2H), 3.97 (br d, J=6.6 Hz, 2H), 3.84 (br s, 2H), 3.44 (br s, 2H), 1.29 (t, J=6.9 Hz, 3H), 1.19 (br s, 1H).

Synthesis of Compound 042:

Compound 042 was synthesized by following a similar procedure to compound 041. Intermediate 26 was subjected to GP16, GP5, GP8, and finally GP13 resulting in crude 042. The residue was purified by prep-HPLC (column: Waters Xbridge 150×25 mm, 5 um; mobile phase: [water ($NH_4HCO_3$)-ACN]; gradient: 25%-55% B over 15 min) and lyophilization to give 20 mg product. Then the product was purified by prep-HPLC (column: Phenomenex luna C18 150*25 mm*10 um; mobile phase: [water(FA)-ACN]; gradient: 18%-48% B over 9 min) and lyophilization. Compound 042 (14.35 mg, 31.82 µmol, 44.26% yield, 100% purity) was obtained as yellow gum. LCMS: $t_R$=0.455 min, m/z=451.2 $[M+H]^+$. NMR: $^1$H NMR (400 MHz, CHLOROFORM-d) δ=12.32-11.97 (m, 1H), 8.45-8.23 (m, 1H), 7.56 (s, 1H), 7.46-7.41 (m, 1H), 7.37-7.32 (m, 3H), 7.29 (s, 3H), 7.14-7.06 (m, 2H), 5.20 (br s, 2H), 4.07 (q, MJ=6.6 Hz, 2H), 3.97-3.82 (m, 2H), 3.52 (br s, 2H), 1.38 (t, J=6.9 Hz, 3H)

Synthesis of Compound 043:

Compound 043 was synthesized by following a similar procedure to compound 041.

Intermediate 26 was subjected to GP16, GP5, then a modified protocol of GP8 was used.

The modified protocol utilized the following conditions: tert-butyl carbamate (5 eq) and $Cs_2CO_3$ (2 eq) and $Pd(OAc)_2$ (0.1 eq) and Xantphos (0.2 eq). The reaction mixture was stirred at 100° C. for 12 h under $N_2$. After isolation of the product finally GP13 was utilized resulting in crude 043. The residue was purified by prep-HPLC (column: Waters Xbridge 150×25 mm, 5 um; mobile phase: [water(ammonia hydroxide v/v)-ACN]; gradient: 10%-40% B over 10 min) and lyophilization. Compound 043 (13.12 mg, 28.74 μmol, 11.51% yield, 100% purity) was obtained as white solid. LCMS: $t_R$=0.438 min, m/z=457.3 $[M+H]^+$. NMR: $^1$H NMR (METHANOL-d4, 400 MHz): δ=8.25 (br s, 1H), 7.79-7.96 (m, 2H), 7.65-7.76 (m, 2H), 7.53-7.64 (m, 1H), 7.32-7.47 (m, 1H), 7.18-7.33 (m, 1H), 6.98-7.17 (m, 1H), 4.95-4.96 (m, 1H), 4.96 (br s, 2H), 4.20-4.25 (m, 1H), 4.04-4.21 (m, 1H), 3.69-3.82 (m, 2H), 3.41-3.55 (m, 1H), 1.33 ppm (br d, J=17.5 Hz, 3H).

Synthesis of Compound 044:

Compound 044 was synthesized by following a similar procedure to compound 043. Intermediate 26 was subjected to GP16, GP5, then a modified protocol of GP8 was used. The modified protocol utilized DMSO as the solvent, and the following reagents: methanamine-hydrochloride (3 eq), rac-(2S)-pyrrolidine-2-carboxylic acid (0.2 eq), CuI (0.2 eq) and $K_2CO_3$ (2 eq). The reaction mixture was stirred at 100° C. for 12 h under $N_2$. The isolated product was subjected to GP13 resulting in crude 044. The residue was purified by prep-HPLC (column: Waters Xbridge 150×25 mm, 5 um; mobile phase: [water (ammonia hydroxide v/v)-ACN]; gradient: 13%-43% B over 10 min) and lyophilization. Compound 044 (20.72 mg, 41.70 μmol, 49.70% yield, 94.7% purity) was obtained as white solid. LCMS: $t_R$0.411 min, m/z=471.2 $[M+H]^+$. NMR: $^1$H NMR (CHLOROFORM-d, 400 MHz): δ=11.90 (br s, 1H), 8.03 (s, 1H), 7.84 (s, 1H), 7.80 (s, 1H), 7.74 (d, J=7.9 Hz, 1H), 7.58-7.65 (m, 1H), 7.47-7.54 (m, 1H), 7.29 (d, J=8.1 Hz, 1H), 7.06-7.14 (m, 2H), 5.11 (br d, J=1.8 Hz, 1H), 4.93 (s, 2H), 4.04 (q, J=6.8 Hz, 2H), 3.86 (br t, J=5.2 Hz, 2H), 3.49 (br d, J=5.1 Hz, 2H), 3.19 (br d, J=3.3 Hz, 3H), 1.33 ppm (t, J=6.9 Hz, 3H).

Synthesis of Compound 045:

Compound 045 was synthesized starting from intermediate 28. Int-28 was subjected to GP17 (amine=2-(benzyloxy) cyclopropan-1-amine), GP5, then finally GP14 resulting in the crude residue of compound 045. The residue was purified by prep-HPLC (column: YMC-Actus Triart C18 150×30 mm, 7 um; mobile phase: [water(FA)-ACN]; gradient: 20%-50% B over 10 min). The eluent was lyophilized to afford compound 045 (73 mg, 158.52 μmol, 27.68% yield, 100% purity) as white solid. LCMS: $t_R$=0.440 min, m/z=461.3 $[M+H]^+$. NMR: $^1$H NMR (CHLOROFORM-d, 400 MHz): δ=8.44 (s, 1H), 8.26 (s, 1H), 7.34-7.42 (m, 2H), 7.28-7.33 (m, 2H), 7.11-7.17 (m, 2H), 7.01-7.08 (m, 1H), 5.19 (d, J=14.3 Hz, 1H), 4.82 (d, J=14.4 Hz, 1H), 4.07 (q, J=6.9 Hz, 2H), 3.12 (br dd, J=6.0, 4.0 Hz, 1H), 2.89 (s, 4H), 1.38 (t, J=7.0 Hz, 3H), 1.00 (td, J=7.9, 4.2 Hz, 1H), 0.57-0.70 ppm (m, 1H)

Synthesis of Compound 046:

Compound 046 was synthesized by following a similar procedure to compound 043. Intermediate 26 was subjected to GP16, GP5, then a modified protocol of GP8 was used. The modified protocol utilized $NH_2Boc$ (5 eq) in dioxane (0.05 M) was added $Cs_2CO_3$ (3 eq) and Xantphos Pd $G_4$ (0.1 eq), the mixture was stirred at 100° C. for 12 h under $N_2$. The isolated product was subjected to GP13 resulting in crude 046. The residue was purified by pre-HPLC (column: Waters Xbridge 150×25 mm, 5 um; mobile phase: [water ($NH_4HCO_3$)-ACN]; gradient: 28%-58% B over 9 min), lyophilized. The residue was purified by SFC (column: DAICEL CHIRALPAK IC (250 mm×30 mm, 10 um); mobile phase: [$CO_2$-ACN/i-PrOH (0.1% $NH_3H_2O$)]; B %: 50%, isocratic elution mode), lyophilized. Compound 046 (26.95 mg, 56.86 μmol, 24.10% yield, 98.3% purity) was obtained as an off-white solid. LCMS: $t_R$=0.461 min, m/z=466.1 $[M+H]^+$. NMR: $^1$H NMR (400 MHz, CHLOROFORM-d) δ=8.07 (s, 1H), 7.81-7.66 (m, 1H), 7.54 (s, 1H), 7.41 (br d, J=6.9 Hz, 1H), 7.32 (br t, J=5.8 Hz, 3H), 7.07 (br d, J=6.5 Hz, 2H), 5.48-5.35 (m, 1H), 4.96 (br s, 2H), 4.08-4.00 (m, 2H), 3.87 (br s, 2H), 3.54-3.43 (m, 2H), 1.35 (br t, J=6.9 Hz, 3H).

Synthesis of Compound 047:

Compound 047 was synthesized by following a similar procedure to compound 047 where the sole modification was the choice of acid used during the secondary amine coupling reaction (GP5). The resulting crude residue was purified by prep-HPLC (column: Waters Xbridge 150×25 mm, 5 um; mobile phase: [water($NH_4HCO_3$)-ACN]; gradient: 22%-52% B over 9 min), lyophilized. Compound 047 (32.84 mg, 73.06 μmol, 37.10% yield, 100% purity) was obtained as a white solid, LCMS: $t_R$=0.445 min, m/z=450.1 $[M+H]^+$. NMR: $^1$H NMR (400 MHz, CHLOROFORM-d) δ=12.44-11.59 (m, 1H), 8.05 (s, 1H), 7.76 (s, 1H), 7.41-7.28 (m, 4H), 7.12-6.96 (m, 3H), 5.28-5.11 (m, 2H), 4.97 (s, 2H), 4.04 (q, J=6.6 Hz, 2H), 3.88 (br s, 2H), 3.53-3.42 (m, 2H), 1.35 (t, J=6.9 Hz, 3H).

Synthesis of Compound 048:

Compound 048 was synthesized by following a similar procedure to compound 043. Intermediate 26 was subjected to GP16, GP5, then a modified protocol of GP8 was used. The modified protocol utilized methanamine-hydrochloride (5 eq) in DMSO (0.05 M) was added $K_2CO_3$ (3 eq) and CuI (0.2 eq), and L-Proline (0.2 eq) the mixture was stirred at 100° C. for 12 h under $N_2$. The isolated product was subjected to GP13 resulting in crude 048. The residue was purified by prep-HPLC (column: Waters Xbridge 150×25 mm, 5 um; mobile phase: [water($NH_4HCO_3$)-ACN]; gradient: 28%-58% B over 9 min), lyophilized. Compound 048 (13.89 mg, 29.97 μmol, 25.69% yield, 100% purity) was obtained as a white solid. LCMS: $t_R$=0.447 min, m/z=464.2 $[M+H]^+$. NMR: $^1$H NMR (400 MHz, CHLOROFORM-d) δ=8.06 (s, 1H), 7.81 (s, 1H), 7.40-7.29 (m, 4H), 7.10-7.00 (m, 3H), 5.54-5.25 (m, 1H), 4.95 (s, 2H), 4.04 (q, J=7.0 Hz, 2H), 3.87 (br t, J=5.2 Hz, 2H), 3.51 (br d, J=5.0 Hz, 2H), 3.22 (br s, 3H), 1.35 (t, J=7.0 Hz, 3H).

Synthesis of Compound 049:

Compound 049 was synthesized by following a similar procedure to compound 047 where the sole modification was the choice of acid used during the secondary amine coupling reaction (GP5). The resulting residue was purified by prep-HPLC (column: Waters Xbridge 150×25 mm, 5 um; mobile phase: [water (ammonia hydroxide v/v)-ACN]; gradient: 23%-53% B over 10 min) and lyophilization. Compound 049 (27.15 mg, 53.29 μmol, 48.26% yield, 94.2% purity) was obtained as white solid. LCMS: $t_R$=0.469 min, m/z=480.3[M+H]$^+$. NMR: $^1$H NMR (CHLOROFORM-d, 400 MHz): δ=11.73-12.28 (m, 0.5H), 8.03 (s, 0.9H), 7.80 (s, 1.0H), 7.53 (s, 1.1H), 7.37-7.44 (m, 1.1H), 7.29-7.34 (m, 3.0H), 7.00-7.11 (m, 2.1H), 5.12-5.22 (m, 1.0H), 4.91-4.92 (m, 1.0H), 4.93 (s, 2.0H), 4.03 (q, J=6.6 Hz, 2.0H), 3.86 (br t, J=5.1 Hz, 2.1H), 3.45-3.57 (m, 2.1H), 3.20 (d, J=4.5 Hz, 3.0H), 1.34 ppm (t, J=7.0 Hz, 4.0H).

Synthesis of Compound 050:

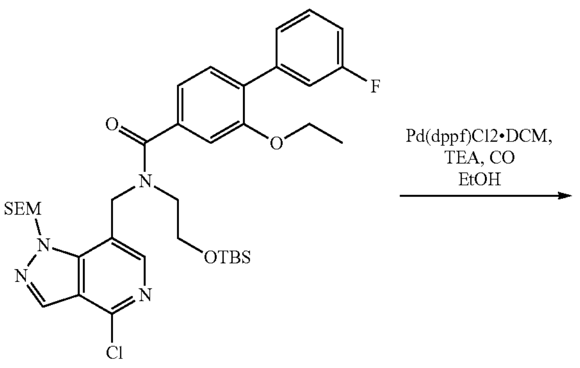

int-30

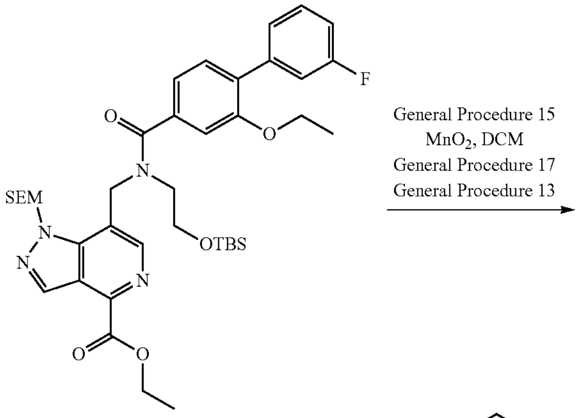

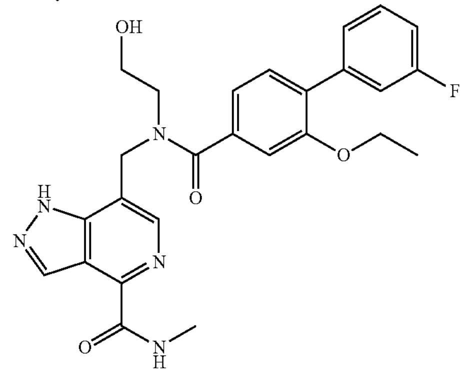

Compound 050

Compound 050 was synthesized using common intermediate 30 from the synthesis of compound 041. Intermediate 30 was subjected to a modified GP12 where the starting material (int-30, 1 eq) was dissolved in EtOH (0.1 M) and treated with $Et_3N$ (3 eq), Pd(dppf)$Cl_2$—$CH_2Cl_2$ (0.05 eq), then degassed and stirred at 80° C. for 12 h under CO (1 eq, 50 PSI) atmosphere. The isolated product was then subjected to GP15, followed by $MnO_2$ (20 eq) in DCM (0.05 M) for 12 h, then GP17, and finally GP13. The residue was purified by prep-HPLC (column: Waters Xbridge 150×25 mm, 5 um;

mobile phase: [water($NH_4HCO_3$)-ACN]; gradient: 18%-48% B over 15 min) and lyophilization. Compound 050 (13.51 mg, 28.29 μmol, 20.43% yield, 100% purity) was obtained as white solid. LCMS: $t_R$=0.438 min, m/z=478.2 [M+H]$^+$. NMR: $^1$H NMR (CHLOROFORM-d, 400 MHz): δ=8.24-8.43 (m, 2H), 7.27-7.40 (m, 4H), 6.92-7.13 (m, 3H), 5.03-5.21 (m, 2H), 4.27 (s, 2H), 3.97-4.09 (m, 2H), 3.77-3.91 (m, 2H), 3.40-3.56 (m, 2H), 2.57-2.67 (m, 2H), 1.34 ppm (br t, J=6.9 Hz, 3H)

Synthesis of Compound 051:

Compound 051 was synthesized by following a similar procedure to compound 041. Intermediate 26 was subjected to GP16, GP5, GP12, and finally GP13. The crude product was purified by prep-HPLC (column: Phenomenex Luna C18 150×25 mm, 10 um; mobile phase: [water(FA)-ACN]; gradient: 18%-48% B over 9 min), and the product was concentrated and lyophilized to give the product. Compound 051 (43.11 mg, 96.12 μmol, 33.31% yield, 100% purity) was obtained as white solid. LCMS: $t_R$=0.451 min, m/z=449.2 [M+H]$^+$. NMR: $^1$H NMR (400 MHz, CHLOROFORM-d) δ ppm 1.36 (t, J=6.88 Hz, 3H) 2.93 (s, 3H) 3.52 (br s, 2H) 3.91 (br d, J=4.00 Hz, 2H) 4.00-4.11 (m, 2H) 5.16 (s, 2H) 7.02-7.09 (m, 3H) 7.28-7.38 (m, 4H) 8.30 (s, 1H) 8.41 (br s, 1H).

Synthesis of Compound 052:

Compound 052 was synthesized by following a similar procedure to compound 041. Intermediate 26 was subjected to GP16, GP4, GP5, GP12, and finally GP13. The crude product was purified by prep-HPLC (column: Waters Xbridge 150×25 mm, 5 um; mobile phase: [water ($NH_4HCO_3$)-ACN]; gradient: 30%-60% B over 9 min) to give the product compound 052 (66.36 mg, 143.48 μmol, 48.60% yield, 100% purity) as white solid. LCMS: $t_R$=0.453 min, m/z=463.2 [M+H]$^+$. NMR: $^1$H NMR (400 MHz, CHLOROFORM-d) δ=8.32-8.24 (m, 1H), 8.22 (s, 1H), 7.40-7.27 (m, 4H), 7.13-7.00 (m, 3H), 5.13 (br d, J=15.0 Hz, 1H), 4.85 (br d, J=14.5 Hz, 1H), 4.40 (br d, J=2.8 Hz, 1H), 4.04 (br d, J=6.0 Hz, 2H), 3.77 (br t, J=10.3 Hz, 1H), 3.66-3.54 (m, 1H), 2.81 (s, 3H), 1.34 (br t, J=6.7 Hz, 3H), 1.27-1.12 (m, 3H)

Synthesis of Compound 053:

Compound 053 was synthesized by following a similar procedure to compound 041. Intermediate 26 was subjected to GP16, GP4, GP5, GP12, GP13. The resulting product was then oxidized with DMP (1.5 eq) in DCM (0.25 M) at 0° C. and stirred for 2 hr. The reaction was filtered, and the filtrate was concentrated to give the crude material which was purified by flash chromatography. Finally, the resulting oxidized product was subjected to Grignard conditions. The starting material was dissolved in THE and treated with MeMgBr (3 M, 579.08 μL, 5 eq) at 0° C. The reaction was stirred at 25° C. for 2 h under $N_2$. The reaction was quenched with sat. aq. $NH_4Cl$ at 0° C. and extracted with EA (×3). The organic phases were combined and washed with brine, dried over anhydrous $Na_2SO_4$, filtered, and concentrated to give a residue. The crude product was purified by prep-HPLC (column: Waters Xbridge 150×25 mm, 5 um; mobile phase: [water($NH_4HCO_3$)-ACN]; gradient: 25%-55% B over 15 min). Compound 053 (20.81 mg, 42.58 μmol, 12.25% yield, 97.5% purity) was obtained as white solid. LCMS: $t_R$=0.459 min, m/z=477.2 [M+H]$^+$. NMR: $^1$H NMR (400 MHz, CHLOROFORM-d) δ=11.75 (br dd, J=5.1, 7.3 Hz, 1H), 8.44-8.35 (m, 1H), 8.23 (s, 1H), 7.40-7.33 (m, 1H), 7.32-7.28 (m, 2H), 7.28-7.27 (m, 1H), 7.07-7.00 (m, 1H), 6.92-6.78 (m, 1H), 5.41 (br s, 1H), 5.53-5.33 (m, 1H), 4.00 (q, J=6.9 Hz, 2H), 3.40 (br s, 2H), 2.89 (br s, 3H), 1.35 (t, J=7.0 Hz, 3H), 1.30-1.17 (m, 5H).

Synthesis of Compound 054:

Compound 054 was synthesized starting from intermediate 28. Int-28 was subjected to GP17, GP5, then finally GP13 resulting in the crude residue of compound 054. The crude product was purified by prep-HPLC (column: Phenomenex luna C18 150×25 mm, 10 um; mobile phase: [water(FA)-ACN]; gradient: 18%-48% B over 9 min) and lyophilization for 12 hr. Compound 054 (10.62 mg, 22.74 μmol, 6.92% yield, 98.6% purity) was obtained as white solid. LCMS: $t_R$=0.449 min, m/z=461.2 $[M+H]^+$. NMR: $^1H$ NMR (400 MHz, CHLOROFORM-d) δ=8.24 (s, 1H), 7.94-7.83 (m, 1H), 7.41-7.34 (m, 1H), 7.34-7.28 (m, 1H), 7.29-7.28 (m, 1H), 7.07-7.03 (m, 1H), 6.84-6.80 (m, 2H), 5.18-5.07 (m, 1H), 5.02 (br s, 1H), 4.90 (br s, 1H), 5.06-4.78 (m, 1H), 4.20 (br s, 1H), 3.93 (br d, J=7.0 Hz, 2H), 2.90 (br s, 3H), 1.33 (t, J=6.8 Hz, 4H).

Synthesis of Compound 055:

Compound 055 was synthesized by following a similar procedure to compound 041. Intermediate 26 was subjected to GP16, GP5, GP8, and finally GP13 resulting in crude 055. The residue was purified by prep-HPLC (column: Waters Xbridge 150×25 mm, 5 um; mobile phase: [water ($NH_4HCO_3$)-ACN]; gradient: 25%-55% B over 9 min), and lyophilized to afford compound 055 (12.03 mg, 27.20 μmol, 18.05% yield, 98% purity) which was obtained as a brown gum. LCMS: $t_R$=0.406 min, m/z=434.2 $[M+H]^+$. NMR: $^1H$ NMR (400 MHz, CHLOROFORM-d) δ=9.11 (br d, J=3.1 Hz, 1H), 8.25 (br s, 2H), 7.39-7.28 (m, 4H), 7.03 (br t, J=7.0 Hz, 3H), 5.03 (br s, 2H), 4.09-3.95 (m, 2H), 3.59-3.33 (m, 2H), 3.00 (br s, 2H), 1.35 (br t, J=6.7 Hz, 3H).

Synthesis of Compound 056 & 057:

Compounds 056 and 057 were synthesized by following a similar procedure to compound 054. Intermediate 28 was subjected to GP17, GP5, and finally GP13 resulting in the crude mixture of 056 and 057. The product was purified by SFC (column: DAICEL CHIRALPAK AD (250 mm×50 mm, 10 um); mobile phase: [$CO_2$-i-PrOH (0.1% $NH_3H_2O$)]; B %: 32%, isocratic elution mode). After SFC, the eluents were concentrated to remove organic solvents and the residual aqueous solutions were lyophilized.

Compound 056 (23.7 mg, 49.10 μmol, 23.30% yield, 98.3% purity) was obtained as off-white solid. LCMS: $t_R$=0.472 min, m/z=4 75.3$[M+H]^+$ NMR: $^1H$ NMR (400 MHz, CHLOROFORM-d) δ=12.50-11.97 (m, 1H), 8.23-8.14 (m, 2H), 7.45-7.31 (m, 5H), 7.14-7.03 (m, 3H), 5.42-5.24 (m, 1H), 4.92-4.76 (m, 1H), 4.67-4.52 (m, 1H), 4.39-4.26 (m, 1H), 4.19-4.03 (m, 3H), 2.59-2.42 (m, 3H), 2.25-2.10 (m, 2H), 1.85-1.80 (m, 1H), 1.82-1.79 (m, 1H), 1.55-1.44 (m, 2H), 1.39 (t, J=6.8 Hz, 4H) SFC: 100% ee.

Compound 057 (38.37 mg, 79.81 μmol, 37.87% yield, 98.7% purity) was obtained as off-white solid. LCMS: $t_R$=0.467 min, m/z=475.3 $[M+H]^+$. $^1H$ NMR: (400 MHz, CHLOROFORM-d) δ=12.48-12.13 (m, 1H), 8.12 (s, 1H), 8.18-8.11 (m, 1H), 7.44-7.28 (m, 5H), 7.13-7.02 (m, 3H), 5.43-5.19 (m, 1H), 4.87-4.68 (m, 1H), 4.60 (br s, 1H), 4.33 (br s, 1H), 4.08 (quin, J=6.7 Hz, 2H), 2.38 (br s, 3H), 2.16 (br s, 1H), 1.87-1.79 (m, 2H), 1.52-1.43 (m, 1H), 1.38 (t, J=6.9 Hz, 3H), 1.26 (br d, J=4.8 Hz, 1H).

Synthesis of Compound 058, 059, 060, and 061:

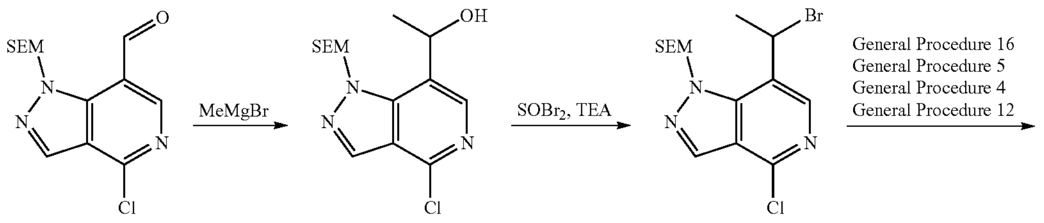

int-27

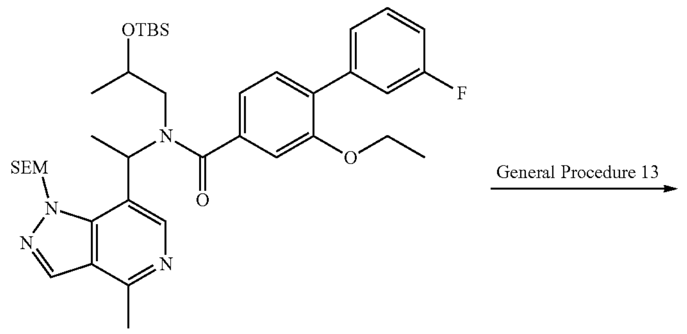

int-29

-continued

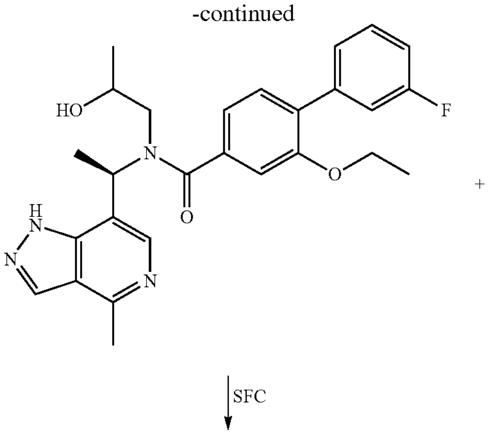

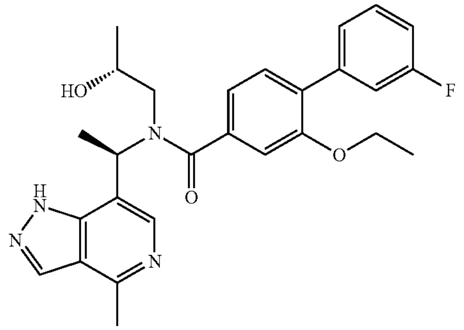

058

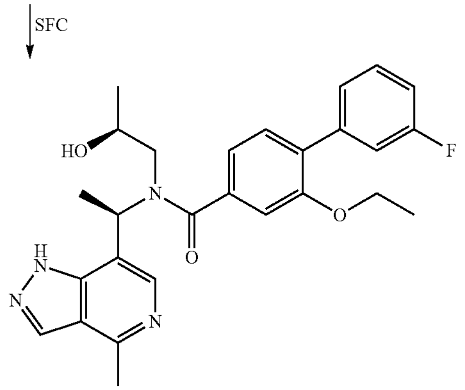

059

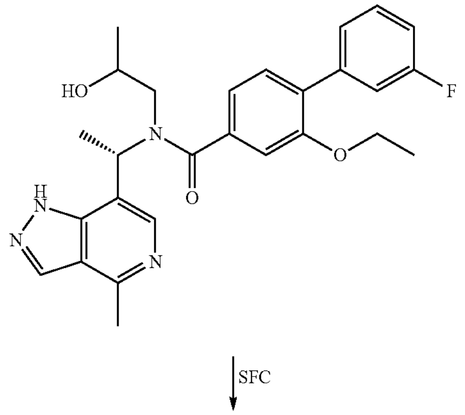

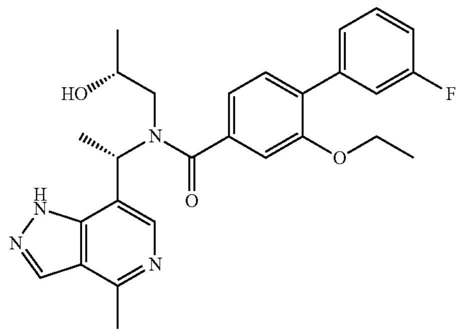

060

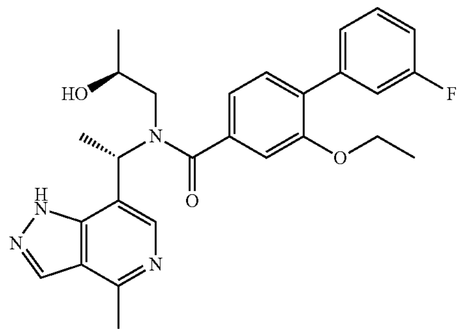

061

Compound 058-061 were synthesized using the synthetic procedure shown above.

Int-27 (1 eq) in THE (0.2M) was treated with MeMgBr (3 M, 3 eq) at −70° C. and stirred for 2 h. The resulting crude product was purified by silica gel chromatography. The purified product was dissolved in DCM and treated with $Et_3N$ (2 eq) and then $SOBr_2$ (2 eq) at 0° C. The reaction was stirred at 20° C. for 12 h under $N_2$ atmosphere. The crude product was purified by silica gel chromatography. The isolated compound was then subject to GP16, GP5, GP4, then GP12 to afford int-29. Intermediate 29 was then subject to GP13 followed by purification by SFC to afford the 4 corresponding products.

Compound 058: LCMS: $t_R$=0.461 min, m/z=477.3 $[M+H]^+$. $^1$H NMR (400 MHz, CHLOROFORM-d) δ=8.23 (s, 1H), 8.18-8.06 (m, 1H), 7.41-7.32 (m, 1H), 7.30-7.24 (m, 4H), 7.07-6.99 (m, 1H), 6.90 (br s, 2H), 3.99 (br s, 2H), 3.79-3.36 (m, 4H), 2.89 (br s, 3H), 1.93 (br d, J=6.8 Hz, 3H), 1.34 (br t, J=6.9 Hz, 3H), 1.04 (br s, 2H). SFC: 100% ee.

Compound 059: LCMS: $t_R$=0.467 min, m/z=477.3 $[M+H]^+$. $^1$H NMR: (400 MHz, CHLOROFORM-d) δ=8.23 (s, 1H), 8.33-8.08 (m, 1H), 7.37-7.34 (m, 1H), 7.39-7.25 (m, 4H), 7.06-7.01 (m, 1H), 6.94 (br s, 2H), 4.00 (br s, 2H), 3.53 (br s, 3H), 3.41 (br s, 1H), 2.88 (br s, 3H), 1.93 (br d, J=7.0 Hz, 3H), 1.35 (t, J=6.9 Hz, 3H), 0.97 (br s, 2H). SFC: 97.95% ee.

Compound 060: LCMS: $t_R$=0.464 min, m/z=477.3 $(M+H^+)$ $^1$H NMR (400 MHz, CHLOROFORM-d) δ=8.30 (br s, 2H), 7.38-7.35 (m, 1H), 7.39-7.34 (m, 1H), 7.33-7.27 (m, 1H), 7.38-7.24 (m, 4H), 7.12 (br s, 1H), 7.06-7.00 (m, 1H), 5.80-5.57 (m, 1H), 4.03 (br s, 3H), 3.87-3.50 (m, 2H), 3.47-3.35 (m, 1H), 2.99 (br s, 3H), 1.97 (br d, J=6.7 Hz, 3H), 1.40-1.31 (m, 3H), 1.04 (br s, 1H), 1.08-0.99 (m, 1H). EE: 99.56%.

Compound 061: LCMS: $t_R$=0.474 min, m/z=477.3 $[M+H]^+$ $^1$H NMR (400 MHz, CHLOROFORM-d) δ=8.27 (s, 1H), 8.41-8.22 (m, 1H), 7.38-7.31 (m, 1H), 7.41-7.31 (m, 1H), 7.31-7.26 (m, 4H), 7.13 (br s, 1H), 7.06-7.00 (m, 1H), 5.71 (br s, 1H), 4.03 (br s, 3H), 3.61 (br s, 2H), 3.46-3.31 (m, 1H), 3.00-2.90 (m, 1H), 2.94 (br s, 2H), 1.96 (br d, J=6.7 Hz, 3H), 1.38-1.26 (m, 3H), 1.08-1.01 (m, 1H), 1.03 (br s, 1H). SFC: 99.10% ee.

Synthesis of Compound 062:

Compound 062 was synthesized starting from int-29 (above). Intermediate 29 was dissolved in DCM (0.1 M) and treated with DMP (3 eq) at 0° C. The reaction was stirred for 1.5 h. The reaction was worked-up and the crude product was purified by prep-HPLC. The purified product was then dissolved in THF (0.15 M) and treated with MeMgBr (3 M, 5 eq) at 0° C. The mixture was stirred at 20° C. for 2 h. The reaction was quenched with sat. NH4Cl (50 mL) at 0° C. and extracted with EA (×3). The organic phases were washed with brine, dried over anhydrous $Na_2SO_4$, filtered, and concentrated to give a residue. The residue was purified by preparative HPLC (column: Waters Xbridge 150×25 mm, 5 um; mobile phase: [water($NH_4HCO_3$)-ACN]; gradient: 36%-66% B over 9 min), LCMS showed the product was not clean and therefore was re-purified by prep-HPLC (column: Phenomenex luna C18 150×25 mm, 10 um; mobile phase: [water(FA)-ACN]; gradient: 15%-45% B over 9 min). Compound 062 (1.62 mg, 3.30 μmol, 2.09% yield, 100% purity) was obtained as white solid. LCMS: $t_R$=0.475 min, m/z=491.3 $[M+H]^+$. $^1$H NMR (400 MHz, CHLOROFORM-d) δ=8.35-8.19 (m, 2H), 7.34 (dd, J=6.0, 8.0 Hz, 2H), 7.24 (br s, 3H), 7.08-6.97 (m, 2H), 6.85 (br s, 1H), 4.12-3.90 (m, 2H), 2.84 (br s, 2H), 1.96 (br d, J=7.0 Hz, 3H), 1.32 (br s, 6H), 1.25 (br s, 3H).

Synthesis of Compound 063

Compound 063 was prepared in a similar manner to the scheme shown for Compound 067 using 2-fluoroethane-1-amine. Compound 063 was isolated as a white solid (76.02 mg, 146.33 μmol, 32.67% yield, 95% purity). LCMS: RT=0.432 min, m/z=494.2 [M+H]+ $^1$H NMR (400 MHz, CHLOROFORM-d) δ=12.38-11.58 (m, 1H), 9.04 (s, 1H), 8.34 (s, 1H), 8.18 (s, 1H), 7.32-7.24 (m, 2H), 7.23-7.19 (m, 2H), 7.01-6.92 (m, 3H), 6.32 (br dd, J=5.3, 10.0 Hz, 1H), 4.56 (t, J=4.8 Hz, 1H), 4.45 (t, J=4.8 Hz, 1H), 3.98 (br dd, J=7.2, 15.4 Hz, 2H), 2.96 (br d, J=4.6 Hz, 1H), 2.92-2.83 (m, 3H), 2.74 (s, 3H), 2.58-2.43 (m, 1H), 2.39-2.27 (m, 1H), 1.29 (t, J=6.9 Hz, 3H).

Synthesis of Compound 064

Compound 064 was prepared in a similar manner to the scheme shown for Compound 067 using bis(2-fluoroethyl) amine. Compound 064 was isolated as a white solid (87.64 mg, 164.73 μmol, 38.13% yield, 98.5% purity). LCMS: Rt=0.422 min, m/z=540.2[M+H]+ HPLC: Rt=1.131 min. 1HNMR: (400 MHz, CHLOROFORM-d) δ=12.26 (br d, J=1.2 Hz, 1H), 9.13 (s, 1H), 8.43 (s, 1H), 8.29 (s, 1H), 7.41-7.28 (m, 4H), 7.10-7.02 (m, 3H), 6.37 (br dd, J=4.4, 10.0 Hz, 1H), 4.64 (t, J=4.8 Hz, 2H), 4.52 (t, J=4.8 Hz, 2H), 4.14-3.99 (m, 2H), 3.02 (t, J=4.8 Hz, 2H), 2.98-2.87 (m, 4H), 2.83 (s, 3H), 2.62-2.50 (m, 1H), 2.44-2.33 (m, 1H), 1.37 (t, J=6.8 Hz, 3H).

Synthesis of Compound 066

Compound 066 was prepared according to the scheme shown for Compound 067 using ethylmethyl amine instead of 2. Compound 066 (17.45 mg, 35.29 μmol, 10.50% yield, 99% purity) was obtained as a white solid. LCMS: RT=0.408 min, m/z=409.3 [M+H]+ $^1$H NMR (400 MHz, CHLOROFORM-d) δ=9.03 (s, 1H), 8.36 (s, 1H), 8.18 (s, 1H), 7.32-7.24 (m, 2H), 7.24-7.17 (m, 2H), 7.06-6.90 (m, 3H), 6.22 (br dd, J=5.0, 8.5 Hz, 1H), 4.11-3.88 (m, 2H), 2.76 (s, 3H), 2.68-2.48 (m, 5H), 2.37 (br d, J=5.1 Hz, 1H), 2.32 (s, 3H), 1.29 (br t, J=6.8 Hz, 3H), 1.06 (br t, J=7.0 Hz, 3H).

Synthesis of Compound 069

Compound 069 was prepared in a similar manner to Compound 073 below and was isolated as a white solid (75.5 mg, 154.89 μmol, 35.12% yield, 99% purity). LCMS: RT=0.380 min, m/z=483.3 [M+2+H]+ $^1$H NMR (400 MHz, CHLOROFORM-d) δ ppm 1.34 (br t, J=6.94 Hz, 3H) 2.54-2.66 (m, 1H) 2.73 (s, 6H) 2.79-2.99 (m, 5H) 3.14-3.26 (m, 1H) 3.97-4.19 (m, 2H) 6.24 (br dd, J=9.32, 4.94 Hz, 1H) 7.10-7.20 (m, 2H) 7.32 (d, J=7.63 Hz, 1H) 7.46-7.53 (m, 1H) 7.60 (br d, J=7.75 Hz, 1H) 7.74 (br d, J=7.88 Hz, 1H) 7.82 (s, 1H) 8.28 (s, 1H) 8.41 (s, 2H) 8.45 (s, 1H) 9.13 (s, 1H).

Synthesis of Compound 070

Compound 070 was prepared following the procedure provided for 077 using 3-fluoroazetidine HCl instead of 2. Compound 070 (50.30 mg, 94.48 μmol, 21.09% yield, 94.96% purity) was obtained as a white solid. LCMS: RT=0.408 min, m/z=506.3 [M+H]+ $^1$H NMR (400 MHz, CHLOROFORM-d) δ=9.05 (s, 1H), 8.32 (s, 1H), 8.20 (s, 1H), 7.33-7.25 (m, 2H), 7.22 (br d, J=7.6 Hz, 2H), 7.04-6.90 (m, 3H), 6.23 (br dd, J=5.5, 9.4 Hz, 1H), 5.26-4.97 (m, 1H), 3.99 (br dd, J=7.2, 17.7 Hz, 2H), 3.77 (br dd, J=6.3, 14.4 Hz, 2H), 3.29-3.16 (m, 2H), 2.77 (br s, 1H), 2.74 (s, 3H), 2.71 (br s, 1H), 2.43-2.16 (m, 2H), 1.29 (t, J=6.9 Hz, 3H).

Synthesis of Compound 073

Compound 073 was prepared following the steps of GP5-8. The resulting product was then oxidized with DMP (1.5 eq) in DCM (0.25 M) at 0° C. and stirred for 2 hr. The reaction was filtered, and the filtrate was concentrated to give the crude material which was purified by flash chromatography. Compound 073 was then prepared following the scheme shown for compound 076. Compound 073 (142.34 mg, 274.69 μmol, 44.81% yield, 99.5% purity) was obtained as white solid. LCMS: Rt=0.396 min, m/z=470.3 (M+H+). $^1$H NMR: (400 MHz, METHANOL-d4) δ=9.15 (s, 1H), 8.50 (br s, 2H), 8.42 (s, 1H), 7.47 (br s, 1H), 7.41-7.33 (m, 4H), 7.32-7.25 (m, 2H), 7.15 (br d, J=7.2 Hz, 1H), 6.33 (br s, 1H), 3.77 (br s, 1H), 3.41-3.33 (m, 1H), 2.95 (br s, 7H), 2.73 (br s, 1H), 3.05-2.61 (m, 1H), 0.84-0.51 (m, 4H).

Synthesis of Compound 074

Compound 074 was prepared following the steps of GP11-13. The resulting product was then oxidized with DMP (1.5 eq) in DCM (0.25 M) at 0° C. and stirred for 2 hr. The reaction was filtered, and the filtrate was concentrated to give the crude material which was purified by flash chromatography. N-methylation was performed by using the oxidized product (190 mg, 429.37 μmol, 1 eq) in DCE (5 mL) was added $Me_2NH$ (2 M, 1.07 mL, 5 eq), AcOH (2.58 mg, 42.94 μmol, 2.46 μL, 0.1 eq) and Molecular sieve 4 A (50 mg, 429.37 μmol, 1 eq) stirred at 20° C. for 4 hr, then added $NaBH(OAc)_3$ (273.00 mg, 1.29 mmol, 3 eq) at 0° C. under $N_2$ and stirred for 12 hr. The reaction mixture was poured into water (20 mL) under $N_2$ and extracted by DCM (20 mL×3), the organic phase was combined and washed with brine (20 mL×2), dried with anhydrous $Na_2SO_4$, filtered and concentrated to give a crude product in vacuo. The residue was purified by prep-HPLC: column: Phenomenex luna C18 150*25 mm*10 um; mobile phase: [water(FA)-ACN]; gradient: 3%-33% B over 10 min and lyophilization to get the product compound 074 (53.48 mg, 111.92 μmol, 26.07% yield, 98.69% purity) was obtained as a yellow gum. LCMS: Rt=0.421 min, m/z=472.3[M+H]+ HPLC: Rt=1.040 min $^1H$ NMR ((400 MHz, CHLOROFORM-d) δ=8.45 (s, 1H), 8.30 (s, 1H), 8.24 (s, 1H), 7.54 (d, J=7.2 Hz, 2H), 7.46-7.31 (m, 4H), 7.16-7.10 (m, 2H), 6.22 (br dd, J=5.6, 9.2 Hz, 1H), 4.14-4.03 (m, 2H), 3.04-2.95 (m, 1H), 2.86 (s, 6H), 2.81-2.69 (m, 2H), 2.61 (s, 6H), 2.58-2.47 (m, 1H), 1.36 (t, J=6.8 Hz, 3H).

Synthesis of Compound 075

Compound 075 was prepared according to the scheme shown for Compound 067 using dimethylamine. A Suzuki-Miyaura. Alkylation was then performed according to GP12 to isolate Compound 075 as a light yellow solid (64.37 mg, 120.18 μmol, 70.45% yield, 100% purity). LCMS: RT=0.422 min, m/z=490.2 [M+H]+ $^1H$ NMR (400 MHz, CHLOROFORM-d) δ=8.48 (s, 1H), 8.29 (s, 1H), 8.23 (s, 1H), 7.35 (td, J=2.9, 7.8 Hz, 2H), 7.31-7.27 (m, 2H), 7.15-7.08 (m, 2H), 7.03 (s, 1H), 6.21 (br d, J=3.4 Hz, 1H), 4.18-3.98 (m, 2H), 3.01-2.89 (m, 1H), 2.88-2.82 (m, 6H), 2.79-2.64 (m, 2H), 2.57 (s, 6H), 2.54-2.47 (m, 1H), 1.36 (t, J=6.8 Hz, 3H).

Synthesis of Compound 040

Compound 040 was prepared following the steps of GP4 and GP11-13, followed by oxidation with DMP in DCM or IBX in DMSO. The crude was treated and purified in the same manner as Compound 036. Compound 040 was then prepared according to the following scheme (see also synthesis of Compound 186 below):

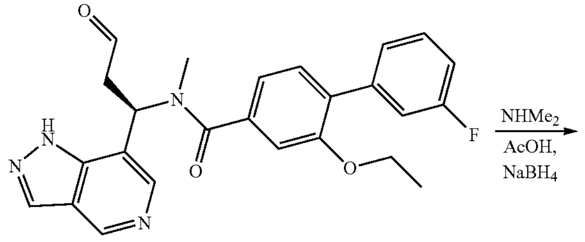

7

-continued

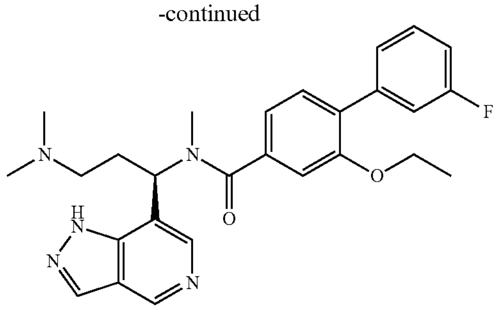

040

To a solution of compound 7 (60 mg, 134.39 μmol, 1 eq) in MeOH (1.5 mL) was added dimethylamine (2 M, 1.5 mL, 22.32 eq), the reaction mixture was stirred at 20° C. for 11 hr. Then NaBH4 (10.17 mg, 268.77 μmol, 2 eq) was added to the solution slowly at 0° C., the reaction mixture was stirred at 20° C. for 1 hr. After the reaction was completed, the reaction mixture was poured into NH4Cl (10 mL) at 0° C., filtered, the filtrate was concentrated under reduced pressure to give a residue. Then the solution was triturated in DCM/MeOH=10:1) and collected by filtration, the filtrate was concentrated under reduced pressure to give crude product. The crude product was purified by prep-HPLC (column: Phenomenex luna C18 150*25 mm*10 um; mobile phase: [water(FA)-ACN]; gradient: 5%-35% B over 9 min) and freeze-dried to give the product. Compound 040 (10.74 mg, 19.97 μmol, 14.86% yield, 97% purity, FA) was obtained as a yellow solid. $^1H$ NMR (400 MHz, CHLOROFORM-d) δ=9.14 (br s, 1H), 8.45 (br s, 1H), 8.34-8.18 (m, 1H), 7.45-7.29 (m, 4H), 7.20-6.97 (m, 3H), 6.31 (br s, 1H), 4.28-3.91 (m, 2H), 2.88 (br s, 3H), 2.69 (br d, J=11.3 Hz, 2H), 2.49 (br s, 6H), 1.49-1.31 (m, 3H). LCMS: Rt=0.417 min, m/z=476.3 (M+H+).

Synthesis of Compound 224

Compound 224 was prepared by treating Compound 040 with Lawesson's reagent in toluene. Compound 224 was isolated as a yellow solid (26.34 mg, 51.43 μmol, 48.92% yield, 96% purity). LCMS: Rt=0.425 min, m/z=492.2 (M+H+). $^1H$ NMR (400 MHz, CHLOROFORM-d) δ=9.16 (s, 1H), 8.54 (s, 1H), 8.50 (s, 1H), 8.30 (s, 1H), 7.76-7.60 (m, 1H), 7.35 (s, 1H), 7.32-7.29 (m, 2H), 7.28-7.22 (m, 1H), 7.07-6.99 (m, 1H), 6.96-6.82 (m, 2H), 4.13-3.98 (m, 2H), 3.07-2.97 (m, 1H), 2.95 (s, 3H), 2.88-2.73 (m, 2H), 2.69-2.62 (m, 1H), 2.60 (s, 6H), 1.36 (t, J=6.9 Hz, 3H).

Synthesis of Compound 039

Compound 039 was prepared in a similar manner to Compound 040 using methylamine instead of dimethylamine and was isolated as a white solid (4.74 mg, 10.27 μmol, 22.93% yield, and 100% purity). LCMS: Rt=0.565 min, m/z=462.3 (M+H+). $^1H$ NMR (400 MHz, CHLOROFORM-d) δ=9.09 (br s, 1H), 8.38-8.20 (m, 2H), 7.46-7.33 (m, 4H), 7.10-7.03 (m, 3H), 4.27-3.94 (m, 4H), 3.84 (br s, 2H), 3.45-3.16 (m, 1H), 3.01 (s, 3H), 2.37-2.27 (m, 4H), 1.41-1.37 (m, 3H).

Compound 145 was prepared using Compound 040 as starting material. To a solution of compound 040 (140 mg, 294.39 μmol, 1 eq) in DCM (3 mL) was added m-CPBA (145.15 mg, 294.39 μmol, 35% purity, 1 eq) at 0° C. The reaction mixture was stirred at 20° C. for 4 h. The mixture was concentrated to get a residue. The crude product was purified by Prep-HPLC (column: Phenomenex luna C18 150*25 mm*10 um; mobile phase: [water (FA)-ACN]; gradient: 8%-38% B over 10 min and lyophilization. Compound 145 (47.64 mg, 95.12 μmol, 32.31% yield, 98.15% purity) was obtained as a white solid. $^1$H NMR (400 MHz, CHLOROFORM-d) δ=9.14 (s, 1H), 8.50 (br s, 1H), 8.41-8.31 (m, 1H), 8.28 (s, 1H), 7.35 (br dd, J=4.0, 7.6 Hz, 2H), 7.30 (br s, 1H), 7.27-7.22 (m, 1H), 7.21-7.11 (m, 2H), 7.07-7.00 (m, 1H), 6.28 (br dd, J=4.4, 9.6 Hz, 1H), 4.16-4.00 (m, 2H), 3.90 (br t, J=10.0 Hz, 1H), 3.75-3.62 (m, 1H), 3.61-3.37 (m, 6H), 3.34-3.21 (m, 1H), 2.91 (s, 3H), 2.78 (br d, J=11.8 Hz, 1H), 1.36 (br t, J=6.8 Hz, 3H). LCMS: Rt=0.430 min, m/z=492.2 (M+H+).

Synthesis of Compound 067

Compound 067 was prepared in a similar manner to Compound 040 using 2-fluoro-N-methylethan-1-amine. Compound 067 (87.64 mg, 164.73 μmol, 38.13% yield, 98.5% purity) as a light yellow solid. LCMS: Rt=0.438 min, m/z=524.2[M+H]+ HPLC: Rt=1.163 min. 1H NMR: (400 MHz, CHLOROFORM-d) δ=9.14 (s, 1H), 8.44 (s, 1H), 8.28 (s, 1H), 7.54 (s, 1H), 7.44-7.40 (m, 1H), 7.37-7.31 (m, 3H), 7.11-7.06 (m, 2H), 6.33 (br dd, J=4.8, 10.2 Hz, 1H), 4.69 (t, J=4.4 Hz, 1H), 4.57 (t, J=4.4 Hz, 1H), 4.16-3.98 (m, 2H), 2.95-2.89 (m, 1H), 2.87-2.75 (m, 6H), 2.65-2.53 (m, 1H), 2.47 (s, 3H), 2.43 (br d, J=7.2 Hz, 1H), 1.37 (t, J=6.8 Hz, 3H).

Synthesis of Compound 136

Compound 136 was prepared in a similar manner to Compound 067 and was obtained as a white solid (22.62 mg, 47.57 μmol, 45.24% yield). LCMS: RT=0.408 min, m/z=476.3 [M+H]+ $^1$H NMR (400 MHz, METHANOL-d4) δ=9.60 (s, 1H), 8.92 (s, 1H), 8.73 (br s, 1H), 7.51 (d, J=7.2 Hz, 2H), 7.45-7.29 (m, 4H), 7.25-7.10 (m, 2H), 6.49 (br d, J=2.2 Hz, 1H), 4.82 (br t, J=4.3 Hz, 2H), 4.19-3.89 (m, 2H), 3.70-3.53 (m, 2H), 3.45 (br s, 2H), 3.14-2.99 (m, 1H), 2.95 (br s, 3H), 2.86-2.64 (m, 1H), 1.33 (br t, J=6.6 Hz, 3H).

Synthesis of Compound 137

Compound 137 was prepared in a similar manner to Compound 067 and was obtained as an off-white solid (27.60 mg, 52.49 μmol, 11.72% yield, 99.2% purity). LCMS: Rt=0.439 min, m/z=522.3 (M+H+) $^1$H NMR (400 MHz, CHLOROFORM-d) δ=12.21 (br s, 1H), 9.15 (s, 1H), 8.45 (s, 1H), 8.29 (s, 1H), 7.44-7.30 (m, 4H), 7.12-7.03 (m, 3H), 6.36 (br dd, J=5.6, 9.2 Hz, 1H), 4.62 (br t, J=5.4 Hz, 1H), 4.50 (br t, J=5.7 Hz, 1H), 4.18-4.00 (m, 2H), 2.85 (s, 3H), 2.69-2.56 (m, 4H), 2.54-2.41 (m, 2H), 2.35 (s, 3H), 1.97-1.82 (m, 2H), 1.40 (t, J=7.0 Hz, 3H).

Synthesis of Compound 138

Compound 138 was prepared in a similar manner to Compound 067 and was obtained as a brown gum (36.48 mg, 71.71 μmol, 85.99% yield, 99% purity). $^1$H NMR (400 MHz, CHLOROFORM-d) δ ppm 1.34 (t, J=6.88 Hz, 3H) 1.78-1.94 (m, 2H) 2.32 (s, 3H) 2.44 (td, J=13.76, 6.75 Hz, 2H) 2.54-2.65 (m, 4H) 2.82 (s, 3H) 3.95-4.14 (m, 2H) 4.40-4.64 (m, 2H) 6.33 (br dd, J=9.01, 5.75 Hz, 1H) 7.02-7.10 (m, 2H) 7.31-7.44 (m, 4H) 7.53 (d, J=7.50 Hz, 2H) 8.25 (s, 1H) 8.42 (s, 1H) 9.11 (s, 1H) 12.23 (br s, 1H). LCMS: Rt=0.427 min, m/z=504.2 (M+H+).

Synthesis of Compound 139

Compound 139 was prepared in a similar manner to Compound 067 and was obtained as an off-white solid (34.01 mg, 69.47 μmol, 14.88% yield). LCMS: Rt=0.420 min, m/z=490.2[M+H]+ HPLC: Rt=1.080 min. 1H NMR: (400 MHz, CHLOROFORM-d) δ=9.06 (s, 1H), 8.51 (s, 1H), 8.41 (s, 1H), 8.24 (s, 1H), 7.52 (d, J=7.2 Hz, 2H), 7.43-7.37 (m, 2H), 7.37-7.31 (m, 2H), 7.11-7.03 (m, 2H), 6.41-6.24 (m, 1H), 4.62 (br t, J=5.6 Hz, 1H), 4.50 (br t, J=5.6 Hz, 1H), 4.08-3.99 (m, 2H), 3.16-3.00 (m, 4H), 2.80 (s, 4H), 2.68-2.57 (m, 1H), 2.17-2.01 (m, 2H), 1.34 (t, J=6.8 Hz, 3H).

Synthesis of Compound 155

Compound 155 was prepared in a similar manner to Compound 067 and was obtained as a white solid (153.25 mg, 306.76 μmol, 65.72% yield, 98% purity). LCMS: Rt=0.392 min, m/z=490.3[M+H]+ $^1$H NMR (400 MHz, CHLOROFORM-d) δ=12.41-12.04 (m, 1H), 9.14 (s, 1H), 8.45 (s, 1H), 8.29 (s, 1H), 7.57 (d, J=7.6 Hz, 2H), 7.46-7.40 (m, 2H), 7.38 (br d, J=7.7 Hz, 2H), 7.15-7.08 (m, 2H), 6.36 (br dd, J=4.8, 10.0 Hz, 1H), 4.69 (t, J=4.6 Hz, 1H), 4.57 (t, J=4.6 Hz, 1H), 4.08 (br dd, J=7.4, 15.6 Hz, 2H), 2.88 (br s, 1H), 2.86 (s, 3H), 2.81 (br s, 1H), 2.77 (s, 2H), 2.63-2.52 (m, 1H), 2.46 (s, 3H), 2.44-2.35 (m, 1H), 1.38 (t, J=6.9 Hz, 3H).

Synthesis of Compound 184

Compound 184 was prepared in a similar manner to Compound 067. Compound 184 (35.11 mg, 66.64 μmol, 22.67% yield, 99% purity) was obtained as a white solid. LCMS: Rt=0.408 min, m/z=522.3[M+H]+ $^1$H NMR (400 MHz, CHLOROFORM-d) δ=13.03-11.15 (m, 1H), 9.14 (s, 1H), 8.45 (s, 1H), 8.28 (s, 1H), 7.43-7.34 (m, 2H), 7.32 (br d, J=7.0 Hz, 2H), 7.14-7.01 (m, 3H), 6.35 (br dd, J=4.9, 9.8 Hz, 1H), 4.66 (t, J=4.8 Hz, 1H), 4.54 (t, J=4.8 Hz, 1H), 4.08 (br dd, J=7.3, 15.8 Hz, 2H), 2.97-2.93 (m, 1H), 2.90-2.85 (m, 2H), 2.84 (s, 3H), 2.83-2.79 (m, 1H), 2.74 (q, J=7.1 Hz, 2H), 2.59-2.50 (m, 1H), 2.43 (br s, 1H), 1.38 (t, J=6.9 Hz, 3H), 1.10 (t, J=7.1 Hz, 3H).

Synthesis Compound 076

Compound 076 (124.7 mg, 241.27 μmol, 28.77% yield, 97.91% purity) was prepared in a similar manner to Compound 040 and was obtained as a yellow gum. LCMS: Rt=0.441 min, m/z=506.2[M+H]+ HPLC: Rt=1.138 min. $^1$H NMR (400 MHz, CHLOROFORM-d) δ=8.39 (s, 2H), 8.35 (s, 1H), 8.27 (s, 1H), 7.55 (s, 1H), 7.44-7.39 (m, 1H), 7.37-7.31 (m, 3H), 7.18-7.12 (m, 2H), 6.20 (br dd, J=5.6, 9.2 Hz, 1H), 4.19-4.00 (m, 2H), 3.29-3.15 (m, 1H), 2.92 (br d, J=4.4 Hz, 1H), 2.90-2.86 (m, 6H), 2.83 (br s, 1H), 2.75 (s, 6H), 2.63 (br dd, J=6.4, 11.6 Hz, 1H), 1.37 (t, J=6.8 Hz, 3H).

Synthesis of Compound 068

Compound 068 was prepared in a similar manner to Compound 076 and was isolated as a yellow solid (155.02 mg, 293.98 μmol, 44.92% yield, 99% purity). LCMS: Rt=0.412 min, m/z=522.5 (M+H+) $^1$H NMR (400 MHz, METHANOL-d4) δ ppm 1.12-1.28 (m, 3H) 2.56-2.66 (m, 1H) 2.72 (br s, 3H) 2.78 (br d, J=8.00 Hz, 1H) 2.89 (br s, 7H) 3.27 (br s, 2H) 3.95 (br s, 2H) 4.97 (s, 2H) 6.21 (br s, 1H) 6.95-7.09 (m, 2H) 7.19-7.33 (m, 4H) 7.41 (s, 1H) 8.25 (s, 2H) 8.28 (br s, 1H) 8.52 (s, 1H).

Synthesis of Compound 096

Compound 096 was prepared in a similar manner to Compound 040. Compound 096 (6090.70 mg, 12.78 mmol, 89.82% yield, 96% purity) was obtained as an off-white solid. LCMS: Rt=0.405 min, m/z=458.2 (M+H+). $^1$H NMR (400 MHz, CHLOROFORM-d) δ=1.35 (br t, J=6.88 Hz, 3H) 2.33 (s, 6H) 2.37-2.42 (m, 1H) 2.46-2.51 (m, 1H) 2.51-2.58 (m, 2H) 2.82 (s, 3H) 3.94-4.15 (m, 2H) 6.32 (br d, J=9.13 Hz, 1H) 7.03-7.12 (m, 2H) 7.30-7.37 (m, 2H) 7.37-7.44 (m, 2H) 7.53 (d, J=7.25 Hz, 2H) 8.25 (s, 1H) 8.42 (s, 1H) 9.10 (s, 1H).

Synthesis of Compound 135

Compound 135 was prepared in a similar manner to Compound 040. Compound 135 (16.76 mg, 36.34 μmol, 29.62% yield, 99% purity) was obtained as off-white solid. LCMS: RT=0.493 min, m/z=457.3 [M+2+H]+ $^1$H NMR (400 MHz, CHLOROFORM-d) δ ppm 1.35 (t, J=6.88 Hz, 3H) 2.34 (s, 6H) 2.36-2.48 (m, 2H) 2.49-2.57 (m, 2H) 2.77 (s, 3H) 3.95-4.14 (m, 2H) 6.37 (br dd, J=9.07, 5.57 Hz, 1H) 7.03-7.09 (m, 2H) 7.17 (t, J=7.57 Hz, 1H) 7.32-7.43 (m, 5H) 7.54 (d, J=7.25 Hz, 2H) 7.75 (d, J=8.00 Hz, 1H) 8.11 (s, 1H) 11.73-12.11 (m, 1H).

Synthesis of Compound 146

Compound 146 was prepared in a similar manner to Compound 076 and was isolated as a white solid (14.62 mg, 32.60 μmol, 4.26% yield, 94% purity). LCMS: RT=0.412 min, m/z=422.2 [M+2+H]+ $^1$H NMR (400 MHz, CHLOROFORM-d) δ ppm 0.64-0.73 (m, 2H) 0.92-1.02 (m, 2H) 1.45 (br t, J=6.82 Hz, 3H) 2.18-2.29 (m, 1H) 2.46-2.58 (m, 1H) 2.65 (s, 6H) 2.76 (br s, 1H) 2.81 (br s, 3H) 2.86 (br s, 1H) 3.00-3.12 (m, 1H) 4.01-4.19 (m, 2H) 6.13-6.27 (m, 1H) 6.81 (d, J=7.75 Hz, 1H) 6.95-7.04 (m, 2H) 8.26 (s, 1H) 8.42 (s, 1H) 8.43-8.52 (m, 1H) 9.12 (s, 1H).

Synthesis of Compound 149

Compound 149 was prepared in a similar manner to Compounds 008 and 076. Compound 149 (20.64 mg, 41.31 μmol, 21.37% yield, 99% purity) was obtained as a white solid. LCMS: Rt=0.392 min, m/z=495.3[M+H]+ $^1$H NMR (400 MHz, CHLOROFORM-d) δ=9.06 (br s, 1H), 8.38 (br s, 2H), 8.20 (s, 1H), 7.68 (s, 1H), 7.53 (s, 2H), 7.42 (br s, 2H), 7.24 (br d, J=7.6 Hz, 1H), 7.17-7.07 (m, 1H), 6.19 (br s, 1H), 3.89-3.60 (m, 1H), 3.05-2.87 (m, 1H), 2.80 (s, 3H), 2.76-2.62 (m, 2H), 2.54 (s, 6H), 2.51-2.40 (m, 1H), 0.88-0.47 (m, 4H).

Synthesis of Compound 156

Compound 156 was prepared in a similar manner to Compounds 008 and 076 and was obtained as a white solid (113.37 mg, 257.68 μmol, 36.88% yield, 99% purity). LCMS: RT=0.413 min, m/z=436.2 [M+2+H]+ $^1$H NMR (400 MHz, CHLOROFORM-d) δ ppm 1.39 (br t, J=6.85 Hz, 3H) 1.75-1.84 (m, 1H) 1.95-2.13 (m, 3H) 2.27-2.36 (m, 2H) 2.47-2.59 (m, 1H) 2.65 (s, 6H) 2.76 (br s, 1H) 2.81 (s, 3H) 2.83-2.90 (m, 1H) 3.00-3.13 (m, 1H) 3.71 (quin, J=8.53 Hz, 1H) 3.93-4.10 (m, 2H) 6.16-6.25 (m, 1H) 6.92 (s, 1H) 7.03 (br d, J=7.58 Hz, 1H) 7.20 (br d, J=7.70 Hz, 1H) 8.25 (s, 1H) 8.42 (br s, 1H) 8.44-8.60 (m, 1H) 9.11 (s, 1H).

Synthesis of Compound 158

Compound 158 was prepared in a similar manner to Compounds 008 and 076 and was obtained as a white solid (54.55 mg, 127.50 μmol, 33.09% yield, 99% purity). LCMS: RT=0.409 min, m/z=424.3 [M+2+H]+ $^1$H NMR (400 MHz, CHLOROFORM-d) δ ppm 1.19 (br t, J=5.44 Hz, 6H) 1.42 (br d, J=4.40 Hz, 3H) 2.53 (br s, 1H) 2.61 (br d, J=4.16 Hz, 6H) 2.73 (br s, 2H) 2.81 (br s, 3H) 2.93-3.06 (m, 1H) 3.25-3.39 (m, 1H) 3.93-4.17 (m, 2H) 6.22 (br s, 1H) 6.97 (br s, 1H) 7.03 (br s, 1H) 7.16-7.24 (m, 1H) 8.25 (br d, J=4.28 Hz, 1H) 8.42 (br s, 1H) 8.48 (br s, 1H) 9.11 (br s, 1H).

Synthesis of Compound 161

Compound 161 was prepared in a similar manner to Compounds 008 and 076 and was obtained as a white solid (80.16 mg, 183.19 μmol, 46.77% yield, 100% purity). LCMS: RT=0.816 min, m/z=438.3 [M+H]+ $^1$H NMR (400 MHz, DMSO-d6) δ=9.07 (s, 1H), 8.40-8.31 (m, 2H), 8.27-8.17 (m, 1H), 7.18 (d, J=7.8 Hz, 1H), 6.91 (d, J=7.8 Hz, 1H), 6.88 (s, 1H), 5.89 (br s, 1H), 3.97 (br dd, J=3.6, 6.3 Hz, 2H), 3.05 (br d, J=7.0 Hz, 1H), 2.85 (s, 3H), 2.42-2.32 (m, 4H), 2.19 (s, 6H), 1.63-1.49 (m, 2H), 1.30 (t, J=6.9 Hz, 3H), 1.16 (d, J=6.9 Hz, 3H), 0.79 (t, J=7.4 Hz, 3H).

Synthesis of Compound 162

Compound 162 was prepared in a similar manner to Compounds 008 and 076 and was obtained as an off-white solid (56.03 mg, 115.70 μmol, 12.91% yield, 98.2% purity). LCMS: Rt=0.440 min, m/z=476.3 (M+H+). $^1$H NMR (400 MHz, CHLOROFORM-d) δ=9.12 (s, 1H), 8.50 (br s, 1H), 8.44 (s, 1H), 8.26 (s, 1H), 7.39-7.32 (m, 2H), 7.27 (s, 2H), 7.16-7.08 (m, 2H), 7.06-6.99 (m, 1H), 6.31-6.20 (m, 1H), 4.17-3.97 (m, 2H), 3.02-2.93 (m, 1H), 2.85 (s, 3H), 2.80-2.68 (m, 2H), 2.58 (s, 6H), 2.56-2.48 (m, 1H), 1.36 (br t, J=6.8 Hz, 3H).

Synthesis of Compound 167

Compound 167 was prepared in a similar manner to Compound 076 using ethanamine instead dimethylamine and $NaBH(OAc)_3$. Compound 167 (112.04 mg, 233.24 μmol, 65.09% yield, 99% purity) was obtained as a white solid. LCMS: RT=0.408 min, m/z=476.3 [M+H]+ $^1$H NMR (400 MHz, CHLOROFORM-d) δ=9.04 (s, 1H), 8.65 (s, 1H), 8.41 (s, 1H), 8.22 (s, 1H), 7.40-7.29 (m, 2H), 7.26 (br dd, J=2.2, 6.1 Hz, 2H), 7.11-7.02 (m, 3H), 6.32 (br d, J=4.8 Hz, 1H), 4.10-3.97 (m, 2H), 3.12 (br s, 2H), 3.06-2.96 (m, 2H), 2.94-2.84 (m, 1H), 2.80 (s, 3H), 2.68 (br d, J=5.9 Hz, 1H), 1.34 (td, J=6.9, 13.4 Hz, 6H).

Synthesis of Compound 180

Compound 180 was prepared in a similar manner to Compound 076. Compound 180 (46.23 mg, 111.22 μmol, 49.38% yield, 99% purity) was isolated as a yellow solid. $^1$H NMR (400 MHz, CHLOROFORM-d) δ ppm 1.33 (br t, J=6.94 Hz, 3H) 2.38-2.51 (m, 1H) 2.55 (s, 6H) 2.62 (br d, J=10.13 Hz, 1H) 2.69 (s, 3H) 2.77 (td, J=11.23, 4.94 Hz, 1H) 2.84-2.96 (m, 1H) 3.96 (dt, J=13.26, 6.75 Hz, 2H) 5.02 (s, 2H) 6.14 (br dd, J=9.26, 5.00 Hz, 1H) 6.84-6.96 (m, 3H) 7.21-7.28 (m, 1H) 8.21 (s, 1H) 8.25 (s, 1H) 8.40 (br s, 1H). LCMS: Rt=0.367 min, m/z=412.2 (M+H+).

Synthesis of Compound 189

Compound 189 was prepared in a similar manner to Compound 040. Compound 189 (16.02 mg, 33.42 μmol, 67.38% yield, 99% purity) was obtained as a brown gum. LCMS: Rt=0.483 min, m/z=475.3 (M+H+). $^1$H NMR (400 MHz, CHLOROFORM-d) δ=1.31-1.45 (m, 3H) 2.31-2.55 (m, 8H) 2.57 (br d, J=6.88 Hz, 2H) 2.71-2.96 (m, 3H) 3.94-4.22 (m, 2H) 6.36 (br dd, J=8.69, 5.44 Hz, 1H) 6.99-7.11 (m, 3H) 7.18 (t, J=7.63 Hz, 1H) 7.28-7.42 (m, 5H) 7.76 (d, J=8.13 Hz, 1H) 8.12 (s, 1H) 11.83-11.95 (m, 1H).

Synthesis of Compound 227

Compound 227 was prepared by treating Compound 189 with m-CPBA. Compound 227 was isolated as a white solid (29.73 mg, 57.57 μmol, 34.15% yield, 95% purity). LCMS: Rt=0.510 min, m/z=491.1 (M+H+). $^1$H NMR (400 MHz, CHLOROFORM-d) δ=1.34 (t, J=6.88 Hz, 3H) 2.69-2.80 (m, 1H) 2.89 (s, 3H) 3.08-3.21 (m, 1H) 3.47 (s, 3H) 3.60 (s, 3H) 3.71-3.79 (m, 1H) 4.02-4.14 (m, 3H) 6.40 (br dd, J=9.82, 5.19 Hz, 1H) 7.03 (br t, J=7.82 Hz, 1H) 7.14-7.23 (m, 3H) 7.28-7.38 (m, 4H) 7.44 (br d, J=7.13 Hz, 1H) 7.76 (d, J=8.13 Hz, 1H) 8.11 (s, 1H).

Synthesis of Compound 193

Compound 193 was prepared in a similar manner to Compound 040 using methylamine and $NaBH(OAc)_3$. Compound 193 (6090.70 mg, 12.78 mmol, 89.82% yield, 96% purity) was obtained as a yellow solid. LCMS: Rt=0.400 min, m/z=444.3 (M+H+). $^1$H NMR (400 MHz, CHLOROFORM-d) δ=9.64-9.43 (m, 1H), 8.85 (br s, 1H), 8.61 (br s, 1H), 7.44-7.33 (m, 2H), 7.30-7.16 (m, 4H), 7.13-6.98 (m, 2H), 6.46-6.17 (m, 1H), 3.93 (br d, J=6.6 Hz, 2H), 3.20 (br d, J=1.6 Hz, 2H), 2.83 (br s, 4H), 2.76-2.68 (m, 3H), 2.67-2.56 (m, 1H), 1.26-1.13 (m, 3H).

Synthesis of Compound 194

Compound 194 was prepared in a similar manner to Compound 040. Compound 194 (61.46 mg, 133.26 μmol, 74.20% yield, 99% purity) was obtained as a white solid. LCMS: Rt 0.475 min, m/z=457.2 (M+H+) $^1$H NMR (400 MHz, CHLOROFORM-d) δ=1.35 (br t, J=6.82 Hz, 3H) 2.35 (s, 6H) 2.37-2.49 (m, 2H) 2.49-2.62 (m, 2H) 2.77 (s, 3H) 3.96-4.17 (m, 2H) 6.37 (br dd, J=8.69, 5.44 Hz, 1H) 7.01-7.12 (m, 2H) 7.17 (t, J=7.57 Hz, 1H) 7.30-7.46 (m, 5H) 7.54 (br d, J=7.38 Hz, 2H) 7.75 (d, J=8.00 Hz, 1H) 8.12 (s, 1H) 11.95 (br s, 1H)

Synthesis of Compound 195

Compound 195 was prepared in a similar manner to Compound 040. Compound 195 (50.81 mg, 106.89 μmol, 90.46% yield, 99% purity) was obtained as a white solid. LCMS: Rt 0.510 min, m/z=471.3 (M+H+) $^1$H NMR (400 MHz, CHLOROFORM-d) δ=11.97 (br s, 1H), 8.13 (s, 1H), 7.77 (d, J=7.9 Hz, 1H), 7.44-7.29 (m, 5H), 7.23-7.13 (m, 2H), 7.12-7.01 (m, 2H), 6.44-6.32 (m, 1H), 4.16-3.95 (m, 2H), 2.79 (s, 3H), 2.63-2.51 (m, 2H), 2.51-2.43 (m, 1H), 2.41 (s, 3H), 2.40-2.38 (m, 1H), 2.37 (s, 6H), 1.37 (t, J=6.9 Hz, 3H).

Synthesis of Compound 196

Compound 196 was prepared in a similar manner to Compound 040. Compound 196 (108.81 mg, 224.81 μmol, 55.02% yield, 99.5% purity) was obtained as a white solid. LCMS: Rt 0.488 min, m/z=482.4, M+H+ $^1$H NMR (400 MHz, CHLOROFORM-d) δ=11.88 (br s, 1H), 8.12 (s, 1H), 7.85 (s, 1H), 7.76 (d, J=8.0 Hz, 2H), 7.62 (d, J=7.8 Hz, 1H), 7.55-7.48 (m, 1H), 7.38 (d, J=7.1 Hz, 1H), 7.31 (br d, J=7.9 Hz, 1H), 7.18 (t, J=7.6 Hz, 1H), 7.10-7.05 (m, 2H), 6.37 (br dd, J=5.6, 9.0 Hz, 1H), 4.18-3.98 (m, 2H), 2.77 (s, 3H), 2.57-2.50 (m, 2H), 2.48-2.37 (m, 2H), 2.35 (s, 6H), 1.36 (br t, J=6.9 Hz, 3H). 13C NMR: (101 MHz, CHLOROFORM-d) δ=172.52 (br s, 1C), 155.91 (br s, 1C), 139.84-138.31 (m, 1C), 136.94, 134.79, 133.84, 133.09, 130.99-129.84 (m, 1C), 128.80, 123.75 (br d, J=46.4 Hz, 1C), 120.61 (br d, J=48.5 Hz, 1C), 119.70-118.63 (m, 1C), 111.99 (br d, J=43.5 Hz, 1C), 64.42, 56.79, 51.04 (br s, 1C), 45.83, 31.95 (br s, 1C), 27.16 (br s, 1C), 14.55.

Synthesis of Compound 197

Compound 197 was prepared in a similar manner to Compound 040 using methylamine and NaBH(OAc)$_3$. Compound 197 (33.25 mg, 71.48 μmol, 31.84% yield, 99% purity) was obtained as a white solid. LCMS: Rt=0.498 min, m/z=461.4 (M+H+) $^1$H NMR (400 MHz, CHLOROFORM-d) δ=1.26-1.40 (m, 3H) 2.57-2.78 (m, 6H) 2.82 (br s, 2H) 3.10-3.30 (m, 2H) 3.94-4.15 (m, 2H) 6.57 (br d, J=5.75 Hz, 1H) 6.95-7.05 (m, 2H) 7.07-7.16 (m, 2H) 7.16-7.25 (m, 3H) 7.29-7.40 (m, 2H) 7.66-7.81 (m, 1H) 8.10 (br s, 1H) 9.43-9.62 (m, 1H) 9.78 (br d, J=5.13 Hz, 1H).

Synthesis of Compound 198

Compound 198 was prepared in a similar manner to Compound 040 using NaBH(OAc)$_3$. Compound 198 (20.24 mg, 39.89 μmol, 15.24% yield, 95.9% purity) was obtained as an off-white solid. LCMS: Rt=0.501 min, m/z=487.3 [M+H]+ $^1$H NMR (400 MHz, CHLOROFORM-d) δ=11.74 (br s, 1H), 7.96 (s, 1H), 7.60 (d, J=8.0 Hz, 1H), 7.25-7.13 (m, 3H), 7.11 (s, 2H), 7.09-6.99 (m, 3H), 6.94 (br d, J=7.6 Hz, 1H), 6.86 (br t, J=7.9 Hz, 1H), 6.20 (br d, J=5.4 Hz, 1H), 3.61 (br s, 1H), 2.63 (s, 3H), 2.41 (br d, J=6.9 Hz, 2H), 2.22 (s, 7H), 0.74-0.51 (m, 4H).

Synthesis of Compound 199

Compound 199 was prepared in a similar manner to Compound 040 using NaBH(OAc)$_3$. Compound 199 (5.6 mg, 11.59 μmol, 17.36% yield, 97% purity) was obtained as a brown solid. LCMS: Rt=0.487 min, m/z=469.2[M+H]+ $^1$H NMR (400 MHz, CHLOROFORM-d) δ=8.13 (s, 1H), 7.79 (d, J=8.0 Hz, 1H), 7.53-7.44 (m, 3H), 7.42-7.32 (m, 5H), 7.24-7.16 (m, 2H), 6.35 (br dd, J=4.9, 9.9 Hz, 1H), 3.89-3.80 (m, 1H), 3.37-3.28 (m, 1H), 3.07-3.00 (m, 1H), 2.86 (s, 9H), 2.79-2.54 (m, 2H), 0.86-0.60 (m, 4H).

Synthesis of Compounds 200 and 201

Compounds 200 and 201 were prepared in a similar manner to Compound 040 using NaBH(OAc)$_3$ and separated by SFC. Compound 200 (62.54 mg, 127.23 μmol, 41.44% yield, 99.4% purity) was obtained as a white solid. LCMS: Rt=0.530 min, m/z=489.3[M+H]+ $^1$H NMR (400 MHz, CHLOROFORM-d) δ=11.82 (br s, 1H), 8.13 (s, 1H), 7.40-7.28 (m, 5H), 7.08-7.01 (m, 3H), 6.95 (d, J=7.2 Hz, 1H), 6.31 (br dd, J=5.8, 9.2 Hz, 1H), 4.14-4.00 (m, 2H), 2.80 (s, 3H), 2.69 (br d, J=6.8 Hz, 2H), 2.63 (s, 3H), 2.60-2.42 (m, 9H), 1.36 (t, J=6.8 Hz, 3H). Compound 201 was obtained as a white solid (62.54 mg, 127.23 μmol, 41.44% yield, 99.4% purity). LCMS: Rt=0.536 min, m/z=489.3 [M+H]+ $^1$H NMR (400 MHz, CHLOROFORM-d) δ=11.92-11.69 (m, 1H), 8.13 (s, 1H), 7.40-7.27 (m, 5H), 7.10-6.99 (m, 3H), 6.95 (d, J=7.2 Hz, 1H), 6.31 (br dd, J=5.6, 9.2 Hz, 1H), 4.16-3.98 (m, 2H), 2.81 (s, 3H), 2.73 (br d, J=6.2 Hz, 2H), 2.66-2.46 (m, 11H), 1.36 (t, J=6.8 Hz, 3H).

Synthesis of Compounds 202 and 203

Compounds 202 and 203 were prepared in a similar manner to Compound 040 using NaBH(OAc)$_3$ and separated by SFC. Compound 202 (28.5 mg, 56.93 μmol, 25.91% yield) was obtained as a white solid. LCMS: Rt=0.529 min, m/z=501.3 [M+H]+ $^1$H NMR (400 MHz, CHLOROFORM-d) δ=11.86 (br s, 1H), 8.18-8.08 (m, 1H), 7.44 (s, 1H), 7.39-7.27 (m, 3H), 7.26-7.17 (m, 2H), 7.10 (dd, J=1.2, 7.8 Hz, 1H), 7.06-6.99 (m, 1H), 6.94 (d, J=7.4 Hz, 1H), 6.33 (br dd, J=5.6, 9.4 Hz, 1H), 3.84-3.72 (m, 1H), 2.78 (s, 3H), 2.64 (s, 5H), 2.53-2.33 (m, 8H), 0.88-0.67 (m, 4H). Compound 203 was obtained as a white solid (14.39 mg, 28.75 μmol, 13.08% yield). LCMS: Rt=0.520 min, m/z=501.3 [M+H]+ $^1$H NMR (400 MHz, CHLOROFORM-d) δ=11.99-11.71 (m, 1H), 8.13 (s, 1H), 7.44 (s, 1H), 7.39-7.27 (m, 3H), 7.24-7.16 (m, 2H), 7.10 (br d, J=6.8 Hz, 1H), 7.02 (dt, J=2.4, 8.2 Hz, 1H), 6.94 (d, J=7.2 Hz, 1H), 6.37-6.28 (m, 1H), 3.77 (br d, J=3.2 Hz, 1H), 2.80 (s, 3H), 2.64 (s, 5H), 2.56-2.39 (m, 8H), 0.88-0.68 (m, 4H).

Synthesis of Compounds 204 and 205

Compounds 204 and 205 were prepared in a similar manner to Compound 040 using NaBH(OAc)$_3$ and separated by SFC. Compound 204 (13.66 mg, 29.01 μmol, 27.30% yield, 99.93% purity) was obtained as a white solid. LCMS: Rt=0.525 min, m/z=471.3 [M+H]+ $^1$H NMR (400 MHz, CHLOROFORM-d) δ=11.95 (br s, 1H), 8.14 (s, 1H), 7.59-7.53 (m, 2H), 7.46-7.40 (m, 2H), 7.38-7.33 (m, 2H), 7.29 (s, 1H), 7.12-7.03 (m, 2H), 6.95 (d, J=7.2 Hz, 1H), 6.34 (br dd, J=5.8, 9.2 Hz, 1H), 4.18-3.96 (m, 2H), 2.78 (s, 3H), 2.65 (s, 3H), 2.59-2.48 (m, 2H), 2.47-2.28 (m, 7H), 1.37 (t, J=6.8 Hz, 3H). Compound 205 was obtained as a white solid (25.12 mg, 50.43 μmol, 47.46% yield, 94.47% purity). LCMS: Rt=0.526 min, m/z=471.3 [M+H]+ $^1$H NMR (400 MHz, CHLOROFORM-d) δ=11.95 (br s, 1H), 8.14 (s, 1H), 7.56 (d, J=7.2 Hz, 2H), 7.46-7.39 (m, 2H), 7.38-7.33 (m, 2H), 7.31 (s, 1H), 7.29 (s, 1H), 7.10-7.04 (m, 2H), 6.95 (d, J=7.2 Hz, 1H), 6.34 (br dd, J=5.8, 9.0 Hz, 1H), 4.17-3.98 (m, 2H), 3.94 (s, 1H), 3.88 (s, 1H), 2.78 (s, 3H), 2.65 (s, 3H), 2.58-2.48 (m, 2H), 2.47-2.31 (m, 8H), 1.37 (t, J=6.8 Hz, 3H).

Synthesis of Compounds 208 and 209

Compounds 208 and 209 were prepared in a similar manner to Compound 040 using NaBH(OAc)$_3$ and separated by SFC. Compound 208 (7.77 mg, 18.97 μmol, 19.92% yield) was obtained as a white solid. LCMS: Rt=0.430 min, m/z=410.2[M+H]+ $^1$H NMR (400 MHz, CHLOROFORM-d) δ=12.58-12.39 (m, 1H), 9.09 (s, 1H), 8.30 (s, 1H), 8.24 (s, 1H), 7.21 (d, J=7.8 Hz, 1H), 7.06 (d, J=7.6 Hz, 1H), 7.00 (s, 1H), 6.33 (br dd, J=5.4, 10.6 Hz, 1H), 4.15-3.98 (m, 2H), 3.45-3.30 (m, 2H), 2.85-2.80 (m, 1H), 2.79 (s, 3H), 2.44 (s, 6H), 1.44 (t, J=6.8 Hz, 3H), 1.21 (d, J=6.6 Hz, 6H). Compound 209 was obtained as a white solid (8.29 mg, 20.24 μmol, 21.26% yield). LCMS: Rt=0.434 min, m/z=410.2[M+H]+ $^1$H NMR (400 MHz, CHLOROFORM-d) δ=12.61-12.39 (m, 1H), 9.09 (s, 1H), 8.30 (s, 1H), 8.24

(s, 1H), 7.21 (d, J=7.8 Hz, 1H), 7.06 (d, J=7.6 Hz, 1H), 7.00 (s, 1H), 6.33 (br dd, J=5.4, 10.6 Hz, 1H), 4.15-3.98 (m, 2H), 3.46-3.28 (m, 2H), 2.86-2.80 (m, 1H), 2.79 (s, 3H), 2.44 (s, 6H), 1.44 (t, J=6.8 Hz, 3H), 1.21 (br d, J=6.8 Hz, 6H).

Synthesis of Compound 211

Compound 211 was prepared in a similar manner to Compound 040 using $NaBH(OAc)_3$ and bis(methyl-$d_3$) amine. Compound 211 (3251.09 mg, 6.75 mmol, 75.35% yield, 100% purity) was obtained as a white solid. LCMS: Rt=0.502 min, m/z=482.2[M+H]+ $^1$H NMR (400 MHz, CHLOROFORM-d) δ=11.44 (br s, 1H), 9.18-9.03 (m, 1H), 8.45-8.43 (m, 1H), 8.41 (br s, 1H), 8.30-8.21 (m, 1H), 7.40-7.29 (m, 2H), 7.29-7.19 (m, 2H), 7.19-7.06 (m, 2H), 7.05-6.94 (m, 1H), 6.23 (br d, J=3.3 Hz, 1H), 4.28-3.87 (m, 2H), 3.29-3.09 (m, 1H), 3.03-2.72 (m, 5H), 2.60 (br s, 1H), 1.50-1.20 (m, 3H).

Synthesis of Compound 212

Compound 212 was prepared in a similar manner to Compound 040. Compound 212 (54.03 mg, 115.97 μmol, 42.53% yield, 98% purity) was obtained as a yellow gum. LCMS: Rt=0.480 min, m/z=457.2 (M+H+). $^1$H NMR (400 MHz, CHLOROFORM-d) δ=1.35 (br t, J=6.88 Hz, 3H) 2.35 (s, 6H) 2.37-2.49 (m, 2H) 2.50-2.62 (m, 2H) 2.77 (s, 3H) 3.95-4.15 (m, 2H) 6.37 (br dd, J=9.01, 5.50 Hz, 1H) 7.00-7.11 (m, 2H) 7.17 (t, J=7.57 Hz, 1H) 7.31-7.45 (m, 5H) 7.54 (d, J=7.38 Hz, 2H) 7.75 (d, J=8.00 Hz, 1H) 8.12 (s, 1H) 11.84-12.04 (m, 1H).

Synthesis of Compound 213

Compound 213 was prepared in a similar manner to Compound 040 using $NaBH(OAc)_3$. Compound 213 (34.17 mg, 150.45 μmol, 70.92% yield, 99.6% purity) was obtained as a white solid. LCMS: Rt=0.524 min, m/z=491.2 [M+H]+ $^1$H NMR (400 MHz, CHLOROFORM-d) δ=8.56 (s, 1H), 8.12 (s, 1H), 7.76 (d, J=8.0 Hz, 1H), 7.54 (s, 1H), 7.43-7.37 (m, 2H), 7.37-7.30 (m, 3H), 7.23-7.14 (m, 1H), 7.13-7.07 (m, 2H), 6.34 (br dd, J=5.3, 9.5 Hz, 1H), 4.16-3.99 (m, 2H), 2.90-2.82 (m, 1H), 2.81-2.75 (m, 3H), 2.75-2.67 (m, 1H), 2.65-2.58 (m, 1H), 2.53 (s, 6H), 2.49-2.30 (m, 1H), 1.36 (t, J=6.9 Hz, 3H).

Synthesis of Compound 206

Compound 206 was prepared by treating Compound 213 with m-CPBA. Compound 206 was isolated as a white solid (13.75 mg, 26.28 μmol, 37.01% yield, 96.9% purity). LCMS: Rt=0.513 min, m/z=507.1[M+H]+ $^1$H NMR (400 MHz, CHLOROFORM-d) δ=8.40 (s, 1H), 8.11 (s, 1H), 7.76 (br d, J=8.0 Hz, 1H), 7.52 (s, 1H), 7.45 (br d, J=7.0 Hz, 1H), 7.39 (br d, J=6.1 Hz, 1H), 7.32-7.28 (m, 1H), 7.29-7.26 (m, 1H), 7.22-7.10 (m, 3H), 6.36 (br dd, J=5.6, 9.1 Hz, 1H), 4.13-3.99 (m, 3H), 3.80-3.57 (m, 3H), 3.48 (br s, 3H), 3.39 (s, 3H), 3.17-3.09 (m, 1H), 2.86 (s, 3H), 2.82-2.68 (m, 1H), 1.34 (br t, J=6.9 Hz, 3H).

Synthesis of Compound 207

Compound 207 was prepared in a similar manner to Compound 206. Compound 207 was isolated as a yellow gum (94.31 mg, 173.08 μmol, 53.93% yield, 98.2% purity). LCMS: Rt=0.515 min, m/z=535.3 [M+H]+. $^1$H NMR (400 MHz, CHLOROFORM-d) δ=8.43 (s, 1H), 8.13 (s, 1H), 7.78 (br d, J=8.0 Hz, 1H), 7.54 (s, 1H), 7.47 (br d, J=7.0 Hz, 1H), 7.41 (br d, J=6.4 Hz, 1H), 7.35-7.30 (m, 3H), 7.26-7.08 (m, 3H), 6.33 (br dd, J=4.5, 9.9 Hz, 1H), 4.17-4.00 (m, 2H), 3.83-3.37 (m, 6H), 3.21 (q, J=10.5 Hz, 1H), 2.87 (s, 3H), 2.71-2.50 (m, 1H), 1.46-1.29 (m, 8H)

Synthesis of Compound 214

Compound 214 was prepared in a similar manner to Compound 040 using $NaBH(OAc)_3$ and N-methyl-ethanamine. Compound 214 (52.67 mg, 103.49 μmol, 46.10% yield, 96% purity) was obtained as a yellow oil. LCMS: Rt=0.483 min, m/z=489.3 (M+H+). $^1$H NMR (400 MHz, CHLOROFORM-d) δ=1.14-1.29 (m, 3H) 1.36 (br t, J=6.88 Hz, 3H) 2.40-2.56 (m, 4H) 2.58-2.70 (m, 1H) 2.72-2.84 (m, 6H) 2.86-2.93 (m, 1H) 3.97-4.18 (m, 2H) 6.33 (br dd, J=9.51, 5.13 Hz, 1H) 6.98-7.07 (m, 1H) 7.07-7.14 (m, 2H) 7.18 (t, J=7.57 Hz, 1H) 7.27-7.43 (m, 5H) 7.76 (d, J=8.00 Hz, 1H) 8.12 (s, 1H) 8.61 (s, 1H).

Synthesis of Compound 215

Compound 215 was prepared in a similar manner to Compound 040 using $NaBH(OAc)_3$ and diethylamine. Compound 215 (48.19 mg, 91.08 μmol, 40.58% yield, 95% purity) was obtained as a yellow gum. LCMS: Rt=0.502 min, m/z=503.3 (M+H+). $^1$H NMR (400 MHz, CHLOROFORM-d) δ=1.18 (t, J=7.13 Hz, 6H) 1.36 (t, J=6.94 Hz, 3H) 2.37-2.53 (m, 1H) 2.57-2.72 (m, 1H) 2.74-3.03 (m, 9H) 3.97-4.18 (m, 2H) 6.33 (br dd, J=9.57, 5.19 Hz, 1H) 6.99-7.07 (m, 1H) 7.07-7.13 (m, 2H) 7.18 (t, J=7.57 Hz, 1H) 7.28-7.45 (m, 5H) 7.76 (d, J=8.13 Hz, 1H) 8.12 (s, 1H) 8.66 (s, 1H).

Synthesis of Compound 216

Compound 216 was prepared by treating Compound 215 with m-CPBA. Compound 216 (66.36 mg, 125.40 μmol, 52.52% yield, 98% purity) was obtained as a white solid. LCMS: Rt=0.525 min, m/z=519.2 (M+H+) $^1$H NMR (400 MHz, CHLOROFORM-d) δ=1.35 (q, J=6.75 Hz, 6H) 1.42 (br t, J=7.07 Hz, 3H) 2.58-2.73 (m, 1H) 2.93 (s, 3H) 3.14-3.25 (m, 1H) 3.43-3.65 (m, 4H) 3.68-3.86 (m, 2H) 4.01-4.17 (m, 2H) 6.36 (br dd, J=10.07, 4.94 Hz, 1H) 6.97-7.06 (m, 1H) 7.14-7.25 (m, 3H) 7.27-7.39 (m, 4H) 7.47 (br d, J=7.00 Hz, 1H) 7.77 (d, J=8.13 Hz, 1H) 8.12 (s, 1H).

Synthesis of Compound 219

Compound 219 was prepared in a similar manner to Compound 040 using $NaBH(OAc)_3$. Compound 219 (240.38 mg, 487.05 μmol, 36.41% yield, 99.8% purity) was obtained as a white solid. LCMS: Rt=0.509 min, m/z=493.4 [M+H]+ $^1$H NMR (400 MHz, CHLOROFORM-d) δ=12.15-11.46 (m, 1H), 8.58-8.53 (m, 1H), 8.12 (s, 1H), 7.77 (d, J=8.0 Hz, 1H), 7.41 (d, J=7.2 Hz, 1H), 7.32 (d, J=8.0 Hz, 1H), 7.19 (t, J=7.6 Hz, 1H), 7.13-7.04 (m, 4H), 6.78 (tt, J=2.4, 8.8 Hz, 1H), 6.34 (br dd, J=5.2, 9.2 Hz, 1H), 4.17-3.99 (m, 2H), 2.81 (s, 3H), 2.80-2.69 (m, 2H), 2.69-2.60 (m, 1H), 2.55 (s, 6H), 2.51 (br d, J=5.6 Hz, 1H), 1.38 (t, J=6.8 Hz, 3H).

Synthesis of Compounds 220 and 221

Compounds 220 and 221 were prepared in a similar manner to Compound 040 using $NaBH(OAc)_3$ and separated by SFC. Compound 220 (10.89 mg, 21.88 μmol, 8.70% yield, 95.8% purity) was obtained as an off-white solid. LCMS: Rt=0.515 min, m/z=477.2 [M+H]+ $^1$H NMR (400 MHz, CHLOROFORM-d) δ=12.19 (br s, 1H), 8.14 (s, 1H), 7.77 (d, J=8.0 Hz, 1H), 7.56 (s, 1H), 7.47-7.42 (m, 1H), 7.37-7.30 (m, 4H), 7.19-7.13 (m, 3H), 6.47-6.37 (m, 1H), 4.15-4.02 (m, 2H), 3.44 (t, J=12.0 Hz, 1H), 2.78 (s, 3H), 2.76-2.71 (m, 1H), 2.47 (s, 6H), 1.39 (t, J=7.2 Hz, 3H). Compound 221 was obtained as a white solid (11.84 mg, 24.53 μmol, 9.75% yield, 98.838% purity). LCMS: Rt=0.510 min, m/z=477.3 [M+H]+ $^1$H NMR (400 MHz, CHLOROFORM-d) δ=12.19 (br s, 1H), 8.14 (s, 1H), 7.77 (d, J=8.0 Hz, 1H), 7.56 (s, 1H), 7.44 (br d, J=7.2 Hz, 1H), 7.37-7.29 (m, 4H), 7.20-7.13 (m, 3H), 6.42 (dd, J=5, 2, 11.2 Hz, 1H), 4.16-4.01 (m, 2H), 3.45 (t, J=12.0 Hz, 1H), 2.81-2.76 (m, 3H), 2.76-2.71 (m, 1H), 2.47 (s, 6H), 1.39 (t, J=7.2 Hz, 3H).

Synthesis of Compound 226

Compound 226 was prepared in a similar manner to Compound 040 using $NaBH(OAc)_3$. Compound 226 (5.02 mg, 11.19 μmol, 64.20% yield, 98.9% purity) was obtained as a white solid. LCMS: Rt=0.430 min, m/z=444.2 [M+H]+ $^1$H NMR (400 MHz, CHLOROFORM-d) δ=12.82-11.85 (m, 1H), 9.58-8.81 (m, 1H), 8.29 (s, 2H), 7.55 (br d, J=7.2 Hz, 2H), 7.44-7.33 (m, 4H), 7.26-7.18 (m, 2H), 6.53-6.38 (m, 1H), 4.19-4.00 (m, 2H), 3.78-3.62 (m, 1H), 3.06-2.96 (m, 1H), 2.91 (br s, 3H), 2.60 (br s, 6H), 1.37 (t, J=6.8 Hz, 3H).

Synthesis of Compound 228

Compound 228 was prepared in a similar manner to Compound 040 using $NaBH(OAc)_3$. Compound 228 (42.5 mg, 88.91 μmol, 20.58% yield, 100% purity) was obtained as a white solid. LCMS: Rt=0.437 min, m/z=478.2 (M+H+) $^1$H NMR (400 MHz, deuterium oxide) δ=9.19 (br s, 1H), 8.48 (br s, 2H), 7.30-6.87 (m, 4H), 6.79 (br d, J=8.4 Hz, 3H), 6.31 (br s, 1H), 3.68 (br d, J=2.0 Hz, 2H), 3.25 (br d, J=4.4 Hz, 3H), 2.77 (s, 4H), 2.70-2.60 (m, 1H), 2.48 (br s, 3H), 0.88 (br s, 3H).

Synthesis of Compound 229

Compound 229 was prepared in a similar manner to Compound 040 using $NaBH(OAc)_3$ and 2-methoxy-N-methylethan-1-amine. Compound 229 (134.75 mg, 246.34 μmol, 57.02% yield, 98% purity) was obtained as a white solid. LCMS: Rt=0.433 min, m/z=536.3 (M+H+) $^1$H NMR (400 MHz, CHLOROFORM-d) δ=9.16 (s, 1H), 8.47 (s, 1H), 8.42 (br s, 1H), 8.30 (s, 1H), 7.55 (s, 1H), 7.43 (br d, J=6.7 Hz, 1H), 7.38-7.30 (m, 3H), 7.23-7.03 (m, 2H), 6.26 (br dd, J=5.0, 9.5 Hz, 1H), 4.23-3.92 (m, 2H), 3.70 (br s, 2H), 3.37 (s, 3H), 3.17 (br d, J=3.1 Hz, 1H), 3.09 (br t, J=4.6 Hz, 2H), 3.05-2.94 (m, 1H), 2.87 (s, 3H), 2.83-2.75 (m, 1H), 2.71 (s, 3H), 2.65-2.50 (m, 1H).

Synthesis of Compound 230

Compound 230 was prepared in a similar manner to Compound 040 using $NaBH(OAc)_3$ and 2-((tert-butyldimethylsilyl)oxy)-N-methylethan-1-amine. The resulting product was treating with $NH_4F$ to remove the TBS protecting group. Compound 230 (82.18 mg, 157.42 μmol, 40.07% yield, 100% purity) was obtained as a white solid. LCMS: Rt=0.444 min, m/z=522.2[M+H]+ $^1$H NMR (400 MHz, CHLOROFORM-d) δ=9.08 (s, 1H), 8.42 (s, 1H), 8.38 (s, 1H), 8.23 (s, 1H), 7.49 (s, 1H), 7.40-7.27 (m, 3H), 7.27-7.22 (m, 1H), 7.07 (br d, J=3.6 Hz, 2H), 6.30 (br dd, J=3.9, 9.6 Hz, 1H), 4.15-3.93 (m, 2H), 3.80 (q, J=4.5 Hz, 2H), 3.15-3.01 (m, 1H), 2.92 (br d, J=4.4 Hz, 3H), 2.82 (s, 3H), 2.74 (br d, J=9.0 Hz, 1H), 2.61 (s, 3H), 2.57 (br d, J=6.8 Hz, 1H), 1.31 (t, J=6.9 Hz, 3H).

Synthesis of Compound 231

Compound 231 was prepared in a similar manner to Compound 040 using $NaBH(OAc)_3$ and methane-$d_3$-amine. Compound 231 (27.06 mg, 57.67 μmol, 65.13% yield, 99% purity) was obtained as a white solid. LCMS: Rt=0.427 min, m/z=465.3 [M+H]+ $^1$H NMR (400 MHz, deuterium oxide) δ=99.51 (s, 1H), 8.87 (s, 1H), 8.54 (s, 1H), 7.37-7.30 (m, 1H), 7.23 (br dd, J=7.8, 18.8 Hz, 2H), 7.15 (br d, J=9.9 Hz, 1H), 7.08-6.95 (m, 3H), 6.37 (br dd, J=4.6, 10.1 Hz, 1H), 3.99 (br dd, J=4.1, 6.8 Hz, 2H), 3.28 (br t, J=7.6 Hz, 2H), 2.88-2.74 (m, 1H), 2.68 (s, 3H), 2.65-2.56 (m, 1H), 1.18 (br t, J=6.9 Hz, 3H).

Synthesis of Compound 232

Compound 232 was prepared in a similar manner to Compound 040. Compound 232 (14.8 mg, 30.68 μmol, 13.91% yield, 97.12% purity) was obtained as a white solid. LCMS: Rt=0.430 min, m/z=444.2 [M+H]+ $^1$H NMR (400 MHz, DMSO-d6) δ=9.76-9.62 (m, 1H), 9.23-9.09 (m, 2H), 9.05-8.82 (m, 1H), 8.67-8.54 (m, 1H), 7.97 (br s, 1H), 7.91-7.86 (m, 1H), 7.82 (br d, J=7.6 Hz, 1H), 7.66-7.61 (m, 1H), 7.50-7.39 (m, 1H), 7.19 (br s, 2H), 6.20 (s, 1H), 4.84-4.34 (m, 2H), 4.19-4.00 (m, 2H), 3.10-2.89 (m, 3H), 2.62 (br s, 5H), 1.27 (br d, J=1.2 Hz, 3H)

Synthesis of Compound 233

Compound 233 was prepared in a similar manner to Compound 040 using $NaBH(OAc)_3$. Compound 233 (27.92 mg, 53.72 μmol, 62.01% yield, 98.8% purity, HCl) was obtained as a yellow solid. LCMS: Rt=0.508 min, m/z=477.2 [M+H]+ $^1$H NMR (400 MHz, METHANOL-d4) δ=8.27 (s, 1H), 7.88 (d, J=8.0 Hz, 1H), 7.61 (br d, J=7.2 Hz, 1H), 7.53 (br s, 1H), 7.45-7.40 (m, 1H), 7.40-7.35 (m, 2H), 7.34-7.28 (m, 2H), 7.19-7.08 (m, 2H), 6.34 (br s, 1H), 4.16-3.97 (m, 2H), 3.30-3.19 (m, 2H), 2.87-2.71 (m, 7H), 2.66-2.57 (m, 1H), 1.32 (br t, J=6.0 Hz, 3H).

Synthesis of Compound 254

Compound 254 was prepared in a similar manner to Compound 206. Compound 254 was isolated as an off-white gum (23.26 mg, 44.38 μmol, 41.59% yield, 99.6% purity). LCMS: Rt=0.432 min, m/z=522.2, M+H+. $^1$H NMR (400 MHz, CHLOROFORM-d) δ=9.05 (br s, 1H), 8.41 (br s, 1H), 8.19 (s, 1H), 7.46 (br s, 1H), 7.33 (br s, 1H), 7.24 (br s, 3H), 7.16-6.99 (m, 2H), 6.21 (br s, 1H), 4.01 (br dd, J=7.1, 12.8 Hz, 2H), 3.73-3.33 (m, 5H), 3.26-3.15 (m, 3H), 3.13-2.98 (m, 1H), 2.84 (br d, J=6.8 Hz, 3H), 1.52-1.18 (m, 6H). 13C NMR: (101 MHz, CHLOROFORM-d) δ=155.95, 145.54 (br d, J=6.2 Hz, 1C), 143.20-141.27 (m, 1C), 139.22, 135.95-132.56 (m, 1C), 130.58 (br s, 1C), 129.36 (br d, J=35.2 Hz, 1C), 127.49 (br d, J=21.1 Hz, 1C), 121.12, 119.90 (br d, J=5.8 Hz, 1C), 115.59 (br s, 1C), 111.96 (br d, J=5.4 Hz, 1C), 65.58-63.30 (m, 1C), 54.78, 50.65 (br d, J=12.0 Hz, 1C), 33.01 (br s, 1C), 22.60 (br s, 1C), 14.56, 9.55-7.98 (m, 1C).

Synthesis of Compound 255

Compound 255 was prepared in a similar manner to Compound 206. Compound 255 was isolated as a yellow gum (43.97 mg, 75.16 μmol, 70.81% yield, 99.5% purity). LCMS: Rt=0.444 min, m/z=536.3, M+H+ $^1$H NMR (400 MHz, CHLOROFORM-d) δ=9.17-9.08 (m, 1H), 8.46 (br d, J=19.8 Hz, 2H), 8.30-8.21 (m, 1H), 7.54 (s, 1H), 7.41 (br d, J=6.5 Hz, 1H), 7.37-7.29 (m, 3H), 7.22-7.07 (m, 2H), 6.32-6.16 (m, 1H), 4.22-3.96 (m, 2H), 3.81-3.37 (m, 5H), 3.27 (br d, J=10.1 Hz, 1H), 2.95-2.86 (m, 3H), 2.84 (br d, J=3.9 Hz, 1H), 2.72 (br d, J=5.5 Hz, 1H), 1.44-1.16 (m, 9H) $^{13}$C NMR: (101 MHz, CHLOROFORM-d) δ=173.43 (br s, 1C), 167.31, 155.99, 146.40-144.80 (m, 1C), 142.53-140.65 (m, 1C), 139.28, 135.98-134.37 (m, 1C), 133.82, 131.83, 130.65 (br s, 1C), 129.41 (d, J=35.2 Hz, 1C), 127.53 (br d, J=22.4 Hz, 1C), 121.06, 120.38-119.38 (m, 1C), 112.04 (br s, 1C), 64.56, 61.47 (br s, 1C), 59.94 (br s, 1C), 58.25 (br s, 1C), 50.69 (br s, 1C), 46.53, 33.06, 22.13 (br s, 1C), 14.61, 10.36, 8.63 (br d, J=41.0 Hz, 1C).

Synthesis of Compounds 256 and 257

Compounds 256 and 257 were prepared in a similar manner to Compound 040 and separated by SFC. Compound 256 (16.55 mg, 35.40 μmol, 34.68% yield, 98.5% purity) was obtained as a yellow solid. LCMS: Rt=0.472 min, m/z=461.2, M+H+ $^1$H NMR (400 MHz, CHLOROFORM-d) δ=12.35-11.83 (m, 1H), 8.13 (s, 1H), 7.76 (d, J=8.0 Hz, 1H), 7.40-7.27 (m, 5H), 7.22-7.09 (m, 3H), 7.03 (br t, J=7.8 Hz, 1H), 6.43 (br dd, J=4.5, 10.9 Hz, 1H), 4.19-3.94 (m, 2H), 3.48 (br t, J=10.9 Hz, 1H), 2.78 (s, 4H), 2.49 (s, 6H), 1.37 (t, J=6.9 Hz, 3H). 13C NMR (101 MHz, CHLOROFORM-d) δ=173.08, 163.64, 161.21, 155.82, 139.88 (br d, J=8.3 Hz, 1C), 136.45, 134.76 (br s, 1C), 131.27, 130.46, 129.33 (d, J=8.3 Hz, 1C), 125.09 (d, J=2.5 Hz, 1C), 123.41, 120.92, 120.01 (br d, J=47.7 Hz, 1C), 116.48 (d, J=22.4 Hz, 1C), 114.03 (d, J=21.1 Hz, 1C), 111.91, 64.32, 57.35, 49.76, 46.22-45.16 (m, 1C), 32.10, 14.60. Compound 257 was obtained as a yellow solid (16.36 mg, 35.27 μmol, 34.56% yield, 99.3% purity). LCMS: Rt=0.473 min, m/z=461.2, M+H+. $^{1}$H NMR (400 MHz, CHLOROFORM-d) δ=12.14 (br s, 1H), 8.13 (s, 1H), 7.76 (d, J=8.1 Hz, 1H), 7.41-7.28 (m, 5H), 7.21-7.10 (m, 3H), 7.03 (br t, J=7.4 Hz, 1H), 6.44 (br dd, J=3.8, 7.3 Hz, 1H), 4.08 (dt, J=8.9, 15.9 Hz, 2H), 3.59-3.41 (m, 1H), 2.79 (s, 4H), 2.49 (br s, 6H), 1.37 (t, J=6.9 Hz, 3H). $^{13}$C NMR (101 MHz, CHLOROFORM-d) δ=173.11 (br s, 1C), 163.65, 161.21, 155.83, 139.89 (br d, J=8.3 Hz, 1C), 136.43 (br s, 1C), 134.76 (br s, 1C), 131.29, 130.47, 129.33 (d, J=8.3 Hz, 1C), 125.09 (d, J=2.1 Hz, 1C), 123.78-122.96 (m, 1C), 121.18-119.07 (m, 1C), 116.48 (d, J=22.4 Hz, 1C), 114.03 (d, J=21.1 Hz, 1C), 111.94, 64.34, 57.34 (br s, 1C), 49.76, 45.74 (br s, 1C), 32.13, 14.60.

Synthesis of Compounds 258 and 259

Compounds 258 and 259 were prepared in a similar manner to Compound 040 using N-methylethanamine and separated by SFC. Compound 258 (22.9 mg, 48.25 μmol, 46.12% yield, 100% purity) was obtained as an off-white solid. LCMS: Rt=0.482 min, m/z=475.2, M+H+ $^{1}$H NMR (400 MHz, CHLOROFORM-d) δ=12.17 (br s, 1H), 8.13 (s, 1H), 7.76 (d, J=8.0 Hz, 1H), 7.41-7.28 (m, 5H), 7.21-7.11 (m, 3H), 7.03 (br t, J=7.6 Hz, 1H), 6.45 (br dd, J=4.0, 11.0 Hz, 1H), 4.24-3.94 (m, 2H), 3.52 (br s, 1H), 2.77 (s, 5H), 2.62 (br s, 1H), 2.46 (br s, 3H), 1.38 (t, J=6.9 Hz, 3H), 1.20 (br t, J=6.9 Hz, 3H). 13C NMR (101 MHz, CHLOROFORM-d) δ=173.08 (br s, 1C), 163.64, 161.21, 155.78, 139.90 (br d, J=7.9 Hz, 1C), 136.55 (br d, J=1.7 Hz, 1C), 134.72 (br s, 1C), 131.24 (br s, 1C), 130.50, 129.32 (br d, J=8.3 Hz, 1C), 125.07 (br s, 1C), 123.39, 120.87 (br s, 1C), 120.02 (br d, J=40.2 Hz, 1C), 116.47 (br d, J=22.0 Hz, 1C), 114.02 (br d, J=21.1 Hz, 1C), 111.90, 64.30, 55.17 (br s, 1C), 51.82 (br s, 1C), 49.62, 41.63 (br s, 1C), 32.12 (br s, 1C), 14.61, 12.52 (br s, 1C). Compound 259 was obtained as an off-white solid (23.18 mg, 48.40 μmol, 46.27% yield, 99.1% purity). LCMS: Rt=0.475 min, m/z=475.2, M+H+ $^{1}$H NMR (400 MHz, CHLOROFORM-d) δ=12.17 (br s, 1H), 8.13 (s, 1H), 7.76 (d, J=8.0 Hz, 1H), 7.42-7.28 (m, 5H), 7.20-7.11 (m, 3H), 7.03 (br t, J=8.0 Hz, 1H), 6.57-6.32 (m, 1H), 4.23-3.92 (m, 2H), 3.51 (br s, 1H), 2.77 (br s, 5H), 2.61 (br d, J=4.5 Hz, 1H), 2.46 (br s, 3H), 1.38 (t, J=6.9 Hz, 3H), 1.20 (br t, J=6.6 Hz, 3H). $^{13}$C NMR (101 MHz, CHLOROFORM-d) δ=173.09, 163.65, 161.21 (br s, 1C), 155.78, 139.91 (br d, J=7.5 Hz, 1C), 134.72 (br s, 1C), 131.26, 130.51, 129.32 (br d, J=8.3 Hz, 1C), 125.08 (br s, 1C), 123.39 (br s, 1C), 120.88 (br s, 1C), 120.02 (br d, J=40.2 Hz, 1C), 116.48 (br d, J=22.0 Hz, 1C), 114.02 (br d, J=21.6 Hz, 1C), 111.91, 64.31, 55.21 (br s, 1C), 51.80 (br s, 1C), 49.63 (br s, 1C), 41.63 (br s, 1C), 32.12 (br s, 1C), 14.61, 12.51 (br d, J=2.1 Hz, 1C).

Synthesis of Compounds 260 and 261

Compounds 260 and 261 were prepared in a similar manner to Compound 040 using diethylamine and separated by SFC. Compound 260 (12.70 mg, 25.84 μmol, 31.56% yield, 99.4% purity) was obtained as a white solid. LCMS: Rt=0.517 min, MS (ESI) m/z: 489.4, M+H+ $^{1}$H NMR (400 MHz, CHLOROFORM-d) δ=12.17 (br s, 1H), 8.13 (s, 1H), 7.76 (d, J=8.0 Hz, 1H), 7.39-7.28 (m, 5H), 7.24-7.13 (m, 3H), 7.03 (br t, J=7.5 Hz, 1H), 6.51-6.38 (m, 1H), 4.16-4.02 (m, 2H), 3.77-3.50 (m, 1H), 3.10-2.87 (m, 4H), 2.79 (br s, 3H), 2.74-2.66 (m, 1H), 1.38 (t, J=6.9 Hz, 3H), 1.17 (br t, J=6.3 Hz, 6H). Compound 261 was obtained as a white solid (11.44 mg, 23.18 μmol, 28.31% yield, 99.0% purity). LCMS: Rt=0.513 min, MS (ESI) m/z: 489.4, M+H+ $^{1}$H NMR (400 MHz, CHLOROFORM-d) δ=12.63-11.40 (m, 1H), 8.04 (s, 1H), 7.68 (br d, J=8.0 Hz, 1H), 7.32-7.19 (m, 5H), 7.13-7.03 (m, 3H), 6.94 (br t, J=7.8 Hz, 1H), 6.37 (br d, J=8.0 Hz, 1H), 4.08-3.91 (m, 2H), 3.57 (br s, 1H), 3.20-2.81 (m, 4H), 2.70 (s, 3H), 2.68-2.58 (m, 1H), 1.29 (br t, J=6.9 Hz, 3H), 1.09 (br t, J=6.8 Hz, 5H).

Synthesis of Compound 262

Compound 262 was prepared in a similar manner to Compound 040 using NaBH(OAc)$_3$ and 2-((tert-butyldimethylsilyl)oxy)-N-methylethan-1-amine. The resulting product was treating with $NH_4F$ to remove the TBS protecting group. Compound 262 (28.97 mg, 57.24 μmol, 35.48% yield, 99.9% purity) was obtained as a white solid. LCMS: Rt=0.415 min, m/z=506.3 M+H+ $^{1}$H NMR (400 MHz, CHLOROFORM-d) δ=9.06 (br s, 1H), 8.48 (br s, 1H), 8.21 (s, 1H), 7.35-7.28 (m, 1H), 7.27-7.17 (m, 3H), 7.13-7.03 (m, 2H), 6.99 (br t, J=8.2 Hz, 1H), 6.38 (br d, J=4.6 Hz, 1H), 4.07-3.96 (m, 2H), 3.78 (br s, 2H), 3.03-2.88 (m, 4H), 2.80 (s, 3H), 2.73 (br d, J=1.8 Hz, 1H), 2.61 (br s, 4H), 1.31 (br t, J=6.8 Hz, 3H). $^{13}$C NMR: (101 MHz, CHLOROFORM-d) δ=173.50, 163.65, 161.22, 156.00, 145.30 (br s, 1C), 142.26, 141.41 (br s, 1C), 139.57 (d, J=8.3 Hz, 1C), 135.20 (br d, J=45.2 Hz, 1C), 131.82 (br s, 1C), 130.57, 129.44 (br d, J=8.3 Hz, 1C), 125.09 (br s, 1C), 120.77, 119.69, 117.21-115.93 (m, 1C), 114.25 (br d, J=21.1 Hz, 1C), 112.02, 64.49, 59.12 (br s, 1C), 57.73, 54.27 (br s, 1C), 49.69 (br s, 1C), 41.62, 32.64 (br s, 1C), 25.20 (br s, 1C), 14.60.

Synthesis of Compound 279

Compound 279 was prepared in a similar manner to Compound 040 using NaBH(OAc)$_3$. Compound 279 (16.94 mg, 32.49 μmol, 10.21% yield, 96% purity) was obtained as a yellow solid. LCMS: Rt=0.420 min, m/z=501.3 (M+H+) $^{1}$H NMR (400 MHz, CHLOROFORM-d) δ=9.11 (s, 1H), 8.47 (br s, 1H), 8.39 (s, 1H), 7.75 (br s, 1H), 7.66 (br d, J=8.4 Hz, 1H), 7.54-7.51 (m, 1H), 7.45 (br d, J=8.0 Hz, 1H), 7.19-7.05 (m, 2H), 6.34-6.22 (m, 1H), 4.23-4.02 (m, 2H), 2.99-2.75 (m, 3H), 2.43 (br s, 4H), 2.36 (br s, 6H), 1.43-1.25 (m, 3H).

Synthesis of Compound 280

Compound 280 was prepared in a similar manner to Compound 040 using methylamine. Compound 280 (11.86 mg, 20.77 μmol, 4.90% yield, 98% purity, 2HCl) was obtained as a yellow solid. LCMS: Rt=0.417 min, m/z=478.2 (M+H+) $^{1}$H NMR (400 MHz, methanol-d) δ=9.72-9.60 (m, 1H), 9.08-8.86 (m, 1H), 8.80-8.62 (m, 1H), 7.75 (s, 1H), 7.66 (dd, J=2.0, 10.0 Hz, 1H), 7.53 (dd, J=1.2, 8.0 Hz, 1H), 7.45 (d, J=7.6 Hz, 1H), 7.29-7.16 (m, 2H), 6.40 (br d, J=4.0 Hz, 1H), 4.23-4.06 (m, 2H), 3.32 (br s, 1H), 3.30 (br s, 1H), 2.92 (br s, 3H), 2.84 (s, 3H), 2.81-2.61 (m, 2H), 1.40-1.31 (m, 3H)

Synthesis of Compound 077

Compound 077 was prepared by the following scheme.

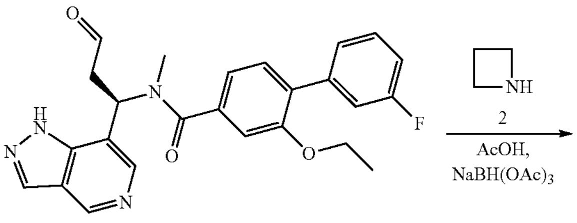

1

-continued

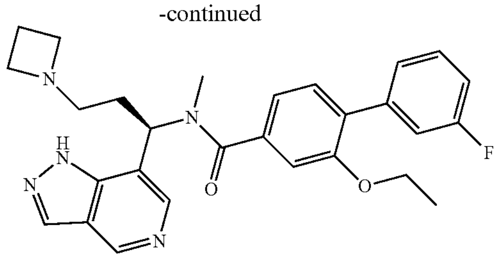

077

To a solution of compound 1 (200 mg, 447.96 μmol, 1 eq) and compound 2 (51.15 mg, 895.91 μmol, 60.46 μL, 2 eq) in DCE (8 mL) was added AcOH (2.69 mg, 44.80 μmol, 2.56 μL, 0.1 eq) and Molecular sieve 4 A (100 mg, 447.96 μmol, 1 eq). The mixture was stirred at 25° C. for 12 hr. To the reaction mixture was added $NaBH(OAc)_3$ (284.82 mg, 1.34 mmol, 3 eq) at 0° C. and stirred at 0° C. for 1 hr. The reaction mixture was filtered, and the filtrate was concentrated under reduced pressure to give a residue. The crude product was purified by prep-HPLC (column: Phenomenex luna C18 150*25 mm*10 um; mobile phase: [water (FA)-ACN]; gradient: 8%-38% B over 9 min) and lyophilized to give a product. Compound 077 (22.84 mg, 45.91 μmol, 10.25% yield, 98% purity) was obtained as a white solid. LCMS: RT=0.433 min, m/z=488.3 [M+H]+ $^1$H NMR (400 MHz, CHLOROFORM-d) δ=12.38-11.71 (m, 1H), 9.03 (s, 1H), 8.32 (s, 1H), 8.18 (s, 1H), 7.33-7.25 (m, 2H), 7.25-7.20 (m, 2H), 7.04-6.93 (m, 3H), 6.20 (br d, J=3.4 Hz, 1H), 4.12-3.86 (m, 2H), 3.22 (t, J=6.9 Hz, 4H), 2.73 (s, 3H), 2.65-2.51 (m, 2H), 2.37-2.25 (m, 1H), 2.22-2.13 (m, 1H), 2.06 (quin, J=7.0 Hz, 2H), 1.29 (br t, J=6.9 Hz, 3H).

Synthesis of Compounds 123 and 124

Compounds 123 and 124 were prepared in a similar manner to compound 077.

Compound 123 (31.73 mg, 66.34 μmol, 34.90% yield, 99% purity) was obtained as a white solid. LCMS: Rt=0.400 min, m/z=474.4[M+H]+ $^1$H NMR (400 MHz, CHLOROFORM-d) δ=12.53 (br s, 1H), 9.02 (s, 1H), 8.20-8.12 (m, 2H), 7.31-7.20 (m, 4H), 7.15-7.09 (m, 2H), 6.96 (br s, 1H), 6.01 (br dd, J=5.6, 9.4 Hz, 1H), 4.13-3.94 (m, 2H), 3.41-3.29 (m, 5H), 3.02-2.95 (m, 1H), 2.74 (s, 3H), 2.14-2.07 (m, 2H), 1.31 (t, J=6.9 Hz, 3H)

Compound 124 (30.08 mg, 62.89 μmol, 33.09% yield, 99% purity) was obtained as a white solid. LCMS: Rt=0.400 min, m/z=474.2[M+H]+ $^1$H NMR (400 MHz, CHLOROFORM-d) δ=12.53 (br s, 1H), 9.02 (s, 1H), 8.21-8.17 (m, 2H), 7.32-7.21 (m, 4H), 7.15-7.08 (m, 2H), 6.99-6.94 (m, 1H), 6.01 (br dd, J=5.6, 9.6 Hz, 1H), 4.09-3.97 (m, 2H), 3.41-3.29 (m, 5H), 2.97 (br dd, J=5.6, 12.0 Hz, 1H), 2.74 (s, 3H), 2.14-2.07 (m, 2H), 1.31 (t, J=6.9 Hz, 3H).

Synthesis of Compounds 129 and 130

Compounds 129 and 130 were prepared in a similar manner to compound 077.

Compound 129 (31.45 mg, 64.10 μmol, 44.65% yield, 99.369% purity) was obtained as a white solid. LCMS: Rt=0.434 min, m/z=488.2 [M+H]+ $^1$H NMR: (400 MHz, CHLOROFORM-d) δ=12.51 (br s, 1H), 9.10 (s, 1H), 8.33 (s, 1H), 8.25 (s, 1H), 7.40-7.27 (m, 4H), 7.18-7.11 (m, 2H), 7.03 (br t, J=7.6 Hz, 1H), 6.32 (br dd, J=4.8, 10.8 Hz, 1H), 4.08 (br dd, J=7.2, 15.2 Hz, 2H), 3.73 (br t, J=11.6 Hz, 1H), 2.94 (br dd, J=5.2, 12.4 Hz, 1H), 2.82 (s, 5H), 2.67 (br d, J=5.6 Hz, 2H), 1.87 (br s, 4H), 1.37 (br t, J=6.8 Hz, 3H).

Compound 130 (35.19 mg, 72.17 μmol, 50.27% yield) was obtained as a white solid. LCMS: Rt=0.438 min, m/z=488.2 [M+H]+ $^1$H NMR: (400 MHz, CHLOROFORM-d) δ=12.51 (br s, 1H), 9.11 (s, 1H), 8.33 (s, 1H), 8.25 (s, 1H), 7.42-7.27 (m, 4H), 7.19-7.10 (m, 2H), 7.06-6.99 (m, 1H), 6.32 (br dd, J=5.2, 10.8 Hz, 1H), 4.16-3.99 (m, 2H), 3.74 (br t, J=11.6 Hz, 1H), 2.94 (dd, J=5.2, 12.4 Hz, 1H), 2.82 (s, 5H), 2.67 (br d, J=7.6 Hz, 2H), 1.87 (br s, 4H), 1.38 (t, J=6.8 Hz, 3H).

Synthesis of Compound 187

Compound 187 was prepared in a similar manner to Compound 077 using N,N-dimethylazetidin-3-amine instead of azetidine. Compound 187 (26.64 mg, 49.30 μmol, 79.72% yield, 95.6% purity) was obtained as a white gum. LCMS: Rt=0.429 min, m/z=517.2 [M+H]+ $^1$H NMR (400 MHz, CHLOROFORM-d) δ=9.11 (s, 1H), 8.36 (br s, 1H), 8.31-8.21 (m, 2H), 7.40-7.32 (m, 2H), 7.32-7.27 (m, 2H), 7.21-7.10 (m, 2H), 7.06-7.00 (m, 1H), 6.17 (br dd, J=5.1, 9.9 Hz, 1H), 4.09 (br dd, J=7.0, 11.1 Hz, 2H), 3.82-3.68 (m, 2H), 3.63 (br s, 1H), 3.38 (br t, J=6.8 Hz, 1H), 3.29 (br t, J=6.9 Hz, 1H), 3.23-3.12 (m, 2H), 2.82 (s, 3H), 2.28 (s, 6H), 1.37 (t, J=6.9 Hz, 3H).

Synthesis of Compound 217

Compound 217 was prepared in a similar manner to compound 077. Compound 217 (18.52 mg, 36.31 μmol, 5.39% yield, 95.4% purity) was obtained as an off-white solid. LCMS: Rt=0.492 min, m/z=487.3[M+H]+ $^1$H NMR (400 MHz, CHLOROFORM-d) δ=12.87 (br s, 1H), 8.12 (br s, 1H), 7.76 (br d, J=7.5 Hz, 1H), 7.44 (br s, 1H), 7.40-7.31 (m, 1H), 7.19 (br s, 1H), 7.12-6.95 (m, 3H), 6.34 (br s, 1H), 4.55-4.38 (m, 2H), 4.12-3.99 (m, 2H), 3.89 (br s, 2H), 3.32 (br s, 2H), 2.93-2.81 (m, 3H), 2.80-2.74 (m, 1H), 2.60 (br s, 1H), 2.42 (br s, 1H), 1.34 (br s, 3H).

Synthesis of Compound 218

Compound 218 was prepared in a similar manner to compound 077. Compound 218 (13.21 mg, 25.13 μmol, 11.85% yield, 95.7% purity) was obtained as an off-white solid. LCMS: Rt=0.528 min, m/z=503.1[M+H]+ $^1$H NMR (400 MHz, CHLOROFORM-d) δ=11.79 (br s, 1H), 8.59 (s, 1H), 8.04 (s, 1H), 7.67 (d, J=8.1 Hz, 1H), 7.46 (s, 1H), 7.33 (br d, J=6.8 Hz, 1H), 7.29-7.21 (m, 4H), 7.09 (t, J=7.6 Hz, 1H), 7.02-6.95 (m, 2H), 6.25 (br dd, J=5.7, 9.4 Hz, 1H), 4.07-3.89 (m, 2H), 3.36 (br t, J=7.1 Hz, 4H), 2.79 (br s, 1H), 2.71-2.66 (m, 4H), 2.62 (br s, 1H), 2.37-2.24 (m, 1H), 2.22-2.10 (m, 3H), 1.28 (br t, J=6.9 Hz, 3H).

Synthesis of Compounds 222 and 223

Compounds 222 and 223 were prepared in a similar manner to Compound 077 using pyrrolidine and separated by SFC. Compound 222 (21.48 mg, 42.38 μmol, 37.49% yield, 96% purity) was obtained as a white solid. LCMS: Rt=0.490 min, m/z=487.2 (M+H+) $^1$H NMR (400 MHz, CHLOROFORM-d) δ=1.38 (t, J=6.88 Hz, 3H) 1.59-1.75 (m, 1H) 1.88 (br s, 5H) 2.64 (br d, J=10.38 Hz, 2H) 2.79 (br s, 5H) 3.66-3.89 (m, 1H) 4.09 (br dd, J=17.01, 7.13 Hz, 2H) 6.40 (br d, J=1.25 Hz, 1H) 7.03 (br t, J=7.32 Hz, 1H) 7.09-7.23 (m, 3H) 7.28-7.39 (m, 5H) 7.76 (br d, J=7.88 Hz, 1H) 8.13 (s, 1H) 12.22 (br d, J=0.88 Hz, 1H). Compound 223 was obtained as a white solid (20.30 mg, 41.30 μmol, 36.54% yield, 99% purity). LCMS: Rt=0.490 min, m/z=487.2 (M+H+). $^1$H NMR (400 MHz, CHLOROFORM-d) δ=1.38 (t, J=6.82 Hz, 3H) 1.68 (br s, 1H) 1.87 (br s, 4H) 2.65 (br d, J=2.38 Hz, 2H) 2.75-2.87 (m, 5H) 3.77 (br t, J=11.69 Hz, 1H) 3.98-4.16 (m, 2H) 6.38 (br d, J=7.63 Hz, 1H) 7.03 (br t, J=8.19 Hz, 1H) 7.11-7.19 (m, 3H) 7.28-7.40 (m, 5H) 7.76 (br d, J=8.00 Hz, 1H) 8.13 (s, 1H) 12.24 (br s, 1H).

Synthesis of Compound 225

Compound 225 was prepared in a similar manner to compound 077 using $NaBH_4$. Compound 225 (18.52 mg, 36.31 μmol, 5.39% yield, 95.4% purity) was obtained as an off-white solid. LCMS: Rt=0.417 min, m/z=500.3 [M+H]+ $^{1}$H NMR (400 MHz, CHLOROFORM-d) δ=9.06 (s, 1H), 8.45 (br s, 1H), 8.35 (s, 1H), 8.19 (s, 1H), 7.39 (s, 1H), 7.32-7.23 (m, 2H), 7.16-7.04 (m, 3H), 6.95 (dt, J=2.1, 8.3 Hz, 1H), 6.16 (br dd, J=5.3, 9.6 Hz, 1H), 4.11-3.64 (m, 5H), 3.21-3.02 (m, 1H), 2.92 (dt, J=5.0, 11.3 Hz, 1H), 2.87-2.69 (m, 3H), 2.62 (br d, J=10.3 Hz, 1H), 2.68-2.50 (m, 1H), 2.47-2.23 (m, 3H), 0.82-0.57 (m, 4H).

Synthesis of Compound 226

Compound 226 was prepared in a similar manner to compound 077 using $NaBH_4$. Compound 226 (5.47 mg, 10.37 μmol, 6.15% yield, 97.8% purity) was obtained as an off-white solid. LCMS: Rt=0.430 min, m/z=516.2[M+H]+ $^{1}$H NMR (400 MHz, CHLOROFORM-d) δ=12.43-11.72 (m, 1H), 9.13 (s, 1H), 8.42 (s, 1H), 8.26 (s, 1H), 7.45 (br d, J=7.7 Hz, 2H), 7.35-7.30 (m, 4H), 7.15 (br d, J=7.7 Hz, 1H), 6.26 (br dd, J=4.6, 9.4 Hz, 1H), 3.80 (br s, 1H), 3.70 (br s, 3H), 3.09-2.96 (m, 1H), 2.88 (s, 3H), 2.63 (br dd, J=2.8, 5.0 Hz, 1H), 2.46-2.29 (m, 3H), 1.36-1.20 (m, 2H), 0.86-0.71 (m, 4H).

Synthesis of Compound 246

Compound 246 was prepared following the procedure provided for 077 using 3-azetidin-3-ol instead of azetidine. Compound 246 (14.80 mg, 29.91 μmol, 98.94% yield, 98.94% purity) was obtained as a white solid. LCMS: RT=0.408 min, m/z=490.3 (M+H+) $^{1}$H NMR (400 MHz, CHLOROFORM-d) δ=9.12 (s, 1H), 8.28 (d, J=4.4 Hz, 2H), 7.41-7.28 (m, 4H), 7.21-7.14 (m, 2H), 7.08-7.01 (m, 1H), 6.14 (br dd, J=4.8, 9.8 Hz, 1H), 4.61-4.52 (m, 1H), 4.18-4.01 (m, 2H), 3.89 (td, J=6.8, 13.6 Hz, 2H), 3.68 (br t, J=11.2 Hz, 1H), 3.34-3.19 (m, 2H), 3.13 (br dd, J=5.2, 12.1 Hz, 1H), 2.83 (s, 3H), 1.39 (t, J=6.8 Hz, 3H).

Synthesis of Compound 247

Compound 247 was prepared following the procedure provided for 077 using 3-pyrrolidin-3-ol instead of azetidine. Compound 247 (5.75 mg, 11.41 μmol, 100.00% yield, 99.95% purity) was obtained as a white solid. LCMS: RT=0.408 min, m/z=504.2 (M+H+) $^{1}$H NMR (400 MHz, CHLOROFORM-d) δ=9.14 (s, 1H), 8.35 (d, J=2.0 Hz, 1H), 8.29 (s, 1H), 7.41-7.28 (m, 4H), 7.17 (br d, J=7.2 Hz, 2H), 7.04 (br t, J=7.8 Hz, 1H), 6.37 (br t, J=11.8 Hz, 1H), 4.49 (br d, J=0.8 Hz, 1H), 4.18-4.01 (m, 2H), 3.84 (dt, J=6.3, 11.6 Hz, 1H), 3.31-3.14 (m, 2H), 3.11-3.00 (m, 2H), 3.00-2.91 (m, 2H), 2.87 (s, 3H), 2.82-2.48 (m, 2H), 2.29 (td, J=6.4, 13.0 Hz, 1H), 2.00-1.83 (m, 1H), 1.38 (t, J=6.8 Hz, 3H).

Synthesis of Compound 264

Compound 264 was prepared following the procedure provided for 077. Compound 264 (12.8 mg, 24.92 μmol, 27.31% yield, 92% purity) was obtained as a white solid. LCMS: RT=0.503 min, m/z=473.2.4 (M+H+). $^{1}$H NMR (400 MHz, CHLOROFORM-d) δ=1.38 (t, J=6.94 Hz, 3H) 2.13-2.27 (m, 2H) 2.78 (s, 3H) 2.93-3.04 (m, 1H) 3.29 (br d, J=1.25 Hz, 1H) 3.41-3.61 (m, 4H) 4.00-4.20 (m, 2H) 6.19 (br dd, J=10.38, 4.63 Hz, 1H) 7.03 (br t, J=7.88 Hz, 1H) 7.10-7.17 (m, 1H) 7.18-7.26 (m, 3H) 7.28-7.41 (m, 4H) 7.75 (d, J=8.00 Hz, 1H) 8.12 (s, 1H).

Synthesis of Compound 281

Compound 281 was prepared following the procedure provided for 077. Compound 281 (5.47 mg, 10.37 μmol, 6.15% yield, 97.8% purity) was obtained as a white solid. LCMS: RT=0.430 min, m/z=516.2[M+H]+ $^{1}$H NMR (400 MHz, CHLOROFORM-d) δ=12.43-11.72 (m, 1H), 9.13 (s, 1H), 8.42 (s, 1H), 8.26 (s, 1H), 7.45 (br d, J=7.7 Hz, 2H), 7.35-7.30 (m, 4H), 7.15 (br d, J=7.7 Hz, 1H), 6.26 (br dd, J=4.6, 9.4 Hz, 1H), 3.80 (br s, 1H), 3.70 (br s, 3H), 3.09-2.96 (m, 1H), 2.88 (s, 3H), 2.63 (br dd, J=2.8, 5.0 Hz, 1H), 2.46-2.29 (m, 3H), 1.36-1.20 (m, 2H), 0.86-0.71 (m, 4H).

Synthesis of Compound 080

Compound 080 was prepared according to the following scheme:

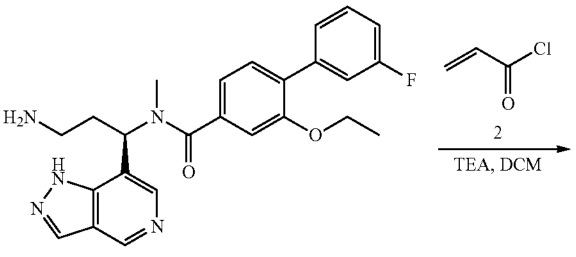

1

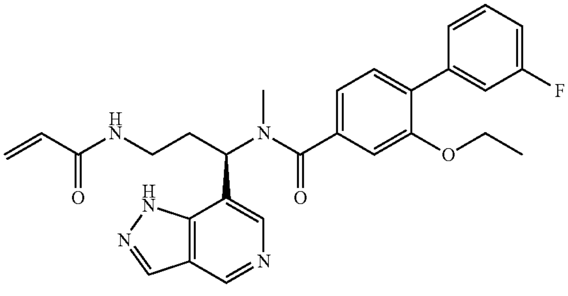

080

To a solution of compound 1 (120 mg, 268.15 μmol, 1 eq) in DCM (3 mL) was added TEA (54.27 mg, 536.31 μmol, 74.65 μL, 2 eq) and compound 2 (24.27 mg, 268.15 μmol, 21.79 μL, 1 eq) at 0° C. The reaction mixture was stirred at 0° C. for 2 h. The reaction mixture was added into water (10 mL) and extracted with DCM (10 ML*3), then the organic phase was dried with Na2SO4 and concentrated under reduce pressure to give the residue. The crude product was purified by Prep-TLC (DCM:MeOH=10:1) to give the product (Rf=0.55). The crude product was purified by Prep-HPLC (column: Phenomenex luna C18 150*25 mm*10 um; mobile phase: [water (FA)-ACN]; gradient: 5%-35% B over 15 min) to give the product Compound 080 (19.88 mg, 38.25 μmol, 14.26% yield, 96.5% purity) as white solid. LCMS: Rt=0.453 min, m/z=502.2 (M+H+) $^{1}$H NMR (400 MHz, CHLOROFORM-d) δ=12.30-11.88 (m, 1H), 9.31-9.00 (m, 1H), 8.62-8.37 (m, 1H), 8.32 (s, 1H), 7.43-7.36 (m, 2H), 7.35-7.30 (m, 2H), 7.19-7.15 (m, 2H), 7.07 (dt, J=1.6, 8.3 Hz, 1H), 6.41-6.30 (m, 2H), 6.27-6.14 (m, 2H), 5.76-5.70 (m, 1H), 4.20-4.05 (m, 2H), 4.00-3.87 (m, 1H), 3.43-3.30 (m, 1H), 2.90 (s, 3H), 2.81-2.69 (m, 1H), 2.51-2.38 (m, 1H), 1.40 (t, J=6.9 Hz, 3H).

Synthesis of Compound 083

Compound 083 was prepared in a similar manner to Compound 076 and was isolated as a brown solid (13.64 mg, 24.25 μmol, 12.40% yield, 96.1% purity). LCMS: Rt=0.478 min, m/z=540.2 (M+H+) $^{1}$H NMR: (400 MHz, CHLOROFORM-d) δ=8.44 (br s, 1H), 8.29 (s, 1H), 8.24 (s, 1H), 7.43 (d, J=2.0 Hz, 2H), 7.35-7.31 (m, 2H), 7.17-7.09 (m, 2H), 6.21 (br dd, J=5.2, 8.8 Hz, 1H), 4.15-4.05 (m, 2H), 3.05-2.95 (m, 1H), 2.86 (s, 3H), 2.83 (s, 3H), 2.75-2.49 (m, 9H), 1.38 (t, J=6.8 Hz, 3H).

Synthesis of Compounds 085 and 087

Compounds 085 and 087 were prepared by the steps of GP1-3 and GP5-8, where the product of GP6 was Boc-protected and the product on GP8 was deprotected under acidic conditions and then purified by SFC column: DAICEL CHIRALPAK AD (250 mm*30 mm, 10 um); mobile phase: [CO2-EtOH (0.1% NH3H2O)]; B %: 62.5%, isocratic elution mode to give two peaks.

Peak 1: Compound 087 (100 mg, 210.12 μmol, 55.28% yield, 99.5% purity) was obtained as a white solid. LCMS: Rt=0.435 min, m/z=474.2 (M+H+)

$^1$H NMR (400 MHz, CHLOROFORM-d) δ=12.34-11.91 (m, 1H), 9.13 (s, 1H), 8.44 (s, 1H), 8.28 (s, 1H), 7.43-7.29 (m, 4H), 7.06 (s, 3H), 6.08-6.01 (m, 1H), 4.20-3.97 (m, 2H), 3.32-3.30 (m, 2H), 3.24-3.03 (m, 2H), 2.87 (s, 3H), 2.64-2.63 (m, 1H), 2.33-2.21 (m, 1H), 1.82-1.81 (m, 1H), 1.39 (t, J=7.2 Hz, 3H).

Peak 2 was re-purified by prep-HPLC column: Unisil 3-100 C18 Ultra 150*50 mm*3 um; mobile phase: [water (FA)-ACN]; gradient: 8%-38% B over 10 min to give Compound 085 (9.94 mg, 18.94 μmol, 4.98% yield, 99% purity, FA) was obtained as a white solid. LCMS: Rt=0.429 min, m/z=474.2 (M+H+) $^1$H NMR (400 MHz, CHLOROFORM-d) δ=9.13 (br s, 1H), 8.44 (s, 1H), 8.28 (s, 1H), 7.43-7.29 (m, 4H), 7.06 (s, 3H), 6.08-6.01 (m, 1H), 4.20-3.97 (m, 2H), 3.32-3.30 (m, 2H), 3.24-3.03 (m, 2H), 2.87 (s, 3H), 2.64-2.63 (m, 1H), 2.33-2.21 (m, 1H), 1.82-1.81 (m, 1H), 1.39 (t, J=7.2 Hz, 3H).

Synthesis of Compounds 088 and 089

Compounds 088 and 089 were prepared by the steps of Scheme 3, GP1-3 and GP5-8, where the product of GP6 was Boc-protected and the product on GP8 was deprotected under acidic conditions and then purified by SFC (column: DAICEL CHIRALPAK AD (250 mm*30 mm, 10 um); mobile phase: [CO2-ACN/i-PrOH (0.1% NH3H2O)]; B %: 55%, isocratic elution mode) and concentrated and lyophilized to get the peak 1. Compound 089 (90 mg, 187.78 μmol, 55.58% yield, 98.8% purity) as an off-white solid.

Peak 2 was re-purified by prep-HPLC (column: Phenomenex luna C18 150*25 mm*10 um; mobile phase: [water (FA)-ACN]; gradient: 5%-35% B over 9 min) and lyophilized to get the crude, the crude was re-purified by SFC (column: DAICEL CHIRALPAK AD (250 mm*30 mm, 10 um); mobile phase: [CO2-ACN/i-PrOH (0.1% NH3H2O)]; B %: 55%, isocratic elution mode) and concentrated and lyophilized to give Compound 088 (9.77 mg, 20.20 μmol, 5.98% yield, 97.89% purity) as a brown gum.

Compound 088: LCMS: Rt=0.425 min, m/z=474.3[M+H]+ $^1$H NMR (400 MHz, CHLOROFORM-d) δ=9.11 (s, 1H), 8.45 (s, 1H), 8.28 (s, 1H), 7.40-7.31 (m, 2H), 7.31-7.28 (m, 1H), 7.27-7.23 (m, 1H), 7.08-6.98 (m, 3H), 6.17-5.85 (m, 1H), 4.18-3.95 (m, 2H), 3.43-3.36 (m, 1H), 3.35-3.22 (m, 1H), 3.17 (br t, J=7.2 Hz, 2H), 3.02-2.95, 2.85 (s, 3H), 2.27-2.16 (m, 1H), 1.47-1.39 (m, 1H), 1.36 (t, J=6.8 Hz, 3H)

Compound 089: LCMS: Rt=0.425 min, m/z=474.2[M+H]+ $^1$H NMR (400 MHz, CHLOROFORM-d) δ=9.11 (s, 1H), 8.45 (s, 1H), 8.26 (s, 1H), 7.40-7.31 (m, 2H), 7.27 (s, 2H), 7.06-7.00 (m, 3H), 6.17-5.85 (m, 1H), 4.18-3.95 (m, 2H), 3.43-3.36 (m, 1H), 3.35-3.22 (m, 1H), 3.08 (br t, J=67.2 Hz, 2H), 3.02-2.95 (m, 1H), 2.82 (s, 3H), 2.22-2.10 (m, 1H), 1.47-1.39 (m, 1H), 1.36 (t, J=6.8 Hz, 3H).

Synthesis of Compound 081

Compound 081 was prepared using Compound 088 as starting material. To a solution of compound 088 in DMA (1 mL) was added formaldehyde (30.85 mg, 380.12 μmol, 28.30 μL, 37% purity, 3 eq) and NaBH(OAc)3 (80.56 mg, 380.12 μmol, 3 eq) at 0° C., the mixture was stirred at 25° C. for 2 hr. The reaction mixture was diluted with water (3 mL) and extracted with DCM (3 mL*3). The combined organic layers dried over Na2SO4, filtered and concentrated under reduced pressure to give a residue. The residue was purified by prep-HPLC (column: YMC-Actus Triart C18 150*30 mm*7 um; mobile phase: [water (FA)-ACN]; gradient: 5%-35% B over 10 min) to give the Compound 081 (38.57 mg, 71.76 μmol, 87.47% yield, 99.28% purity, FA) was obtained as a white solid. LCMS: RT=0.428 min, m/z=488.2 [M+H]+ $^1$H NMR (400 MHz, $D_2O$) δ=9.04 (s, 1H), 8.40 (s, 1H), 8.20 (s, 1H), 7.27-7.26 (m, 2H), 7.25-7.15 (m, 2H), 6.89-6.78 (m, 3H), 6.20-5.80 (m, 1H), 4.00-3.94 (m, 2H), 3.70-3.55 (m, 1H), 3.31-3.01 (m, 2H), 2.95-2.85 (m, 1H), 2.78 (s, 3H), 2.45 (s, 3H), 2.38-2.32 (m, 2H), 2.00-1.96 (m, 1H), 1.28 (br t, J=7.2 Hz, 3H).

Synthesis of Compound 082

Compound 082 was according to Compound 081 using Compound 089 as starting material. Compound 082 (22.96 mg, 46.84 μmol, 44.36% yield, 99.46% purity) was obtained as an off-white solid. LCMS: Rt=0.435 min, m/z=488.3[M+H]+ $^1$H NMR (400 MHz, CHLOROFORM-d) δ=12.33 (br s, 1H), 9.33 (s, 1H), 8.61 (s, 1H), 8.48 (s, 1H), 7.62-7.55 (m, 2H), 7.53-7.48 (m, 2H), 7.27 (s, 3H), 6.33 (br s, 1H), 4.36-4.21 (m, 2H), 3.77-3.57 (m, 1H), 3.32 (br t, J=8.0 Hz, 1H), 3.04 (s, 4H), 2.72-2.63 (m, 5H), 2.60-2.30 (m, 1H), 1.76-1.63 (m, 1H), 1.59 (t, J=7.2 Hz, 3H).

Synthesis of Compound 090

Compound 090 was prepared following the steps of GP4-8. The resulting product was then oxidized and N-methylated using the same procedure described for Compound 074. Compound 090 (8.78 mg, 16.56 μmol, 13.73% yield, 99.32% purity) was obtained as white solid. LCMS: Rt=0.457 min, m/z=526.3 (M+H+) $^1$H NMR: (400 MHz, CHLOROFORM-d) δ=9.13 (s, 1H), 8.48 (br s, 1H), 8.44 (s, 1H), 8.27 (s, 1H), 7.43 (d, J=2.0 Hz, 2H), 7.36-7.30 (m, 2H), 7.19-7.01 (m, 2H), 6.28 (br d, J=8.8 Hz, 1H), 4.16-4.03 (m, 2H), 2.83 (s, 3H), 2.73-2.62 (m, 2H), 2.51 (s, 6H), 2.01 (s, 2H), 1.38 (t, J=7.2 Hz, 3H).

Synthesis of Compound 091

Compound 091 was prepared following the steps of GP4-8. The resulting product was then oxidized and N-methylated using the same procedure described for Compound 074. Compound 091 (111.31 mg, 231.52 μmol, 32.02% yield, 98.09% purity) was obtained as white solid. LCMS: Rt=0.428 min, m/z=472.3 (M+H+) $^1$H NMR: (400 MHz, CHLOROFORM-d) δ=9.30-9.19 (m, 1H), 8.58-8.49 (m, 1H), 8.37 (s, 1H), 7.48-7.42 (m, 2H), 7.39 (br d, J=6.4 Hz, 2H), 7.27-7.21 (m, 2H), 7.16-7.08 (m, 1H), 6.34 (br d, J=8.1 Hz, 1H), 4.25-4.10 (m, 2H), 3.29-3.20 (m, 1H), 2.96 (s, 3H), 2.95-2.85 (m, 2H), 2.77 (s, 6H), 2.74-2.57 (m, 1H), 1.46 (t, J=6.8 Hz, 3H).

Synthesis of Compounds 092 and 097:

Compounds 092 and 097 were synthesized following the steps of GP1-3 and GP5-9, then GP11-13. The crude compounds 092 and 097 was purified by SFC (column: DAICEL CHIRALPAK AD (250 mm×50 mm, 10 um); mobile phase: [$CO_2$:i-PrOH (0.1% $NH_3H_2O$)]; B %: 30%, isocratic elution mode). The eluent was concentrated to remove organic solvents and the residual aqueous solution was lyophilized to afford the desired products.

Compound 092 (80 mg, 174.10 μmol, 33.33% yield) was obtained as an off-white solid. LCMS: $t_R$=0.418 min, m/z=460.2 $[M+H]^+$ NMR: $^1$H NMR (400 MHz, CHLOROFORM-d) δ=9.06 (s, 1H), 8.20-8.10 (m, 2H), 7.31-7.26 (m, 1H), 7.30-7.10 (m, 3H), 7.00-6.89 (m, 3H), 6.43 (br d, J=10.0 Hz, 1H), 4.05-3.93 (m, 2H), 3.87 (s, 2H), 3.82 (br d, J=7.6 Hz, 1H), 3.80-3.75 (m, 1H), 3.36 (br s, 1H), 2.68 (s, 3H), 1.28 (t, J=6.8 Hz, 3H).

Compound 097 (60 mg, 118.69 μmol, 22.72% yield) was obtained as an off-white solid. LCMS: $t_R$=0.418 min, m/z=460.2 $[M+H]^+$ NMR: $^1$H NMR (400 MHz, CHLOROFORM-d) δ=9.06 (s, 1H), 8.52 (br s, 1H), 8.30-8.19 (m, 2H), 7.35-7.29 (m, 1H), 7.21-7.16 (m, 3H), 7.00 (br s, 2H), 6.93 (br d, J=8.0 Hz, 1H), 6.58 (br d, J=11.2 Hz, 1H), 4.42-4.32 (m, 1H), 4.30-4.24 (m, 1H), 4.22-4.08 (m, 2H), 4.00-3.90 (m, 2H), 3.80-3.70 (m, 1H), 2.69 (s, 3H), 1.27 (t, J=6.8 Hz, 3H).

Synthesis of Compound 095

Compound 095 was prepared following the steps of GP4-8. The resulting product was then oxidized and N-methylated using the same procedure described for Compound 074. Compound 095 (1851.73 mg, 3.64 mmol, 46.49% yield, 99.9% purity) was isolated as light-yellow gum. LCMS: Rt=0.432 min, m/z=508.3 (M+H+) $^1$H NMR (400 MHz, CHLOROFORM-d) δ=9.10 (s, 1H), 8.39 (s, 1H), 8.25 (s, 1H), 8.21 (s, 2H), 7.28 (td, J=3.0, 7.8 Hz, 2H), 7.25-7.19 (m, 2H), 7.07-7.01 (m, 2H), 6.99-6.93 (m, 1H), 6.23 (br dd, J=4.5, 10.3 Hz, 1H), 4.75-4.68 (m, 1H), 4.63-4.56 (m, 1H), 4.08-3.92 (m, 2H), 3.09-3.01 (m, 1H), 3.01-2.91 (m, 2H), 2.84 (td, J=6.2, 9.4 Hz, 1H), 2.78 (s, 3H), 2.72-2.58 (m, 1H), 2.54 (s, 3H), 2.49-2.36 (m, 1H), 1.29 (t, J=6.9 Hz, 3H).

Synthesis of Compound 079:

Compound 079 was prepared using Compound 097 as starting material. To a solution of 097 (40 mg, 79.12 μmol, 1 eq) and formaldehyde (19.27 mg, 237.37 μmol, 17.67 μL, 37% purity, 3 eq) in DMA (0.5 mL) was added AcOH (475.14 μg, 7.91 μmol, 0.1 eq). The mixture was stirred at 25° C. for 0.5 h, then $NaBH(OAc)_3$ (50.31 mg, 237.37 μmol, 3 eq) was added at 0° C. The mixture was stirred at 25° C. for 0.5 h and filtered to isolate the filtrate. The residue was purified by prep-HPLC (column: Phenomenex luna C18 150*25 mm*10 um; mobile phase: [water (FA)-CAN]; gradient: 5%-35% B over 15 min) and lyophilized to get the crude product. The crude product was repurified by prep-HPLC (column: Phenomenex luna C18 150*25 mm*10 um; mobile phase: [water (FA)-ACN]; gradient: 5%-35% B over 15 min) and lyophilized. Compound 079 (15.55 mg, 29.85 μmol, 37.72% yield, 99.73% purity) was obtained as a white solid. LCMS: Rt=0.431 min, m/z=474.2[M+H]+ $^1$H NMR (400 MHz, CHLOROFORM-d) δ=12.81-11.30 (m, 1H), 9.12 (s, 1H), 8.54 (br s, 1H), 8.34-8.21 (m, 2H), 7.41-7.32 (m, 2H), 7.31-7.26 (m, 2H), 7.09-6.99 (m, 3H), 6.34 (br d, J=10.8 Hz, 1H), 4.13-4.00 (m, 2H), 3.95-3.79 (m, 3H), 3.43 (t, J=5.6 Hz, 1H), 3.14 (br s, 1H), 2.80 (s, 3H), 2.51 (s, 3H), 1.37 (t, J=6.8 Hz, 3H).

Synthesis of Compound 210

Compound 210 was prepared in a similar manner to Compound 157 and was then treated with m-CPBA in DCM. Compound 210 (1736.51 mg, 3.38 mmol, 55.50% yield, 99% purity) was obtained as an off-white solid. LCMS: RT=0.449 min, m/z=508.2[M+H]+ $^1$H NMR (400 MHz, CHLOROFORM-d) δ=9.08 (s, 1H), 8.46 (s, 1H), 8.35 (s, 1H), 8.22 (s, 1H), 7.49 (s, 1H), 7.36 (br d, J=6.3 Hz, 1H), 7.28 (br d, J=6.8 Hz, 2H), 7.25 (s, 1H), 7.14-7.04 (m, 2H), 6.26 (br dd, J=6.0, 8.6 Hz, 1H), 4.15-3.85 (m, 2H), 3.82-3.53 (m, 2H), 3.44 (s, 3H), 3.36 (s, 3H), 3.19 (br d, J=9.5 Hz, 1H), 2.96-2.66 (m, 4H), 1.32 (br t, J=6.8 Hz, 3H).

Synthesis of Compound 105

Compound 105 was prepared according to the steps of GP16, GP5, GP8, and GP9 and was isolated as a white solid (41.43 mg, 87.97 μmol, 10.03% yield, 98% purity). LCMS: Rt=0.383 min, m/z=462.3[M+H]+ $^1$H NMR (400 MHz, CHLOROFORM-d) δ=9.05 (s, 1H), 8.48 (s, 1H), 8.24-8.19 (m, 1H), 7.39-7.30 (m, 2H), 7.25 (br s, 2H), 7.10-6.99 (m, 3H), 5.07 (br s, 2H), 4.07-3.72 (m, 4H), 3.33-2.77 (m, 4H), 1.38-1.17 (m, 6H).

Synthesis of Compound 106

Compound 106 was prepared in a similar manner to Compound 067 using (3S,5R)-3,5-difluoropiperidine and was isolated as a white solid. (44.36 mg, 81.69 μmol, 38.42% yield, 99% purity). LCMS: RT=0.433 min, m/z=538.2 [M+H]+ $^1$H NMR (400 MHz, CHLOROFORM-d) δ=9.04 (br s, 1H), 8.31 (br s, 1H), 8.19 (s, 1H), 7.31-7.23 (m, 2H), 7.23-7.18 (m, 2H), 6.97-6.87 (m, 3H), 5.03 (s, 2H), 4.50 (br s, 1H), 4.38 (br s, 1H), 3.94 (br d, J=4.3 Hz, 2H), 3.39 (br s, 2H), 2.61-2.33 (m, 6H), 2.14-1.86 (m, 2H), 1.26 (br t, J=6.2 Hz, 3H).

Synthesis of Compound 107

Compound 107 was prepared in a similar manner to Compound 067 using (3R,4R)-3,4-difluoropyrrolidine and isolated as a white solid (60.40 mg, 114.21 μmol, 46.67% yield, 99% purity). LCMS: Rt=0.423 min, m/z=524.2[M+H]+ $^1$H NMR (400 MHz, CHLOROFORM-d) δ ppm 0.83 (br t, J=6.88 Hz, 3H) 1.99-2.44 (m, 6H) 2.96 (br s, 2H) 3.51 (br s, 2H) 4.39-4.66 (m, 4H) 6.38-6.60 (m, 3H) 6.74-6.88 (m, 4H) 7.69-7.91 (m, 2H) 8.60 (s, 1H) 11.40-11.81 (m, 1H).

Synthesis of Compound 108

Compound 108 was prepared in a similar manner to Compound 067 using (3R,4S)-3,4-difluoropyrrolidine and was isolated as a white solid. LCMS: Rt=0.417 min, m/z=524.2[M+H]+ $^1$H NMR (400 MHz, CHLOROFORM-d) δ ppm 1.35 (br t, J=6.75 Hz, 3H) 2.54-2.92 (m, 6H) 3.46 (br s, 2H) 4.03 (br s, 2H) 4.85 (br s, 1H) 4.99 (br s, 1H) 5.04 (br s, 2H) 6.91-7.09 (m, 3H) 7.29 (br d, J=7.00 Hz, 2H) 7.32-7.42 (m, 2H) 8.23-8.39 (m, 2H) 9.12 (br s, 1H) 11.87-12.24 (m, 1H).

Synthesis of Compound 109

Compound 109 was prepared in a similar manner to Compound 067 using 3-fluoropiperidine and was isolated as a white solid (27.36 mg, 54.06 μmol, 24.91% yield, 99.9% purity). LCMS: Rt=0.419 min, m/z=506.2 (M+H+). $^1$H NMR: (400 MHz, CHLOROFORM-d) δ=12.34-11.77 (m, 1H), 9.03 (br s, 1H), 8.30-8.10 (m, 2H), 7.33-7.21 (m, 3H), 7.18 (br s, 1H), 7.01-6.80 (m, 3H), 5.18-4.93 (m, 3H), 4.04-3.83 (m, 2H), 3.56-3.33 (m, 2H), 2.77-2.61 (m, 4H), 2.39-1.76 (m, 4H), 1.27 (br t, J=6.8 Hz, 3H).

Synthesis of Compound 110

Compound 110 was prepared in a similar manner to Compound 067 using 4-fluoropiperidine and was isolated as a light yellow oil (117 mg, 180.04 μmol, 50.66% yield). LCMS: Rt=0.502 min, m/z=650.2[M+H]+

Synthesis of Compound 111

Compound 111 was prepared in a similar manner to Compound 067 using (3S,5S)-3,5-difluoropiperidine and was isolated as a white solid (67.67 mg, 123.36 μmol, 49.63% yield, 98% purity). LCMS: RT=0.442 min, m/z=538.3 [M+H]+ $^1$H NMR (400 MHz, CHLOROFORM-d) δ=12.49-11.64 (m, 1H), 9.15 (s, 1H), 8.38 (br s, 1H), 8.29 (s, 1H), 7.36 (td, J=5.2, 7.9 Hz, 2H), 7.31 (br d, J=7.3 Hz, 2H), 7.09-6.93 (m, 3H), 5.28-5.14 (m, 1H), 5.11-4.98 (m, 1H), 4.96-4.68 (m, 2H), 4.05 (br d, J=6.6 Hz, 2H), 3.47 (br s, 2H), 2.76-2.60 (m, 2H), 2.59-2.51 (m, 2H), 2.49 (br s, 2H), 2.11-1.99 (m, 2H), 1.37 (t, J=6.9 Hz, 3H).

Synthesis of Compound 112

Compound 112 was prepared in a similar manner to Compound 117. Compound 112 was isolated as a white solid (40.16 mg, 82.21 μmol, 20.19% yield, 99% purity). LCMS: Rt=0.420 min, m/z=484.5[M+H]+ $^1$H NMR (400 MHz, CHLOROFORM-d) δ=13.03-11.91 (m, 1H), 9.09 (br s, 1H), 8.26 (s, 2H), 7.53 (br d, J=7.6 Hz, 2H), 7.46-7.38 (m, 2H), 7.37-7.29 (m, 2H), 7.00 (br d, J=5.3 Hz, 2H), 5.06 (br s, 2H), 3.98 (br s, 2H), 3.52 (br s, 2H), 2.58 (br s, 2H), 2.33 (br s, 4H), 1.61 (br s, 4H), 1.46 (br s, 2H), 1.34 (br t, J=6.9 Hz, 3H).

Synthesis of Compound 113

Compound 113 was prepared in a similar manner to Compound 067 using 3,3-difluoropiperidine and was isolated as a white solid (58.1 mg, 107.65 μmol, 52.86% yield, 99.6% purity). LCMS: Rt=0.447 min, m/z=538.2[M+H]+ HPLC: Rt=1.220 min. 1HNMR: (400 MHz, CHLOROFORM-d) δ=12.31-11.89 (m, 1H), 9.13 (s, 1H), 8.35 (br s, 1H), 8.27 (s, 1H), 7.40-7.32 (m, 2H), 7.29 (br d, J=7.8 Hz, 2H), 7.09-6.93 (m, 3H), 5.10 (s, 2H), 4.04 (br d, J=6.8 Hz, 2H), 3.46 (br s, 2H), 2.69-2.44 (m, 4H), 2.29 (br s, 2H), 1.93-1.78 (m, 4H), 1.36 (t, J=6.8 Hz, 3H).

Synthesis of Compound 114

Compound 114 was prepared according to the steps of GP16, GP5, GP8, GP9, followed by oxidation IBX in DMSO. The oxidized product was then coupled with 3-fluoropiperidine following the procedure for Compound 067, then deprotected with TFA in DCM (GP9). Compound 114 was isolated as a white solid (53.39 mg, 92.88 μmol, 32.42% yield, 98.4% purity). LCMS: Rt=0.429 min, m/z=520.2 (M+H+) $^1$H NMR: (400 MHz, chloroform-d) δ=9.07 (s, 1H), 8.30 (br s, 1H), 8.24 (s, 1H), 8.19 (s, 1H), 7.32-7.20 (m, 3H), 7.17 (br s, 1H), 7.03-6.78 (m, 3H), 5.09-4.94 (m, 2H), 4.68-4.39 (m, 1H), 3.93 (br s, 2H), 3.43 (br s, 2H), 2.74-2.34 (m, 4H), 2.25 (br d, J=1.3 Hz, 2H), 1.84-1.54 (m, 3H), 1.43 (br s, 1H), 1.27 (br t, J=6.9 Hz, 3H).

Synthesis of Compound 115

Compound 115 was prepared in a similar manner to Compound 117. The amine starting material was prepared according to the following scheme:

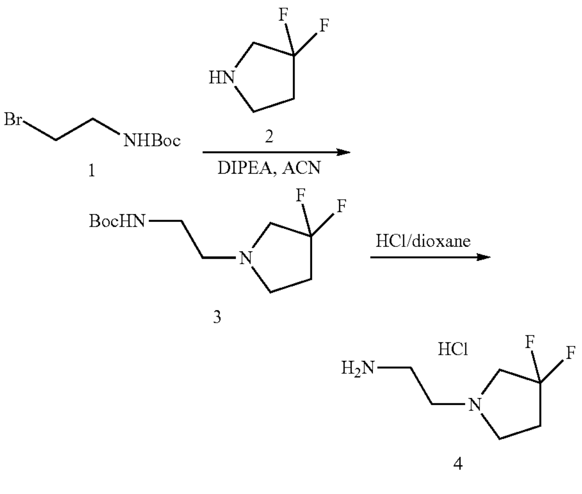

Compound 115 was isolated as a white solid (84.22 mg, 159.26 μmol, 18.49% yield, 99% purity). LCMS: Rt=0.443 min, m/z=524.2[M+H]+ $^1$H NMR (400 MHz, CHLOROFORM-d) δ ppm 1.36 (t, J=6.94 Hz, 3H) 2.19 (br s, 2H) 2.52 (br s, 2H) 2.66 (br s, 4H) 3.43-3.55 (m, 2H) 4.03 (br s, 2H) 5.05 (s, 2H) 6.88-7.10 (m, 3H) 7.29 (br d, J=7.38 Hz, 2H) 7.31-7.41 (m, 2H) 8.22-8.41 (m, 2H) 9.12 (s, 1H) 11.94-12.26 (m, 1H).

Synthesis of Compound 116

Compound 116 was prepared in a similar manner to Compound 117. Compound 116 was isolated as a white solid (61.75 mg, 131.09 μmol, 22.22% yield, 95% purity). LCMS: Rt=0.410 min, m/z=448.2 (M+H+) $^1$H NMR: (400 MHz, CHLOROFORM-d) δ=12.56-12.10 (m, 1H), 9.23-8.95 (m, 1H), 8.45-8.06 (m, 2H), 7.41-7.31 (m, 2H), 7.26-7.13 (m, 2H), 7.03 (br t, J=7.3 Hz, 3H), 5.02 (br s, 2H), 4.15-3.88 (m, 2H), 3.68-3.37 (m, 2H), 3.01-2.74 (m, 2H), 2.61-2.24 (m, 3H), 1.40-1.29 (m, 3H).

Synthesis of Compound 117

Compound 117 was prepared according to the steps of GP16, GP5, GP8, and GP9. Compound 117 was isolated as a white solid (148.3 mg, 292.70 μmol, 41.10% yield, 99% purity). LCMS: Rt=0.413 min, m/z=502.2[M+H]+ $^1$H NMR (400 MHz, CHLOROFORM-d) δ=10.59-9.39 (m, 3H), 9.11 (br s, 1H), 8.47-8.22 (m, 3H), 7.40-7.28 (m, 3H), 7.25 (br s, 1H), 7.17-6.88 (m, 3H), 5.08 (s, 2H), 3.98 (br s, 2H), 3.91-3.54 (m, 2H), 3.50-2.19 (m, 6H), 1.98-1.62 (m, 4H), 1.55 (br s, 2H), 1.33 (br t, J=6.4 Hz, 3H).

Synthesis of Compound 118

Compound 118 was prepared in a similar manner to Compound 117. Compound 118 was isolated as a white solid (99.03 mg, 194.69 μmol, 27.42% yield, 99% purity). LCMS: Rt=0.408 min, m/z=504.2[M+H]+ $^1$H NMR (400 MHz, CHLOROFORM-d) δ=9.12 (br s, 1H), 8.54-7.88 (m, 3H), 7.40-7.27 (m, 2H), 7.26-7.23 (m, 1H), 7.08-6.79 (m, 3H), 5.06 (br s, 2H), 3.99 (br s, 2H), 3.79-3.28 (m, 6H), 2.78-2.49 (m, 2H), 2.47-1.78 (m, 4H), 1.35 (br t, J=6.6 Hz, 3H).

Synthesis of Compound 119

Compound 119 was prepared in a similar manner to Compound 117. Compound 119 was isolated as a white solid (52.61 mg, 106.82 μmol, 15.62% yield, 99% purity). LCMS: Rt=0.420 min, m/z=488.2[M+H]+ $^1$H NMR (400 MHz, CHLOROFORM-d) δ ppm 1.33 (br t, J=6.50 Hz, 3H) 1.79-2.17 (m, 4H) 2.40-3.17 (m, 4H) 3.25-3.51 (m, 2H) 3.58-3.90 (m, 2H) 3.98 (br s, 2H) 5.08 (br s, 2H) 6.92-7.12 (m, 3H) 7.27 (s, 2H) 7.30-7.40 (m, 2H) 8.07-8.58 (m, 3H) 9.09 (br s, 1H) 10.68-11.21 (m, 3H).

Synthesis of Compound 120

Compound 120 was prepared in a similar manner to Compound 117. Compound 119 was isolated as a white solid (95.96 mg, 194.04 μmol, 27.60% yield, 99% purity). LCMS: Rt=0.421 min, m/z=490.3[M+H]+ $^1$H NMR (400 MHz, CHLOROFORM-d) δ ppm 0.84-1.34 (m, 6H) 1.37 (br t, J=6.75 Hz, 3H) 2.43-3.02 (m, 4H) 3.10-3.51 (m, 2H) 3.57-3.94 (m, 2H) 4.04 (br d, J=5.00 Hz, 2H) 5.14 (br s, 2H) 6.97-7.15 (m, 3H) 7.28-7.33 (m, 2H) 7.35-7.44 (m, 2H) 8.06-8.61 (m, 3H) 9.14 (br s, 1H) 10.22-11.01 (m, 3H).

Synthesis of Compounds 121 and 122

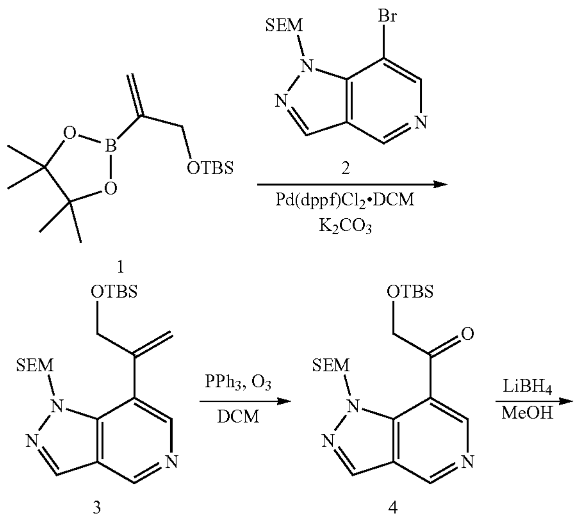

-continued

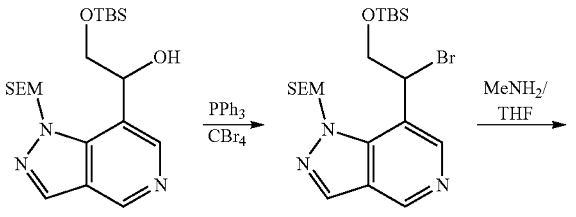

5

6

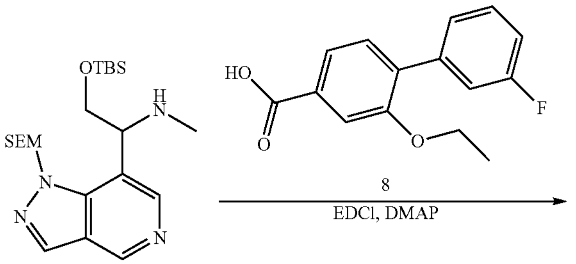

7

8

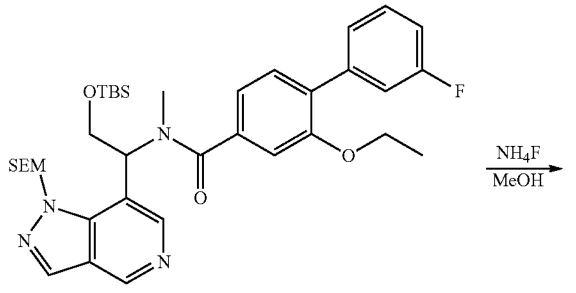

9

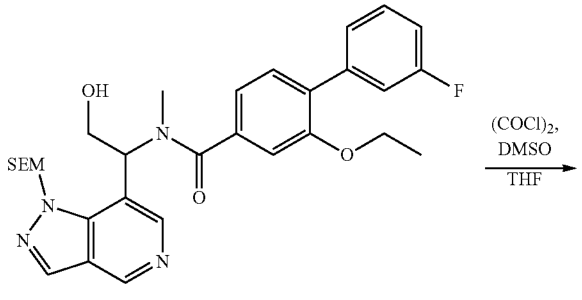

10

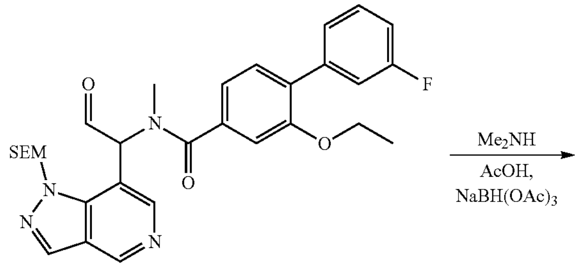

11

-continued

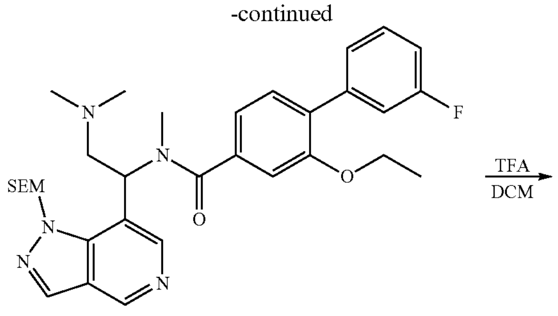

12

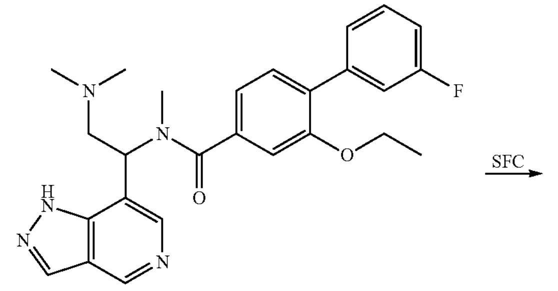

13

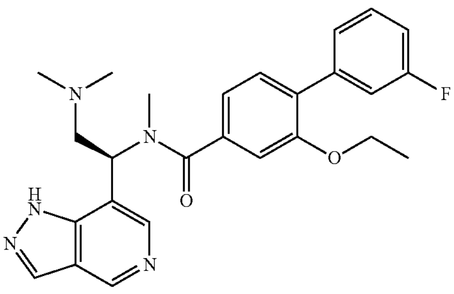

121

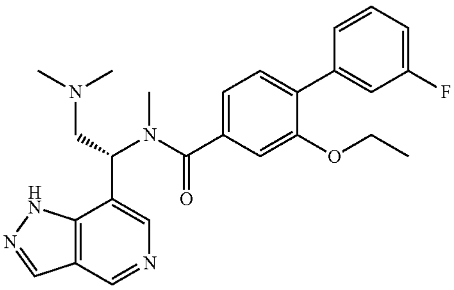

122

To a solution of compound 1 (10 g, 33.52 mmol, 1 eq) and compound 2 (11.01 g, 33.52 mmol, 1 eq) in dioxane (100 mL) and $H_2O$ (10 mL) was added $K_2CO_3$ (9.27 g, 67.05 mmol, 2 eq) and $Pd(dppf)Cl_2{\cdot}CH_2Cl_2$ (1.37 g, 1.68 mmol, 0.05 eq). The mixture was stirred at 100° C. for 12 h under $N_2$ atmosphere. The reaction mixture was poured into $H_2O$ (300 mL) under $N_2$ and extracted by EtOAc (200 mL×3), the organic phase was combined and washed with brine (200 mL×3), dried with anhydrous $Na_2SO_4$, filtered and concentrated to give a residue. The resulting residue was purified by silica gel column chromatography (PE:EA=1:0 to 3:1) to give the product (Rf=0.5). Compound 3 (11.5 g, 27.40 mmol, 81.73% yield) was obtained as a brown oil. $^1$H NMR: (400 MHz, CHLOROFORM-d) δ=9.05 (br s, 1H), 8.21 (br d, J=10.0 Hz, 1H), 8.19 (s, 1H), 5.78 (s, 3H), 5.30 (d, J=1.2

Hz, 1H), 4.47 (s, 2H), 3.62-3.50 (m, 2H), 0.89 (s, 9H), 0.85 (d, J=8.4 Hz, 2H), 0.02 (s, 6H), −0.04 (s, 9H)

To a solution of compound 3 (5.5 g, 13.10 mmol, 1 eq) in DCM (60 mL) and MeOH (60 mL) was added ozone (628.99 mg, 13.10 mmol, 1 eq) at −70° C. for 0.5h, then added $PPh_3$ (6.87 g, 26.21 mmol, 2 eq) in DCM (5 mL) at −70° C., the mixture was stirred at 20° C. for 1 hr. The reaction was concentrated to give a crude product. The resulting residue was purified by silica gel column chromatography (PE:EA=1:0 to 3:1) to give the product (Rf=0.35). Compound 4 (5.1 g, 12.09 mmol, 92.29% yield) was obtained as a yellow oil. $^1H$ NMR: (400 MHz, METHANOL-$d_4$) δ=9.26 (s, 1H), 8.81 (s, 1H), 8.42 (s, 1H), 5.90 (s, 2H), 4.93 (s, 2H), 3.30-3.25 (m, 2H), 0.89 (s, 9H), 0.74 (dd, J=7.6, 8.8 Hz, 2H), 0.15 (s, 6H), −0.11 (s, 9H)

To a solution of compound 4 (5 g, 11.86 mmol, 1 eq) in MeOH (55 mL) was added $LiBH_4$ (2 M, 17.79 mL, 3 eq) at 0° C. under $N_2$ atmosphere, the mixture was stirred at 20° C. for 2 hr under $N_2$ atmosphere. The combined mixture was poured into sat. $NH_4Cl$. aq (50 mL) at 0° C., and the aqueous phase was extracted with EA (80 mL×3). The combined organic phase was dried with $Na_2SO_4$ and concentrated to give the crude product. The resulting residue was purified by silica gel column chromatography (PE:EA=1:0 to 1:1) to give the product (Rf=0.4). Compound 5 (5.7 g, crude) was obtained as a yellow oil. $^1H$ NMR: (400 MHz, METHANOL-$d_4$) δ=9.02 (s, 1H), 8.54 (s, 1H), 8.31 (s, 1H), 6.15 (d, J=11.6 Hz, 1H), 5.85 (d, J=11.6 Hz, 1H), 5.51 (dd, J=5.6, 7.6 Hz, 1H), 4.16-4.12 (m, 1H), 3.87 (dd, J=8.0, 9.6 Hz, 1H), 3.62-3.53 (m, 2H), 0.89-0.78 (m, 2H), 0.71 (s, 9H), −0.06 (s, 9H), −0.10 (s, 3H), −0.24 (s, 3H)

To a solution of compound 5 (5.7 g, 13.45 mmol, 1 eq) in DCM (60 mL) was added $CBr_4$ (8.92 g, 26.91 mmol, 2 eq) and $PPh_3$ (5.29 g, 20.18 mmol, 1.5 eq) in DCM (20 mL) at 0° C., the mixture was stirred at 20° C. for 2 h. The mixture was concentrated to give a crude product. The resulting residue was purified by silica gel column chromatography (PE:EA=1:0 to 3:1) to give the product (Rf=0.5). Compound 6 (2.31 g, 4.75 mmol, 35.29% yield) was obtained as a yellow oil. $^1H$ NMR: (400 MHz, METHANOL-$d_4$) δ=9.06 (s, 1H), 8.67 (s, 1H), 8.35 (s, 1H), 6.09-6.03 (m, 1H), 6.02-5.95 (m, 2H), 4.43-4.29 (m, 2H), 3.63-3.51 (m, 2H), 0.93-0.82 (m, 2H), 0.75 (s, 9H), 0.03 (s, 3H), −0.04-−0.08 (m, 12H)

To a solution of compound 6 (2.31 g, 4.75 mmol, 1 eq) in DMF (25 mL) was added $K_2CO_3$ (1.31 g, 9.49 mmol, 2 eq) and $MeNH_2$ (2 M, 11.87 mL, 5 eq), the mixture was stirred at 30° C. for 12 h. The reaction mixture was poured in water (30 mL), and extracted with EA (50 mL×3). The combined organic layers were washed by brine (50 mL×3) and dried over $Na_2SO_4$ and concentrated under reduced pressure to give a residue. Compound 7 (2.2 g, crude) was obtained as a yellow oil. LCMS: Rt=0.509 min, m/z=437.3 $[M+H]^+$ To a solution of compound 7 (2.2 g, 3.78 mmol, 1 eq) and compound 8 (1.08 g, 4.16 mmol, 1.1 eq) in DCM (20 mL) was added EDCI (1.09 g, 5.67 mmol, 1.5 eq) and DMAP (46.15 mg, 377.80 μmol, 0.1 eq), the mixture was stirred at 25° C. for 1 hr. The mixture was concentrated to give a crude product. The resulting residue was purified by silica gel column chromatography (PE:EA=1:1) to give the product (Rf=0.4). Compound 9 (2.4 g, 3.53 mmol, 93.56% yield) was obtained as a yellow oil. LCMS: Rt=0.646 min, m/z=679.4 $[M+H]^+$ To a solution of compound 9 (2.1 g, 3.09 mmol, 1 eq) in MeOH (30 mL) was added $NH_4F$ (1.15 g, 30.93 mmol, 10 eq), the mixture was stirred at 60° C. for 5 hr. The reaction mixture was poured in water (50 mL) and extracted with EA (50 mL×3). The combined organic layers were washed by brine (50 mL×3) and dried over $Na_2SO_4$ and concentrated under reduced pressure to give a residue. The resulting residue was purified by silica gel column chromatography (PE:EA=1:0 to 0:1) to give the product. (Rf=0.3). Compound 10 (1.37 g, 2.43 mmol, 78.51% yield) was obtained as a yellow solid. LCMS: Rt=0.603 min, m/z=565.2 $[M+H]^+$ ıH NMR: (400 MHz, METHANOL-$d_4$) 6=9.06 (s, 1H), 8.67 (s, 1H), 8.35 (s, 1H), 6.09-6.03 (m, 1H), 6.02-5.95 (m, 2H), 4.43-4.29 (m, 2H), 3.63-3.51 (m, 2H), 0.93-0.82 (m, 2H), 0.75 (s, 9H), 0.03 (s, 3H), −0.04-−0.08 (m, 12H)

To a solution of $(COCl)_2$ (289.94 mg, 2.28 mmol, 199.96 μL, 3 eq) in DCM (10 mL) at −70° C. was added a solution of DMSO (178.48 mg, 2.28 mmol, 178.48 μL, 3 eq) in DCM (2 mL). The mixture was stirred for 30 min at −70° C., and a solution of compound 10 (430 mg, 761.44 μmol, 1 eq) in DCM (5 mL) was added to the mixture and stirred at −70° C. for 0.5 h. The mixture was treated with TEA (462.29 mg, 4.57 mmol, 635.89 μL, 6 eq) and allowed to warm to 20° C. slowly, then the mixture was stirred at 20° C. for 0.5 h. The reaction mixture was poured in water (20 mL) and extracted with DCM (30 mL×3). The combined organic layers were washed by brine (30 mL×3) and dried over $Na_2SO_4$ and concentrated under reduced pressure to give a residue. Compound 11 (400 mg, crude) was obtained as a yellow solid. $^1H$ NMR: (400 MHz, METHANOL-$d_4$) δ=9.94 (s, 1H), 9.19 (s, 1H), 8.31 (s, 1H), 8.26 (s, 1H), 7.38-7.35 (m, 2H), 7.34-7.31 (m, 2H), 7.20 (s, 1H), 7.17 (br d, J=7.6 Hz, 1H), 7.05 (br s, 1H), 6.73 (s, 1H), 5.83 (br d, J=6.4 Hz, 1H), 5.79-5.74 (m, 1H), 4.12-4.08 (m, 2H), 3.57-3.50 (m, 2H), 2.97 (s, 3H), 1.39 (s, 3H), 0.89-0.83 (m, 2H), −0.06 (s, 9H)

To a mixture of compound 11 (300 mg, 533.14 μmol, 1 eq) and N-methylmethanamine (2 M, 2.67 mL, 10 eq) in DCE (10 mL) was added AcOH (32.02 mg, 533.14 μmol, 30.52 μL, 1 eq) and 4 A MS (60 mg) at 20° C. The mixture was stirred at 30° C. for 12 h. Then $NaBH(OAc)_3$ (1.13 g, 5.33 mmol, 10 eq) was added and the mixture was stirred at 30° C. for 3 h. $NaBH_3CN$ (167.52 mg, 2.67 mmol, 5 eq) was added to the reaction mixture, then the mixture was stirred at 30° C. for 1 h. The reaction mixture was poured into saturated $NaHCO_3$ (20 mL) and extracted with DCM (30 mL×3). The combined organic layers were washed by brine (50 mL) and dried over $Na_2SO_4$ and concentrated under reduced pressure to give a residue. The crude product was purified by reversed-phase HPLC (0.1% FA condition) and lyophilized to give the product. Compound 12 (73 mg, 123.35 μmol, 23.14% yield) was obtained as a yellow oil. LCMS: Rt=0.522 min, m/z=592.3 $[M+H]^+$ To a mixture of compound 12 (90 mg, 152.08 μmol, 1 eq) in DCM (1 mL) was added TFA (1.54 g, 13.46 mmol, 1 mL, 88.52 eq) at 0° C., then the mixture was stirred at 25° C. for 3 h. The reaction mixture was poured into saturated $NaHCO_3$ (20 mL) and extracted with DCM (30 mL×3). The combined organic layers were washed by brine (50 mL) and dried over $Na_2SO_4$ and concentrated under reduced pressure to give a residue. The residue was purified by prep-HPLC (column: Waters Xbridge 150×25 mm×5 um; mobile phase: [water ($NH_4HCO_3$)-ACN]; gradient: 35%-65% B over 15 min), the purified solution was lyophilized to give a white solid. Compound 13 (45 mg, 97.50 μmol, 64.11% yield) was obtained as a white solid. LCMS: Rt=0.423 min, m/z=462.2 $[M+H]^{30}$ The residue was purified by SFC (column: DAICEL CHIRALCEL OD (250 mm×30 mm, 10 um); mobile phase: [$CO_2$-i-PrOH (0.1% $NH_3 \cdot H_2O$)]; B %: 23%, isocratic elution mode), the purified solution was concentrated to give a white solid.

Compound 121 (19.18 mg, 41.21 μmol, 42.27% yield, 99.163% purity) was obtained as a white solid. LCMS: Rt=0.426 min, m/z=462.1 $[M+H]^+$ $^1H$ NMR: (400 MHz, CHLOROFORM-d) δ=12.44 (br s, 1H), 9.11 (s, 1H), 8.33 (s, 1H), 8.25 (s, 1H), 7.41-7.27 (m, 4H), 7.19-7.11 (m, 2H), 7.07-7.00 (m, 1H), 6.35 (br dd, J=5.6, 10.4 Hz, 1H), 4.18-3.99 (m, 2H), 3.43 (t, J=11.6 Hz, 1H), 2.82 (s, 4H), 2.46 (s, 6H), 1.38 (t, J=6.8 Hz, 3H)

Compound 122 (20.70 mg, 44.41 μmol, 45.55% yield, 99.019% purity) was obtained as a white solid. LCMS: Rt=0.424 min, m/z=462.2 $[M+H]^+$ $^1H$ NMR: (400 MHz, CHLOROFORM-d) δ=12.44 (br s, 1H), 9.11 (s, 1H), 8.33 (s, 1H), 8.25 (s, 1H), 7.41-7.27 (m, 4H), 7.20-7.10 (m, 2H), 7.07-6.99 (m, 1H), 6.35 (br dd, J=5.6, 10.4 Hz, 1H), 4.19-3.99 (m, 2H), 3.43 (br t, J=11.6 Hz, 1H), 2.89-2.75 (m, 4H), 2.46 (s, 6H), 1.37 (t, J=6.8 Hz, 3H)

Synthesis of Compounds 125 and 126

Compounds 125 and 126 were prepared in a similar manner to compounds 121 and 122.

Compound 125 (14.05 mg, 29.36 μmol, 35.09% yield, 99.9% purity) was obtained as a white solid. LCMS: Rt=0.821 min, m/z=478.2 [M+H]+ $^1H$ NMR: (400 MHz, CHLOROFORM-d) δ=12.36 (br s, 1H), 9.03 (s, 1H), 8.25 (s, 1H), 8.18 (s, 1H), 7.47 (s, 1H), 7.35 (br d, J=6.8 Hz, 1H), 7.28-7.22 (m, 3H), 7.11-7.03 (m, 2H), 6.28 (br dd, J=5.2, 10.4 Hz, 1H), 4.10-3.92 (m, 2H), 3.36 (t, J=11.6 Hz, 1H), 2.82-2.70 (m, 4H), 2.39 (s, 6H), 1.30 (t, J=6.8 Hz, 3H)

Compound 126 (14.2 mg, 29.62 μmol, 35.39% yield, 99.7% purity) was obtained as a white solid. LCMS: Rt=0.820 min, m/z=478.2 [M+H]+ $^1H$ NMR: (400 MHz, CHLOROFORM-d) δ=9.41 (br s, 1H), 8.72 (br s, 1H), 8.54 (br s, 1H), 7.45 (s, 1H), 7.42-7.19 (m, 7H), 6.71 (br s, 1H), 4.55 (br d, J=2.4 Hz, 1H), 4.16-3.97 (m, 2H), 3.97-3.77 (m, 1H), 3.03 (br s, 9H), 1.31-1.25 (m, 3H).

Synthesis of Compounds 127 and 128

Compounds 127 and 128 were prepared in a similar manner to compounds 121 and 122.

Compound 127 (29.79 mg, 59.99 μmol, 41.96% yield, 98.598% purity) was obtained as a white solid. LCMS: Rt=0.439 min, m/z=490.2 [M+H]+ $^1H$ NMR: (400 MHz, CHLOROFORM-d) δ=12.44 (br s, 1H), 9.11 (s, 1H), 8.34 (s, 1H), 8.25 (s, 1H), 7.41-7.27 (m, 4H), 7.19-7.12 (m, 2H), 7.06-6.99 (m, 1H), 6.36 (br dd, J=4.8, 11.2 Hz, 1H), 4.08 (br dd, J=6.8, 13.2 Hz, 2H), 3.50 (br t, J=12.0 Hz, 1H), 3.04 (dd, J=4.8, 12.8 Hz, 1H), 2.90-2.78 (m, 5H), 2.73-2.65 (m, 2H), 1.38 (t, J=6.8 Hz, 3H), 1.13 (t, J=7.2 Hz, 6H)

Compound 128 (31.17 mg, 63.08 μmol, 44.12% yield, 99.08% purity) was obtained as a white solid. LCMS: Rt=0.441 min, m/z=490.3 [M+H]+ $^1H$ NMR: (400 MHz, CHLOROFORM-d) δ=12.44 (br s, 1H), 9.11 (s, 1H), 8.34 (s, 1H), 8.25 (s, 1H), 7.41-7.27 (m, 4H), 7.20-7.11 (m, 2H), 7.07-6.99 (m, 1H), 6.36 (br dd, J=4.8, 11.2 Hz, 1H), 4.08 (br dd, J=6.8, 13.2 Hz, 2H), 3.50 (t, J=12.0 Hz, 1H), 3.04 (dd, J=4.8, 12.8 Hz, 1H), 2.92-2.76 (m, 5H), 2.68 (qd, J=6.8, 13.6 Hz, 2H), 1.38 (t, J=6.8 Hz, 3H), 1.13 (t, J=7.2 Hz, 6H).

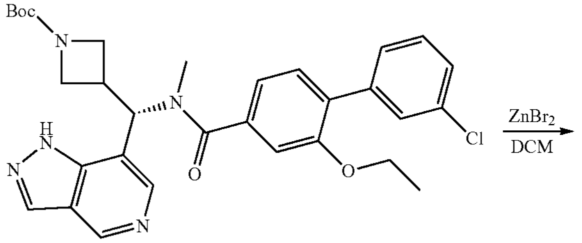

1

-continued

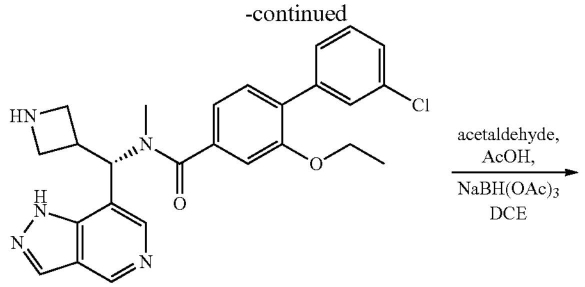

2

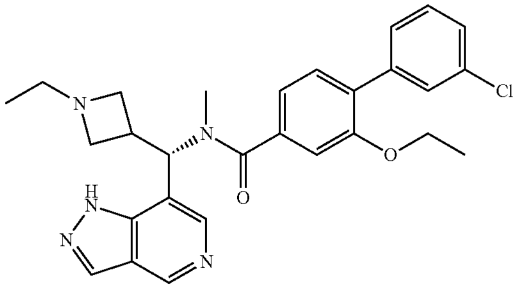

133

To a solution of compound 1 (500.00 mg, 867.93 μmol, 1 eq) in DCM (10 mL) was added ZnBr2 (977.29 mg, 4.34 mmol, 217.17 μL, 5 eq). The mixture was stirred at 25° C. for 3 hr. The reaction mixture was concentrated under reduced pressure to give a residue, which was purified by reversed-phase HPLC (0.1% FA condition) and lyophilized to give compound 2 (360 mg, 733.66 μmol, 84.53% yield, 97% purity) as white solid. LCMS: RT=0.441 min, m/z=476.2 [M+H]+ $^1H$ NMR (400 MHz, CHLOROFORM-d) δ=9.13 (s, 1H), 8.54 (s, 1H), 8.26 (d, J=10.1 Hz, 2H), 7.48 (s, 1H), 7.37-7.33 (m, 1H), 7.30 (br d, J=4.5 Hz, 2H), 7.26-7.22 (m, 1H), 7.06 (s, 1H), 6.97 (br d, J=7.7 Hz, 1H), 6.63-6.54 (m, 1H), 4.37 (br t, J=8.7 Hz, 1H), 4.26 (br t, J=8.8 Hz, 1H), 4.20-4.11 (m, 2H), 4.06-3.98 (m, 2H), 3.80-3.73 (m, 1H), 2.82-2.72 (m, 3H), 1.33 (t, J=6.8 Hz, 3H).

To a solution of compound 2 (200 mg, 420.20 μmol, 1 eq) in DCE (4 mL) was added one drop of AcOH and acetaldehyde (55.53 mg, 1.26 mmol, 70.74 μL, 3 eq) and stirred at 25° C. for 5 min. Then NaBH(OAc)3 (267.17 mg, 1.26 mmol, 3 eq) was added to the mixture and the mixture was stirred at 25° C. for 0.5 hr. The reaction mixture was partitioned between ethyl acetate (30 mL×2) and water (30 mL). The combined organic layers were dried over sodium sulfate anhydrous, filtered and concentrated under reduced pressure to give a residue, which was purified by prep-HPLC (column: Phenomenex luna C18 150*25 mm*10 um; mobile phase: [water (FA)-ACN]; gradient: 8%-38% B over 15 min) and lyophilized to give Compound 133 (12.06 mg, 22.82 μmol, 21.72% yield, 95.363% purity) as white solid. LCMS: RT=0.452 min, m/z=504.2 [M+H]+ $^1H$ NMR (400 MHz, CHLOROFORM-d) δ=9.13 (s, 1H), 8.58 (s, 1H), 8.35 (s, 1H), 8.28 (s, 1H), 7.53 (s, 1H), 7.43-7.37 (m, 1H), 7.32 (dd, J=3.1, 6.5 Hz, 3H), 7.07-7.00 (m, 2H), 6.31 (br d, J=10.9 Hz, 1H), 4.18-4.08 (m, 2H), 4.08-3.95 (m, 3H), 3.68 (br s, 1H), 3.37 (br d, J=6.6 Hz, 1H), 2.95-2.89 (m, 2H), 2.87 (s, 3H), 1.37 (t, J=6.9 Hz, 3H), 1.17 (t, J=7.2 Hz, 3H).

Synthesis of Compounds 132 and 133

Compounds 132 and 133 were prepared in a similar manner to Compound 131.

Compound 132 (50.12 mg, 91.33 μmol, 67.21% yield, 96.51% purity, FA) was isolated as colorless gum. LCMS:

RT=0.436 min, m/z=484.4 [M+H]+ $^1$H NMR (400 MHz, DMSO-d6) δ=11.16-10.75 (m, 1H), 9.33 (br s, 1H), 8.72-8.57 (m, 1H), 8.45 (br s, 1H), 8.13 (s, 1H), 7.52 (d, J=7.2 Hz, 2H), 7.41 (t, J=7.6 Hz, 2H), 7.34 (br d, J=7.2 Hz, 2H), 7.11 (br s, 2H), 6.58-6.26 (m, 1H), 4.51-4.31 (m, 1H), 4.28-4.15 (m, 1H), 4.13-3.92 (m, 5H), 3.77-3.63 (m, 1H), 2.80 (br s, 3H), 1.29-1.23 (m, 3H), 1.19 (br d, J=6.2 Hz, 6H).

Compound 133 (19.64 mg, 38.13 μmol, 30.61% yield, 97.372% purity, FA) was isolated as a white solid. LCMS: RT=0.451 min, m/z=456.1 [M+H]+ $^1$H NMR (400 MHz, CHLOROFORM-d) δ=9.15 (s, 1H), 8.47-8.44 (m, 1H), 8.36 (s, 1H), 8.29 (s, 1H), 7.53 (d, J=7.2 Hz, 2H), 7.45-7.38 (m, 2H), 7.35 (m, 2H), 7.09-7.00 (m, 2H), 6.36-6.26 (m, 1H), 4.37-4.27 (m, 1H), 4.17 (m, 2H), 4.10-4.00 (m, 2H), 3.97-3.88 (m, 1H), 3.64-3.54 (m, 1H), 2.91 (s, 3H), 2.79 (s, 3H), 1.36 (t, J=6.8 Hz, 3H).

Synthesis of Compound 134

Compound 134 was prepared in a similar manner to Compound 131. Compound 134 (7.40 mg., 13.86 μmol, 15.30% yield, 96.578% purity, FA) was obtained as a white solid. LCMS: RT=0.469 min, m/z=470.2 [M+H]+ $^1$H NMR (400 MHz, CHLOROFORM-d) δ=9.13 (s, 1H), 8.58 (s, 1H), 8.32 (s, 1H), 8.27 (s, 1H), 7.57-7.49 (m, 2H), 7.45-7.38 (m, 2H), 7.37-7.31 (m, 2H), 7.05 (br d, J=2.2 Hz, 2H), 6.29 (br d, J=11.2 Hz, 1H), 4.10-3.97 (m, 4H), 3.88 (br s, 1H), 3.48 (br s, 1H), 3.19 (br s, 1H), 2.84 (s, 3H), 2.81-2.74 (m, 2H), 1.35 (t, J=6.8 Hz, 3H), 1.10 (t, J=7.2 Hz, 3H).

Synthesis of Compounds 141-144

Compounds 141-144 were prepared in a similar manner to Compounds 008 and 131.

Compound 141 (19.01 mg, 39.12 μmol, 9.12% yield, 96% purity) was obtained as white solid. LCMS: RT=0.404 min, m/z=467.3 [M+H]+ $^1$H NMR (400 MHz, CHLOROFORM-d) δ=9.13 (s, 1H), 8.61-8.52 (m, 1H), 8.28 (s, 1H), 8.24 (br s, 1H), 7.80 (s, 1H), 7.72 (d, J=7.8 Hz, 1H), 7.62 (d, J=7.8 Hz, 1H), 7.55-7.47 (m, 1H), 7.25 (s, 1H), 7.04 (br s, 1H), 6.99 (br d, J=8.0 Hz, 1H), 6.58-6.44 (m, 1H), 4.30 (br s, 1H), 4.22-3.97 (m, 6H), 3.73-3.65 (m, 1H), 2.84-2.73 (m, 3H), 1.38-1.30 (m, 3H).

Compound 142 (21.92 mg, 45.11 μmol, 10.52% yield, 96% purity) was obtained as white solid. LCMS: RT=0.412 min, m/z=467.3 [M+H]+ $^1$H NMR (400 MHz, CHLOROFORM-d) δ=9.17-9.12 (m, 1H), 8.49-8.42 (m, 1H), 8.32-8.28 (m, 1H), 8.25 (s, 1H), 7.81 (s, 1H), 7.73 (br d, J=8.0 Hz, 1H), 7.63 (d, J=7.8 Hz, 1H), 7.54-7.48 (m, 1H), 7.29-7.28 (m, 1H), 7.08-6.97 (m, 2H), 6.54-6.45 (m, 1H), 4.37-4.31 (m, 1H), 4.21-4.02 (m, 6H), 3.73 (br d, J=2.4 Hz, 1H), 2.84-2.78 (m, 3H), 1.34 (t, J=6.8 Hz, 3H).

Compound 143 (14.29 mg, 28.86 μmol, 19.24% yield, 97.064% purity) was isolated as yellow gum. LCMS: RT=0.416 min, m/z=481.2 (M+H+). $^1$H NMR (400 MHz, CHLOROFORM-d) δ=9.14 (s, 1H), 8.54-8.48 (m, 1H), 8.34-8.26 (m, 2H), 7.84 (s, 1H), 7.75 (br d, J=7.8 Hz, 1H), 7.66-7.60 (m, 1H), 7.56-7.48 (m, 1H), 7.34-7.29 (m, 1H), 7.08-7.01 (m, 2H), 6.34-6.26 (m, 1H), 4.05 (br s, 3H), 3.95 (br d, J=7.8 Hz, 2H), 3.67-3.58 (m, 1H), 3.31 (br s, 1H), 2.83 (s, 3H), 2.61 (s, 3H), 1.36 (br t, J=6.8 Hz, 3H).

Compound 144 (25.19 mg, 47.94 μmol, 31.95% yield, 91.462% purity) was isolated as yellow gum. LCMS: RT=0.410 min, m/z=481.2 [M+H]+ $^1$H NMR (400 MHz, CHLOROFORM-d) δ=9.14 (s, 1H), 8.51 (br s, 1H), 8.34-8.26 (m, 2H), 7.84 (s, 1H), 7.79-7.72 (m, 1H), 7.63 (br d, J=7.8 Hz, 1H), 7.55-7.49 (m, 1H), 7.35-7.29 (m, 1H), 7.09-7.02 (m, 2H), 6.34-6.23 (m, 1H), 4.08 (br d, J=6.6 Hz, 3H), 3.96 (br d, J=8.4 Hz, 2H), 3.63 (br s, 1H), 3.36-3.27 (m, 1H), 2.83 (s, 3H), 2.62 (s, 3H), 1.37 (br t, J=6.8 Hz, 3H).

Synthesis of Compound 148

Compound 148 was prepared in a similar manner as Compound 131. Compound 148 (16.70 mg, 30.63 μmol, 24.30% yield, 93% purity) was isolated as a white solid. LCMS: RT=0.450 min, m/z=490.3 (M+H)+ $^1$H NMR (400 MHz, DMSO-d6) δ=9.10 (s, 1H), 8.40 (s, 1H), 8.37-8.29 (m, 2H), 7.57 (s, 1H), 7.49-7.35 (m, 4H), 7.11-6.97 (m, 2H), 6.28 (br d, J=2.4 Hz, 1H), 4.03 (br s, 2H), 3.74-3.71 (m, 2H), 3.32 (br s, 2H), 3.02 (br s, 1H), 2.77 (br s, 3H), 2.37 (br s, 3H), 1.23 (br t, J=6.6 Hz, 3H).

Synthesis of Compounds 150 and 151

Compounds 150 and 151 were prepared in a similar manner to Compound 131 using TFA instead of zinc bromide.

Compound 150 (19.12 mg, 85.28 μmol, 28.87% yield, 99% purity, FA salt) as was obtained as a white solid. LCMS: Rt=0.426 min, m/z=448.2 (M+H+). $^1$H NMR (400 MHz, DMSO-d6) δ=9.13 (s, 1H), 8.44 (s, 1H), 8.39 (s, 1H), 8.29 (s, 1H), 7.50 (d, J=7.6 Hz, 2H), 7.40 (t, J=7.6 Hz, 2H), 7.35-7.30 (m, 2H), 7.13-6.94 (m, 2H), 6.52-6.26 (m, 1H), 4.25-4.14 (m, 1H), 4.01 (br d, J=2.4 Hz, 4H), 3.91 (br d, J=3.6 Hz, 2H), 2.80-2.64 (m, 3H), 1.22 (br t, J=6.4 Hz, 3H).

Compound 151 (47 mg, 104.80 μmol, 47.30% yield, 98.45% purity) was a white gum. LCMS: RT=0.421 min, m/z=442.2 [M+H]+ $^1$H NMR (400 MHz, DMSO-d6) δ=9.12 (s, 1H), 8.41 (d, J=3.0 Hz, 2H), 8.35 (s, 1H), 7.52 (d, J=7.4 Hz, 2H), 7.41 (t, J=7.6 Hz, 2H), 7.36-7.27 (m, 2H), 7.15-6.93 (m, 2H), 6.53-6.31 (m, 1H), 4.19-4.10 (m, 2H), 4.00-3.74 (m, 4H), 3.59-3.52 (m, 1H), 2.78 (s, 3H), 1.23 (t, J=6.0 Hz, 3H).

Synthesis of Compounds 154-156

Compounds 152-154 were prepared in a similar manner to Compounds 008 and 131.

Compound 152 (300 mg, crude) was obtained as a white solid. LCMS: Rt=0.423 min, m/z=456.2[M+H]+ $^1$H NMR (400 MHz, CHLOROFORM-d) δ=9.13 (s, 1H), 8.60 (br s, 1H), 8.47 (s, 1H), 8.28 (s, 1H), 7.50-7.44 (m, 2H), 7.40-7.34 (m, 2H), 7.34-7.27 (m, 2H), 7.03-6.97 (m, 2H), 6.06 (br s, 1H), 4.09-3.91 (m, 2H), 3.82-3.60 (m, 2H), 3.51-3.22 (m, 3H), 2.88 (s, 3H), 2.36-2.16 (m, 1H), 1.82-1.63 (m, 1H), 1.30 (t, J=6.8 Hz, 3H).

Compound 153 (18.01 mg, 37.76 μmol, 27.98% yield, 95.52% purity) as a white solid. LCMS: Rt=0.421 min, m/z=456.2[M+H]+ $^1$H NMR (400 MHz, CHLOROFORM-d) 6=9.12 (s, 1H), 8.60 (br s, 1H), 8.46 (s, 1H), 8.28 (s, 1H), 7.51-7.44 (m, 2H), 7.40-7.34 (m, 2H), 7.34-7.27 (m, 2H), 7.04-6.97 (m, 2H), 6.06 (br s, 1H), 4.07-3.91 (m, 2H), 3.80-3.61 (m, 2H), 3.50-3.23 (m, 3H), 2.87 (s, 3H), 2.34-2.17 (m, 1H), 1.77-1.63 (m, 1H), 1.30 (t, J=7.2 Hz, 3H).

Compound 154 (82.53 mg, 175.26 μmol, 53.23% yield, 99.72% purity) was prepared using Compound 152 as starting material and was isolated as a white solid. LCMS: Rt=0.431 min, m/z=470.3[M+H]+ $^1$H NMR (400 MHz, CHLOROFORM-d) δ=9.13 (s, 1H), 8.49 (br s, 1H), 8.41 (s, 1H), 8.28 (s, 1H), 7.56-7.51 (m, 2H), 7.44-7.38 (m, 2H), 7.37-7.31 (m, 2H), 7.09-7.04 (m, 2H), 6.10-5.91 (m, 1H), 4.14-3.96 (m, 2H), 3.91-3.75 (m, 1H), 3.74-3.58 (m, 1H), 3.32 (br s, 1H), 3.01-2.79 (m, 5H), 2.71 (s, 3H), 2.31 (br s, 1H), 1.78-1.62 (m, 1H), 1.35 (t, J=6.8 Hz, 3H).

Synthesis of Compounds 159 and 160

Compounds 159 and 160 were prepared in a similar manner to Compounds 152 and 154.

Compound 159 (106.39 mg, 231.21 μmol, 64.24% yield, 99% purity) was obtained as white solid. $^1$H NMR (400 MHz, CHLOROFORM-d) δ ppm 1.26-1.36 (m, 3H) 2.08 (br dd, J=12.32, 7.82 Hz, 1H) 2.40 (br d, J=6.25 Hz, 1H) 2.84 (s, 3H) 2.88-2.95 (m, 1H) 3.33-3.59 (m, 3H) 3.69 (br d, J=6.88 Hz, 1H) 3.92-4.09 (m, 2H) 6.12 (br d, J=1.13 Hz, 1H)

6.95-7.02 (m, 2H) 7.28-7.42 (m, 4H) 7.50 (br d, J=7.25 Hz, 2H) 8.21-8.25 (m, 1H) 8.44 (s, 1H) 8.47 (br s, 1H) 9.05 (s, 1H). LCMS: Rt=0.426 min, m/z=456.2 (M+H+).

Compound 160 (74.66 mg, 157.40 μmol, 47.80% yield, 99% purity) was obtained as off-white solid. $^1$H NMR (400 MHz, CHLOROFORM-d) δ ppm 1.34 (t, J=6.94 Hz, 3H) 2.07-2.20 (m, 1H) 2.43-2.55 (m, 1H) 2.58-2.65 (m, 1H) 2.66 (s, 3H) 2.87 (s, 3H) 3.17 (br s, 1H) 3.30-3.55 (m, 2H) 3.85 (br s, 1H) 3.94-4.11 (m, 2H) 6.04 (br d, J=1.63 Hz, 1H) 6.99-7.05 (m, 2H) 7.30-7.36 (m, 2H) 7.37-7.43 (m, 2H) 7.52 (d, J=7.75 Hz, 2H) 8.28 (s, 1H) 8.43 (s, 1H) 8.51 (s, 1H) 9.13 (s, 1H). LCMS: Rt=0.437 min, m/z=470.2 (M+H+).

Synthesis of Compounds 168-171

Compounds 168-171 were prepared in a similar manner to Compound 131.

Compound 168 (34.35 mg, 69.37 μmol, 8.76% yield, 92% purity) was obtained as white solid. LCMS: RT=0.433 min, m/z=456.1 [M+H]+ $^1$H NMR (400 MHz, CHLOROFORM-d) δ=9.13 (s, 1H), 8.52 (s, 1H), 8.28 (s, 1H), 8.23 (s, 1H), 7.35-7.28 (m, 4H), 7.16 (br d, J=6.8 Hz, 1H), 7.03 (s, 1H), 6.98 (d, J=7.6 Hz, 1H), 6.46 (br d, J=10.8 Hz, 1H), 4.33-4.23 (m, 1H), 4.22-4.11 (m, 2H), 4.09-3.97 (m, 3H), 3.73-3.65 (m, 1H), 2.81 (s, 3H), 2.39 (s, 3H), 1.34 (t, J=6.8 Hz, 3H).

Compound 169 (6.92 mg, 13.59 μmol, 22.73% yield, 95% purity) was prepared using Compound 168 as starting material and was isolated as an off-white solid. LCMS: RT=0.470 min, m/z=484.3 (M+H+) $^1$H NMR (400 MHz, CHLOROFORM-d) δ=9.12 (s, 1H), 8.59 (br s, 1H), 8.29 (s, 1H), 8.27 (s, 1H), 7.37-7.33 (m, 3H), 7.32-7.28 (m, 1H), 7.16 (br d, J=7.2 Hz, 1H), 7.07-6.99 (m, 2H), 6.34 (br d, J=10.4 Hz, 1H), 4.14-3.99 (m, 2H), 3.91-3.78 (m, 2H), 3.76 (br d, J=7.2 Hz, 1H), 3.30 (br s, 1H), 3.04-2.98 (m, 1H), 2.81 (s, 3H), 2.68-2.63 (m, 2H), 2.40 (s, 3H), 1.36 (t, J=6.8 Hz, 3H), 1.04 (t, J=7.2 Hz, 3H).

Compound 170 (17.86 mg, 37.64 μmol, 5.50% yield, 96% purity) was obtained as an off-white solid. LCMS: RT=0.465 min, m/z=456.3 [M+H]+ $^1$H NMR (400 MHz, CHLOROFORM-d) δ=9.13 (s, 1H), 8.55 (s, 1H), 8.28 (s, 1H), 8.22 (s, 1H), 7.35-7.28 (m, 4H), 7.16 (br d, J=7.2 Hz, 1H), 7.03 (s, 1H), 6.98 (d, J=7.8 Hz, 1H), 6.47 (br d, J=11.2 Hz, 1H), 4.27 (br t, J=8.4 Hz, 1H), 4.19-4.11 (m, 2H), 4.06-3.98 (m, 3H), 3.71-3.66 (m, 1H), 2.81 (s, 3H), 2.39 (s, 3H), 1.34 (t, J=6.8 Hz, 3H).

Compound 171 (8.77 mg, 17.59 μmol, 22.06% yield, 97% purity) was prepared using Compound 170 as starting material and was isolated as a white solid. LCMS: RT=0.476 min, m/z=484.3 (M+H)+ $^1$H NMR (400 MHz, CHLOROFORM-d) δ=9.12 (s, 1H), 8.60 (br s, 1H), 8.29 (s, 1H), 8.27 (s, 1H), 7.37-7.33 (m, 3H), 7.32-7.28 (m, 1H), 7.17 (br d, J=7.2 Hz, 1H), 7.07-7.01 (m, 2H), 6.34 (br d, J=10.5 Hz, 1H), 4.12-4.00 (m, 2H), 3.89-3.80 (m, 2H), 3.77 (br d, J=7.2 Hz, 1H), 3.31 (br s, 1H), 3.07-3.00 (m, 1H), 2.81 (s, 3H), 2.67 (q, J=7.2 Hz, 2H), 2.40 (s, 3H), 1.36 (t, J=7.0 Hz, 3H), 1.05 (t, J=7.2 Hz, 3H).

Synthesis of Compound 172

Compound 172 was prepared in a similar manner to Compound 133. Compound 172 (8.36 mg, 18.45 μmol, 7.32% yield, 93% purity) was isolated as a white solid. LCMS: RT=0.461 min, m/z=504.2 (M+H)+ $^1$H NMR (400 MHz, DMSO-d6) δ=9.10 (s, 1H), 8.43-8.33 (m, 2H), 8.27 (br s, 1H), 7.57 (s, 1H), 7.49-7.36 (m, 4H), 7.10-6.95 (m, 2H), 6.37-6.15 (m, 1H), 4.04 (br s, 2H), 3.68 (br s, 2H), 3.26 (br s, 2H), 2.95 (br d, J=2.9 Hz, 1H), 2.77 (br s, 3H), 2.56 (br s, 2H), 1.24 (br t, J=6.8 Hz, 3H), 0.90 (br t, J=6.8 Hz, 3H).

Synthesis of Compounds 176 and 177

Compounds 173 and 174 were prepared in a similar manner to Compound 131.

Compound 173 (26.82 mg, 52.60 μmol, 32.06% yield, 95.62% purity) was obtained as a brown solid. LCMS: Rt=0.433 min, m/z=488.2[M+H]+ $^1$H NMR (400 MHz, CHLOROFORM-d) δ=12.14 (br d, J=1.6 Hz, 1H), 9.11 (s, 1H), 8.26 (s, 2H), 7.41-7.27 (m, 4H), 7.10-6.97 (m, 3H), 6.38 (br d, J=10.8 Hz, 1H), 4.17-3.98 (m, 2H), 3.76-3.59 (m, 3H), 3.22-3.10 (m, 1H), 2.87 (br t, J=6.0 Hz, 1H), 2.78 (s, 3H), 2.62-2.44 (m, 2H), 1.37 (t, J=6.8 Hz, 3H), 0.98 (t, J=7.2 Hz, 3H)

Compound 174 (20.01 mg, 39.10 μmol, 23.83% yield, 95.26% purity) was isolated as a brown solid. LCMS: Rt=0.430 min, m/z=488.1[M+H]+ $^1$H NMR (400 MHz, CHLOROFORM-d) δ=12.14 (br s, 1H), 9.11 (s, 1H), 8.26 (s, 2H), 7.41-7.27 (m, 4H), 7.12-6.95 (m, 3H), 6.38 (br d, J=10.8 Hz, 1H), 4.16-3.96 (m, 2H), 3.75-3.58 (m, 3H), 3.18-3.10 (m, 1H), 2.86 (br t, J=5.6 Hz, 1H), 2.78 (s, 3H), 2.59-2.47 (m, 2H), 1.37 (t, J=6.8 Hz, 3H), 0.98 (t, J=7.2 Hz, 3H).

Synthesis of Compounds 175 and 176

Compounds 175 and 176 were prepared in a similar manner to Compound 131.

Compound 175 (71.06 mg, 141.67 μmol, 39.48% yield, 100% purity) was isolated as a solid. LCMS: Rt=0.443 min, m/z=502.3 [M+H]+ $^1$H NMR (400 MHz, CHLOROFORM-d) δ=12.32-11.95 (m, 1H), 9.11 (s, 1H), 8.36-8.21 (m, 2H), 7.41-7.32 (m, 2H), 7.31-7.28 (m, 1H), 7.27 (s, 1H), 7.09-7.00 (m, 3H), 6.33 (br d, J=10.4 Hz, 1H), 4.20-3.94 (m, 2H), 3.79-3.59 (m, 3H), 3.14 (br s, 1H), 2.94-2.84 (m, 1H), 2.79 (s, 3H), 2.47-2.37 (m, 1H), 1.37 (t, J=6.8 Hz, 3H), 1.01-0.91 (m, 6H).

Compound 176 (42.23 mg, 84.19 μmol, 23.46% yield, 100% purity) was isolated as a solid. LCMS: Rt=0.437 min, m/z=502.3[M+H]+ $^1$H NMR (400 MHz, CHLOROFORM-d) δ=12.13 (br s, 1H), 9.11 (s, 1H), 8.34-8.19 (m, 2H), 7.41-7.32 (m, 2H), 7.32-7.27 (m, 2H), 7.09-7.00 (m, 3H), 6.35 (br d, J=10.4 Hz, 1H), 4.16-4.00 (m, 2H), 3.72-3.58 (m, 3H), 3.11 (br t, J=4.8 Hz, 1H), 2.88-2.82 (m, 1H), 2.79 (s, 3H), 2.45-2.34 (m, 1H), 1.37 (t, J=6.8 Hz, 3H), 1.00-0.91 (m, 6H).

Synthesis of Compound 177

Compound 177 was prepared in a similar manner to Compound 131. Compound 177 (12.24 mg, 25.40 μmol, 26.08% yield, 97.46% purity) was obtained as a white solid. LCMS: RT=0.429 min, m/z=470.4 [M+H]+ $^1$H NMR (400 MHz, CHLOROFORM-d) δ=9.13 (s, 1H), 8.57 (br s, 1H), 8.33 (s, 1H), 8.28 (s, 1H), 7.59-7.49 (m, 2H), 7.44-7.38 (m, 2H), 7.35 (d, J=7.6 Hz, 2H), 7.08-7.00 (m, 2H), 6.28 (br d, J=11.2 Hz, 1H), 4.15-3.99 (m, 4H), 3.95 (br d, J=7.6 Hz, 1H), 3.62-3.50 (m, 1H), 3.27 (t, J=7.2 Hz, 1H), 2.92-2.78 (m, 5H), 1.35 (t, J=6.8 Hz, 3H), 1.12 (t, J=7.2 Hz, 3H).

Synthesis of Compounds 178 and 179

Compound 178 was prepared in a similar manner to Compound 131 using Compound 151 as starting material.

Compound 178 (15.66 mg, 34.08 μmol, 23.15% yield, 99.13% purity) was obtained as a white solid. LCMS: RT=0.453 min, m/z=456.1 [M+H]+ $^1$H NMR (400 MHz, CHLOROFORM-d) δ=9.15 (s, 1H), 8.52 (s, 1H), 8.38-8.23 (m, 2H), 7.58-7.52 (m, 2H), 7.47-7.40 (m, 2H), 7.39-7.34 (m, 2H), 7.09-7.02 (m, 2H), 6.40-6.24 (m, 1H), 4.15-4.01 (m, 3H), 3.93 (m, 2H), 3.55 (br t, J=6.8 Hz, 1H), 3.31-3.20 (m, 1H), 2.85 (s, 3H), 2.59 (s, 3H), 1.38 (t, J=7.2 Hz, 3H).

Compound 179 (29.06 mg, 60.09 μmol, 44.22% yield, 100% purity) was obtained as an off-white gum. LCMS: RT=0.499 min, m/z=484.2 [M+H]+ $^1$H NMR (400 MHz, CHLOROFORM-d) δ=12.57-11.71 (m, 1H), 9.13 (s, 1H), 8.59 (s, 1H), 8.33 (s, 1H), 8.28 (s, 1H), 7.57-7.50 (m, 2H), 7.45-7.39 (m, 2H), 7.36 (d, J=7.4 Hz, 2H), 7.09-7.02 (m, 2H), 6.27 (br d, J=10.8 Hz, 1H), 4.13-4.02 (m, 2H), 4.00-3.80 (m, 3H), 3.41 (br t, J=6.8 Hz, 1H), 3.13 (br t, J=7.2 Hz, 1H), 2.84 (s, 3H), 2.71-2.67 (m, 1H), 1.36 (t, J=7.2 Hz, 3H), 1.08 (t, J=6.8 Hz, 6H).

Synthesis of Compounds 181 and 182

Compounds 181 and 182 were prepared in a similar manner to the first step shown for Compound 131.

Compound 181 (22 mg, 43.45 μmol, 4.32% yield, 94% purity FA) as white solid. LCMS: Rt=0.437 min, m/z=476.1 (M+H+) 1H NMR (400 MHz, DMSO-d6) δ=9.13 (s, 1H), 8.44 (s, 1H), 8.40-8.37 (m, 1H), 8.30 (s, 1H), 7.56 (s, 1H), 7.48-7.36 (m, 4H), 7.05 (br s, 2H), 6.42 (br d, J=3.2 Hz, 1H), 4.19 (br t, J=8.0 Hz, 1H), 4.03 (br d, J=2.8 Hz, 4H), 3.91 (br s, 2H), 2.71 (br s, 3H), 1.27-1.20 (m, 3H).

Compound 182 (23 mg, 45.42 μmol, 5.84% yield, 94% purity) as a white solid. LCMS: Rt=0.436 min, m/z=476.2 (M+H)+ $^1$H NMR: (400 MHz, DMSO-d6) δ=9.12 (s, 1H), 8.43 (s, 1H), 8.41 (s, 1H), 8.32 (s, 1H), 7.55 (s, 1H), 7.50-7.34 (m, 4H), 7.18-6.95 (m, 2H), 6.41 (br d, J=5.6 Hz, 1H), 4.21 (br d, J=8.8 Hz, 1H), 4.04 (br s, 4H), 3.93 (br d, J=2.4 Hz, 2H), 2.72 (br s, 3H), 1.23 (br t, J=6.0 Hz, 3H).

Synthesis of Compound 183

Compound 183 was prepared in a similar manner to Compound 131 using Compound 181 as starting material. Compound 183 (16.14 mg, 30.63 μmol, 24.30% yield, 93% purity) was isolated as a white solid. LCMS: Rt=0.437 min, m/z=476.1 (M+H+) $^1$H NMR: (400 MHz, DMSO-d6) δ=9.09 (s, 1H), 8.39 (s, 1H), 8.37-8.33 (m, 1H), 7.57 (s, 1H), 7.49-7.35 (m, 4H), 7.08-6.94 (m, 2H), 6.25 (br s, 1H), 4.03 (br s, 2H), 3.62 (br d, J=4.8 Hz, 1H), 3.55-3.48 (m, 2H), 3.26 (br s, 1H), 3.07 (br s, 1H), 2.75 (br d, J=12.4 Hz, 3H), 2.22 (s, 3H), 1.27-1.20 (m, 3H).

Synthesis of Compounds 065 and 071

Compounds 065 and 071 were prepared in a similar manner to Compound 131.

Compound 065 (26.07 mg, 46.38 μmol, 22.61% yield, 94.92% purity, FA) was isolated as a white solid. LCMS: Rt=0.443 min, m/z=488.3[M+H]+ $^1$H NMR (400 MHz, CHLOROFORM-d) δ=8.50 (s, 1H), 8.24 (s, 1H), 8.16 (s, 1H), 7.40-7.32 (m, 2H), 7.29 (br s, 1H), 7.27-7.23 (m, 1H), 7.06-6.99 (m, 3H), 6.25 (br d, J=10.4 Hz, 1H), 4.14-3.94 (m, 5H), 3.63 (br s, 1H), 3.32 (br s, 1H), 2.84 (s, 3H), 2.81 (s, 3H), 2.63 (s, 3H), 1.36 (t, J=6.8 Hz, 3H).

Compound 071 (7.98 mg, 14.71 μmol, 7.17% yield, 98.38% purity, FA) was isolated as a white solid. LCMS: Rt=0.429 min, m/z=488.3[M+H]+ $^1$H NMR (400 MHz, CHLOROFORM-d) δ=8.50 (s, 1H), 8.24 (s, 1H), 8.16 (s, 1H), 7.41-7.32 (m, 2H), 7.31-7.27 (m, 2H), 7.09-6.97 (m, 3H), 6.26 (br d, J=10.8 Hz, 1H), 4.13-4.01 (m, 3H), 4.00-3.88 (m, 2H), 3.61-3.54 (m, 1H), 3.26 (br s, 1H), 2.85 (s, 3H), 2.81 (s, 3H), 2.60 (s, 3H), 1.37 (t, J=6.8 Hz, 3H).

Synthesis of Compound 190

Compound 190 was prepared in a similar manner to Compound 131. Compound 190 (8.36 mg, 18.45 μmol, 7.32% yield, 93% purity) was obtained as a white solid. LCMS: RT=0.461 min, m/z=504.2 (M+H)+ $^1$H NMR (400 MHz, CHLOROFORM-d) δ=9.10 (s, 1H), 8.43-8.33 (m, 2H), 8.27 (br s, 1H), 7.57 (s, 1H), 7.49-7.36 (m, 4H), 7.10-6.95 (m, 2H), 6.37-6.15 (m, 1H), 4.04 (br s, 2H), 3.68 (br s, 2H), 3.26 (br s, 2H), 2.95 (br d, J=2.9 Hz, 1H), 2.77 (br s, 3H), 2.56 (br s, 2H), 1.24 (br t, J=6.8 Hz, 3H), 0.90 (br t, J=6.8 Hz, 3H).

Synthesis of Compound 241

Compound 241 was prepared in a similar manner to Compound 131_using formaldehyde instead of acetaldehyde and TFA instead of zinc bromide. Compound 241 (18.07 mg, 35.84 μmol, 7.01% yield, 97% purity) was obtained as a brown gum. LCMS: RT=0.748 min, m/z=489.2[M+H]+ $^1$H NMR (400 MHz, CHLOROFORM-d) δ=11.92 (br s, 1H), 8.13 (s, 1H), 7.76 (d, J=7.9 Hz, 1H), 7.54 (s, 1H), 7.43-7.39 (m, 1H), 7.34-7.29 (m, 3H), 7.22-7.18 (m, 1H), 7.15 (d, J=7.7 Hz, 1H), 7.04 (s, 1H), 6.99 (d, J=7.7 Hz, 1H), 6.45 (br d, J=10.8 Hz, 1H), 4.12-3.99 (m, 2H), 3.77-3.68 (m, 1H), 3.66-3.58 (m, 2H), 3.17 (br t, J=6.2 Hz, 1H), 2.86 (s, 1H), 2.71 (s, 3H), 2.42-2.36 (m, 3H), 1.37 (t, J=7.0 Hz, 3H).

Synthesis of Compounds 282 and 283

Compounds 282 and 283 were isolated by chiral separation of Compound 241 via SFC. Compound 282 (216.06 mg, 441.39 μmol, 47.97% yield, 99.9% purity) was obtained as an off-white gum. LCMS: RT=0.560 min, m/z=489.2 [M+H]+ $^1$H NMR (400 MHz, CHLOROFORM-d) δ=11.87 (br s, 1H), 8.12-8.07 (m, 1H), 7.73 (d, J=7.9 Hz, 1H), 7.51 (s, 1H), 7.41-7.37 (m, 1H), 7.29 (s, 2H), 7.25-7.23 (m, 1H), 7.19-7.16 (m, 1H), 7.14-7.09 (m, 1H), 7.01 (s, 1H), 6.97 (d, J=7.7 Hz, 1H), 6.42 (br d, J=10.9 Hz, 1H), 4.09-3.98 (m, 2H), 3.78-3.73 (m, 1H), 3.66 (br d, J=3.5 Hz, 2H), 3.19 (br t, J=6.4 Hz, 1H), 2.91-2.85 (m, 1H), 2.69 (s, 3H), 2.39 (s, 3H), 1.36-1.31 (m, 3H). Compound 283 (148.12 mg, 302.90 μmol, 32.92% yield, 100% purity) was obtained as an off-white gum. LCMS: RT=0.568 min, m/z=489.1 [M+H]+ $^1$H NMR (400 MHz, CHLOROFORM-d) δ=11.91 (br s, 1H), 8.12 (s, 1H), 7.75 (d, J=7.9 Hz, 1H), 7.54 (s, 1H), 7.43-7.39 (m, 1H), 7.36-7.29 (m, 3H), 7.22-7.17 (m, 1H), 7.16-7.12 (m, 1H), 7.04 (s, 1H), 6.99 (d, J=7.8 Hz, 1H), 6.45 (br d, J=10.9 Hz, 1H), 4.12-3.98 (m, 2H), 3.75-3.68 (m, 1H), 3.66-3.56 (m, 2H), 3.16 (br t, J=6.1 Hz, 1H), 2.90-2.82 (m, 1H), 2.71 (s, 3H), 2.38 (s, 3H), 1.40-1.33 (m, 3H).

Synthesis of Compound 296

Compound 296 was prepared in a similar manner to Compound 131_using formaldehyde instead of acetaldehyde and $NaBH_2CN$ instead of zinc bromide. Compound 296 (200 mg, 415.62 μmol, 27.22% yield, 98.2% purity) was obtained as a white solid. LCMS: RT=0.542 min, m/z=473.1 [M+H]+.

Synthesis of Compounds 297 and 298

Compounds 297 and 298 were isolated by chiral separation of Compound 296 via SFC. Compound 297 (95.3 mg, 198.44 μmol, 46.89% yield, 98.4% purity) was obtained as a white solid. LCMS: RT=0.549 min, m/z=473.1 [M+H]+ $^1$H NMR (400 MHz, CHLOROFORM-d) δ=11.92 (br s, 1H), 8.12 (s, 1H), 7.76 (d, J=7.8 Hz, 1H), 7.40-7.27 (m, 4H), 7.22-7.17 (m, 1H), 7.17-7.12 (m, 1H), 7.07-6.98 (m, 3H), 6.45 (br d, J=10.8 Hz, 1H), 4.13-3.98 (m, 2H), 3.75-3.67 (m, 1H), 3.67-3.56 (m, 2H), 3.16 (br t, J=6.1 Hz, 1H), 2.89-2.81 (m, 1H), 2.71 (s, 3H), 2.38 (s, 3H), 1.37 (t, J=7.0 Hz, 3H). Compound 298 (68.17 mg, 141.52 μmol, 33.44% yield, 98.1% purity) was obtained as a white solid. LCMS: RT=0.540 min, m/z=473.1 [M+H]+ $^1$H NMR (400 MHz, CHLOROFORM-d) δ=8.12 (s, 1H), 7.75 (d, J=7.8 Hz, 1H), 7.40-7.28 (m, 4H), 7.22-7.17 (m, 1H), 7.17-7.11 (m, 1H), 7.07-6.98 (m, 3H), 6.45 (br d, J=10.8 Hz, 1H), 4.13-3.99 (m, 2H), 3.76-3.67 (m, 1H), 3.62 (br s, 2H), 3.16 (br t, J=6.2 Hz, 1H), 2.86 (s, 1H), 2.71 (s, 3H), 2.38 (s, 3H), 1.37 (t, J=6.9 Hz, 3H).

Synthesis of Compound 140

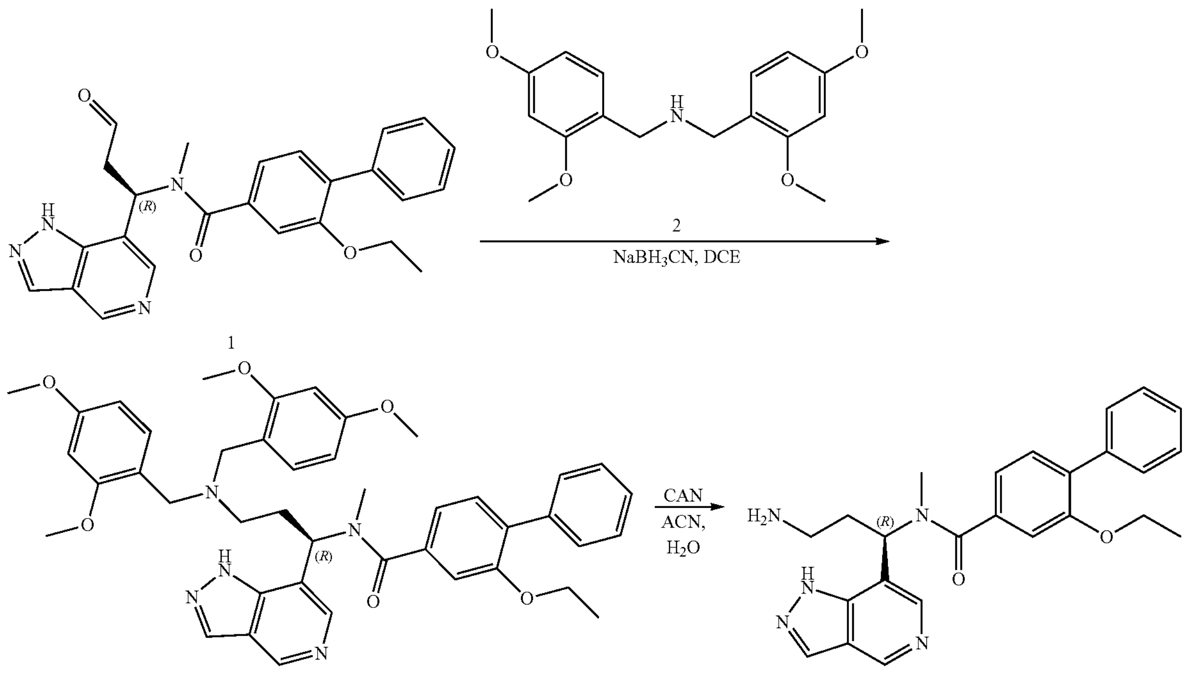

1

3

140

To a solution of compound 2 (333.32 mg, 1.05 mmol, 1.5 eq) in DCE (8 mL) was added compound 1 (300 mg, 700.15 μmol, 1 eq), HOAc (21.02 mg, 350.07 μmol, 20.04 μL, 0.5 eq) and Molecular sieve 4 A (150 mg, 700.15 μmol, 1 eq) stirred at 25° C. for 12 hr, then added NaBH(OAc)3 (148.39 mg, 700.15 μmol, 1 eq) at 0° C. and stirred at 25° C. for 2 hr. The reaction mixture was added into water (50 mL) and extracted with EtOAc (50 ML*3), then the organic phase was dried with Na2SO4 and concentrated under reduce pressure to give the residue. The crude product was purified by prep-TLC (PE:EA=0:1) and concentrated under reduced pressure to give the product (Rf=0.4). Compound 3 (400 mg, 438.44 μmol, 62.62% yield, 80% purity) was obtained as light-yellow oil. LCMS: Rt=0.507 min, m/z=730.5 (M+H+)

To a solution of compound 3 (270 mg, 369.93 μmol, 1 eq) in ACN (2.8 mL) and H2O (1.2 mL) was added CAN (608.41 mg, 1.11 mmol, 553.10 μL, 3 eq) at 0° C. The reaction mixture was stirred at 50° C. for 12 h. The reaction mixture was purified directly. The residue was purified by prep-HPLC (column: Phenomenex luna C18 150*25 mm*10 um; mobile phase: [water (FA)-ACN]; gradient: 2%-32% B over 15 min) and lyophilized to afford product. Compound 140 (38.32 mg, 88.33 μmol, 23.88% yield, 99% purity) was obtained as white solid. $^1$H NMR (400 MHz, CHLOROFORM-d) δ ppm 1.20 (br t, J=6.63 Hz, 3H) 2.51-2.82 (m, 5H) 3.09-3.32 (m, 2H) 3.81-3.96 (m, 2H) 6.27 (br s, 1H) 6.94-7.00 (m, 2H) 7.13 (br d, J=7.63 Hz, 1H) 7.26-7.32 (m, 4H) 7.37 (br d, J=6.88 Hz, 2H) 8.14 (s, 1H) 8.44 (br s, 2H) 8.96 (br s, 1H). LCMS: Rt=0.416 min, m/z=430.2 (M+H+).

Synthesis of Compound 147

Compound 147 was prepared in a similar manner to compound 140 with an additional coupling step using propionic acid with EDCI and DMAP in DCM. To a solution of starting material (26 mg, 58.10 μmol, 1 eq) and propionic acid (4.30 mg, 58.10 μmol, 4.33 μL, 1 eq) in DCM (1 mL) was added EDCI (16.71 mg, 87.15 μmol, 1.5 eq) and DMAP (709.79 μg, 5.81 μmol, 0.1 eq), the mixture was stirred at 25° C. for 12 hr. The crude product was purified by prep-HPLC (column: Phenomenex luna C18 150*25 mm*10 um; mobile phase: [water (FA)-ACN]; gradient: 18%-48% B over 9 min), and the product was concentrated and freeze-dried to give the product. The product was purified by prep-HPLC (column: Phenomenex luna C18 150*25 mm*10 um; mobile phase: [water (FA)-ACN]; gradient: 18%-48% B over 9 min), and the product was concentrated and freeze-dried to give the product. Compound 147 (7.41 mg, 14.57 μmol, 28.22% yield, 99% purity) was obtained as brown gum. $^1$H NMR (400 MHz, CHLOROFORM-d) δ ppm 1.19 (t, J=7.57 Hz, 3H) 1.37 (t, J=6.94 Hz, 3H) 2.28 (q, J=7.50 Hz, 2H) 2.34-2.41 (m, 1H) 2.66 (dddd, J=13.98, 10.69, 7.29, 3.56 Hz, 1H) 2.85 (s, 3H) 3.20-3.33 (m, 1H) 3.73-3.86 (m, 1H) 4.02-4.15 (m, 2H) 6.04 (br t, J=5.75 Hz, 1H) 6.29 (br dd, J=11.26, 4.25 Hz, 1H) 7.00-7.07 (m, 1H) 7.10-7.16 (m, 2H) 7.27-7.32 (m, 2H) 7.32-7.39 (m, 2H) 8.27 (s, 1H) 8.40 (br s, 1H) 9.12 (br s, 1H). LCMS: Rt=0.458 min, m/z=504.2 (M+H+).

Synthesis of Compound 157

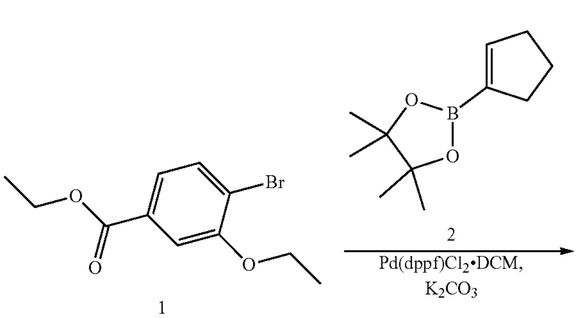

1

-continued

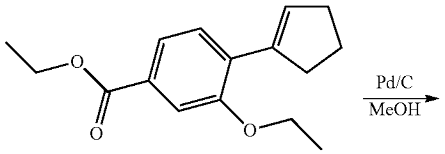

3

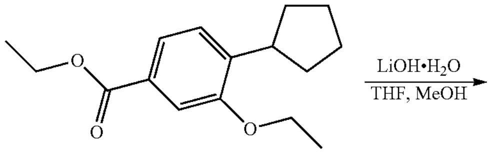

4

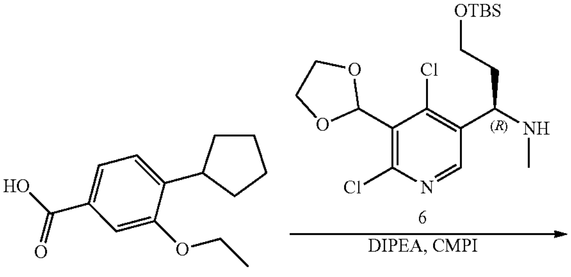

6

5

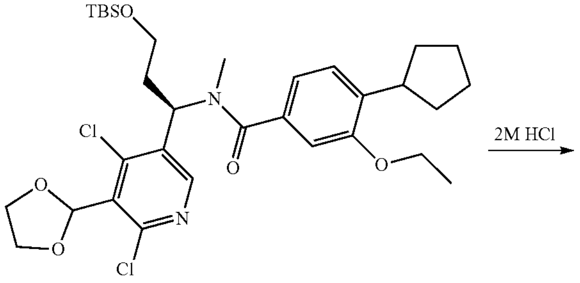

7

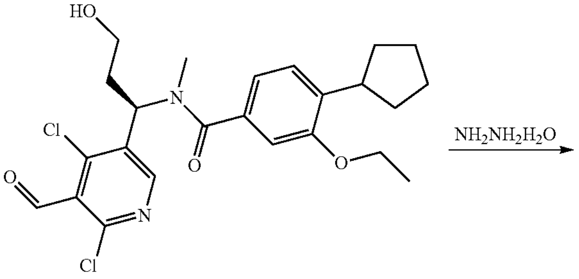

8

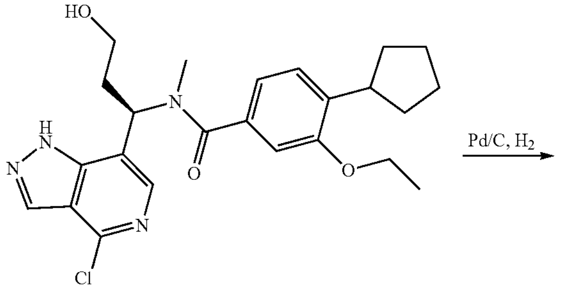

9

-continued

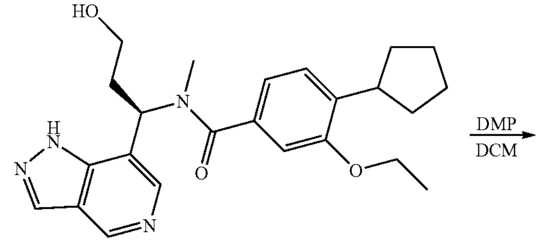

10

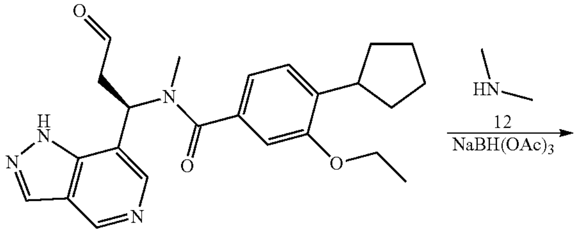

11

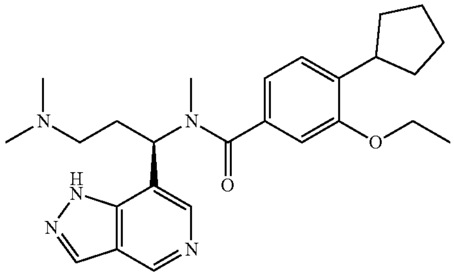

157

To a solution of the compound 1 (13.51 g, 49.46 mmol, 1 eq) and compound 2 (9.6 g, 49.46 mmol, 1 eq) in the dioxane (130 mL) and $H_2O$ (13 mL) was added $K_2CO_3$ (13.67 g, 98.93 mmol, 2 eq) and Pd(dppf)$Cl_2$·$CH_2Cl_2$ (4.04 g, 4.95 mmol, 0.1 eq) under $N_2$, then the mixture was stirred at 100° C. for 12 h. The mixture was poured into water (100 mL) and extracted with EtOAc (100 mL×2), then the organic phase was washed by brine (100 mL), dried over $Na_2SO_4$ and concentrated to give a residue. The residue was purified by column chromatography ($SiO_2$, PE/EtOAc=1/0 to 10/1), the spot (PE/EtOAc=10/1, Rf=0.6) was collected. Compound 3 (11.6 g, 44.56 mmol, 90.08% yield) was obtained as yellow liquid. $^1$H NMR (400 MHz, CHLOROFORM-d) δ=7.61 (dd, J=1.2, 8.0 Hz, 1H), 7.55 (s, 1H), 7.34-7.30 (m, 1H), 6.67 (br s, 1H), 4.38 (q, J=7.2 Hz, 2H), 4.17 (q, J=7.2 Hz, 2H), 2.79 (dt, J=2.0, 7.6 Hz, 2H), 2.58 (dt, J=2.4, 7.2 Hz, 2H), 1.97 (quin, J=7.6 Hz, 2H), 1.51 (t, J=6.8 Hz, 3H), 1.42-1.38 (m, 3H)

To a solution of the Pd/C (4.74 g, 4.46 mmol, 10% purity, 0.1 eq) in the MeOH (130 mL) was added compound 3 (11.6 g, 44.56 mmol, 1 eq) under $N_2$, the suspension was degassed under vacuum and purged with $H_2$ several times. The mixture was stirred under $H_2$ (50 psi) at 30° C. for 12 h. The mixture filtered and the filtrate was collected to concentrated. Compound 4 (10.6 g, crude) was obtained as yellow oil which was used directly for the next step. $^1$H NMR (400 MHz, CHLOROFORM-d) δ=7.59 (dd, J=1.6, 8.0 Hz, 1H), 7.49 (d, J=1.2 Hz, 1H), 7.25 (s, 1H), 4.40-4.34 (m, 2H), 4.11 (q, J=6.8 Hz, 2H), 3.43-3.31 (m, 1H), 2.09-1.97 (m, 2H), 1.85-1.76 (m, 2H), 1.74-1.67 (m, 2H), 1.64-1.59 (m, 2H), 1.47-1.43 (m, 3H), 1.41-1.37 (m, 3H)

To a solution of compound 4 (10.6 g, 40.41 mmol, 1 eq) in the THF (35 mL), MeOH (35 mL) and $H_2O$ (35 mL) was added $LiOH·H_2O$ (5.09 g, 121.22 mmol, 3 eq), then the mixture was stirred at 25° C. for 12 h. The mixture was adjusted to pH=2 with 1N HCl solution. The reaction mixture was poured into $H_2O$ (200 mL) and extracted by EtOAc (200 mL×3), the organic phase was combined and washed with brine (200 mL), dried over $Na_2SO_4$ and concentrated to give a crude product. Compound 5 (9.6 g, crude) was obtained as white solid which was used directly for the next step. LCMS: Rt=0.352 min, m/z=233.3 ($M+H^+$)

To a solution of compound 5 (3 g, 12.80 mmol, 1 eq) and compound 6 (5.40 g, 12.80 mmol, 1 eq) in the DMF (50 mL) was added CMPI (4.91 g, 19.21 mmol, 1.5 eq) and DIEA (4.96 g, 38.41 mmol, 6.69 mL, 3 eq), then the mixture was stirred at 50° C. for 12 h. The reaction mixture was poured into $H_2O$ (100 mL) and extracted by EtOAC (100 mL×3), the organic phase was combined and washed with brine (100 mL), dried with $Na_2SO_4$ and concentrated to give a residue. The residue was purified by column chromatography ($SiO_2$, PE/EtOAc=1/0 to 3/1), the spot (PE/EtOAc=3/1, Rf=0.5) was collected. Compound 7 (3.5 g, 5.49 mmol, 42.86% yield) was obtained as yellow oil. LCMS: Rt=0.736 min, m/z=637.2 ($M+H^+$) $^1H$ NMR (400 MHz, CHLOROFORM-d) δ=8.62-8.45 (m, 1H), 7.17 (d, J=7.6 Hz, 1H), 6.88-6.78 (m, 2H), 6.49 (br s, 1H), 6.10-5.77 (m, 1H), 4.33 (br s, 2H), 4.12-4.08 (m, 2H), 4.07-3.96 (m, 2H), 3.87-3.68 (m, 2H), 3.38-3.25 (m, 1H), 2.94-2.65 (m, 3H), 2.51-2.36 (m, 1H), 2.33 (br d, J=6.8 Hz, 1H), 2.04-1.97 (m, 2H), 1.82-1.72 (m, 2H), 1.71-1.64 (m, 2H), 1.53 (br s, 2H), 1.41 (br t, J=6.8 Hz, 3H), 0.92-0.84 (m, 9H), 0.10--0.02 (m, 6H)

To a solution of the compound 7 (3.50 g, 5.49 mmol, 1 eq) in the THF (20 mL) was added HCl (2 M, 19.94 mL, 7.27 eq), then the mixture was stirred at 40° C. for 12 h. The mixture was adjusted pH to 9-10 by $NaHCO_3$ and extracted by EtOAc (50 mL×2), then the organic phase was washed by brine (50 mL), dried over $Na_2SO_4$ and concentrated to give a residue. Compound 8 (3.3 g, crude) was obtained as yellow oil. The crude product was used directly for the next step. LCMS: Rt=0.599 min, m/z=479.2 ($M+H^+$)

To a solution of the compound 8 (3.3 g, 6.88 mmol, 1 eq) in the dioxane (30 mL) was added $N_2H_4·H_2O$ (834.29 mg, 15.83 mmol, 808.42 μL, 95% purity, 2.3 eq), then the mixture was stirred at 70° C. for 2 h. The mixture was poured into ice water (40 mL) and extracted with EtOAc (40 mL×2), then the organic phase was washed by brine (40 mL), dried over $Na_2SO_4$ and concentrated to give a residue. The residue was purified by column chromatography ($SiO_2$, PE/EtOAc=1/0 to 0/1), the spot (PE/EtOAc=0/1, Rf=0.6) was collected. Compound 8 (1 g, 2.19 mmol, 31.79% yield) was obtained as yellow oil. LCMS: Rt=0.590 min, m/z=457.3 ($M+H^+$) $^1H$ NMR (400 MHz, CHLOROFORM-d) δ=12.57-12.07 (m, 1H), 8.23 (s, 1H), 8.12 (s, 1H), 7.20 (d, J=7.6 Hz, 1H), 6.97-6.91 (m, 2H), 6.39 (br dd, J=4.4, 10.4 Hz, 1H), 4.08-3.98 (m, 2H), 3.95-3.84 (m, 2H), 3.39-3.27 (m, 1H), 2.77 (s, 3H), 2.63-2.53 (m, 1H), 2.45-2.35 (m, 1H), 2.22-2.12 (m, 1H), 2.04-1.96 (m, 2H), 1.84-1.75 (m, 2H), 1.74-1.62 (m, 4H), 1.43 (t, J=6.8 Hz, 3H)

To a solution of the Pd/C (100 mg, 93.97 μmol, 10% purity, 4.29e-2 eq) in the MeOH (10 mL) was added compound 9 (1 g, 2.19 mmol, 1 eq) and DIEA (282.83 mg, 2.19 mmol, 381.17 μL, 1 eq) under $N_2$, the suspension was degassed under vacuum and purged with $H_2$ several times. The mixture was stirred under $H_2$ (20 psi) at 30° C. for 12 h. The mixture filtered and the filtrate was collected to concentrated. The residue was used to next step without purification. Compound 10 (1.2 g, crude) was obtained as yellow oil which was used directly for the next step. LCMS: RT=0.464 min, m/z=423.3 (M+H+)

To a solution of compound 10 (1.2 g, 2.84 mmol, 1 eq) in the DCM (12 mL) was added Dess-Martin (2.41 g, 5.68 mmol, 1.76 mL, 2 eq) at 0° C. and stirred for 1 h. The reaction mixture was poured into $H_2O$ (20 mL) and extracted by DCM (20 mL×2), the organic phase was combined and washed with brine (20 mL×2), dried over $Na_2SO_4$, filtered and concentrated to give a crude product. The residue was purified by reversed-phase HPLC (0.1% FA condition). Compound 11 (740 mg, 1.76 mmol, 61.96% yield) was obtained as brown oil. LCMS: Rt=0.448 min, m/z=421.2 (M+H+)

To a solution of compound 11 (400 mg, 951.24 μmol, 1 eq) and compound 12 (2 M, 1.43 mL, 3 eq) in the DCE (8 mL) was added 4 A MS (0.4 g) and AcOH (5.71 mg, 95.12 μmol, 5.45 μL, 0.1 eq) and stirred at 25° C. for 12 h. Then the mixture was added $NaBH(OAc)_3$ (604.82 mg, 2.85 mmol, 3 eq) at 0° C. and stirred at 25° C. for 3 h. The reaction mixture was filtered. The filter liquor was poured into $H_2O$ (20 mL) under $N_2$ and extracted by DCM (20 mL×3), the organic phase was combined and washed with brine (20 mL×3), dried over Na2SO4, filtered and concentrated to give a crude product in vacuum. The residue was purified by Prep-HPLC (column: Phenomenex luna C18 150*25 mm*10 um; mobile phase: [water (FA)-ACN]; gradient: 10%-40% B over 10 min). Compound 157 (77 mg, 171.27 μmol, 18.00% yield, 96.3% purity) was obtained as white solid. LCMS: Rt=0.473 min, m/z=450.2 (M+H+) $^1H$ NMR (400 MHz, CHLOROFORM-d) δ=9.10 (s, 1H), 8.49 (s, 1H), 8.41 (s, 1H), 8.24 (s, 1H), 7.22 (d, J=7.6 Hz, 1H), 7.03-6.90 (m, 2H), 6.25 (br d, J=8.4 Hz, 1H), 4.11-3.99 (m, 2H), 3.38-3.29 (m, 1H), 2.80 (s, 3H), 2.77-2.70 (m, 1H), 2.69-2.58 (m, 2H), 2.46 (d, J=1.2 Hz, 6H), 2.45-2.38 (m, 1H), 2.08-1.93 (m, 2H), 1.82-1.72 (m, 2H), 1.72-1.63 (m, 2H), 1.61-1.50 (m, 2H), 1.42 (br t, J=6.8 Hz, 3H).

Synthesis of Compound 210

Compound 210 was prepared in a similar manner to Compound 079 and was then treated with m-CPBA in DCM. Compound 210 (8.99 mg, 18.11 μmol, 6.12% yield, 98.6% purity) was obtained as an off-white gum. LCMS: RT=0.441 min, m/z=490.2[M+H]+ $^1H$ NMR (400 MHz, METHANOL-d4) δ=9.24 (br s, 1H), 8.61-8.47 (m, 1H), 8.43-8.28 (m, 1H), 7.49-7.21 (m, 6H), 7.11-7.01 (m, 1H), 6.36-5.29 (m, 1H), 5.08-4.95 (m, 1H), 4.49-4.15 (m, 2H), 4.12-3.91 (m, 1H), 3.27-3.07 (m, 1H), 3.03 (s, 3H), 3.00-2.80 (m, 2H), 2.76-2.65 (m, 3H), 1.41-1.26 (m, 3H).

Synthesis of Compound 185

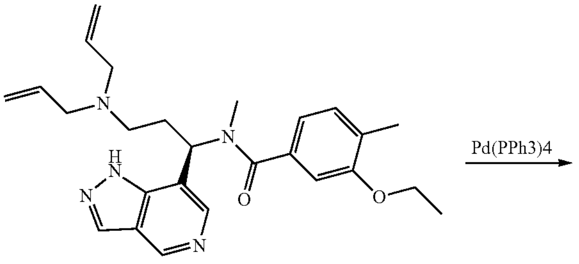

1

-continued

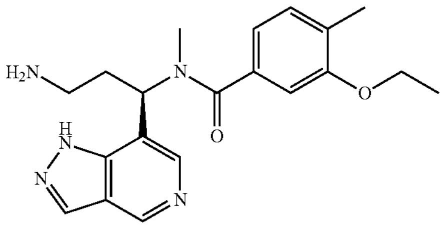

185

To a solution of compound 1 (200 mg, 446.86 μmol, 1 eq) in EtOH (8 mL) was added 4-methylbenzenesulfinic acid (418.80 mg, 2.68 mmol, 6 eq) and Pd(PPh3)4 (129.09 mg, 111.71 μmol, 0.25 eq). The mixture was stirred at 40° C. for 12 h under N2. The reaction mixture was added into saturated NaHCO3 (30 mL) and extracted with DCM (30 mL×3), then the organic phase was dried with Na2SO4 and concentrated under reduce pressure to give the residue. The residue was purified by prep-HPLC (column: Waters Xbridge 150×25 mm×5 um; mobile phase: [water ($NH_4HCO_3$)-ACN]; gradient: 10%-40% B over 15 min), the purified solution was lyophilized to give a white solid. Then the residue was purified by prep-HPLC (column: Unisil 3-100 C18 Ultra 150×50 mm×3 um; mobile phase: [water (FA)-ACN]; gradient: 1%-28% B over 10 min), the purified solution was lyophilized to give a white solid. Compound 185 (95.46 mg, 226.79 μmol, 50.75% yield, 98.229% purity, FA) was obtained as a white solid. LCMS: Rt=0.411 min, m/z=368.1 [M+H]+ $^1$H NMR: (400 MHz, CHLOROFORM-d) δ=8.95 (s, 1H), 8.51 (br s, 1H), 8.35 (br s, 1H), 8.12 (s, 1H), 6.92 (br d, J=7.6 Hz, 1H), 6.78 (br d, J=3.6 Hz, 2H), 6.19 (br s, 1H), 3.95-3.75 (m, 2H), 3.23-2.96 (m, 2H), 2.57 (br s, 5H), 2.07 (s, 3H), 1.28 (br t, J=6.4 Hz, 3H).

Synthesis of Compound 186

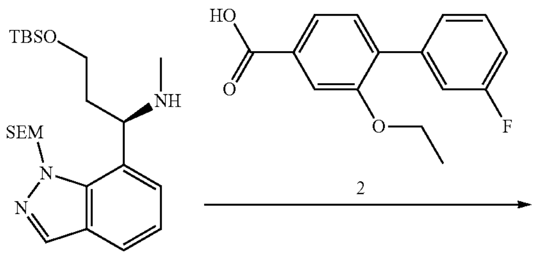

1

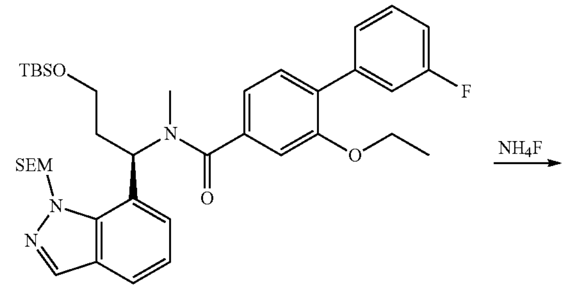

3

-continued

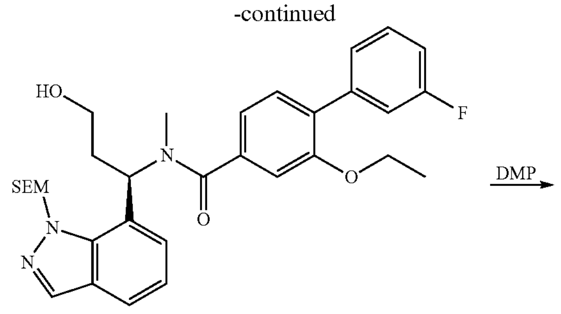

4

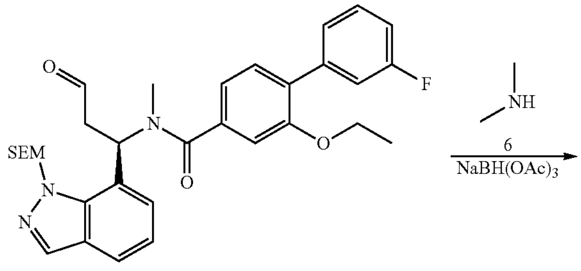

5

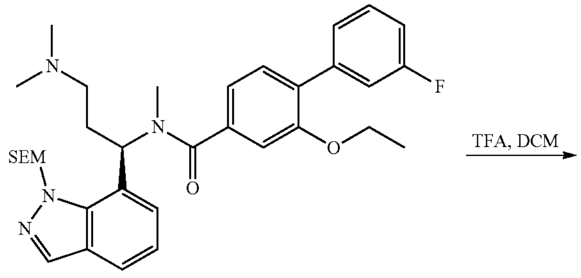

7

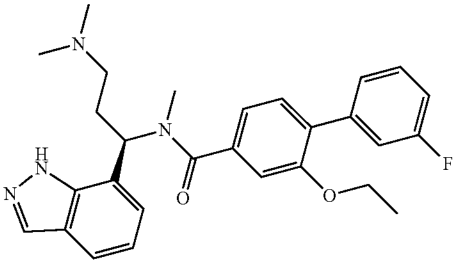

186

To a solution of compound 1 (150 mg, 333.50 μmol, 1 eq) and compound 2 (86.80 mg, 333.50 μmol, 1 eq) in DMF (3 mL) was added CMPI (127.80 mg, 500.25 μmol, 1.5 eq) and DIPEA (4.60 g, 35.59 mmol, 6.20 mL, 3 eq) at 25° C. The mixture was stirred at 50° C. for 12 hr. The reaction mixture was poured into $H_2O$ (30 mL) and extracted by EtOAc (30 mL×3), the organic phase was combined and washed with brine (30 mL×3), dried with anhydrous $Na_2SO_4$, filtered and concentrated to give a crude product in vacuum. The crude product was purified by prep-TLC (PE:EA=2:1) and concentrated under reduced pressure to give the product (Rf=0.6) compound 3 (90 mg, 126.15 μmol, 37.83% yield, 97% purity) as a light-yellow oil. LCMS: RT=0.776 min, m/z=692.5 [M+H]+

To a solution of compound 3 (90 mg, 130.05 μmol, 1 eq) in MeOH (1 mL) was added NH4F (48.17 mg, 1.30 mmol, 10 eq), the mixture was stirred at 60° C. for 2 h. The mixture was stirred at 40° C. for 5 h. The reaction mixture was poured into H2O (10 mL), and extracted with EA (10 mL×3). The combined organic phase was dried with $Na_2SO_4$ and concentrated to give the crude product. Compound 4 (76 mg, crude) as a light yellow oil. The crude product was used directly for the next step. LCMS: RT=0.638 min, m/z=578.4 [M+H]+

To a solution of compound 4 (100 mg, 173.08 μmol, 1 eq) in DMSO (2 mL) was added IBX (96.93 mg, 346.16 μmol, 2 eq). The reaction mixture was stirred at 25° C. for 3h. The reaction mixture was poured into $H_2O$ (10 mL) under $N_2$ and extracted by DCM (10 mL×3), the organic phase was combined and washed with brine (10 mL×3), dried with anhydrous $Na_2SO_4$, filtered and concentrated to give a crude product in vacuum. The crude product was purified by prep-TLC (PE:EA=0:1) and concentrated to give the product (Rf=0.8) compound 7 (84 mg, 81.70 μmol, 47.20% yield, 56% purity) was obtained as light-yellow oil. LCMS: RT=0.676 min, m/z=576.3 [M+H]+

To a solution of compound 7 (152 mg, 385.33 μmol, 1 eq), $Me_2NH$ (2 M, 963.33 μL, 5 eq) in DCE (3 mL) was added AcOH (3.86 mg, 64.26 μmol, 3.68 μL, 0.5 eq) and Molecular sieve 4 A (20 mg, 128.53 μmol, 1 eq). Then the reaction mixture was stirred at 25° C. for 11h. Then $NaBH(OAc)_3$ (81.72 mg, 385.59 μmol, 3 eq) was added to the solution at 0° C. The reaction mixture was stirred at 25° C. for 1 h. The reaction mixture was added into water (20 mL) and extracted with EA (20 ML*3), then the organic phase was dried with $Na_2SO_4$ and concentrated under reduce pressure to give the residue. The crude product was purified by prep-TLC (PE:EA=0:1) and concentrated under reduced pressure to give the product (Rf=0.1). Compound 7 (54.55 mg, 127.50 μmol, 33.09% yield, 99% purity) was obtained as light-yellow oil. LCMS: RT=0.506 min, m/z=475.4 [M+2+H]+

To a solution of compound 7 (30 mg, 49.60 μmol, 1 eq) in DCM (0.3 mL) was added TFA (2.30 g, 20.19 mmol, 1.50 mL, 407.13 eq), The reaction mixture was stirred at 25° C. for 1 hr. The reaction mixture was adjusted PH=8. The filter liquor was added into $H_2O$ (20 mL) at 25° C. under $N_2$ and extracted by DCM (20 mL×3), the organic phase was dried with anhydrous $Na_2SO_4$, filtered and concentrated to give a crude product in vacuum. The crude product was purified by prep-HPLC (column: Waters Xbridge C18 150*25 mm*5 um; mobile phase: [$H_2O$ (0.05% $NH_3H_2O$)-ACN]; gradient: 50%-80% B over 11.0 min), and concentrated under reduced pressure to give the product. Compound 186 (16.02 mg, 33.42 μmol, 67.38% yield, 99% purity) was obtained as brown gum. LCMS: Rt=0.483 min, m/z=475.3 (M+H+). $^1$H NMR (400 MHz, CHLOROFORM-d) δ ppm 1.31-1.45 (m, 3H) 2.31-2.55 (m, 8H) 2.57 (br d, J=6.88 Hz, 2H) 2.71-2.96 (m, 3H) 3.94-4.22 (m, 2H) 6.36 (br dd, J=8.69, 5.44 Hz, 1H) 6.99-7.11 (m, 3H) 7.18 (t, J=7.63 Hz, 1H) 7.28-7.42 (m, 5H) 7.76 (d, J=8.13 Hz, 1H) 8.12 (s, 1H) 11.83-11.95 (m, 1H).

Synthesis of Compound 188

Compound 188 was prepared following Scheme 4, GP1, GP5, GP13, and G16 using nitromethane and reducing with iron and ammonium chloride. The remaining of the synthesis is shown below.

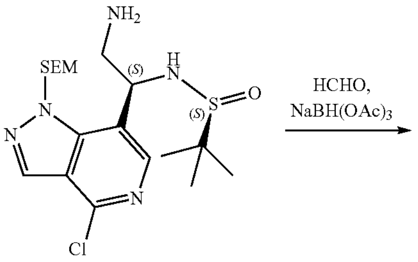

7

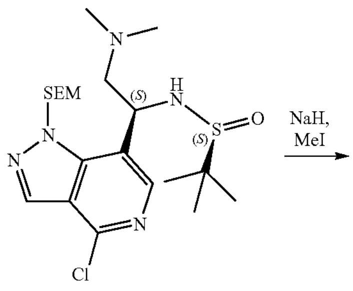

8

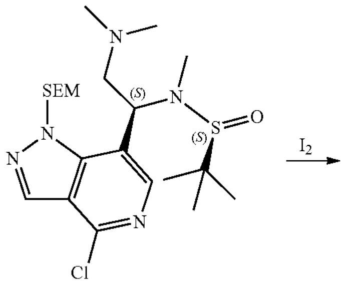

9

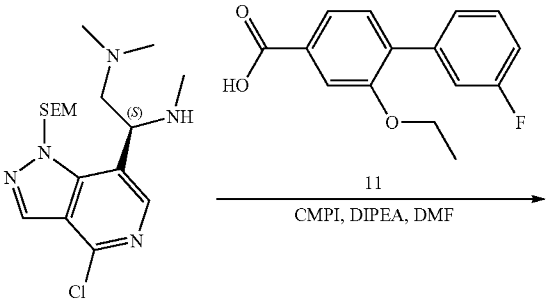

10

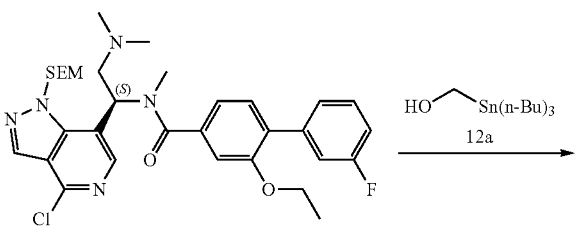

12

-continued

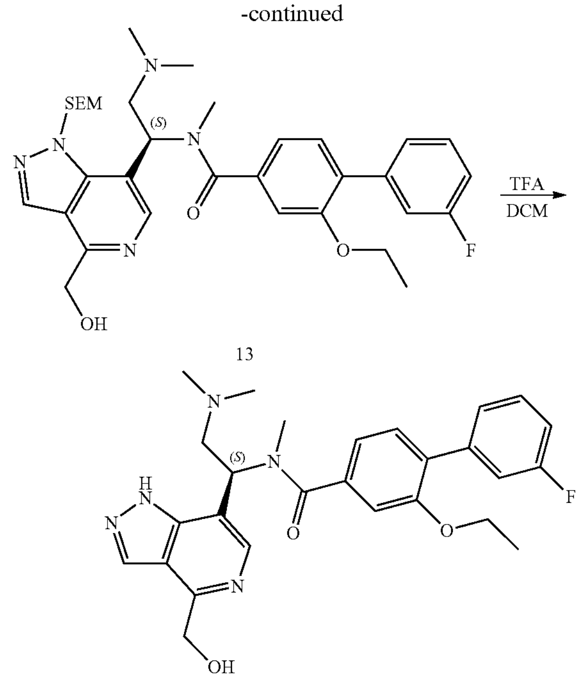

13

188

To a solution of compound 7 (1.45 g, 3.25 mmol, 1 eq) in the MeOH (25 mL) was added HCHO (1.32 g, 16.25 mmol, 1.21 mL, 37% purity, 5 eq) and $NaBH_3CN$ (817.08 mg, 13.00 mmol, 4 eq), then the mixture was stirred at 20° C. for 1 h under $N_2$. The reaction mixture was quenched with aq.sat.$NH_4Cl$ (50 mL) at 0° C. under nitrogen protect and then extracted with EA (50 mL*3), the combined organic were washed with brine (50 mL), then the organic phase was dried with $Na_2SO_4$ and concentrated under reduce pressure to give the residue. The residue was purified by column chromatography ($SiO_2$, Commercial hexanes: Ethyl acetate=0/1 to I/O). Compound 8 (1.4 g, 2.95 mmol, 90.84% yield, N/A purity) as yellow oil. LCMS: Rt=0.497 min, m/z=474.3 [M+H]+ $^1$H NMR (400 MHz, CHLOROFORM-d) δ=8.40 (br s, 1H), 8.19 (s, 1H), 6.29-5.99 (m, 1H), 5.88-5.60 (m, 1H), 5.49-5.08 (m, 1H), 3.72-3.47 (m, 2H), 2.63-2.29 (m, 5H), 1.37-1.15 (m, 10H), 1.11-0.77 (m, 2H), 0.00 (s, 9H)

To a 100 mL vial was added compound 8 (1.30 g, 2.74 mmol, 1 eq) and THF (20 mL), the flask was evacuated and back filled with nitrogen for three times. Then cooled to 0° C., NaH (164.51 mg, 4.11 mmol, 60% purity, 1.5 eq) was added at 0° C. in portions under nitrogen protected, the mixture was stirred at 0° C. for 1 h, then MeI (377.00 mg, 2.66 mmol, 165.35 μL, 9.69e-1 eq) was added to the mixture at 0-10° C., the mixture was allow warm up to 25° C. and stirred at 25° C. for 1 hr. The reaction mixture was added $NH_4Cl$ (300 ML) in $N_2$, then extracted with EA (300×2) then extracted with brine (300 mL×3), then the organic phase was dried with $Na_2SO_4$ and concentrated under reduce pressure to give the residue. The residue was purified by column chromatography ($SiO_2$, Commercial hexanes: Ethyl acetate=1/0 to 0/1). Compound 9 (700 mg, 1.43 mmol, 52.30% yield, N/A purity) as yellow solid. LCMS: RT=0.472 min, m/z=488.2 [M+H]+ $^1$H NMR (400 MHz, CHLOROFORM-d) δ=8.27 (s, 1H), 8.15 (s, 1H), 6.00 (d, J=11.8 Hz, 1H), 5.76 (d, J=11.8 Hz, 1H), 5.36 (t, J=7.7 Hz, 1H), 3.60-3.40 (m, 2H), 3.13-2.86 (m, 2H), 2.70 (s, 3H), 2.42-2.23 (m, 6H), 1.26-1.10 (m, 9H), 1.00-0.72 (m, 2H), −0.03 (s, 9H)

To a solution of compound 9 (700.00 mg, 1.43 mmol, 1 eq) in THF (5 mL) was added HCl (2 M, 5 mL, 6.97 eq). The reaction mixture was stirred at 20° C. for 1 hr. The reaction mixture was added $NaHCO_3$ (10 ML) in $N_2$, then extracted with EA (10×2) then extracted with brine (10 mL×3), then the organic phase was dried with $Na_2SO_4$ and concentrated under reduce pressure to give the residue. The crude was used into next step without farther purification. Compound 10 (520 mg, 947.94 μmol, 66.11% yield, 70% purity) as yellow solid. LCMS: RT=0.454 min, m/z=384.2 [M+H]+ $^1$H NMR (400 MHz, CHLOROFORM-d) δ=8.43 (s, 1H), 8.19-8.13 (m, 1H), 3.62-3.58 (m, 3H), 2.35-2.32 (m, 6H), 1.94-1.84 (m, 3H), 1.78-1.66 (m, 3H), 1.02-0.77 (m, 3H), −0.02--0.04 (m, 9H)

To a solution of Compound 10 (480 mg, 1.25 mmol, 1 eq) and Compound 11 (325.33 mg, 1.25 mmol, 1 eq) in DMF (5 mL) was added CMPI (638.72 mg, 2.50 mmol, 2 eq) and DIEA (484.67 mg, 3.75 mmol, 653.20 μL, 3 eq), the mixture was stirred at 50° C. for 2 hr. The reaction mixture was added $NH_4Cl$ (30 ML) in $N_2$, then extracted with EA (30×2) then extracted with brine (30 mL×3), then the organic phase was dried with $Na_2SO_4$ and concentrated under reduce pressure to give the residue. The residue was purified by column chromatography ($SiO_2$, Commercial hexanes: Ethyl acetate=1/0 to 0/1). Compound 12 (350 mg, 463.88 μmol, 37.11% yield, 83% purity) as yellow solid. LCMS: RT=0.614 min, m/z=626.2 [M+H]+ $^1$H NMR (400 MHz, CHLOROFORM-d) δ=8.32 (s, 1H), 8.20 (s, 1H), 7.40-7.31 (m, 2H), 7.30 (br s, 1H), 7.07-6.92 (m, 4H), 6.72-6.29 (m, 2H), 5.83-5.63 (m, 1H), 4.08-3.97 (m, 2H), 3.62-3.39 (m, 2H), 2.94-2.83 (m, 3H), 2.41 (s, 6H), 1.38-1.32 (m, 3H), 1.00-0.74 (m, 3H), −0.04 (s, 9H)

To a solution of Compound 12 and compound 12a (384.54 mg, 1.20 mmol, 3 eq) in dioxane (3 mL) was added Xphos Pd $G_4$ (34.35 mg, 39.92 μmol, 0.1 eq). The reaction mixture was stirred at 80° C. for 16 hr. After the reaction was cooled into 20° C. and being filtered at 20° C. under $N_2$, the filtrate was extracted with ethyl acetate (20 mL×2). The combined organic phase was evaporated under reduced pressure. The combined filter cake was quenched with 1 N HCl aqueous at 0° C. under $N_2$. The residue was purified by column chromatography ($SiO_2$, Commercial hexanes:Ethyl acetate=10/1 to 0/1) and by prep-TLC ($SiO_2$, DCM:MeOH=10:1). Compound 13 (80 mg, 128.66 μmol, 32.23% yield, N/A purity) as yellow solid. LCMS: RT=0.853 min, m/z=622.4 [M+H]+

To a solution of Compound 13 (75 mg, 120.61 μmol, 1 eq) in HFIP (1 mL) was added MsOH (23.18 mg, 241.23 μmol, 17.24 μL, 2 eq). The reaction mixture was stirred at 30° C. for 2 hr. The reaction was concentrated under reduce pressure to give the residue. The residue was purified by prep-HPLC (column: Phenomenex Luna C18 150*25 mm*10 um; mobile phase: [$H_2O$ (0.225% FA)-ACN]; gradient: 1%-30% B over 15.0 min) and lyophilizated to give product. Compound 188 (5.89 mg, 11.77 μmol, 9.75% yield, 98.19% purity) as white solid. LCMS: RT=0.423 min, m/z=492.2 [M+H]+ $^1$H NMR (400 MHz, CHLOROFORM-d) δ=8.28 (br dd, J=4.8, 11.8 Hz, 2H), 7.39-7.34 (m, 2H), 7.35-7.28 (m, 4H), 7.17 (br d, J=4.4 Hz, 1H), 7.10-6.97 (m, 1H), 6.45-6.35 (m, 1H), 5.19-5.04 (m, 2H), 4.16-4.02 (m, 2H), 3.63-3.43 (m, 1H), 2.91 (br d, J=10.0 Hz, 2H), 2.86 (br d, J=4.4 Hz, 3H), 2.53 (br s, 6H), 1.46-1.32 (m, 3H).

Compound 234

Compound 234 was prepared in accordance with the following scheme

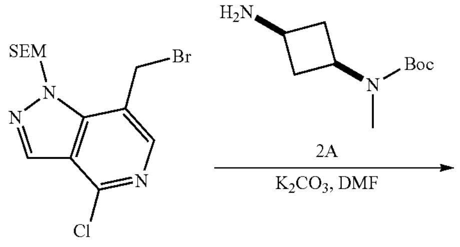

1

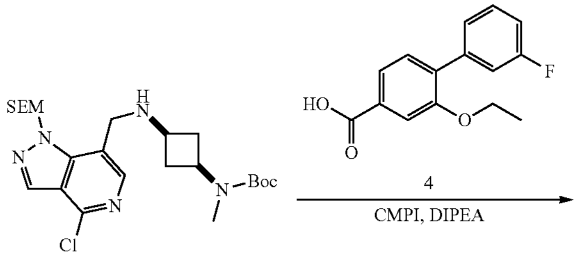

3

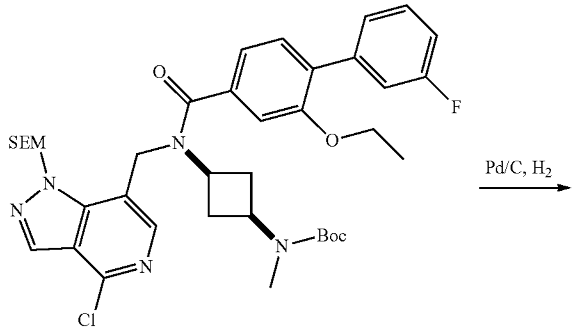

5

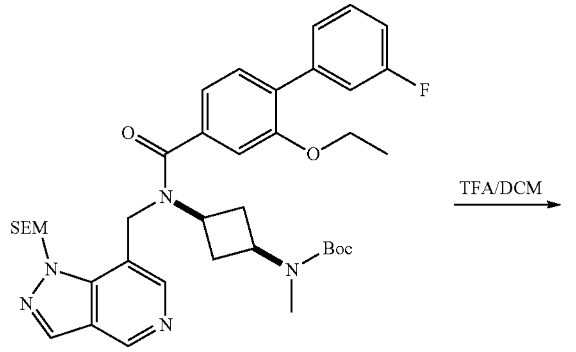

6

-continued

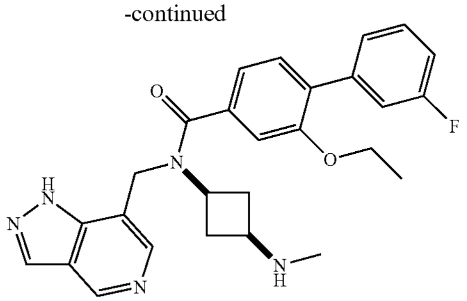

234

To a solution of compound 1 (282.17 mg, 748.96 μmol, 1 eq) and compound 2A (450 mg, 2.25 mmol, 3 eq) in DMF (4 mL) was added $K_2CO_3$ (310.54 mg, 2.25 mmol, 3 eq). Then the reaction was stirred at 25° C. for 12 h. The reaction mixture was added water (15 mL) and extracted by EA (15 mL×3). The organic phase was dried over anhydrous sodium sulfate, filtered and concentrated under vacuo to give a residue. The crude product was purified by RP-HPLC (spherical C18 20-45 mm 100 A 80 g; mobile phase: [water (0.1% FA)-ACN]; B %: 40%-55% (DP collected)) and lyophilized, compound 3 (280 mg, 564.38 μmol, 75.36% yield) was obtained as a white oil, $^1$H NMR (400 MHz, CHLOROFORM-d) δ=8.20 (s, 1H), 8.15 (s, 1H), 6.09 (s, 2H), 4.17 (s, 2H), 3.65-3.56 (m, 2H), 3.16-3.06 (m, 1H), 2.84 (s, 3H), 2.53 (br d, J=6.6 Hz, 3H), 1.96 (br dd, J=2.3, 4.7 Hz, 2H), 1.51 (s, 9H), 0.96-0.86 (m, 2H), 0.00 (s, 9H)

To a solution of compound 3 (260 mg, 524.07 μmol, 1 eq) and compound 4 (163.67 mg, 628.88 μmol, 1.2 eq) in DMF (4 mL) was added CMPI (200.83 mg, 786.11 μmol, 1.5 eq) and DIEA (203.19 mg, 1.57 mmol, 273.84 μL, 3 eq). The mixture was stirred at 50° C. for 12 hr. The reaction mixture was poured into $H_2O$ (10 mL) under $N_2$ and extracted by EtOAC (10 mL×3), the organic phase was combined and washed with brine (10 mL×3), dried with anhydrous $Na_2SO_4$, filtered and concentrated to give a crude product in vacuum. The crude product was purified by prep-HPLC (column: Phenomenex luna C18 150*25 mm*10 um; mobile phase: [$H_2O$ (0.225% FA)-ACN]; gradient: 80%-100% B over 9.0 min) and lyophilized. Compound 5 (193 mg, 261.39 μmol, 49.88% yield) was obtained as a white gum. $^1$H NMR (400 MHz, CHLOROFORM-d) δ=8.18 (s, 1H), 8.03 (s, 1H), 7.39-7.33 (m, 4H), 7.08 (br s, 3H), 5.92 (br s, 2H), 5.43-5.30 (m, 2H), 4.38-4.24 (m, 1H), 4.11-3.99 (m, 2H), 3.97-3.79 (m, 1H), 3.63-3.47 (m, 2H), 2.73 (s, 3H), 2.44 (br dd, J=2.5, 11.2 Hz, 4H), 1.41 (s, 9H), 1.39 (br s, 3H), 0.90 (br d, J=1.8 Hz, 2H), 0.00 (s, 9H)

To a 35 ml hydrogenation flask with a magnetic stir bar was added Pd/C (34.59 mg, 32.50 μmol, 10% purity, 0.15 eq) and followed by the addition of MeOH (4 mL) under argon, then added compound 5 (160 mg, 216.70 μmol, 1 eq) in MeOH (4 mL) and DIEA (28.01 mg, 216.70 μmol, 37.74 μL, 1 eq) under $N_2$. The reaction mixture was stirred at 25° C. for 3 h under $H_2$ (15 psi). The reaction mixture was filtered under $N_2$ with diatomite and the filter cake was recycling, filter liquor was concentrated to give the crude. Compound 6 was obtained as a colorless oil. LCMS: RT=0.617 min, m/z=704.4 [M+H]+

A mixture of compound 6 (150 mg, 213.09 μmol, 1 eq) in DCM (2 mL) and TFA (2 mL) was at stirred at 25° C. for 1 hr. The solvent was removed under reduced pressure. The crude product was purified by prep-HPLC (column: Boston Green ODS 150*30 mm*5 um; mobile phase: [$H_2O$ (0.225% FA)-ACN]; gradient: 5%-35% B over 11.0 min) and lyophilized. Compound 234 (24.92 mg, 51.57 μmol, 24.20% yield, 98% purity) was obtained as a white solid. LCMS: RT=0.451 min, m/z=474.1 [M+H]+ $^1$H NMR (400 MHz, CHLOROFORM-d) δ=8.95 (br s, 1H), 8.68-8.39 (m, 2H), 8.13 (s, 1H), 7.35-7.25 (m, 2H), 7.25-7.20 (m, 2H), 7.01-6.88 (m, 3H), 5.20 (br s, 2H), 4.42-4.11 (m, 1H), 3.96 (br d, J=4.0 Hz, 2H), 3.05 (br s, 1H), 2.70 (br d, J=0.8 Hz, 2H), 2.42 (s, 5H), 1.29 (br t, J=6.8 Hz, 3H).

Synthesis of Compound 244

Compound 244 was prepared by reacting Compound 234 with formaldehyde in the presence of $NaBH(OAc)_3$. Compound 244 (9.47 mg, 18.82 μmol, 8.65% yield, 96.9% purity) was obtained as an off-white gum. LCMS: RT=0.425 min, m/z=488.2 [M+H]+ $^1$H NMR (400 MHz, CHLOROFORM-d) δ=12.13 (br s, 1H), 9.03 (s, 1H), 8.45 (s, 1H), 8.17 (s, 1H), 7.32-7.20 (m, 4H), 7.01-6.93 (m, 1H), 6.90-6.84 (m, 2H), 5.06 (br s, 2H), 3.98 (q, J=6.8 Hz, 3H), 2.13 (br d, J=7.9 Hz, 5H), 2.03 (s, 6H), 1.30 (t, J=6.9 Hz, 3H).

Synthesis of Compound 235

Compound 235 was prepared following the protocol above for Compound 234 starting with a different diastereomer of compound 2A. Compound 235 (23.00 mg, 48.33 μmol, 17.01% yield, 99.5% purity) was obtained as a white solid. LCMS: RT=0.401 min, m/z=474.3 [M+H]+ $^1$H NMR (400 MHz, CHLOROFORM-d) δ=9.10 (s, 1H), 8.38 (br s, 1H), 8.25 (s, 1H), 8.17 (br s, 1H), 7.39-7.33 (m, 1H), 7.33-7.28 (m, 3H), 7.06-6.99 (m, 1H), 6.97 (s, 1H), 6.93 (br d, J=6.8 Hz, 1H), 5.08 (br s, 2H), 4.92 (br s, 1H), 4.02 (br d, J=6.4 Hz, 2H), 3.41 (br s, 1H), 2.81-2.50 (m, 2H), 2.31 (br s, 3H), 2.24 (br d, J=1.2 Hz, 2H), 1.34 (t, J=6.8 Hz, 3H).

Synthesis of Compound 240

Compound 240 was prepared by reacting Compound 235 with formaldehyde in the presence of $NaBH(OAc)_3$. Compound 240 (21.06 mg, 42.11 μmol, 52.48% yield, 97.5% purity) was obtained as a white solid. LCMS: RT=0.412 min, m/z=488.3 [M+H]+ $^1$H NMR (400 MHz, CHLOROFORM-d) δ=9.13 (s, 1H), 8.45 (br s, 1H), 8.28 (s, 1H), 8.17 (br s, 1H), 7.41-7.34 (m, 2H), 7.34-7.28 (m, 2H), 7.07-7.01 (m, 1H), 6.97 (s, 1H), 6.94 (br d, J=7.3 Hz, 1H), 5.13 (br s, 2H), 4.81 (br t, J=8.3 Hz, 1H), 4.06 (q, J=6.9 Hz, 2H), 3.10-2.87 (m, 1H), 2.53 (br s, 2H), 2.42-2.31 (m, 2H), 2.26 (br s, 6H), 1.38 (t, J=6.9 Hz, 3H).

Synthesis of Compound 236

Compound 236 was prepared in a similar manner to Compound 234 starting with a different diastereomer of compound 2A. Compound 236 (22.42 mg, 45.07 μmol, 32.47% yield, 98.5% purity) was obtained as a white solid. LCMS: RT=0.425 min, m/z=490.2 [M+H]+ $^1$H NMR (400 MHz, CHLOROFORM-d) δ=12.14 (br s, 1H), 9.12 (s, 1H), 8.45 (s, 1H), 8.26 (s, 1H), 7.56 (s, 1H), 7.46-7.42 (m, 1H), 7.38-7.34 (m, 1H), 7.33 (s, 1H), 7.31 (s, 1H), 6.99-6.92 (m, 2H), 5.13 (br s, 2H), 4.72 (t, J=8.4 Hz, 1H), 4.06 (q, J=6.8 Hz, 2H), 3.24 (br t, J=7.6 Hz, 1H), 2.54-2.43 (m, 2H), 2.26 (s, 3H), 1.96-1.87 (m, 2H), 1.37 (t, J=6.8 Hz, 3H).

Synthesis of Compound 242

Compound 242 was prepared by reacting Compound 236 with formaldehyde in the presence of $NaBH(OAc)_3$. Compound 242 was obtained as a white solid. LCMS: RT=0.412 min, m/z=488.3 [M+H]+ $^1$H NMR (400 MHz, CHLOROFORM-d) δ=12.30-12.04 (m, 1H), 9.12 (s, 1H), 8.47 (s, 1H), 8.27 (s, 1H), 7.55 (s, 1H), 7.46-7.41 (m, 1H), 7.37-7.30 (m, 3H), 6.97-6.90 (m, 2H), 5.15 (br s, 2H), 4.66 (quin, J=8.4 Hz, 1H), 4.05 (q, J=7.2 Hz, 2H), 2.70 (dt, J=3.6, 7.6 Hz, 1H), 2.50-2.40 (m, 2H), 2.15-2.08 (m, 2H), 2.06 (s, 6H), 1.37 (t, J=6.8 Hz, 3H).

Synthesis of Compound 237

Compound 237 was prepared in a similar manner to Compound 234 starting with a different diastereomer of compound 2A. Compound 237 (45.17 mg, 98.16 μmol, 70.71% yield, 99% purity) was obtained as a white solid. LCMS: RT=0.400 min, m/z=456.3 [M+H]+ $^1$H NMR (400 MHz, CHLOROFORM-d) δ=9.07 (br s, 1H), 8.45-8.30 (m, 1H), 8.30-8.12 (m, 2H), 7.52 (br d, J=7.2 Hz, 2H), 7.41-7.35 (m, 2H), 7.34-7.29 (m, 2H), 6.98 (s, 1H), 6.94 (br d, J=6.4 Hz, 1H), 5.07 (br s, 2H), 4.91 (br s, 1H), 3.99 (br d, J=5.2 Hz, 2H), 3.45 (br s, 1H), 2.85-2.52 (m, 2H), 2.32 (br s, 5H), 1.31 (br t, J=6.8 Hz, 3H).

Synthesis of Compound 243

Compound 243 was prepared by reacting Compound 237 with formaldehyde in the presence of $NaBH(OAc)_3$. Compound 243 (44.59 mg, 94.01 μmol, 13.84% yield, 99% purity) was obtained as a white solid. LCMS: RT=0.397 min, m/z=470.2 [M+H]+ $^1$H NMR (400 MHz, CHLOROFORM-d) δ=12.21 (br s, 1H), 9.12 (s, 1H), 8.47 (s, 1H), 8.26 (s, 1H), 7.56 (d, J=7.2 Hz, 2H), 7.46-7.39 (m, 2H), 7.38-7.31 (m, 2H), 6.97-6.90 (m, 2H), 5.15 (br s, 2H), 4.68 (quin, J=8.4, Hz, 1H), 4.04 (q, J=7.2 Hz, 2H), 2.70 (dt, J=3.6, 7.6 Hz, 1H), 2.51-2.38 (m, 2H), 2.16-2.08 (m, 2H), 2.06 (s, 6H), 1.36 (t, J=6.8 Hz, 3H).

Synthesis of Compound 238

Compound 238 was prepared in a similar manner to Compound 234. Compound 238 (24.59 mg, 45.17 μmol, 27.11% yield, 90% purity) was obtained as a yellow gum. LCMS: RT=0.434 min, m/z=490.2 [M+H]+ $^1$H NMR (400 MHz, CHLOROFORM-d) δ=12.13 (s, 1H), 9.12 (s, 1H), 8.50 (s, 1H), 8.27 (s, 1H), 7.57 (s, 1H), 7.47-7.43 (m, 1H), 7.40-7.32 (m, 4H), 7.01-6.94 (m, 2H), 5.16 (br s, 2H), 4.07 (q, J=6.8 Hz, 3H), 2.84-2.73 (m, 1H), 2.38-2.30 (m, 5H), 2.14-2.01 (m, 2H), 1.39 (t, J=6.8 Hz, 3H).

Synthesis of Compound 239

Compound 239 was prepared in a similar manner to Compound 234. Compound 239 (24.59 mg, 45.17 μmol, 27.11% yield, 90% purity) was obtained as an off-white gum. LCMS: RT=0.417 min, m/z=456.3 [M+H]+ $^1$H NMR (400 MHz, CHLOROFORM-d) δ=12.30-11.98 (m, 1H), 9.12 (s, 1H), 8.49 (s, 1H), 8.27 (s, 1H), 7.57 (d, J=7.8 Hz, 2H), 7.48-7.40 (m, 2H), 7.39-7.34 (m, 2H), 7.00-6.95 (m, 2H), 5.15 (br s, 2H), 4.15-3.98 (m, 3H), 2.77 (br t, J=7.1 Hz, 1H), 2.34 (s, 5H), 2.11-1.99 (m, 2H), 1.38 (t, J=6.9 Hz, 3H).

Synthesis of Compound 245

Compound 245 was prepared by reacting Compound 239 with formaldehyde in the presence of $NaBH(OAc)_3$. Compound 244 (30.22 mg, 63.71 μmol, 43.32% yield, 99% purity) was obtained as a white solid. LCMS: RT=0.405 min, m/z=470.3 [M+H]+ $^1$H NMR (400 MHz, CHLOROFORM-d) δ=12.22 (br d, J=3.0 Hz, 1H), 9.10 (s, 1H), 8.52 (s, 1H), 8.25 (s, 1H), 7.56 (d, J=7.3 Hz, 2H), 7.45-7.39 (m, 2H), 7.38-7.32 (m, 2H), 6.98-6.93 (m, 2H), 5.14 (br s, 2H), 4.05 (q, J=6.9 Hz, 3H), 2.25-2.17 (m, 5H), 2.11 (s, 6H), 1.36 (t, J=6.9 Hz, 3H).

Synthesis of Compound 248

Compound 248 was prepared following the protocol above for Compound 234 starting with a tert-butyl (((1s, 3s)-3-aminocyclobutyl)methyl)carbamate instead of 2A followed by deprotection with TFA. Compound 248 (7.02 mg, 14.68 μmol, 2.52% yield, 99% purity) was obtained as a white solid. LCMS: RT=0.420 min, m/z=474.2 (M+H+) $^1$H NMR (400 MHz, CHLOROFORM-d) δ=8.96-8.80 (m, 1H), 8.71-8.55 (m, 1H), 8.51-8.40 (m, 1H), 7.93 (br s, 1H), 7.40-7.31 (m, 4H), 7.08-6.99 (m, 3H), 5.29-5.17 (m, 2H), 4.45-4.27 (m, 1H), 4.08 (br d, J=6.4 Hz, 2H), 3.11-2.95 (m, 2H), 2.46-2.29 (m, 2H), 2.25-2.10 (m, 3H), 1.42-1.35 (m, 3H).

Synthesis of Compound 249

Compound 249 was prepared by reacting Compound 248 with formaldehyde in the presence of $NaBH(OAc)_3$. Compound 249 (17.72 mg, 34.27 μmol, 10.82% yield, 97% purity) was obtained as a white solid. LCMS: RT=0.427 min, m/z=502.2 (M+H+) $^1$H NMR (400 MHz, CHLOROFORM-d) δ=12.21-11.96 (m, 1H), 9.12 (s, 1H), 8.44 (s, 1H), 8.26 (s, 1H), 7.40-7.31 (m, 4H), 7.05 (br t, J=88 Hz, 1H), 6.98-6.92 (m, 2H), 5.23-5.04 (m, 2H), 4.32-4.18 (m, 1H), 4.10-4.03 (m, 2H), 2.48-2.34 (m, 2H), 2.33-2.20 (m, 6H), 2.19-2.12 (m, 2H), 2.02 (br d, J=6.4 Hz, 3H), 1.38 (dt, J=2.0, 6.8 Hz, 3H).

Synthesis of Compound 250

Compound 250 was prepared following the protocol above for Compound 234 starting with a tert-butyl ((1s,3s)-3-aminocyclobutyl)carbamate instead of 2A followed by deprotection with TFA. Compound 250 (17.33 mg, 37.80 μmol, 43.40% yield) was obtained as a white solid. LCMS: RT=0.485 min, m/z=459.2 [M+H]+ $^1$H NMR (400 MHz, CHLOROFORM-d) δ=8.49 (br s, 1H), 8.01 (br s, 1H), 7.70 (br d, J=7.6 Hz, 1H), 7.44 (br d, J=3.2 Hz, 1H), 7.40-7.28 (m, 4H), 7.15 (br t, J=7.6 Hz, 1H), 7.04 (br t, J=7.2 Hz, 1H), 7.00-6.92 (m, 2H), 5.26-5.09 (m, 2H), 4.04 (br d, J=1.6 Hz, 3H), 3.27-2.91 (m, 1H), 2.46-2.30 (m, 2H), 2.29-2.10 (m, 2H), 1.36 (br s, 3H)

Synthesis of Compound 251

Compound 251 was prepared by reacting Compound 250 with formaldehyde in the presence of $NaBH(OAc)_3$. Compound 251 (54 mg, 110.98 μmol, 22.12% yield) was obtained as a white solid. LCMS: RT=0.497 min, m/z=487.3 [M+H]+ $^1$H NMR (400 MHz, CHLOROFORM-d) δ=8.38 (s, 1H), 8.24 (s, 1H), 7.82-7.77 (m, 1H), 7.64-7.39 (m, 4H), 7.26 (br s, 5H), 5.21-4.97 (m, 2H), 4.39-4.13 (m, 2H), 2.36 (br s, 3H), 2.22-1.81 (m, 9H), 1.46-1.13 (m, 3H).

Synthesis of Compound 252

Compound 252 was prepared in a similar manner to Compound 234. Compound 252 (65.97 mg, 126.83 μmol, 22.29% yield, 99.7% purity) was obtained as a white solid. LCMS: RT=0.501 min, m/z=473.3 [M+H]+. $^1$H NMR (400 MHz, CHLOROFORM-d) δ=8.63 (br s, 1H), 8.04 (s, 1H), 7.69 (d, J=8.1 Hz, 1H), 7.56-7.39 (m, 1H), 7.39-7.27 (m, 4H), 7.15 (t, J=7.5 Hz, 1H), 7.07-6.99 (m, 3H), 5.22 (br s, 2H), 4.50-4.14 (m, 1H), 4.13-3.59 (m, 2H), 3.10-2.81 (m, 1H), 2.60-2.40 (m, 2H), 2.36 (br s, 5H), 1.46-1.22 (m, 3H).

Synthesis of Compound 253

Compound 253 was prepared in a similar manner to Compound 251. Compound 253 (10.2 mg, 18.88 μmol, 59.91% yield, 93.3% purity) was obtained as a white solid. LCMS: RT=0.443 min, m/z=504.2 [M+H]+ $^1$H NMR (400 MHz, CHLOROFORM-d) δ=12.47-11.89 (m, 1H), 9.10 (s, 1H), 8.52 (s, 1H), 8.25 (s, 1H), 7.56 (s, 1H), 7.44 (td, J=1.8, 6.8 Hz, 1H), 7.37-7.30 (m, 3H), 6.97-6.92 (m, 2H), 5.13 (br s, 2H), 4.13-3.96 (m, 3H), 2.20 (br d, J=8.1 Hz, 5H), 2.11 (s, 6H), 1.37 (t, J=6.9 Hz, 3H).

Synthesis of Compound 265

Compound 265 was prepared in a similar manner to Compound 251. Compound 265 (78.16 mg, 158.09 μmol, 23.88% yield, 97% purity) was obtained as a white solid. LCMS: RT=0.460 min, m/z=480.2 [M+H]+. $^1$H NMR (400 MHz, CHLOROFORM-d) δ=8.64 (s, 1H), 8.06 (s, 1H), 7.84 (br s, 1H), 7.75 (br d, J=0.9 Hz, 1H), 7.70 (d, J=8.1 Hz, 1H), 7.63 (br d, J=7.6 Hz, 1H), 7.56-7.41 (m, 2H), 7.29 (br d, J=5.4 Hz, 1H), 7.15 (t, J=7.6 Hz, 1H), 7.04 (s, 2H), 5.20 (br s, 2H), 4.36-3.69 (m, 3H), 3.09-2.88 (m, 1H), 2.55-2.40 (m, 2H), 2.35 (br s, 5H), 1.39-1.24 (m, 3H).

Synthesis of Compound 266

Compound 266 was prepared in a similar manner to Compound 251. Compound 266 (41.16 mg, 80.34 μmol, 19.20% yield, 94.98% purity) was obtained as a brown gum. LCMS: RT=0.526 min, m/z=487.2 [M+H]+ $^1$H NMR (400 MHz, CHLOROFORM-d) δ=8.64 (br s, 1H), 8.08 (s, 1H), 7.37 (br d, J=6.0 Hz, 2H), 7.34-7.29 (m, 3H), 7.07-7.03 (m, 1H), 7.01 (br s, 2H), 6.91 (br d, J=7.2 Hz, 1H), 5.16 (br s, 2H), 4.18-3.91 (m, 3H), 3.01-2.83 (m, 1H), 2.61 (s, 3H), 2.43-2.38 (m, 3H), 2.36 (br s, 4H), 1.34 (br d, J=6.0 Hz, 3H).

Synthesis of Compound 277

Compound 277 was prepared in a similar manner to Compound 234. Compound 277 (20.48 mg, 37.75 μmol, 23.10% yield, 92.9% purity) was obtained as a yellow solid. LCMS: RT=0.433 min, m/z=504.2 [M+H]+. $^1$H NMR (400 MHz, CHLOROFORM-d) δ=12.57-11.61 (m, 1H), 8.33 (s, 1H), 8.22 (s, 1H), 7.56 (s, 1H), 7.45-7.41 (m, 1H), 7.37-7.31 (m, 3H), 6.97-6.90 (m, 2H), 5.09 (br s, 2H), 4.11-3.99 (m, 3H), 2.85 (s, 3H), 2.74 (br t, J=7.2 Hz, 1H), 2.32 (s, 5H), 2.10-1.99 (m, 2H), 1.37 (t, J=6.9 Hz, 3H).

Synthesis of Compound 278

Compound 278 was prepared in a similar manner to Compound 234. Compound 278 (62.83 mg, 121.65 μmol, 39.70% yield, 94.4% purity) was obtained as a white solid. LCMS: RT=0.412 min, m/z=488.2 [M+H]+. $^1$H NMR (400 MHz, CHLOROFORM-d) δ=12.47-11.72 (m, 1H), 8.32 (s, 1H), 8.21 (s, 1H), 7.40-7.28 (m, 4H), 7.08-7.01 (m, 1H), 6.97-6.91 (m, 2H), 5.08 (br s, 2H), 4.11-3.99 (m, 3H), 2.85 (s, 3H), 2.73 (s, 1H), 2.36-2.27 (m, 5H), 2.03 (td, J=9.2, 11.3 Hz, 2H), 1.37 (t, J=6.8 Hz, 3H).

Synthesis of Compound 267

Compound 267 was prepared following the procedures of GP2, GP3, and GP5 with (R)-2-methyl-N—((S)-(1-((2-(trimethylsilyl)ethoxy)methyl)-1H-pyrazolo[4,3-c]pyridin-7-yl)(1-trityl-1H-imidazol-4-yl)methyl)propane-2-sulfinamide as starting material and MsOH/$NH_2OH$—HCl are reagents in GP3. Compound 267 was obtained as a white solid (45 mg, 94.71 μmol, 3.86% yield, 99.02% purity). LCMS: RT=0.420 min, m/z=471.2 [M+H]+ $^1$H NMR (400 MHz, CHLOROFORM-d) δ=13.07-12.82 (m, 1H), 9.76-9.56 (m, 1H), 9.13 (s, 1H), 8.77-8.54 (m, 1H), 8.26 (s, 1H), 7.83 (s, 1H), 7.61-7.40 (m, 1H), 7.39-7.33 (m, 1H), 7.33 (br s, 3H), 7.07-6.98 (m, 3H), 4.12-3.95 (m, 2H), 3.19-2.99 (m, 3H), 1.35 (t, 3H).

Synthesis of Compound 284

Compound 284 was prepared in a similar manner to Compound 250. Compound 284 (9.02 mg, 18.31 μmol, 21.95% yield, 99.24% purity) was obtained as a yellow solid. LCMS: RT=0.526 min, m/z=487.2 [M+H]+ $^1$H NMR (400 MHz, CHLOROFORM-d) δ=8.54-8.45 (m, 1H), 8.02 (br s, 1H), 7.55 (br s, 1H), 7.41 (br s, 1H), 7.37-7.29 (m, 4H), 7.01-6.94 (m, 2H), 6.91 (br d, J=7.2 Hz, 1H), 5.19-5.06 (m, 2H), 4.15-3.89 (m, 3H), 3.21-2.98 (m, 1H), 2.60 (s, 3H), 2.43-2.19 (m, 4H), 1.35 (br s, 3H)

Synthesis of Compound 285

Compound 285 was prepared by reacting Compound 284 with formaldehyde in the presence of $NaBH(OAc)_3$. Compound 285 (63.32 mg, 122.46 μmol, 66.54% yield) was obtained as a yellow gum. LCMS: RT=0.522 min, m/z=517.1 [M+H]+ $^1$H NMR (400 MHz, CHLOROFORM-d) δ=8.06 (s, 1H), 7.51 (br s, 1H), 7.39 (br s, 2H), 7.32-7.27 (m, 3H), 7.08-6.97 (m, 2H), 6.92 (br d, J=7.2 Hz, 1H), 5.16 (br s, 2H), 4.24-3.58 (m, 2H), 2.74-2.56 (m, 8H), 2.51 (br s, 6H), 1.43-1.22 (m, 3H).

Synthesis of Compound 286

Compound 286 was prepared in a similar manner to Compound 234. Compound 286 (4.23 mg, 8.41 μmol, 15.42% yield) was obtained as a yellow solid. LCMS:

RT=0.515 min, m/z=503.1 [M+H]+ $^1$H NMR (400 MHz, CHLOROFORM-d) δ=12.05-11.68 (m, 1H), 8.12 (s, 1H), 7.56 (s, 1H), 7.45-7.41 (m, 1H), 7.37-7.28 (m, 5H), 6.96-6.92 (m, 2H), 6.90 (d, J=7.2 Hz, 1H), 5.11 (br s, 2H), 4.09-3.97 (m, 3H), 2.73-2.67 (m, 1H), 2.64 (s, 3H), 2.30 (s, 3H), 2.28 (br s, 1H), 2.03-1.95 (m, 2H), 1.36 (br t, J=6.8 Hz, 3H).

Synthesis of Compound 287

Compound 287 was prepared in a similar manner to Compound 250. Compound 287 (19.77 mg, 40.46 μmol, 14.29% yield, 97.4% purity) was obtained as an off-white solid. LCMS: RT=0.406 min, m/z=476.1 [M+H]+ $^1$H NMR (400 MHz, CHLOROFORM-d) δ=9.08 (br s, 1H), 8.66-8.33 (m, 1H), 8.24 (s, 1H), 7.56 (s, 1H), 7.46-7.41 (m, 1H), 7.37-7.29 (m, 3H), 7.10-6.89 (m, 2H), 5.26-4.90 (m, 2H), 4.16-3.68 (m, 4H), 2.22-2.05 (m, 1H), 1.82-1.69 (m, 2H), 1.35 (br t, J=6.8 Hz, 3H), 1.27-1.13 (m, 1H).

Synthesis of Compound 288

Compound 288 was prepared by reacting Compound 287 with formaldehyde in the presence of $NaBH(OAc)_3$. Compound 288 (22.09 mg, 42.91 μmol, 14.59% yield, 97.9% purity) was obtained as a white solid. LCMS: RT=0.423 min, m/z=504.3 [M+H]+ $^1$H NMR (400 MHz, CHLOROFORM-d) δ=12.72-12.30 (m, 1H), 9.05 (br s, 1H), 8.61-8.28 (m, 1H), 8.19 (s, 1H), 7.49 (s, 1H), 7.36 (br d, J=6.4 Hz, 1H), 7.33-7.27 (m, 2H), 7.22 (s, 1H), 6.91 (br s, 2H), 5.23 (br d, J=8.4 Hz, 1H), 4.87 (br d, J=14.8 Hz, 1H), 4.28 (br d, J=1.2 Hz, 1H), 4.13-3.83 (m, 2H), 3.24 (br d, J=1.6 Hz, 1H), 1.98-1.70 (m, 9H), 1.29 (br s, 4H).

Synthesis of Compound 289

Compound 289 was prepared in a similar manner to Compound 250. Compound 289 (42.13 mg, 89.49 μmol, 12.47% yield, 99.1% purity) was obtained as a white solid. LCMS: RT=0.409 min, m/z=467.2 [M+H]+ $^1$H NMR (400 MHz, CHLOROFORM-d) δ=9.11 (s, 1H), 8.46 (s, 1H), 8.26 (s, 1H), 7.86 (d, J=0.8 Hz, 1H), 7.77 (dd, J=1.0, 7.9 Hz, 1H), 7.63 (dd, J=1.0, 7.8 Hz, 1H), 7.53 (d, J=7.9 Hz, 1H), 7.31 (d, J=7.5 Hz, 1H), 7.03-6.91 (m, 2H), 5.12 (br s, 2H), 4.12-4.03 (m, 2H), 3.92 (br s, 1H), 2.98 (br t, J=7.6 Hz, 1H), 2.35 (br d, J=6.4 Hz, 2H), 2.04-1.94 (m, 2H), 1.36 (t, J=6.8 Hz, 3H)

Synthesis of Compound 290

Compound 290 was prepared by reacting Compound 289 with formaldehyde in the presence of $NaBH(OAc)_3$. Compound 290 (108.52 mg, 218.76 μmol, 51.03% yield, 99.7% purity) was obtained as a white solid. LCMS: RT=0.413 min, m/z=495.2 [M+H]+ $^1$H NMR (400 MHz, CHLOROFORM-d) δ=12.16 (br d, J=1.5 Hz, 1H), 9.11 (s, 1H), 8.52 (s, 1H), 8.25 (s, 1H), 7.87 (s, 1H), 7.82-7.74 (m, 1H), 7.68-7.60 (m, 1H), 7.57-7.49 (m, 1H), 7.32 (d, J=8.1 Hz, 1H), 7.03-6.92 (m, 2H), 5.14 (br s, 2H), 4.15-3.95 (m, 3H), 2.28-2.14 (m, 5H), 2.11 (s, 6H), 1.37 (t, J=6.9 Hz, 3H).

Synthesis of Compound 291

Compound 291 was prepared in a similar manner to Compound 234. Compound 291 (32.05 mg, 66.03 μmol, 31.29% yield, 99% purity) was obtained as a white solid. LCMS: RT=0.409 min, m/z=481.2 [M+H]+ $^1$H NMR (400 MHz, CHLOROFORM-d) δ=9.11 (s, 1H), 8.48 (s, 1H), 8.26 (s, 1H), 7.87 (s, 1H), 7.78 (br d, J=8.0 Hz, 1H), 7.64 (br d, J=7.6 Hz, 1H), 7.56-7.49 (m, 1H), 7.32 (d, J=8.0 Hz, 1H), 7.01-6.94 (m, 2H), 5.14 (br s, 2H), 4.11-3.99 (m, 3H), 2.75 (br t, J=7.2 Hz, 1H), 2.32 (s, 5H), 2.09-1.98 (m, 2H), 1.37 (t, J=6.8 Hz, 3H).

Synthesis of Compound 292

Compound 292 was prepared in a similar manner to Compound 250. Compound 292 (32.32 mg, 65.26 μmol, 12.76% yield, 94% purity) was obtained as a white solid. LCMS: RT=0.485 min, m/z=466.3 [M+H]+ $^1$H NMR (400 MHz, CHLOROFORM-d) δ=8.10 (s, 1H), 7.85 (s, 1H), 7.79-7.71 (m, 2H), 7.62 (d, J=7.7 Hz, 1H), 7.55-7.47 (m, 1H), 7.38 (br d, J=6.8 Hz, 1H), 7.29 (br s, 1H), 7.14 (t, J=7.5 Hz, 1H), 7.01-6.92 (m, 2H), 5.15 (br s, 2H), 4.03 (br s, 2H), 3.94-3.79 (m, 1H), 2.95 (br s, 1H), 2.30 (br s, 2H), 2.05-1.92 (m, 2H), 1.34 (br t, J=6.1 Hz, 3H)

Synthesis of Compound 293

Compound 293 was prepared by reacting Compound 292 with formaldehyde in the presence of $NaBH(OAc)_3$. Compound 293 (44.03 mg, 82.96 μmol, 9.66% yield, 93% purity) was obtained as a white solid. LCMS: RT=0.455 min, m/z=494.3 [M+H]+ $^1$H NMR (400 MHz, CHLOROFORM-d) δ=8.09 (s, 1H), 7.82 (br s, 1H), 7.72 (br d, J=8.1 Hz, 2H), 7.61 (br d, J=7.6 Hz, 1H), 7.53-7.47 (m, 1H), 7.35-7.27 (m, 2H), 7.18 (t, J=7.6 Hz, 1H), 7.12-6.96 (m, 2H), 5.25 (br s, 2H), 4.16-3.66 (m, 2H), 2.92-2.15 (m, 12H), 1.39-1.18 (m, 3H).

Synthesis of Compound 294

Compound 294 was prepared in a similar manner to Compound 250. Compound 294 (32.37 mg, 69.39 μmol, 15.96% yield, 98.5% purity) was obtained as a white solid. LCMS: RT=0.392 min, m/z=460.1 [M+H]+ $^1$H NMR (400 MHz, CHLOROFORM-d) δ=13.39-12.31 (m, 1H), 9.03 (br s, 1H), 8.43 (br s, 1H), 8.19 (s, 1H), 7.36-7.30 (m, 1H), 7.29 (br s, 1H), 7.25 (br d, J=7.2 Hz, 2H), 7.06-6.88 (m, 3H), 5.08 (br s, 1H), 4.92 (br d, J=14.8 Hz, 1H), 3.98 (br s, 3H), 3.69 (q, J=8.4 Hz, 1H), 2.07 (br s, 1H), 1.75-1.65 (m, 2H), 1.30 (br t, J=6.4 Hz, 3H), 1.19 (br d, J=17.6 Hz, 1H).

Synthesis of Compound 295

Compound 295 was prepared in a similar manner to Compound 250. Compound 295 (15.26 mg, 31.42 μmol, 7.93% yield, 98% purity) was obtained as a white solid. LCMS: RT=0.431 min, m/z=476.2 [M+H]+ $^1$H NMR (400 MHz, CHLOROFORM-d) δ=9.53 (s, 1H), 8.86 (br s, 1H), 8.33 (br s, 1H), 7.47 (s, 1H), 7.38-7.26 (m, 5H), 7.18 (d, J=7.8 Hz, 1H), 5.49-5.19 (m, 2H), 4.84-4.79 (m, 1H), 4.29-4.15 (m, 1H), 4.13-3.97 (m, 2H), 2.96 (quin, J=10.6 Hz, 1H), 2.43-2.29 (m, 1H), 2.19 (br d, J=8.1 Hz, 1H), 2.09-1.97 (m, 1H), 1.31 (t, J=7.0 Hz, 3H).

Synthesis of Compound 301

Compound 301 was prepared in a similar manner to Compound 250. Compound 301 (10.14 mg, 30.88 μmol, 14.54% yield, 98% purity) was obtained as a white solid. LCMS: RT=0.424 min, m/z=476.2 [M+H]+ $^1$H NMR (400 MHz, CHLOROFORM-d) δ=12.30-11.90 (m, 1H), 9.11 (s, 1H), 8.47 (s, 1H), 8.26 (s, 1H), 7.55 (s, 1H), 7.45-7.41 (m, 1H), 7.36-7.30 (m, 3H), 6.97-6.91 (m, 2H), 5.13 (br s, 2H), 4.05 (q, J=6.9 Hz, 2H), 3.98-3.88 (m, 1H), 3.04-2.92 (m, 1H), 2.41-2.29 (m, 2H), 2.05-1.93 (m, 2H), 1.37 (t, J=6.8 Hz, 3H).

Synthesis of Compound 302

Compound 302 was prepared in a similar manner to Compound 240 using Compound 301 as starting material. Compound 302 (25.75 mg, 48.31 μmol, 11.84% yield, 97.2% purity) was obtained as a white solid. LCMS: RT=0.446 min, m/z=518.3 [M+H]+ $^1$H NMR (400 MHz, CHLOROFORM-d) δ=12.49-11.80 (m, 1H), 8.39 (s, 1H), 8.21 (s, 1H), 7.56 (s, 1H), 7.46-7.40 (m, 1H), 7.38-7.30 (m, 3H), 6.98-6.90 (m, 2H), 5.12 (br s, 2H), 4.05 (q, J=7.0 Hz, 3H), 2.85 (s, 3H), 2.35-2.19 (m, 5H), 2.15 (br s, 6H), 1.37 (t, J=6.9 Hz, 3H).

Synthesis of Compound 303

Compound 303 was prepared in a similar manner to Compound 250. Compound 303 (15.59 mg, 31.87 μmol, 4.08% yield, 96.8% purity) was obtained as a white solid. LCMS: RT=0.417 min, m/z=474.3 [M+H]+ $^1$H NMR (400 MHz, CHLOROFORM-d) δ=12.25-11.90 (m, 1H), 8.31 (s, 1H), 8.22 (s, 1H), 7.40-7.32 (m, 2H), 7.32-7.27 (m, 2H), 7.08-7.01 (m, 1H), 6.96-6.90 (m, 2H), 5.08 (br s, 2H), 4.05 (q, J=6.9 Hz, 2H), 3.96-3.86 (m, 1H), 3.02-2.90 (m, 1H), 2.86 (s, 3H), 2.40-2.28 (m, 2H), 2.02-1.92 (m, 2H), 1.37 (t, J=7.0 Hz, 3H).

Synthesis of Compound 304

Compound 304 was prepared in a similar manner to Compound 240 using Compound 303 as starting material. Compound 304 (108.54 mg, 213.79 μmol, 33.75% yield, 98.8% purity) was obtained as a white solid. LCMS: RT=0.413 min, m/z=502.3 [M+H]+ $^1$H NMR (400 MHz, CHLOROFORM-d) δ=12.15 (br s, 1H), 8.37 (s, 1H), 8.21 (s, 1H), 7.41-7.33 (m, 2H), 7.33-7.28 (m, 2H), 7.08-7.01 (m, 1H), 6.97-6.91 (m, 2H), 5.09 (br s, 2H), 4.10-3.97 (m, 3H), 2.85 (s, 3H), 2.27-2.15 (m, 5H), 2.10 (s, 6H), 1.37 (t, J=6.9 Hz, 3H).

Example 2: THP-1 Cell-Based NLRP3 Activation Assay

THP-1 cells are cultured in complete media (CM) until they reach logarithmic growth and achieve a viability >90%. CM is composed of RPMI-1640 (+Glutamax)/10% fetal bovine serum/55 μM β-mercaptoethanol/pen/strep. Cells are spun down and resuspended to 1,000,000 cells/mL in CM containing either 20 nM or 500 nM PMA. 150,000 cells (150 μL) are then added to each well of a 96-well TC plate and incubated for either 24 hr or 3 hr, respectively, in a standard cell culture incubator (37° C.; 5% $CO_2$). After this incubation, the plate is tilted and media carefully removed. 200 μL of CM containing 100 ng/mL LPS is then added to the wells and the cells incubated an additional 3 hrs. The media is again removed and replaced with Opti-Mem medium containing pre-determined dilutions of test compounds in replicate wells. After a 30 min incubation, 10 μM nigericin (final concentration) in Opti-Mem medium with the corresponding concentration of compound is added to the wells for an additional 1 hr. Positive control wells contain 10 μM nigericin in Opti-Mem in the absence of test compound, while negative control wells contain Opti-Mem only. Supernatants are then transferred to a fresh 96-well plate for storage and assayed for IL-1β (human; DuoSet; R&D) and for TNFα (human; DuoSet; R&D) levels and relative pyroptosis using a CytoTox 96 Kit (do not freeze prior to testing; Promega). Once supernatants are removed, the relative viability of adherent cells in the 96-well TC plate are determined using a CellTiter-Glo® luminescent cell viability assay (Promega).

Table 4 below provides $IC_{50}$ data for the compounds disclosed herein where "A" is indicative of an $IC_{50}$ value of <100 nM, "B" is indicative of an $IC_{50}$ value between 100 nM and 500 nM, "C" is indicative of an $IC_{50}$ value between 500 nM and 1 uM, "D" is indicative of an $IC_{50}$ value between 1 uM and 15 uM, and "E" is indicative of an $IC_{50}$ value >15 uM.

TABLE 4

| No. | $IC_{50}$ |
|---|---|
| 001 | A |
| 002 | A |
| 003 | A |
| 004 | A |
| 005 | A |
| 006 | A |
| 007 | A |
| 008 | D |

TABLE 4-continued

| No. | $IC_{50}$ |
|---|---|
| 009 | A |
| 010 | D |
| 011 | D |
| 012 | B |
| 013 | A |
| 014 | A |
| 015 | A |
| 016 | E |
| 017 | A |
| 018 | A |
| 019 | A |
| 020 | B |
| 021 | B |
| 022 | A |
| 023 | A |
| 024 | A |
| 025 | A |
| 026 | A |
| 027 | A |
| 028 | E |
| 029 | A |
| 030 | E |
| 031 | E |
| 032 | B |
| 033 | A |
| 034 | E |
| 035 | A |
| 036 | A |
| 037 | A |
| 038 | A |
| 039 | D |
| 040 | A |
| 041 | A |
| 042 | A |
| 043 | B |
| 044 | B |
| 045 | A |
| 046 | A |
| 047 | B |
| 048 | A |
| 049 | A |
| 050 | D |
| 051 | A |
| 052 | E |
| 053 | A |
| 054 | E |
| 055 | A |
| 056 | A |
| 057 | B |
| 058 | A |
| 059 | D |
| 060 | E |
| 061 | E |
| 062 | A |
| 063 | A |
| 064 | A |
| 065 | A |
| 066 | A |
| 067 | A |
| 068 | A |
| 070 | A |
| 071 | A |
| 072 | A |
| 073 | A |
| 074 | A |
| 075 | A |
| 076 | A |
| 077 | A |
| 078 | A |
| 079 | A |
| 080 | A |
| 081 | A |
| 082 | A |
| 083 | A |
| 084 | A |
| 085 | A |
| 086 | A |
| 087 | A |

TABLE 4-continued

| No. | $IC_{50}$ |
|---|---|
| 088 | B |
| 089 | A |
| 090 | A |
| 091 | A |
| 092 | B |
| 093 | A |
| 094 | A |
| 095 | A |
| 096 | A |
| 097 | A |
| 098 | A |
| 099 | A |
| 100 | A |
| 101 | A |
| 102 | A |
| 103 | A |
| 104 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | B |
| 119 | A |
| 120 | A |
| 121 | A |
| 122 | C |
| 123 | C |
| 124 | — |
| 125 | A |
| 126 | A |
| 127 | A |
| 128 | A |
| 129 | C |
| 130 | A |
| 131 | A |
| 132 | D |
| 133 | A |
| 134 | D |
| 135 | A |
| 136 | A |
| 137 | A |
| 138 | A |
| 139 | A |
| 140 | A |
| 141 | A |
| 142 | D |
| 143 | A |
| 144 | A |
| 145 | D |
| 146 | B |
| 147 | A |
| 148 | A |
| 149 | A |
| 150 | D |
| 151 | A |
| 152 | C |
| 153 | A |
| 154 | A |
| 155 | A |
| 156 | A |
| 157 | A |
| 158 | D |
| 159 | A |
| 160 | A |
| 161 | A |
| 162 | A |
| 163 | A |
| 164 | A |
| 165 | A |
| 166 | A |

TABLE 4-continued

| No. | $IC_{50}$ |
|---|---|
| 167 | A |
| 168 | A |
| 169 | A |
| 170 | A |
| 171 | A |
| 172 | A |
| 173 | A |
| 174 | A |
| 175 | A |
| 176 | B |
| 177 | A |
| 178 | A |
| 179 | A |
| 180 | C |
| 181 | A |
| 182 | A |
| 183 | A |
| 184 | A |
| 185 | D |
| 186 | A |
| 187 | A |
| 188 | A |
| 189 | A |
| 190 | A |
| 192 | B |
| 193 | A |
| 194 | A |
| 195 | A |
| 196 | A |
| 197 | A |
| 198 | A |
| 199 | A |
| 200 | B |
| 201 | B |
| 202 | A |
| 203 | A |
| 204 | B |
| 205 | A |
| 206 | A |
| 207 | A |
| 208 | D |
| 209 | A |
| 210 | D |
| 211 | A |
| 212 | A |
| 213 | A |
| 214 | A |
| 215 | A |
| 216 | A |
| 217 | A |
| 218 | A |
| 219 | A |
| 220 | B |
| 221 | A |
| 222 | C |
| 223 | A |
| 224 | A |
| 225 | A |
| 226 | B |
| 227 | A |
| 228 | A |
| 229 | A |
| 230 | A |
| 231 | A |
| 232 | A |
| 233 | A |
| 234 | D |
| 235 | B |
| 236 | A |
| 237 | D |
| 238 | A |
| 239 | A |
| 240 | C |
| 241 | A |
| 242 | B |
| 243 | D |
| 244 | A |
| 245 | A |

TABLE 4-continued

| No. | $IC_{50}$ |
|---|---|
| 246 | A |
| 247 | A |
| 248 | A |
| 249 | A |
| 250 | A |
| 251 | A |
| 252 | A |
| 253 | A |
| 254 | A |
| 255 | A |
| 256 | B |
| 257 | A |
| 258 | B |
| 259 | A |
| 260 | D |
| 261 | A |
| 262 | A |
| 263 | A |
| 264 | A |
| 265 | A |
| 266 | A |
| 267 | B |
| 277 | A |
| 278 | A |
| 279 | A |
| 280 | A |
| 281 | D |
| 282 | A |
| 283 | A |
| 284 | A |
| 285 | A |
| 286 | A |
| 287 | C |
| 288 | B |
| 289 | A |
| 290 | A |
| 291 | A |
| 292 | A |
| 293 | A |
| 294 | C |
| 295 | B |
| 297 | B |
| 298 | A |
| 299 | D |
| 300 | B |

Example 3: Compound 007 NLRP3 Epitope Determination

NLRP3 belongs to the family of NOD-like receptors (NLRs), which are classified as AAA+ ATPases (ATPases associated with diverse cellular activities). AAA+ ATPases are triphosphate-nucleotide binding domains whose central β-sheet is defined by a characteristic parallel β2-β3-β4-β1-β5 topology, where the P-loop (or Walker A motif) is directly following the first β-strand (β1) and the Walker B motif is located on the third β-strand (β3) (Hochheiser and Geyer, 2023). The structure of the P-loop domain is characterized by a three-layered αβα sandwich of repeating β-loop-α units, also known as Rossmann-fold, where the β-strands are arranged in parallel orientation and surrounded by α-helices. NLRs constitute the subgroup of STAND ATPases within the AAA+ superfamily, which contain a C-terminal helical domain (HD1) followed by a winged helix domain (WHD) relative to the ATPase activity containing nucleotide-binding domain (NBD).

Compound 007 of the disclosure was used as an exemplary compound for determining the epitope to NLRP3, using cryogenic electron microscopy (cryo-EM).

Figure 2:
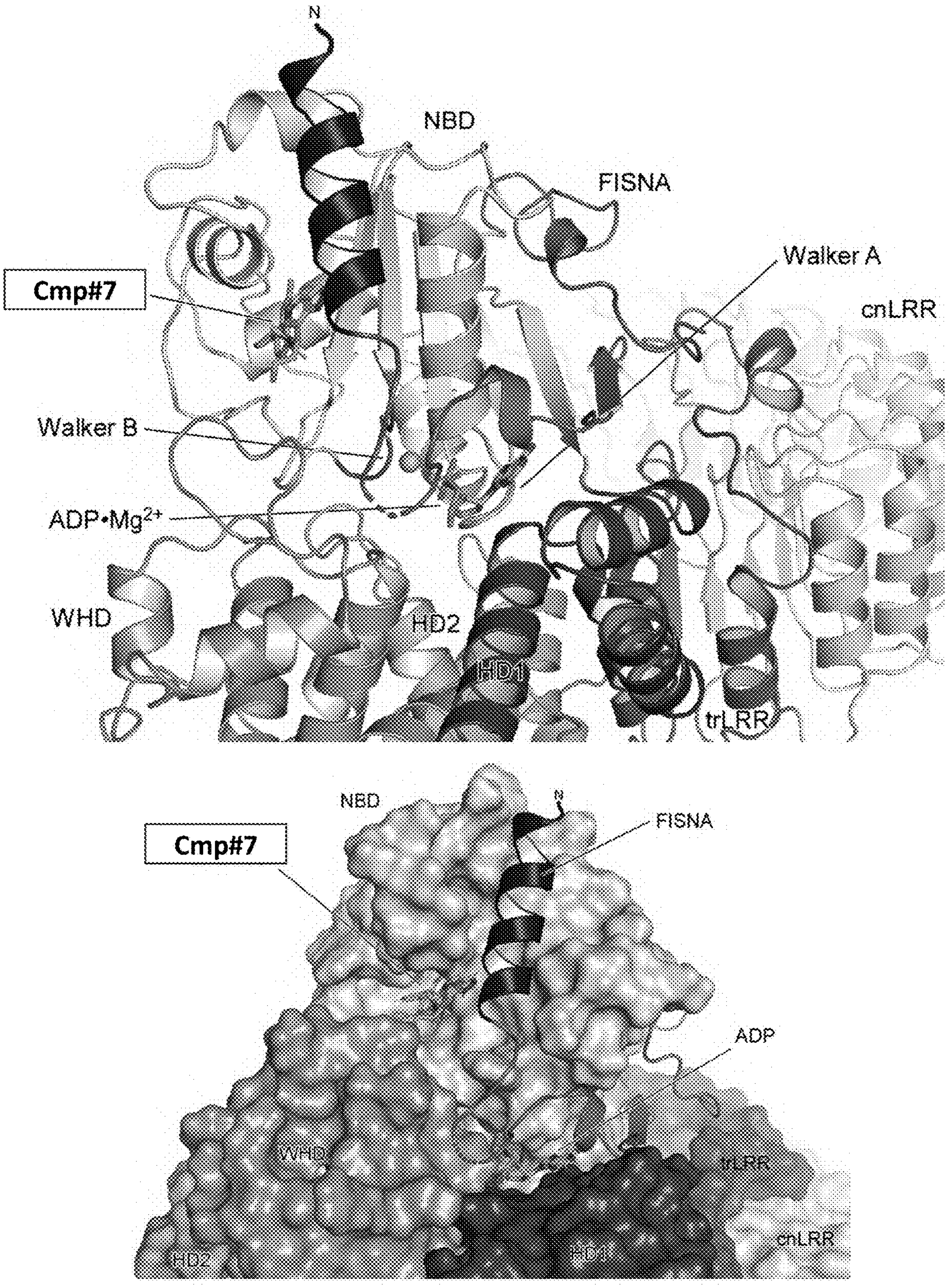
FIG. 2 depicts ribbon-structure images of Compound 007 and ADP binding on two different sites of the NLRP3 NBD.
Figure 6:
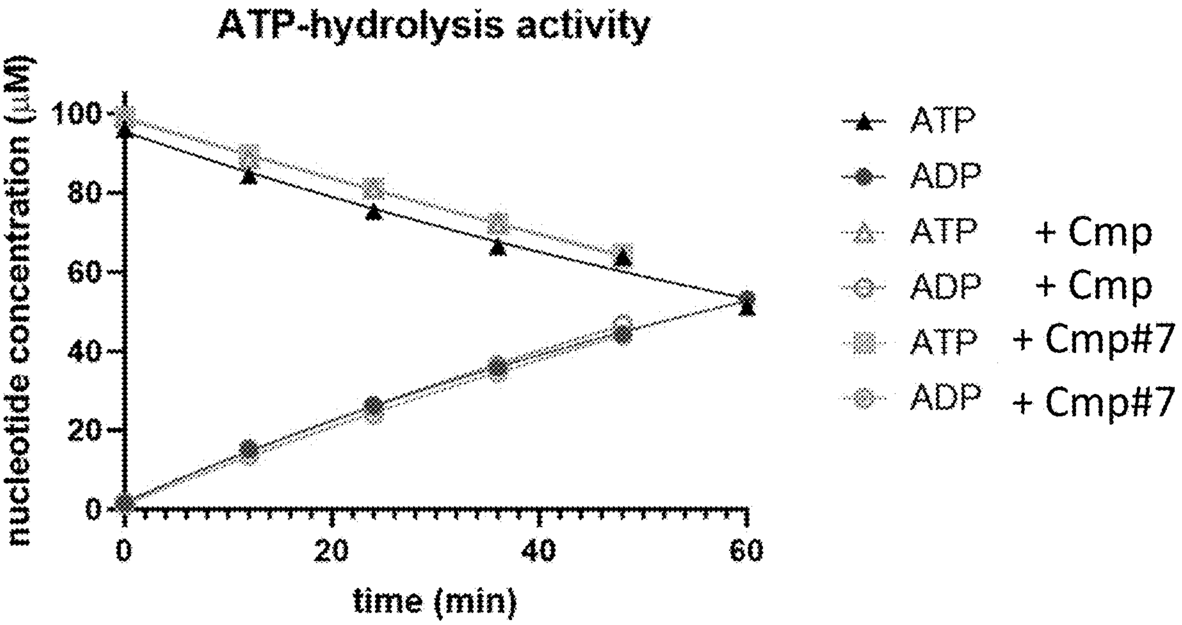
FIG. 6 depicts ATP hydrolysis over time by Compound 007 and an additional 5-azaindazole-containing compound incubated with NLRP3.

The results of the cryo-EM assay found that Compound 007 binds in a pocket on the surface of the NACHT domain of NLRP3 (FIG. 1). The specific binding site is mostly composed of residues from the nucleotide-binding domain (NBD) but opposite to the ATP-binding site from the perspective of the central β-sheet (FIG. 2). The binding site is consistent with the finding that the 5-azaindazole-containing compounds either do not inhibit, or are very weak inhibitors of the intrinsic ATP-hydrolysis activity of NLRP3 (FIG. 6).

Figure 3:
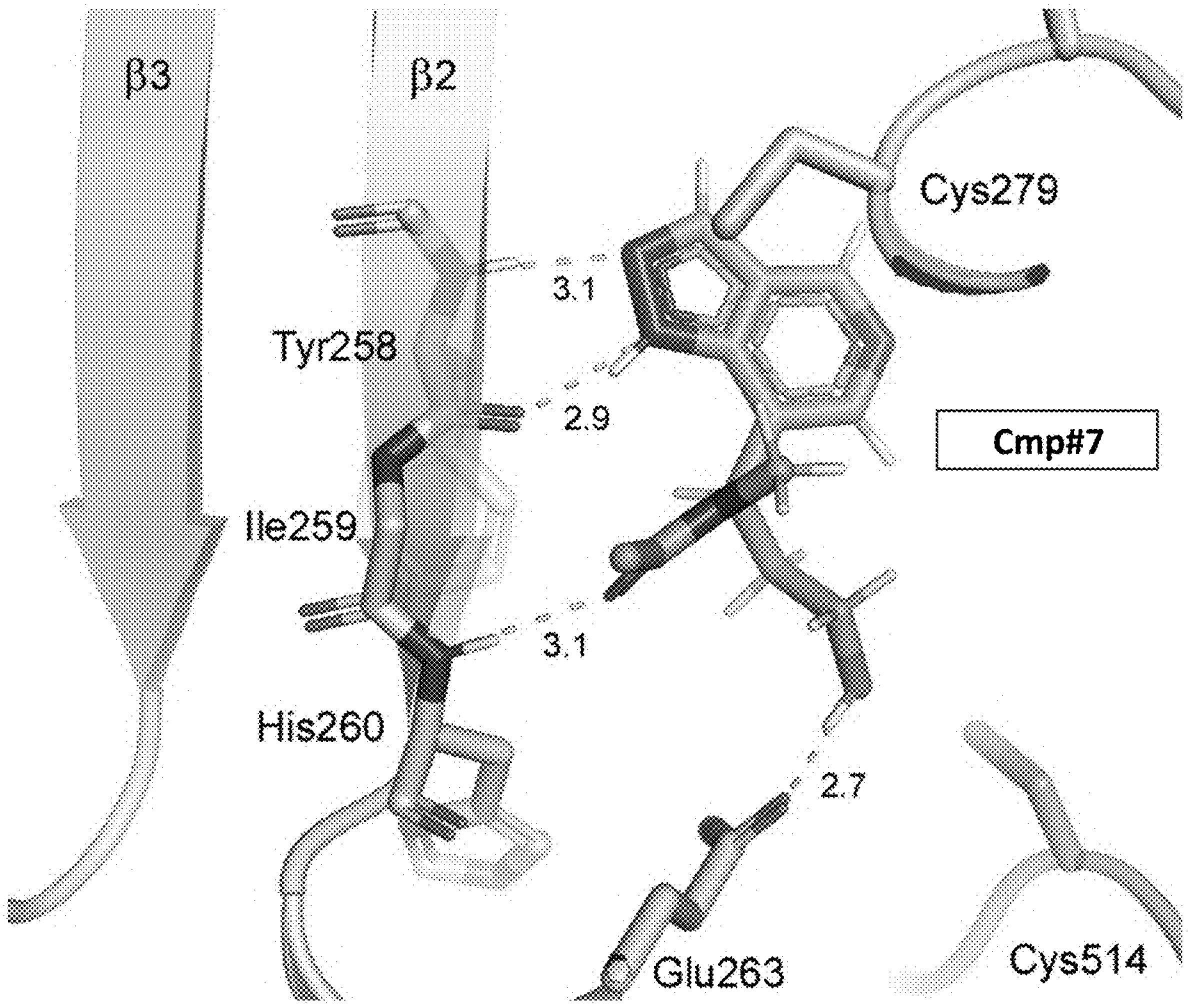
FIG. 3 depicts a ribbon-structure image of a hydrogen-bond network of Compound 007 to the β2 main chain of NLRP3.
Figure 4:
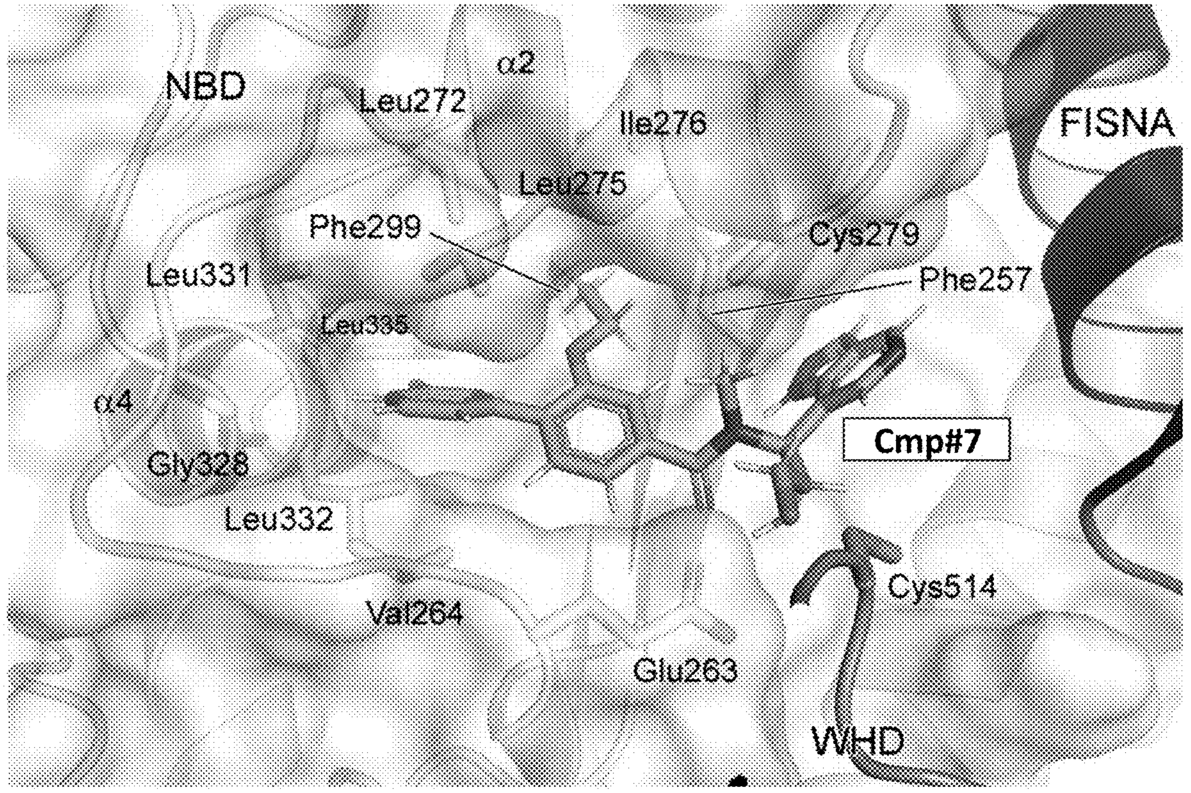
FIG. 4 depicts a ribbon-structure image of the biphenyl moiety of Compound 007 binding into a hydrophobic pocket on NLRP3.

The defining feature of the interaction between the 5-azaindazole-containing compounds (Hartman et al., Bioorg. Med. Chem. Lett. 102: 129675. 2024) and NLRP3 is the formation of three hydrogen bonds to the backbone atoms of the terminal β-strand β2 in the NBD of NLRP3 (FIG. 3). The two nitrogen atoms (N32 and N31) form two donor-acceptor pairs with the backbone NH and CO groups of Tyr258 at a distance of 3.1 and 2.9 Angstroem, respectively, in perfect geometry (FIG. 3). This specific interaction is complemented by a third hydrogen bond between the CO moiety (O23) of the central peptide bond unit to the backbone NH group of His260 at 3.1 Angstroem (FIG. 3). The following biphenyl unit binds into a hydrophobic crevice formed by helices α2 and α4 of the NBD, where it interacts with the side chains of residues Leu275, Leu272, Leu335, Leu331, Leu332, Val264, the β-methylene group of Glu263, and Gly328 in a counterclockwise listing (FIG. 4). The ethoxy moiety in the meta-position of the first benzene ring of Compound 007 reaches out into a hydrophobic crevice formed by the side chains of Phe299, Leu272, Ile276 and Phe257 of NLRP3 contributing to the specificity of the interaction. The fluorine atom of the second benzene ring is embedded between the side chains of Leu331, Leu332 and L335 of NBD helix α4. The two benzene rings of the biphenyl unit are twisted relative to each other by 45° (FIG. 4).

Figure 5:
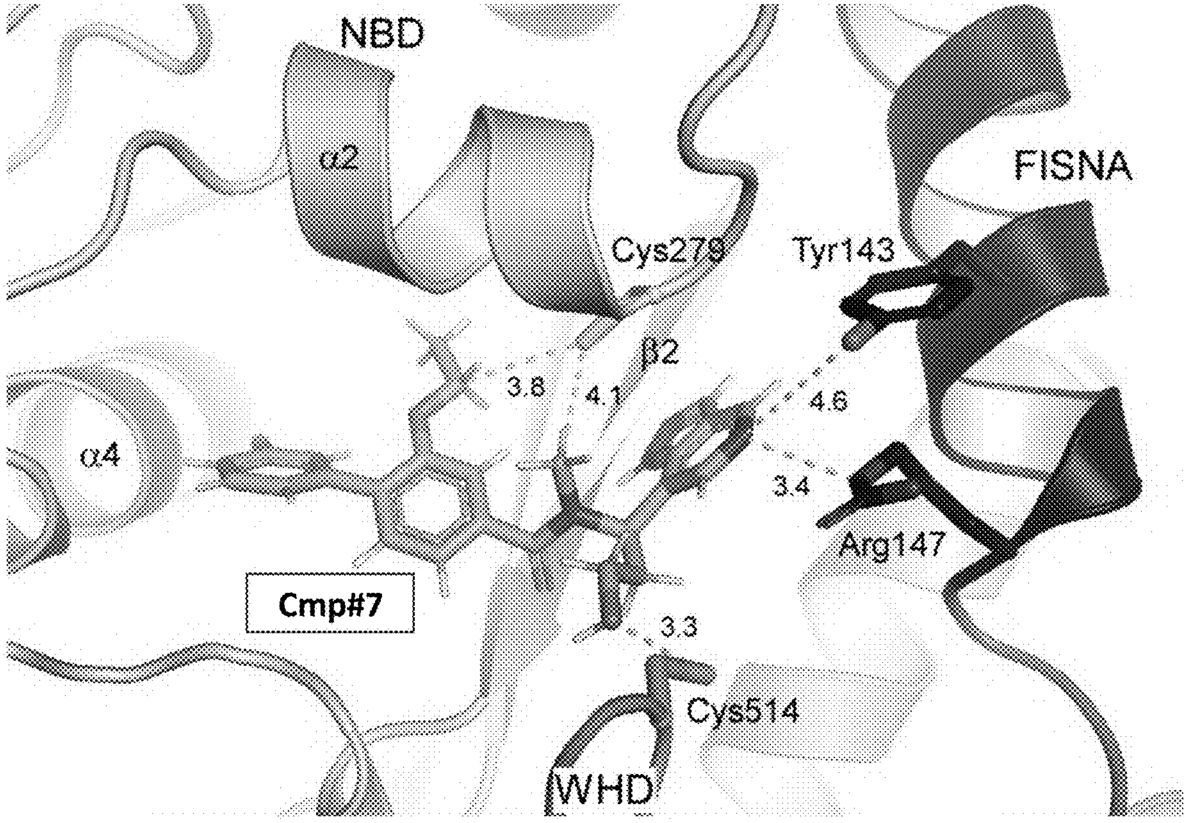
FIG. 5 depicts a ribbon-structure image of Compound 007 in proximity to Cys279 and Cys514 of NLRP3.

The benzylic Ca position (C04) position of the 5-azaindazole is chiral and in the (R)-configuration. The hydroxy group of the 2-hydroxyethyl moiety forms a hydrogen bond to the carboxyl side chain group of Glu263 (FIG. 3). Additional interactions are made to residue Cys514 at the tip of the β-sandwich loop in the winged-helix-domain (WHD) of NLRP3 at a distance of 3.3 Angstroem between the oxygen (001) and the sulfur atoms (FIG. 4). The methyl group at the NC position of the central peptide bond (C24) is in proximity (4.1 Angstroem) to the sidechain of Cys279 (FIG. 5).

The binding of Compound 007 to NLRP3 is complemented by an interaction of the nitrogen atom (N27) of the 5-azaindazole, which is in 3.4 and 4.6 Angstroem distance to the side chains of Arg147 and Tyr143 of the FISNA domain, respectively, coordinating the interaction of the inhibitor to the first subdomain of the NACHT (FIG. 4). Overall, the inhibitor Compound 007 performs interactions with 25 residues of the three subdomains NBD, FISNA and WHD, with Leu275 and Cys279 making the largest contribution to the buried surface area (BSA) of NLRP3 with 56 and 42 $Å^2$, respectively.

Methods—Example 3

Cloning, Expression and Purification of Human NLRP3

Full length, human NLRP3 (3-1036, UniProt accession code Q96P20), codon-optimized for *Spodoptera frugiperda*, was cloned in an in-house modified pACE-Bac1 vector containing an N-terminal MBP-tag, followed by a Tobacco etch virus (TEV) protease cleavage site. For recombinant protein expression of MBP-NLRP3, 1 L of Sf9 insect cells were infected with 3% v/v viral stock of the second virus passage. The expression culture was incubated for 72 h at 27° C. and 80 rpm, and was subsequently harvested by centrifugation at 2000 rpm for 20 min. Cell pellets were washed with PBS and subsequently used for protein purification or flash-frozen in liquid nitrogen and stored at −80° C. For protein purification, a 1 L cell pellet was solubilized in lysis buffer (50 mM HEPES pH 7.5, 150 mM NaCl, 0.5 mM TCEP, 1 mM ADP, 10 mM $MgCl_2$) to which 1 μM Compound 007 from a 10 mM stock solution in DMSO was added. The lysis buffer was supplemented with 1 mM phenylmethylsulfonyl-fluoride (PMSF), followed by sonication (10 sec on; 5 sec off for 4 min at 40% intensity) on ice. The cell lysate was centrifuged at 25,000 rpm for 1 h and the supernatant was subsequently filtered with a 0.45 μm syringe filter, before it was applied onto a lysis buffer equilibrated 5 ml MBP-trap column (GE Healthcare) connected to an ÄKTA-Start FPLC system. The column was subsequently washed with 10 column volumes (CVs) of lysis buffer and the protein was eluted with 5 CVs of lysis buffer supplemented with 15 mM maltose. The NLRP3·Compound 007 complex was further purified using a Superose 6 increase 10/300 GL column (GE Healthcare) equilibrated with lysis buffer. Elution fractions were analyzed by SDS-PAGE and negative stain electron microscopy (EM), before they were plunge frozen for cryo-EM analysis.

A NACHT-transition LRR construct of human NLRP3 (aa 131-694) was subcloned into an in-house modified pACE-Bac1 vector containing an N-terminal MBP-tag, followed by a Tobacco etch virus (TEV) protease cleavage site. The Bac-to-Bac system was used to generate baculovirus infected Sf9 insect cells. For the expression of recombinant human NLRP3, insect cells were infected with 3% v/v of a viral stock of the second passage. The expression culture was incubated for 72 h at 27° C. and 80 rpm, and subsequently harvested by centrifugation at 2000 rpm for 20 min. The cell pellet was washed with PBS and either used for subsequent protein purification or frozen in liquid nitrogen and stored at −80° C. till further use. For protein purification, cells were resuspended in buffer A (20 mM Tris-HCl pH 7.8, 150 mM NaCl, 5 mM β-mercaptoethanol, 10 mM $MgCl_2$, 1 mM ADP) supplemented with 1 mM PMSF and 1 μg/ml DNAse 1, and lysed by sonication (6 sec on; 5 sec off for 4 min at 40% intensity on ice). The lysate was cleared from cell debris by centrifugation at 70,000×g for >30 minutes. The protein containing an N-terminal MBP tag was captured using a MBPTrap column (GE Healthcare) and the unbound fraction was washed off with buffer A. After elution with buffer A containing 10 mM maltose, TEV protease (1:50 w/w) was added for cleavage of the MBP-tag and the protein was dialyzed against buffer B (20 mM HEPES pH 7.8, 150 mM NaCl, 10 mM $MgCl_2$, 1 mM ADP, 1 mM TCEP, 500 mM L-Arginine); overnight at 4° C. using the snake skin dialysis tubing with 3.5 kDa MWCO (Thermo Scientific). Protein was further purified using a Superdex 75 gel filtration column 16/600 (GE Healthcare) that was connected to a MBPTrap column for prolonged retention of the cleaved MBP tag and pre-equilibrated with buffer C (20 mM HEPES pH 7.8, 150 mM NaCl, 10 mM $MgCl_2$, 1 mM ADP, 1 mM TCEP, 150 mM L-Arginine). Peak fractions containing monomeric NLRP3 were pooled, concentrated to 9.0 mg/ml (Amicon 10 kDa MWCO), snap frozen in liquid nitrogen, and stored at −80° C. For biochemical analysis, the protein was purified in absence of ADP and Compound 007. Due to lower solubility of the protein, the concentration was adjusted to 1 mg/ml.

Cryo-EM Grid Preparation, Data Collection and Processing

The purified NLRP3·Compound 007 complex was applied onto glow-discharged EM-grids (Quantifoil Cu300 R2/1+2 nm carbon support film), incubated for 30s at 100% humidity and 4° C., before it was blotted for 5s with blot force 5 and plunge frozen into liquid ethane using a Vitrobot mark IV plunge freezing device (Thermo Fisher Scientific). For dataset acquisition using the SerialEM version 4 automation software, 4,720 electron-event representation (EER) movies each consisting of 1122 raw frames were recorded on a Cs-corrected Krios Titan microscope operated at 300 kV and equipped with a Falcon4i camera at a total dose of 66.22 $e^{-}/A^2$ and a defocus range of −0.80 to −1.80 μm. For Cryo-EM data processing in cryoSPARC, the raw EER data were fractioned onto 40 movie frames with a unsampling factor of 2. Resulting movie stacks were aligned using the patch motion correction and patch CTF correction jobs. Using the blob picker, 3,114,152 particles were picked and detected of which 2,058,399 were extracted (search particle diameter 280 nm, 588 box size), of which 559,748 particles remained after multiple rounds of 2D classification. From these particles, three ab-initio models were generated, which were further subjected to heterogenous refinement. One model (468,974 particles) was further subjected to a non-uniform (NU)-refinement, followed by 3D classification allowing for ten 3D-classes. One class, comprising 30,200 particles, was further refined by another NU-refinement yielding a final reconstruction of the NLRP3·Compound 007 complex at 3.00 Å resolution (0.143 FSC). In this reconstruction, Compound 007 is clearly visible in the cryo-EM density map at a surface accessible binding pocket composed of the nucleotide-binding domain.

Thermal Shift Assay

Nano-differential scanning fluorimetry (nanoDSF) measurements were performed on a Prometheus NT.48 (NanoTemper) device to determine the thermal stability of the protein-ligand samples. For stability characterizations, NLRP3 was mixed with buffer or ligand in the presence of 2% DMSO. The sample was incubated for 30 minutes on ice before loading into capillaries (NanoTemper). The measurement was setup with a temperature ramp ranging from 15-95° C., a slope of 1.5° C./min, and 90% laser intensity.

HPLC-Based ATPase Assay

For the analysis of the intrinsic ATP hydrolysis, 3 μM full length, wild type NLRP3 (peak 1) was incubated for 30 minutes on ice in the presence of 2% DMSO or 100 μM BAL-0028 or 100 μM Compound 007. After incubation, 100 μM of ATP was added and the reaction was incubated for 60 minutes at 25° C. Every 10 minutes a 10 μl sample was injected onto a 1260 Infinity II LC system connected to a reversed phase C18-silica column (Chromolith Performance, Merck) that was pre-equilibrated with buffer D (30 mM $K_2HPO_4$, 70 mM $KH_2PO_4$, 10 mM TBA-Br, 4% v/v acetonitrile; pH 6.5). The detector was setup to measure at 259 nm wavelength. Detected peaks for ADP and ATP were integrated and the ratio was used to calculate the molar concentrations of educt and product.

Surface Plasmon Resonance Spectroscopy

Surface plasmon resonance (SPR) spectroscopy experiments were performed on a Biacore 8K (GE Healthcare) device. The system was flushed with running buffer (10 mM HEPES pH 7.4, 200 mM NaCl, 0.5 mM ADP, 0.5 mM tris(2-carboxyethyl)phosphine (TCEP), 2 mM $MgCl_2$, 1 g/L carboxymethyl dextran (CMD), 0.05% Tween20, 2% DMSO) at 25° C. A streptavidin functionalized sensor chip (Series S Sensor Chip SA, Cytiva) was conditioned with three consecutive injections of 1 M NaCl in 50 mM NaOH (10 μL/min) for 1 min. After purification of biotinylated NLRP3 (131-694) that was expressed as wildtype or mutants in the FreeStyle™ 293-F expression system, the protein was immobilized onto the sensor chip at 2 μL/min for 3000 s. The flow system was washed using 50% isopropanol in 1 M NaCl and 50 mM NaOH. Free streptavidin binding sites were blocked by four consecutive injections of Biotin-PEG (1000 nM, Mn 2,300 Da) for 2 min at 10 μL/min. For binding measurements in the single cycle mode, increasing concentrations of 2.3 to 600 nM BAL compounds were injected at 30 μL/min (association 240 s, dissociation 60/360 s). Data were collected at a rate of 10 Hz. The binding data were double referenced by blank cycle and reference flow cell subtraction. Data were corrected by a 4-point solvent correction. For determination of dissociation constants, processed data were fitted to a 1:1 interaction model using the Biacore Insight Evaluation Software (version 3.0.12.15655). For improved comparability of the NLRP3 variants and to account for their different immobilization levels, the measurements were normalized to the theoretical Rmax resulting in the bound fraction.

Example 4: Diet-Induced Obesity (DIO) Studies

Compound 040 ("Cmpd 40") was used to evaluate weight loss promotion in a diet-induced obesity (DIO) mouse model. The treatment groups were as follows:

0. Lean/vehicle (VEH) (50 mM Citrate buffer, PO), n=10
1. DIO/VEH (50 mM Citrate buffer, PO), n=12
2. DIO/Cmpd 40 (5 mpk, QD, PO), n=12
3. DIO/Cmpd 40 (20 mpk, QD, PO), n=12
4. DIO/Cmpd 40 (50 mpk, QD, PO), n=12
5. DIO/Cmpd 40 (100 mpk, QD, PO), n=16 (n=8 were ended earlier for PK, remaining n=8 were dosed at 75 mpk since day 9)
6. DIO/Semaglutide (10 ug/kg, QD, SC), n=12

Figure 7:
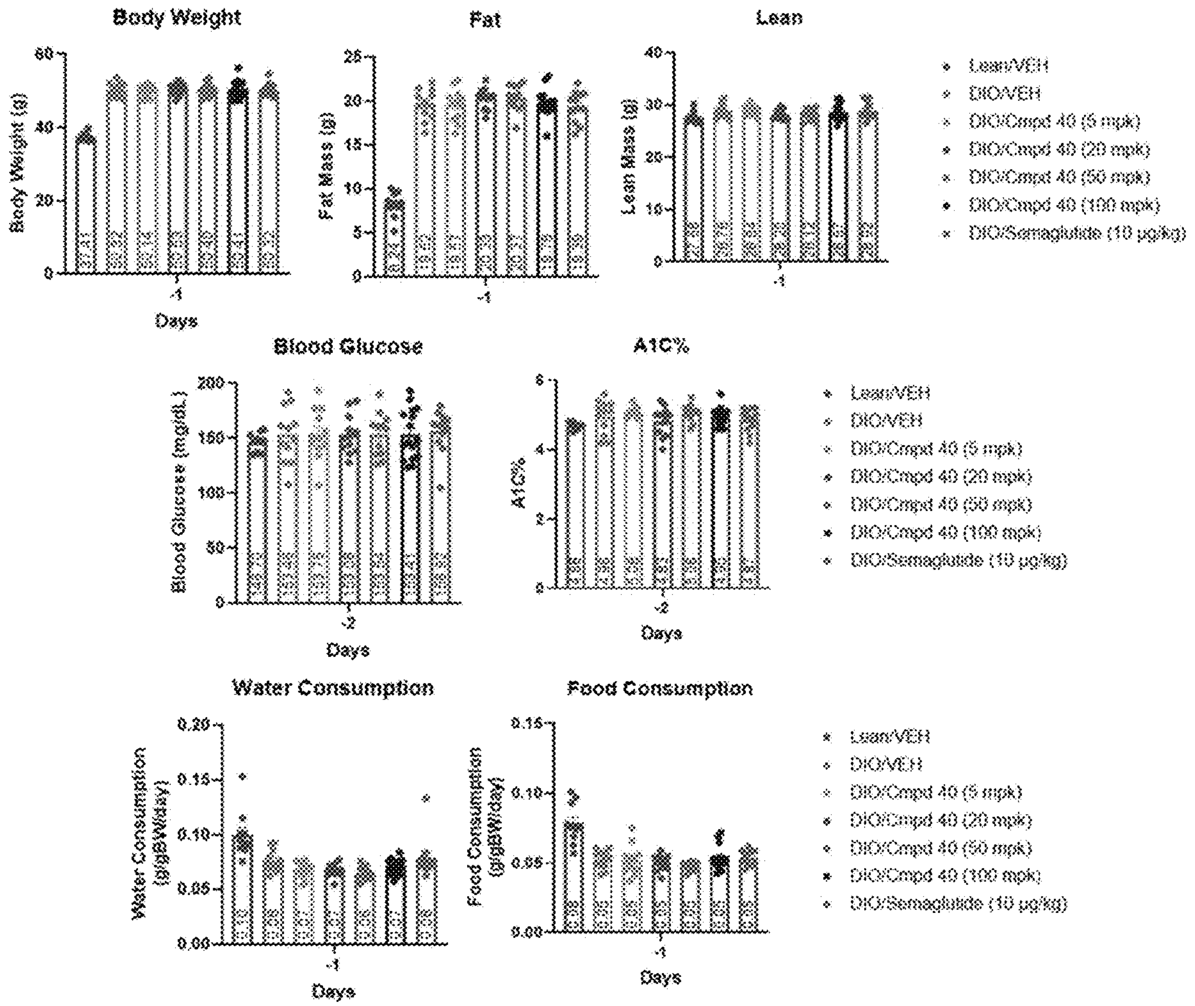
FIG. 7 depicts randomization of mice for treatment.

Compound 040 was administered orally (PO) in a 50 mM citrate buffer (pH 4). Semaglutide was administered orally in a 20 mM citrate buffer (pH 7). The PO volume was 5 ul/gBW; and the subcutaneous (SC) volume was 4 ul/gBW. Mice were evaluated daily for body weight, food consumption, and water consumption. The mice were also evaluated weekly for body composition. Baseline and endpoint A1C and fasting glucose, endpoint HOMA-IR were also measured. The DIO mice were randomized for the drug treatment on the basis of equivalent body weight, body composition (fat mass, lean mass), 6 h fasting blood glucose, baseline blood A1C level, water consumption and food consumption as shown in FIG. 7.

Figure 8:
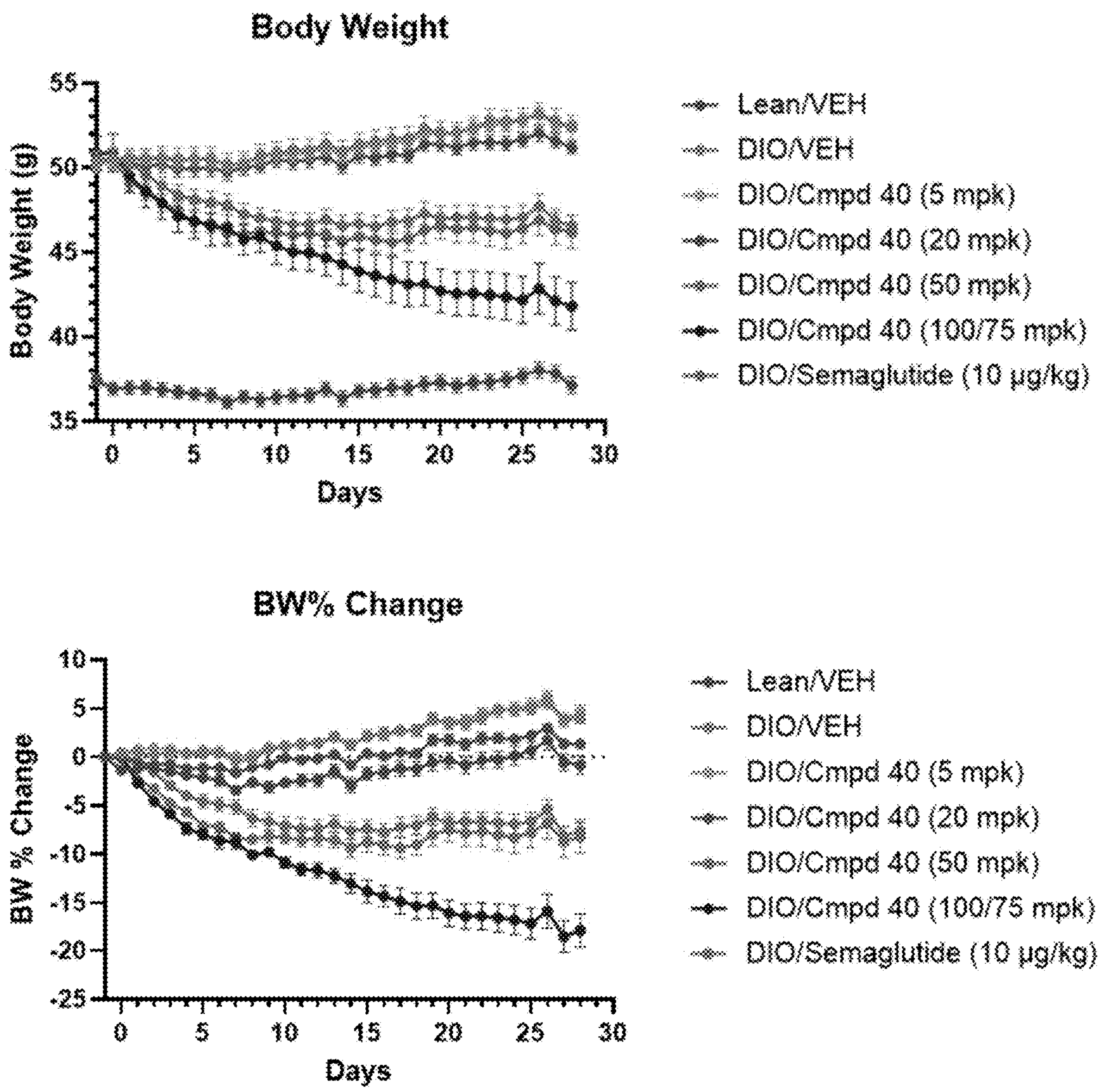
FIG. 8 depicts the body weight and body weight percent changes in a diet-induced obesity (DIO) mouse model using Compound 040 or semaglutide.

The body weight change and body weight percentage changes are shown in FIG. 8 for mice receiving Compound 40 compared to a vehicle or semaglutide. Compound 40 showed a dose-dependent effect on reducing body weight of DIO mice. Table 5 summarizes the data shown in FIG. 8

TABLE 5

| Groups | Day 28 BW % change vs. baseline | Day 28 BW % change vs. DIO/VEH |
|---|---|---|
| DIO/VEH | 4.0 | 0.0 |
| DIO/Cmpd 40 (5 mpk, po, qd) | 4.6 | 0.6 |
| DIO/Cmpd 40 (20 mpk, po, qd) | 1.3 | −2.7 |
| DIO/Cmpd 40 (50 mpk, po, qd) | −7.6 | −11.6 |
| DIO/Cmpd 40 (100/75 mpk, po, qd) | −17.9 | −22.0 |
| DIO/Semaglutide (10 μg/kg, sc, qd) | −8.2 | −12.2 |

Figure 9:
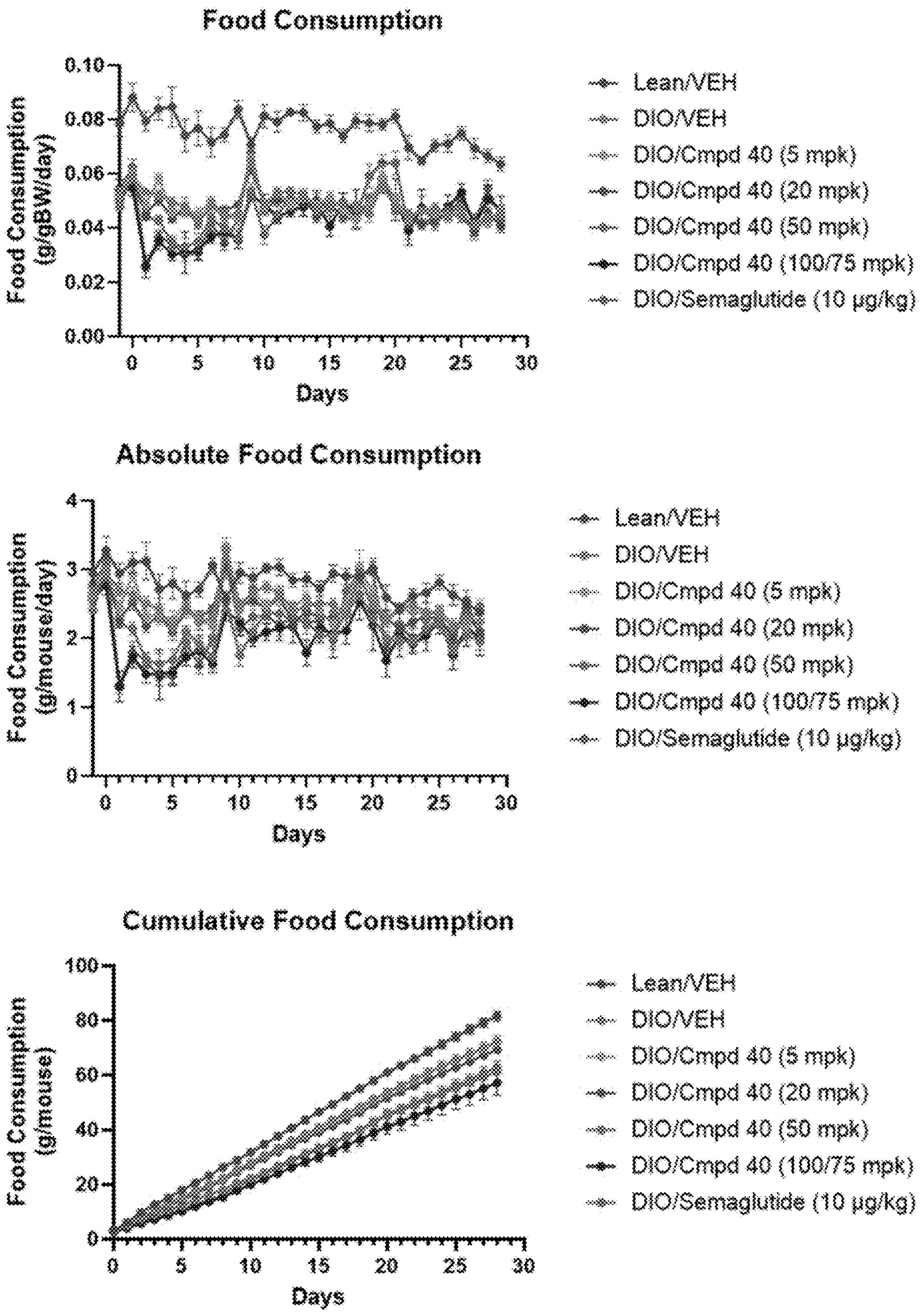
FIG. 9 depicts the food consumption in the DIO mouse model using Compound 040 or semaglutide.

The changes in food consumption in mice receiving no treatment (VEH), Compound 40, and semaglutide are shown in FIG. 9. Compound 40 showed a dose-dependent effect on reducing food consumption.

Figure 10:
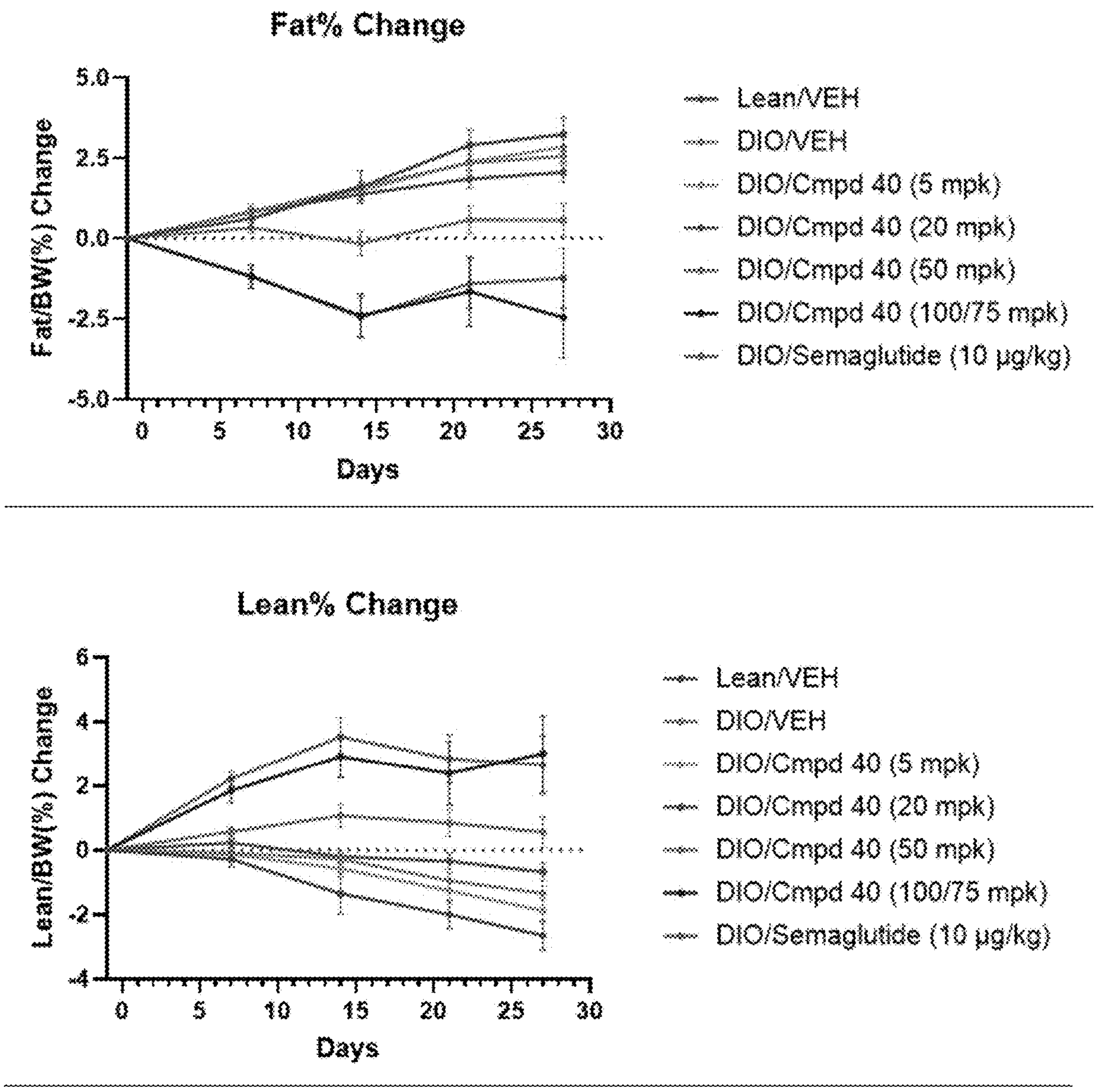
FIG. 10 depicts the change in fat mass and lean mass percentages in the DIO mouse model using Compound 040 or semaglutide.

The changes in fat and lean percentages in mice receiving no treatment (VEH), Compound 40, and semaglutide are shown in FIG. 10. Compound 40 showed a dose-dependent effect on reducing fat mass to body weight percentage and maintaining lean mass to body weight percentage.

Figure 11:
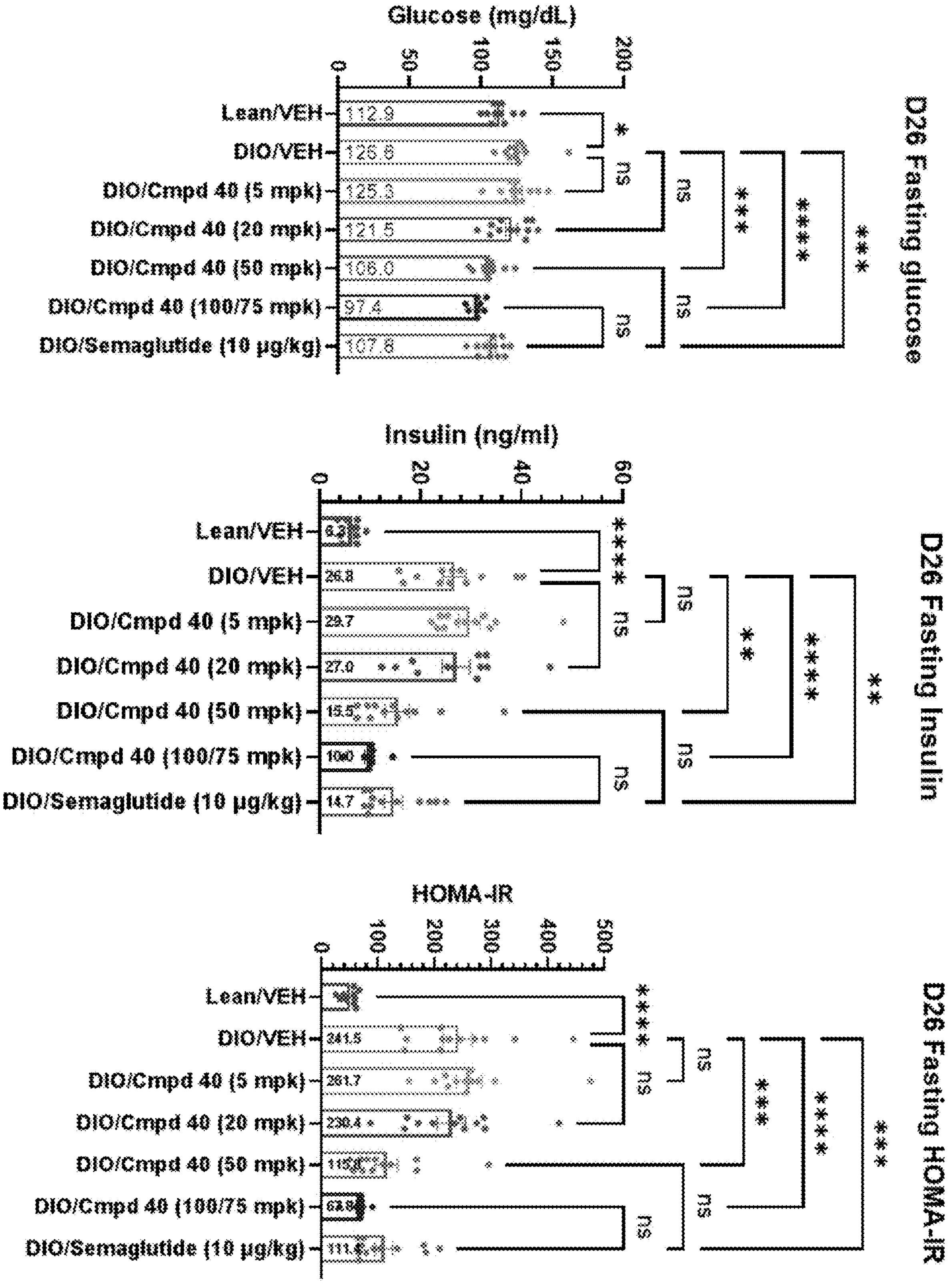
FIG. 11 depicts glucose metabolism in the DIO mouse model using Compound 040 or semaglutide.

Compound 40, at doses of 50 mpk or higher, significantly reduced fasting glucose and improved insulin sensitivity in DIO mice as shown in FIG. 11.

Figure 12:
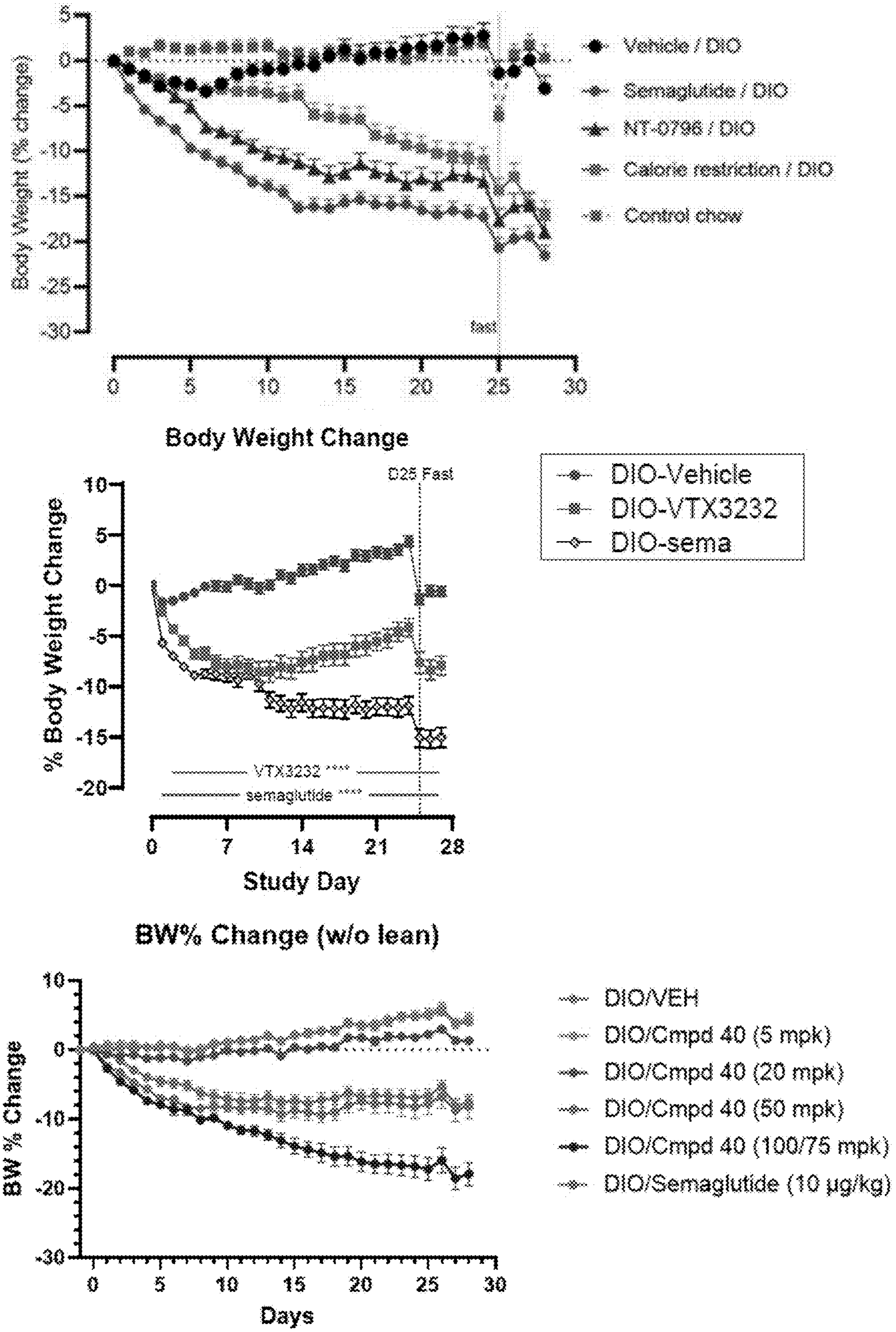
FIG. 12 depicts the body weight changes in the DIO mouse model to compare NT-0796, calorie restriction, VTX3232, Compound 040 and semaglutide.

FIG. 12. depicts a weight loss comparison between DIO mice receiving vehicle, semaglutide, NT-0796, WTX3232, or Compound 40

Figure 13:
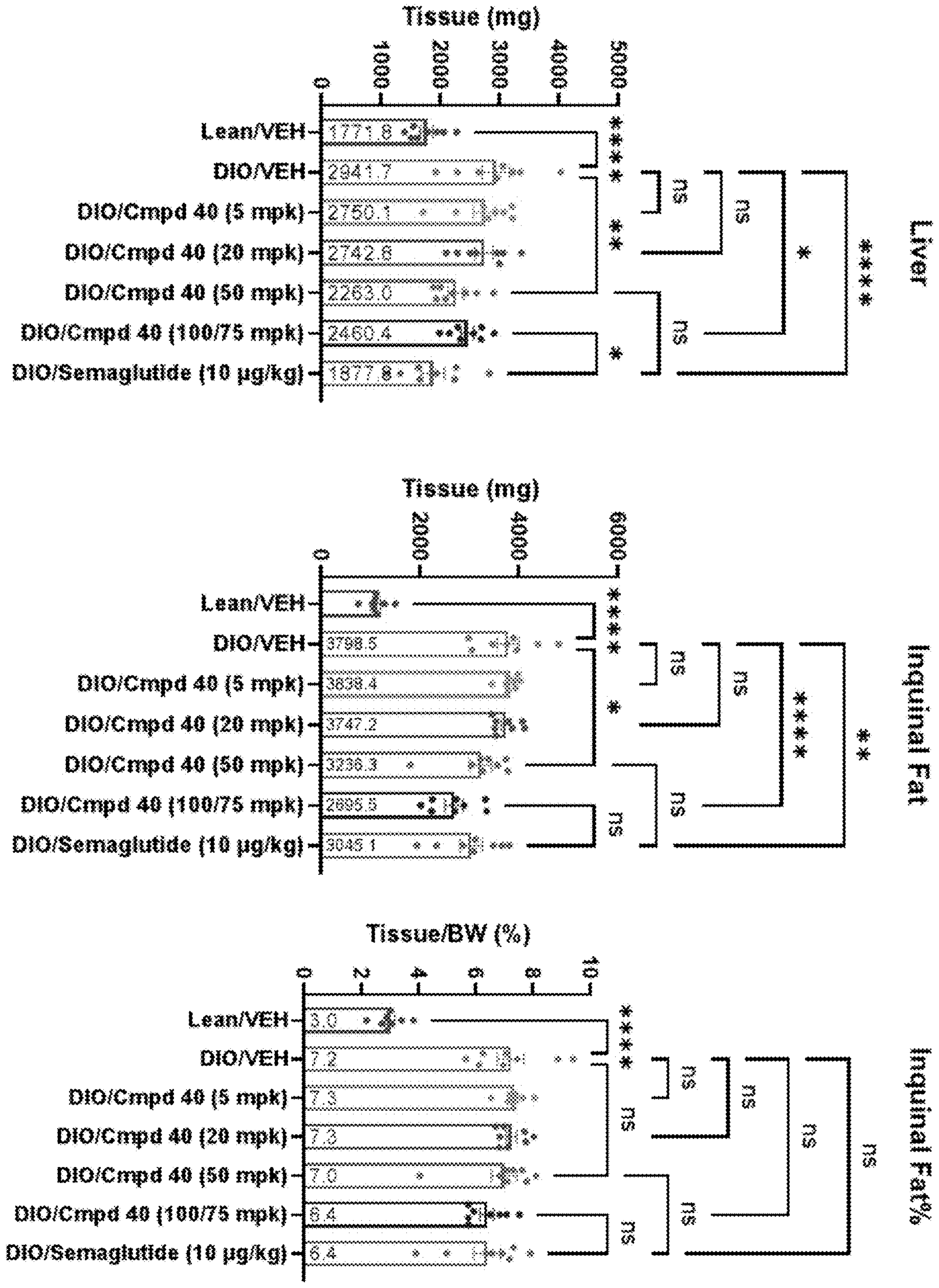
FIG. 13 depicts the terminal tissue weights or tissue to body weight percent of DIO mice after Compound 040 or semaglutide treatment for 4 weeks.

Compound 40, at doses of 50 mpk or higher, significantly reduced liver weight and inguinal fat weight. The inguinal fat to body weight percentage or muscle tissues to body weight percentage of Compound 40-treated DIO mice had no significant difference from Semaglutide treated mice as shown in FIG. 13.

Figure 14:
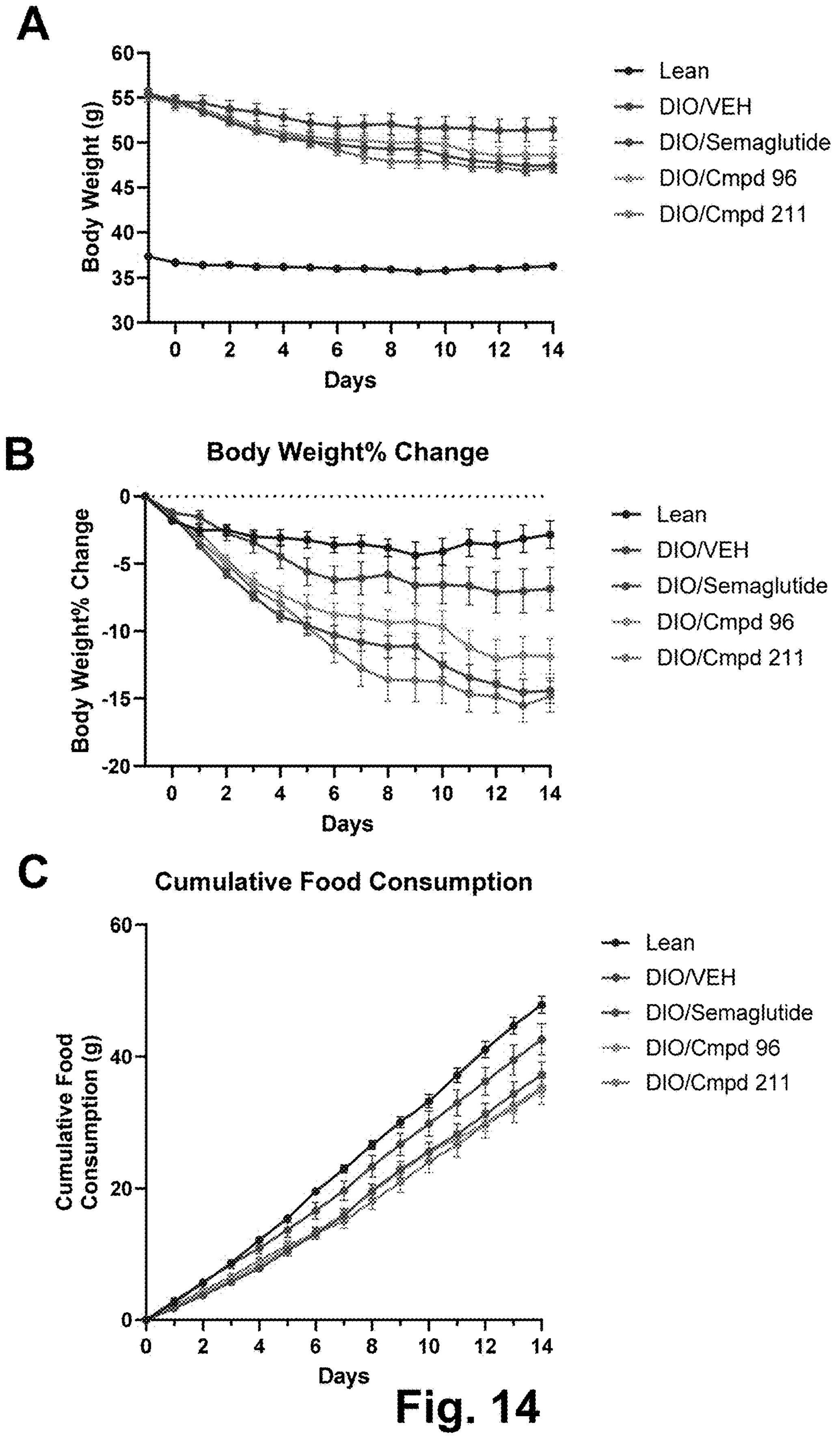
FIG. 14 depicts the body weight (A), body weight percent change (B), and cumulative food consumption (C) in the DIO mouse model using Compound 096, Compound 211, or semaglutide.

The body weight change and body weight percentage changes are shown in FIGS. 14A and 14B for mice receiving Compound 096 or Compound 211 compared to a vehicle or semaglutide. Compounds 096 and 211 showed a dose-dependent effect on reducing body weight of DIO mice. Table 6 summarizes the data shown in FIG. 14

TABLE 6

| Groups | Day 14 BW % change vs. baseline |
|---|---|
| DIO/VEH | −2.8 |
| DIO/Cmpd 096 (50 mpk, po, qd) | −11.9 |
| DIO/Cmpd 211 (50 mpk, po, qd) | −14.9 |
| DIO/Semaglutide (10 μg/kg, sc, qd) | −14.4 |

Figure 15:
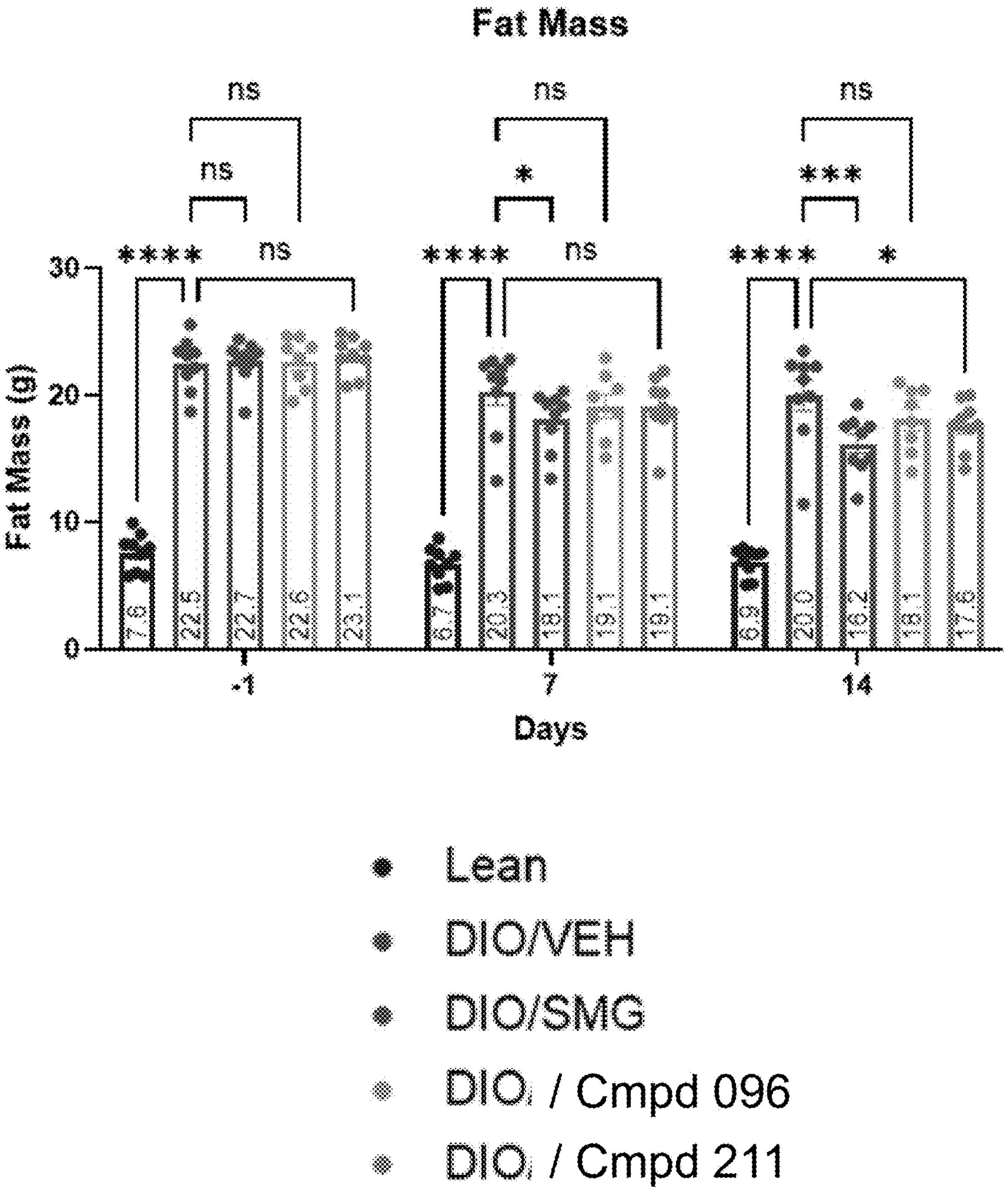
FIG. 15 depicts the fat mass in the DIO mouse model using Compound 096, Compound 211, or semaglutide.

The changes in food consumption in mice receiving no treatment (VEH), Compound 096, Compound 211, and semaglutide are shown in FIG. 14. Compounds 096 and 211 showed a dose-dependent effect on reducing food consumption, which also caused a change in fat mass as shown in FIG. 15.

As can be seen in the above example and corresponding Figures, Compound 40, Compound 096, and Compound 211 significantly reduced body weight and food consumption of high fat DIO mice, which is comparable to the effect of Semaglutide.

Example 5: Foot Gout Model

Figure 16:
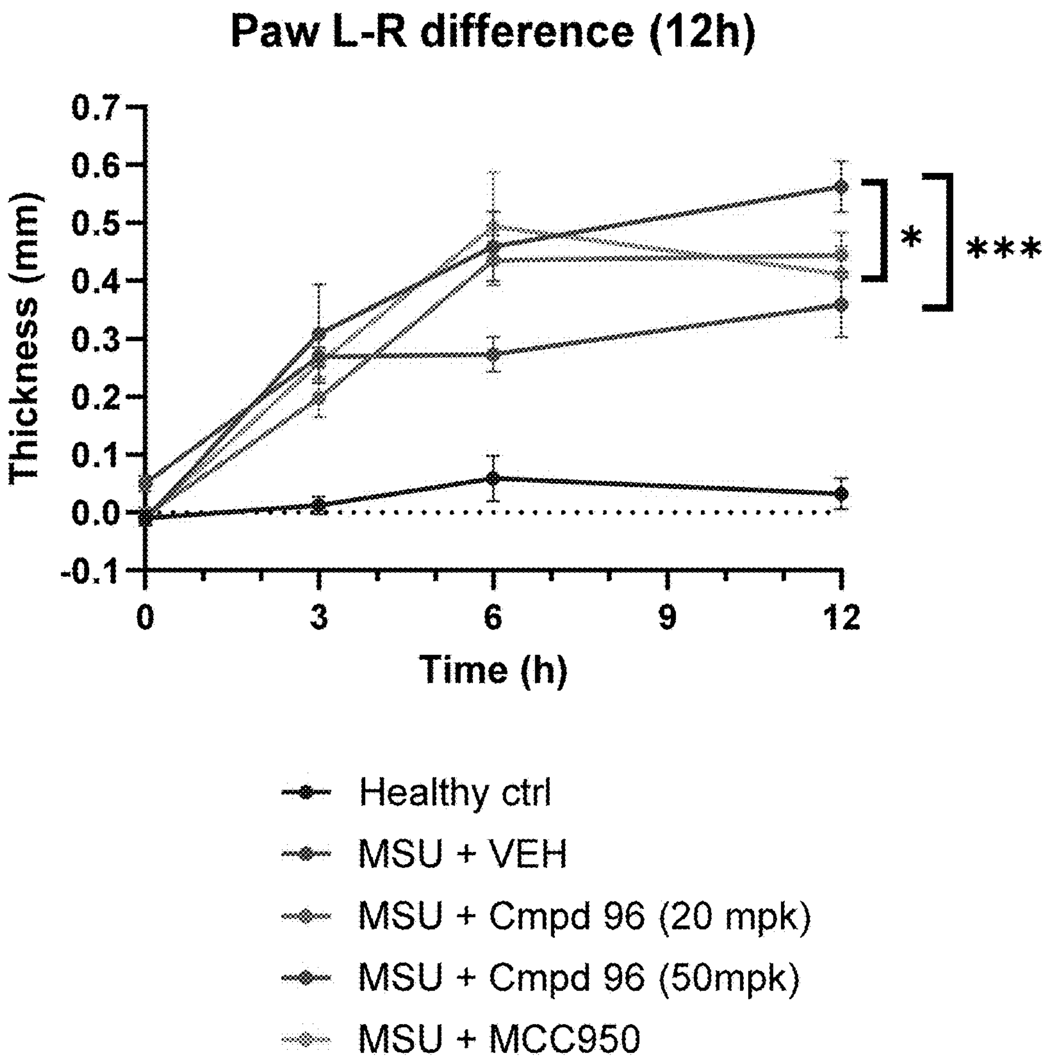
FIG. 16 depicts the swelling reduction effect of Compound 096 and MCC950 in a foot gout model.
Figure 17:
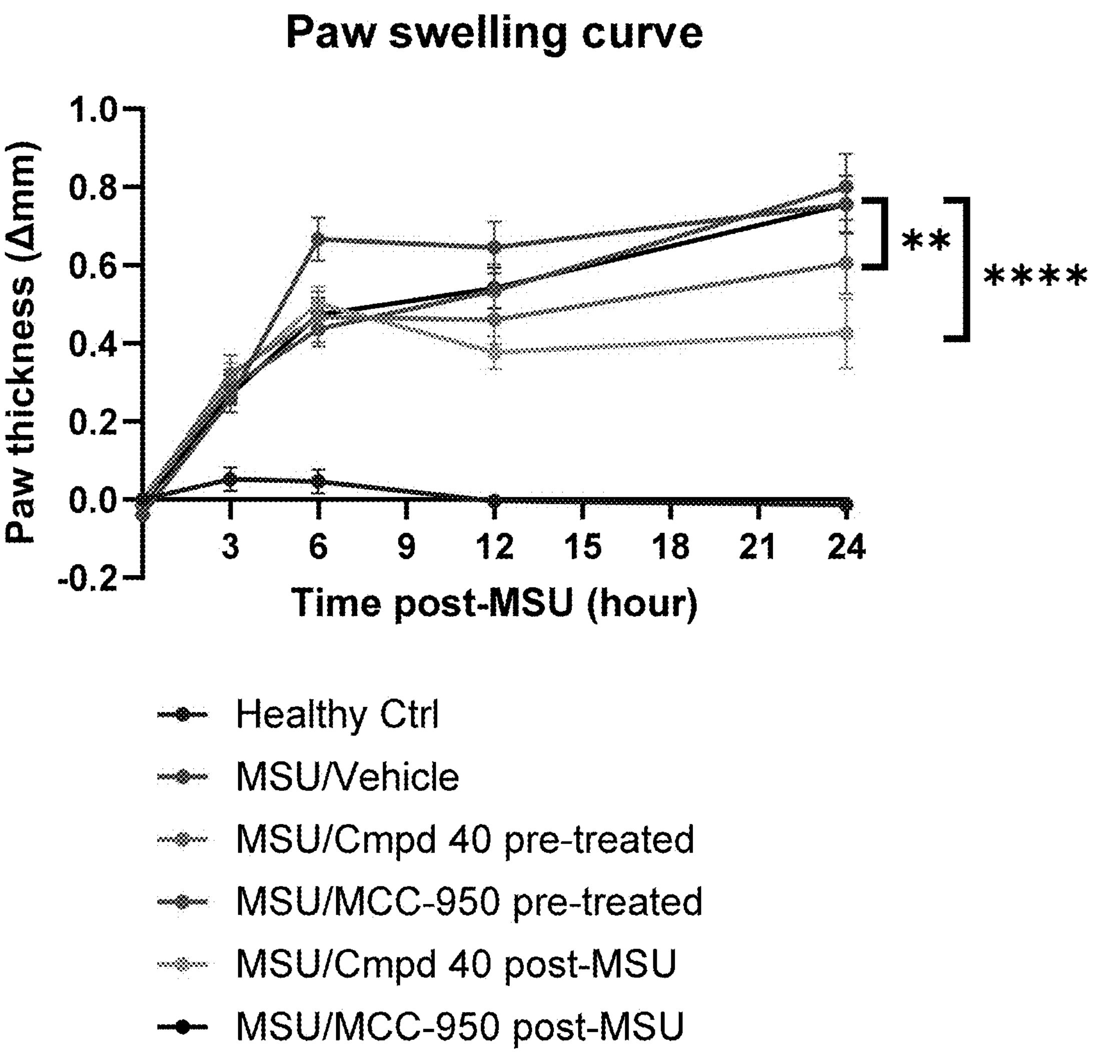
FIG. 17 depicts the reduction in paw swelling in a mouse gout model using Compound 040 or MCC950.

Compound 096 and Compound 040 reduce swelling in a foot gout mouse model in a dose dependent manner as shown in FIG. 16 and FIG. 17. Compound 040 can be used as both a preventative and therapeutic treatment.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula I:

(I)

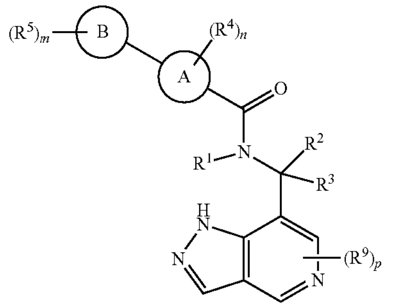

or a pharmaceutically acceptable salt thereof;

wherein

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of H, $C_{1-6}$ alkyl, $C_{3-6}$ cycloalkyl, $C_{1-6}$ alkoxy, $OC_{3-6}$ cycloalkyl, O($C_{0-6}$ alkylene-$C_{6-10}$ aryl), and $C_{0-6}$ alkylene-$C_{6-10}$ aryl, wherein alkyl and cycloalkyl are optionally substituted with OH, OC(O)$C_{1-6}$ alkyl, C(O)$C_{1-6}$ alkyl, $N(R^a)_2$, and halo;

each $R^a$ is independently H, $C_{1-6}$ alkyl, $C_{3-6}$ cycloalkyl, and C(O)$C_{1-6}$ alkyl;

$R^2$ is H or $C_{1-6}$ alkyl;

$R^3$ is selected from the group consisting of $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, NH($C_{1-6}$ alkyl), N($C_{1-6}$ alkyl)($C_{1-6}$ haloalkyl), NH($C_{1-6}$ haloalkyl), N($C_{1-6}$ alkyl)$_2$, N($C_{1-6}$ haloalkyl)$_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; and the nitrogen atom of NH($C_{1-6}$ alkyl), N($C_{1-6}$ alkyl)($C_{1-6}$ haloalkyl), NH($C_{1-6}$ haloalkyl), N($C_{1-6}$ alkyl)$_2$, and N($C_{1-6}$ haloalkyl)$_2$ is optionally oxidized and one or more carbon atoms of the alkyl groups on the nitrogen atom are optionally substituted with 1-6 deuterium atoms or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, NH($C_{1-6}$ alkyl), N($C_{1-6}$ alkyl)$_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, NH($C_{1-6}$ alkyl), N($C_{1-6}$ alkyl)$_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

2. The compound of claim 1, wherein

Ring A is $C_{6-10}$ aryl;

Ring B is $C_{6-10}$ aryl;

$R^1$ is $C_{1-6}$ alkyl;

$R^2$ is H;

$R^3$ is selected from the group consisting of $C_{1-6}$ alkyl, $C_{3-6}$ cycloalkyl, and 3-6 membered heterocycloalkyl, all of which are substituted by OH, $C_{1-6}$ alkoxy, $NH_2$, $NH(C_{1-6}$ alkyl), $N(C_{1-6}$ alkyl$)_2$, halo, $SO_2R^6$, or $C_{1-3}$ alkylene-5-10 membered heteroaryl;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2$R6;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, $SO_2R^6$, and halo;

m is 0, 1, 2, or 3;

n is 0, 1, 2, or 3; and p is 0, 1, 2, or 3.

3. The compound of claim 1, wherein

Ring A is $C_{6-10}$ aryl;

Ring B is $C_{6-10}$ aryl;

$R^1$ is $C_{1-6}$ alkyl;

$R^2$ is H;

$R^3$ is selected from the group consisting of $C_{1-6}$ alkyl, $C_{3-6}$ cycloalkyl, and 3-6 membered heterocycloalkyl, all of which are substituted by OH, $NH(C_{1-6}$ alkyl), $N(C_{1-6}$ alkyl$)_2$, or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which is substituted by OH;

each $R^4$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $NHC(O)C_{1-6}$ alkyl, CN, and $C_{1-6}$ haloalkyl;

each $R^5$ is independently selected from the group consisting of $C_{1-6}$ alkyl, halo, OH, $C_{1-6}$ alkoxy, $OC_{3-6}$ cycloalkyl, $NH_2$, $NH(C_{1-6}$ alkyl), $N(C_{1-6}$ alkyl$)_2$, $CONH_2$, $CONH(C_{1-6}$ alkyl), CN, and $C_{1-6}$ haloalkyl;

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

4. The compound of claim 1, wherein the compound of Formula I is a compound of Formula Ia:

(Ia)

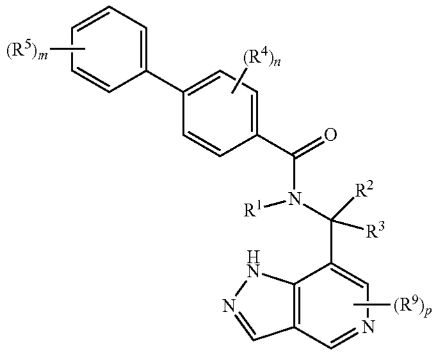

or a pharmaceutically acceptable salt thereof.

5. The compound of claim 1, wherein $R^1$ is $C_{1-6}$ alkyl; $R^2$ is H;

each $R^4$ is independently selected from the group consisting of halo, $C_{1-6}$ alkoxy, $OC_{3-6}$ cycloalkyl, and $C_{1-6}$ haloalkyl;

each $R^5$ is independently selected from the group consisting of $C_{1-6}$ alkyl, halo, CN, and $C(O)NH(C_{1-6}$ alkyl); and each $R^9$ is independently selected from the group consisting of $C_{1-3}$ alkyl, $C_{1-6}$ alkoxy, $C_{1-3}$ alkyl-OH, and halo.

6. The compound of claim 1, wherein $R^3$ is $C_{1-6}$ alkyl substituted by OH, $NH(C_{1-6}$ alkyl), $N(C_{1-6}$ alkyl$)_2$, or $C_{1-3}$ alkoxy.

7. The compound of claim 1, wherein m is 0, 1, or 2, n is 1; and p is 0 or 1.

8. The compound of claim 1, wherein the compound of Formula I is selected from

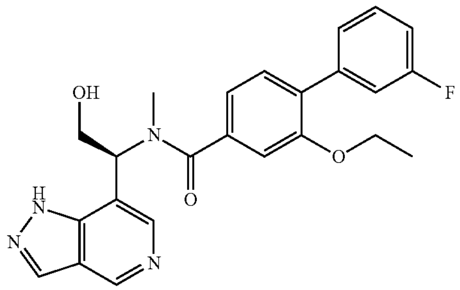

-continued
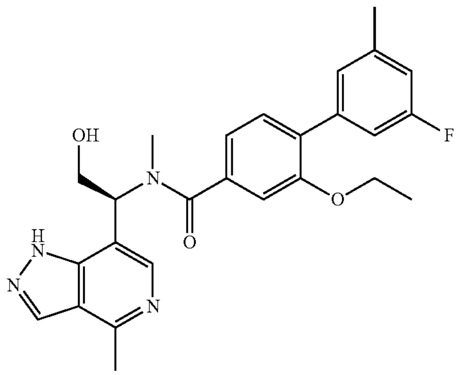
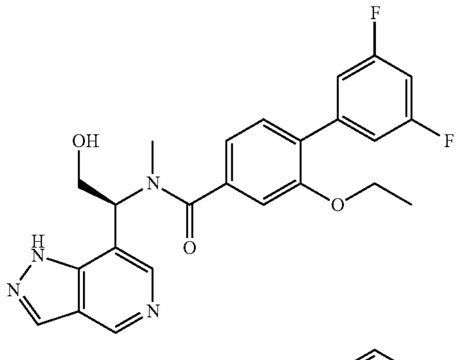
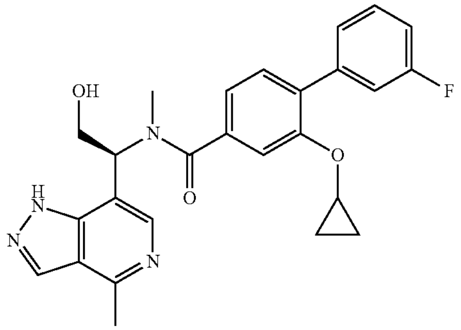
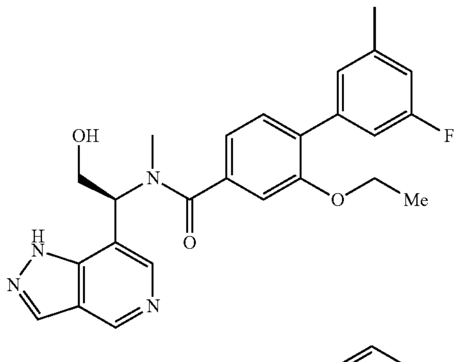
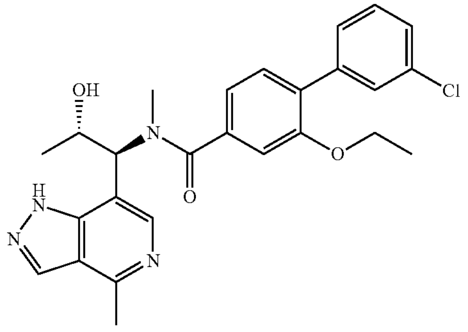
-continued
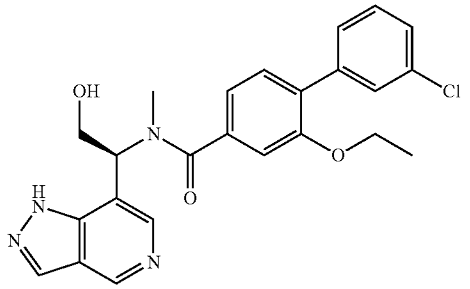
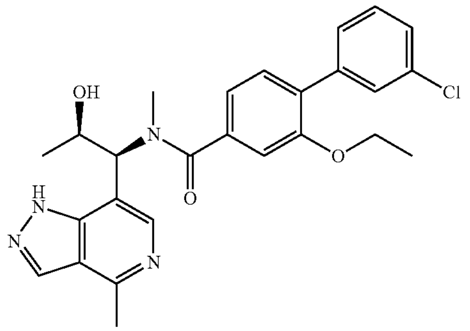
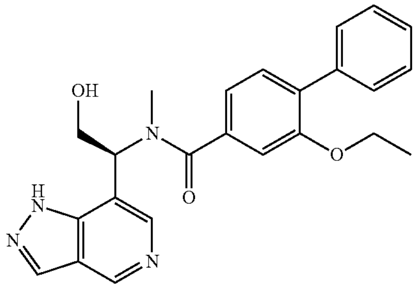
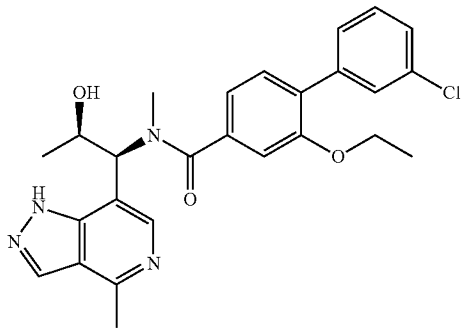
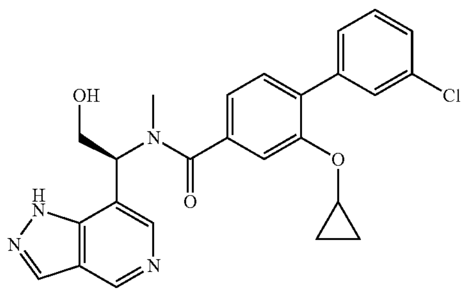

-continued
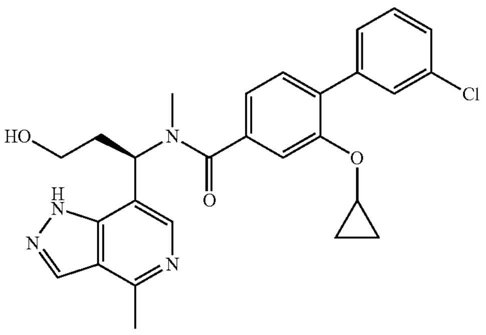
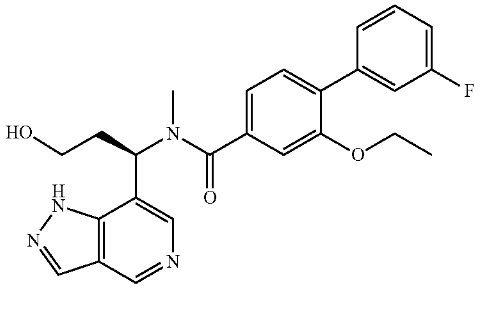
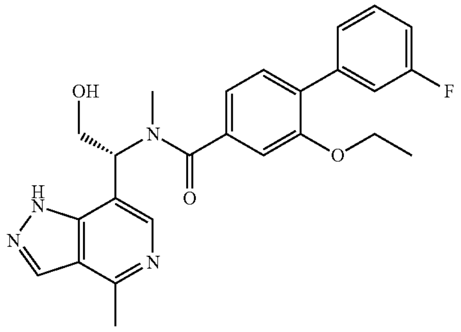
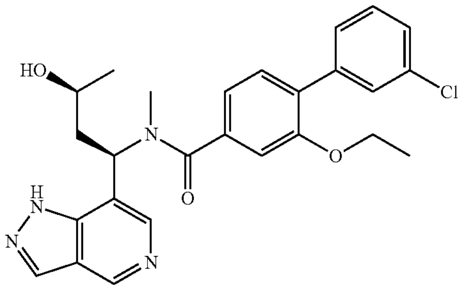
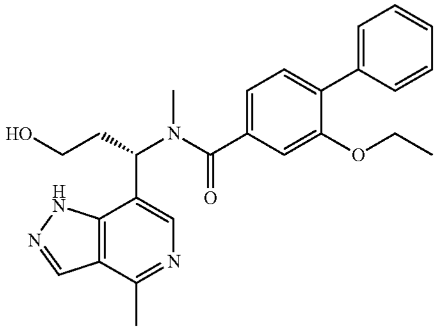
-continued
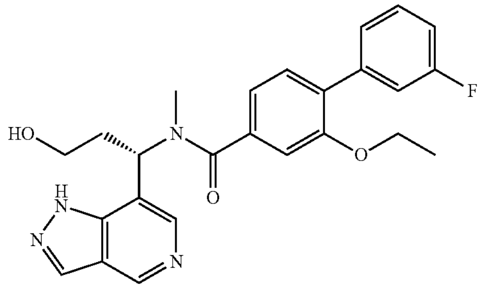
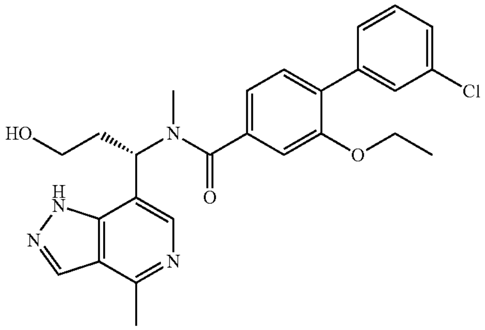
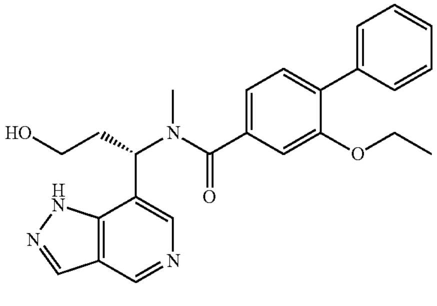
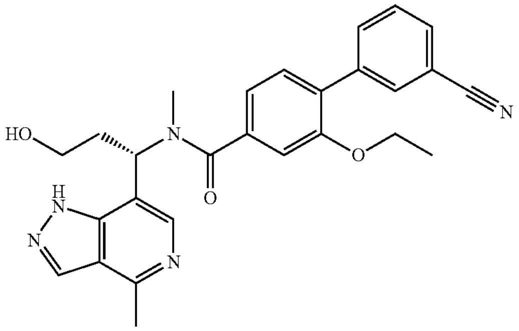
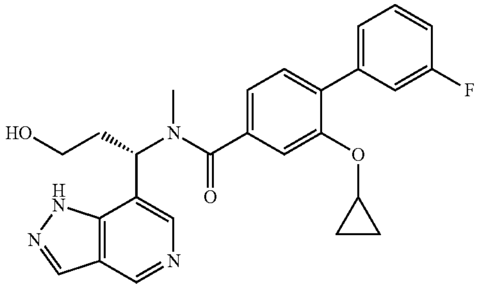

-continued
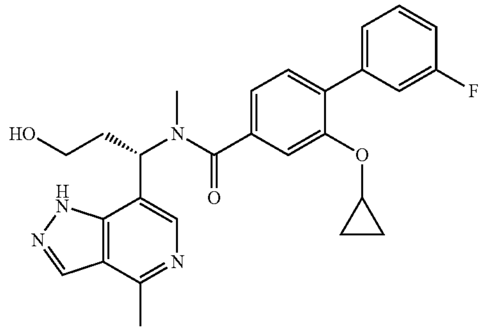
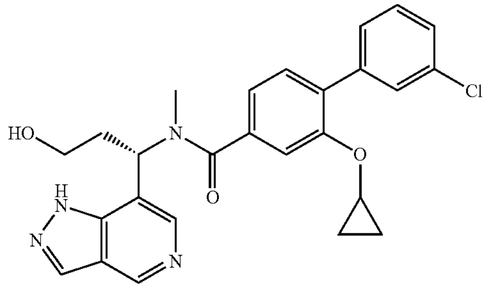
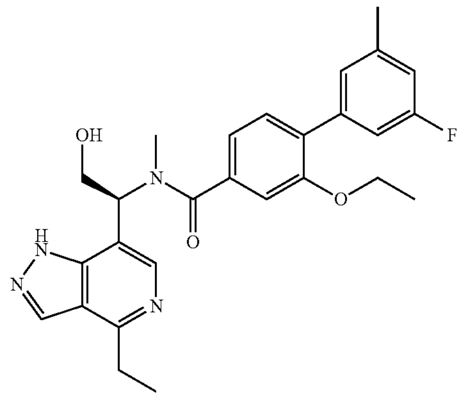
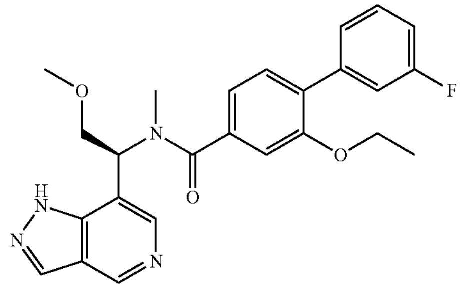
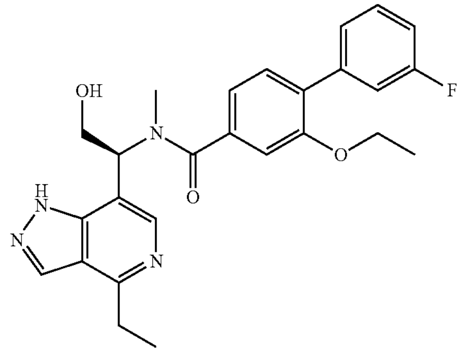
-continued
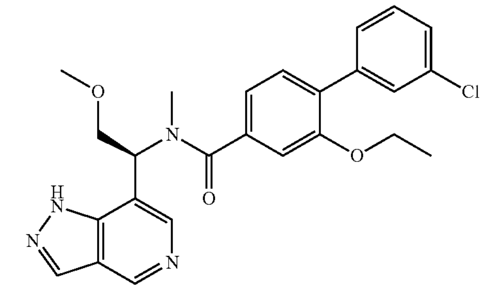
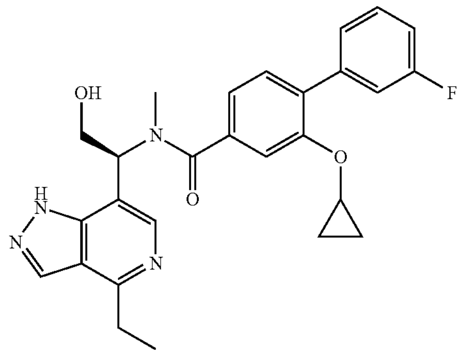
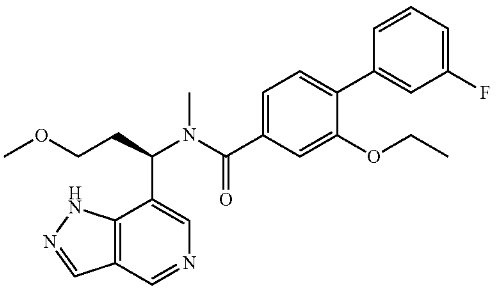
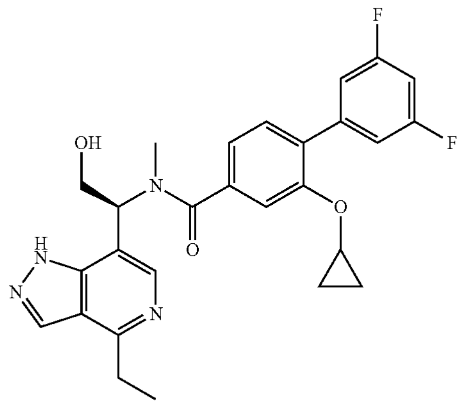
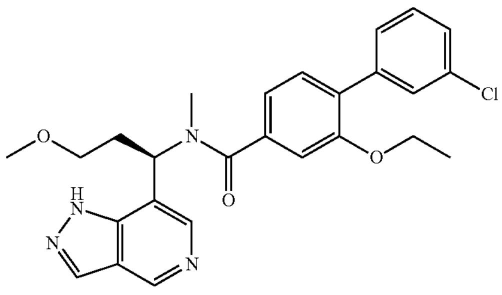

-continued
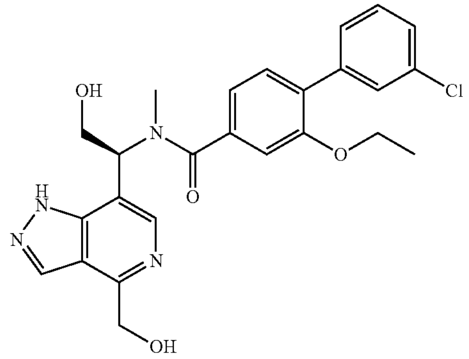
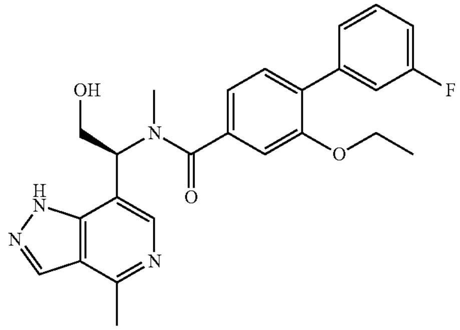
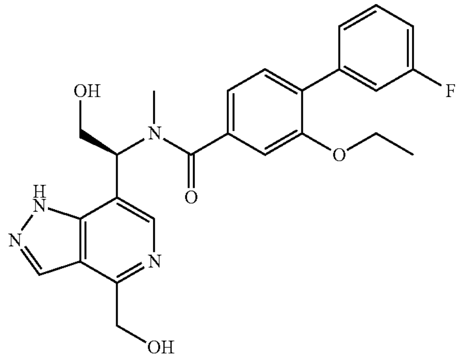
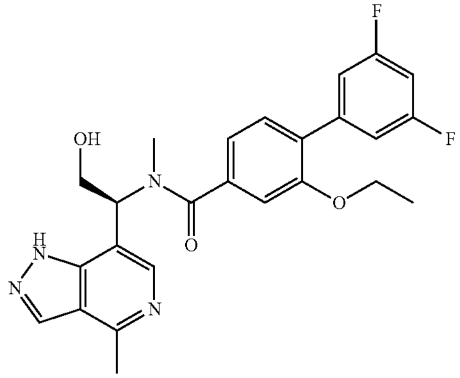
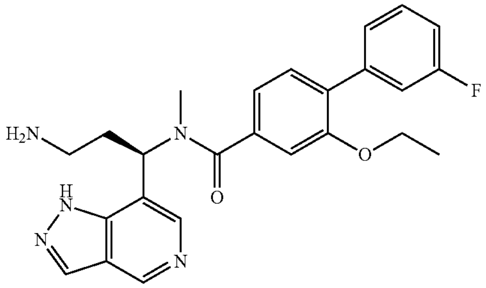
-continued
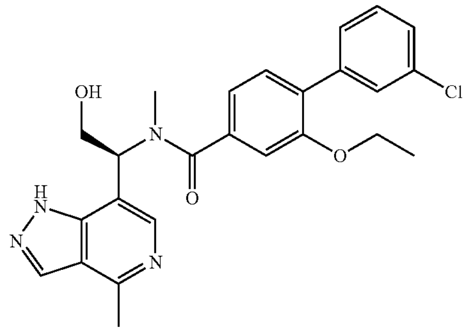
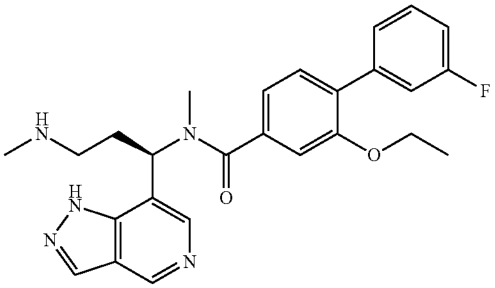
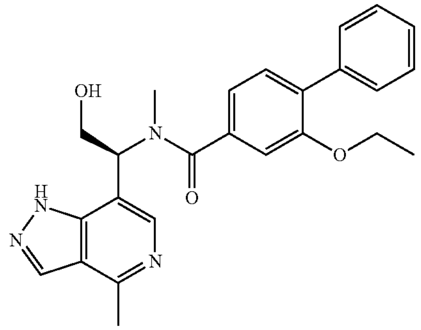
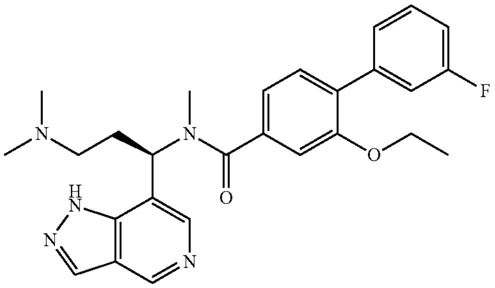
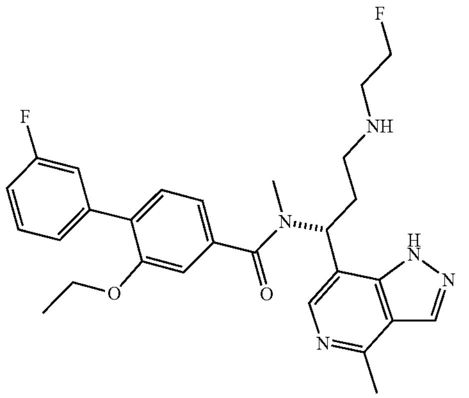

-continued
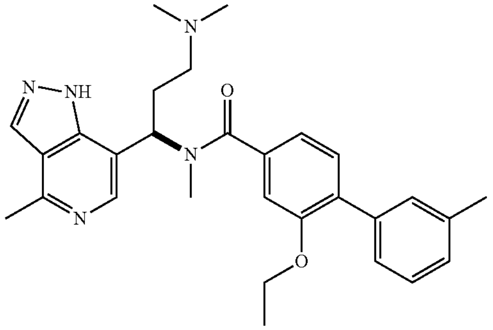
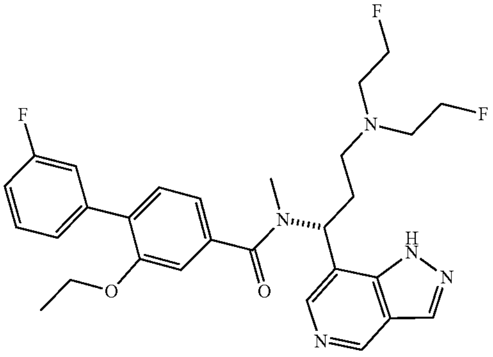
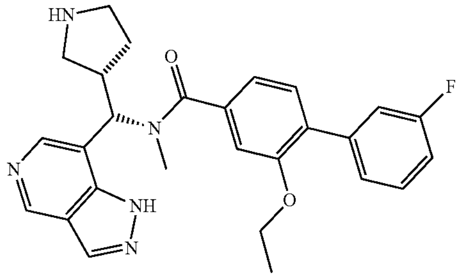
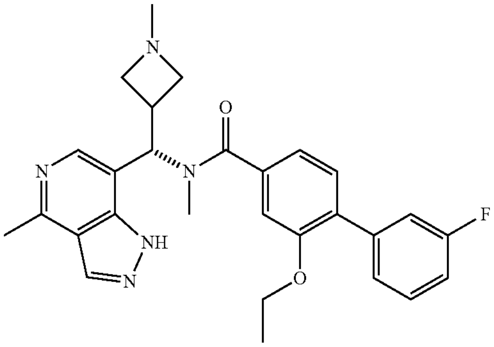
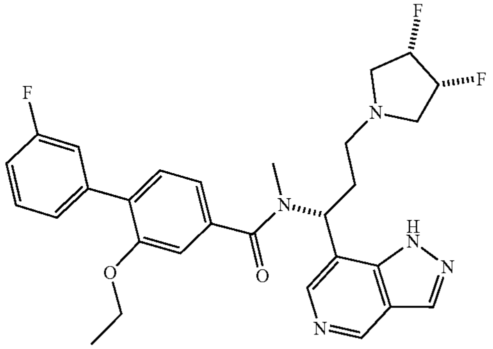
-continued
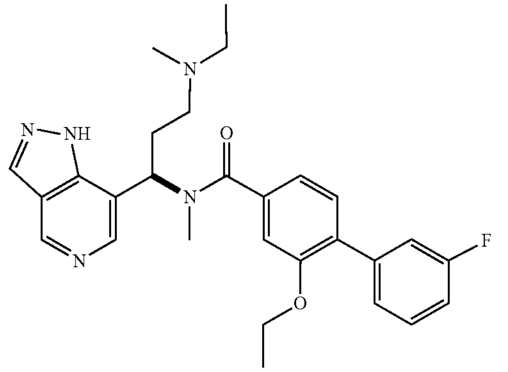
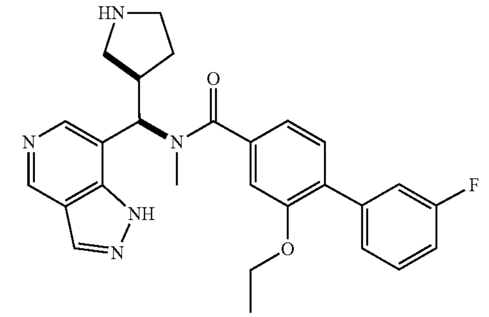
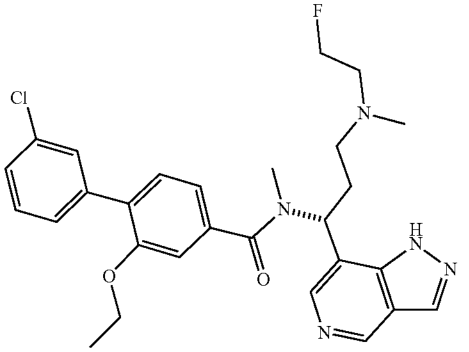
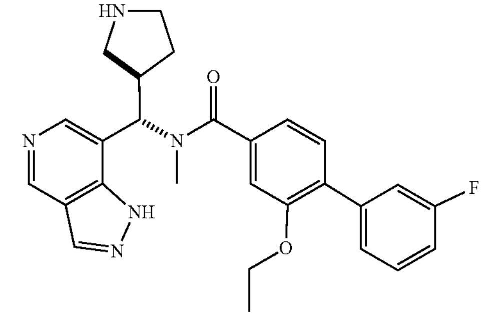
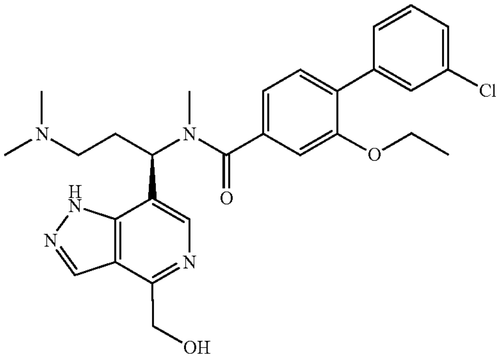

-continued
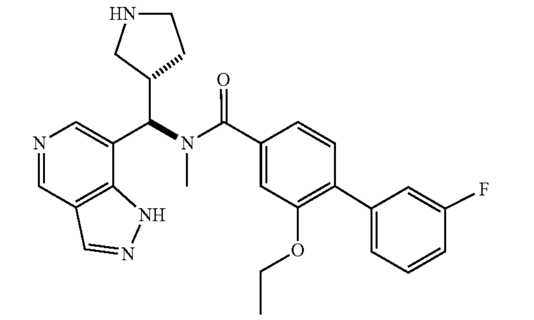
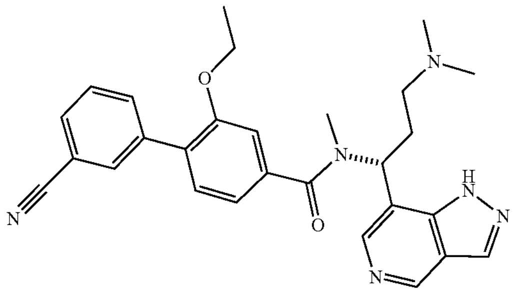
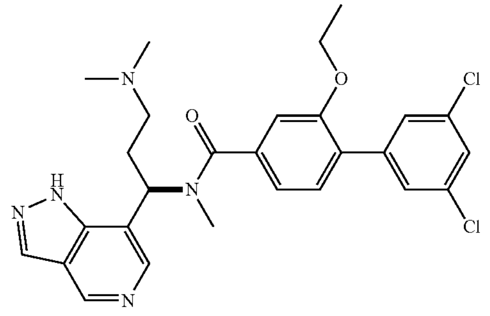
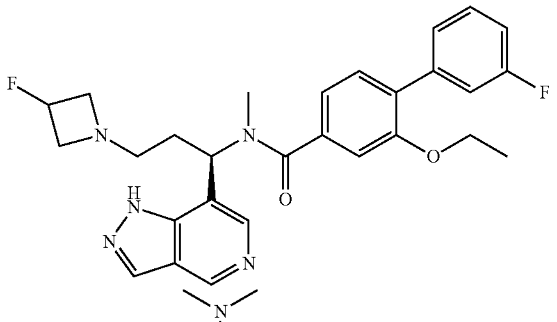
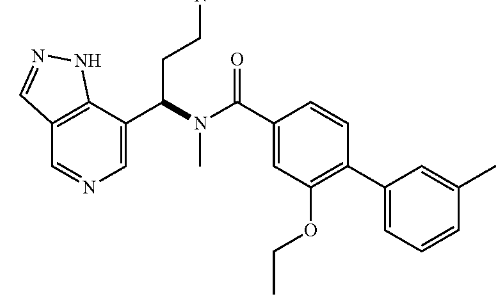
-continued
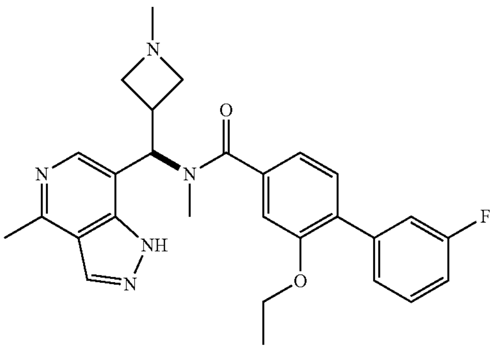
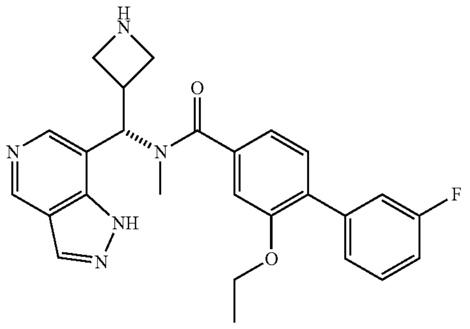
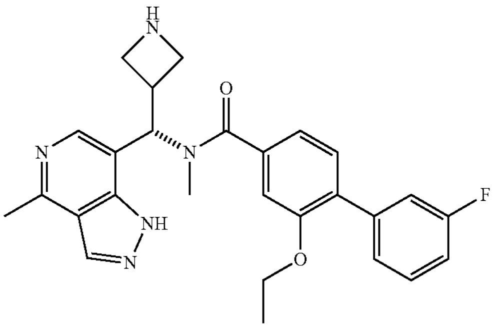
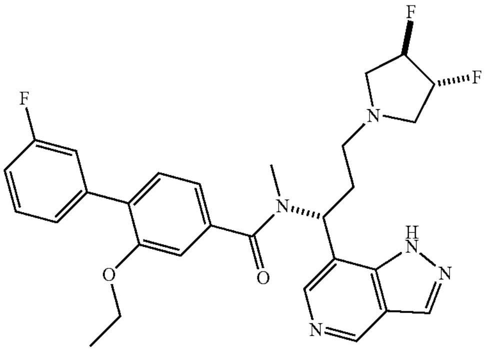
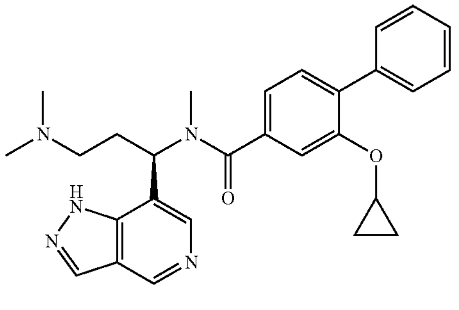

-continued
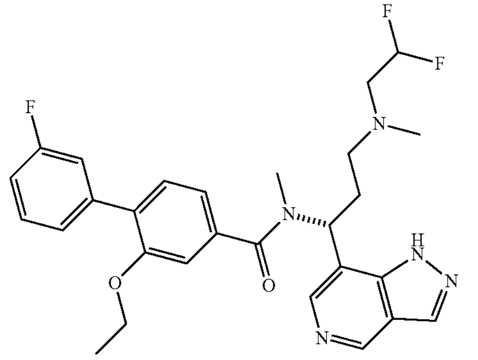
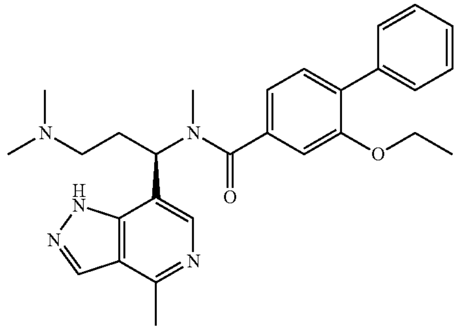
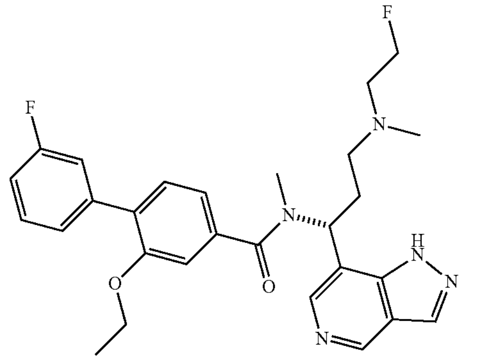
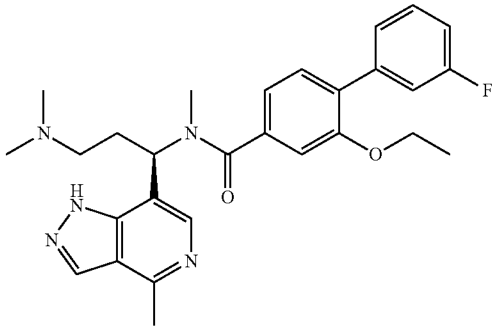
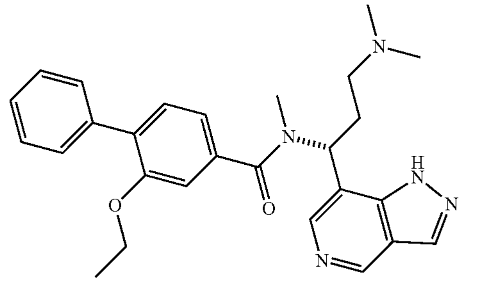
-continued
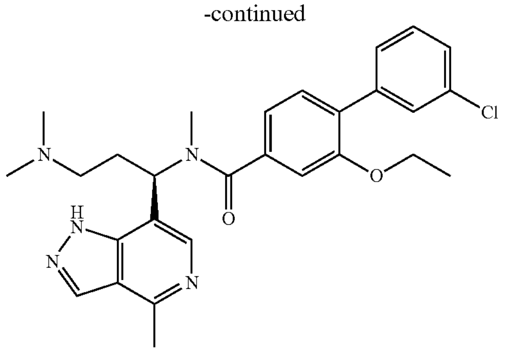
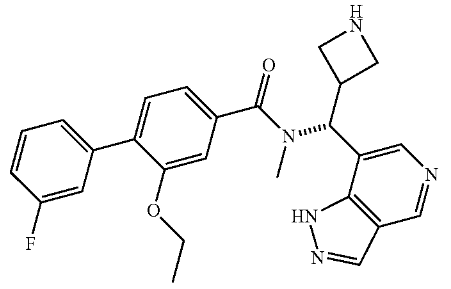
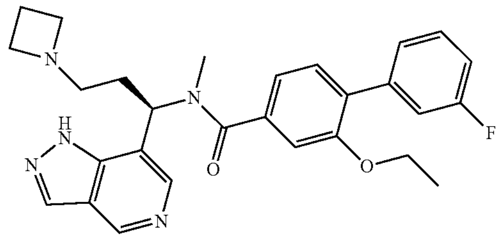
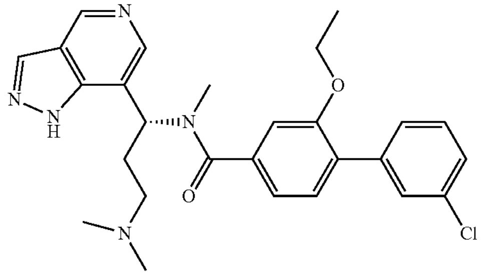
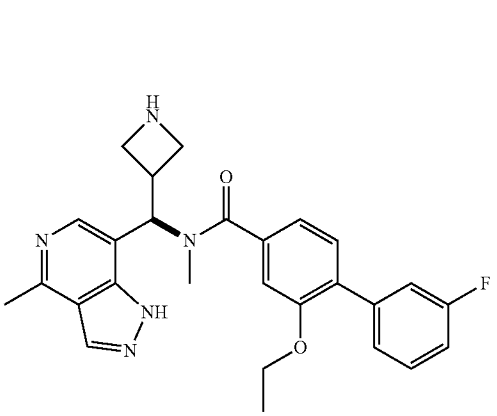

-continued
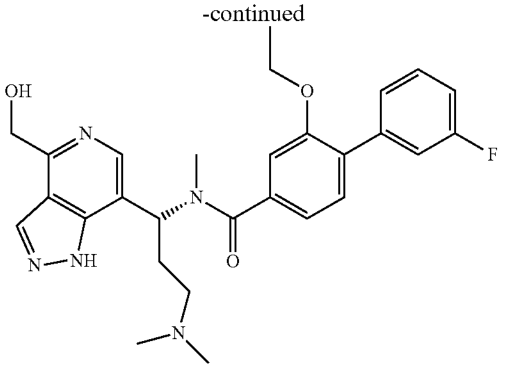
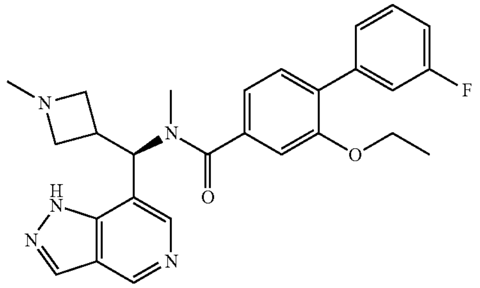
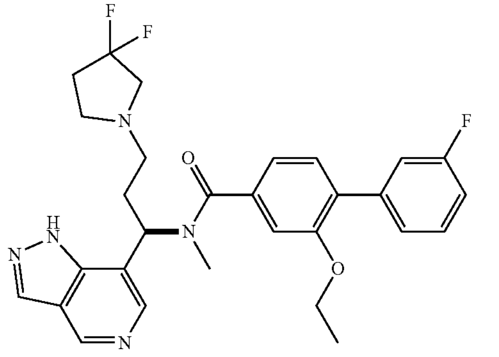
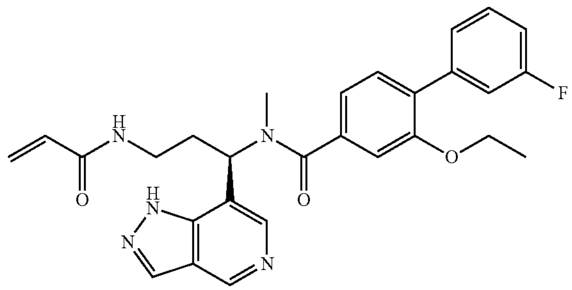
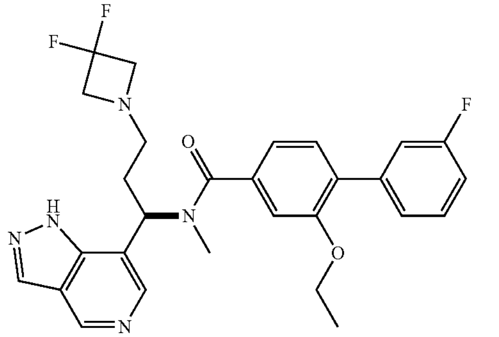
-continued
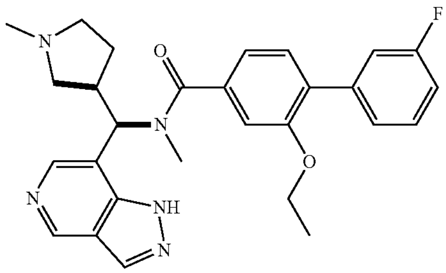
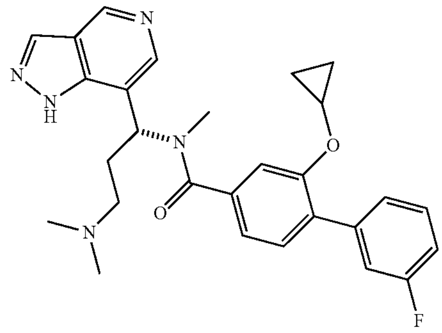
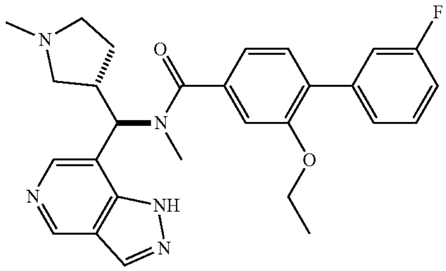
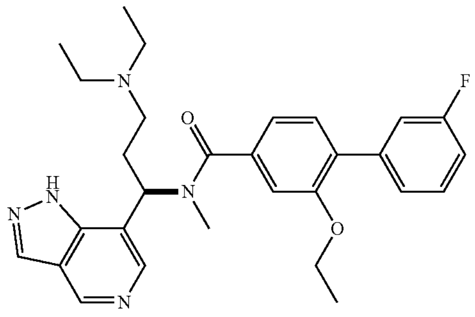
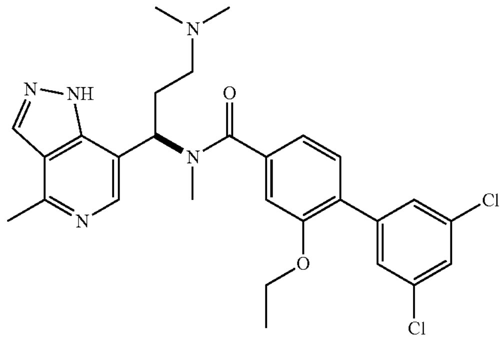

-continued
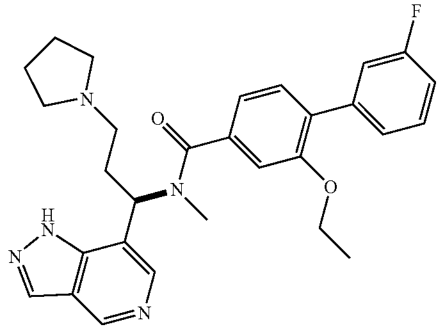
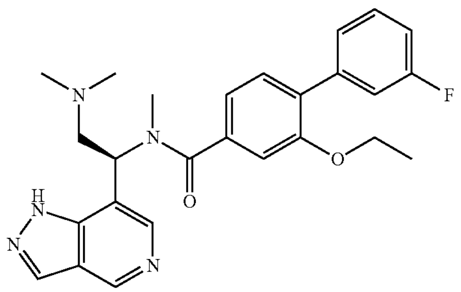
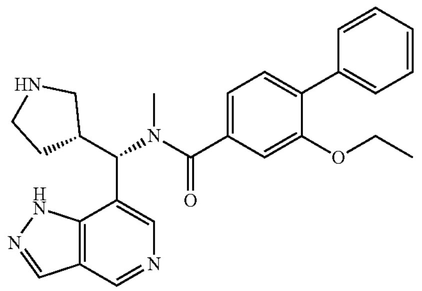
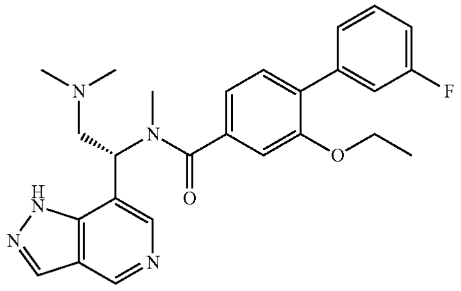
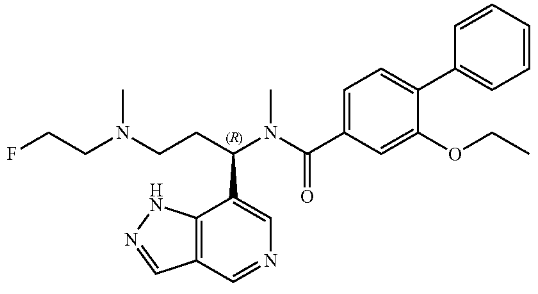
-continued
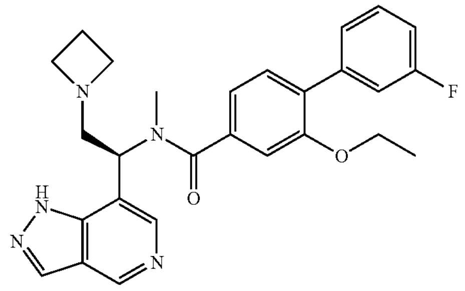
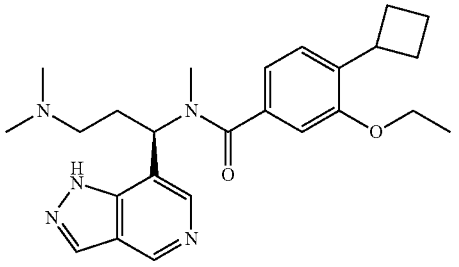
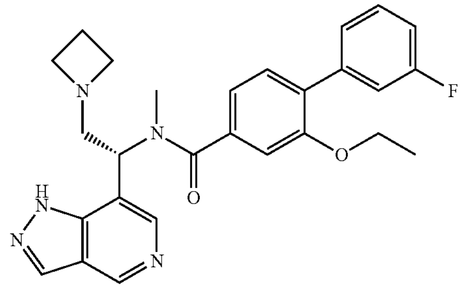
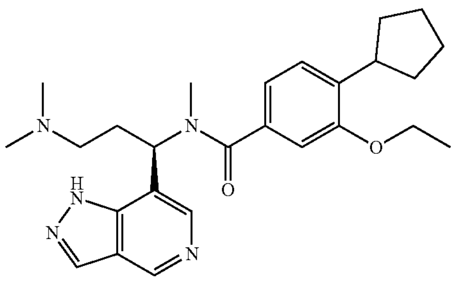
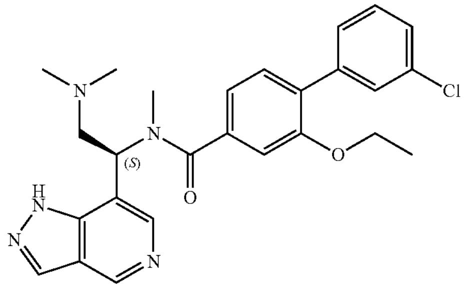
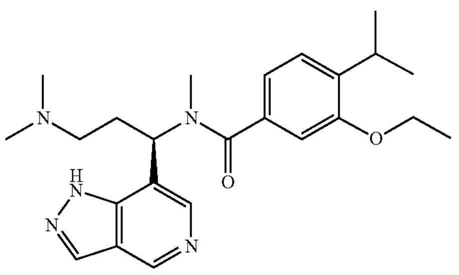

-continued
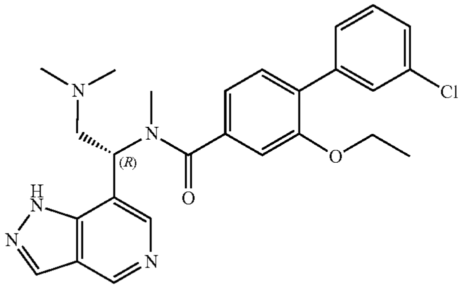
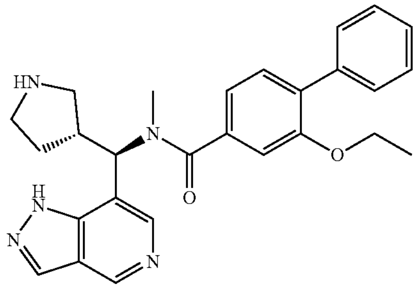
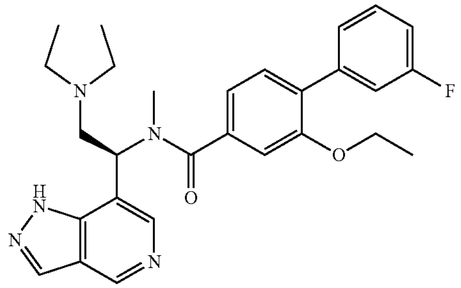
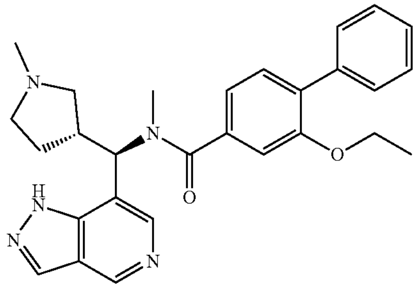
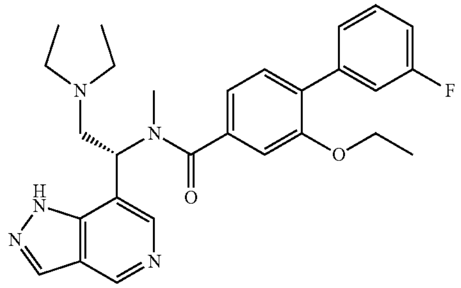
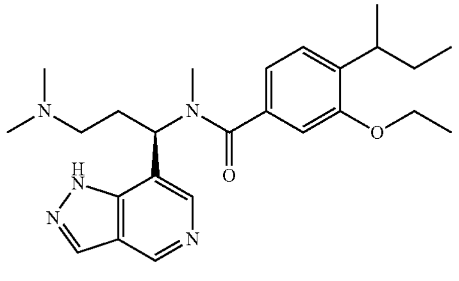
-continued
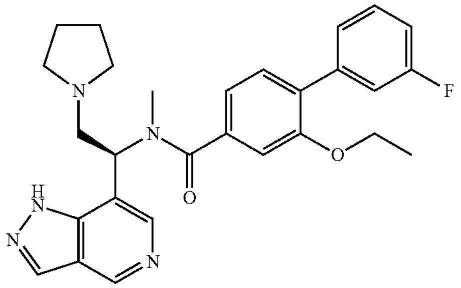
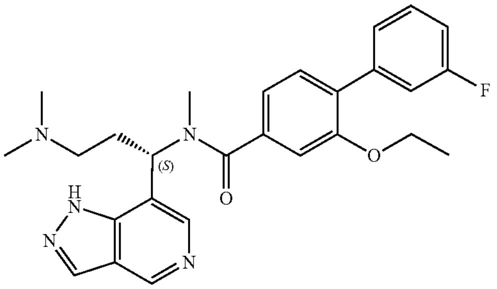
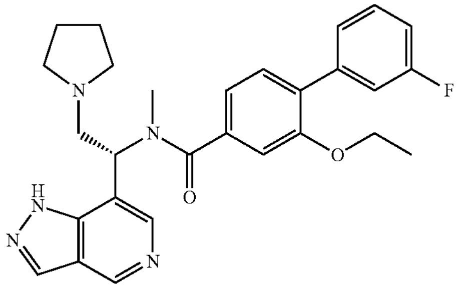
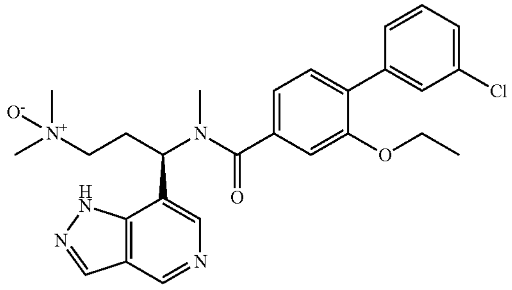
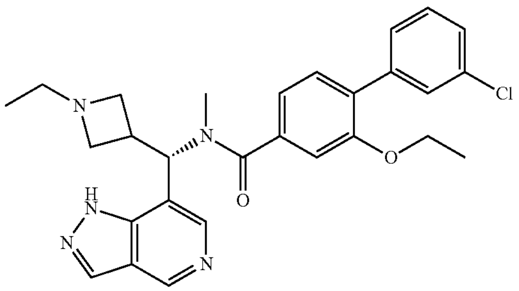
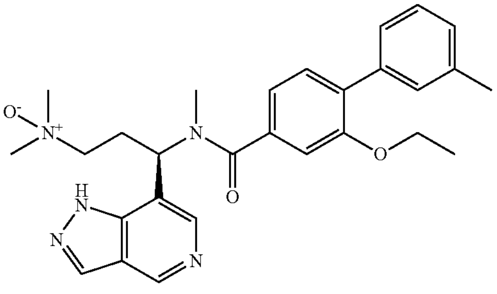

-continued
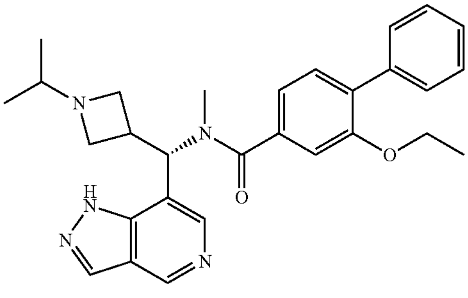
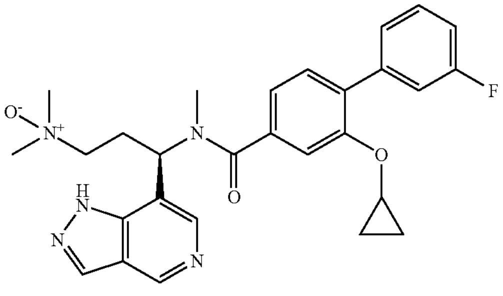
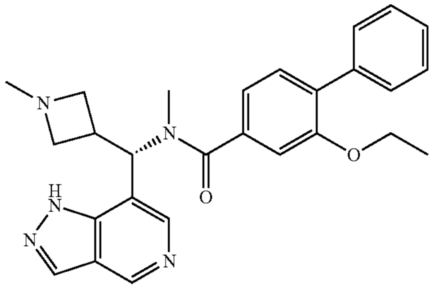
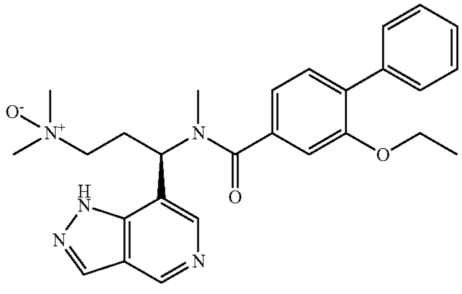
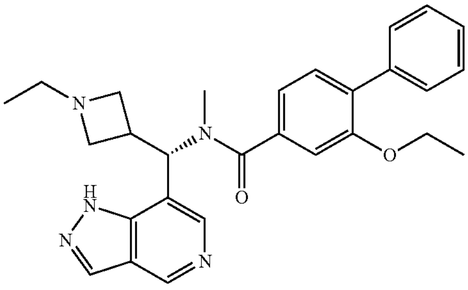
-continued
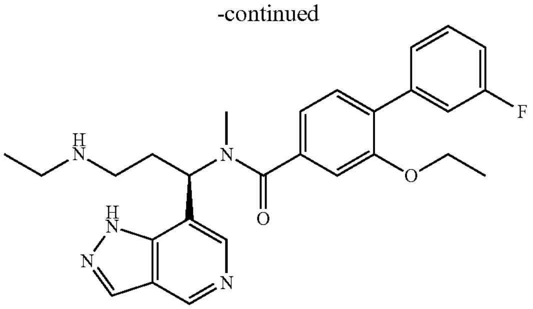
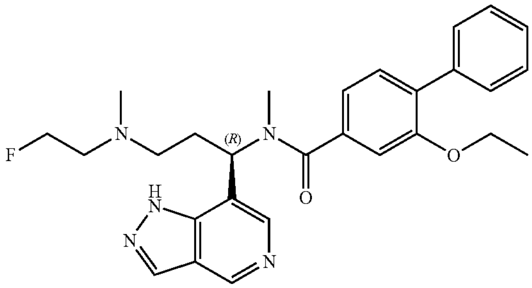
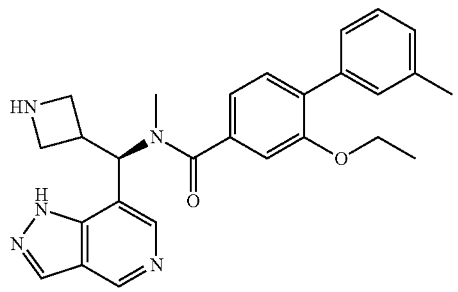
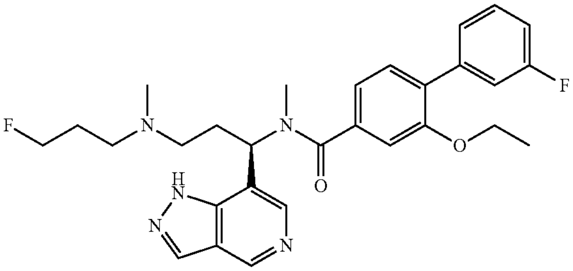
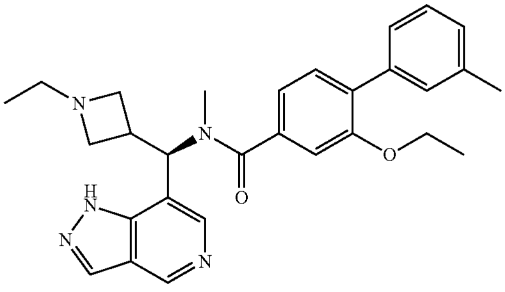
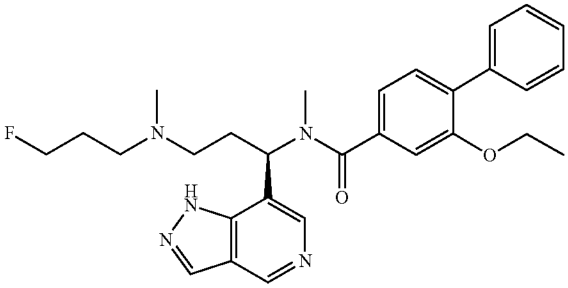

-continued
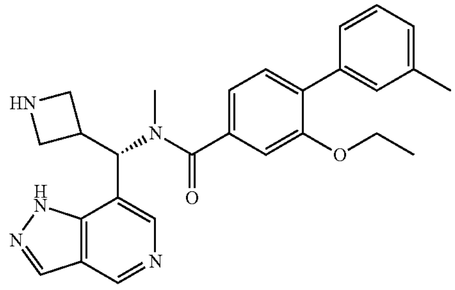
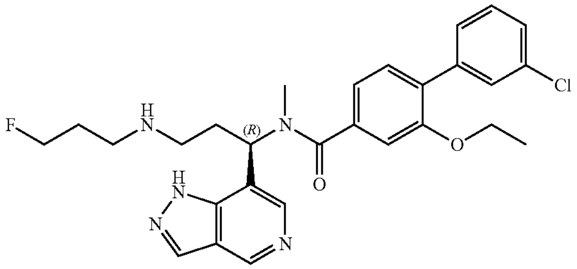
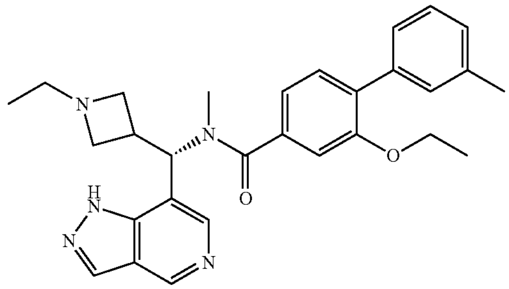
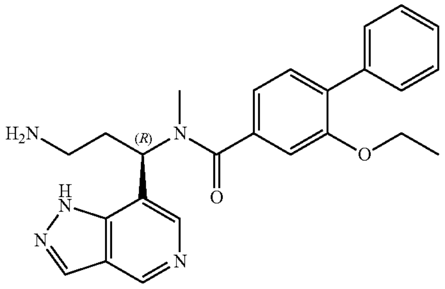
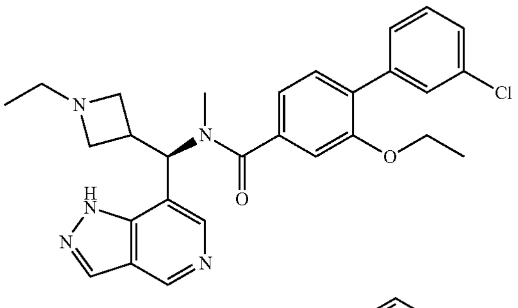
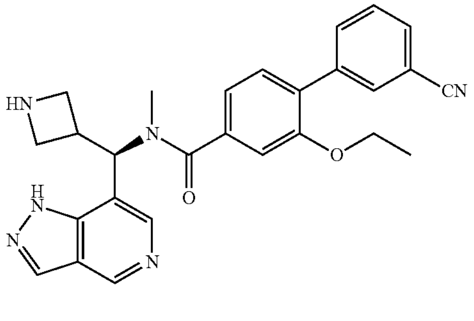
-continued
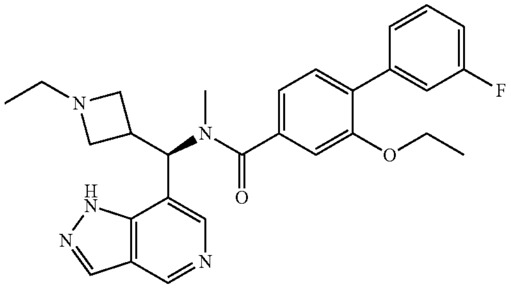
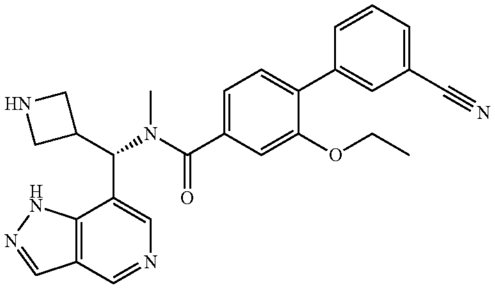
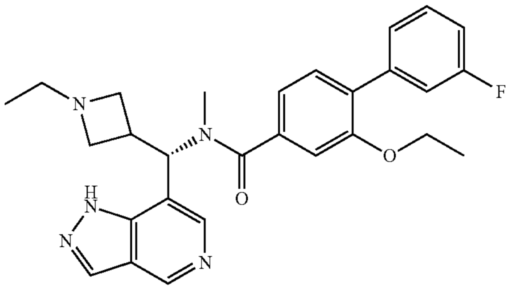
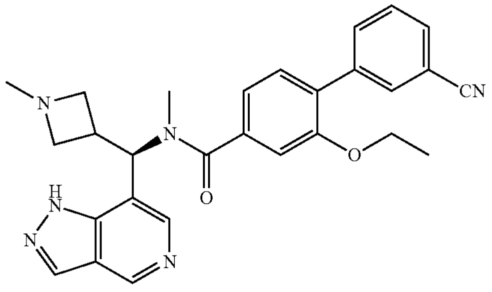
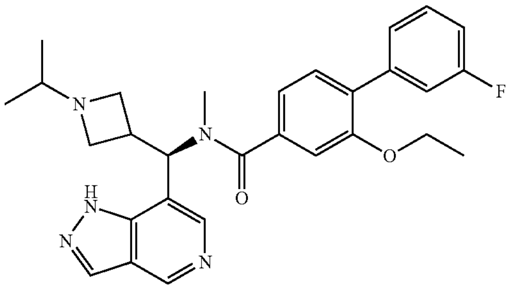

-continued
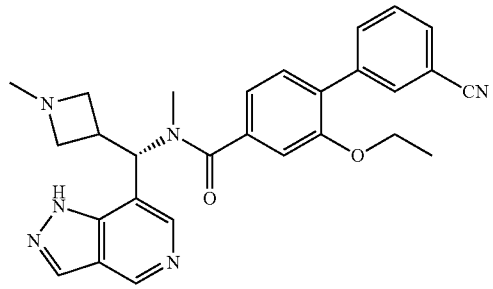
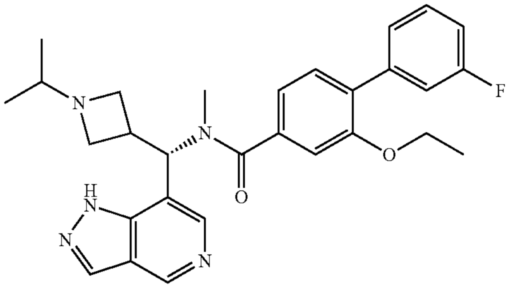
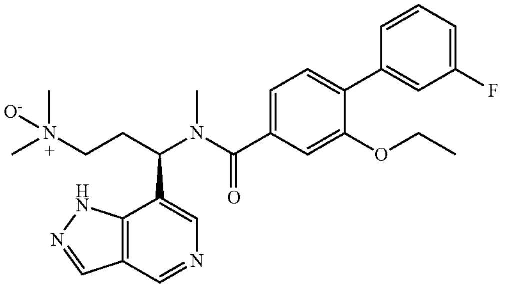
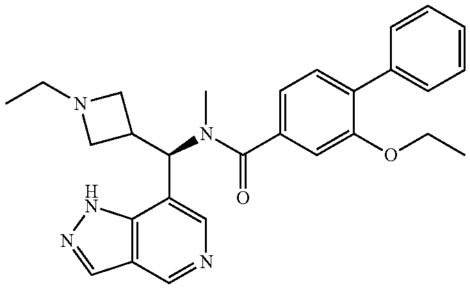
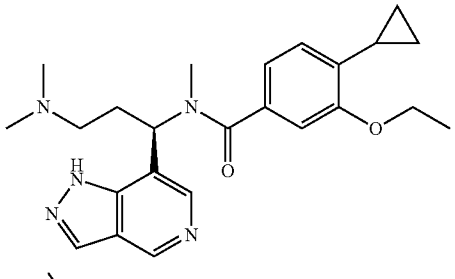
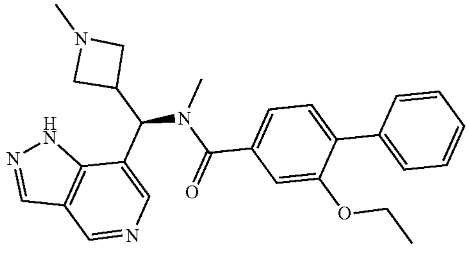
-continued
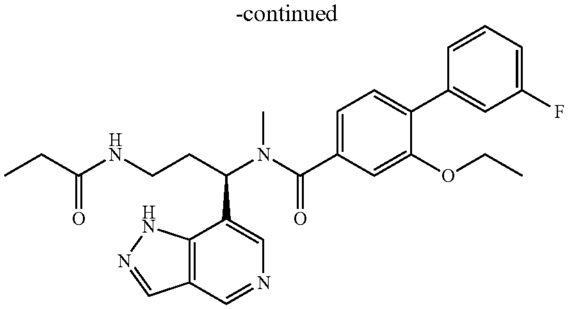
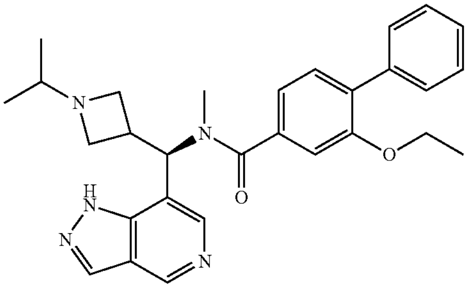
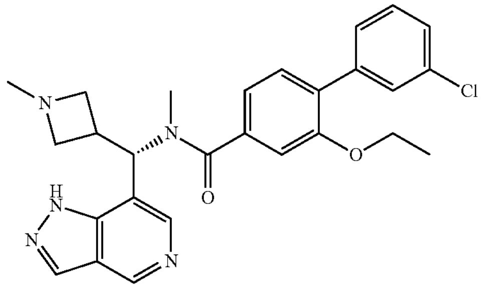
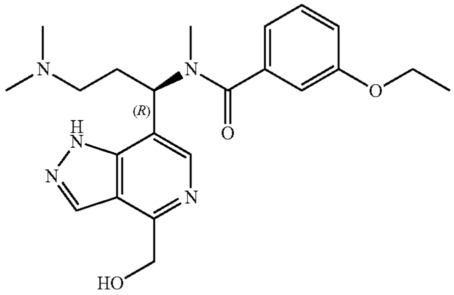
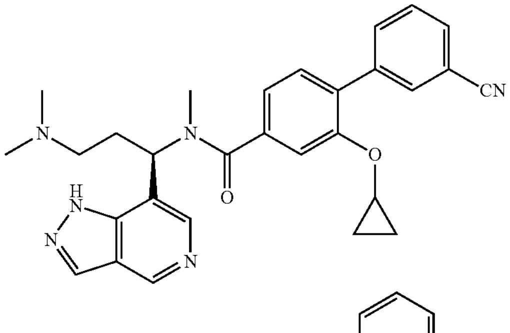
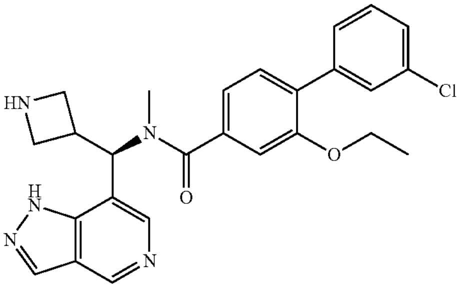

-continued
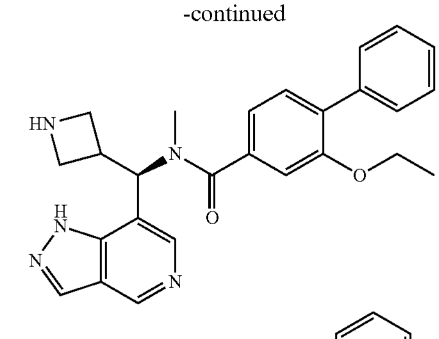
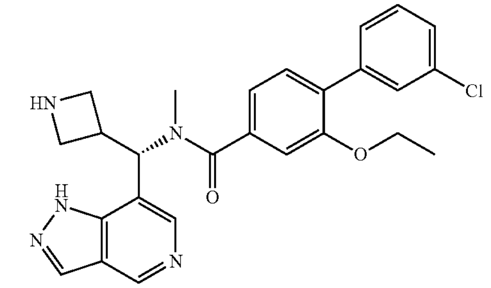
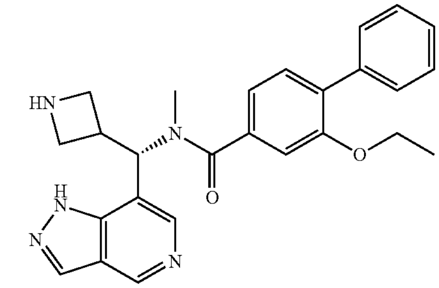
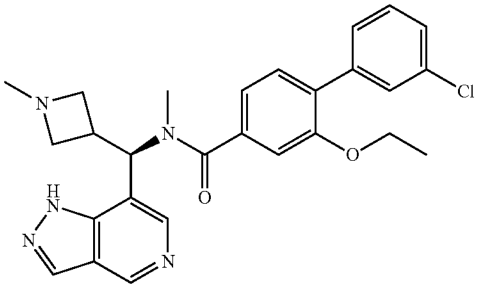
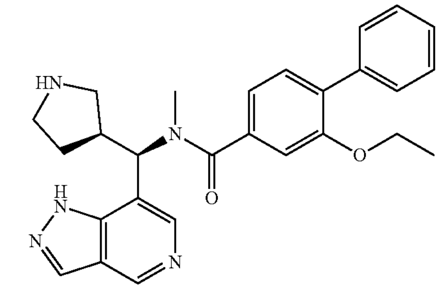
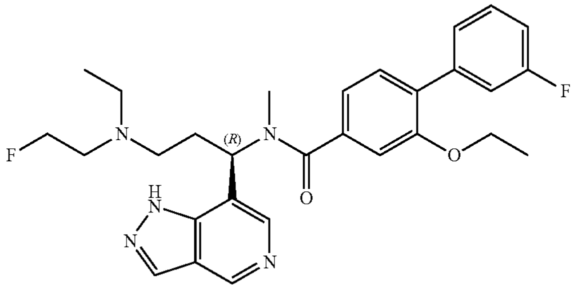
-continued
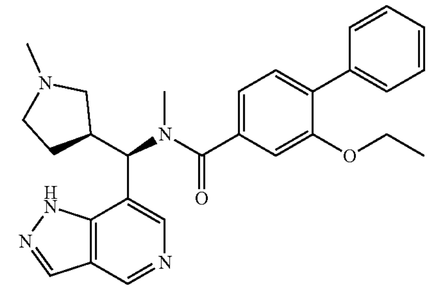
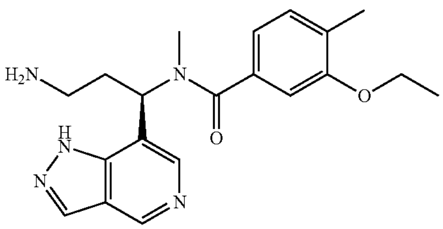
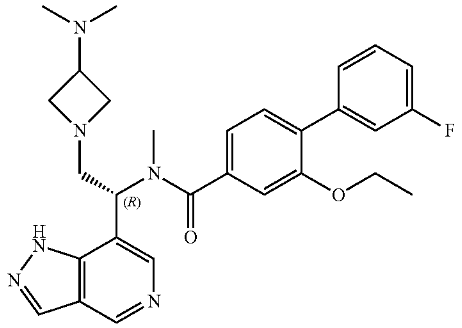
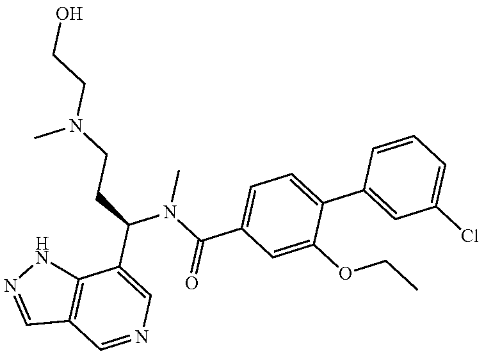
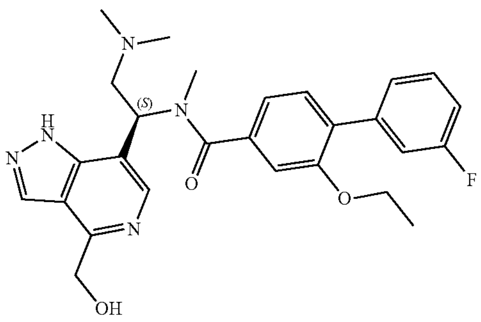

-continued
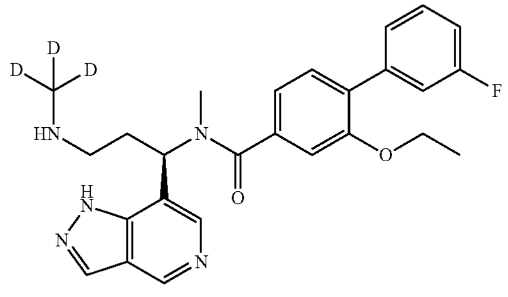
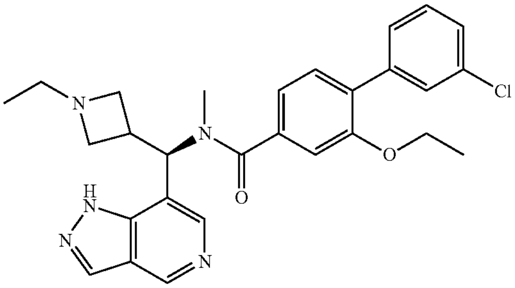
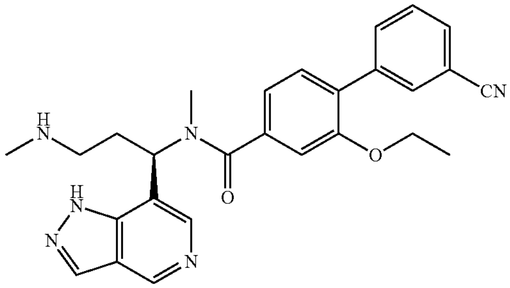
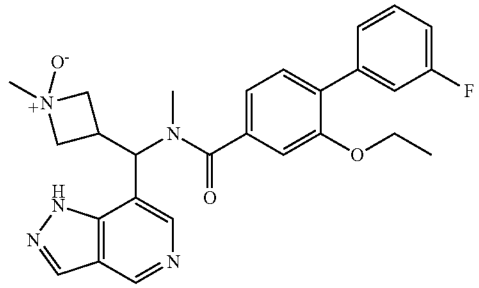
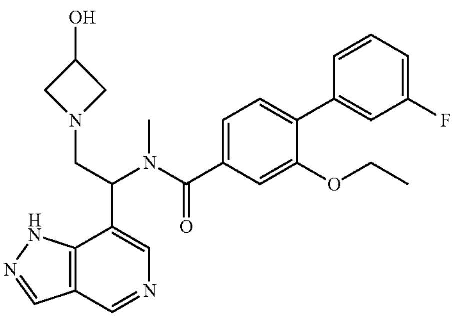
-continued
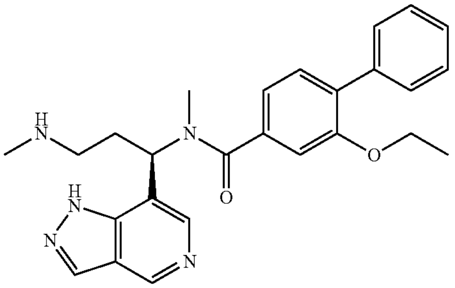
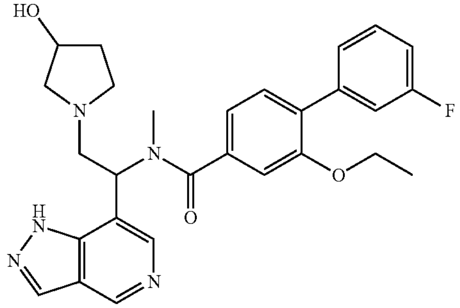
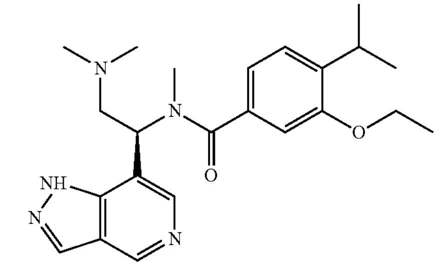
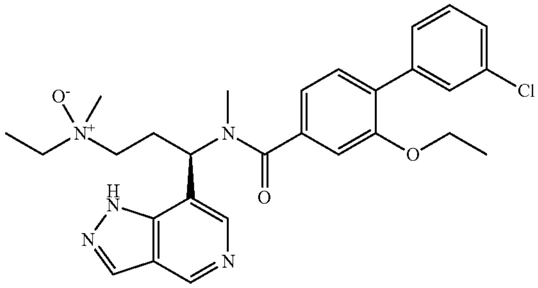
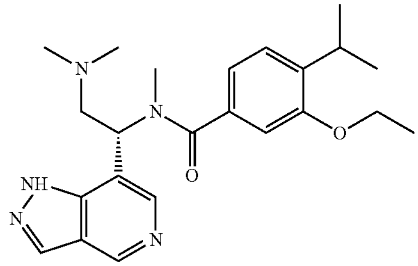
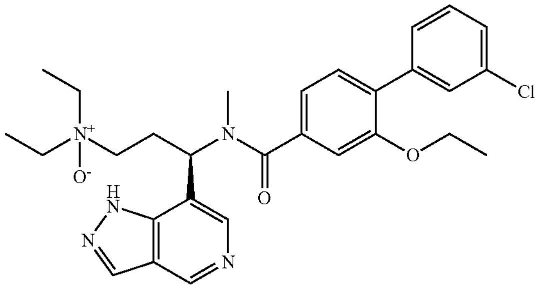

-continued
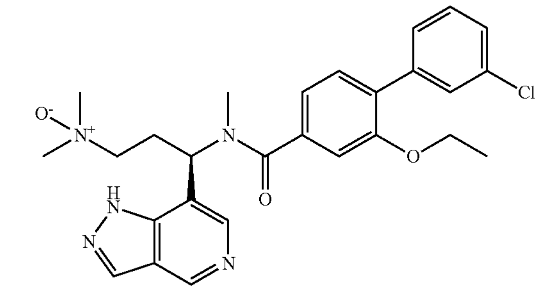
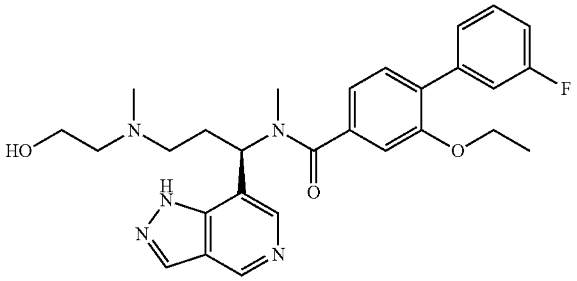
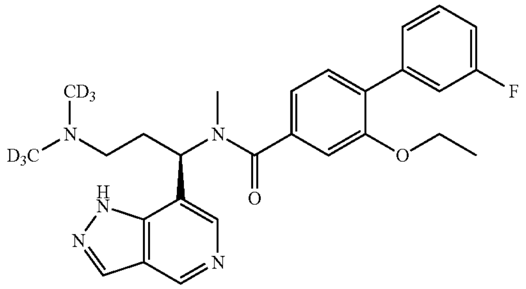
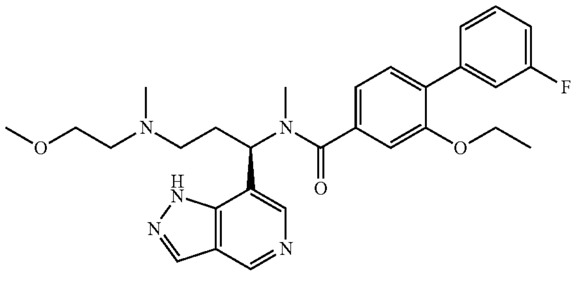
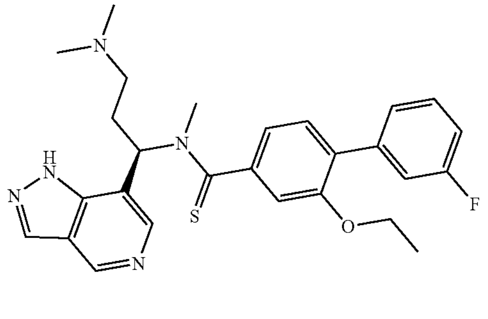
-continued
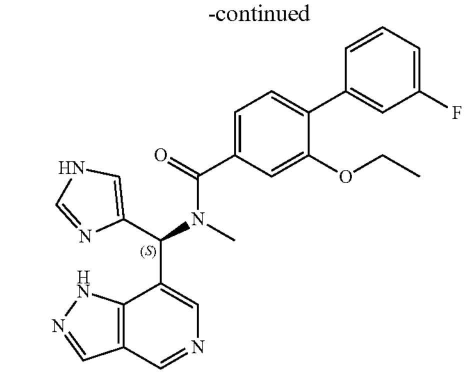
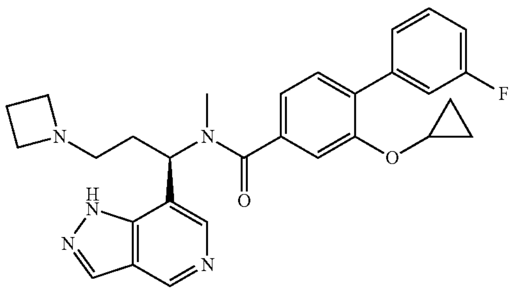
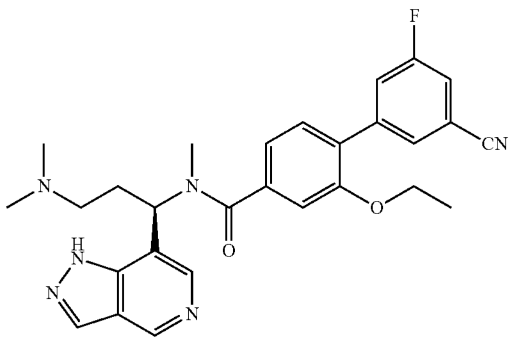
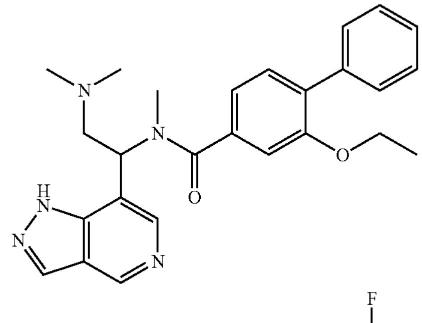
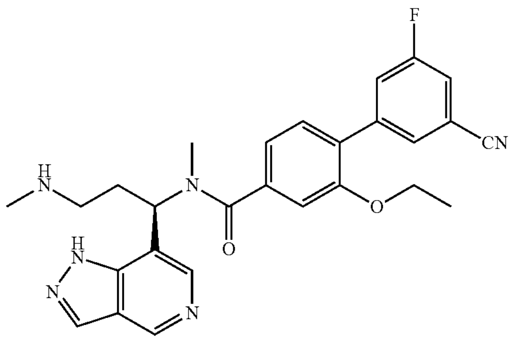

-continued

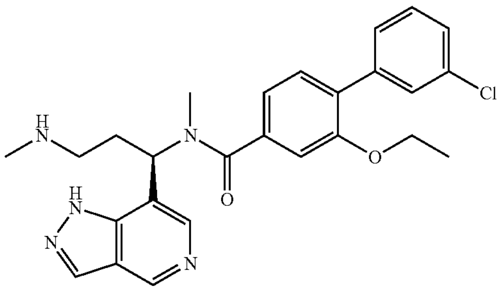

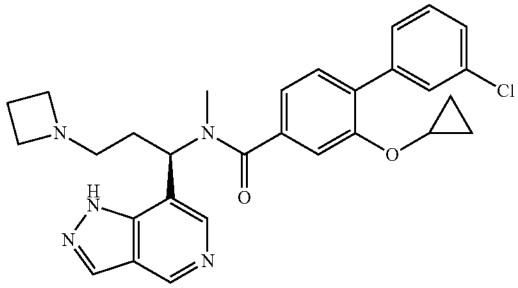

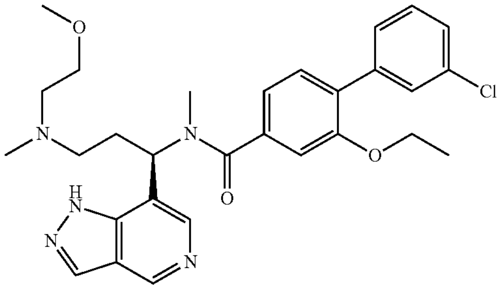

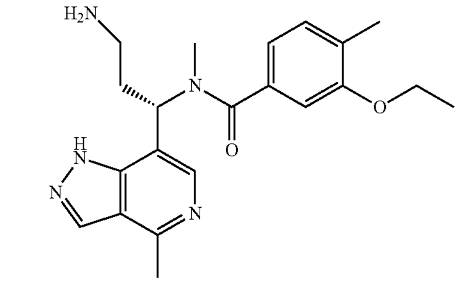

or a pharmaceutically acceptable salt thereof.

9. A compound of Formula II:

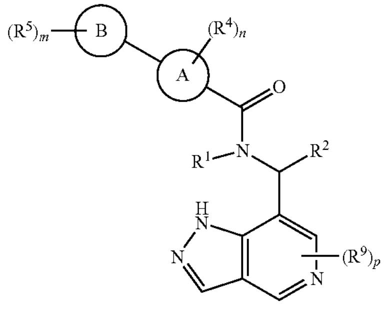

(II)

or a pharmaceutically acceptable salt thereof;

wherein

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of $C_{1-6}$ alkyl, $C_{3-6}$ cycloalkyl, $C_{0-6}$ alkylene-$C_{6-10}$ aryl, and 3-7 membered heterocycloalkyl, wherein $C_{1-6}$ alkyl, $C_{3-6}$ cycloalkyl, and $C_{0-6}$ alkylene-$C_{6-10}$ aryl are substituted with OH, halo, $SO_2R^6$, $OC(O)C_{1-6}$ alkyl, $C(O)C_{1-6}$ alkyl, 3-6 membered heterocycloalkyl, and $N(R^a)_2$, wherein 3-6 membered heterocycloalkyl is optionally substituted by one or two halo;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkyl-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, COR, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ alkoxy, $C_{1-6}$ alkyl-OH, $C_{1-6}$ alkyl-$NH(C_{1-3}$ alkyl), halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

10. The compound of claim 9, wherein

Ring A is $C_{6-10}$ aryl;

Ring B is $C_{6-10}$ aryl;

$R^1$ is selected from the group consisting of $C_{1-6}$ alkyl, $C_{3-6}$ cycloalkyl, $C_{1-6}$ alkoxy, $OC_{3-6}$ cycloalkyl, $O(C_{0-6}$ alkylene-$C_{6-10}$ aryl), and $C_{0-6}$ alkylene-$C_{6-10}$ aryl, all of which are substituted with OH, halo, $SO_2R^6$, $OC(O)C_{1-6}$ alkyl, $C(O)C_{1-6}$ alkyl, and $N(R^a)_2$;

each $R^a$ is independently H, $C_{1-6}$ alkyl, $C_{3-6}$ cycloalkyl, and $C(O)C_{1-6}$ alkyl;

$R^2$ is H or $C_{1-6}$ alkyl;

each $R^4$ is independently selected from the group consisting of halo, OH, $C_{1-6}$ alkoxy, $OC_{3-6}$ cycloalkyl, CN, and $C_{1-6}$ haloalkyl;

each $R^5$ is independently selected from the group consisting of $C_{1-6}$ alkyl, $C_{1-6}$ haloalkyl, halo, CN, $CONH_2$, and $CONH(C_{1-6}$ alkyl);

each $R^9$ is independently selected from the group consisting of $C_{1-6}$ alkyl, $C_{1-6}$ alkoxy, $C_{1-6}$ alkyl-OH, halo, CN, OH, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

11. The compound of claim 9, wherein

Ring A is phenyl;

Ring B is phenyl;

$R^1$ is selected from the group consisting of $C_{1-6}$ alkyl and $C_{3-6}$ cycloalkyl, both of which are substituted with OH;

$R^2$ is H or $C_{1-6}$ alkyl;

each $R^4$ is independently selected from the group consisting of halo, OH, $C_{1-6}$ alkoxy, $OC_{3-6}$ cycloalkyl, and $C_{1-6}$ haloalkyl;

each $R^5$ is independently selected from the group consisting of $C_{1-6}$ alkyl, $C_{1-6}$ haloalkyl, halo, CN, $CONH_2$, and $CONH(C_{1-6}$ alkyl);

each $R^9$ is independently selected from the group consisting of $C_{1-6}$ alkyl, $C_{1-6}$ alkoxy, $C_{1-6}$ alkyl-OH, halo, CN, OH, $NH_2$, $NH(C_{1-6}$ alkyl), and $N(C_{1-6}$ alkyl$)_2$;

m is 0, 1, or 2;

n is 0, 1, or 2; and p is 0 or 1.

12. The compound of claim 9, wherein the compound of Formula II is a compound of Formula IIa:

(IIa)

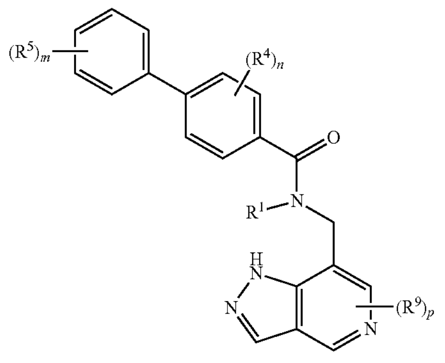

or a pharmaceutically acceptable salt thereof.

13. The compound of claim 9, wherein $R^1$ is $C_{1-6}$ alkyl substituted by OH.

14. The compound of claim 9, wherein each $R^4$ is independently selected from the group consisting of $C_{1-6}$ alkoxy and $OC_{3-6}$ cycloalkyl;

each $R^5$ is independently selected from the group consisting of halo, CN, $CONH_2$, and $CONH(C_{1-6}$ alkyl); and each $R^9$ is independently selected from the group consisting of $C_{1-6}$ alkyl-OH, halo, OH, $NH_2$, $NH(C_{1-6}$ alkyl), and $N(C_{1-6}$ alkyl$)_2$.

15. The compound of claim 9, wherein m is 0, 1, or 2;

n is 1; and p is 0 or 1.

16. The compound of claim 9, wherein the compound of Formula II is selected from

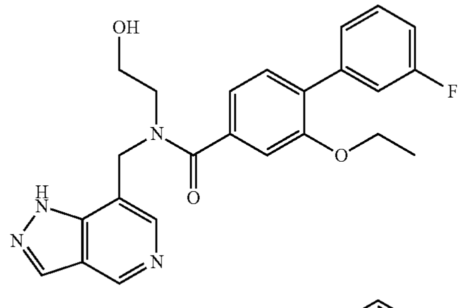

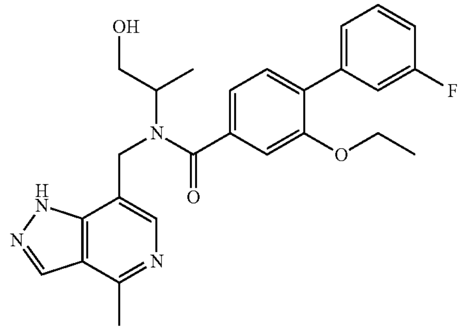

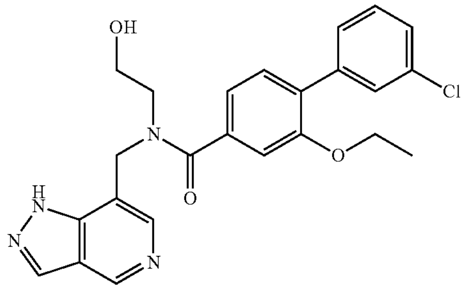

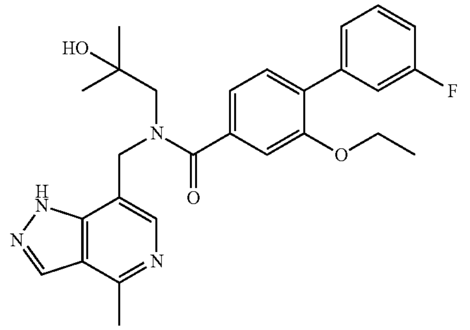

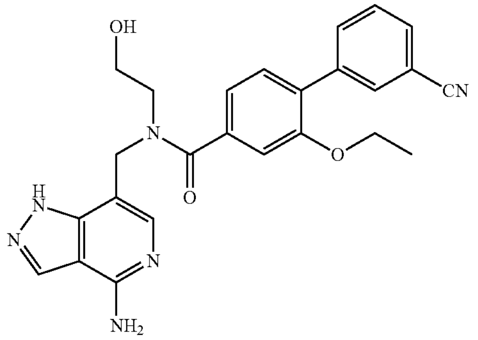

-continued
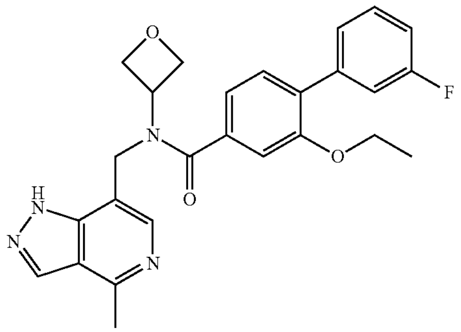
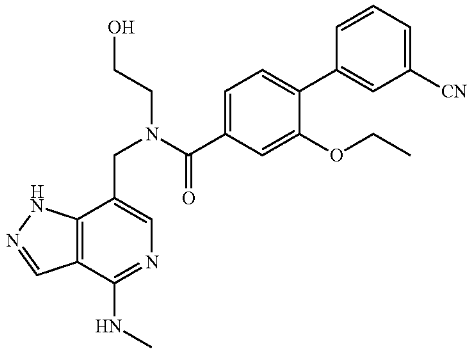
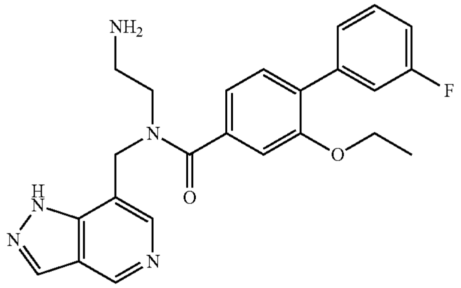
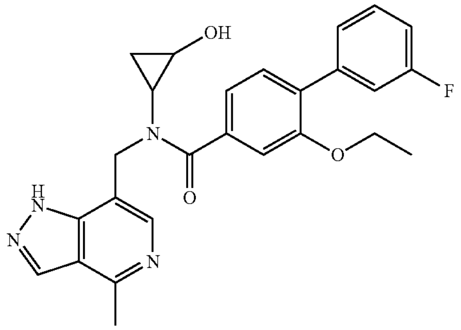
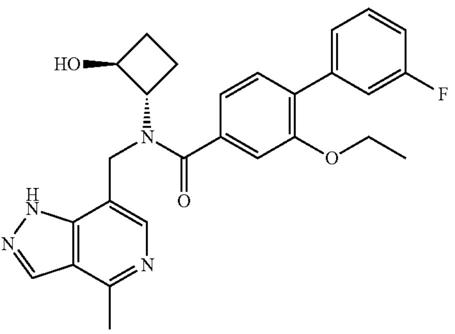
-continued
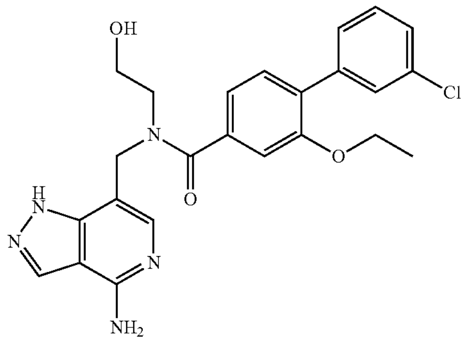
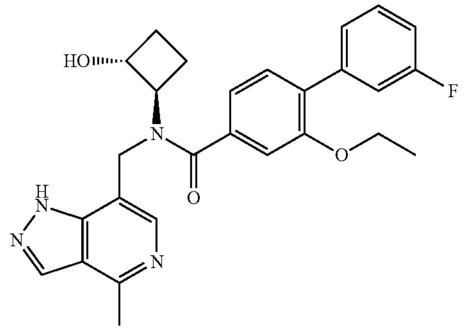
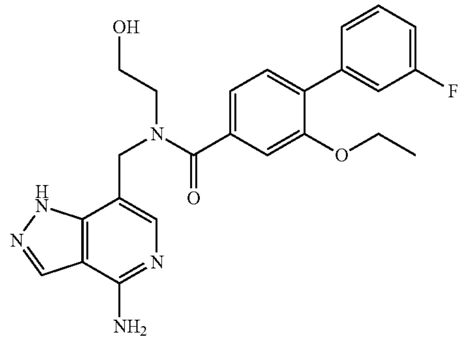
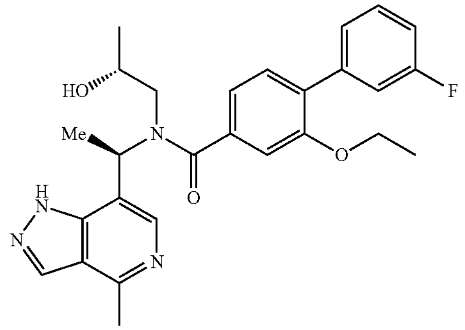
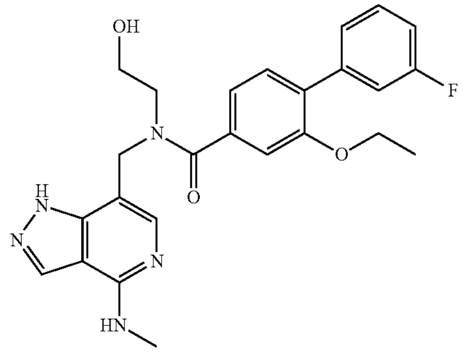

-continued
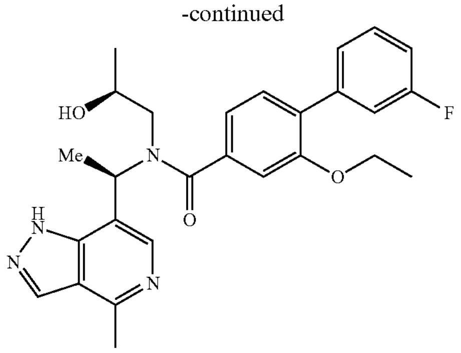
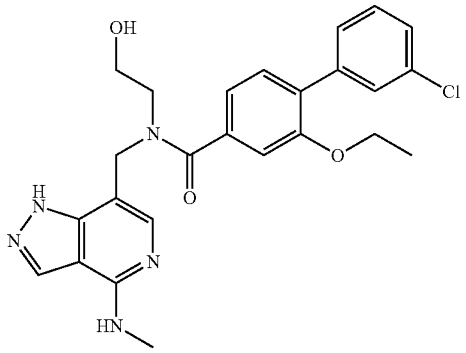
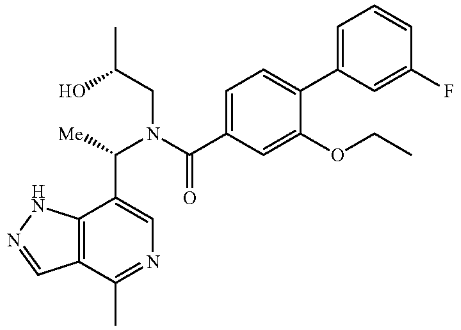
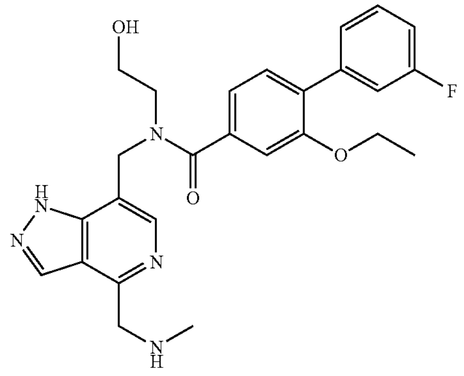
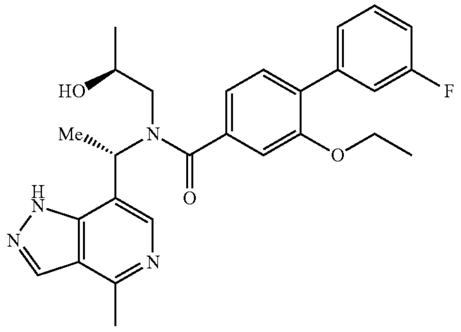
-continued
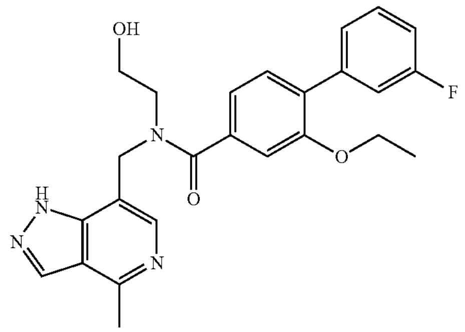
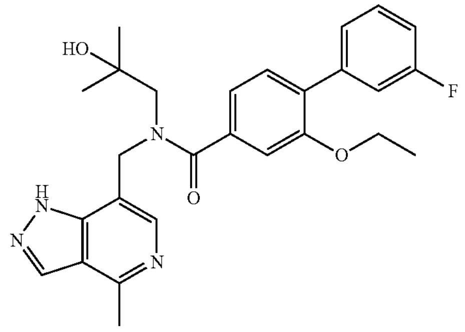
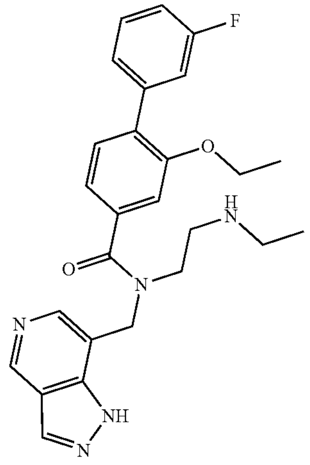
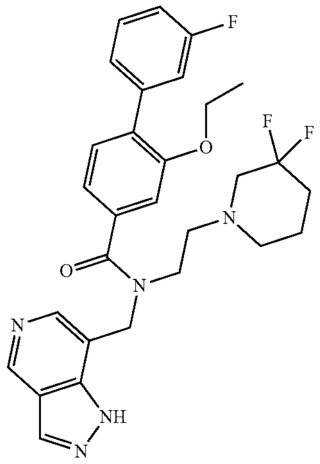

-continued
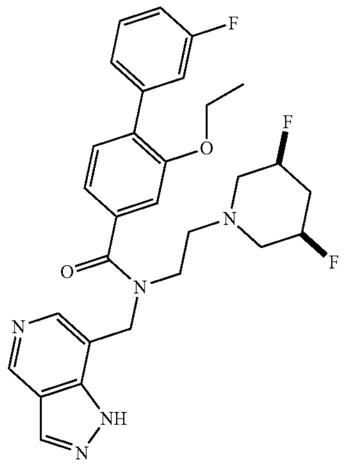
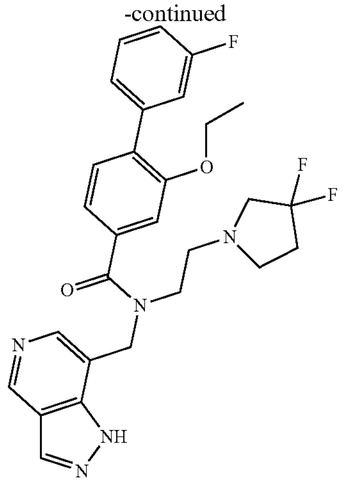
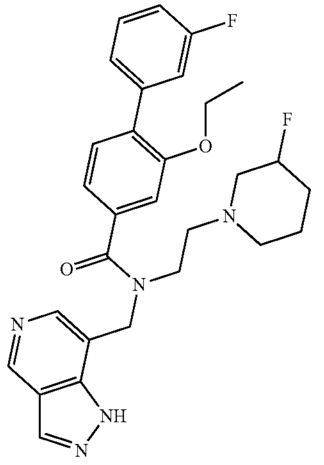
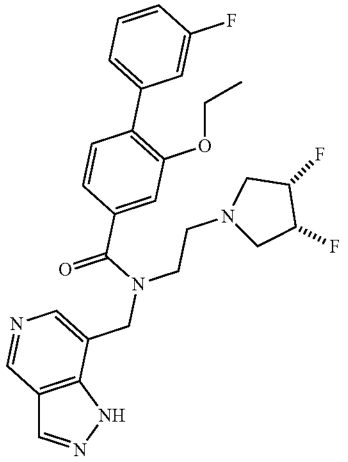
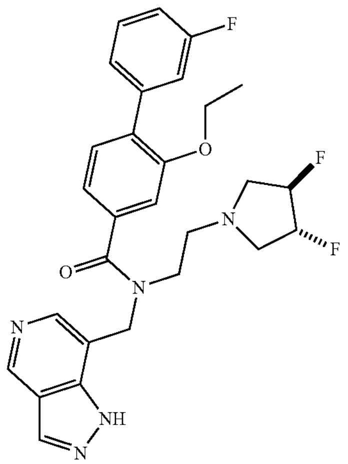
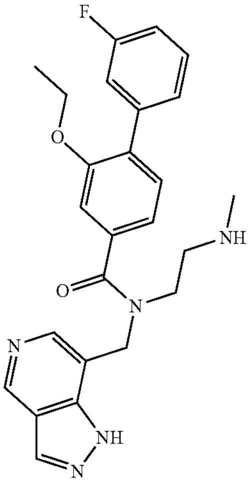
-continued -continued
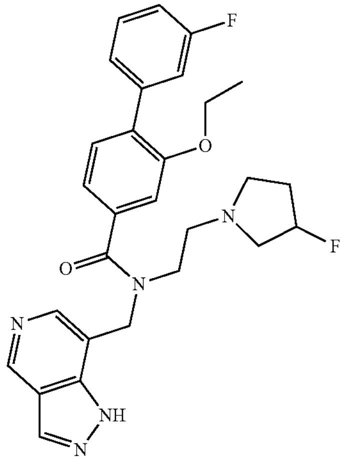
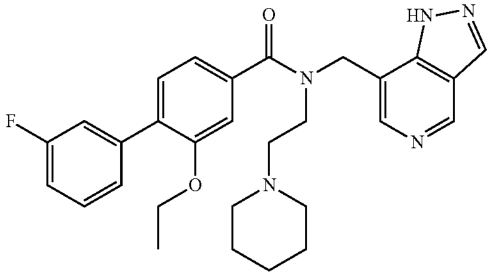
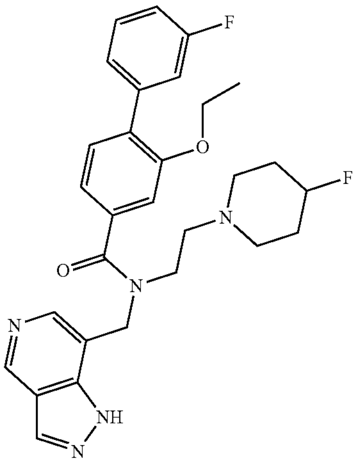
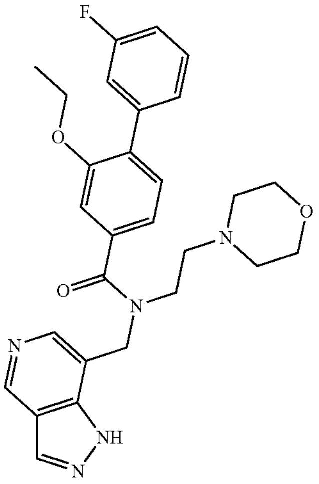
-continued
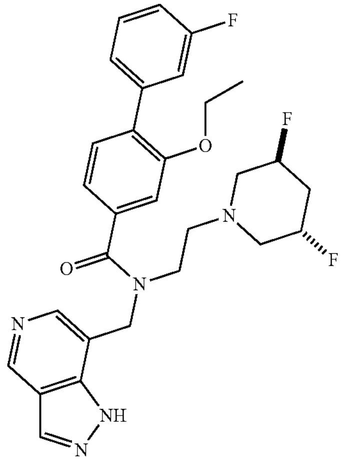
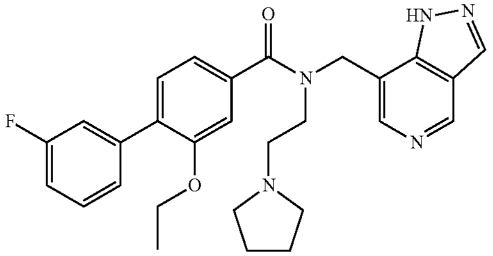
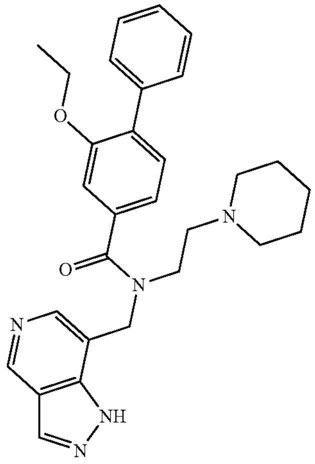
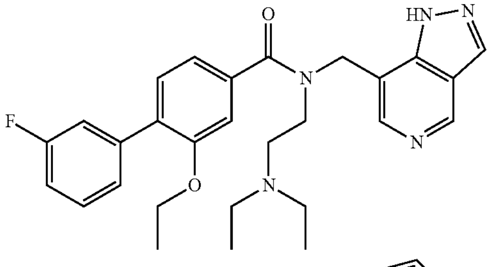
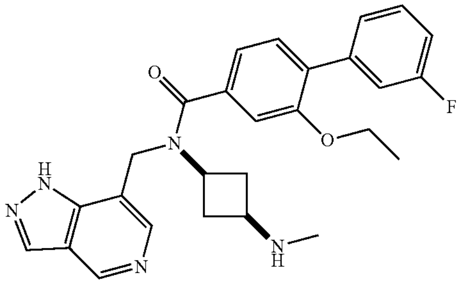

-continued
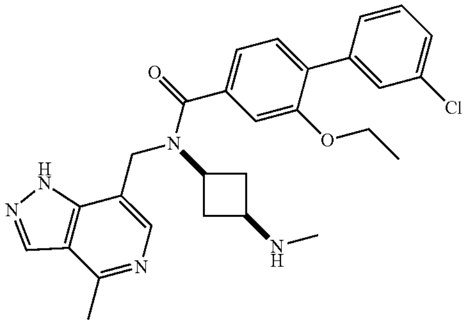
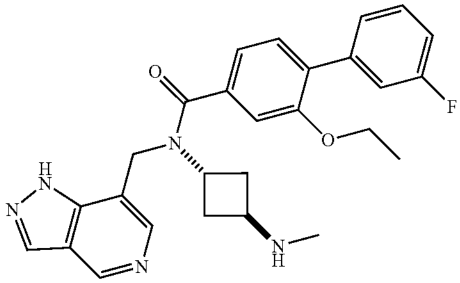
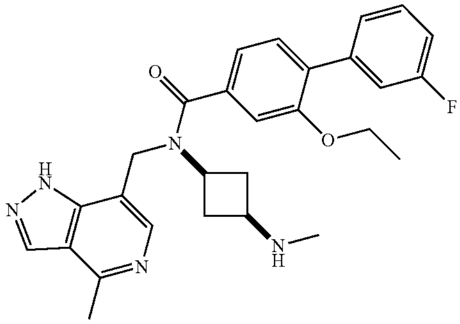
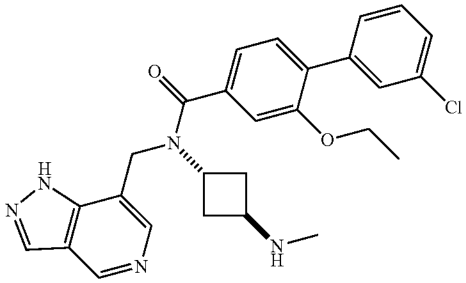
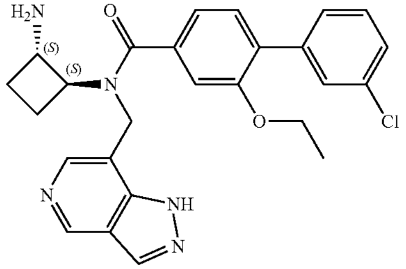
-continued
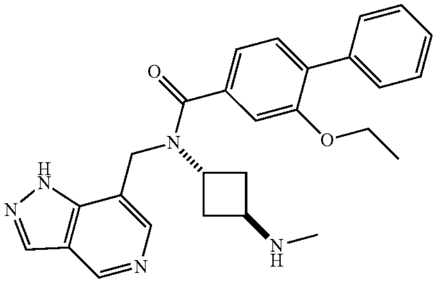
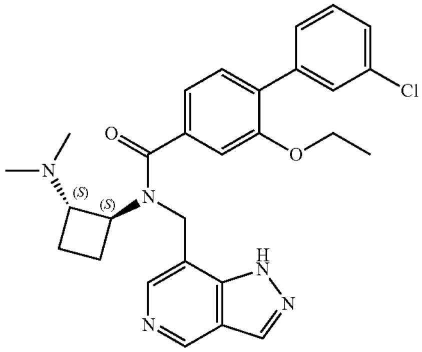
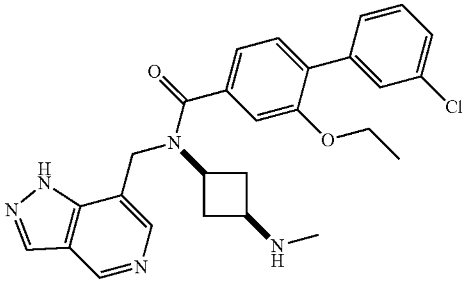
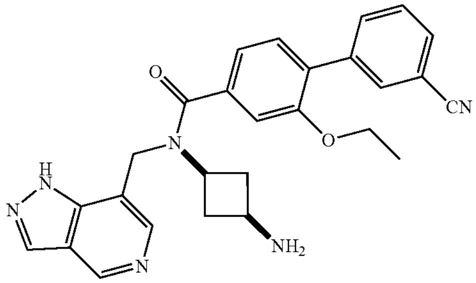
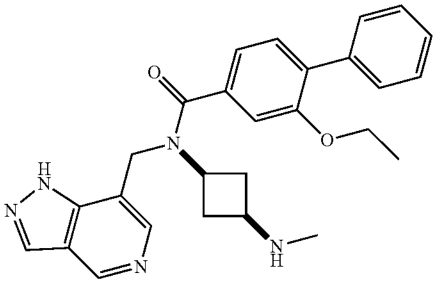

-continued
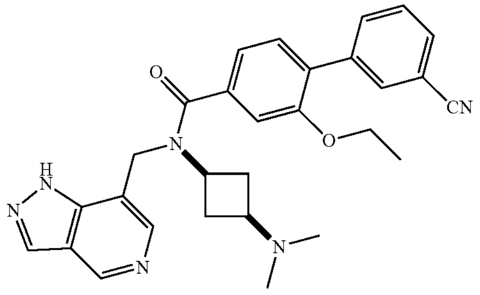
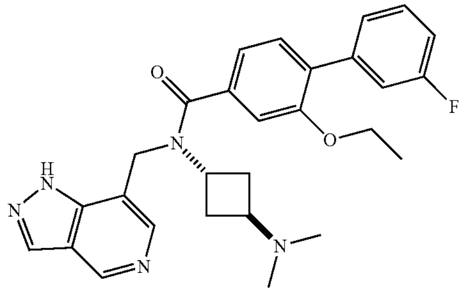
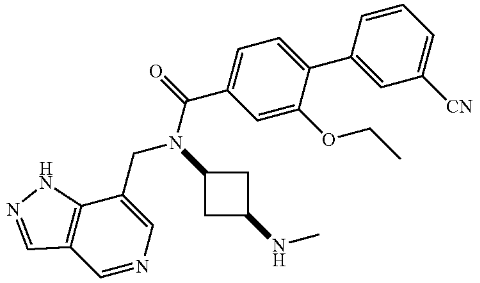
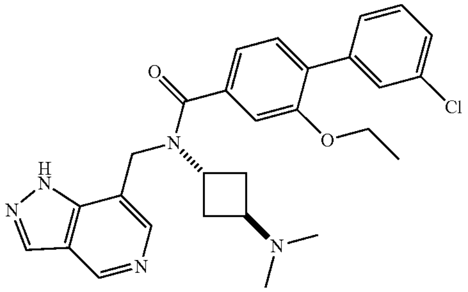
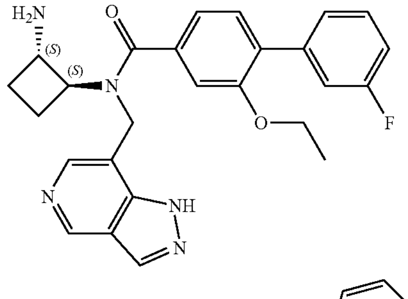
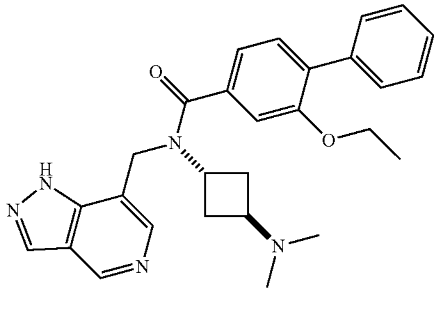
-continued
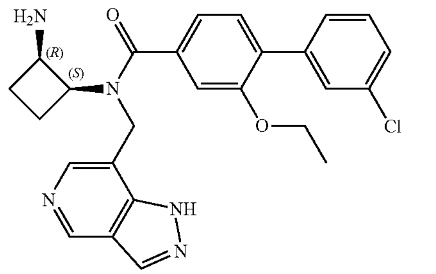
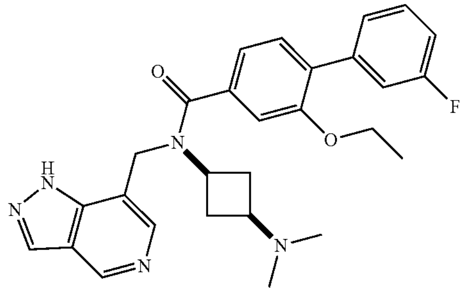
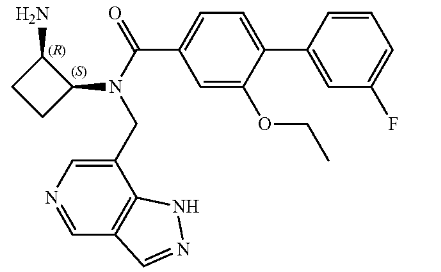
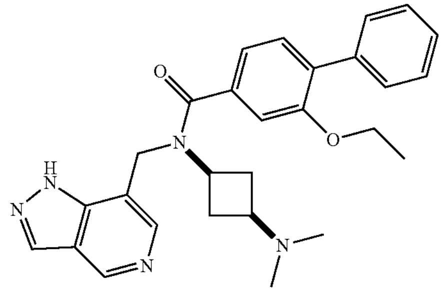
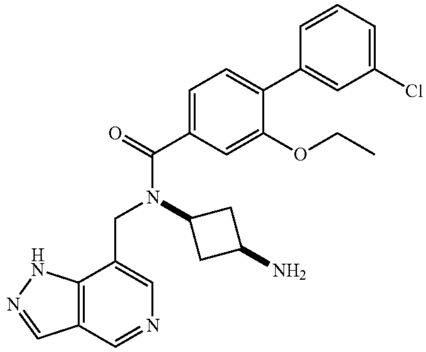

-continued

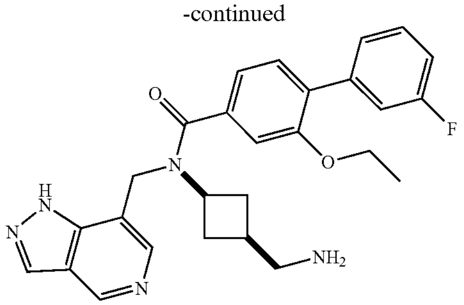

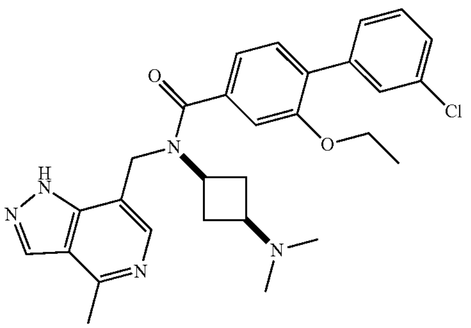

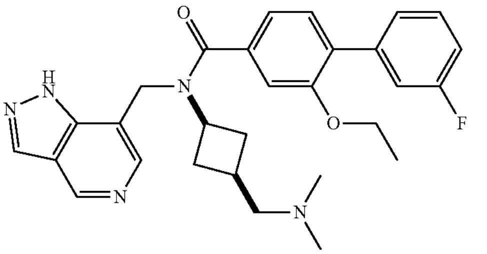

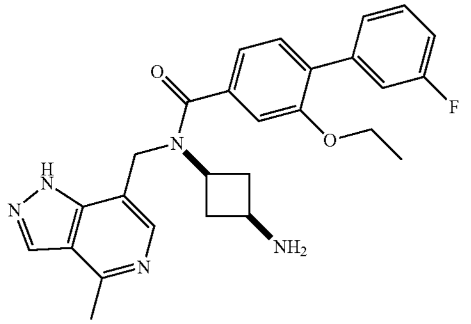

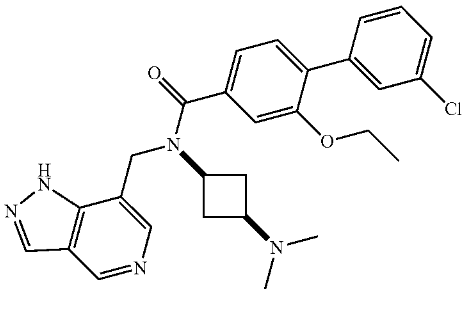

-continued

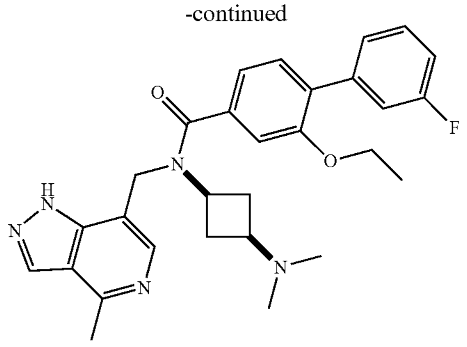

or a pharmaceutically acceptable salt thereof.

17. A compound of Formula III:

(III)

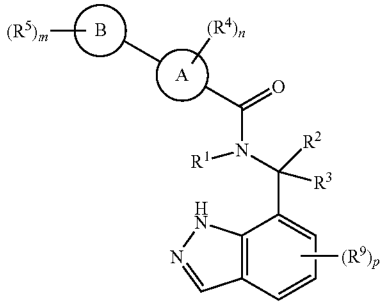

or a pharmaceutically acceptable salt thereof;

wherein

Ring A is selected from the group consisting of $C_{6-10}$ aryl, $C_{3-10}$ cycloalkyl, and 4-10 membered heterocycloalkyl;

Ring B is selected from the group consisting of $C_{6-10}$ aryl, 5-6 membered heteroaryl, $C_{3-6}$ cycloalkyl, and 3-6 membered heterocycloalkyl;

alternatively, Ring B and $R^5$ are absent;

$R^1$ is selected from the group consisting of H, $C_{1-6}$ alkyl, $C_{3-6}$ cycloalkyl, $OC_{3-6}$ cycloalkyl, $O(C_{0-6}$ alkylene-$C_{6-10}$ aryl), and $C_{0-6}$ alkylene-$C_{6-10}$ aryl, wherein alkyl and cycloalkyl are optionally substituted with OH, OC(O)$C_{1-6}$ alkyl, C(O)$C_{1-6}$ alkyl, $N(R^a)_2$, and halo;

each $R^a$ is independently H, $C_{1-6}$ alkyl, $C_{3-6}$ cycloalkyl, and C(O)$C_{1-6}$ alkyl;

$R^2$ is H or $C_{1-6}$ alkyl;

$R^3$ is selected from the group consisting of H, $C_{1-6}$ alkyl, $C_{3-6}$ cycloalkyl, 3-6 membered heterocycloalkyl, and 5-10 membered heteroaryl, wherein $C_{1-6}$ alkyl and $C_{3-6}$ cycloalkyl are substituted by OH, $C_{1-6}$ alkoxy, $NH_2$, NH($C_{1-6}$ alkyl), N($C_{1-6}$ alkyl)($C_{1-6}$ haloalkyl), NH($C_{1-6}$ haloalkyl), N($C_{1-6}$ alkyl)$_2$, N($C_{1-6}$ haloalkyl)$_2$, halo, $SO_2R^6$, $NHCOR^6$, 3-6 membered heterocycloalkyl optionally substituted with one or two halo or OH, or $C_{0-3}$ alkylene-5-10 membered heteroaryl, wherein 3-6 membered heterocycloalkyl is independently optionally oxidized and independently optionally substituted by $C_{1-6}$ alkyl; and the nitrogen atom of $NH_2$, NH($C_{1-6}$ alkyl), N($C_{1-6}$ alkyl)($C_{1-6}$ haloalkyl), NH($C_{1-6}$ haloalkyl), N($C_{1-6}$ alkyl)$_2$, and N($C_{1-6}$ haloalkyl)$_2$ is optionally oxidized and one or more carbon atoms of the alkyl groups on the nitrogen atom are optionally substituted with 1-6 deuterium atoms or $C_{1-6}$ alkoxy;

alternatively, $R^2$ and $R^3$, together with the atom to which they are attached, form a ring selected from the group consisting of $C_{3-7}$ cycloalkyl and 3-7 membered heterocycloalkyl, both of which are substituted by OH, $C_{1-6}$ alkoxy, or $C_{1-4}$ alkylene-O—$C_{1-4}$ alkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkylene-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkylene-$C_{6-10}$ aryl, $C_{0-6}$ alkylene-5-10 membered heteroaryl, $C_{1-6}$ alkoxy, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $C_{1-6}$ alkoxy, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $C_{1-6}$ alkoxy, halo, $NH_2$, $NH(C_{1-6}$ alkyl), and $N(C_{1-6}$ alkyl$)_2$;

each $R^9$ is independently selected from the group consisting of $C_{1-6}$ alkyl, CN, $SO_2R^6$, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

18. The compound of claim 17, wherein the compound of Formula III is a compound selected from

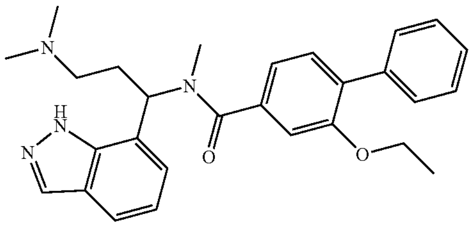

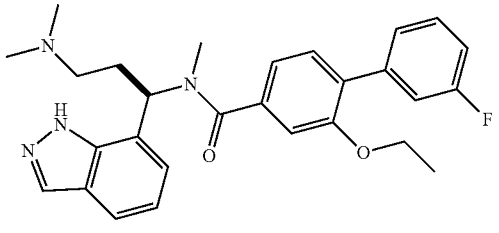

-continued

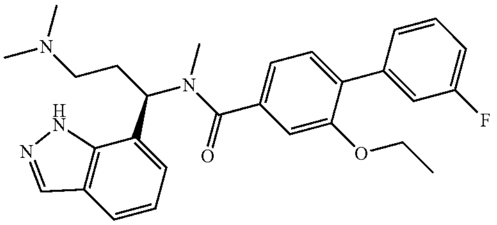

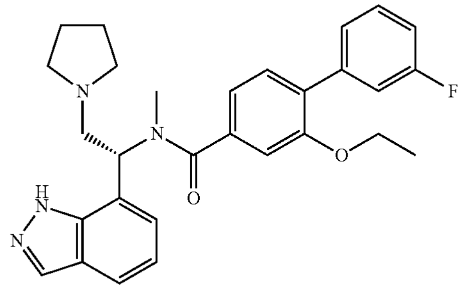

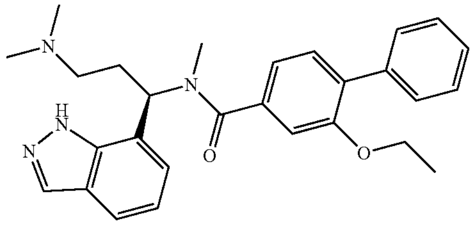

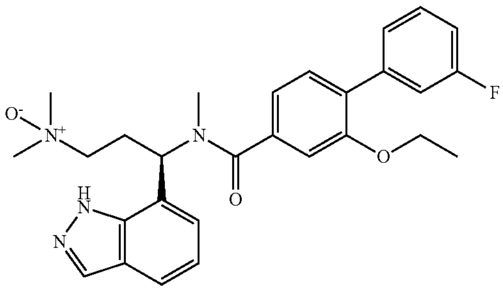

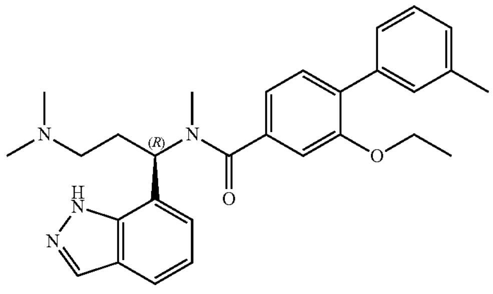

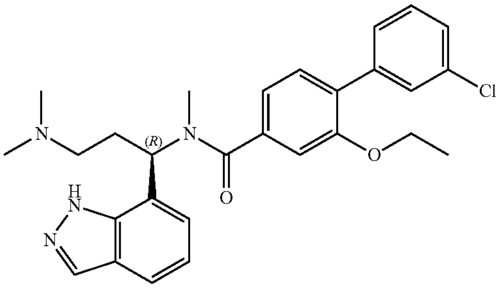

-continued
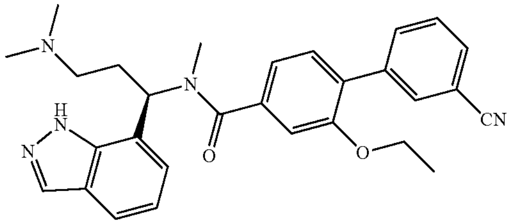
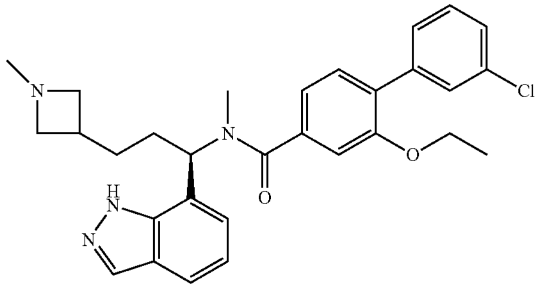
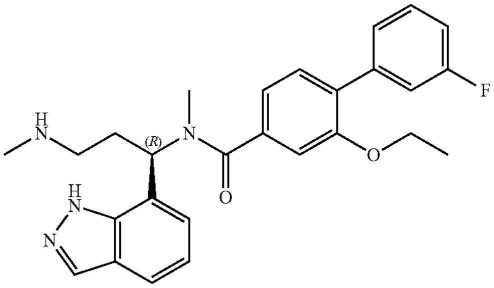
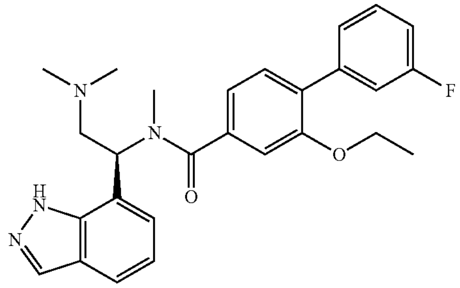
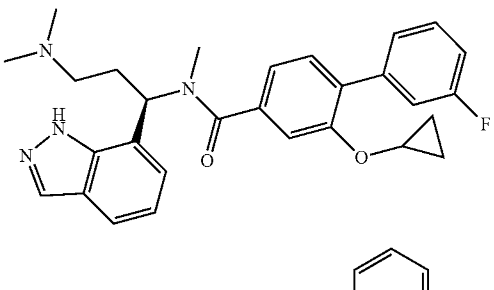
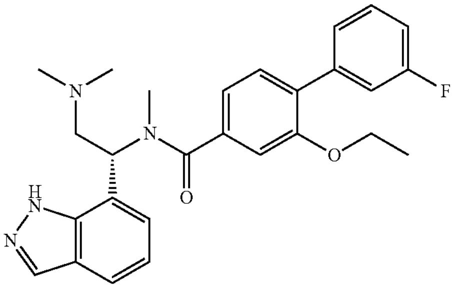
-continued
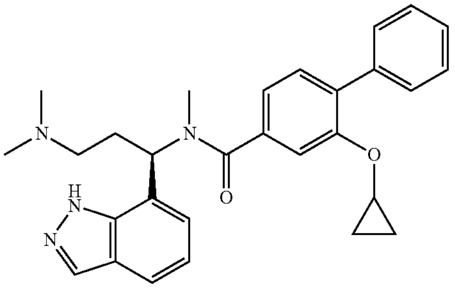
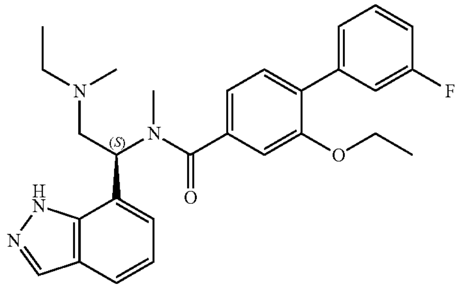
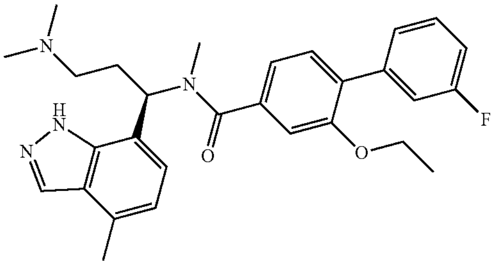
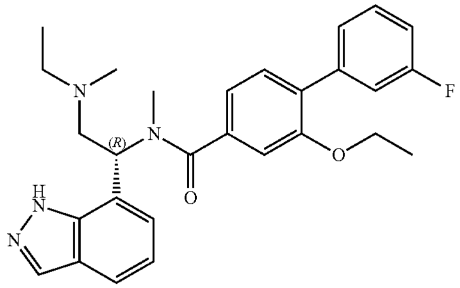
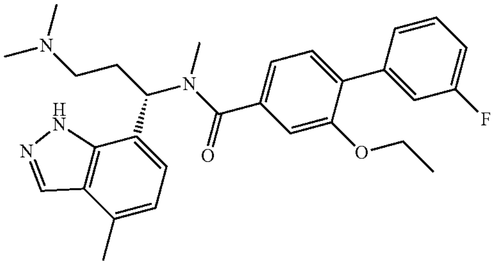
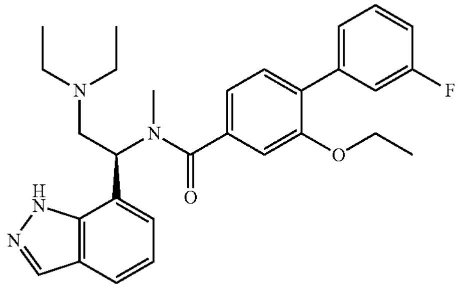

-continued
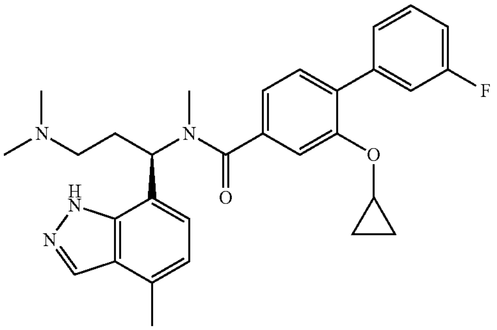
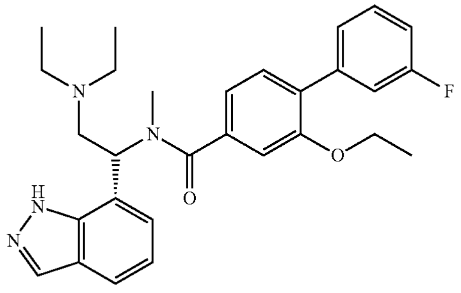
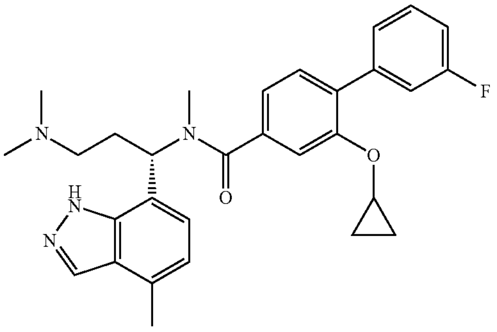
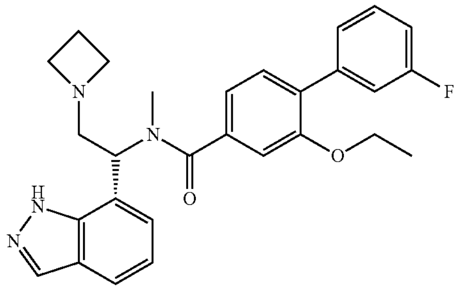
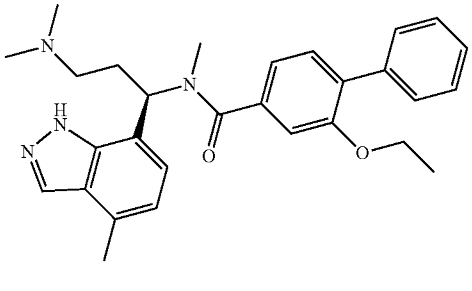
-continued
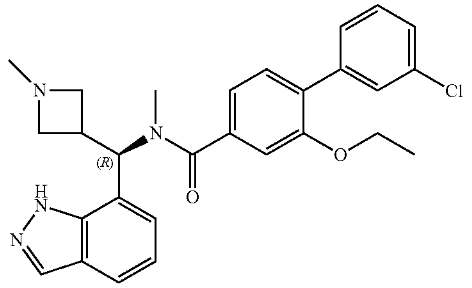
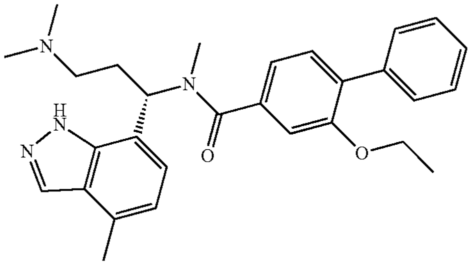
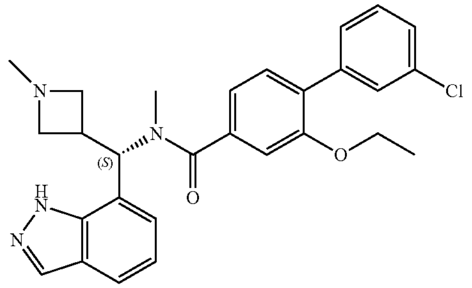
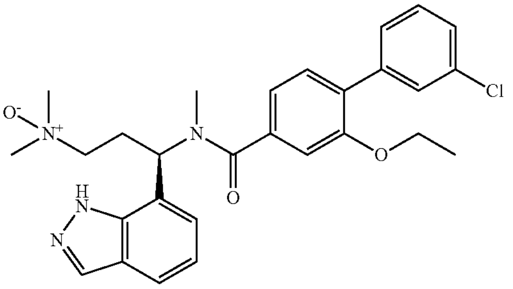
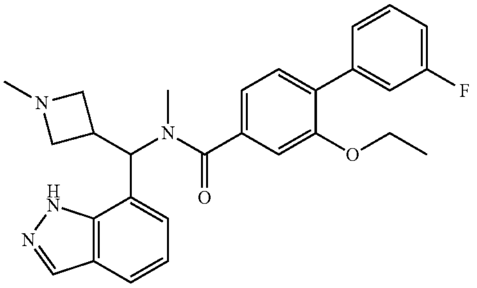
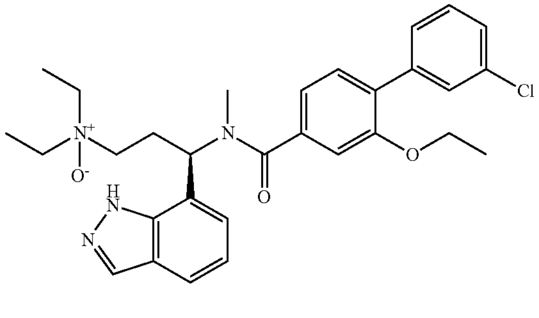

-continued
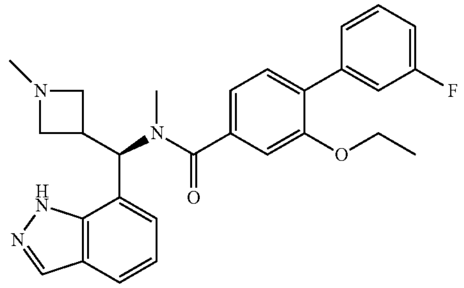
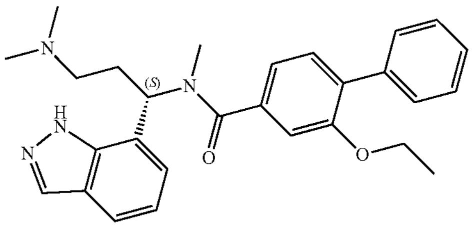
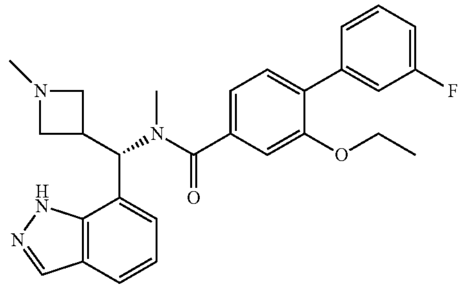
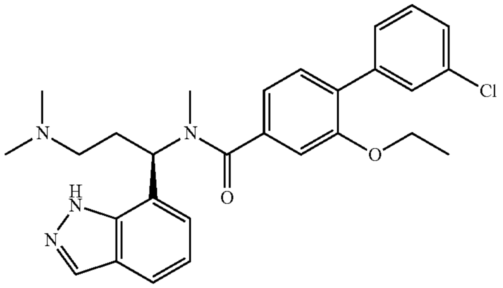
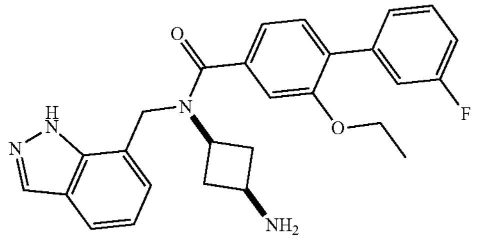
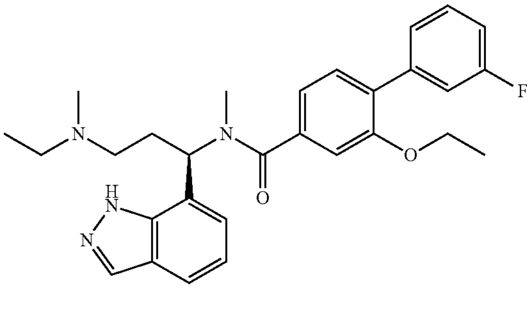
-continued
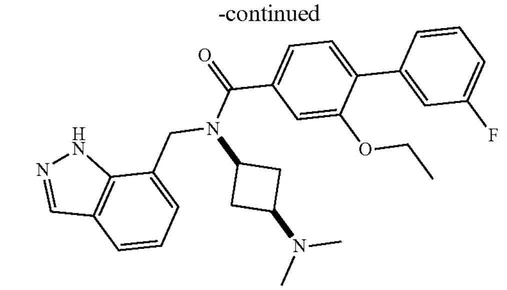
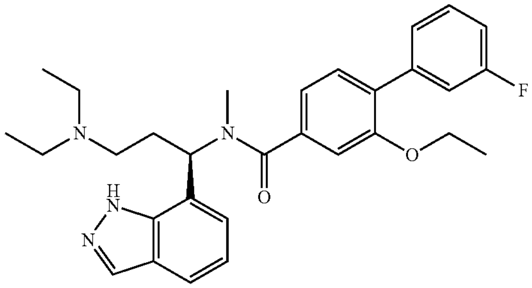
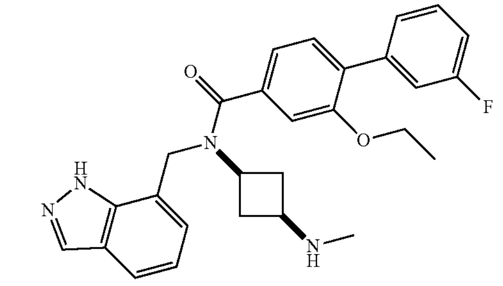
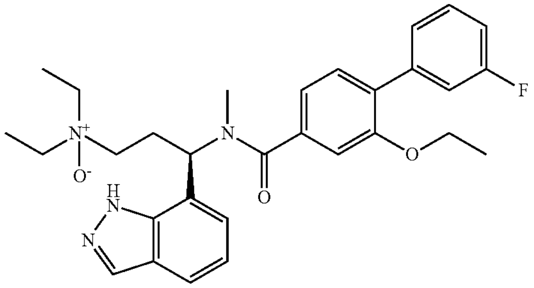
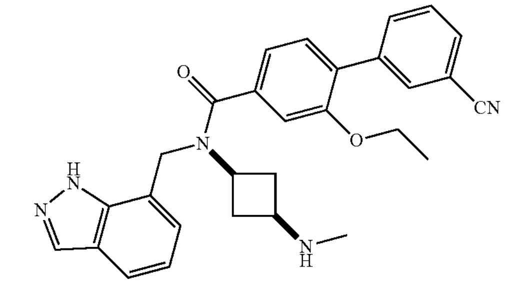
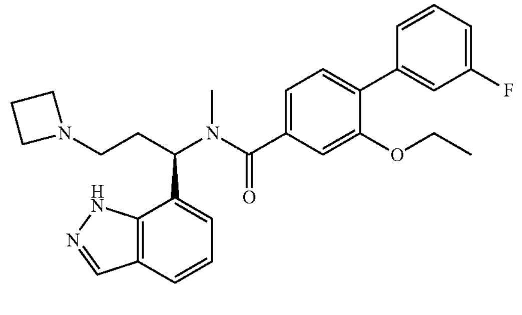

-continued

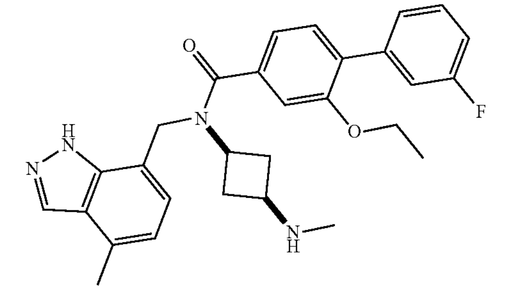

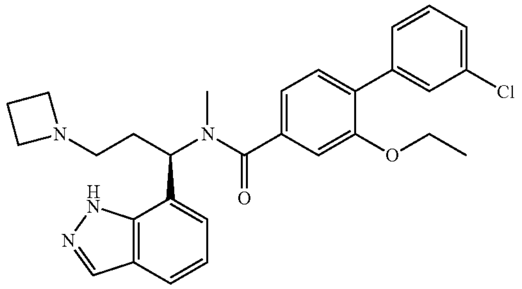

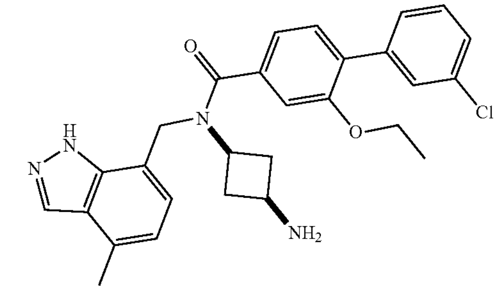

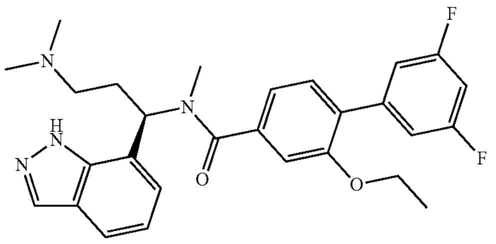

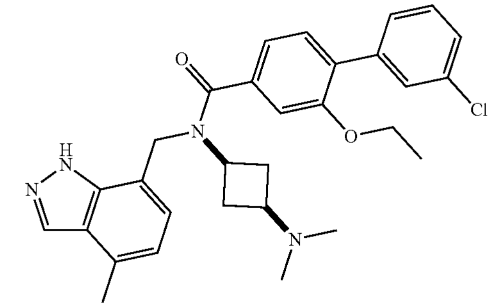

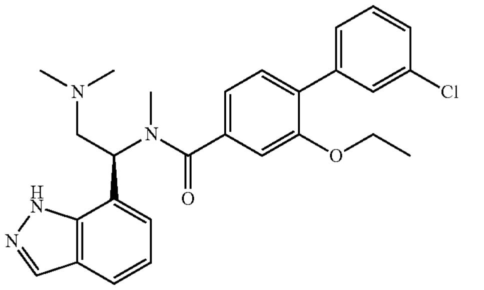

-continued

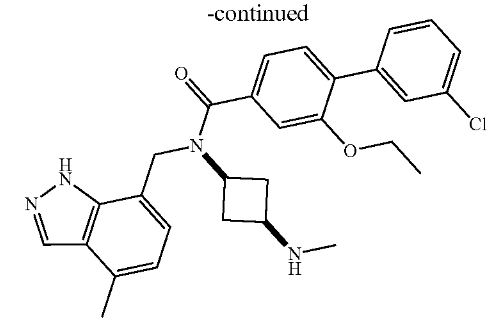

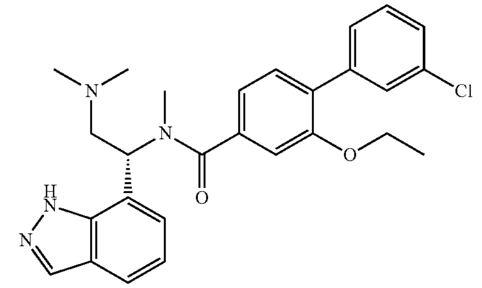

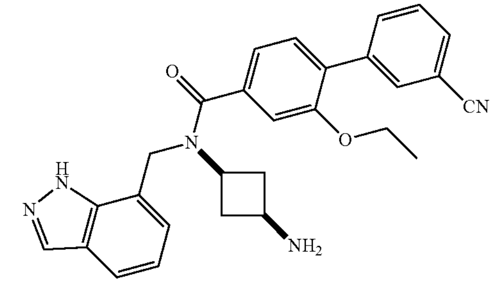

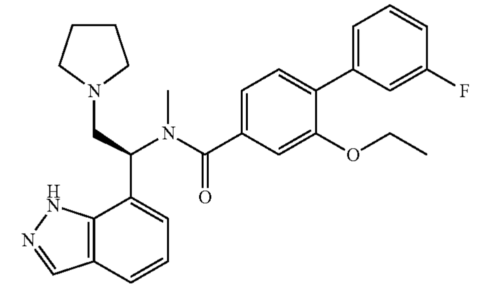

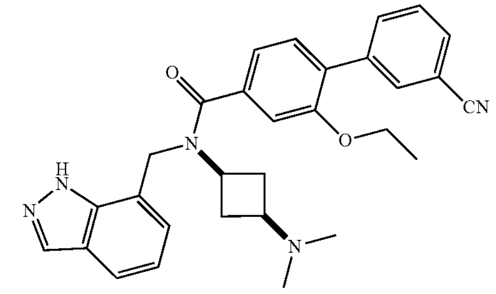

or a pharmaceutically acceptable salt thereof.

19. The compound of claim 1 wherein the compound binds to one or more amino acids of Y143, R147, F257, Y258, H260, E263, V264, L272, L275, I276, C279, F299, G328, L331, L332, L335, and C514 of a NLRP3 amino acid sequence of SEQ ID NO: 1.

20. A pharmaceutical composition comprising a compound of claim 1, or a pharmaceutically acceptable salt thereof, and a pharmaceutically acceptable excipient.

21. A method of inhibiting NLRP3 inflammasome in a subject in need thereof comprising administering to the subject a therapeutically effective amount of a compound according to claim 1.

22. A method of treating obesity in a subject in need thereof, comprising administering to the subject a therapeutically effective amount of a compound according to claim 1, or a pharmaceutically acceptable salt thereof.

23. A method of improving lipid metabolism in a subject in need thereof, comprising administering to the subject a therapeutically effective amount of a compound according to claim 1, or a pharmaceutically acceptable salt thereof.

24. A method of treating an ocular disease in a subject in need thereof comprising administering to the subject a therapeutically effective amount of a compound according to claim 1, or a pharmaceutically acceptable salt thereof.

25. A method of treating gout in a subject in need thereof comprising administering to the subject a therapeutically effective amount of a compound according to claim 1, or a pharmaceutically acceptable salt thereof.

26. The compound of claim 1, wherein the compound of Formula I is selected from the group consisting of

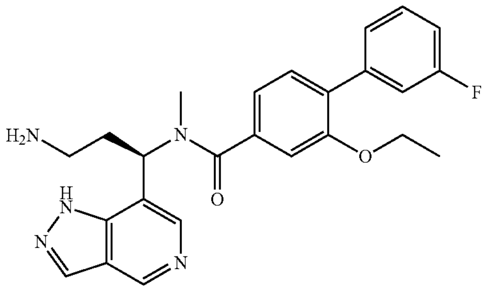

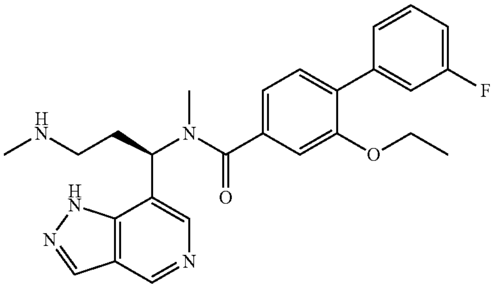

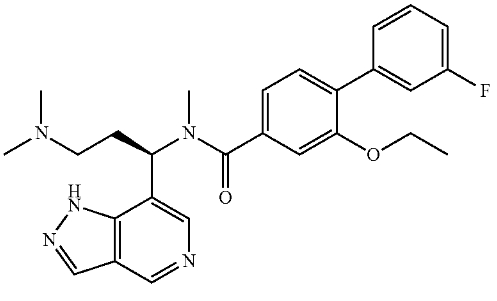

or a pharmaceutically acceptable salt thereof.

27. The compound of claim 1, wherein the compound of Formula I is

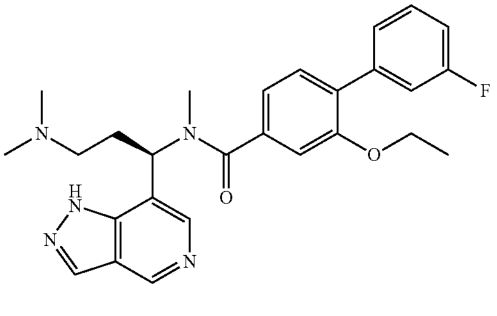 [SMILES: CCOc1cc(C(=O)N(C)[C@H](CCN(C)C)c2cncc3cn[nH]c23)ccc1-c1cccc(F)c1]

or a pharmaceutically acceptable salt thereof.

28. The compound of claim 1, wherein the compound of Formula I is

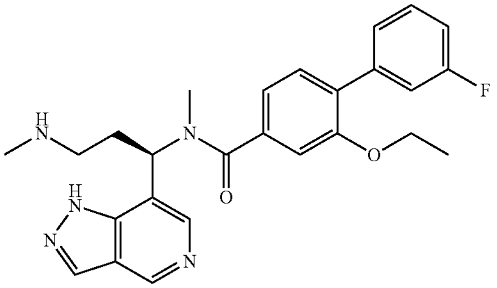 [SMILES: CCOc1cc(C(=O)N(C)[C@H](CCNC)c2cncc3cn[nH]c23)ccc1-c1cccc(F)c1]

or a pharmaceutically acceptable salt thereof.

29. The compound of claim 1, wherein the compound of Formula I is

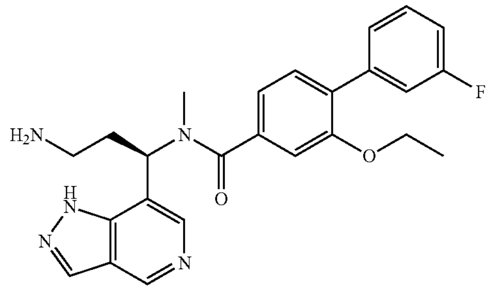 [SMILES: CCOc1cc(C(=O)N(C)[C@H](CCN)c2cncc3cn[nH]c23)ccc1-c1cccc(F)c1]

or a pharmaceutically acceptable salt thereof.

* * * * *